(12) United States Patent
Mautino et al.

(10) Patent No.: US 10,047,066 B2
(45) Date of Patent: Aug. 14, 2018

(54) IDO INHIBITORS

(75) Inventors: Mario Mautino, Ames, IA (US); Firoz Jaipuri, Ames, IA (US); Agnieszka Marcinowicz-Flick, Ames, IA (US); Tanay Kesharwani, Ames, IA (US); Jesse Waldo, Ames, IA (US)

(73) Assignee: NEWLINK GENETICS CORPORATION, Ames, IA (US)

( * ) Notice: Subject to any disclaimer, the term of this patent is extended or adjusted under 35 U.S.C. 154(b) by 855 days.

(21) Appl. No.: 12/744,860

(22) PCT Filed: Dec. 1, 2008

(86) PCT No.: PCT/US2008/085167
§ 371 (c)(1),
(2), (4) Date: Nov. 17, 2010

(87) PCT Pub. No.: WO2009/073620
PCT Pub. Date: Jun. 11, 2009

(65) Prior Publication Data
US 2011/0053941 A1 Mar. 3, 2011

Related U.S. Application Data

(60) Provisional application No. 61/050,646, filed on May 6, 2008, provisional application No. 60/991,518, filed on Nov. 30, 2007.

(51) Int. Cl.
*A61K 31/5375* (2006.01)
*A61K 31/135* (2006.01)
(Continued)

(52) U.S. Cl.
CPC .......... *C07D 333/56* (2013.01); *A61K 31/138* (2013.01); *A61K 31/506* (2013.01); *C07C 259/06* (2013.01); *C07C 311/48* (2013.01); *C07C 327/44* (2013.01); *C07C 327/48* (2013.01); *C07C 333/20* (2013.01); *C07D 209/14* (2013.01); *C07D 209/18* (2013.01); *C07D 213/40* (2013.01); *C07D 215/26* (2013.01); *C07D 253/07* (2013.01); *C07D 261/20* (2013.01); *C07D 263/22* (2013.01); *C07D 277/36* (2013.01); *C07D 277/64* (2013.01); *C07D 279/06* (2013.01); *C07D 307/80* (2013.01); *C07D 307/81* (2013.01); *C07D 333/58* (2013.01); *C07D 333/60* (2013.01); *C07D 335/06* (2013.01);
(Continued)

(58) Field of Classification Search
CPC .. C07D 333/56; C07D 277/64; C07D 307/80; C07D 279/06; C07D 277/36; C07D 401/06; C07D 209/18; C07D 215/26; C07D 333/60; C07D 307/81; C07D 471/04; C07D 217/26; C07C 327/48; C07C 259/06; C07C 311/48; A61K 31/506; A61K 31/437; A61K 31/472

USPC ....................................................... 514/238.2
See application file for complete search history.

(56) References Cited

U.S. PATENT DOCUMENTS 3,192,110 A   6/1965   Biel et al.
3,215,706 A   11/1965  Lutz
(Continued)

FOREIGN PATENT DOCUMENTS

CA        952113 A   *   7/1974
EP        0 578 847 A1   7/1992
(Continued)

OTHER PUBLICATIONS

Nicolaus, Bruno J. R.; Pagani, Giuseppe; Testa, Emilio, O,N-Substituted hydroxylamines. II. Synthesis and properties of O-(phenylalkyl)hydroxylamines, Helvetica Chimica Acta (1962), 45, 1381-95.*

(Continued)

*Primary Examiner* — Sarah Pihonak
*Assistant Examiner* — Jason Deck
(74) *Attorney, Agent, or Firm* — McDonnell Boehnen Hulbert & Berghoff LLP

(57) ABSTRACT

Presently provided are methods for (a) modulating an activity of indoleamine 2,3-dioxygenase comprising contacting an indoleamine 2,3-dioxygenase with a modulation effective amount of a compound as described in one of the aspects described herein; (b) treating indoleamine 2,3-dioxygenase (IDO) mediated immunosuppression in a subject in need thereof, comprising administering an effective indoleamine 2,3-dioxygenase inhibiting amount of a compound as described in one of the aspects described herein; (c) treating a medical conditions that benefit from the inhibition of enzymatic activity of indoleamine-2,3-dioxygenase comprising administering an effective indoleamine 2,3-dioxygenase inhibiting amount of a compound as described in one of the aspects described herein; (d) enhancing the effectiveness of an anti-cancer treatment comprising administering an anti-cancer agent and a compound as described in one of the aspects described herein; (e) treating tumor-specific immunosuppression associated with cancer comprising administering an effective indoleamine 2,3-dioxygenase inhibiting amount of a compound as described in one of the aspects described herein; and (f) treating immunosuppression associated with an infectious disease, e.g., HIV-I infection, comprising administering an effective indoleamine 2,3-dioxygenase inhibiting amount a compound as described in one of the aspects described herein.

1 Claim, No Drawings

(51) Int. Cl.

| | | |
|---|---|---|
| *A61K 31/404* | (2006.01) | |
| *A61K 31/381* | (2006.01) | |
| *A61K 31/505* | (2006.01) | |
| *C07D 209/14* | (2006.01) | |
| *C07D 405/12* | (2006.01) | |
| *C07D 333/56* | (2006.01) | |
| *A61K 31/138* | (2006.01) | |
| *A61K 31/506* | (2006.01) | |
| *C07C 259/06* | (2006.01) | |
| *C07C 311/48* | (2006.01) | |
| *C07C 327/44* | (2006.01) | |
| *C07C 327/48* | (2006.01) | |
| *C07C 333/20* | (2006.01) | |
| *C07D 209/18* | (2006.01) | |
| *C07D 213/40* | (2006.01) | |
| *C07D 215/26* | (2006.01) | |
| *C07D 253/07* | (2006.01) | |
| *C07D 261/20* | (2006.01) | |
| *C07D 263/22* | (2006.01) | |
| *C07D 277/36* | (2006.01) | |
| *C07D 279/06* | (2006.01) | |
| *C07D 307/81* | (2006.01) | |
| *C07D 333/58* | (2006.01) | |
| *C07D 333/60* | (2006.01) | |
| *C07D 335/06* | (2006.01) | |
| *C07D 401/06* | (2006.01) | |
| *C07D 409/12* | (2006.01) | |
| *C07D 417/06* | (2006.01) | |
| *C07D 417/12* | (2006.01) | |
| *C07D 277/64* | (2006.01) | |
| *C07D 307/80* | (2006.01) | |
| *A61P 37/00* | (2006.01) | |
| *A61K 31/4045* | (2006.01) | |
| *C07D 403/12* | (2006.01) | |
| *C07D 401/12* | (2006.01) | |
| *A61K 31/4709* | (2006.01) | |
| *C07D 413/12* | (2006.01) | |
| *A61K 31/423* | (2006.01) | |
| *C07C 333/04* | (2006.01) | |
| *A61K 31/27* | (2006.01) | |
| *C07D 213/53* | (2006.01) | |
| *A61K 31/4406* | (2006.01) | |
| *A61K 31/4402* | (2006.01) | |
| *A61K 31/36* | (2006.01) | |
| *A61K 31/47* | (2006.01) | |
| *A61K 31/357* | (2006.01) | |
| *A61K 31/428* | (2006.01) | |

(52) U.S. Cl.
CPC ......... *C07D 401/06* (2013.01); *C07D 405/12* (2013.01); *C07D 409/12* (2013.01); *C07D 417/06* (2013.01); *C07D 417/12* (2013.01)

(56) References Cited

U.S. PATENT DOCUMENTS

| | | | |
|---|---|---|---|
| 3,226,446 A | 12/1965 | Drain et al. | |
| 3,240,802 A | 3/1966 | Robertson | |
| 3,245,878 A | 4/1966 | Berger et al. | |
| 3,245,879 A | 4/1966 | Purdy et al. | |
| 3,262,978 A | 7/1966 | Robertson | |
| 3,284,299 A | 11/1966 | McGrath et al. | |
| 3,313,824 A | 4/1967 | Paquette | |
| 3,329,677 A | 7/1967 | Schumann | |
| 3,342,678 A | 9/1967 | Berger et al. | |
| 3,349,135 A | 10/1967 | Drain et al. | |
| 3,375,273 A | 3/1968 | Drain et al. | |
| 3,378,592 A | 4/1968 | Lutz | |
| 3,758,546 A | 9/1973 | Kasztreiner et al. | |
| 3,766,235 A | 10/1973 | Kisfaludy et al. | |
| 4,009,175 A | 2/1977 | Hester, Jr. | |
| 4,144,393 A | 3/1979 | Bradshaw et al. | |
| 4,287,194 A * | 9/1981 | Kosa et al. | 514/247 |
| 4,331,665 A | 5/1982 | Teraji et al. | |
| 4,332,798 A | 6/1982 | Teraji et al. | |
| 4,390,534 A | 6/1983 | Teraji et al. | |
| 4,472,194 A | 9/1984 | Van Assche et al. | |
| 4,840,945 A | 6/1989 | Ohnishi et al. | |
| 4,923,896 A | 5/1990 | Trivedi | |
| 5,081,248 A | 1/1992 | Zama et al. | |
| 5,120,849 A | 6/1992 | Wild et al. | |
| 5,155,127 A | 10/1992 | Trivedi | |
| 5,233,035 A | 8/1993 | Hara et al. | |
| 5,322,852 A | 6/1994 | Frei et al. | |
| 5,358,955 A | 10/1994 | Brooks et al. | |
| 5,378,716 A | 1/1995 | Hamanaka et al. | |
| 5,403,835 A | 4/1995 | Nakagawa et al. | |
| 5,407,902 A | 4/1995 | Oda et al. | |
| 5,438,052 A | 8/1995 | Angehrn et al. | |
| 5,455,238 A | 10/1995 | Aszodi et al. | |
| 5,512,581 A | 4/1996 | Brooks et al. | |
| 5,516,806 A | 5/1996 | Frei et al. | |
| 5,587,372 A | 12/1996 | Aszodi et al. | |
| 5,594,009 A | 1/1997 | Hudkins et al. | |
| 5,606,095 A | 2/1997 | Pfiffner et al. | |
| 5,616,806 A | 4/1997 | Nagata et al. | |
| 5,705,511 A | 1/1998 | Hudkins et al. | |
| 6,057,269 A | 5/2000 | Klintz et al. | |
| 6,107,291 A | 8/2000 | Russo-Rodriguez et al. | |
| 6,121,459 A | 9/2000 | Schwindt et al. | |
| 6,221,865 B1 | 4/2001 | Sebti et al. | |
| 6,451,840 B1 | 9/2002 | Munn et al. | |
| 6,482,416 B2 | 11/2002 | Munn et al. | |
| 6,552,006 B2 | 4/2003 | Raz et al. | |
| 6,635,677 B2 | 10/2003 | Gerson et al. | |
| 6,936,416 B2 | 8/2005 | Zhu et al. | |
| 7,160,539 B2 | 1/2007 | Munn et al. | |
| 7,312,200 B2 | 12/2007 | Malsam et al. | |
| 7,384,558 B2 | 6/2008 | Hai et al. | |
| 7,465,448 B2 | 12/2008 | Munn et al. | |
| 7,598,287 B2 | 10/2009 | Munn et al. | |
| 7,705,022 B2 | 4/2010 | Prendergast et al. | |
| 7,714,139 B2 | 5/2010 | Prendergast et al. | |
| 7,799,776 B2 | 9/2010 | Andersen et al. | |
| 8,034,953 B2 | 10/2011 | Combs et al. | |
| 8,324,282 B2 * | 12/2012 | Gerson et al. | 514/645 |
| 2002/0002152 A1 | 1/2002 | Craig et al. | |
| 2002/0035136 A1 | 3/2002 | Liu et al. | |
| 2003/0139361 A1 | 7/2003 | Yuda et al. | |
| 2003/0194803 A1 | 10/2003 | Mellow et al. | |
| 2003/0212028 A1 | 11/2003 | Raz et al. | |
| 2003/0225133 A1 | 12/2003 | Dutta | |
| 2005/0186289 A1 | 8/2005 | Munn et al. | |
| 2005/0191276 A1 | 9/2005 | Gurtner et al. | |
| 2005/0238651 A1 | 10/2005 | Gurtner et al. | |
| 2005/0249666 A1 | 11/2005 | Nakamura et al. | |
| 2006/0142214 A1* | 6/2006 | Or et al. | 514/28 |
| 2006/0160883 A1 | 7/2006 | Stoops | |
| 2006/0165665 A1 | 7/2006 | Min et al. | |
| 2006/0241186 A1 | 10/2006 | Gerson et al. | |
| 2006/0258719 A1 | 11/2006 | Combs et al. | |
| 2006/0270618 A1 | 11/2006 | Bevec | |
| 2006/0292618 A1 | 12/2006 | Mellor et al. | |
| 2007/0048769 A1 | 3/2007 | Mellor et al. | |
| 2007/0077224 A1 | 4/2007 | Munn et al. | |
| 2007/0077234 A1 | 4/2007 | Munn et al. | |
| 2007/0082853 A1 | 4/2007 | Or et al. | |
| 2007/0092881 A1 | 4/2007 | Ohnishi et al. | |
| 2007/0099844 A1 | 5/2007 | Prendergast et al. | |
| 2007/0203140 A1 | 8/2007 | Combs et al. | |

FOREIGN PATENT DOCUMENTS

| | | |
|---|---|---|
| EP | 0 544 958 A1 | 6/1993 |
| EP | 0 658 547 A1 | 6/1995 |
| EP | 0 838 452 A1 | 4/1998 |

(56) References Cited

FOREIGN PATENT DOCUMENTS

| | | | |
|---|---|---|---|
| EP | 0 949 243 A1 | 10/1999 | |
| EP | 1 281 707 A1 | 2/2003 | |
| EP | 1 595 865 A1 | 11/2005 | |
| GB | 1034198 | 10/1963 | |
| GB | 964 721 A | 7/1964 | |
| GB | 1 042 191 A | 9/1966 | |
| GB | 1 264 261 | 2/1972 | |
| GB | 1 331 203 | 9/1973 | |
| GB | 1331203 | 9/1973 | |
| GB | 1 496 757 | 1/1978 | |
| IL | 35932 A | 11/1974 | |
| JP | 2005232009 A | * | 9/2005 |
| WO | WO 2002034745 a1 | * | 5/2002 |
| WO | 04/018479 A1 | 3/2004 | |
| WO | 2004/093871 A1 | 11/2004 | |
| WO | 2004/094409 A1 | 11/2004 | |
| WO | 2006/005185 A1 | 1/2006 | |
| WO | 2007/050963 A1 | 5/2007 | |
| WO | 08/008398 A1 | 1/2008 | |
| WO | 08/024725 A1 | 2/2008 | |
| WO | 08/150447 A1 | 12/2008 | |

OTHER PUBLICATIONS

Tadashi Amagasa, Masami Ogawa and Soji Sugai, Plant Cell Physiol. 33(7): 1025-1029 (1992), Effects of Aminooxyacetic Acid and Its Derivatives on Flowering in Pharbitis nil.*
Sugimoto et al., "Crystal structure of human indoleamine 2,3-dioxygenase: Catalytic mechanism of O2 incorporation by a heme-containing dioxygenase", PNAS, Feb. 21, 2006, vol. 103, No. 8, pp. 2611-2616.
Berger, Bradley J., "Antimalarial Activities of Aminooxy compounds", Antimicrobial Agents and Chemotherapy, Sep. 2000, vol. 44, No. 9, pp. 2540-2542.
Cady et al., "1-Methyl-DL-tryptophan, B-(3-Benzofuranyl)-DL-alanine (the Oxygen Analog of Tryptophan), and B-[3-Benzo(b)thienyl]-DL-alanine (the Sulfur Analog of Tryptophan) Are Competitive Inhibitors for Indoleamine 2,3-Dioxygense", Archives Of Biochemistry And Biophysics, vol. 291, No. 2, Dec., pp. 326-333, 1991.
Scott et al., "Potential Inhibitors of Tyrosine Hydroxylase and Dopamine-B-Hydroxylase", Journal of Pharmaceutical Sciences, vol. 73, No. 11, Nov. 1984, pp. 1531-1535.
Hamor et al., "Benzyloxyamines as Possible Inhibitors of Histamine Biosynthesis", Journal of Pharmaceutical Sciences, vol. 59, No. 12, Dec. 1970, pp. 1752-1756.
Levine et al., "Inhibition of histamine synthesis in the rat by a-hydrazino analog of histidine and 4-bromo-3-hydroxy benzyloxyamine", Biochemical Pharmacology, 1965, vol. 14, pp. 139-149, Pergamon Press Ltd., Printed in Great Britain.
Schumann et al., "Hydroxylamine Chemistry. IV. O-Aralkylhydroxylamines", J. Medicinal Chem., 1964, vol. 7 (3), pp. 329-334.
Ludwig et al., "The Synthesis of Hydroxylamine Derivatives Possessing Hypocholesteremic Activity", J. Medicinal Chem., Jul. 1967, vol. 10 (4), pp. 556-564.
High et al., "Probing the 'Active Site' of Diamine Oxidase: Structure-Activity Relations for Histamine Potentiation by O-Alkylhydroxylamines on Colonic Epithelium", The Journal Of Pharmacology And Experimental Therapeutics, 1999, vol. 288, No. 2, pp. 490-501.
Leinweber, "Mechanism of Histidine Decarboxylase Inhibition by NSD-1055 and Related Hydroxylamines", Mol. Pharmacol. 4, 1968, pp. 337-348.
Levine, "Histamine Synthesis in Man: Inhibition by 4-Bromo-3-Hydroxybenzyloxyamine", Science, Nov. 25, 1966, vol. 154, pp. 1017-1019.
Vottero et al., "Inhibitors of human indoleamine 2,3-dioxygenase identified with a target-based screen in yeast", Biotechnol. J. 2006, vol. 2, Issue 3, pp. 282-288.

Malachowski et al., "A new cancer immunosuppression target: indoleamine 2,3-dioxygenase (IDO). A review of the IDO mechanism, inhibition and therapeutic applications", Drugs of the Future 2005, vol. 30 Issue 9, pp. 897-909.
Gaspari et al., "Structure-Activity Study of Brassinin Derivatives as Indoleamine 2,3-Dioxygenase Inhibitors", J. Med. Chem. 2006, vol. 49, pp. 684-692.
Brastianos et al., J. Am. Chem. Soc. 2006, 128 (50), pp. 16046-16047.
Pereira et al., J. Nat. Prod., 2006, 69 (10), pp. 1496-1499.
Martin, D.G. et al., "Hydroxylamine Chemistry. V. Aralkoxyguanidines", Journal of Medicinal Chemistry, vol. 8, 1965, p. 456-459.
Undheim, K. et al., "Semisynthetic Penicillins. IV. Preparation of α-(Ylideneimino-oxy) carboxylic Acids", Acta Chemica Scandinavica, vol. 19, nb. 2, 1965, p. 317-324.
Schumann, E.L. et al., "Hydroxylamine Chemistry. IV. O-Aralkylhydroxylamines", Journal of Medicinal Chemistry, vol. 7, 1964, p. 329-334.
Schumann, E.L. et al., "The Synthesis and γ-Aminobutyric Acid Transaminase Inhibition of Aminoöxy Acids and Related Compounds", Journal of Medicinal and Pharmaceutical Chemistry, vol. 5, 1962, p. 464-477.
Bellasio, E. et al., "O- And N-Substituted Hydroxylamines. Paper VII—Synthesis of O- and N-benzhydrylhydroxylamine and derivatives", Farmaco, Edizione Scientifica, vol. 23, 1968, p. 372-382.
Chen, Fei; Song, Ke-Sheng; Wu, Yun-Dong; Yang, Dan. Synthesis and conformational studies of γ-aminoxy peptides. Journal of the American Chemical Society; vol. 130; nb. 2; (2008); p. 743-755.
Bates, Roderick W.; Nemeth, Joseph A.; Snell, Robert H. Synthesis of Sedamine by Cycloisomerisation of an Allenic Hydroxylamine. Synthesis; 7; (2008); p. 1033-1038.
Bates, Roderick W.; Snell, Robert H.; Winbush, Susann. Synthesis of N,O-heterocycles by intramolecular conjugate addition of a hydroxylamine. Synlett; 7; (2008); p. 1042-1044.
Foot, Oliver F.; Knight, David W.; Low, Ai Cheng Lilian; Li, YingFa. On the viability of 5-endo-dig cyclisations of O-propargylic hydroxylamine derivatives, leading to 2,5-dihydroisoxazoles (3-isoxazolines). Tetrahedron Letters; vol. 48; nb. 4; (2007); p. 647-650.
Clive, Derrick L. J.; Pham, Mai P.; Subedi, Rajendra. Carbocyclization by Radical Closure onto O-Trityl Oximes: Dramatic Effect of Diphenyl Diselenide. Journal of the American Chemical Society; vol. 129; nb. 9; (2007); p. 2713-2717.
Peng, Jinsong; Jiang, Dahong; Lin, Wenqing; Chen, Yuanwei. Palladium-catalyzed sequential one-pot reaction of aryl bromides with O-homoallylhydroxylamines: Synthesis of N-aryl-β-amino alcohols. Organic and Biomolecular Chemistry; vol. 5; nb. 9; (2007); p. 1391-1396.
Sibi, Mukund P.; Itoh, Kennosuke. Organocatalysis in Conjugate Amine Additions. Synthesis of β-Amino Acid Derivatives. Journal of the American Chemical Society; vol. 129; nb. 26; (2007); p. 8064-8065.
Dongol, Krishna Gopal; Tay, Boon Ying Palladium(O)-catalyzed cascade one-pot synthesis of isoxazolidines Tetrahedron Letters; vol. 47; nb. 6; (2006); p. 927-930.
Dongol, Krishna Gopal; Tay, Boon Ying; Xiang, Kai; Thiemann, Thies. Palladium(II)-Catalyzed Synthesis of Isoxazolidines: Using a Catalytic Copper Acetate and Molecular Oxygen as the Cooxidant Synthetic Communications; vol. 36; nb. 9; (2006); p. 1247-1257.
Pennicott, Lewis; Lindell, Stephen. The Preparation of 2-Isoxazolines from O-Propargylic Hydroxylamines via a Tandem Rearrangement-Cyclisation Reaction Synlett; 3; (2006); p. 463-465.
Janza, Birgit; Studer, Armido. Stereoselective cyclization reactions of IBX-generated alkoxyamidyl radicals Journal of Organic Chemistry; vol. 70; nb. 17; (2005); p. 6991-6994.
Maillard, Ludovic T.; Benohoud, Meryem; Durand, Philippe; Badet, Bernard.A New Supported Reagent for the Parallel Synthesis of Primary and Secondary O-Alkyl Hydroxylamines Through a Base-Catalyzed Mitsunobu Reaction. Journal of Organic Chemistry; vol. 70; nb. 16; (2005); p. 6303-6312.
Yamagiwa, Noriyuki; Qin, Hongbo; Matsunaga, Shigeki; Shibasaki, Masakatsu. Lewis Acid-Lewis acid Heterobimetallic Cooperative

(56) References Cited

OTHER PUBLICATIONS

Catalysis: Mechanistic Studies and Application in Enantioselective Aza-Michael Reaction. Journal of the American Chemical Society; vol. 127; nb. 38; (2005); p. 13419-13427.
Cooper, Tracey S.; Laurent, Pierre; Moody, Christopher J.; Takle, Andrew K. Asymmetric synthesis of N-protected amino acids by the addition of organolithium carboxyl synthons to ROPHy/SOPHyderived aldoximes and ketoximes. Organic and Biomolecular Chemistry; vol. 2; nb. 2; (2004); p. 265-276.
Wetter, Christian; Gierlich, Johannes; Knoop, Christoph Alexander; Mueller, Christoph; Schulte, Tobias; Studer, Armido. Steric and Electronic Effects in Cyclic Alkoxyamines-Synthesis and Applications as Regulators for Controlled/Living Radical Polymerization. Chemistry—A European Journal; vol. 10; nb. 5; (2004); p. 1156-1166.
Atobe, Masakazu; Yamazaki, Naoki; Kibayashi, Chihiro Enantioselective synthesis of primary 1-(aryl)alkylamines by nucleophilic 1,2-addition of organolithium reagents to hydroxyoxime ethers and application to asymmetric synthesis of G-protein-coupled receptor ligands. Journal of Organic Chemistry; vol. 69; nb. 17; (2004); p. 5595-5607.
Pegurier, Cecile; Morellato, Laurence; Chahed, Eminn; Andrieux, Jean; Nicolas, Jean-Paul; Boutin, Jean A.; Bennejean, Caroline; Delagrange, Philippe; Langlois, Michel; Mathe-Allainmat, Monique Synthesis of New Arylalkoxy Amido Derivatives as Melatoninergic Ligands. Bioorganic & Medicinal Chemistry; vol. 11; nb. 5; (2003); p. 789-800.
Bates, Roderick W.; Sa-Ei, Kanicha. O-Alkenyl Hydroxylamines: A New Concept for Cyclofunctionalization. Organic Letters; vol. 4; nb. 24; (2002); p. 4225-4228.
Jin, Xiu Lan; Sugihara, Hiroyasu; Daikai, Kazuhiro; Tateishi, Hiroki; Jin, Yong Zhi; Furuno, Hiroshi; Inanaga, Junji. Chiral rare earth metal complex-catalyzed conjugate addition of O-alkylhydroxylamines. An efficient synthetic entry into optically active 2-acyl aziridines. Tetrahedron; vol. 58; nb. 41; (2002); p. 8321-8330.
Rossello, Armando; Bertini, Simone; Lapucci, Annalina; Macchia, Marco; Martinelli, Adriano; Rapposelli, Simona; Herreros, Esperanza;Macchia, Bruno Synthesis, Antifungal Activity, and Molecular Modeling Studies of New Inverted Oxime Ethers of Oxiconazole Journal of Medicinal Chemistry; vol. 45; nb. 22; (2002); p. 4903-4912.
Dutta, Aloke K.; Fei, Xiang-Shu; Beardsley, Patrick M.; Newman, Jennifer L.; Reith, Maarten E.A. Structure-Activity Relationship Studies of 4[2-(Diphenylmethoxy)ethyl]-1-benzylpiperidine Derivatives and Their N-Analogues: Evaluation of Behavioral Activity of O- and N-Analogues and Their Binding to Monoamine Transporters Journal of Medicinal Chemistry; vol. 44; nb. 6; (2001); p. 937-948.
Yamazaki, Naoki; Atobe, Masakazu; Kibayashi, Chihiro. Nucleophilic addition of methyllithium to chiral oxime ethers: asymmetric preparation of 1-(aryl)ethylamines and application to a synthesis of calcimimetics (+)-NPS R-568 and its thio analogue Tetrahedron Letters; vol. 42; nb. 30; (2001); p. 5029-5032.
Ishikawa, Teruhiko; Kawakami, Masatomo; Fukui, Miyuki; Yamashita, Ayako; Urano, Jin; Saito, Seiki Novel [2,3]Sigmatropic Rearrangement for Carbon-Nitrogen Bond Formation. Journal of the American Chemical Society; vol. 123; nb. 31; (2001); p. 7734-7735.
Tanaka, Ken; Katsurada, Manabu; Ohno, Fumihiko; Shiga, Yasushi; Oda, Masatsugu; Miyagi, Miwa; Takehara, Jun; Okano, Kazuya Practical Asymmetric Synthesis of (S)- MA20565, a Wide-Spectrum Agricultural Fungicide Journal of Organic Chemistry; vol. 65; nb. 2; (2000); p. 432-437.
Kolasa, Teodozyj; Gunn, David E.; Bhatia, Pramila; Woods, Keith W.; Gane, Todd; Stewart, Andrew O.; Bouska, Jenifer B.; Harris, Richard R.; Hulkower, Keren I.; Malo, Peter E.; Bell, Randy L.; et al. Heteroarylmethoxyphenylalkoxyiminoalkylcarboxylic Acids as Leukotriene Biosynthesis Inhibitors Journal of Medicinal Chemistry; vol. 43; nb. 4; (2000); p. 690-705.
Kolasa, Teodozyj; Gunn, David E.; Bhatia, Pramila; Basha, Anwer; Craig, Richard A.; Stewart, Andrew O.; Bouska, Jennifer B.; Harris, Richard R.; Hulkower, Keren I.; Malo, Peter E.; Bell, Randy L.; et al. Symmetrical Bis (heteroarylmethoxyphenyl) alkylcarboxylic Acids as Inhibitors of Leukotriene Biosynthesis Journal of Medicinal Chemistry; vol. 43; nb. 17; (2000); p. 3322-3334.
Moody, Christopher J.; Hunt, James C. A. Synthesis of Virenamide B, a Cytotoxic Thiazole-Containing Peptide Journal of Organic Chemistry; vol. 64; nb. 23; (1999); p. 8715-8717.
Gallagher, Peter T.; Hunt, James C. A.; Lightfoot, Andrew P.; Moody, Christopher J. Chiral oximes in asymmetric synthesis. Part 2. Addition of butyllithium to benzaldehyde O-(1-phenylalkyl)oximes Journal of the Chemical Society, Perkin Transactions 1: Organic and Bio-Organic Chemistry (1972-1999); nb. 17; (1997); p. 2633-2638.
Kolasa, Teodozyj; Gunn, David E.; Stewart, Andrew O.; Brooks, Clint D. W. Synthesis and Resolution of 2(Cyclohexyl-4-(2-quinolylmethoxy)phenyl) methoxyiminopropionic acid, Leukotriene Biosynthesis Inhibitors Tetrahedron: Asymmetry; vol. 7; nb. 9; (1996); p. 2645-2654.
Brown, David S.; Gallagher, Peter T.; Lightfoot, Andrew P.; Moody, Christopher J.; Slawin, Alexandra M. Z.; Swann, Elizabeth Chiral Oximes in Asymmetric Synthesis. Addition of Organometallic Reagents to O-(1-Phenylethyl) Aldoximes Tetrahedron; vol. 51; nb. 42; (1995); p. 11473-11488.
Ace, Karl W.; Hussain, Nigel; Lathbury, David C.; Morgan, David O. Synthesis of an α-(Aminooxy)arylacetic Ester by the Reaction of an α-Diazo Ester with N-Hydroxyphthalimide. Tetrahedron Letters; vol. 36; nb. 44; (1995); p. 8141-8144.
Dieter, R. Karl; Datar, Ravindra 1,2-Nucleophilic additions of organolithium reagents to chiral oxime ethers Canadian Journal of Chemistry; vol. 71; nb. 6; (1993); p. 814-823.
Muir, G.; Jones, R. L.; Will, S. G.; Winwick, T.; Peesapati, V.; et al. Thromboxane receptor active analogues based on the 6-oxabicyclo<3.2.1>octane ring system European Journal of Medicinal Chemistry; vol. 28; nb. 7-8; (1993); p. 609-624.
Iwagami, Hisao; Yatagai, Masanobu; Nakazawa, Masakazu; Orita, Haruo; Honda, Yutaka; et al. Synthesis of a Chiral α-(Aminooxy)arylacetic Ester. II. A Route through a Chiral 2-Hydroxy-2-phenylacetic Acid Derivative Bulletin of the Chemical Society of Japan; vol. 64; nb. 1; (1991); p. 175-182.
Iwagami, Hisao; Nakazawa, Masakazu; Yatagai, Masanobu; Hijiya, Toyoto; Honda, Yutaka; et al. Synthesis of Chiral α-(Aminooxy)arylacetic Ester. I. A Route through Optical Resolution of a Racemic α-(Phthalimidooxy)arylacetic Acid Bulletin of the Chemical Society of Japan; vol. 63; nb. 11; (1990); p. 3073-3081.
Kolasa, Teodozyj; Sharma, Sushil K.; Miller, Marvin J. α-N-Hydroxyamino Acid Derivatives Tetrahedron; vol. 44; nb. 17; (1988); p. 5431-5440.
Stanciuc, Gabriela; Caproiu, M. Teodor; Caragheorgheopol, Agneta; Caldararu, Horia; Balaban, Alexandru T.; Walter, Robert I. Factors Affecting the Stability and Equilibria of Free Radicals. XIII. N-Alkoxy- and N-Aralkoxypicrylamines and ESR Spectra of the Corresponding Capto-Dative Persistent Aminyls. Journal of Magnetic Resonance (1969-1992); vol. 75; nb. 1; (1987); p. 63-72.
Kolasa, Teodozyj; Miller, Marvin J.A Simple Method for Distinguishing Optical Isomers of Chiral Amines, Hydroxylamines, Amino Acids, and Peptides. Journal of Organic Chemistry; vol. 51; nb. 15; (1986); p. 3055-3058.
Dixon, Dabney White; Weiss, Randy H. Oxidation of 1,2-Bis(hydroxylamines). Journal of Organic Chemistry; vol. 49; nb. 23; (1984); p. 4487-4494.
Atherton, Frank R.; Lambert, Robert W. Synthesis of 2(R)-<3(S)-Acylamino-2-OXO-1-Azetidinyloxy>-Acetic Acids. Tetrahedron; vol. 40; nb. 6; (1984); p. 1039-1046.
Grochowski, Jurczak, "A New Synthesis of O-Alkylhydroxylamines", Synthesis, (1976), p. 682.
Kasztreiner et al., "Synthesis of O-Substituted Hydroxylamines", Acta Chimica Academiae Scientiarum Hungaricae; vol. 84; (1975); p. 167,179.
Schalke; Hall. Journal of the Chemical Society, Perkin Transactions 1: Organic and Bio-Organic Chemistry (1972-1999); (1975); p. 2417,2421.

(56) References Cited

OTHER PUBLICATIONS

Criechio,R. et al., "Oximes of 3-Formylrifamycin SV. Synthesis, Antibacterial Activity, and Other Biological Properties", Journal of Medicinal Chemistry; vol. 17; (1974); p. 396-403.
Carey,F.A. et al., "O-Nitrene and O-Nitrenium Cation Intermediates in Reactions of O-Substituted Hydroxylamines", Journal of Organic Chemistry; vol. 38, 1973, p. 3107-3114.
Cieslak et al., "Semisynthetic Penicillins. IV. A New Method of Synthesis of Ampicillin", Acta Poloniae Pharmaceutica; vol. 25; (1968); p. 259-260.
Ludwig,B.J. et al., The Synthesis of Hydroxylamine Derivatives Processing Hypocholesteremic Activity, Journal of Medicinal Chemistry, vol. 10, 1967, p. 556-564.
Okamoto, M.; Fujiwara, M.; Kodama, E.; Yamamoto, O.; Shigeta, S.; Mitsuya, H.; Konno, K.; Yokota, T.; and Baba, M. Antiviral Chemistry & Chemotherapy (1999), 10(2), 71-77.
Guidance for Industry, U.S. Department of Health and Human Services, Food and Drug Administration, Center for Drug Evaluation and Research (CDER), Center for Biologics Evaluation and Research (CBER), Nov. 2003, Revision 1, pp. 1-8.

\* cited by examiner

IDO INHIBITORS

CROSS-REFERENCE TO RELATED APPLICATIONS

The present application is a national stage entry of PCT/US2008/085167, filed on Dec. 1, 2008, which claims the benefit of the filing dates of U.S. Provisional Application Ser. No. 60/991,518 filed 30 Nov. 2007; and U.S. Provisional Application Ser. No. 61/050,646, filed 6 May 2008. The entire contents of the foregoing applications are incorporated by reference herein in their entirety.

BACKGROUND OF THE INVENTION

Field of the Invention

The present disclosure relates to compounds and methods for inhibition of indoleamine 2,3-dioxygenase; further the disclosure relates to method of treatment of diseases and disorders mediated by indoleamine 2,3-dioxygenase.

Summary of the Related Art

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process.

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL-2) was believed to result from IDO released by the tumor cells in response to IFN-γ secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO inhibition can enhance the levels of virus-specific T cells and, concomitantly, reduce the number of virally infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, Nature Med., 11:312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, Science 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest., 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival.

IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8).

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo[b]thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

According to the various aspects of the present disclosure are provided methods for (a) modulating an activity of indoleamine 2,3-dioxygenase comprising contacting an indoleamine 2,3-dioxygenase with a modulation effective amount of a compound as described in one of the aspects described herein; (b) treating indoleamine 2,3-dioxygenase (IDO) mediated immunosuppression in a subject in need thereof, comprising administering an effective indoleamine 2,3-dioxygenase inhibiting amount of a compound as described in one of the aspects described herein; (c) treating a medical conditions that benefit from the inhibition of enzymatic activity of indoleamine-2,3-dioxygenase comprising administering an effective indoleamine 2,3-dioxygenase inhibiting amount of a compound as described in one of the aspects described herein; (d) enhancing the effectiveness of an anti-cancer treatment comprising administering an anti-cancer agent and a compound as described in one of the aspects described herein; (e) treating tumor-specific immunosuppression associated with cancer comprising administering an effective indoleamine 2,3-dioxygenase inhibiting amount of a compound as described in one of the aspects described herein; and (f) treating immunsupression associated with an infectious disease, e.g., HIV-1 infection, comprising administering an effective indoleamine 2,3-dioxygenase inhibiting amount of a compound as described in one of the aspects described herein.

In a particular aspect, the present disclosure provides methods for (a) modulating activity of indoleamine 2,3-dioxygenase comprising contacting indoleamine 2,3-dioxygenase with an effective modulating amount of a compound of formula (XXI); (b) treating indoleamine 2,3-dioxygenase (IDO) mediated immunosuppression in a subject in need thereof, comprising administering an effective indoleamine 2,3-dioxygenase inhibiting amount of a compound of formula (XXI); (c) treating a medical conditions that benefit from the inhibition of enzymatic activity of indoleamine-2, 3-dioxygenase comprising administering an effective indoleamine 2,3-dioxygenase inhibiting amount of a compound of formula (XXI); (d) enhancing the effectiveness of an anti-cancer treatment comprising administering an anti-cancer agent and a compound of Formula (XXI); (e) treating tumor-specific immunosuppression associated with cancer comprising administering an effective indoleamine 2,3-dioxygenase inhibiting amount of a compound of Formula (XXI); and (f) treating immunsupression associated with an infectious disease, e.g., HIV-1 infection, comprising administering an effective indoleamine 2,3-dioxygenase inhibiting amount of a compound of Formula (XXI),

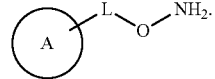

(XXI)

DETAILED DESCRIPTION OF THE INVENTION

In one aspect, methods are provided for (a) modulating an activity of indoleamine 2,3-dioxygenase comprising contacting an indoleamine 2,3-dioxygenase with a modulation effective amount of Formula (I); (b) treating indoleamine 2,3-dioxygenase (IDO) mediated immunosuppression in a subject in need thereof, comprising administering an effective indoleamine 2,3-dioxygenase inhibiting amount of a compound of Formula (I); (c) treating a medical conditions that benefit from the inhibition of enzymatic activity of indoleamine-2,3-dioxygenase comprising administering an effective indoleamine 2,3-dioxygenase inhibiting amount of a compound of Formula (I); (d) enhancing the effectiveness of an anti-cancer treatment comprising administering an anti-cancer agent and a compound of Formula (I); (e) treating tumor-specific immunosuppression associated with cancer comprising administering an effective indoleamine 2,3-dioxygenase inhibiting amount of a compound of Formula (I); and (f) treating immunsupression associated with an infectious disease, e.g., HIV-1 infection, comprising administering an effective indoleamine 2,3-dioxygenase inhibiting amount of a compound of Formula (I),

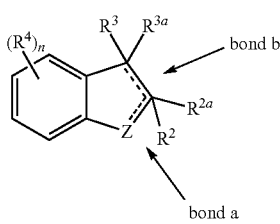
(I)

or a pharmaceutically acceptable salt thereof, wherein
n is 0, 1, 2, 3 or 4;

Z is —N=, —N$^+$(R$^1$)=, —N(R$^{10}$)—, —O—, or —S—, provided that when Z is —N$^+$(R$^1$)=, then a pharmaceutically acceptable anion is present;

bonds a and b are independently a single or double bond provided that (i) when bond a is a double bond, then Z is —N= and R$^{2a}$ is absent; and (ii) when bond b is a double bond, then Z is —N(R$^1$)—, —O—, or —S— and R$^{2a}$ and R$^{3a}$ are absent;

R$^1$ is —R$^N$, C$_3$-C$_8$cycloalkyl, aryl, heteroaryl, arylC$_1$-C$_6$alkyl, heteroarylC$_1$-C$_6$alkyl, or -G$^1$;

R$^{10}$ is —R$^1$ or —OR;

R$^2$ and R$^3$ are each independently —R$^1$, halogen, cyano, nitro, —OR, —OOH, —N(R$^N$)$_2$, —N(H)(OH), —ONH$_2$, —ON(R$^N$)C(O)OR;

or R$^2$ and R$^3$ taken together with the atoms to which they are attached form a fused 5 or 6 membered aryl or a 5 or 6 membered heteroaryl group, wherein the aryl and heteroaryl groups are optionally substituted with one or more R$^4$ groups;

R$^{2a}$ and R$^{3a}$ are independently hydrogen, C$_1$-C$_6$alkyl, hydroxyC$_1$-C$_6$alkyl, cyano, —OOH, —OH, or G$^1$;

or R$^2$ and R$^{2a}$ taken together form =R$^D$; or R$^3$ and R$^{3a}$ taken together form =R$^D$;

each R$^4$ is independently hydrogen, halogen, cyano, nitro, —OR, —N(R$^N$)$_2$, —C(O)OR, —C(O)N(R$^N$)$_2$, —CH$_2$COOR, C$_1$-C$_6$alkyl, C$_2$-C$_6$alkenyl, C$_2$-C$_6$alkynyl, C$_3$-C$_8$cycloalkyl, heterocyclyl, aryl, or heteroaryl;

each G$^1$ is independently —C(O)NH(R$^{70}$), —CH$_2$—R$^{500}$, -L$^1$-R$^5$, or -L$^{10}$-R$^{50}$, wherein R$^{70}$ is (i) phenyl substituted with one or two groups which are each independently halogen, C$_1$-C$_6$alkyl, —COOH, —NH$_2$, —SH, or —OH; or (ii) a 5 or 6 membered heteroaryl, optionally substituted with one or two groups which are each independently halogen, C$_1$-C$_6$alkyl, —COOH, —NH$_2$, —SH, or —OH;

L$^1$ is —C$_2$-C$_6$alkyl-, —C$_2$-C$_6$alkenyl-, —C$_2$-C$_6$alkynyl-, wherein the alkyl, alkenyl, or alkynyl group is optionally substituted with one or two groups which are independently phenyl, halogen, —OR, or —N(R$^N$)$_2$; and R$^5$ is cyano, nitro, —NH$_2$, —NH(C$_1$-C$_6$alkyl), —NH(OH), —OH, —C(O)OR, —C(O)NH$_2$, —C(O)R, —C(NH)NH$_2$, —C(NOH)NH$_2$, —C(O)N(H)OH, —OC(O)NH$_2$, —N(H)C(O)OR, —N(H)C(O)NH$_2$, —N(OH)C(O)R, —C(O)CF$_3$, —C(O)CH$_3$, —S(O)R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, —C(O)S(OR), —C(O)S(N(R)$_2$), —N(H)SC(O)CH$_3$, —O—SC(O)R, —P(O)(OR)$_2$, —C(O)CH$_2$P(O)(OR)$_2$, —C(O)N(H)R$^{70}$, —C(S)N(H)R$^{70}$, —NHC(O)R$^{70}$, —NHC(S)R$^{70}$, —NHC(O)NHR$^{70}$, —NHC(S)NHR$^{70}$, or —N(H)C(S)SR$^8$, wherein R$^8$ is —C$_1$-C$_6$ alkyl-G$^4$, wherein G$^4$ is (i) aryl or heteroaryl, each optionally substituted with one or more groups which are each independently halogen, —OR, —N(R$^N$)$_2$, —C(O)OR, —C(O)N(R$^N$)$_2$, —C(O)R, —OC(O)R, C$_1$-C$_6$ alkyl, C$_2$-C$_6$ alkenyl, C$_2$-C$_6$ alkynyl, aryl, heteroaryl, or heterocyclyl;

or (ii) saturated or unsaturated heterocyclyl, each optionally substituted with one or more groups which are each independently =R$^D$, halogen, —OR, —N(R$^N$)$_2$, —C(O)OR, —C(O)N(R$^N$)$_2$, —C(O)R, —OC(O)R, C$_1$-C$_6$ alkyl, C$_2$-C$_6$ alkenyl, C$_2$-C$_6$ alkynyl, aryl, heteroaryl, or heterocyclyl;

or (iii) hydrogen, cyano, —N(R$^N$)$_2$, —NR$^N$(OH), —OR, —ONH$_2$, —C(O)OR, —C(O)N(R$^N$)$_2$, —C(O)R, —C(O)N(H)OH, —N(H)C(O)NH$_2$, or —P(O)(OR)$_2$;

L$^{10}$ is a bond or —C$_1$-C$_6$alkyl-,

R$^{50}$ is a group of the formula,

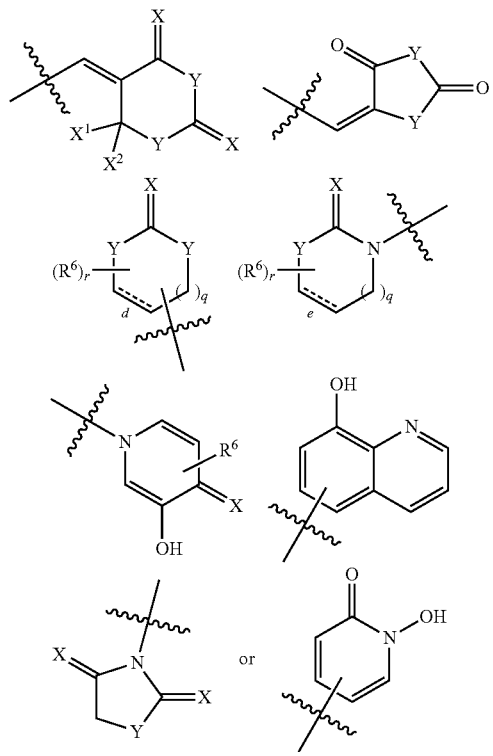

wherein q is 0 or 1; r is 0, 1, or 2;

bonds d and e are independently a single or double bond;

each R$^6$ is independently hydrogen, C$_1$-C$_6$ alkyl, C$_1$-C$_6$ haloalkyl, or phenyl;

each X is independently =O or =S;

X$^1$ and X$^2$ are both hydrogen or X$^1$ and X$^2$ taken together form =R$^D$; and each Y is independently —O—, —S—, or —N(R$^N$)—;

R$^{500}$ is —C(O)OR, —C(O)NH$_2$, —C(O)N(H)R$^{70}$, —C(S)N(H)R$^{70}$, —NHC(O)NHR$^{70}$, —NHC(S)NHR$^{70}$, —NHC(O)R$^{70}$, —NHC(S)R$^{70}$, —N(H)C(O)NH$_2$, —C(O)CF$_3$, —C(O)CH$_3$, —C(O)N(H)OH, —N(OH)C(O)R, —N(H)C(S)SR$^8$, or —R$^{50}$;

each R is independently hydrogen, C$_1$-C$_6$alkyl, C$_1$-C$_6$haloalkyl, C$_2$-C$_6$alkenyl, C$_2$-C$_6$alkynyl, phenyl or benzyl, wherein each of group is optionally substituted with one or more groups which are independently halogen, hydroxyl, C$_1$-C$_6$alkoxy, amino, carboxy, and carbamoyl;

each R$^D$ is independently =O, =S, =N(R$^N$), =N(OR), =N(NH$_2$), or =N(CN); and each $R^N$ is independently (i) hydrogen; (ii) $C_1$-$C_6$alkyl, $C_2$-$C_6$alkenyl, $C_2$-$C_6$alkynyl, phenyl, or benzyl, wherein each group is optionally substituted with one or more groups which are independently halogen, hydroxyl, $C_1$-$C_6$alkoxy, amino, carboxy, and carbamoyl; or (iii) formyl, —C(O)$C_1$-$C_6$ alkyl, —C(O)O$C_1$-$C_6$alkyl, —C(O)N(H)$C_1$-$C_6$alkyl, or —S(O)$_2$$C_1$-$C_6$alkyl;

provided that (a) one and only one $G^1$ is present;

(b) when bond b is a double bond, Z is —N(H)—, O, or S, $R^3$ is —(CH$_2$)$_{1-3}$—N(H)C(S)S—$R^8$, then $R^8$ is not —CH$_2$-$G^4$;

(c) the compound is not β-(3-benzofuranyl)alanine, β-(3-benzo[b]thienyl)alanine, 1-methyltryptophan, 1-ethyltryptophan, hexyl (1H-indol-3-yl)methylcarbamodithioate and 2-amino-(3-indolin-3-yl)propanoic acid; and (d) when bond b is a double bond, Z is —N(H)—, —N(CH$_3$)—, or —N(CH$_2$CH$_3$)—, $R^3$ is -$G^1$, and $G^1$ is —CH$_2$CH(NH($R^N$))COOR, —CH$_2$C(CH$_3$)(NH$_2$)COOR, —CH(CH$_3$)CH(NH$_2$)COOH, —CH$_2$CH$_2$NH$_2$, —CH$_2$CH$_2$COOH, —CH$_2$CH(OH)COOH, or —CH=CH—COOR, then either n is not 0 or $R^2$ is not hydrogen and $R^2$ or $R^4$ are not $C_1$-$C_2$alkyl, aryl, halogen, —OH, —OCH$_3$, OCH$_2$Ph, —COOH, or nitro.

In an embodiment of the first aspect, the compound is of one of formulae (Ia)-(In),

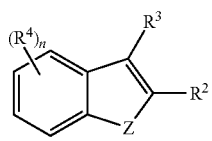
(Ia)

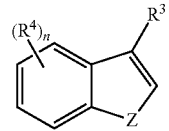
(Ib)

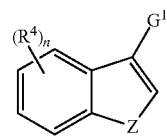
(Ic)

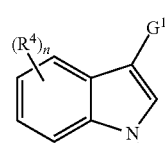
(Id)

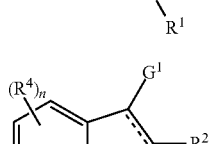
(Ie)

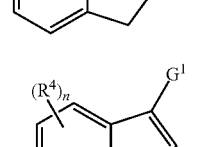
(If)

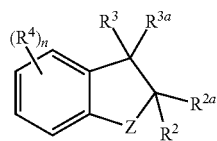
(Ig)

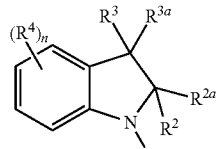
(Ih)

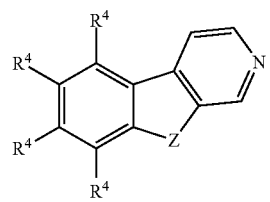
(Ii)

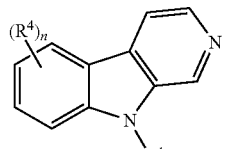
(Ij)

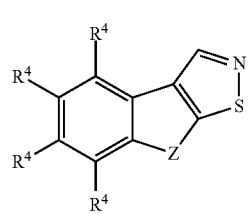
(Ik)

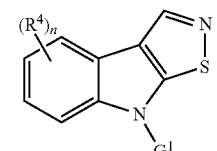
(Il)

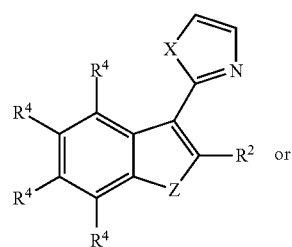
(Im) or

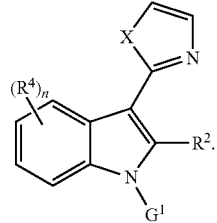
(In)

and the remaining variables are as defined for formula (I).

In an embodiment of the first aspect, the compound is of one of formulae (I) and (Ia)-(In), and $G^1$ is —C(O)NH($R^{70}$), wherein $R^{70}$ is a phenyl substituted with one or two groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is —C(O)NH($R^{70}$), wherein $R^{70}$ is a 5-membered heteroaryl optionally substituted with one or two groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is —C(O)NH($R^{70}$), wherein $R^{70}$ is a thiazolyl optionally substituted with one to three groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is -$L^1$-$R^5$, wherein $L^1$ is —$C_2$-$C_6$alkyl- wherein the alkyl group is optionally substituted with one or two groups which are independently phenyl, halogen, —OR, or —N($R^N$)$_2$; and $R^5$ is cyano, nitro, —$NH_2$, —NH($C_1$-$C_6$alkyl), —NH(OH), —OH, —C(O)OR, —C(O)$NH_2$, —C(NH)$NH_2$, —C(O)N(H)OH, —OC(O)$NH_2$, —N(H)C(O)OR, —N(H)C(O)$NH_2$, —N(OH)C(O)$NH_2$, —C(O)$CF_3$, —N(H)S(O)R, —N(H)S(O)$_2$R, —N(H)SC(O)$CH_3$, —P(O)(OR)$_2$, —C(O)N(H)$R^{70}$, —NHC(S)$R^{70}$, —NHC(S)NH$R^{70}$, or —N(H)C(S)S$R^8$.

In an embodiment of the first aspect, the compound is of one of formulae (I) and (Ia)-(In), and $G^1$ is —$C_2$-$C_6$alkyl-C(O)NH($R^{70}$).

In an embodiment of the first aspect, the compound is of one of formulae (I) and (Ia)-(In), and $G^1$ is —$C_2$-$C_6$alkyl-C(O)NH($R^{70}$), wherein $R^{70}$ is a phenyl substituted with one or two groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is —$C_2$-$C_6$alkyl-C(O)NH($R^{70}$), wherein $R^{70}$ is a phenyl substituted with one or two groups which are each independently —$NH_2$, —SH, or —OH.

In an embodiment of the first aspect, the compound is of one of formulae (I) and (Ia)-(In), and $G^1$ is —$C_2$-$C_6$alkyl-C(O)NH($R^{70}$), wherein $R^{70}$ is thiazolyl optionally substituted with one or two groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is —$C_2$-$C_6$alkyl-C(O)NH($R^{70}$), wherein $R^{70}$ is thiazolyl.

In an embodiment of the first aspect, the compound is of one of formulae (I) and (Ia)-(In), and $G^1$ is —$C_2$-$C_6$alkyl-NHC(S)$R^{70}$.

In an embodiment of the first aspect, the compound is of one of formulae (I) and (Ia)-(In), and $G^1$ is —$C_2$-$C_6$alkyl-NHC(S)$R^{70}$, wherein $R^{70}$ is a phenyl substituted with one or two groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is —$C_2$-$C_6$alkyl-NHC(S)$R^{70}$, wherein $R^{70}$ is a phenyl substituted with one or two groups which are each independently —$NH_2$, —SH, or —OH.

In an embodiment of the first aspect, the compound is of one of formulae (I) and (Ia)-(In), and $G^1$ is —$C_2$-$C_6$alkyl-NHC(S)$R^{70}$, wherein $R^{70}$ is thiazolyl optionally substituted with one or two groups which are each independently halogen, $C_1$-$C_6$alkyl, —COOH, —$NH_2$, —SH, or —OH.

In an embodiment of the first aspect, the compound is of one of formulae (I) and (Ia)-(In), and $G^1$ is —$C_2$-$C_6$alkyl-NHC(S)$R^{70}$, wherein $R^{70}$ is thiazolyl.

In an embodiment of the first aspect, the compound is of one of formulae (I) and (Ia)-(In), and $G^1$ is —$C_2$-$C_6$alkyl-N(H)C(S)S$R^8$.

In an embodiment of the first aspect, the compound is of one of formulae (I) and (Ia)-(In), and $G^1$ is —$CH_2CH_2$N(H)C(S)S$R^8$.

In an embodiment of the first aspect, the compound is of one of formulae (I) and (Ia)-(In), and $G^1$ is —$C_2$-$C_6$alkyl-N(H)C(S)S$R^8$, wherein $R^8$ is —$C_1$-$C_6$ alkyl-$G^4$, wherein $G^4$ is aryl or heteroaryl, each optionally substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is —$CH_2CH_2$N(H)C(S)S$R^8$, wherein $R^8$ is —$C_1$-$C_6$ alkyl-$G^4$, wherein $G^4$ is aryl or heteroaryl, each optionally substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is —$CH_2CH_2$N(H)C(S)S$R^8$, wherein $R^8$ is —$C_1$-$C_6$ alkyl-$G^4$, wherein $G^4$ is phenyl optionally substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is —$CH_2CH_2$N(H)C(S)S$R^8$, wherein $R^8$ is —$C_1$-$C_6$ alkyl-$G^4$, wherein $G^4$ is phenyl substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is —$CH_2CH_2$N(H)C(S)S$R^8$, wherein $R^8$ is —$CH_2CH_2G^4$, wherein $G^4$ is aryl or heteroaryl, each optionally substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is —$CH_2CH_2$N(H)C(S)S$R^8$, wherein $R^8$ is —$CH_2CH_2G^4$, wherein $G^4$ is phenyl optionally substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is —$CH_2CH_2$N(H)C(S)S$R^8$, wherein $R^8$ is —$CH_2CH_2G^4$, wherein $G^4$ is phenyl substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the first aspect, the compound is of one of formulae (I) and (Ia)-(In), and $G^1$ is -$L^{10}$-$R^{50}$.

In an embodiment of the first aspect, the compound is of one of formulae (I) and (Ia)-(In), and $G^1$ is -$L^{10}$-$R^{50}$, herein $L^{10}$ is a bond, and $R^{50}$ is a group of the formula,

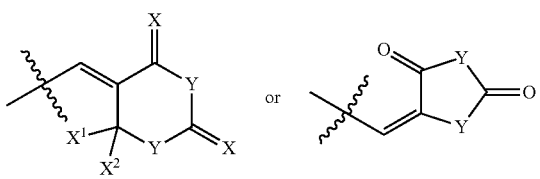

In an embodiment of the first aspect, the compound is of one of formulae (I) and (Ia)-(In), and $G^1$ is -$L^{10}$-$R^{50}$, wherein $L^{10}$ is —$C_1$-$C_6$alkyl-, and $R^{50}$ is a group of the formula,

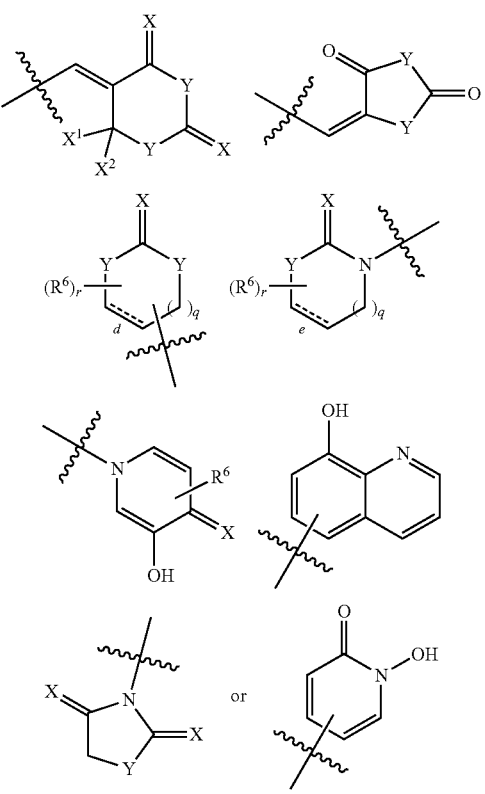

In an embodiment of the first aspect, the compound is of one of formulae (I) and (Ia)-(In), and $G^1$ is -$L^{10}$-$R^{50}$, wherein $L^{10}$ is —$C_1$-$C_6$alkyl-, and $R^{50}$ is a group of the formula,

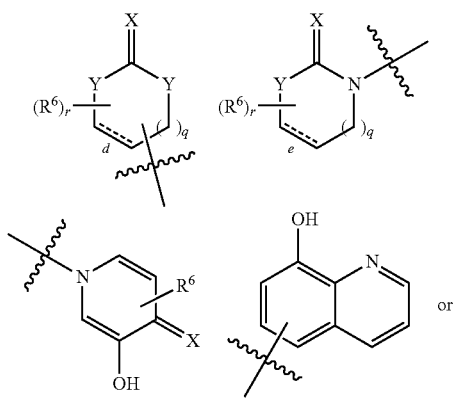

In an embodiment of the first aspect, the compound is of one of formulae (I) and (Ia)-(In), and $G^1$ is —$CH_2$—$R^{500}$, wherein $R^{500}$ is —C(O)OR, —C(O)NH_2, —C(O)N(H)R^{70}, —C(S)N(H)R^{70}, —NHC(O)NHR^{70}, —NHC(S)NHR^{70}, —NHC(O)R^{70}, —NHC(S)R^{70}, —N(H)C(O)NH_2, —C(O)CF_3, —C(O)CH_3, —C(O)N(H)OH, —N(OH)C(O)R, or —$R^{50}$.

In a an embodiment of the first aspect, the compound is of one of formulae (I) and (Ia)-(In), and $G^1$ is —$CH_2$—$R^{500}$, wherein $R^{500}$ is —C(O)OR.

In an embodiment of the first aspect, the compound is of one of formulae (I) and (Ia)-(In), and $G^1$ is —$CH_2$—$R^{500}$, wherein $R^{500}$ is —C(O)NH_2.

In an embodiment of the first aspect, the compound is of one of formulae (I) and (Ia)-(In), and $G^1$ is —$CH_2$—$R^{50}$.

In an embodiment of the first aspect, the compound is of one of formulae (I) and (Ia)-(In), and $G^1$ is —$CH_2C(O)CF_3$.

In a second aspect, methods are provided for (a) modulating an activity of indoleamine 2,3-dioxygenase comprising contacting an indoleamine 2,3-dioxygenase with a modulation effective amount of Formula (II); (b) treating indoleamine 2,3-dioxygenase (IDO) mediated immunosuppression in a subject in need thereof, comprising administering an effective indoleamine 2,3-dioxygenase inhibiting amount of a compound of Formula (II); (c) treating a medical conditions that benefit from the inhibition of enzymatic activity of indoleamine-2,3-dioxygenase comprising administering an effective indoleamine 2,3-dioxygenase inhibiting amount of a compound of formula (II); (d) enhancing the effectiveness of an anti-cancer treatment comprising administering an anti-cancer agent and a compound of Formula (II); (e) treating tumor-specific immunosuppression associated with cancer comprising administering an effective indoleamine 2,3-dioxygenase inhibiting amount of a compound of Formula (II); and (f) treating immunsupression associated with an infectious disease, e.g., HIV-1 infection, comprising administering an effective indoleamine 2,3-dioxygenase inhibiting amount of a compound of Formula (II), (II)

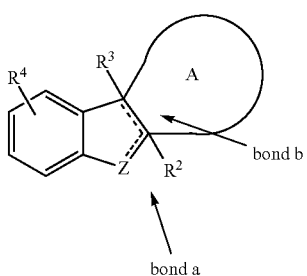

or a pharmaceutically acceptable salt thereof, wherein bonds a and b are each a single or double bond provided that (i) when bond a is a single bond, then Z is —O—, —S— or —N(R$^N$)—;

(ii) when bond a is a double bond, then R$^2$ is absent and Z is —N=;

(iii) when bond b is a double bond, then R$^2$ and R$^3$ are absent and Z is —O—, —S— or —N(R$^N$)—; and (iv) only one of bonds a and b is a double bond;

R$^2$ and R$^3$ are independently hydrogen, hydroxy, C$_1$-C$_6$alkyl, or -G$^1$;

R$^4$ is hydrogen, halogen, cyano, nitro, —OR, —SR, —N(R$^N$)$_2$, —C(O)OR, —C(O)N(R$^N$)$_2$, —C(NR$^N$)CH$_3$, C$_1$-C$_6$alkyl, C$_1$-C$_6$haloalkyl, C$_2$-C$_6$alkenyl, C$_2$-C$_6$ alkynyl, C$_3$-C$_8$ cycloalkyl, heterocyclyl, aryl, or heteroaryl, wherein the aryl and heteroaryl groups are optionally substituted with one or more groups which are independently halogen, cyano, nitro, —OR, SR, —N(R$^N$)$_2$, —C(O)OR, —C(O)N (R$^N$)$_2$, —C(N—NH$_2$)CH$_3$, C$_1$-C$_6$alkyl, or C$_1$-C$_6$haloalkyl, and the aryl and heteroaryl groups are optionally fused to a 3-8 membered unsaturated heterocyclyl group; and ring A is a 3-8 membered saturated or unsaturated cycloalkyl or 3-8 membered saturated or unsaturated heterocyclyl group wherein ring A is optionally substituted by one or more groups which are each independently =O, =S, =N(R$^N$), =N(OR), =N(NH$_2$), =N(CN), R$^4$, or G$^1$;

G$^1$ is independently -L$^1$-R$^5$ wherein

L$^1$ is —C$_1$-C$_6$alkyl-, —C$_2$-C$_6$alkenyl-, —C$_2$-C$_6$alkynyl-, wherein the alkyl, alkenyl, or alkynyl group is optionally substituted with one or two groups which are independently phenyl, halogen, —OR, or —N(R$^N$)$_2$; and R$^5$ is cyano, nitro, —NH$_2$, —NH(OH), —OH, —C(O) OR, —C(O)NH$_2$, —C(O)R, —C(NH)NH$_2$, —C(NOH)NH$_2$, —C(O)N(H)OH, —N(H)C(O)R, —N(H)C(S)R, —N(H)C (O)OR, —N(OH)C(O)R, —C(O)CF$_3$, —C(O)CH$_3$, —S(O) R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, or —P(O) (OR)$_2$; and each R is independently hydrogen, C$_1$-C$_6$alkyl, C$_1$-C$_6$haloalkyl, C$_2$-C$_6$alkenyl, C$_2$-C$_6$alkynyl, phenyl, benzyl, heteroaryl, or heteroarylC$_1$-C$_6$alkyl, wherein each group is optionally substituted with one or more groups which are independently halogen, hydroxyl, C$_1$-C$_6$alkoxy, amino, carboxy, and carbamoyl; and each R$^N$ is independently (i) hydrogen; (ii) C$_1$-C$_6$alkyl, C$_2$-C$_6$alkenyl, C$_2$-C$_6$alkynyl, phenyl, or benzyl, wherein each group is optionally substituted with one or more groups which are independently halogen, hydroxyl, C$_1$-C$_6$alkoxy, amino, carboxy, and carbamoyl; or (iii) formyl, —C(O)C$_1$-C$_6$alkyl, —C(O)OC$_1$-C$_6$alkyl, —C(O)N(H)C$_1$-C$_6$alkyl, or —S(O)$_2$C$_1$-C$_6$alkyl;

provided that the compound is not 7-methoxy-1-methyl-4,9-dihydro-3H-pyrido[3,4-b]indole, 1-methyl-4,9-dihydro-3H-pyrido[3,4-b]indol-7-ol, 2,3,4,9-tetrahydro-1H-pyrido[3,4-b)]indole, and 7-methoxy-4,9-dihydro-3H-pyrido[3,4-b)]indol-1-ol.

In an embodiment of the second aspect, G$^1$ is -L$^1$-R$^5$ wherein L$^1$ is —C$_1$-C$_6$alkyl- or —C$_2$-C$_6$alkenyl-, wherein the alkyl or alkenyl group is optionally substituted with one or two groups which are independently —OR or —N(R$^N$)$_2$; and R$^5$ is cyano, —NH$_2$, —NH(OH), —OH, —C(O)OR, —C(O)NH$_2$, —C(O)R, —C(NH)NH$_2$, —C(NOH)NH$_2$, —C(O)N(H)OH, —N(H)C(O)R, N(H)C(S)R, —N(H)C(O) OR, or —N(OH)C(O)R.

In an embodiment of the second aspect, G$^1$ is -L$^1$-R$^5$ wherein L$^1$ is —C$_1$-C$_6$alkyl-optionally substituted with one group which is —OR or —N(R$^N$)$_2$; and R$^5$ is —NH$_2$, —NH(OH), —OH, —C(O)OR, —C(O)NH$_2$, —C(O)N(H) OH, —N(H)C(O)R, or —N(H)C(O)OR.

In an embodiment of the second aspect, G$^1$ is -L$^1$-R$^5$ wherein L$^1$ is —C$_1$-C$_3$alkyl-substituted —N(R$^N$)$_2$, and R$^5$ is —C(O)OR, —C(O)NH$_2$, or —C(O)N(H)OH.

In another embodiment of the second aspect, the compound is of one of formulae (II)-(IIe),

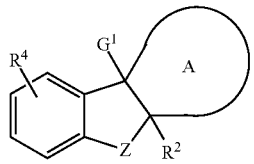

(IIa)

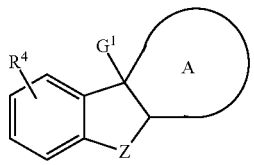

(IIb)

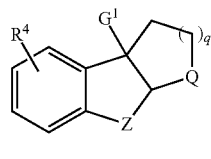

(IIc)

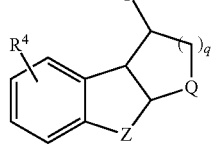

(IId)

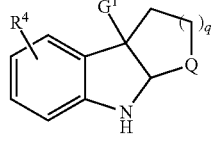

(IIe)

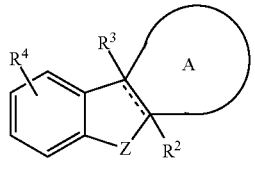

(IIf)

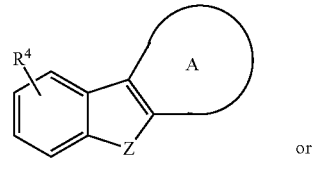

(IIg)

or

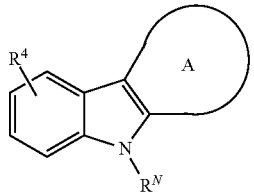

(IIh)

wherein Q is —O—, —N(H)—, —S—; q is 0, 1, or 2, and the remaining variables are as defined for formula (II).

In one embodiment of the second aspect, the compound is of one of formulae (II) and (II)-(II) and $G^1$ is as defined in any one of the preceding embodiments of the second aspect.

In another embodiment of the second aspect, the compound is of the formula,

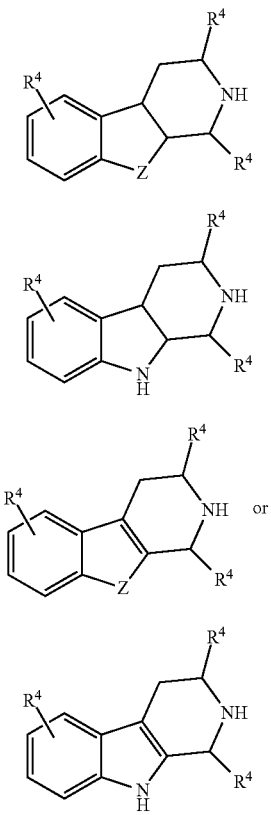

and the remaining variables are as defined for formula (II).

In an embodiment of the second aspect, the compound is according to one of the formulae (II), and (IIi)-(III) and one $R^4$ is —OR, —SR, —N(R$^N$)$_2$, —C(O)OR, or —C(O)N(R$^N$)$_2$.

In another embodiment of the second aspect, the compound is according to one of the formulae (II), and (IIi)-(III) and one $R^4$ is —C(O)OR or —C(O)N(R$^N$)$_2$.

In a third aspect, methods are provided for (a) modulating an activity of indoleamine 2,3-dioxygenase comprising contacting an indoleamine 2,3-dioxygenase with a modulation effective amount of Formula (III); (b) treating indoleamine 2,3-dioxygenase (IDO) mediated immunosuppression in a subject in need thereof, comprising administering an effective indoleamine 2,3-dioxygenase inhibiting amount of a compound of Formula (III); (c) treating a medical conditions that benefit from the inhibition of enzymatic activity of indoleamine-2,3-dioxygenase comprising administering an effective indoleamine 2,3-dioxygenase inhibiting amount of a compound of formula (III); (d) enhancing the effectiveness of an anti-cancer treatment comprising administering an anti-cancer agent and a compound of Formula (III), (e) treating tumor-specific immunosuppression associated with cancer comprising administering an effective indoleamine 2,3-dioxygenase inhibiting amount of a compound of Formula (III); and (f) treating immunsupression associated with an infectious disease, e.g., HIV-1 infection, comprising administering an effective indoleamine 2,3-dioxygenase inhibiting amount of a compound of Formula (III),

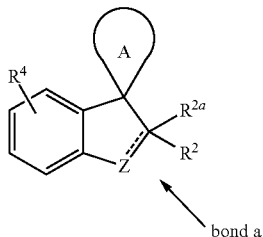

or a pharmaceutically acceptable salt thereof, wherein

Z is —N═, —N(R$^N$), —O—, or —S—;

bond a is a single or double bond provided that when bond a is a double bond, then Z is —N═ and R$^{2a}$ is absent;

$R^2$ and $R^{2a}$ are each hydrogen, or $R^2$ and $R^{2a}$ taken together form ═R$^D$;

ring A is a spiro ring which is either (i) a saturated or unsaturated $C_4$-$C_8$cycloalkyl optionally substituted with one or more groups which are each independently R$^{20}$ or R$^{21}$; or (ii) a saturated or unsaturated 3-8 membered heterocyclyl optionally substituted with one or more groups which are each independently R$^{20}$ or R$^{21}$;

$R^4$ is independently hydrogen, halogen, cyano, nitro, —OR, —N(R$^N$)$_2$, —C(O)OR, —C(O)N(R$^N$)$_2$, $C_1$-$C_6$alkyl, $C_2$-$C_6$alkenyl, $C_2$-$C_6$alkynyl, $C_3$-$C_8$cycloalkyl, heterocyclyl, aryl, or heteroaryl;

each R$^{20}$ is independently ═R$^D$, ═$C_3$-$C_8$cycloalkyl, or ═heterocyclyl;

each R$^{21}$ is independently halogen or -L$^1$-R$^5$, wherein

L$^1$ is a bond, —$C_1$-$C_6$alkyl-, —$C_2$-$C_6$alkenyl-, —$C_2$-$C_6$alkynyl-, wherein the alkyl, alkenyl, or alkynyl group is optionally substituted with one or two groups which are independently phenyl, halogen, —OR, or —N(R$^N$)$_2$; and $R^5$ is cyano, nitro, —NH$_2$, —NH(OH), —OH, —C(O)OR, —C(O)N(R)$_2$, —C(O)R, —C(NH)NH$_2$, —C(NOH)NH$_2$, —C(O)N(H)OH, —N(H)C(O)R, —N(H)C(S)R, —N(H)C(O)OR, —N(OH)C(O)R, —C(O)CF$_3$, —C(O)CH$_3$, —S(O)R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, or —P(O)(OR)$_2$;

each R is independently hydrogen, $C_1$-$C_6$alkyl, $C_1$-$C_6$haloalkyl, $C_2$-$C_6$alkenyl, $C_2$-$C_6$alkynyl, phenyl or benzyl, wherein each group is optionally substituted with one or more groups which are independently halogen, hydroxyl, $C_1$-$C_6$alkoxy, amino, carboxy, and carbamoyl;

each R$^D$ is independently ═O, ═S, ═N(R$^N$), ═N(OR), ═N(NH$_2$), or ═N(CN); and each R$^N$ is independently (i) hydrogen; (ii) $C_1$-$C_6$alkyl, $C_2$-$C_6$alkenyl, $C_2$-$C_6$alkynyl, phenyl, or benzyl, wherein each group is optionally substituted with one or more groups which are independently halogen, hydroxyl, $C_1$-$C_6$alkoxy, amino, carboxy, and carbamoyl; or (iii) formyl, —C(O)$C_1$-$C_6$ alkyl, —C(O)O$C_1$-$C_6$alkyl, —C(O)N(H)$C_1$-$C_6$alkyl, or —S(O)$_2$$C_1$-$C_6$alkyl.

In an embodiment of the third aspect, the compound is of one of formulae (IIa)-(IIId),

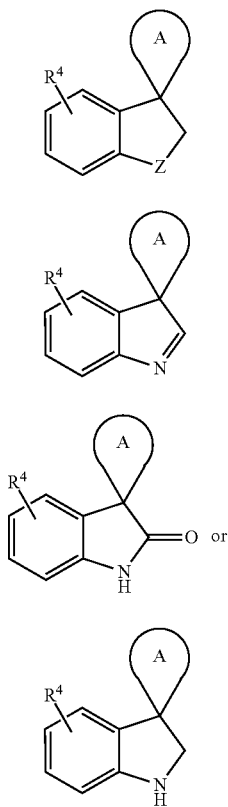

(IIIa)

(IIIb)

(IIIc)

(IIId)

wherein X is —O—, —S—, or —NH—, and the remaining variables are as defined for formula (III).

In an embodiment of the third aspect, the compound is of one of formulae (IIIe)-(IIIh),

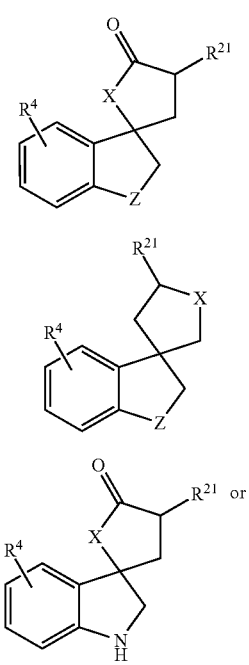

(IIIe)

(IIIf)

(IIIg)

(IIIh)

wherein X is —O—, —S—, or —NH—, and the remaining variables are as defined for formula (III).

In an embodiment of the third aspect, the compound is of one of formulae (III) and (IIIe)-(IIIh) and $R^{21}$ is -$L^1$-$R^5$.

In another embodiment of the third aspect, the compound is of one of formulae (III) and (IIIe)-(IIIh) and $R^{21}$ is -$L^1$-$R^5$, wherein $L^1$ is a bond or —$C_1$-$C_6$alkyl- optionally substituted with —OR or —N($R^N$)$_2$.

In an embodiment of the third aspect, the compound is of one of formulae (III) and (IIIe)-(IIIh) and $R^{21}$ is -$L^1$-$R^5$, wherein $L^1$ is a bond or —$C_1$-$C_6$alkyl- optionally substituted with —OR or —N($R^N$)$_2$; and $R^5$ is cyano, —NH$_2$, —NH(OH), —OH, —C(O)OR, —C(O)N(R)$_2$, —C(O)N(H)OH, —N(H)C(O)R, —N(H)C(O)OR, —S(O)N(R)$_2$, —S(O)$_2$N(R)$_2$, —N(H)S(O)R, —N(H)S(O)$_2$R, or —P(O)(OR)$_2$.

In an embodiment of the third aspect, the compound is of one of formulae (III) and (IIIe)-(IIIh) and $R^{21}$ is -$L^1$-$R^5$, wherein $L^1$ is a bond or —$C_1$-$C_6$alkyl- optionally substituted with —OR or —N($R^N$)$_2$; and $R^5$ is —NH$_2$, —C(O)OR, —C(O)N(R)$_2$, or —C(O)N(H)OH.

In a fourth aspect, methods are provided for (a) modulating an activity of indoleamine 2,3-dioxygenase comprising contacting an indoleamine 2,3-dioxygenase with a modulation effective amount of Formula (IV); (b) treating indoleamine 2,3-dioxygenase (IDO) mediated immunosuppression in a subject in need thereof, comprising administering an effective indoleamine 2,3-dioxygenase inhibiting amount of a compound of Formula (IV); (c) treating a medical conditions that benefit from the inhibition of enzymatic activity of indoleamine-2,3-dioxygenase comprising administering an effective indoleamine 2,3-dioxygenase inhibiting amount of a compound of formula (IV); (d) enhancing the effectiveness of an anti-cancer treatment comprising administering an anti-cancer agent and a compound of Formula (IV); (e) treating tumor-specific immunosuppression associated with cancer comprising administering an effective indoleamine 2,3-dioxygenase inhibiting amount of a compound of Formula (IV); and (f) treating immunsupression associated with an infectious disease, e.g., HIV-1 infection, comprising administering an effective indoleamine 2,3-dioxygenase inhibiting amount of a compound of Formula (IV),

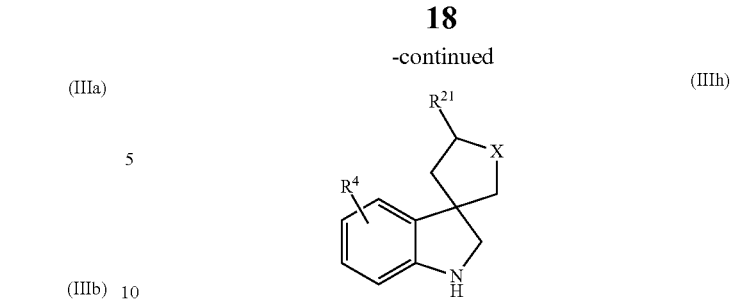

(IV)

or a pharmaceutically acceptable salt thereof, wherein bond a is a single or double bond;
Y is =$R^D$;
both X are —S— or —N($R^N$)—;

R¹ and R² are independently C₁-C₆alkyl, —OR, —N(R^N)₂, or —SR;

or R¹ and R² taken together with the carbon atoms to which they are attached form (i) a fused phenyl ring optionally substituted with one or more groups which are independently halogen, cyano, nitro, C₁-C₆alkyl, —OR, —N(R^N)₂, or —SR; or (ii) a fused 5-8 membered heterocyclyl ring optionally substituted with one or more groups which are independently =R^D, C₁-C₆alkyl, —OR, —N(R^N)₂, or —SR;

each R is independently hydrogen, C₁-C₆alkyl, C₁-C₆haloalkyl, C₂-C₆alkenyl, C₂-C₆alkynyl, phenyl or benzyl, wherein each of group is optionally substituted with one or more groups which are independently halogen, hydroxyl, cyano, C₁-C₆alkoxy, amino, carboxy, and carbamoyl;

each R^D is independently =O, =S, =N(R^N), =N(OR), =N(NH₂), or =N(CN); and each R^N is independently (i) hydrogen, hydroxyl, cyano, or amino; (ii) C₁-C₆alkyl, C₂-C₆alkenyl, C₂-C₆alkynyl, phenyl, or benzyl, wherein each group is optionally substituted with one or more groups which are independently halogen, hydroxyl, C₁-C₆alkoxy, amino, carboxy, and carbamoyl; or (iii) formyl, —C(O)C₁-C₆alkyl, —C(O)OC₁-C₆alkyl, —C(O)N(H)C₁-C₆alkyl, or —S(O)₂C₁-C₆alkyl;

provided that when X and Z are both N(R^N), then one is not NH.

In an embodiment of the fourth aspect, the compound is of formulae (IVa),

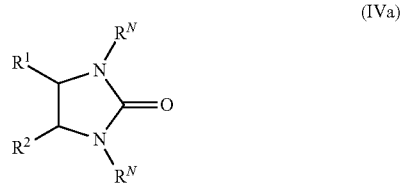

(IVa)

wherein R¹, R², and R^N are as defined for formula (IV).

In an embodiment of the fourth aspect, the compound is of formulae (IV) or (IVa), and R¹ and R² are independently —OR, or R¹ and R² taken together with the carbon atoms to which they are attached form a fused 5-8 membered heterocyclyl ring.

In an embodiment of the fourth aspect, the compound is of formulae (IV) or (IVa), and each R^N is independently hydrogen, hydroxyl, or C₁-C₆alkyl optionally substituted with one halogen, hydroxyl, C₁-C₆alkoxy, amino, carboxy or carbamoyl group.

In another embodiment of the fourth aspect, the compound is of formulae (IVb),

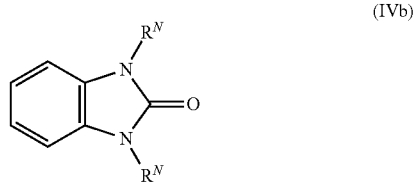

(IVb)

wherein R^N is as defined for formula (IV).

In an embodiment of the fourth aspect, the compound is of formulae (IV) or (IVb), and each R^N is independently hydrogen, hydroxyl, or C₁-C₆alkyl optionally substituted with one halogen, hydroxyl, C₁-C₆alkoxy, amino, carboxy or carbamoyl group.

In another embodiment of the fourth aspect, the compound is of formulae (IVc),

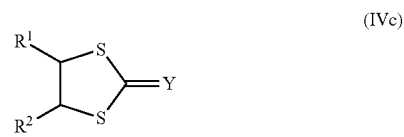

(IVc)

wherein R¹, R², and Y are as defined for formula (IV).

In an embodiment of the fourth aspect, the compound is of formulae (IV) or (IVc), and R¹ and R² each —SR, or R¹ and R² taken together with the carbon atoms to which they are attached form a fused 5-8 membered heterocyclyl ring optionally substituted with =R^D, C₁-C₆alkyl, —OR, —N(R^N)₂, or —SR.

In an embodiment of the fourth aspect, the compound is of formulae (IV) or (IVc), and R¹ and R² each —SR, or R¹ and R² taken together with the carbon atoms to which they are attached form a fused 5-8 membered heterocyclyl ring optionally substituted with =R^D, C₁-C₆alkyl, —OR, —N(R^N)₂, or —SR, wherein each R is independently hydrogen or C₁-C₆alkyl, substituted with one halogen, hydroxyl, cyano, C₁-C₆alkoxy, amino, carboxy, or carbamoyl group.

In a fifth aspect, methods are provided for (a) modulating an activity of indoleamine 2,3-dioxygenase comprising contacting an indoleamine 2,3-dioxygenase with a modulation effective amount of Formula (V); (b) treating indoleamine 2,3-dioxygenase (IDO) mediated immunosuppression in a subject in need thereof, comprising administering an effective indoleamine 2,3-dioxygenase inhibiting amount of a compound of Formula (V); (c) treating a medical conditions that benefit from the inhibition of enzymatic activity of indoleamine-2,3-dioxygenase comprising administering an effective indoleamine 2,3-dioxygenase inhibiting amount of a compound of formula (V); (d) enhancing the effectiveness of an anti-cancer treatment comprising administering an anti-cancer agent and a compound of Formula (V); (e) treating tumor-specific immunosuppression associated with cancer comprising administering an effective indoleamine 2,3-dioxygenase inhibiting amount of a compound of Formula (V); and (f) treating immunsupression associated with an infectious disease, e.g., HIV-1 infection, comprising administering an effective indoleamine 2,3-dioxygenase inhibiting amount of a compound of Formula (V),

(V)

or a pharmaceutically acceptable salt thereof, wherein X, Y, and Z are independently —N=, —N⁺(R³)=, —N(R³)—, —C(R⁴)=, —O—, or —S—; provided (i) one and only one of X, Y, and Z is —N(R³)—, —O—, or —S—, (ii) no more than one of X, Y, and Z is —N⁺(R³)=; (iii) when one of X, Y, and Z is —N(R³)—, —O—, or —S— and the other two are both —C(R⁴)=, then R¹ and R² taken together are not a phenyl ring; (iv) when X and Z are —N(R³)— and —N= or —N= and —N(R³)—, then R³ is not hydrogen; (v) provided that when one of X, Y, and Z is —N⁺(R³)=, then a pharmaceutically acceptable anion is present; and (vi) R¹, R², and R³ or R⁴ are not simultaneously H.

R¹, R², and R⁴ are independently hydrogen, halogen, cyano, nitro, —OR, —SR, —N(R$^N$)₂, —N(H)NH₂, —C(O)R, —C(O)N(R$^N$)₂, $C_1$-$C_6$ alkyl, $C_1$-$C_6$halo alkyl, —$C_1$-$C_6$ alkyl-OR, —$C_1$-$C_6$alkyl-SR, —$C_1$-$C_6$alkyl-N(R$^N$)₂, —$C_1$-$C_6$alkyl-C(O)OR, —$C_1$-$C_6$alkyl-C(O)N(R$^N$)₂, $C_2$-$C_6$alkenyl, $C_2$-$C_6$alkynyl, $C_3$-$C_8$cycloalkyl, heterocyclyl, aryl, heteroaryl, or G¹, wherein the aryl and heteroaryl groups are optionally substituted with one or more groups which are independently halogen, cyano, nitro, —OR, —SR, —N(R$^N$)₂, —C(O)OR, —C(O)N(R$^N$)₂, $C_1$-$C_6$alkyl, $C_1$-$C_6$halo alkyl, —$C_1$-$C_6$ alkyl-OR, —$C_1$-$C_6$alkyl-SR, —$C_1$-$C_6$alkyl-N(R$^N$)₂, —$C_1$-$C_6$ alkyl-C(O)OR, or —$C_1$-$C_6$ alkyl-C(O)N(R$^N$)₂;

R³ is hydroxyl, amino, cyano, R$^N$ or G¹;

or R¹ and R² taken together with the atoms to which they are attached form a fused ring which is G²;

or R³ and R⁴, when present on adjacent atoms, taken together with the atoms to which they are attached form a fused ring which is G²;

or two R⁴, when present on adjacent carbon atoms, taken together with the atoms to which they are attached form a fused ring which is G²;

G² is (i) a saturated or unsaturated 4-8 membered cycloalkyl optionally substituted with one or more groups which are each independently R²⁰ or R²¹;

(ii) a saturated or unsaturated 4-8 membered heterocyclyl optionally substituted with one or more groups which are each independently R²⁰ or R²¹;

(iii) phenyl optionally substituted with one or more R²¹ groups, or (iv) a 5 or 6 membered heteroaryl group optionally substituted with one or more R²¹ groups; wherein each R²⁰ is independently =R$^D$, =$C_3$-$C_8$cycloalkyl, or =heterocyclyl; and each R²¹ is independently halogen, hydroxyl, amino, cyano, $C_1$-$C_6$alkyl, $C_1$-$C_6$halo alkyl, or G¹;

each G¹ is independently —C(CH₃)=NOCH₂C(O)OH, —C(CH₃)=NOCH₂C(O)NH₂, —C(CH₃)=NOC(O)C(O)NH₂, —C(O)NH(R⁷⁰), —W-L¹-R⁵ or -L¹⁰-R⁵⁰, wherein R⁷⁰ is (i) phenyl substituted with one or two groups which are each independently halogen, $C_1$-$C_6$alkyl, —COOH, —NH₂, —SH, —OCH₃ or —OH; or (ii) a 5 or 6 membered heteroaryl, optionally substituted with one or two groups which are each independently halogen, $C_1$-$C_6$alkyl, —COOH, —NH₂, —SH, or —OH;

W is a bond, —S(O)—, —S(O)₂—, —C(O)N(R$^N$)—, —C(O)O—, —C(O)S—, —OC(O)—, —N(R$^N$)C(O)—, —O—, —S—, or —N(R$^N$)=;

L¹ is —$C_1$-$C_6$alkyl-, —$C_2$-$C_6$alkenyl-, —$C_2$-$C_6$alkynyl-, wherein the alkyl, alkenyl, or alkynyl group is optionally substituted with one or two groups which are independently phenyl, halogen, —OR, or —N(R$^N$)₂; and R⁵ is cyano, nitro, amino, —OR, mercapto, —NH(OH), —NHN(H)R, —C(O)OR, —C(O)NH₂, —C(O)R, —C(NH)NH₂, —C(NOH)NH₂, —C(O)N(H)OH, —N(H)C(O)OR, —N(OH)C(O)R, —C(O)CF₃, —S(O)R, —S(O)₂R, —S(O)OR, —S(O)₂OR, —S(O)N(R)₂, —S(O)₂N(R)₂, —SC(NH)NH₂, —N(H)S(O)R, —N(H)S(O)₂R, —C(O)S(OR), —C(O)S(N(R)₂), —N(H)SC(O)CH₃, —P(O)(OR)₂, —C(O)N(H)R⁷⁰, —C(S)N(H)R⁷⁰, —C(O)N(H)N=C(H)R, —C(O)N(H)N(H)R, —SC(NH)NH₂, —C(O)NH(R⁷⁰), —C(S)NH(R⁷⁰), —NHC(O)R⁷⁰, —NHC(S)R⁷⁰, —NHC(O)NHR⁷⁰, —NHC(S)NHR⁷⁰, or —N(H)C(S)SR⁸, wherein R⁸ is -L²-G⁴, wherein L² is —$C_1$-$C_6$ alkyl- optionally substituted with one or more groups which are each independently —OR, —N(R$^N$)₂, —N(R$^N$)C(O)R, —N(R$^N$)C(O)OR, —C(O)OR, —C(O)N(R)₂, $C_1$-$C_6$ alkyl, $C_2$-$C_6$ alkenyl, $C_2$-$C_6$ alkynyl, aryl, heteroaryl, or heterocyclyl; and G⁴ is (i) hydrogen; (ii) aryl or heteroaryl, each optionally substituted with one or more groups which are each independently halogen, —OR, —N(R$^N$)₂, —C(O)OR, —C(O)N(R$^N$)₂, —C(O)R, —OC(O)R, $C_1$-$C_6$ alkyl, $C_2$-$C_6$ alkenyl, $C_2$-$C_6$ alkynyl, aryl, heteroaryl, or heterocyclyl;

(iii) saturated or unsaturated heterocyclyl, each optionally substituted with one or more groups which are each independently =R$^D$, halogen, —OR, —N(R$^N$)₂, —C(O)OR, —C(O)N(R$^N$)₂, —C(O)R, —OC(O)R, $C_1$-$C_6$ alkyl, $C_2$-$C_6$ alkenyl, $C_2$-$C_6$ alkynyl, aryl, heteroaryl, or heterocyclyl;

or (iv) cyano, —N(R$^N$)₂, —NR$^N$(OH), —OR, —ONH₂, —C(O)OR, —C(O)N(R$^N$)₂, —C(O)R, —C(O)N(H)OH, —N(H)C(O)OR, —N(H)C(O)NH₂, —N(OH)C(O)R, or —P(O)(OR)₂;

L¹⁰ is a bond or —$C_1$-$C_6$alkyl-,

R⁵⁰ is a group of the formula,

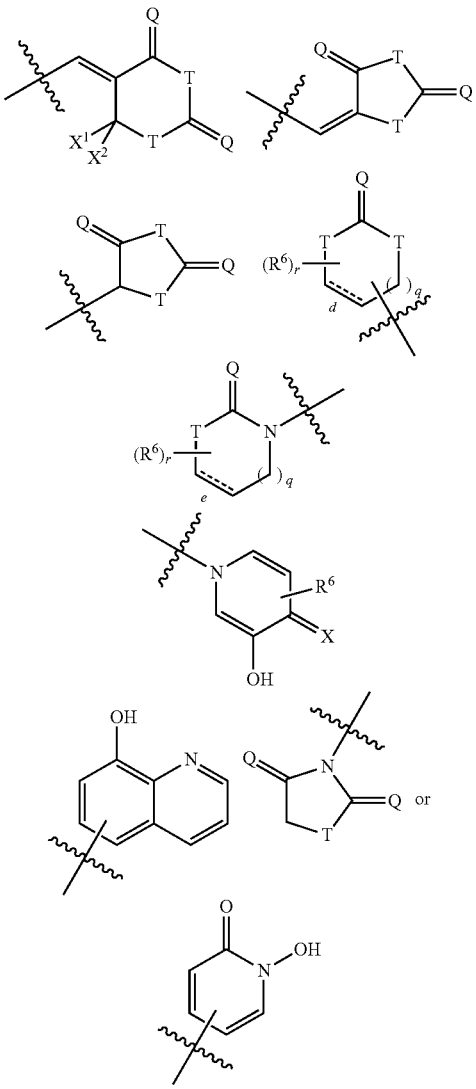

wherein q is 0 or 1; r is 0, 1, or 2;

bonds d and e are independently a single or double bond;

each R⁶ is independently hydrogen, $C_1$-$C_6$ alkyl, $C_1$-$C_6$ haloalkyl, or phenyl;

each Q is independently =O or =S;

each T is independently is —O—, —S—, or —N($R^N$)—; and $X^1$ and $X^2$ are both hydrogen or $X^1$ and $X^2$ taken together form =$R^D$;

each R is independently hydrogen, $C_1$-$C_6$alkyl, $C_1$-$C_6$haloalkyl, $C_2$-$C_6$alkenyl, $C_2$-$C_6$alkynyl, phenyl or benzyl, wherein each of group is optionally substituted with one or more groups which are independently halogen, hydroxyl, $C_1$-$C_6$alkoxy, amino, carboxy, and carbamoyl;

each $R^D$ is independently =O, =S, =N($R^N$), =N(OR), =N($NH_2$), or =N(CN); and each $R^N$ is independently (i) hydrogen; (ii) $C_1$-$C_6$alkyl, $C_2$-$C_6$alkenyl, $C_2$-$C_6$alkynyl, phenyl, or benzyl, wherein each group is optionally substituted with one or more groups which are independently halogen, hydroxyl, $C_1$-$C_6$alkoxy, amino, carboxy, and carbamoyl; or (iii) formyl, —C(O)$C_1$-$C_6$alkyl, —C(O)O$C_1$-$C_6$alkyl, —C(O)N(H)$C_1$-$C_6$alkyl, or —S(O)$_2$$C_1$-$C_6$alkyl;

provided that (i) one and only one $G^1$ is present; (ii) no more than one $G^2$ is present; (iii) the compound is not 2-amino-3-(1H-azaindol-3-yl)propanoic acid; and 2-amino-3-(1H-pyrrolo[2,3-b]pyridin-3-yl)propanoic acid; and (iv) when $G^1$ is —$(CH_2)_{1-3}$—N(H)C(S)S-$L^2$-$G^4$, then $L^2$ is not methylene.

In an embodiment of the fifth aspect, the compound is according to one of formulae (Va)-(Vj),

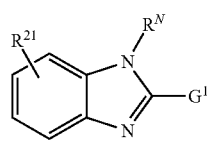
(Va)

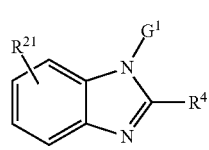
(Vb)

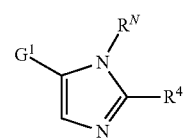
(Vc)

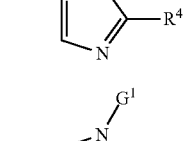
(Vd)

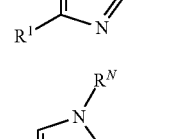
(Ve)

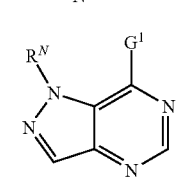
(Vf)

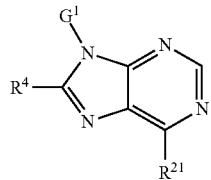
(Vg)

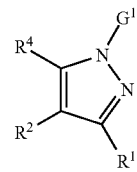
(Vh)

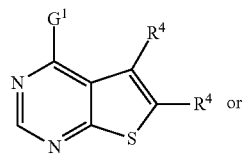
(Vi)

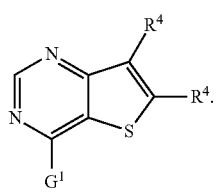
(Vj)

and the remaining variables are as defined for formula (V).

In another embodiment of the fifth aspect, the compound is according to one of formulae (Vk)-(Vo),

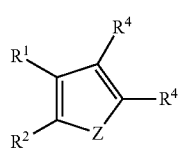
(Vk)

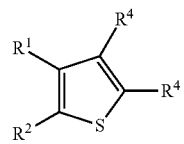
(Vl)

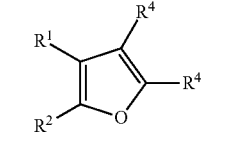
(Vm)

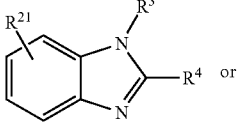
(Vn)

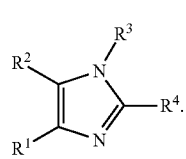
(Vo)

and the remaining variables are as defined for formula (V).

In an embodiment of the fifth aspect, the compound is of any one of formulae (V) and (Va)-(Vo), and $G^1$ is -$L^1$-$R^5$.

In an embodiment of the fifth aspect, the compound is of any one of formulae (V) and (Va)-(Vo), and $G^1$ is -$L^1$-$R^5$, wherein $L^1$ is —$C_1$-$C_6$alkyl- or —$C_2$-$C_6$alkenyl-, wherein the alkyl or alkenyl is optionally substituted with one groups which is —OR or —N($R^N$)$_2$.

In a an embodiment of the fifth aspect, the compound is of any one of formulae (V) and (Va)-(Vo), and $G^1$ is -$L^1$-$R^5$, wherein $L^1$ is —$C_1$-$C_6$alkyl- or —$C_2$-$C_6$alkenyl-, wherein the alkyl or alkenyl is optionally substituted with one groups which is —OR or —N($R^N$)$_2$; and $R^5$ is cyano, nitro, amino, hydroxyl, mercapto, —NH(OH), —NHN(H)R, —C(O)OR, —C(O)NH$_2$, —C(O)N(H)OH, —N(H)C(O)R, —N(H)C(O)OR, —S(O)R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, or —P(O)(OR)$_2$.

In another embodiment of the fifth aspect, the compound is of any one of formulae (V) and (Va)-(Vo), and $G^1$ is -$L^1$-$R^5$, wherein $L^1$ is —$C_1$-$C_6$alkyl- and $R^5$ is —N(H)C(S)SR$^8$.

In another embodiment of the fifth aspect, the compound is of any one of formulae (V) and (Va)-(Vo), and $G^1$ is —W-$L^1$-$R^5$ wherein W is —S(O)—, —S(O)$_2$—, —C(O)N(R$^N$)—, —C(O)O—, —C(O)S—, —OC(O)—, —N(R$^N$)C(O)—, —O—, —S—, or —N(H)—.

In another embodiment of the fifth aspect, the compound is of any one of formulae (V) and (Va)-(Vo), and $G^1$ is —W-$L^1$-$R^5$, wherein W is —S(O)—, —S(O)$_2$—, —C(O)N(R$^N$)—, —O—, —S—, or —N(H)—.

In another embodiment of the fifth aspect, the compound is of any one of formulae (V) and (Va)-(Vo), and $G^1$ is —W-$L^1$-$R^5$, wherein W is —S(O)— or —S(O)$_2$—.

In another embodiment of the fifth aspect, the compound is of any one of formulae (V) and (Va)-(Vo), and $G^1$ is —W-$L^1$-$R^5$, wherein W is —C(O)N(R$^N$)—.

In another embodiment of the fifth aspect, the compound is of any one of formulae (V) and (Va)-(Vo), and $G^1$ is —W-$L^1$-$R^5$, wherein W is —O—, —S—, or —N(H)—.

In another embodiment of the fifth aspect, the compound is of any one of formulae (V) and (Va)-(Vo), and $G^1$ is -$L^{10}$-$R^{50}$.

In an embodiment of the fifth aspect, the compound is of any one of formulae (V) and (Va)-(Vo), and $G^1$ is -$L^{10}$-$R^{50}$, wherein $L^{10}$ is a bond In an embodiment of the fifth aspect, the compound is of any one of formulae (V) and (Va)-(Vo), and $G^1$ is -$L^{10}$-$R^{50}$, wherein $L^{10}$ is a bond; and $R^{50}$ is a group of the formula,

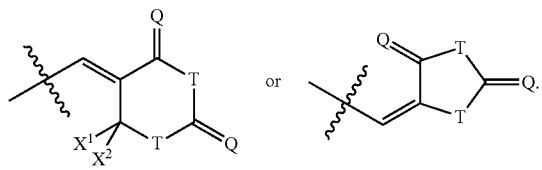

In another embodiment of the fifth aspect, the compound is of any one of formulae (V) and (Va)-(Vo), and $G^1$ is -$L^{10}$-$R^{50}$, wherein $L^{10}$ is —$C_1$-$C_6$alkyl-.

In another embodiment of the fifth aspect, the compound is of any one of formulae (V) and (Va)-(Vo), and $G^1$ is -$L^{10}$-$R^{50}$, wherein $L^{10}$ is —$C_1$-$C_6$alkyl-; and $R^{50}$ is a group of the formula,

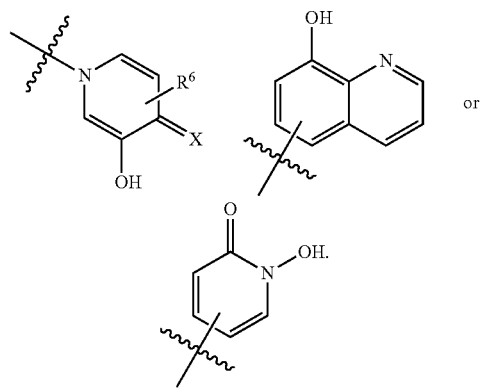

In a sixth aspect, methods are provided for (a) modulating an activity of indoleamine 2,3-dioxygenase comprising contacting an indoleamine 2,3-dioxygenase with a modulation effective amount of Formula (VI); (b) treating indoleamine 2,3-dioxygenase (IDO) mediated immunosuppression in a subject in need thereof, comprising administering an effective indoleamine 2,3-dioxygenase inhibiting amount of a compound of Formula (VI); (c) treating a medical conditions that benefit from the inhibition of enzymatic activity of indoleamine-2,3-dioxygenase comprising administering an effective indoleamine 2,3-dioxygenase inhibiting amount of a compound of formula (VI); (d) enhancing the effectiveness of an anti-cancer treatment comprising administering an anti-cancer agent and a compound of Formula (VI); (e) treating tumor-specific immunosuppression associated with cancer comprising administering an effective indoleamine 2,3-dioxygenase inhibiting amount of a compound of Formula (VI); and (f) treating immunsupression associated with an infectious disease, e.g., HIV-1 infection, comprising administering an effective indoleamine 2,3-dioxygenase inhibiting amount of a compound of Formula (VI),

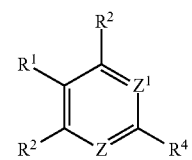
(VI)

or a pharmaceutically acceptable salt thereof, wherein Z is —C(R$^4$)=, —N=, or —N$^+$(R$^3$)=, and $Z^1$ is —C(R$^4$)=, or —N=, provided that at least one of Z and $Z^1$ is —N=, and when Z is —N$^+$(R$^3$)=, then a pharmaceutically acceptable anion is present;

$R^1$, $R^2$, and $R^4$ are independently hydrogen, halogen, cyano, nitro, —OR, —SR, —N(R$^N$)$_2$, —C(O)R, —C(O)O(R), —C(O)N(R$^N$)$_2$, —S(O)R, —S(O)$_2$R, $C_1$-$C_6$alkyl, $C_2$-$C_6$alkenyl, $C_2$-$C_6$alkynyl, $C_3$-$C_8$cycloalkyl, heterocyclyl, aryl, heteroaryl, or $G^1$;

or R¹ and R² taken together with the atoms to which they are attached form a fused
  (i) phenyl ring optionally substituted with one or more R⁴;
  (ii) pyridyl or pyridiniumyl ring, each optionally substituted with one or more R⁴; or
  (iii) 4-8 membered saturated or unsaturated cycloalkyl or 4-8 membered saturated or unsaturated heterocyclyl ring, each optionally substituted with one or more =$R^D$ or —R⁴;
R³ is $R^N$ or G¹;
each G¹ is independently -L¹-R⁵, -Q-L¹-R⁵, -L¹⁰-R⁵⁰, -Q-L¹⁰-R⁵⁰, —C(O)N(H)$R^N$—N(H)C(O)$R^N$, —C(O)N(H)R⁷⁰, —N(H)C(S)SR⁷⁰, or -Q-L¹-R⁷⁰, wherein
  Q is —O—, —S—, or —N($R^N$)—;
  L¹ is —C₁-C₆alkyl-, —C₂-C₆alkenyl-, —C₂-C₆alkynyl-, wherein the alkyl, alkenyl, or alkynyl group is optionally substituted with one or two groups which are independently phenyl, halogen, —OR, or —N($R^N$)₂; and
  R⁷⁰ is (i) phenyl substituted with one or two groups which are each independently halogen, C₁-C₆alkyl, —COOH, —NH₂, —SH, or —OH; or (ii) a 5 or 6 membered heteroaryl, optionally substituted with one or two groups which are each independently halogen, C₁-C₆alkyl, —COOH, —NH₂, —SH, or —OH;
R⁵ is cyano, nitro, amino, hydroxyl, mercapto, —NH(OH), —N(R)N(H)C(O)NH₂, —C(O)R, —C(O)CF₃, —C(O)CH₃, —C(O)OR, —C(O)NH₂, —C(O)N(H)R⁷⁰, —C(S)N(H)R⁷⁰, —C(O)N(H)OH, —C(NH)NH₂, —C(NOH)NH₂, —C(NNH₂)R, —C(H)=NN(H)C(O)R; —N(H)C(O)OR, —N(OH)C(O)R, —S(O)R, —S(O)₂R, —S(O)OR, —S(O)₂OR, —S(O)N(R)₂, —S(O)₂N(R)₂, —N(H)S(O)R, —N(H)S(O)₂R, —C(O)S(OR), —C(O)S(N(R)₂), —N(H)SC(O)CH₃, —P(O)(OR)₂, —C(O)N(H)N=CH(C₁-C₆alkyl), —NHC(O)R⁷⁰, —NHC(S)R⁷⁰, —NHC(O)NHR⁷⁰, —NHC(S)NHR⁷⁰, —NHC(S)N(H)NH₂, —N(H)C(S)SR⁸, or —C(S)N(H)N(H)C(O)NH₂, wherein
  R⁸ is -L²-G⁴, wherein
  L² is —C₂-C₆ alkyl- optionally substituted with one or more groups which are each independently —OR, —N($R^N$)₂, —C(O)OR, —C(O)N($R^N$)₂, C₁-C₆ alkyl, C₂-C₆ alkenyl, C₂-C₆ alkynyl, aryl, heteroaryl, or heterocyclyl; and
  G⁴ is (i) aryl or heteroaryl, each optionally substituted with one or more groups which are each independently halogen, —OR, —N($R^N$)₂, —C(O)OR, —C(O)N($R^N$)₂, —C(O)R, —OC(O)R, C₁-C₆ alkyl, C₁-C₆ haloalkyl, C₂-C₆ alkenyl, C₂-C₆ alkynyl, aryl, heteroaryl, or heterocyclyl;
  (ii) saturated or unsaturated heterocyclyl, each optionally substituted with one or more groups which are each independently =$R^D$, halogen, —OR, —N($R^N$)₂, —C(O)OR, —C(O)N($R^N$)₂, —C(O)R, —OC(O)R, C₁-C₆ alkyl, C₂-C₆ alkenyl, C₂-C₆ alkynyl, aryl, heteroaryl, or heterocyclyl;
  or (iii) cyano, —N($R^N$)₂, —N$R^N$(OH), —OR, —ONH₂, —C(O)OR, —C(O)N($R^N$)₂, —C(O)R, —C(O)N(H)OH, —N(H)C(O)OR, —N(H)C(O)NH₂, —N(OH)C(O)R, or —P(O)(OR)₂; and
L¹⁰ is a bond or L¹;
R⁵⁰ is a group of the formula,

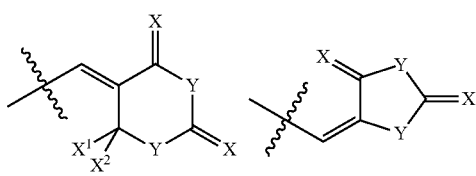

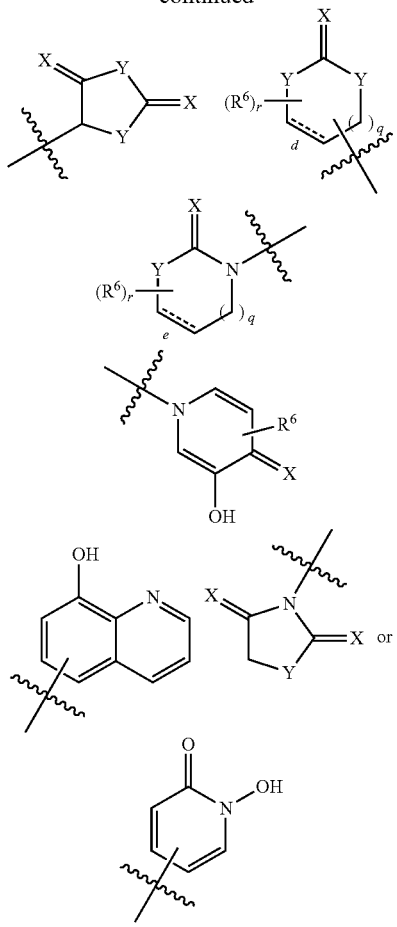

wherein q is 0 or 1; r is 0, 1, or 2;
bonds d and e are independently a single or double bond;
each X is independently =O or =S;
X¹ and X² are both hydrogen or X¹ and X² taken together form =$R^D$; and
each Y is independently —O—, —S—, or —N($R^N$)—,
each R⁶ is independently hydrogen, C₁-C₆alkyl, C₁-C₆haloalkyl, or phenyl;
each R is independently (i) hydrogen or (ii) C₁-C₆alkyl, C₂-C₆alkenyl, C₂-C₆alkynyl, aryl, heteroaryl, cycloalkyl, or heterocyclyl, wherein each is optionally substituted with one or more groups which are independently halogen, hydroxyl, cyano, nitro, C₁-C₆alkoxy, amino, carboxy, and carbamoyl; and
each $R^D$ is =O, =S, =N($R^N$), =N(OR), =N(NH₂), or =N(CN);
each $R^N$ is independently (i) hydrogen; (ii) C₁-C₆alkyl, C₂-C₆alkenyl, or C₂-C₆alkynyl, wherein each group is optionally substituted with one or more groups which are independently halogen, hydroxyl, C₁-C₆alkoxy, amino, carboxy, and carbamoyl; or (iii) —C(O)C₁-C₆alkyl, —C(O)OC₁-C₆alkyl, —C(O)N(H)C₁-C₆alkyl, or —S(O)₂C₁-C₆alkyl;
provided that (i) one and only one G¹ is present; (ii) the compound is not 2-amino-3-(quinolin-3-yl)propanoic acid; and (iii) when G¹ is —(CH₂)₁₋₃—N(H)C(S)S-L²-G⁴, then L² is not methylene.
In an embodiment of the sixth aspect, the compound is of any one of formulae (VIa)-(VIe),

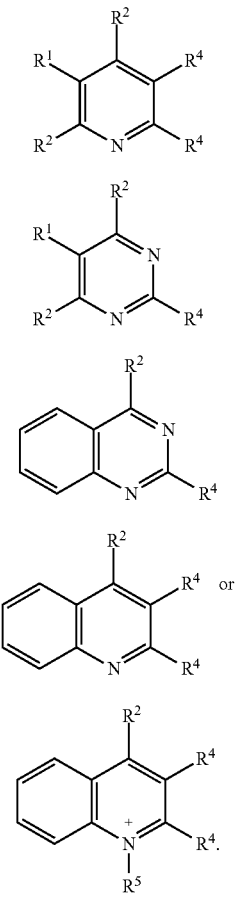

(VIa)

(VIb)

(VIc)

(VId)

(VIe)

and the remaining variables are as defined for formula (VI).

In an embodiment of the sixth aspect, the compound is of any one of formulae (VI) and (VIa)-(VIe), and $G^1$ is -$L^1$-$R^5$.

In an embodiment of the sixth aspect, the compound is of any one of formulae (VI) and (VIa)-(VIe), and $G^1$ is -$L^1$-$R^5$, wherein $L^1$ is —$C_1$-$C_6$alkyl-.

In an embodiment of the sixth aspect, the compound is of any one of formulae (VI) and (VIa)-(VIe), and $G^1$ is -$L^1$-$R^5$, wherein $L^1$ is —$C_1$-$C_6$alkyl-; and $R^5$ is cyano, nitro, amino, hydroxyl, mercapto, —NH(OH), —C(O)R, —C(O)CF$_3$, —C(O)OR, —C(O)NH$_2$, —C(O)N(H)R$^{70}$, —C(S)N(H)R$^{70}$, —C(O)N(H)OH, —N(H)C(O)R$^{70}$, —N(H)C(S)R$^{70}$, —N(H)C(O)OR, —S(O)R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, —P(O)(OR)$_2$, or —N(H)C(S)SR$^8$.

In another embodiment of the sixth aspect, the compound is of any one of formulae (VI) and (VIa)-(VIe), and $G^1$ is -$L^{10}$-$R^{50}$.

In an embodiment of the sixth aspect, the compound is of any one of formulae (VI) and (VIa)-(VIe), and $G^1$ is -$L^{10}$-$R^{50}$, wherein $R^{50}$ is a group of the formula,

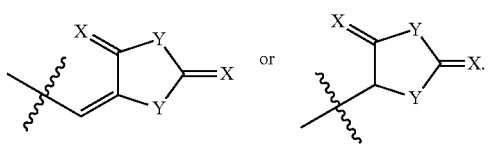

In another embodiment of the sixth aspect, the compound is of any one of formulae (VI) and (VIa)-(VIe), and $G^1$ is —C(O)N(H)R$^{70}$.

In another embodiment of the sixth aspect, the compound is of any one of formulae (VI) and (VIa)-(VIe), and $G^1$ is —N(H)C(S)SR$^{70}$.

In another embodiment of the sixth aspect, the compound is of any one of formulae (VI) and (VIa)-(VIe), and $G^1$ is -Q-$L^1$-$R^{70}$.

In a seventh aspect, methods are provided for (a) modulating an activity of indoleamine 2,3-dioxygenase comprising contacting an indoleamine 2,3-dioxygenase with a modulation effective amount of Formula (VII); (b) treating indoleamine 2,3-dioxygenase (IDO) mediated immunosuppression in a subject in need thereof, comprising administering an effective indoleamine 2,3-dioxygenase inhibiting amount of a compound of Formula (VII); (c) treating a medical conditions that benefit from the inhibition of enzymatic activity of indoleamine-2,3-dioxygenase comprising administering an effective indoleamine 2,3-dioxygenase inhibiting amount of a compound of formula (VII); (d) enhancing the effectiveness of an anti-cancer treatment comprising administering an anti-cancer agent and a compound of Formula (VII); (e) treating tumor-specific immunosuppression associated with cancer comprising administering an effective indoleamine 2,3-dioxygenase inhibiting amount of a compound of Formula (VII); and (f) treating immunsupression associated with an infectious disease, e.g., HIV-1 infection, comprising administering an effective indoleamine 2,3-dioxygenase inhibiting amount of a compound of Formula (VII),

(VII)

or a pharmaceutically acceptable salt thereof, wherein
n is 0, 1, 2, or 3;
$R^1$, $R^2$, and $R^4$ are independently hydrogen, halogen, cyano, nitro, —OR, —SR, —N($R^N$)$_2$, —N($R^N$)(OR), —C(O)R, —C(H)($R^N$)ONH$_2$, —C(H)($R^8$)ONH$_2$, —C(O)O(R), —C(O)N($R^N$)$_2$, —S(O)R, —S(O)$_2$R, $C_1$-$C_6$alkyl, hydroxy$C_1$-$C_6$alkyl, amino$C_1$-$C_6$alkyl, $C_1$-$C_6$halo alkyl, $C_2$-$C_6$alkenyl, $C_2$-$C_6$alkynyl, $C_3$-$C_8$cycloalkyl, heterocyclyl, aryl, or $G^1$;

or $R^1$ and $R^2$ taken together with the atoms to which they are attached form (i) a fused phenyl ring optionally substituted with one or more $R^4$ groups;

(ii) a 6-membered fused unsaturated heterocyclyl ring optionally substituted with one to three groups which are independently =$R^D$ or —$R^4$;

(iii) a 6-membered fused unsaturated cycloalkyl ring optionally substituted with one to three —$R^4$ groups;

(iv) a 4- or 5-membered fused unsaturated heterocyclyl ring optionally substituted with one to three groups which are independently =$R^D$, halogen, cyano, nitro, —OR, —SR, —N($R^N$)$_2$, —N($R^N$)(OR), —C(O)R, —C(O)O(R), —C(O)N($R^N$)$_2$, —S(O)R, —S(O)$_2$R, $C_1$-$C_6$alkyl, $C_2$-$C_6$alkenyl, $C_2$-$C_6$alkynyl, $C_3$-$C_8$cycloalkyl, heterocyclyl, aryl, or heteroaryl, each G¹ is independently —C(O)NH(R⁷⁰), —C(H)=NN(H)C(=R^D)NH₂, -Q-L¹-R⁵, or -L¹⁰-R⁵⁰, or -L¹⁰-R⁵⁰⁰, wherein R⁷⁰ is (i) phenyl optionally substituted with one or two groups which are each independently halogen, C₁-C₆alkyl, —COOH, —NH₂, —SH, or —OH; or (ii) a 5 or 6 membered heteroaryl, optionally substituted with one or two groups which are each independently halogen, C₁-C₆alkyl, —COOH, —NH₂, —SH, or —OH;

Q is a bond, —C(O)—, —S(O)—, —S(O)₂—, —C(O)N(R^N)—, —C(O)O—, —C(O)S—, —OC(O)—, —N(R^N)C(O)—, —O—, —S—, —N(R^N)—, —CH(R)O—, —CH(R)S—, or —CH(R)N(R^N)—;

L¹ is —C₁-C₆alkyl-, —C₂-C₆alkenyl-, —C₂-C₆alkynyl-, wherein the alkyl, alkenyl, or alkynyl group is optionally substituted with one or two groups which are independently phenyl, halogen, —OR, or —N(R^N)₂; and R⁵ is cyano, nitro, —NH₂, —NH(OH), —N(R)N(H)C(O)NH₂, —OH, —ONH₂, —C(O)OR, —C(O)NH₂, —C(O)R, —C(NH)NH₂, —C(NOH)NH₂, —C(O)N(H)OH, —C(H)=NN(H)C(O)R; —N(H)C(O)OR, —N(H)C(O)NH₂, —N(OH)C(O)R, —OC(O)NH₂, —ON(H)C(NH)NH₂, —C(O)CF₃, —C(O)CH₃, —S(O)R, —S(O)₂R, —S(O)OR, —S(O)₂OR, —S(O)N(R)₂, —S(O)₂N(R)₂, —N(H)S(O)R, —N(H)S(O)₂R, —C(O)S(OR), —C(O)S(N(R)₂), —N(H)SC(O)CH₃, —P(O)(OR)₂, —C(O)N(H)R⁷⁰, —C(S)N(H)R⁷⁰, —NHC(O)R⁷⁰, —NHC(S)R⁷⁰, —NHC(O)NHR⁷⁰, —NHC(S)NHR⁷⁰, —NHC(S)N(H)NH₂, —N(H)C(S)SR⁸, or —C(S)N(H)N(H)C(O)NH₂, wherein R⁸ is -L²-G⁴, wherein L² is —C₁-C₆ alkyl- optionally substituted with one or more groups which are each independently —OR, —N(R^N)₂, —C(O)OR, —C(O)N(R^N)₂, C₁-C₆ alkyl, C₂-C₆ alkenyl, C₂-C₆ alkynyl, aryl, heteroaryl, or heterocyclyl; and G⁴ is (i) aryl or heteroaryl, each optionally substituted with one or more groups which are each independently halogen, —OR, —N(R^N)₂, —C(O)OR, —C(O)N(R^N)₂, —C(O)R, —OC(O)R, C₁-C₆ alkyl, C₂-C₆ alkenyl, C₂-C₆ alkynyl, aryl, heteroaryl, or heterocyclyl;

(ii) saturated or unsaturated heterocyclyl, each optionally substituted with one or more groups which are each independently =R^D, halogen, —OR, —N(R^N)₂, —C(O)OR, —C(O)N(R^N)₂, —C(O)R, —OC(O)R, C₁-C₆ alkyl, C₂-C₆ alkenyl, C₂-C₆ alkynyl, aryl, heteroaryl, or heterocyclyl;

or (iii) cyano, —N(R^N)₂, —NR^N(OH), —OR, —ONH₂, —C(O)OR, —C(O)N(R^N)₂, —C(O)R, —C(O)N(H)OH, —N(H)C(O)OR, —N(H)C(O)NH₂, —N(OH)C(O)R, or —P(O)(OR)₂; and L¹⁰ is a bond or L¹, R⁵⁰ is a group of the formula,

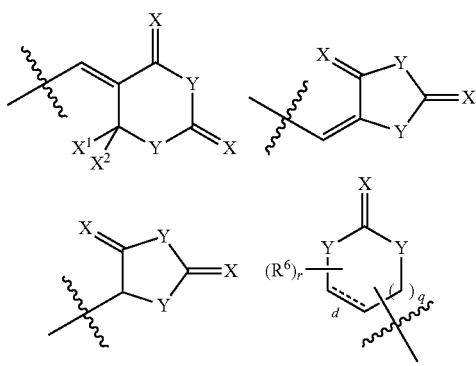

wherein q is 0 or 1; r is 0, 1 or 2;

bonds d and e are independently a single or double bond;

each R⁶ is independently hydrogen, C₁-C₆alkyl, C₁-C₆haloalkyl, or phenyl;

each X is independently =O, =N(R^N), or =S;

X¹ and X² are both hydrogen or X¹ and X² taken together form =R^D; and each Y is independently —O—, —S—, or —N(R^N)—, and R⁵⁰⁰ is —N(R^N)C(NH)N(H)R⁵⁰¹, wherein R⁵⁰¹ is hydrogen, —NH₂, or —C(NH)NH₂;

each R is independently hydrogen, C₁-C₆alkyl, C₁-C₆haloalkyl, C₂-C₆alkenyl, C₂-C₆alkynyl, phenyl or benzyl, wherein each of group is optionally substituted with one or more groups which are independently halogen, hydroxyl, C₁-C₆alkoxy, amino, carboxy, and carbamoyl;

each R^D is independently =O, =S, =N(R^N), =N(OR), =N(NH₂), or =N(CN); and each R^N is independently (i) hydrogen; (ii) C₁-C₆alkyl, C₂-C₆alkenyl, C₂-C₆alkynyl, phenyl, or benzyl, wherein each group is optionally substituted with one or more groups which are independently halogen, hydroxyl, C₁-C₆alkoxy, amino, carboxy, and carbamoyl; or (iii) formyl, —C(O)C₁-C₆alkyl, —C(O)OC₁-C₆alkyl, —C(O)N(H)C₁-C₆alkyl, or —S(O)₂C₁-C₆alkyl;

provided that (i) one and only one G¹ is present; and (ii) the compound is not 2-amino-4-(2-aminophenyl)butanoic acid; and 2-amino-4-(2-amino-3-hydroxyphenyl)butanoic acid;

(iii) when G¹ is —(CH₂)₁₋₃—N(H)C(S)S-L²-G⁴, then L² is not methylene; and (iv) the compound is not of the formula,

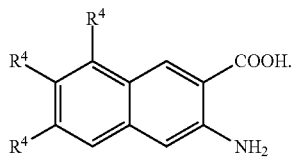

In an embodiment of the seventh aspect, the compound is according to formulae (VIIa) or (VIIb),

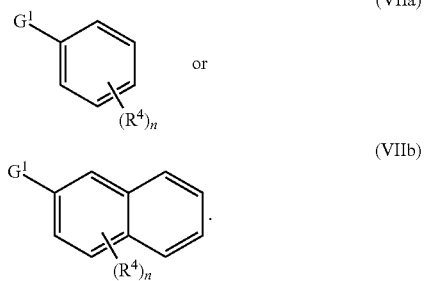

and the remaining variables are as defined for formula (VII).

In another embodiment of the seventh aspect, the compound is according to formulae (VII), (VIIa) or (VIIb), and $G^1$ is —C(O)NH($R^{70}$).

In an embodiment of the seventh aspect, the compound is according to formulae (VII), (VIIa) or (VIIb), and $G^1$ is —C(H)=NN(H)C(=$R^{D1}$)NH$_2$, wherein $R^{D1}$ is =O, =N(OH), or =N(H).

In another embodiment of the seventh aspect, the compound is according to formulae (VII), (VIIa) or (VIIb), and $G^1$ is -$L^1$-$R^5$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- or —$C_2$-$C_6$alkenyl-, wherein the alkyl or alkenyl, or alkynyl group is optionally substituted with one —OR or —N($R^N$)$_2$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- or —$C_2$-$C_6$alkenyl-, wherein the alkyl or alkenyl, or alkynyl group is optionally substituted with one —OR or —N($R^N$)$_2$; and $R^5$ is cyano, —NH$_2$, —NH(OH), —OH, —ONH$_2$, —C(O)OR, —C(O)NH$_2$, —C(O)R, —C(NH)NH$_2$, —C(NOH)NH$_2$, —C(O)N(H)OH, —N(H)C(O)$R^{70}$, —N(H)C(O)OR, —N(H)C(O)NH$_2$, —OC(O)NH$_2$, —C(O)CF$_3$, —C(O)CH$_3$, —S(O)R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, —N(H)SC(O)CH$_3$, —P(O)(OR)$_2$, —C(O)N(H)$R^{70}$, —C(S)N(H)$R^{70}$, —NHC(O)NH$R^{70}$, —NHC(S)NH$R^{70}$, or —N(H)C(S)SR$^8$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- optionally substituted with one —OR or —N($R^N$)$_2$; and $R^5$ is cyano, —NH$_2$, —NH(OH), —OH, —ONH$_2$, —C(O)OR, —C(O)NH$_2$, —C(O)R, —C(O)N(H)OH, —N(H)C(O)$R^{70}$, —C(O)CF$_3$, —C(O)N(H)$R^{70}$, —C(S)N(H)$R^{70}$, —NHC(O)NH$R^{70}$, or —NHC(S)NH$R^{70}$.

In an embodiment of the seventh aspect, the compound is according to formulae (VII), (VIIa) or (VIIb), $R^5$ is —ONH$_2$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- optionally substituted with one —OR or —N($R^N$)$_2$; and $R^5$ is —ONH$_2$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- and $R^5$ is —ONH$_2$.

In an embodiment of the seventh aspect, the compound is according to formulae (VII), (VIIa) or (VIIb), and $G^1$ is -$L^1$-$R^5$, wherein $L^1$ is —$C_1$-$C_3$alkyl- and $R^5$ is —ONH$_2$ and $R^4$ is halogen, nitro, —OR, or —CF$_3$.

In an embodiment of the seventh aspect, the compound is according to formulae (VII), (VIIa) or (VIIb), and $G^1$ is -$L^1$-$R^5$, wherein $L^1$ is —$C_1$-$C_3$alkyl- and $R^5$ is —ONH$_2$, $R^4$ is halogen, nitro, —OR, —CF$_3$ and n=1, 2 or 3.

In an embodiment of the seventh aspect, the compound is according to formulae (VII), (VIIa) or (VIIb), and $R^4$ is —C(H)($R^N$)ONH$_2$.

In an embodiment of the seventh aspect, the compound is according to formulae (VII), (VIIa) or (VIIb), and $R^4$ is —C(H)($R^8$)ONH$_2$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- optionally substituted with one —OR or —N($R^N$)$_2$; and $R^5$ is —C(O)N(H)$R^{70}$ or —C(S)N(H)$R^{70}$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- optionally substituted with one —OR or —N($R^N$)$_2$; and $R^5$ is —C(O)N(H)$R^{70}$ or —C(S)N(H)$R^{70}$, wherein $R^{70}$ is phenyl substituted with one or two groups which are each independently halogen, $C_1$-$C_6$alkyl, —COOH, —NH$_2$, —SH, or —OH.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- optionally substituted with one —OR or —N($R^N$)$_2$; and $R^5$ is —C(O)N(H)$R^{70}$ or —C(S)N(H)$R^{70}$, wherein $R^{70}$ is phenyl substituted with one or two groups which are each independently —NH$_2$, —SH, or —OH.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl- optionally substituted with one —OR or —N($R^N$)$_2$; and $R^5$ is —C(O)N(H)$R^{70}$ or —C(S)N(H)$R^{70}$, wherein $R^{70}$ is thiazolyl.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl-; and $R^5$ is —N(H)C(S)SR$^8$.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl-; and $R^5$ is —N(H)C(S)SR$^8$, wherein $R^8$ is -$L^2$-$G^4$, wherein $L^2$ is —$C_1$-$C_6$ alkyl- optionally substituted with one or more groups which are each independently —OR, —N($R^N$)$_2$, —C(O)OR, —C(O)N($R^N$)$_2$; and $G^4$ is aryl or heteroaryl, each optionally substituted with one or more groups which are each independently halogen, —OR, —N($R^N$)$_2$, —C(O)OR, —C(O)N($R^N$)$_2$, —C(O)R, —OC(O)R, $C_1$-$C_6$ alkyl, $C_2$-$C_6$ alkenyl, $C_2$-$C_6$ alkynyl, aryl, heteroaryl, or heterocyclyl.

In an embodiment of the seventh aspect, the compound is according to formulae (VII), (VIIa) or (VIIb), and $G^1$ is -$L^1$-$R^5$, wherein $L^1$ is —$C_1$-$C_6$alkyl-; and $R^5$ is —N(H)C(S)SR$^8$, wherein $R^8$ is -$L^2$-$G^4$, wherein $L^2$ is —$C_1$-$C_6$ alkyl- optionally substituted with one or more groups which are each independently —OR, —N($R^N$)$_2$, —C(O)OR, —C(O)N($R^N$)$_2$; and $G^4$ is phenyl optionally substituted with one or more groups which are each independently halogen, —OR, —N(R$^N$)$_2$, —C(O)OR, —C(O)N(R$^N$)$_2$, —C(O)R, —OC(O)R, C$_1$-C$_6$ alkyl, C$_2$-C$_6$ alkenyl, C$_2$-C$_6$ alkynyl, aryl, heteroaryl, or heterocyclyl.

In an embodiment of the seventh aspect, the compound is according to formulae (VII), (VIIa) or (VIIb), and G$^1$ is -L$^1$-R$^5$, wherein L$^1$ is —C$_1$-C$_6$alkyl-; and R$^5$ is —N(H)C(S)SR$^8$, wherein R$^8$ is -L$^2$-G$^4$, wherein L$^2$ is —C$_1$-C$_6$ alkyl- optionally substituted with one or more groups which are each independently —OR, —N(R$^N$)$_2$, —C(O)OR, —C(O)N(R$^N$)$_2$; and G$^4$ is phenyl substituted with one or two groups which are each independently halogen, —OR, —N(R$^N$)$_2$, —C(O)OR, —C(O)N(R$^N$)$_2$, —C(O)R, —OC(O)R, or C$_1$-C$_6$ alkyl.

In an embodiment of the seventh aspect, the compound is according to formulae (VII), (VIIa) or (VIIb), and G$^1$ is -L$^1$-R$^5$, wherein L$^1$ is —C$_1$-C$_6$alkyl-; and R$^5$ is —N(H)C(S)SR$^8$, wherein R$^8$ is -L$^2$-G$^4$, wherein L$^2$ is —C$_1$-C$_6$ alkyl- optionally substituted with one or more groups which are each independently —OR, —N(R$^N$)$_2$, —C(O)OR, —C(O)N(R$^N$)$_2$; and G$^4$ is a saturated or unsaturated heterocyclyl, each optionally substituted with one or more groups which are each independently =R$^D$, halogen, —OR, —N(R$^N$)$_2$, —C(O)OR, —C(O)N(R$^N$)$_2$, —C(O)R, —OC(O)R, C$_1$-C$_6$ alkyl, C$_2$-C$_6$ alkenyl, C$_2$-C$_6$ alkynyl, aryl, heteroaryl, or heterocyclyl.

In an embodiment of the seventh aspect, the compound is according to formulae (VII), (VIIa) or (VIIb), and G$^1$ is -L$^1$-R$^5$, wherein L$^1$ is —C$_1$-C$_6$alkyl-; and R$^5$ is —N(H)C(S)SR$^8$, wherein R$^8$ is -L$^2$-G$^4$, wherein L$^2$ is —C$_1$-C$_6$ alkyl- optionally substituted with one or more groups which are each independently —OR, —N(R$^N$)$_2$, —C(O)OR, —C(O)N(R$^N$)$_2$; and G$^4$ is cyano, —N(R$^N$)$_2$, —NR$^N$(OH), —OR, —ONH$_2$, —C(O)OR, —C(O)N(R$^N$)$_2$, —C(O)R, —C(O)N(H)OH, —N(H)C(O)NH$_2$, or —P(O)(OR)$_2$.

In an embodiment of the seventh aspect, the compound is according to formulae (VII), (VIIa) or (VIIb), and G$^1$ is -L$^1$-R$^5$, wherein L$^1$ is —C$_1$-C$_6$alkyl-; and R$^5$ is —N(H)C(S)SR$^8$, wherein R$^8$ is -L$^2$-G$^4$, wherein L$^2$ is —C$_1$-C$_6$ alkyl- substituted with one —N(R$^N$)$_2$, or —C(O)OR$_2$; and G$^4$ is —N(R$^N$)$_2$, —C(O)OR, or —C(O)N(R$^N$)$_2$.

In an embodiment of the seventh aspect, the compound is according to formulae (VII), (VIIa) or (VIIb), and G$^1$ is -L$^1$-R$^5$, wherein L$^1$ is —C$_1$-C$_6$alkyl-; and R$^5$ is —N(H)C(S)SR$^8$, wherein R$^8$ is -L$^2$-G$^4$, wherein L$^2$ is —C$_1$-C$_6$ alkyl- substituted with one —N(R$^N$)$_2$; and G$^4$ is —C(O)OR or —C(O)N(R$^N$)$_2$.

In an embodiment of the seventh aspect, the compound is according to formulae (VII), (VIIa) or (VIIb), and G$^1$ is -Q-L$^1$-R$^5$, wherein Q is —C(O)—, —S(O)—, —S(O)$_2$—, —C(O)N(R$^N$)—, —C(O)O—, —C(O)S—, —OC(O)—, —N(R$^N$)C(O)—, —O—, —S—, —N(R$^N$)—, —CH(R)O—, —CH(R)S—, or —CH(R)N(R$^N$)—.

In an embodiment of the seventh aspect, the compound is according to formulae (VII), (VIIa) or (VIIb), and G$^1$ is -Q-L$^1$-R$^5$, wherein Q is —C(O)—, —S(O)—, —S(O)$_2$—, —C(O)N(R$^N$)—, —C(O)O—, —C(O)S—, —OC(O)—, —N(R$^N$)C(O)—.

In an embodiment of the seventh aspect, the compound is according to formulae (VII), (VIIa) or (VIIb), and G$^1$ is -Q-L$^1$-R$^5$, wherein Q is —C(O)—, —S(O)—, —S(O)$_2$—, —C(O)N(R$^N$)—, —C(O)O—, —C(O)S—, —OC(O)—, or —N(R$^N$)C(O)—.

In an embodiment of the seventh aspect, the compound is according to formulae (VII), (VIIa) or (VIIb), and G$^1$ is -Q-L$^1$-R$^5$, wherein Q is —C(O)— or —S(O)$_2$—.

In an embodiment of the seventh aspect, the compound is according to formulae (VII), (VIIa) or (VIIb), and G$^1$ is -Q-L$^1$-R$^5$, wherein Q is —C(O)N(R$^N$)—.

In an embodiment of the seventh aspect, the compound is according to formulae (VII), (VIIa) or (VIIb), and G$^1$ is -Q-L$^1$-R$^5$, wherein Q is —O—, —S—, or —N(R$^N$)—.

In an embodiment of the seventh aspect, the compound is according to formulae (VII), (VIIa) or (VIIb), and G$^1$ is -Q-L$^1$-R$^5$, wherein Q is —CH(R)O—, —CH(R)S—, or —CH(R)N(R$^N$)—.

In another embodiment of the seventh aspect, the compound is according to formulae (VII), (VIIa) or (VIIb), and G$^1$ is -L$^{10}$-R$^{50}$.

In an embodiment of the seventh aspect, the compound is according to formulae (VII), (VIIa) or (VIIb), and G$^1$ is -L$^{10}$-R$^{50}$, wherein L$^{10}$ is a bond and R$^{50}$ is a group of the formula,

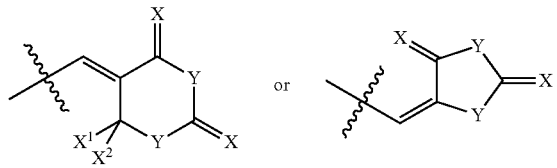

In another embodiment of the seventh aspect, the compound is according to formulae (VII), (VIIa) or (VIIb), and G$^1$ is -L$^{10}$-R$^{50}$, wherein L$^{10}$ is —C$_1$-C$_6$alkyl- and R$^{50}$ is a group of the formula,

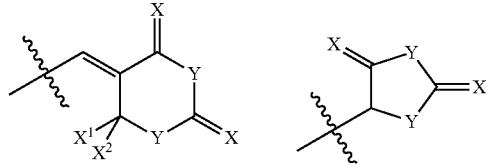

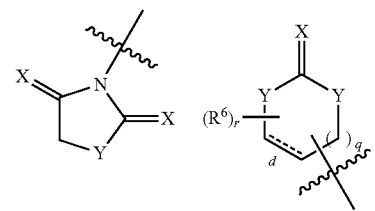

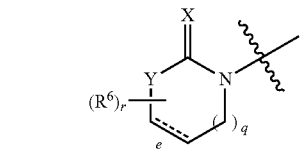

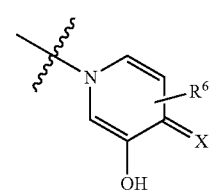

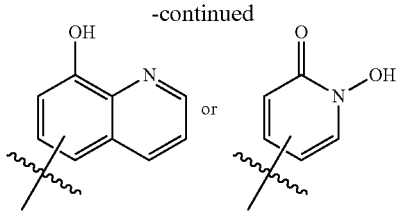

In a eighth aspect, methods are provided for (a) modulating an activity of indoleamine 2,3-dioxygenase comprising contacting an indoleamine 2,3-dioxygenase with a modulation effective amount of Formula (VIII); (b) treating indoleamine 2,3-dioxygenase (IDO) mediated immunosuppression in a subject in need thereof, comprising administering an effective indoleamine 2,3-dioxygenase inhibiting amount of a compound of Formula (VIII); (c) treating a medical conditions that benefit from the inhibition of enzymatic activity of indoleamine-2,3-dioxygenase comprising administering an effective indoleamine 2,3-dioxygenase inhibiting amount of a compound of formula (VIII); (d) enhancing the effectiveness of an anti-cancer treatment comprising administering an anti-cancer agent and a compound of Formula (VIII); (e) treating tumor-specific immunosuppression associated with cancer comprising administering an effective indoleamine 2,3-dioxygenase inhibiting amount of a compound of Formula (VIII); and (f) treating immunsupression associated with an infectious disease, e.g., HIV-1 infection, comprising administering an effective indoleamine 2,3-dioxygenase inhibiting amount of a compound of Formula (VIII),

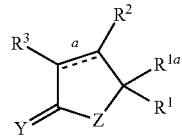

(VIII)

or a pharmaceutically acceptable salt thereof, wherein
bond a is a single or double bond;
Y is =O, =S, or =N($R^{10}$), wherein
$R^{10}$ is (i) hydrogen, hydroxyl, $C_1$-$C_6$alkoxy, amino, or cyano; or (ii) $C_1$-$C_6$alkyl, $C_2$-$C_6$alkenyl, $C_2$-$C_6$alkynyl, phenyl, or benzyl, wherein each group is optionally substituted with one or more groups which are independently halogen, hydroxyl, $C_1$-$C_6$alkoxy, amino, carboxy, and carbamoyl; or (iii) formyl, —C(O)$C_1$-$C_6$alkyl, —C(O)O$C_1$-$C_6$alkyl, —C(O)N(H)$C_1$-$C_6$alkyl, or —S(O)$_2$$C_1$-$C_6$alkyl;
Z is —O—, —S—, or —N($R^{20}$)—, wherein
$R^{20}$ is hydrogen, $C_1$-$C_6$alkyl, —C(O)R, —C(O)OR, —C(O)N(R)$_2$, —S(O)R, or —S(O)$_2$R;
$R^1$ is —$C_1$-$C_6$alkyl-COOR, or aryl optionally substituted with halogen;
$R^{1a}$ is hydrogen, —COOR, or —C(O)N(R)$_2$;
$R^2$ is hydrogen, —C(O)R, or hydroxyl;
$R^3$ is hydrogen or hydroxyl; and
each R is independently hydrogen, $C_1$-$C_6$alkyl, $C_1$-$C_6$haloalkyl, $C_2$-$C_6$alkenyl, $C_2$-$C_6$alkynyl, aryl, or aryl$C_1$-$C_6$alkyl, wherein each of group is optionally substituted with one or more groups which are independently halogen, hydroxyl, $C_1$-$C_6$alkoxy, amino, carboxy, and carbamoyl.

In an embodiment of the eighth aspect, the compound is according to formulae (VIIIa),

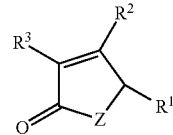

(VIIIa)

and the remaining variables are as defined for formula (VIII).

In a ninth aspect, methods are provided for (a) modulating an activity of indoleamine 2,3-dioxygenase comprising contacting an indoleamine 2,3-dioxygenase with a modulation effective amount of Formula (IX); (b) treating indoleamine 2,3-dioxygenase (IDO) mediated immunosuppression in a subject in need thereof, comprising administering an effective indoleamine 2,3-dioxygenase inhibiting amount of a compound of Formula (IX); (c) treating a medical conditions that benefit from the inhibition of enzymatic activity of indoleamine-2,3-dioxygenase comprising administering an effective indoleamine 2,3-dioxygenase inhibiting amount of a compound of formula (IX); (d) enhancing the effectiveness of an anti-cancer treatment comprising administering an anti-cancer agent and a compound of Formula (IX); (e) treating tumor-specific immunosuppression associated with cancer comprising administering an effective indoleamine 2,3-dioxygenase inhibiting amount of a compound of Formula (IX); and (f) treating immunsupression associated with an infectious disease, e.g., HIV-1 infection, comprising administering an effective indoleamine 2,3-dioxygenase inhibiting amount of a compound of Formula (IX),

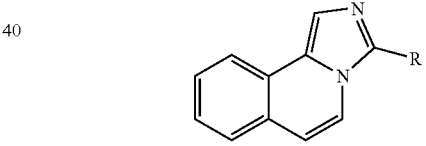

(IX)

or a pharmaceutically acceptable salt thereof, wherein
R is hydrogen or -$L^1$-$R^1$, wherein
$L^1$ is —$C_1$-$C_6$alkyl-, —$C_2$-$C_6$alkenyl-, —$C_2$-$C_6$alkynyl-, wherein the alkyl, alkenyl, or alkynyl group is optionally substituted with one or two groups which are independently phenyl, halogen, —OR, or —N($R^N$)$_2$; and
$R^1$ is hydrogen, cyano, nitro, —NH$_2$, —NH(OH), —OH, —ONH$_2$, —C(O)OR, —C(O)N(H)R, —C(S)N(H)R, —C(O)R, —C(=$R^D$)NH$_2$, —C(O)N(H)OH, —N(H)C(O)R, —N(H)C(S)R, —N(H)C(O)OR, —N(OH)C(O)R, —OC(O)NH$_2$, —C(O)CF$_3$, —C(O)CH$_3$, —S(O)R, —S(O)$_2$R, —S(O)OR, —S(O)$_2$OR, —S(O)N(R)$_2$, —S(O)$_2$N(R)$_2$, —N(H)S(O)R, —N(H)S(O)$_2$R, —P(O)(OR)$_2$, —NHC(O)NHR, —NHC(S)NHR, —SC(S)N(R)$_2$, or —N(R)C(S)SR,
each R is independently hydrogen, $C_1$-$C_6$alkyl, $C_1$-$C_6$haloalkyl, $C_2$-$C_6$alkenyl, $C_2$-$C_6$alkynyl, phenyl or benzyl, wherein each of group is optionally substituted with one or more groups which are independently halogen, hydroxyl, $C_1$-$C_6$alkoxy, amino, carboxy, and carbamoyl;
each $R^D$ is independently =O, =S, =N($R^N$), =N(OR), =N(NH$_2$), or =N(CN); and each $R^N$ is independently (i) hydrogen; (ii) $C_1$-$C_6$alkyl, $C_2$-$C_6$alkenyl, $C_2$-$C_6$alkynyl, phenyl, or benzyl, wherein each group is optionally substituted with one or more groups which are independently halogen, hydroxyl, $C_1$-$C_6$alkoxy, amino, carboxy, and carbamoyl; or (iii) formyl, —C(O)$C_1$-$C_6$ alkyl, —C(O)O$C_1$-$C_6$alkyl, —C(O)N(H)$C_1$-$C_6$alkyl, or —S(O)$_2$$C_1$-$C_6$alkyl.

In an tenth aspect, methods are provided for (a) modulating an activity of indoleamine 2,3-dioxygenase comprising contacting an indoleamine 2,3-dioxygenase with a modulation effective amount of Formula (Xa, Xb, or Xc); (b) treating indoleamine 2,3-dioxygenase (IDO) mediated immunosuppression in a subject in need thereof, comprising administering an effective indoleamine 2,3-dioxygenase inhibiting amount of a compound of Formula (Xa, Xb, or Xc); (c) treating a medical conditions that benefit from the inhibition of enzymatic activity of indoleamine-2,3-dioxygenase comprising administering an effective indoleamine 2,3-dioxygenase inhibiting amount of a compound of formula (Xa, Xb, or Xc); (d) enhancing the effectiveness of an anti-cancer treatment comprising administering an anti-cancer agent and a compound of Formula (Xa, Xb, or Xc); (e) treating tumor-specific immunosuppression associated with cancer comprising administering an effective indoleamine 2,3-dioxygenase inhibiting amount of a compound of Formula (Xa, Xb, or Xc); and (f) treating immunsupression associated with an infectious disease, e.g., HIV-1 infection, comprising administering an effective indoleamine 2,3-dioxygenase inhibiting amount of a compound of Formula (Xa, Xb, or Xc),

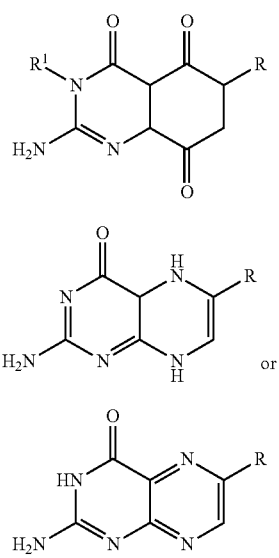

or a pharmaceutically acceptable salt thereof, wherein
$R^1$ is, when present, hydrogen or $C_1$-$C_6$alkyl, and
R is -$L^1$-$R^1$, wherein
$L^1$ is —$C_1$-$C_6$alkyl-, —$C_2$-$C_6$alkenyl-, —$C_2$-$C_6$alkynyl-, wherein the alkyl, alkenyl, or alkynyl group is optionally substituted with one or two groups which are independently phenyl, halogen, —OR or —N($R^N$)$_2$; and
$R^1$ is hydrogen, cyano, nitro, —NH$_2$, —NH(OH), —OH, —ONH$_2$, —C(O)R, —C(O)N(H)R, —C(S)N(H)R, —C(O)R, —C(=$R^D$)NH$_2$, —C(O)N(H)OH, —N(H)C(O)R, —N(H)C(S)R, —N(H)C(O)OR, —N(OH)C(O)R, —OC(O)NH$_2$, —C(O)CF$_3$, —C(O)CH$_3$, —S(O)R, —S(O)OR, —S(O)N(R)$_2$, —N(H)S(O)R, —S(O)$_2$R, —S(O)$_2$OR, —S(O)$_2$N(R)$_2$, —N(H)S(O)$_2$R, —P(O)(OR)$_2$, —NHC(O)NHR, —NHC(S)NHR, —SC(S)N(R)$_2$, or —N(R)C(S)SR, each R is independently hydrogen, $C_1$-$C_6$alkyl, $C_1$-$C_6$haloalkyl, $C_2$-$C_6$alkenyl, $C_2$-$C_6$alkynyl, phenyl or benzyl, wherein each of group is optionally substituted with one or more groups which are independently halogen, hydroxyl, $C_1$-$C_6$alkoxy, amino, carboxy, and carbamoyl;

each $R^D$ is independently =O, =S, =N($R^N$), =N(OR), =N(NH$_2$), or =N(CN); and each $R^N$ is independently (i) hydrogen; (ii) $C_1$-$C_6$alkyl, $C_2$-$C_6$alkenyl, $C_2$-$C_6$alkynyl, phenyl, or benzyl, wherein each group is optionally substituted with one or more groups which are independently halogen, hydroxyl, $C_1$-$C_6$alkoxy, amino, carboxy, and carbamoyl; or (iii) formyl, —C(O)$C_1$-$C_6$ alkyl, —C(O)O$C_1$-$C_6$alkyl, —C(O)N(H)$C_1$-$C_6$alkyl, or —S(O)$_2$$C_1$-$C_6$alkyl.

In an eleventh aspect, methods are provided for (a) modulating an activity of indoleamine 2,3-dioxygenase comprising contacting an indoleamine 2,3-dioxygenase with a modulation effective amount any compound listed in Tables 1-11; (b) treating indoleamine 2,3-dioxygenase (IDO) mediated immunosuppression in a subject in need thereof, comprising administering an effective indoleamine 2,3-dioxygenase inhibiting amount of any compound listed in Tables 1-11; (c) treating a medical conditions that benefit from the inhibition of enzymatic activity of indoleamine-2,3-dioxygenase comprising administering an effective indoleamine 2,3-dioxygenase inhibiting amount of any compound listed in Tables 1-11; (d) enhancing the effectiveness of an anti-cancer treatment comprising administering an anti-cancer agent and any compound listed in Tables 1-11; (e) treating tumor-specific immunosuppression associated with cancer comprising administering an effective indoleamine 2,3-dioxygenase inhibiting amount of any compound listed in Tables 1-11; and (f) treating immunsupression associated with an infectious disease, e.g., HIV-1 infection, comprising administering an effective indoleamine 2,3-dioxygenase inhibiting amount of any compound listed in Tables 1-11.

In an embodiment of the eleventh aspect, the compound is any one compound listed in Table 1.

In an embodiment of the eleventh aspect, the compound is any one compound listed in Table 2.

In an embodiment of the eleventh aspect, the compound is any one compound listed in Table 3.

In an embodiment of the eleventh aspect, the compound is any one compound listed in Table 4.

In an embodiment of the eleventh aspect, the compound is any one compound listed in Table 5.

In an embodiment of the eleventh aspect, the compound is any one compound listed in Table 6.

In an embodiment of the eleventh aspect, the compound is any one compound listed in Table 7.

In an embodiment of the eleventh aspect, the compound is any one compound listed in Table 8.

In an embodiment of the eleventh aspect, the compound is any one compound listed in Table 9.

In an embodiment of the eleventh aspect, the compound is any one compound listed in Table 10.

In an embodiment of the eleventh aspect, the compound is any one compound listed in Table 11.

TABLE 1

| Cmpd # | Structure | Name |
|---|---|---|
| 00001 | 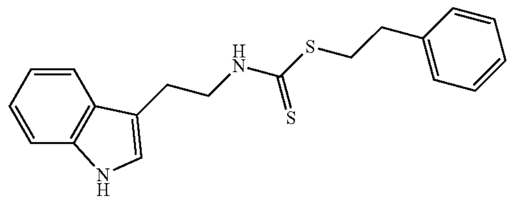 [SMILES: S=C(NCCc1c[nH]c2ccccc12)SCCc1ccccc1] | phenethyl 2-(1H-indol-3-yl)ethylcarbamodithioate |
| 00002 | 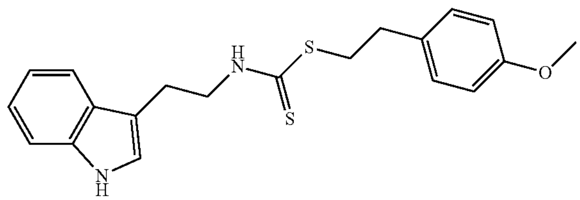 [SMILES: COc1ccc(CCSC(=S)NCCc2c[nH]c3ccccc23)cc1] | 4-methoxyphenethyl 2-(1H-indol-3-yl)ethylcarbamodithioate |
| 00003 | 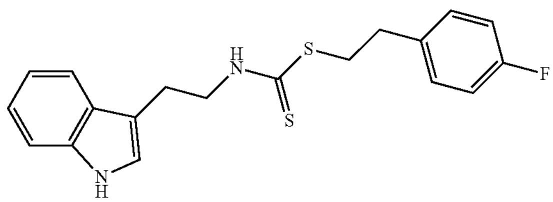 [SMILES: Fc1ccc(CCSC(=S)NCCc2c[nH]c3ccccc23)cc1] | 4-fluorophenethyl 2-(1H-indol-3-yl)ethylcarbamodithioate |
| 00004 | 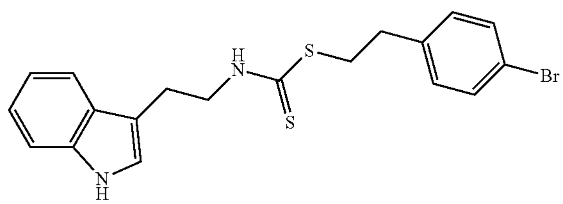 [SMILES: S=C(NCCc1c[nH]c2ccccc12)SCCc1ccc(Br)cc1] | 4-bromophenethyl 2-(1H-indol-3-yl)ethylcarbamodithioate |
| 00006 | 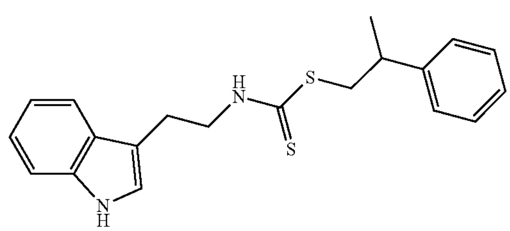 [SMILES: CC(CSC(=S)NCCc1c[nH]c2ccccc12)c1ccccc1] | 2-phenylpropyl 2-(1H-indol-3-yl)ethylcarbamodithioate |
| 00007 | 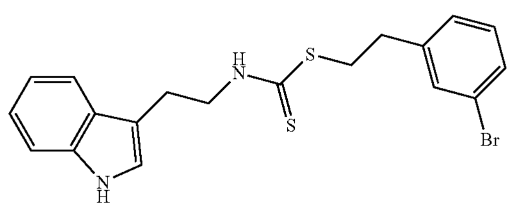 [SMILES: S=C(NCCc1c[nH]c2ccccc12)SCCc1cccc(Br)c1] | 3-bromophenethyl 2-(1H-indol-3-yl)ethylcarbamodithioate |
| 00008 | 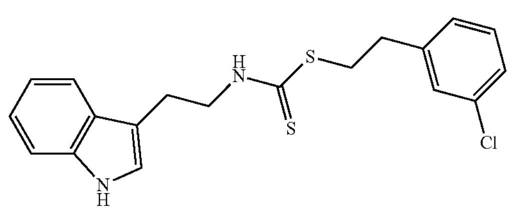 [SMILES: S=C(NCCc1c[nH]c2ccccc12)SCCc1cccc(Cl)c1] | 3-chlorophenethyl 2-(1H-indol-3-yl)ethylcarbamodithioate |

TABLE 1-continued

| Cmpd # | Structure | Name |
|---|---|---|
| 00009 | 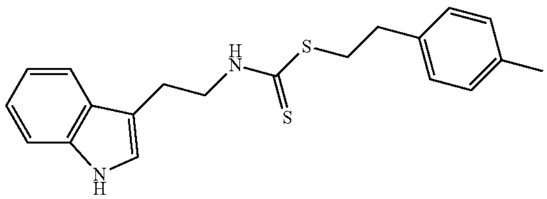 [SMILES: Cc1ccc(CCSC(=S)NCCc2c[nH]c3ccccc23)cc1] | 4-methylphenethyl 2-(1H-indol-3-yl)ethylcarbamodithioate |
| 00010 | 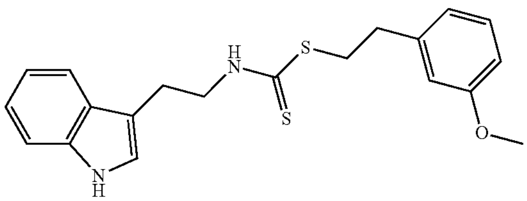 [SMILES: COc1cccc(CCSC(=S)NCCc2c[nH]c3ccccc23)c1] | 3-methoxyphenethyl 2-(1H-indol-3-yl)ethylcarbamodithioate |
| 00012 | 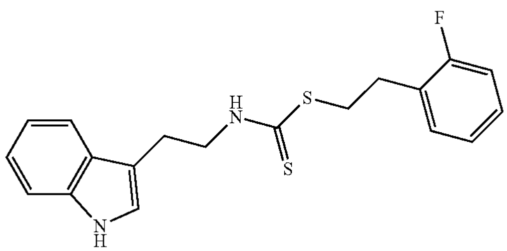 [SMILES: Fc1ccccc1CCSC(=S)NCCc1c[nH]c2ccccc12] | 2-fluorophenethyl 2-(1H-indol-3-yl)ethylcarbamodithioate |
| 00020 | 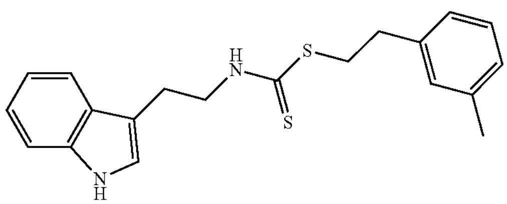 [SMILES: Cc1cccc(CCSC(=S)NCCc2c[nH]c3ccccc23)c1] | 3-methylphenethyl 2-(1H-indol-3-yl)ethylcarbamodithioate |
| 00021 | 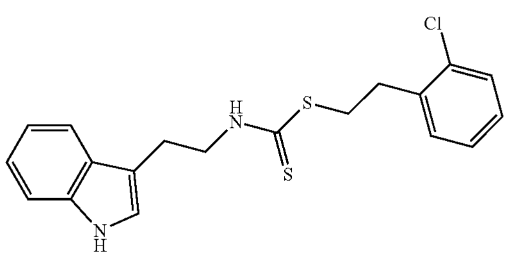 [SMILES: S=C(NCCc1c[nH]c2ccccc12)SCCc1ccccc1Cl] | 2-chlorophenethyl 2-(1H-indol-3-yl)ethylcarbamodithioate |
| 00030 | 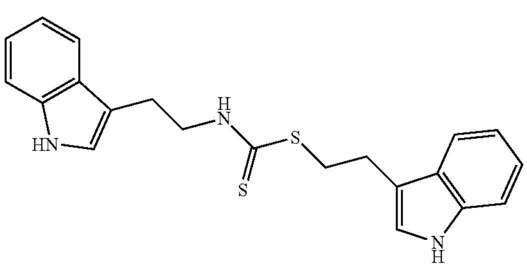 [SMILES: S=C(NCCc1c[nH]c2ccccc12)SCCc1c[nH]c2ccccc12] | 2-(1H-indol-3-yl)ethyl 2-(1H-indol-3-yl)ethylcarbamodithioate |
| 00047 | 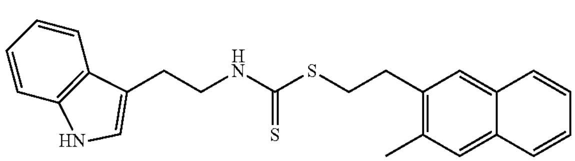 [SMILES: Cc1cc2ccccc2cc1CCSC(=S)NCCc1c[nH]c2ccccc12] | 2-(3-methylnaphthalen-2-yl)ethyl 2-(1H-indol-3-yl)ethylcarbamodithioate |

TABLE 1-continued

| Cmpd # | Structure | Name |
|---|---|---|
| 00053 | 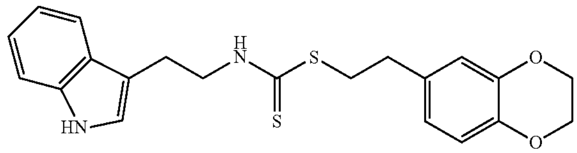 [SMILES: S=C(NCCc1c[nH]c2ccccc12)SCCc1ccc2c(c1)OCCO2] | 2-(2,3-dihydrobenzo[b][1,4]dioxin-6-yl)ethyl 2-(1H-indol-3-yl)ethylcarbamodithioate |
| 00062 | 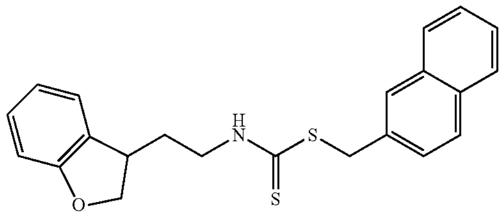 [SMILES: S=C(NCCC1COc2ccccc21)SCc1ccc2ccccc2c1] | naphthalen-2-ylmethyl 2-(2,3-dihydrobenzofuran-3-yl)ethylcarbamodithioate |
| 00078 | 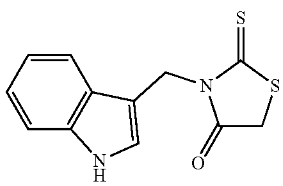 [SMILES: O=C1CSC(=S)N1Cc1c[nH]c2ccccc12] | 3-((1H-indol-3-yl)methyl)-2-thioxothiazolidin-4-one |
| 00080 | 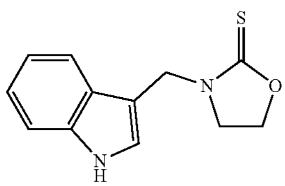 [SMILES: S=C1OCCN1Cc1c[nH]c2ccccc12] | 3-((1H-indol-3-yl)methyl)oxazolidine-2-thione |
| 00239 | 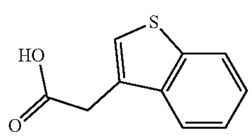 [SMILES: O=C(O)Cc1csc2ccccc12] | 2-(benzo[b]thiophen-3-yl)acetic acid |
| 00288 | 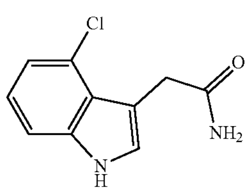 [SMILES: NC(=O)Cc1c[nH]c2cccc(Cl)c12] | 2-(4-chloro-1H-indol-3-yl)acetamide |
| 00293 | 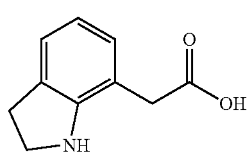 [SMILES: O=C(O)Cc1cccc2c1NCC2] | 2-(indolin-7-yl)acetic acid |
| 00307 | 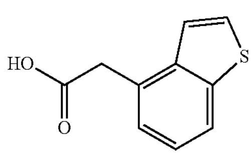 [SMILES: O=C(O)Cc1cccc2sccc12] | 2-(benzo[b]thiophen-4-yl)acetic acid |
| 00325 | 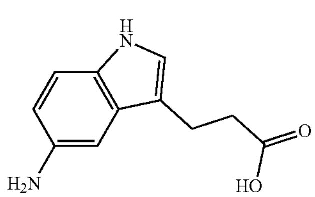 [SMILES: Nc1ccc2[nH]cc(CCC(=O)O)c2c1] | 3-(5-amino-1H-indol-3-yl)propanoic acid |

TABLE 1-continued

| Cmpd # | Structure | Name |
|---|---|---|
| 00327 | 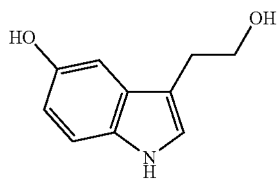 [SMILES: OCCc1c[nH]c2ccc(O)cc12] | 3-(2-hydroxyethyl)-1H-indol-5-ol |
| 00335 | 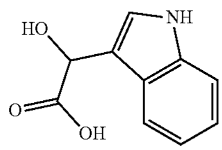 [SMILES: O=C(O)C(O)c1c[nH]c2ccccc12] | 2-hydroxy-2-(1H-indol-3-yl)acetic acid |
| 0352 | 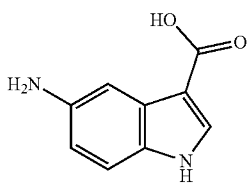 [SMILES: Nc1ccc2[nH]cc(C(=O)O)c2c1] | 5-amino-1H-indole-3-carboxylic acid |
| 00386 | 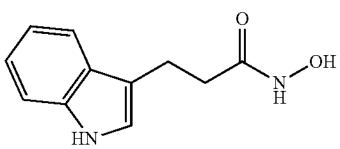 [SMILES: O=C(CCc1c[nH]c2ccccc12)NO] | N-hydroxy-3-(1H-indol-3-yl)propanamide |
| 00388 | 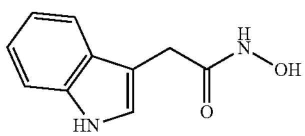 [SMILES: O=C(Cc1c[nH]c2ccccc12)NO] | N-hydroxy-2-(1H-indol-3-yl)acetamide |
| 00390 | 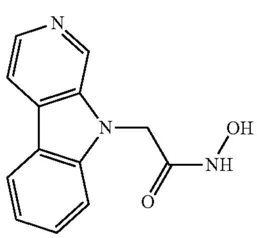 [SMILES: O=C(Cn1c2ccccc2c2ccncc21)NO] | N-hydroxy-2-(9H-pyrido[3,4-b]indol-9-yl)acetamide |
| 00391 | 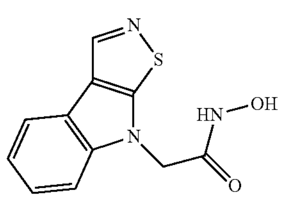 [SMILES: O=C(Cn1c2ccccc2c2cnsc21)NO] | N-hydroxy-2-(8H-isothiazolo[5,4-b]indol-8-yl)acetamide |
| 00392 | 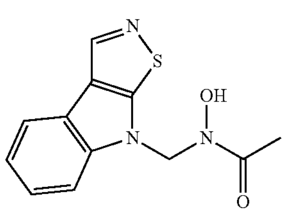 [SMILES: CC(=O)N(O)Cn1c2ccccc2c2cnsc21] | N-((8H-isothiazolo[5,4-b]indol-8-yl)methyl)-N-hydroxyacetamide |

TABLE 1-continued

| Cmpd # | Structure | Name |
|---|---|---|
| 00552 | 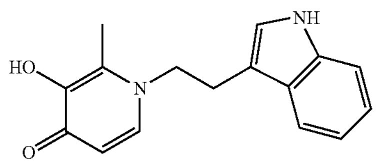 [SMILES: Cc1c(O)c(=O)ccn1CCc1c[nH]c2ccccc12] | 1-(2(1H-indol-3-yl)ethyl)-3-hydroxy-2-methylpyridin-4(1H)-one |
| 00553 | 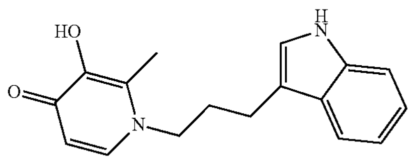 [SMILES: Cc1c(O)c(=O)ccn1CCCc1c[nH]c2ccccc12] | 1-(3-(1H-indol-3-yl)propyl)-3-hydroxy-2-methylpyridin-4(1H)-one |
| 00554 | 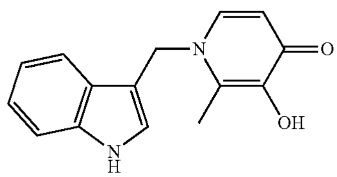 [SMILES: Cc1c(O)c(=O)ccn1Cc1c[nH]c2ccccc12] | 1-((1H-indol-3-yl)methyl)-3-hydroxy-2-methylpyridin-4(1H)-one |
| 00555 | 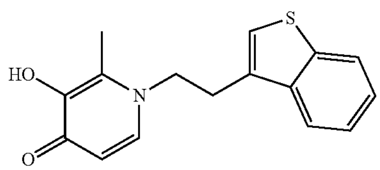 [SMILES: Cc1c(O)c(=O)ccn1CCc1csc2ccccc12] | 1-(2-(benzo[b]thiophen-3-yl)ethyl)-3-hydroxy-2-methylpyridin-4(1H)-one |
| 00562 | 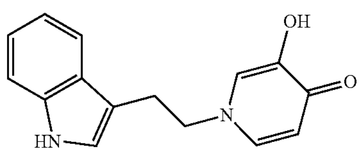 [SMILES: O=c1ccn(CCc2c[nH]c3ccccc23)cc1O] | 1-(2-(1H-indol-3-yl)ethyl)-3-hydroxypyridin-4(1H)-one |
| 00563 | 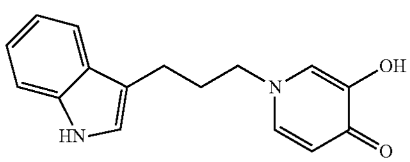 [SMILES: O=c1ccn(CCCc2c[nH]c3ccccc23)cc1O] | 1-(3-(1H-indol-3-yl)propyl)-3-hydroxypyridin-4(1H)-one |
| 00564 | 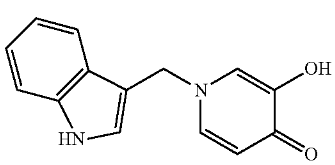 [SMILES: O=c1ccn(Cc2c[nH]c3ccccc23)cc1O] | 1-((1H-indol-3-yl)methyl)-3-hydroxypyridin-4(1H)-one |
| 00565 | 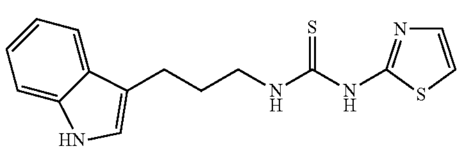 [SMILES: S=C(NCCCc1c[nH]c2ccccc12)Nc1nccs1] | 1-(3-(1H-indol-3-yl)propyl)-3-(thiazol-2-yl)thiourea |
| 00566 | 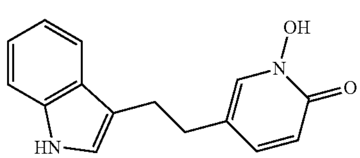 [SMILES: O=c1ccc(CCc2c[nH]c3ccccc23)cn1O] | 5-(2-(1H-indol-3-yl)ethyl)-1-hydroxypyridin-2(1H)-one |

TABLE 1-continued

| Cmpd # | Structure | Name |
|---|---|---|
| 00568 | 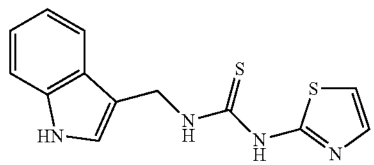 [SMILES: S=C(NCc1c[nH]c2ccccc12)Nc1nccs1] | 1-((1H-indol-3-yl)methyl)-3-(thiazol-2-yl)thiourea |
| 00571 | 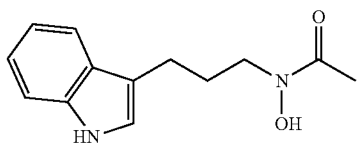 [SMILES: CC(=O)N(O)CCCc1c[nH]c2ccccc12] | N-(3-(1H-indol-3-yl)propyl)-N-hydroxyacetamide |
| 00577 | 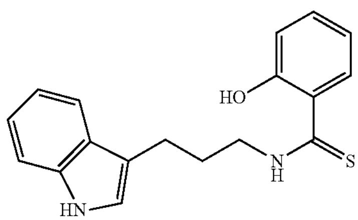 [SMILES: Oc1ccccc1C(=S)NCCCc1c[nH]c2ccccc12] | N-(3-(1H-indol-3-yl)propyl)-2-hydroxybenzothioamide |
| 00588 | 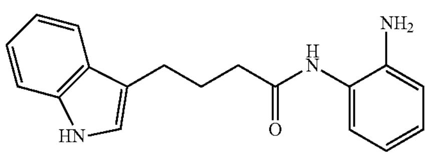 [SMILES: Nc1ccccc1NC(=O)CCCc1c[nH]c2ccccc12] | N-(2-aminophenyl)-4-(1H-indol-3-yl)butanamide |
| 00589 | 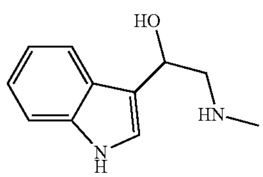 | 1-(1H-indol-3-yl)-2-(methylamino)ethanol |
| 00590 | 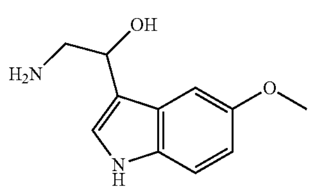 | 2-amino-1-(5-methoxy-1H-indol-3-yl)ethanol |
| 00592 | 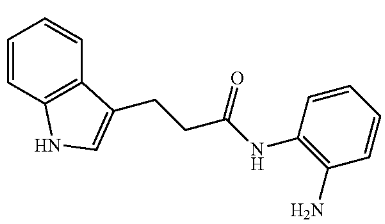 [SMILES: Nc1ccccc1NC(=O)CCc1c[nH]c2ccccc12] | N-(2-aminophenyl)-3-(1H-indol-3-yl)propanamide |
| 00596 | 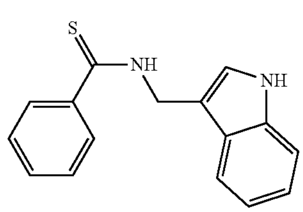 [SMILES: S=C(NCc1c[nH]c2ccccc12)c1ccccc1] | N-((1H-indol-3-yl(methyl)benzothioamide |

TABLE 1-continued

| Cmpd # | Structure | Name |
| --- | --- | --- |
| 00601 | 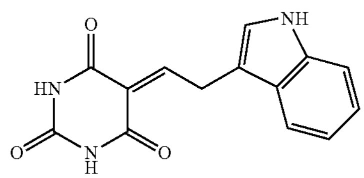 [SMILES: O=C1NC(=O)C(=CCc2c[nH]c3ccccc23)C(=O)N1] | 5-(2-(1H-indol-3-yl)ethylidene)pyrimidine-2,4,6(1H,3H,5H)-trione |
| 00603 | 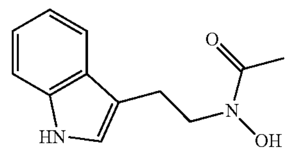 [SMILES: CC(=O)N(O)CCc1c[nH]c2ccccc12] | N-(2-(1H-indol-3-yl)ethyl)-N-hydroxyacetamide |
| 00604 | 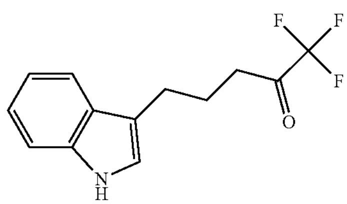 [SMILES: O=C(CCCc1c[nH]c2ccccc12)C(F)(F)F] | 1,1,1-trifluoro-5-(1H-indol-3-yl)pentan-2-one |
| 00606 | 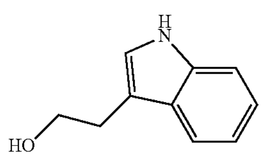 [SMILES: OCCc1c[nH]c2ccccc12] | 2-(1H-indol-3-yl)ethanol |
| 00611 | 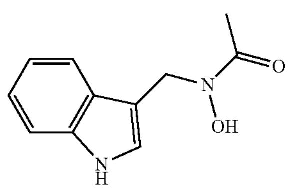 | N-((1H-indol-3-yl)methyl)-N-hydroxyacetamide |
| 00613 | 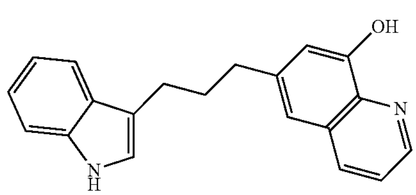 [SMILES: Oc1cc(CCCc2c[nH]c3ccccc23)cc2cccnc12] | 6-(3-(1H-indol-3-yl)propyl)quinolin-8-ol |
| 00630 | 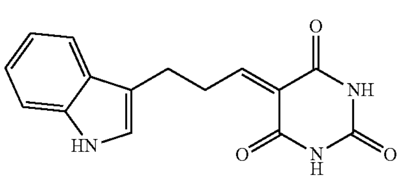 [SMILES: O=C1NC(=O)C(=CCCc2c[nH]c3ccccc23)C(=O)N1] | 5-(3-(1H-indol-3-yl)propylidene)pyrimidine-2,4,6(1H,3H,5H)-trione |
| 00632 | 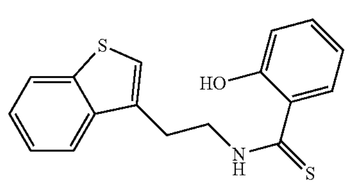 [SMILES: Oc1ccccc1C(=S)NCCc1csc2ccccc12] | N-(2-(benzo[b]thiophen-3-yl)ethyl)-2-hydroxybenzothioamide |

TABLE 1-continued

| Cmpd # | Structure | Name |
| --- | --- | --- |
| 00636 | 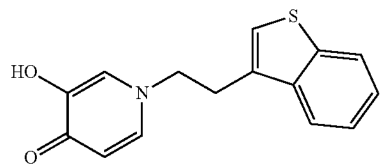 [SMILES: O=c1ccn(CCc2csc3ccccc23)cc1O] | 1-(2-(benzo[b]thiophen-3-yl)ethyl)-3-hydroxypyridin-4(1H)-one |
| 00637 | 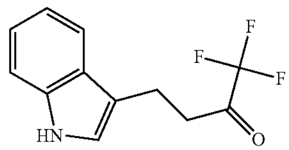 [SMILES: O=C(CCc1c[nH]c2ccccc12)C(F)(F)F] | 1,1,1-trifluoro-4-(1H-indol-3-yl)butan-2-one |
| 00644 | 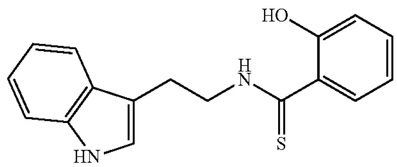 [SMILES: Oc1ccccc1C(=S)NCCc1c[nH]c2ccccc12] | N-(2-(1H-indol-3-yl)ethyl)-2-hydroxybenzothioamide |
| 00646 | 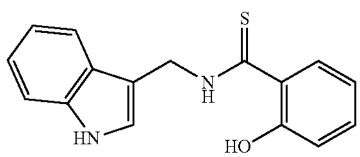 [SMILES: Oc1ccccc1C(=S)NCc1c[nH]c2ccccc12] | N-((1H-indol-3-yl)methyl)-2-hydroxybenzothioamide |
| 00655 | 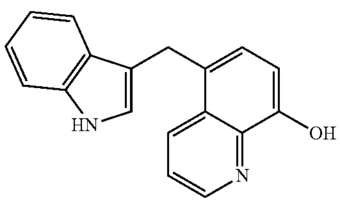 [SMILES: Oc1ccc(Cc2c[nH]c3ccccc23)c2cccnc12] | 5-((1H-indol-3-yl)methyl)quinolin-8-ol |
| 00660 | 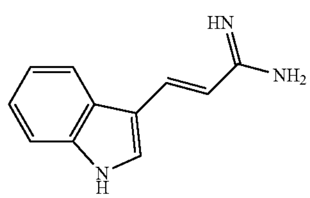 [SMILES: N=C(N)/C=C/c1c[nH]c2ccccc12] | (E)-3-(1H-indol-3-yl)acrylimidamide |
| 00667 | 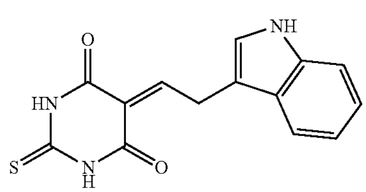 [SMILES: O=C1NC(=S)NC(=O)C1=CCc1c[nH]c2ccccc12] | 5-(2-(1H-indol-3-yl)ethylidene)-2-thioxodihydropyrimidine-4,6(1H,5H)-dione |
| 00672 | 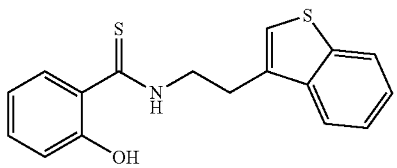 [SMILES: Oc1ccccc1C(=S)NCCc1csc2ccccc12] | N-(2-(benzo[b]thiophen-3-yl)ethyl)-2-hydroxybenzothioamide |

TABLE 1-continued

| Cmpd # | Structure | Name |
|---|---|---|
| 00673 | 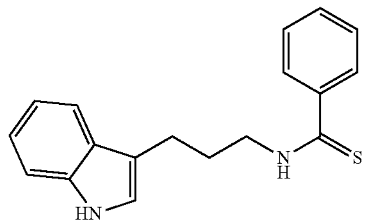 [SMILES: S=C(NCCCc1c[nH]c2ccccc12)c1ccccc1] | N-(3-(1H-indol-3-yl)propyl)benzothioamide |
| 00695 | 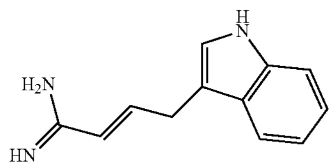 [SMILES: N=C(N)/C=C/Cc1c[nH]c2ccccc12] | (E)-4-(1H-indol-3-yl)but-2-enimidamide |
| 00717 | 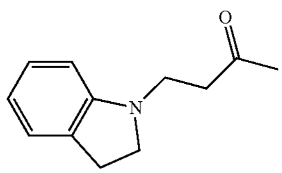 | 4-(indolin-1-yl)butan-2-one |
| 00725 | 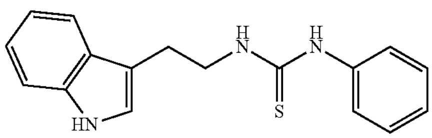 [SMILES: S=C(NCCc1c[nH]c2ccccc12)Nc1ccccc1] | 1-(2-(1H-indol-3-yl)ethyl)-3-phenylthiourea |
| 00729 | 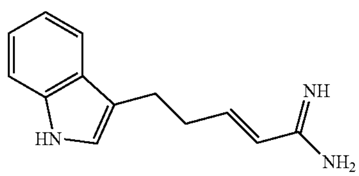 [SMILES: N=C(N)/C=C/CCc1c[nH]c2ccccc12] | (E)-5-(1H-indol-3-yl)pent-2-enimidamide |
| 00737 | 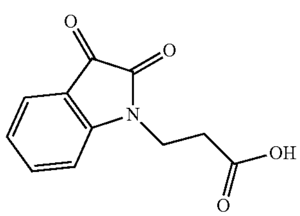 [SMILES: O=C(O)CCN1C(=O)C(=O)c2ccccc21] | 3-(2,3-dioxoindolin-1-yl)propanoic acid |
| 00739 | 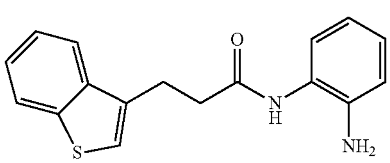 [SMILES: Nc1ccccc1NC(=O)CCc1csc2ccccc12] | N-(2-aminophenyl)-3-(benzo[b]thiophen-3-yl)propanamide |
| 00741 | 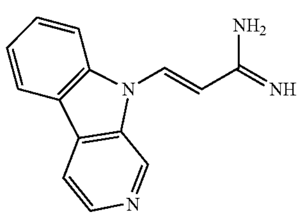 [SMILES: N=C(N)/C=C/n1c2ccccc2c2ccncc21] | (E)-3-(9H-pyrido[3,4-b]indol-9-yl)acrylimidamide |

TABLE 1-continued

| Cmpd # | Structure | Name |
|---|---|---|
| 00745 | 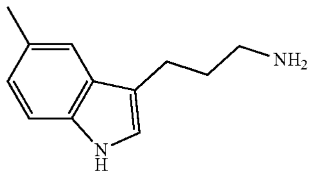 | 3-(5-methyl-1H-indol-3-yl)propan-1-amine |
| 00749 | 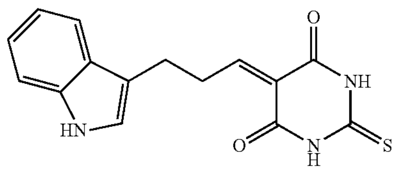 [SMILES: O=C1NC(=S)NC(=O)C1=CCCc1c[nH]c2ccccc12] | 5-(3-(1H-indol-3-yl)propylidene)-2-thioxodihydropyrimidine-4,6(1H,5H)-dione |
| 00758 | 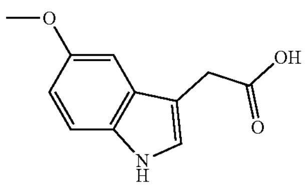 | 2-(5-methoxy-1H-indol-3-yl)acetic acid |
| 00764 | 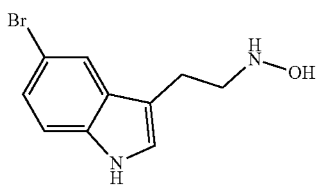 [SMILES: ONCCc1c[nH]c2ccc(Br)cc12] | N-(2-(5-bromo-1H-indol-3-yl)ethyl)hydroxylamine |
| 00789 | 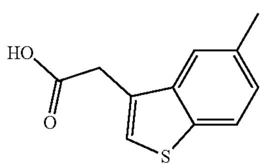 | 2-(5-methylbenzo[b]thiophen-3-yl)acetic acid |
| 00796 | 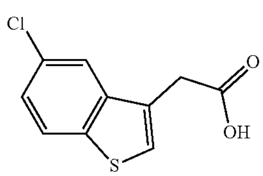 [SMILES: O=C(O)Cc1csc2ccc(Cl)cc12] | 2-(5-chlorobenzo[b]thiophen-3-yl)acetic acid |
| 00813 | 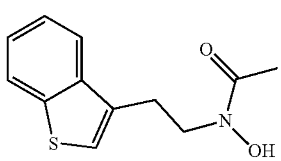 [SMILES: CC(=O)N(O)CCc1csc2ccccc12] | N-(2-(benzo[b]thiophen-3-yl)ethyl)-N-hydroxyacetamide |
| 00819 | 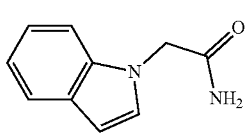 [SMILES: NC(=O)Cn1ccc2ccccc21] | 2-(1H-indol-1-yl)acetamide |

TABLE 1-continued
| Cmpd # | Structure | Name |
|---|---|---|
| 00820 | 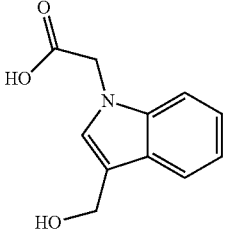 [SMILES: O=C(O)Cn1cc(CO)c2ccccc21] | 2-(3-(hydroxymethyl)-1H-indol-1-yl)acetic acid |
| 00840 | 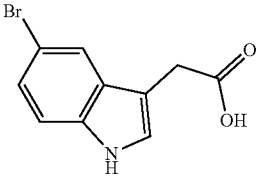 [SMILES: O=C(O)Cc1c[nH]c2ccc(Br)cc12] | 2-(5-bromo-1H-indol-3-yl)acetic acid |
| 00843 | 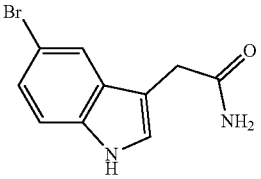 [SMILES: NC(=O)Cc1c[nH]c2ccc(Br)cc12] | 2-(5-bromo-1H-indol-3-yl)acetamide |
| 00850 | 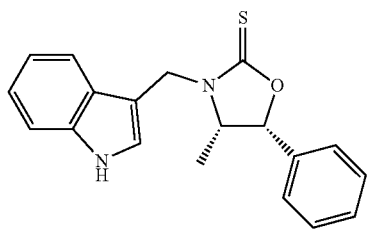 [SMILES: C[C@H]1[C@@H](c2ccccc2)OC(=S)N1Cc1c[nH]c2ccccc12] | (4S,5R)-3-((1H-indol-3-yl)methyl)-4-methyl-5-phenyloxazolidine-2-thione |
| 00852 | 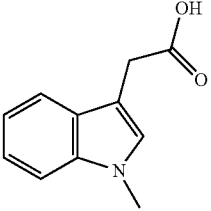 | 2-(1-methyl-1H-indol-3-yl)acetic acid |
| 00872 | 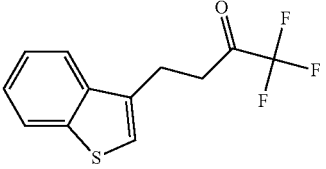 [SMILES: O=C(CCc1csc2ccccc12)C(F)(F)F] | 4-(benzo[b]thiophen-3-yl)-1,1,1-trifluorobutan-2-one |
| 00882 | 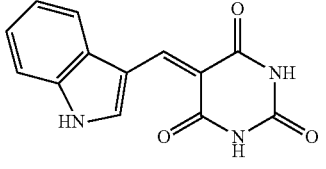 [SMILES: O=C1NC(=O)C(=Cc2c[nH]c3ccccc23)C(=O)N1] | 5-((1H-indol-3-yl)methylene)pyrimidine-2,4,6(1H,3H,5H)-trione |

TABLE 1-continued

| Cmpd # | Structure | Name |
|---|---|---|
| 00888 | 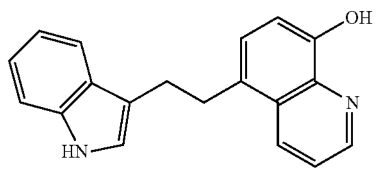 [SMILES: Oc1ccc(CCc2c[nH]c3ccccc23)c2cccnc12] | 5-(2-(1H-indol-3-yl)ethyl)quinolin-8-ol |
| 00894 | 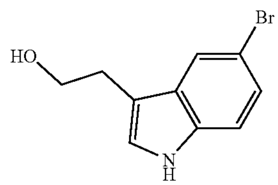 [SMILES: OCCc1c[nH]c2ccc(Br)cc12] | 2-(5-bromo-1H-indol-3-yl)ethanol |
| 00898 | 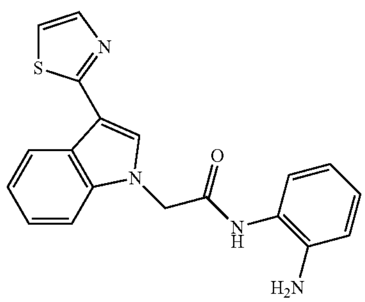 [SMILES: Nc1ccccc1NC(=O)Cn1cc(-c2nccs2)c2ccccc21] | N-(2-aminophenyl)-2-(3-(thiazol-2-yl)-1H-indol-1-yl)acetamide |
| 00924 | 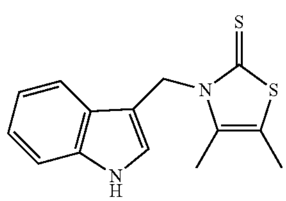 [SMILES: Cc1sc(=S)n(Cc2c[nH]c3ccccc23)c1C] | 3-((1H-indol-3-yl)methyl)-4,5-dimethylthiazole-2(3H)-thione |
| 00931 | 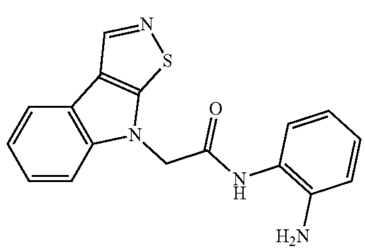 [SMILES: Nc1ccccc1NC(=O)Cn1c2ccccc2c2cnsc21] | N-(2-aminophenyl)-2-(8H-isothiazolo[5,4-b]indol-8-yl)acetamide |
| 00940 | 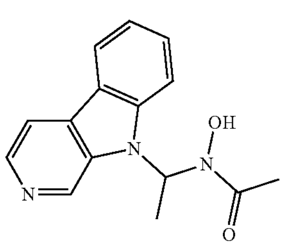 [SMILES: CC(=O)N(O)C(C)n1c2ccccc2c2ccncc21] | N-(1-(9H-pyrido[3,4-b]indol-9-yl)ethyl)-N-hydroxyacetamide |
| 00949 | 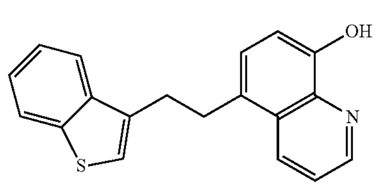 [SMILES: Oc1ccc(CCc2csc3ccccc23)c2cccnc12] | 5-(2-(benzo[b]thiophen-3-yl)ethyl)quinolin-8-ol |

TABLE 1-continued

| Cmpd # | Structure | Name |
|---|---|---|
| 00950 | 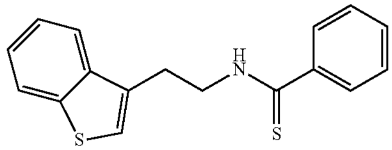 [SMILES: S=C(NCCc1csc2ccccc12)c1ccccc1] | N-(2-(benzo[b]thiophen-3-yl)ethyl)benzothioamide |
| 00952 | 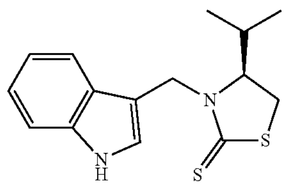 [SMILES: CC(C)[C@H]1CSC(=S)N1Cc1c[nH]c2ccccc12] | (S)-3-((1H-indol-3-yl)methyl)-4-isopropylthiazolidine-2-thione |
| 00953 | 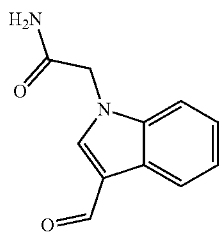 [SMILES: NC(=O)Cn1cc(C=O)c2ccccc21] | 2-(3-formyl-1H-indol-1-yl)acetamide |
| 00957 | 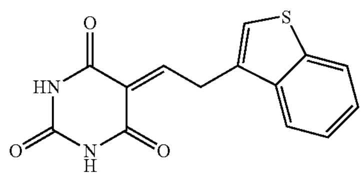 [SMILES: O=C1NC(=O)C(=CCc2csc3ccccc23)C(=O)N1] | 5-(2-(benzo[b]thiophen-3-yl)ethylidene)pyrimidine-2,4,6(1H,3H,5H)-trione |
| 00963 | 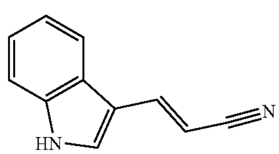 [SMILES: N#C/C=C/c1c[nH]c2ccccc12] | (E)-3-(1H-indol-3-yl)acrylonitrile |
| 00989 | 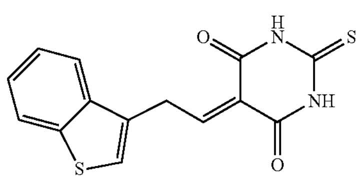 [SMILES: O=C1NC(=S)NC(=O)C1=CCc1csc2ccccc12] | 5-(2-(benzo[b]thiophen-3-yl)ethylidene)-2-thioxodihydropyrimidine-4,6(1H,5H)-dione |
| 00998 | 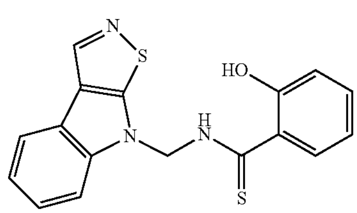 [SMILES: Oc1ccccc1C(=S)NCn1c2ccccc2c2cnsc21] | N-((8H-isothiazolo[5,4-b]indol-8-yl)methyl)-2-hydroxybenzothioamide |
| 01001 | 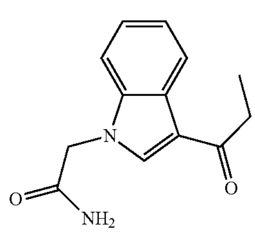 [SMILES: CCC(=O)c1cn(CC(N)=O)c2ccccc12] | 2-(3-propionyl-1H-indol-1-yl)acetamide |

TABLE 1-continued

| Cmpd # | Structure | Name |
|---|---|---|
| 01007 | 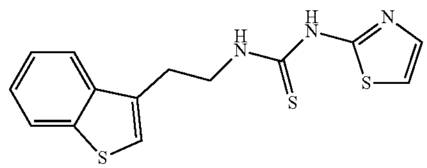 [SMILES: S=C(NCCc1csc2ccccc12)Nc1nccs1] | 1-(2-(benzo[b]thiophen-3-yl)ethyl)-3-(thiazol-2-yl)thiourea |
| 01009 | 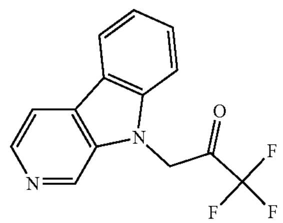 [SMILES: O=C(Cn1c2ccccc2c2ccncc21)C(F)(F)F] | 1,1,1-trifluoro-3-(9H-pyrido[3,4-b]indol-9-yl)propan-2-one |
| 01015 | 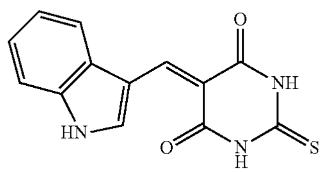 [SMILES: O=C1NC(=S)NC(=O)C1=Cc1c[nH]c2ccccc12] | 5-((1H-indol-3-yl)methylene)-2-thioxodihydropyrimidine-4,6(1H,5H)-dione |
| 01017 | 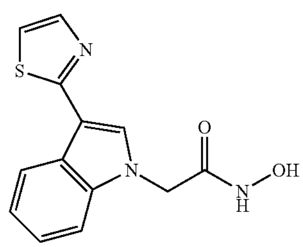 [SMILES: O=C(Cn1cc(-c2nccs2)c2ccccc21)NO] | N-hydroxy-2-(3-(thiazol-2-yl)-1H-indol-1-yl)acetamide |
| 01027 | 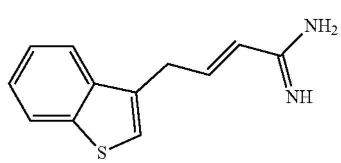 [SMILES: N=C(N)/C=C/Cc1csc2ccccc12] | (E)-4-(benzo[b]thiophen-3-yl)but-2-enimidamide |
| 01043 | 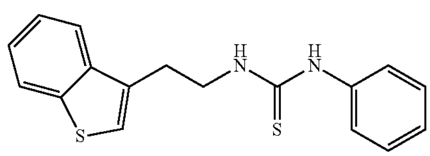 [SMILES: S=C(NCCc1csc2ccccc12)Nc1ccccc1] | 1-(2-(benzo[b]thiophen-3-yl)ethyl)-3-phenylthiourea |
| 01048 | 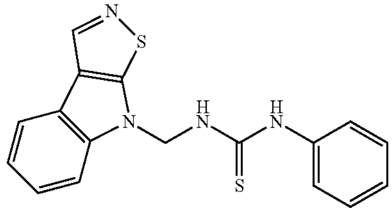 [SMILES: S=C(NCn1c2ccccc2c2cnsc21)Nc1ccccc1] | 1-((8H-isothiazolo[5,4-b]indol-8-yl)methyl)-3-phenylthiourea |
| 01060 | 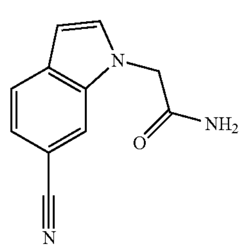 [SMILES: N#Cc1ccc2ccn(CC(N)=O)c2c1] | 2-(6-cyano-1H-indol-1-yl)acetamide |

TABLE 1-continued

| Cmpd # | Structure | Name |
| --- | --- | --- |
| 01063 | 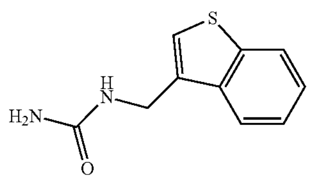 [SMILES: NC(=O)NCc1csc2ccccc12] | 1-(benzo[b]thiophen-3-ylmethyl)urea |
| 01087 | 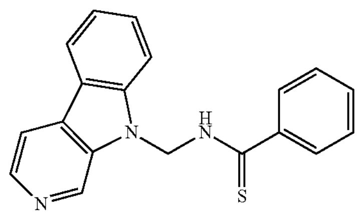 [SMILES: S=C(NCn1c2ccccc2c2ccncc21)c1ccccc1] | N-((9H-pyrido[3,4-b]indol-9-yl)methyl)benzothioamide |
| 01091 | 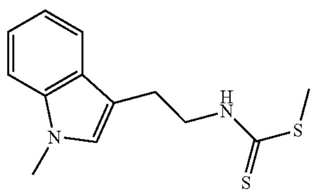 [SMILES: CSC(=S)NCCc1cn(C)c2ccccc12] | methyl 2-(1-methyl-1H-indol-3-yl)ethylcarbamodithioate |
| 01094 | 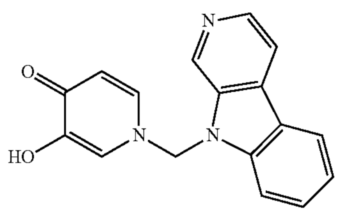 [SMILES: O=c1ccn(Cn2c3ccccc3c3ccncc32)cc1O] | 1-((9H-pyrido[3,4-b]indol-9-yl)methyl)-3-hydroxypyridin-4(1H)-one |
| 01114 | 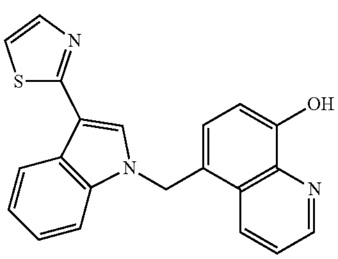 [SMILES: Oc1ccc(Cn2cc(-c3nccs3)c3ccccc32)c2cccnc12] | 5-((3-(thiazol-2-yl)-1H-indol-1-yl)methyl)quinolin-8-ol |
| 01119 | 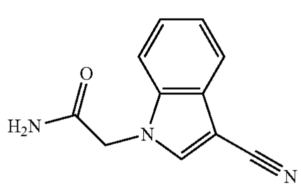 [SMILES: N#Cc1cn(CC(N)=O)c2ccccc12] | 2-(3-cyano-1H-indol-1-yl)acetamide |
| 01120 | 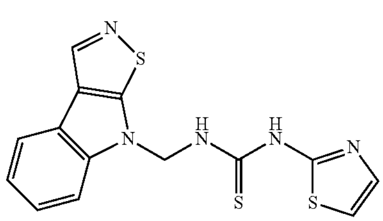 [SMILES: S=C(NCn1c2ccccc2c2cnsc21)Nc1nccs1] | 1-((8H-isothiazolo[5,4-b]indol-8-yl)methyl)-3-(thiazol-2-yl)thiourea |

TABLE 1-continued

| Cmpd # | Structure | Name |
|---|---|---|
| 01125 | 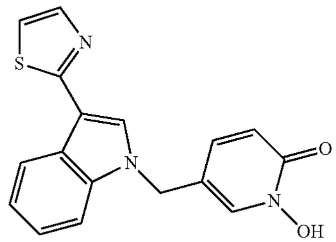 [SMILES: O=c1ccc(Cn2cc(-c3nccs3)c3ccccc32)cn1O] | 1-hydroxy-5-((3-(thiazol-2-yl)-1H-indol-1-yl)methyl)pyridin-2(1H)-one |
| 01127 | 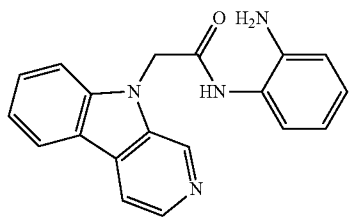 [SMILES: Nc1ccccc1NC(=O)Cn1c2ccccc2c2ccncc21] | N-(2-aminophenyl)-2-(9H-pyrido[3,4-b]indol-9-yl)acetamide |
| 01128 | 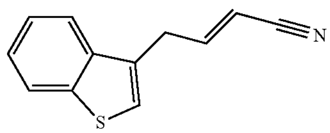 [SMILES: N#C/C=C/Cc1csc2ccccc12] | (E)-4-(benzo[b]thiophen-3-yl)but-2-enenitrile |
| 01133 | 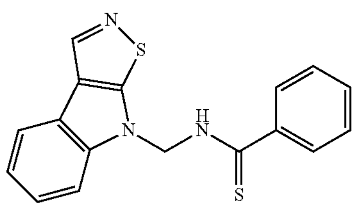 [SMILES: S=C(NCn1c2ccccc2c2cnsc21)c1ccccc1] | N-((8H-isothiazolo[5,4-b]indol-8-yl)methyl)benzothioamide |
| 01135 | 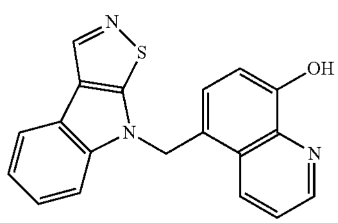 [SMILES: Oc1ccc(Cn2c3ccccc3c3cnsc32)c2cccnc12] | 5-((8H-isothiazolo[5,4-b]indol-8-yl)methyl)quinolin-8-ol |
| 01143 | 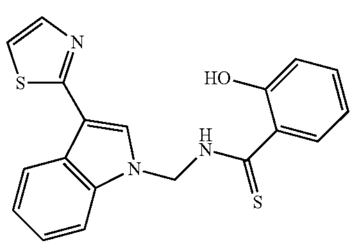 [SMILES: Oc1ccccc1C(=S)NCn1cc(-c2nccs2)c2ccccc21] | 2-hydroxy-N-((3-(thiazol-2-yl)-1H-indol-1-yl)methyl)benzothioamide |
| 01153 | 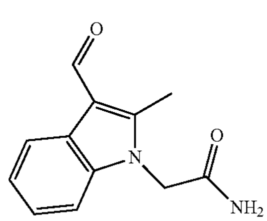 [SMILES: Cc1c(C=O)c2ccccc2n1CC(N)=O] | 2-(3-formyl-2-methyl-1H-indol-1-yl)acetamide |

TABLE 1-continued

| Cmpd # | Structure | Name |
|---|---|---|
| 01165 | 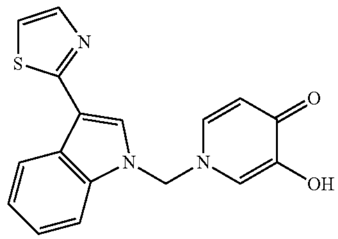 [SMILES: O=c1ccn(Cn2cc(-c3nccs3)c3ccccc32)cc1O] | 3-hydroxy-1-((3-(thiazol-2-yl)-1H-indol-1-yl)methyl)pyridin-4(1H)-one |
| 01169 | 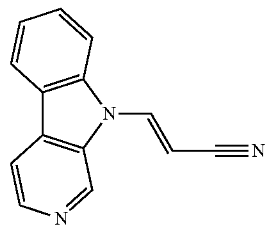 [SMILES: N#C/C=C/n1c2ccccc2c2ccncc21] | (E)-3-(9H-pyrido[3,4-b]indol-9-yl)acrylonitrile |
| 01183 | 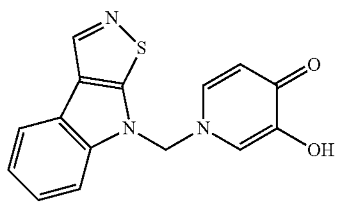 [SMILES: O=c1ccn(Cn2c3ccccc3c3cnsc32)cc1O] | 1-((8H-isothiazolo[5,4-b]indol-8-yl)methyl)-3-hydroxypyridin-4(1H)-one |
| 01185 | 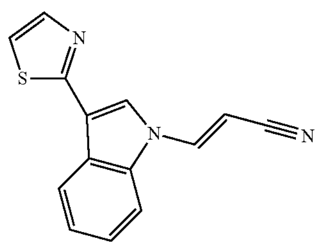 [SMILES: N#C/C=C/n1cc(-c2nccs2)c2ccccc21] | (E)-3-(3-(thiazol-2-yl)-1H-indol-1-yl)acrylonitrile |
| 01188 | 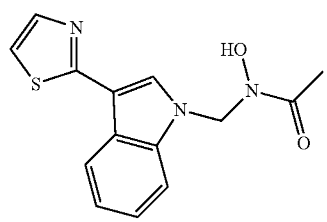 [SMILES: CC(=O)N(O)Cn1cc(-c2nccs2)c2ccccc21] | N-hydroxy-N-((3-(thiazol-2-yl)-1H-indol-1-yl)methyl)acetamide |
| 01190 | 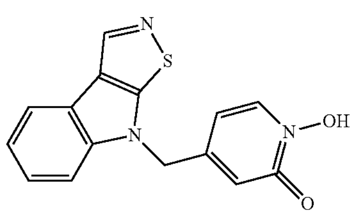 | 4-((8H-isothiazolo[5,4-b]indol-8-yl(methyl)-1-hydroxypyridin-2(1H)-one |
| 01200 | 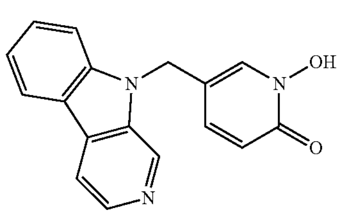 [SMILES: O=c1ccc(Cn2c3ccccc3c3ccncc32)cn1O] | 5-((9H-pyrido[3,4-b]indol-9-yl)methyl)-1-hydroxypyridin-2(1H)-one |

TABLE 1-continued

| Cmpd # | Structure | Name |
|---|---|---|
| 01206 | 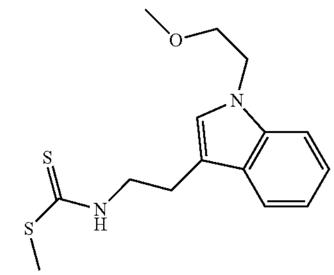 [SMILES: COCCn1cc(CCNC(=S)SC)c2ccccc21] | methyl 2-(1-(2-methoxyethyl)-1H-indol-3-yl)ethylcarbamodithioate |
| 01214 | 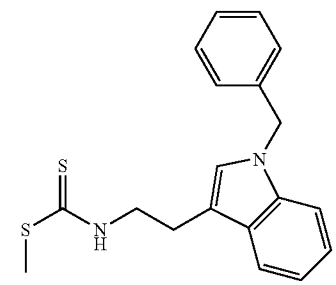 [SMILES: CSC(=S)NCCc1cn(Cc2ccccc2)c2ccccc12] | methyl 2-(1-benzyl-1H-indol-3-yl)ethylcarbamodithioate |
| 01219 | 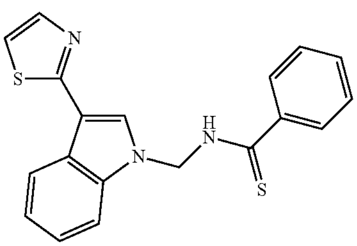 [SMILES: S=C(NCn1cc(-c2nccs2)c2ccccc21)c1ccccc1] | N-((3-(thiazol-2-yl)-1H-indol-1-yl)methyl)benzothioamide |
| 01228 | 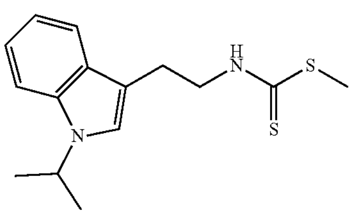 [SMILES: CSC(=S)NCCc1cn(C(C)C)c2ccccc12] | methyl 2-(1-isopropyl-1H-indol-3-yl)-ethylcarbamodithioate |
| 01230 | 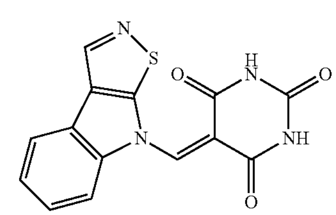 [SMILES: O=C1NC(=O)C(=Cn2c3ccccc3c3cnsc32)C(=O)N1] | 5-((8H-isothiazolo[5,4-b]indol-8-yl)methylene)pyrimidine-2,4,6(1H,3H,5H)-trione |
| 01232 | 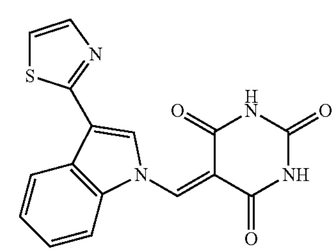 [SMILES: O=C1NC(=O)C(=Cn2cc(-c3nccs3)c3ccccc32)C(=O)N1] | 5-((3-(thiazol-2-yl)-1H-indol-1-yl)methylene)pyrimidine-2,4,6(1H,3H,5H)-trione |

TABLE 1-continued

| Cmpd # | Structure | Name |
|---|---|---|
| 01233 | 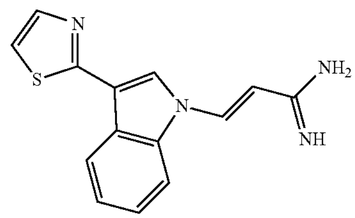 [SMILES: N=C(N)/C=C/n1cc(-c2nccs2)c2ccccc21] | (E)-3-(3-(thiazol-2-yl)-1H-indol-1-yl)acrylimidamide |
| 01235 | 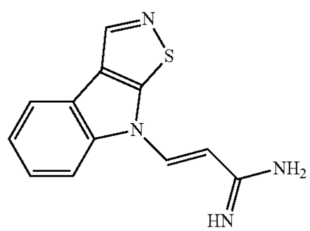 [SMILES: N=C(N)/C=C/n1c2ccccc2c2cnsc21] | (E)-3-(8H-isothiazolo[5,4-b]indol-8-yl)acrylimidamide |
| 01238 | 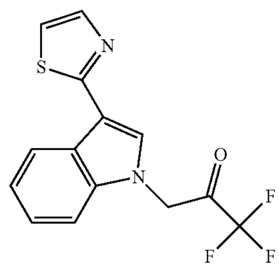 [SMILES: O=C(Cn1cc(-c2nccs2)c2ccccc21)C(F)(F)F] | 1,1,1-trifluoro-3-(3-(thiazol-2-yl)-1H-indol-1-yl)propan-2-one |
| 01241 | 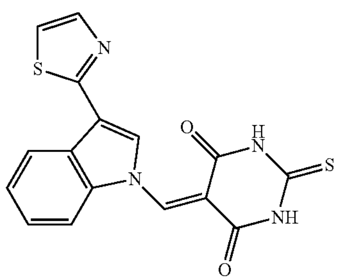 [SMILES: O=C1NC(=S)NC(=O)C1=Cn1cc(-c2nccs2)c2ccccc21] | 5-((3-(thiazol-2-yl)-1H-indol-1-yl)methylene)-2-thioxodihydropyrimidine-4,6(1H,5H)-dione |
| 01244 | 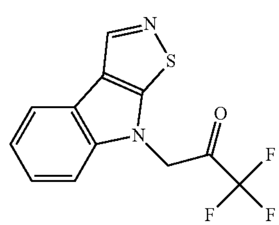 [SMILES: O=C(Cn1c2ccccc2c2cnsc21)C(F)(F)F] | 1,1,1-trifluoro-3-(8H-isothiazolo[5,4-b]indol-8-yl)propan-2-one |
| 01246 | 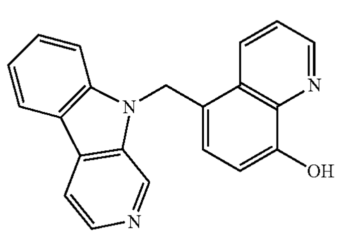 [SMILES: Oc1ccc(Cn2c3ccccc3c3ccncc32)c2cccnc12] | 5-((2-((1Z,3Z)-penta-1,3-dienyl)-1H-pyrrolo[2,3-c]pyridin-1-yl)methyl)quinolin-8-ol |

TABLE 1-continued

| Cmpd # | Structure | Name |
|---|---|---|
| 01247 | 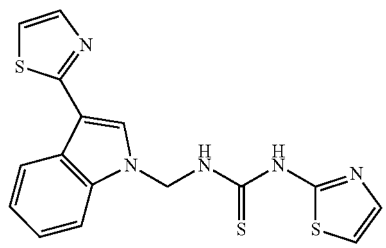 [SMILES: S=C(NCn1cc(-c2nccs2)c2ccccc21)Nc1nccs1] | 1-(thiazol-2-yl)-3-((3-(thiazol-2-yl)-1H-indol-1-yl)methyl)thiourea |
| 01249 | 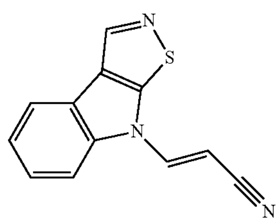 [SMILES: N#C/C=C/n1c2ccccc2c2cnsc21] | (E)-3-(8H-isothiazolo[5,4-b]indol-8-yl)acrylonitrile |
| 01254 | 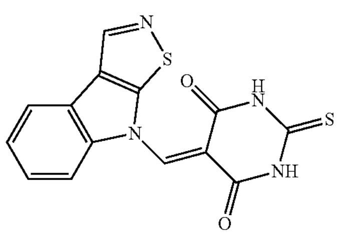 [SMILES: O=C1NC(=S)NC(=O)C1=Cn1c2ccccc2c2cnsc21] | 5-((8H-isothiazolo[5,4-b]indol-8-yl)methylene)-2-thioxodihydropyrimidine-4,6(1H,5H)-dione |
| 01256 | 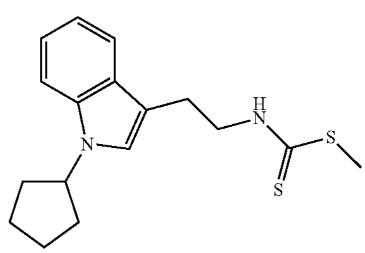 [SMILES: CSC(=S)NCCc1cn(C2CCCC2)c2ccccc12] | methyl 2-(1-cyclopentyl-1H-indol-3-yl)-ethylcarbamodithioate |
| 01258 | 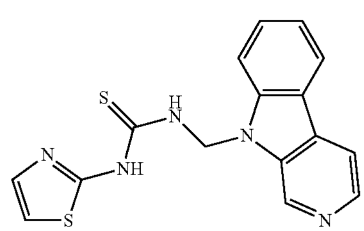 [SMILES: S=C(NCn1c2ccccc2c2ccncc21)Nc1nccs1] | -((9H-pyrido[3,4-b]indol-9-yl)methyl)-3-(thiazol-2-yl)thiourea |
| 01259 | 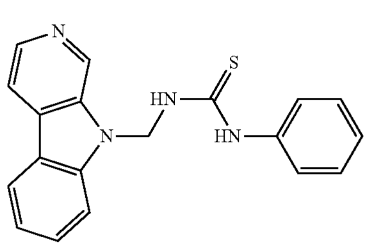 [SMILES: S=C(NCn1c2ccccc2c2ccncc21)Nc1ccccc1] | 1-((9H-pyrido[3,4-b]indol-9-yl)methyl)-3-phenylthiourea |

TABLE 1-continued

| Cmpd # | Structure | Name |
|---|---|---|
| 01260 | 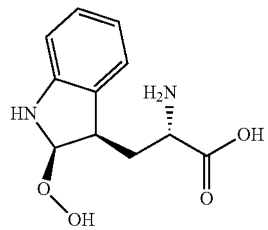 [SMILES: N[C@@H](C[C@@H]1c2ccccc2N[C@@H]1OO)C(=O)O] | (S)-2-amino-3-((2R,3R)-2-hydroperoxyindolin-3-yl)propanoic acid |
| 01261 | 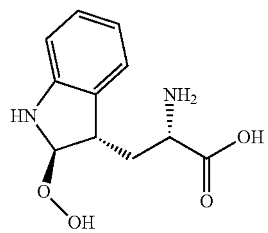 [SMILES: N[C@@H](C[C@H]1c2ccccc2N[C@@H]1OO)C(=O)O] | (S)-2-amino-3-((2R,3S)-2-hydroperoxyindolin-3-yl)propanoic acid |
| 01262 | 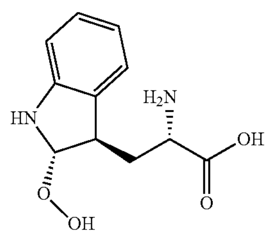 [SMILES: N[C@@H](C[C@@H]1c2ccccc2N[C@H]1OO)C(=O)O] | (S)-2-amino-3-((2S,3R)-2-hydroperoxyindolin-3-yl)propanoic acid |
| 01263 | 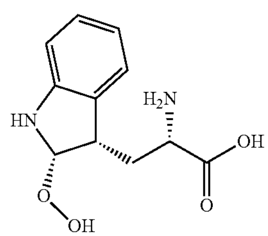 [SMILES: N[C@@H](C[C@H]1c2ccccc2N[C@H]1OO)C(=O)O] | (S)-2-amino-3-((2S,3S)-2-hydroperoxyindolin-3-yl)propanoic acid |
| 01264 | 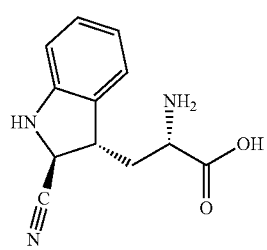 [SMILES: N#C[C@H]1Nc2ccccc2[C@@H]1C[C@H](N)C(=O)O] | (S)-2-amino-3-((2S,3S)-2-cyanoindolin-3-yl)propanoic acid |
| 01265 | 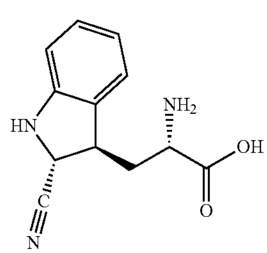 [SMILES: N#C[C@@H]1Nc2ccccc2[C@H]1C[C@H](N)C(=O)O] | (S)-2-amino-3-((2R,3R)-2-cyanoindolin-3-yl)propanoic acid |

TABLE 1-continued

| Cmpd # | Structure | Name |
| --- | --- | --- |
| 01266 | 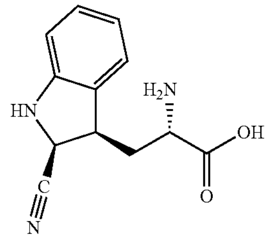 [SMILES: N#C[C@H]1Nc2ccccc2[C@H]1C[C@H](N)C(=O)O] | (S)-2-amino-3-((2S,3R)-2-cyanoindolin-3-yl)propanoic acid |
| 01267 | 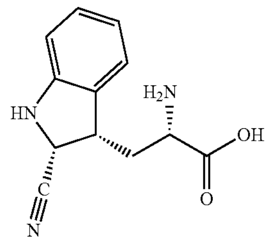 [SMILES: N#C[C@@H]1Nc2ccccc2[C@@H]1C[C@H](N)C(=O)O] | (S)-2-amino-3-((2R,3S)-2-cyanoindolin-3-yl)propanoic acid |
| 01268 | 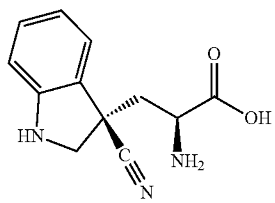 [SMILES: N#C[C@@]1(C[C@H](N)C(=O)O)CNc2ccccc21] | (S)-2-amino-3-((R)-3-cyanoindolin-3-yl propanoic acid |
| 01269 | 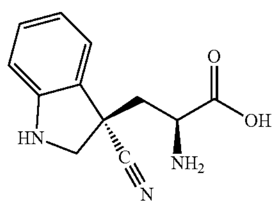 [SMILES: N#C[C@]1(C[C@H](N)C(=O)O)CNc2ccccc21] | (S)-2-amino-3-((S)-3-cyanoindolin-3-yl)propanoic acid |
| 01270 | 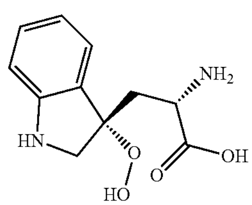 [SMILES: N[C@@H](C[C@@]1(OO)CNc2ccccc21)C(=O)O] | (S)-2-amino-3-((S)-3-hydroperoxyindolin-3-yl)propanoic acid |
| 01271 | 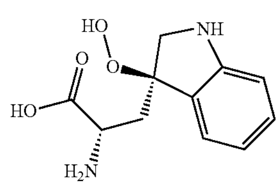 [SMILES: N[C@@H](C[C@]1(OO)CNc2ccccc21)C(=O)O] | (S)-2-amino-3-((R)-3-hydroperoxyindolin-3-yl)propanoic acid |
| 01274 | 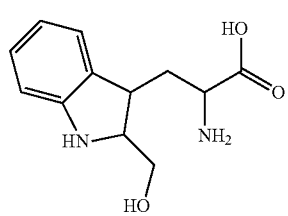 [SMILES: NC(CC1c2ccccc2NC1CO)C(=O)O] | 2-amino-3-(2-(hydroxymethyl)indolin-3-yl)propanoic acid |

TABLE 1-continued

| Cmpd # | Structure | Name |
|---|---|---|
| 01275 | 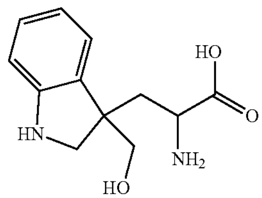 [SMILES: NC(CC1(CO)CNc2ccccc21)C(=O)O] | 2-amino-3-(3-(hydroxymethyl)indolin-3-yl)propanoic acid |
| 01277 | 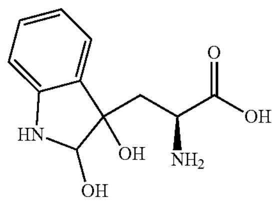 [SMILES: N[C@@H](CC1(O)c2ccccc2NC1O)C(=O)O] | (2S)-2-amino-3-(2,3-dihydroxyindolin-3-yl)propanoic acid |
| 01278 | 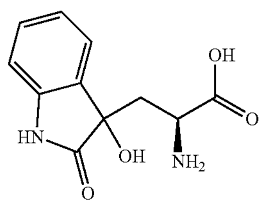 [SMILES: N[C@@H](CC1(O)C(=O)Nc2ccccc21)C(=O)O] | (2S)-2-amino-3-(3-hydroxy-2-oxoindolin-3-yl)propanoic acid |
| 01279 | 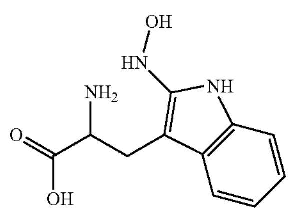 [SMILES: NC(Cc1c(NO)[nH]c2ccccc12)C(=O)O] | 2-amino-3-(2-(hydroxyamino)-1H-indol-3-yl)propanoic acid |
| 01280 | 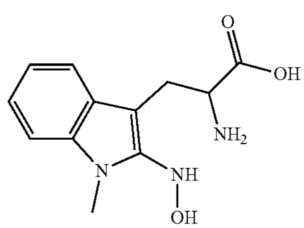 [SMILES: Cn1c(NO)c(CC(N)C(=O)O)c2ccccc21] | 2-amino-3-(2-(hydroxyamino)-1-methyl-1H-indol-3-yl)propanoic acid |
| 01281 | 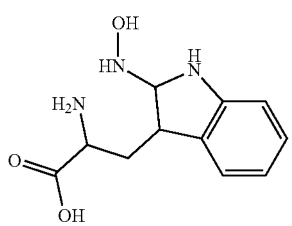 [SMILES: NC(CC1c2ccccc2NC1NO)C(=O)O] | 2-amino-3-(2-(hydroxyamino)indolin-3-yl)propanoic acid |
| 01282 | 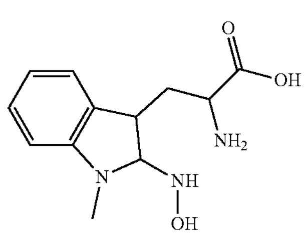 [SMILES: CN1c2ccccc2C(CC(N)C(=O)O)C1NO] | 2-amino-3-(2-(hydroxyamino)-1-methylindolin-3-yl)propanoic acid |

TABLE 1-continued

| Cmpd # | Structure | Name |
|---|---|---|
| 01283 | 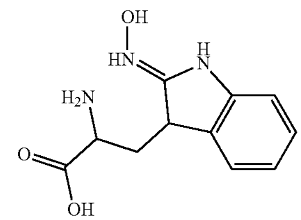 [SMILES: NC(CC1/C(=N/O)Nc2ccccc21)C(=O)O] | (Z)-2-amino-3-(2-(hydroxyimino)indolin-3-yl)propanoic acid |
| 01284 | 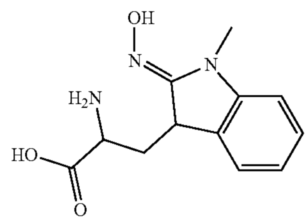 [SMILES: CN1/C(=N\O)C(CC(N)C(=O)O)c2ccccc21] | (Z)-2-amino-3-(2-(hydroxyimino)-1-methylindolin-3-yl)propanoic acid |
| 01285 | 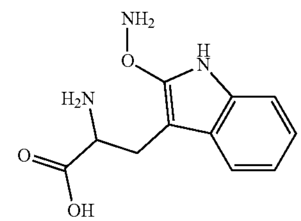 [SMILES: NOc1[nH]c2ccccc2c1CC(N)C(=O)O] | 2-amino-3-(2-(aminooxy)-1H-indol-3-yl(propanoic acid |
| 01286 | 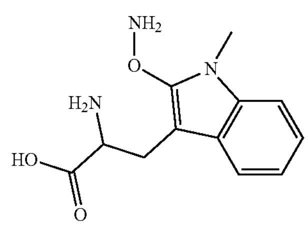 [SMILES: Cn1c(ON)c(CC(N)C(=O)O)c2ccccc21] | 2-amino-3-(2-(aminooxy)-1-methyl-1H-indol-3-yl)propanoic acid |
| 01287 | 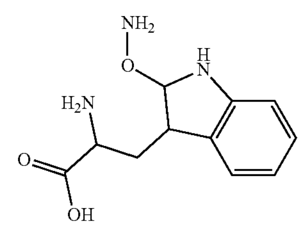 [SMILES: NOC1Nc2ccccc2C1CC(N)C(=O)O] | 2-amino-3-(2-(aminooxy)indolin-3-yl)-propanoic acid |
| 01288 | 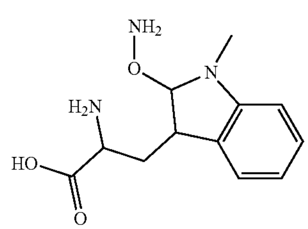 [SMILES: CN1c2ccccc2C(CC(N)C(=O)O)C1ON] | 2-amino-3-(2-(aminooxy)-1-methylindolin-3-yl)propanoic acid |
| 01291 | 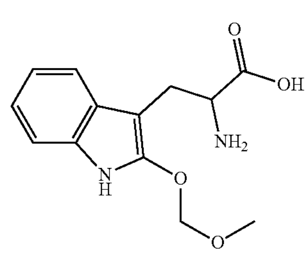 [SMILES: COCOc1[nH]c2ccccc2c1CC(N)C(=O)O] | 2-amino-3-(2-(methoxymethoxy)-1H-indol-3-yl)propanoic acid |

TABLE 1-continued

| Cmpd # | Structure | Name |
|---|---|---|
| 01292 | 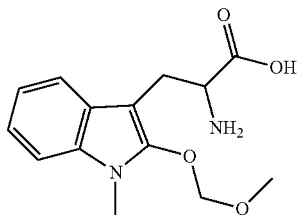 [SMILES: COCOc1c(CC(N)C(=O)O)c2ccccc2n1C] | 2-amino-3-(2-(methoxymethoxy)-1-methyl-1H-indol-3-yl)propanoic acid |
| 01293 | 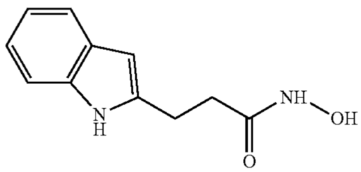 [SMILES: O=C(CCc1cc2ccccc2[nH]1)NO] | N-hydroxy-3-(1H-indol-2-yl)propanamide |
| 01294 | 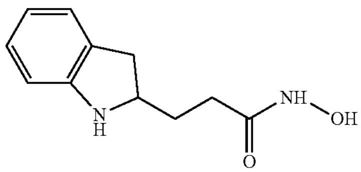 [SMILES: O=C(CCC1Cc2ccccc2N1)NO] | N-hydroxy-3-(indolin-2-yl)propanamide |
| 01295 | 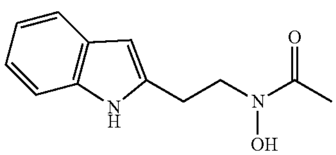 [SMILES: CC(=O)N(O)CCc1cc2ccccc2[nH]1] | N-(2-(1H-indol-2-yl)ethyl)-N-hydroxyacetamide |
| 01296 | 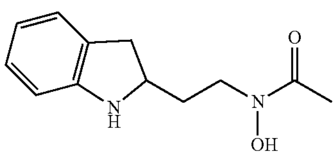 [SMILES: CC(=O)N(O)CCC1Cc2ccccc2N1] | N-hydroxy-N-(2-(indolin-2-yl)ethyl)acetamide |
| 01298 | 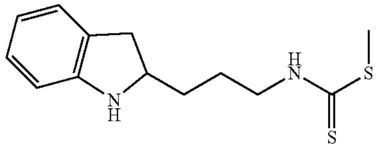 [SMILES: CSC(=S)NCCCC1Cc2ccccc2N1] | methyl 3-(indolin-2-yl)propyl-carbamodithioate |
| 01299 | 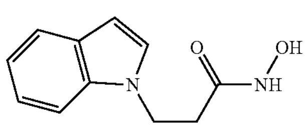 [SMILES: O=C(CCn1ccc2ccccc21)NO] | N-hydroxy-3-(1H-indol-1-yl)propanamide |
| 01300 | 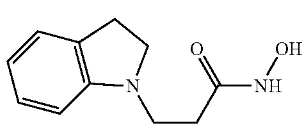 [SMILES: O=C(CCN1CCc2ccccc21)NO] | N-hydroxy-3-(indolin-1-yl)propanamide |
| 01301 | 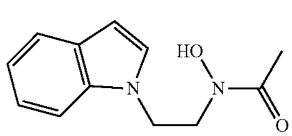 [SMILES: CC(=O)N(O)CCn1ccc2ccccc21] | N-(2-(1H-indol-1-yl)ethyl)-N-hydroxyacetamide |
| 01302 | 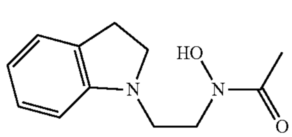 [SMILES: CC(=O)N(O)CCN1CCc2ccccc21] | N-hydroxy-N-(2-(indolin-1-yl)ethyl)acetamide |

TABLE 1-continued

| Cmpd # | Structure | Name |
|---|---|---|
| 01305 | 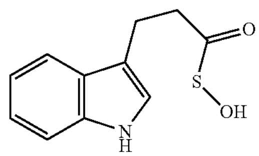 [SMILES: O=C(CCc1c[nH]c2ccccc12)SO] | 3-(1H-indol-3-yl)propane(thioperoxoic)O-acid |
| 01306 | 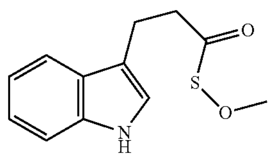 [SMILES: COSC(=O)CCc1c[nH]c2ccccc12] | SO-methyl 3-(1H-indol-3-yl)propane(thioperoxoate) |
| 01307 | 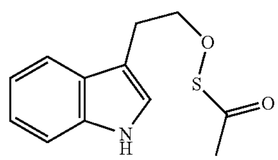 [SMILES: CC(=O)SOCCc1c[nH]c2ccccc12] | SO-2-(1H-indol-3-yl)ethyl ethane(thioperoxoate) |
| 01308 | 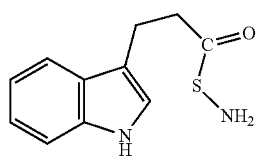 [SMILES: NSC(=O)CCc1c[nH]c2ccccc12] | S-(3-(1H-indol-3-yl)propanoyl)-thiohydroxylamine |
| 01309 | 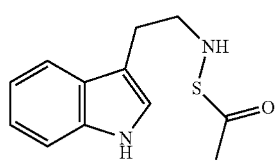 [SMILES: CC(=O)SNCCc1c[nH]c2ccccc12] | N-(2-(1H-indol-3-yl)ethyl)-S-acetylthiohydroxylamine |
| 01310 | 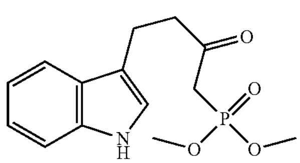 [SMILES: COP(=O)(CC(=O)CCc1c[nH]c2ccccc12)OC] | dimethyl 4-(1H-indol-3-yl)-2-oxobutylphosphonate |
| 01361 | 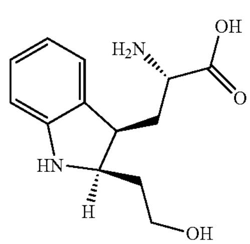 [SMILES: N[C@@H](C[C@@H]1c2ccccc2N[C@@H]1CCO)C(=O)O] | (S)-2-amino-3-((2R,3R)-2-(2-hydroxyethyl)indolin-3-yl)propanoic acid |
| 01362 | 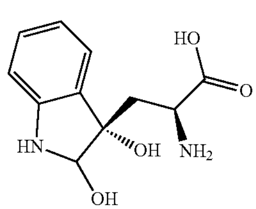 [SMILES: N[C@@H](C[C@]1(O)c2ccccc2NC1O)C(=O)O] | (2S)-2-amino-3-((3S)-2,3-dihydroxyindolin-3-yl)propanoic acid |

TABLE 1-continued

| Cmpd # | Structure | Name |
|---|---|---|
| 01364 | 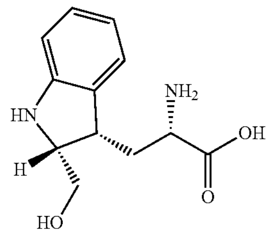 [SMILES: N[C@@H](C[C@H]1c2ccccc2N[C@H]1CO)C(=O)O] | (S)-2-amino-3-((2R,3S)-2-(hydroxylmethyl)indolin-3-yl)propanoic acid |
| 01367 | 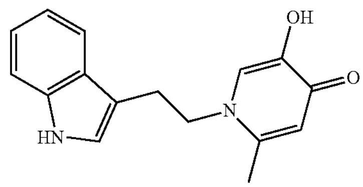 [SMILES: Cc1cc(=O)c(O)cn1CCc1c[nH]c2ccccc12] | 1-(2-(1H-indol-3-yl)ethyl)-5-hydroxy-2-methylpyridin-4(1H)-one |
| 01370 | 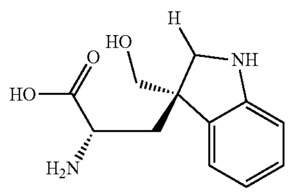 [SMILES: N[C@@H](C[C@@]1(CO)CNc2ccccc21)C(=O)O] | (S)-2-amino-3-((S)-3-(hydroxylmethyl)indolin-3-yl)propanoic acid |
| 01371 | 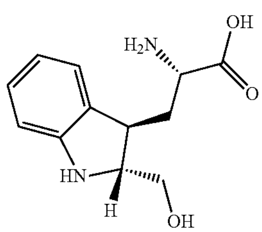 [SMILES: N[C@@H](C[C@@H]1c2ccccc2N[C@H]1CO)C(=O)O] | (S)-2-amino-3-((2R,3R)-2-(hydroxylmethyl)indolin-3-yl)propanoic acid |
| 01372 | 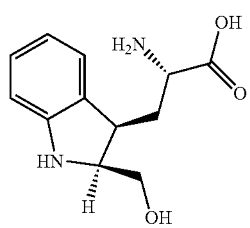 [SMILES: N[C@@H](C[C@@H]1c2ccccc2N[C@@H]1CO)C(=O)O] | (S)-2-amino-3-((2S,3R)-2-(hydroxylmethyl)indolin-3-yl)propanoic acid |
| 01373 | 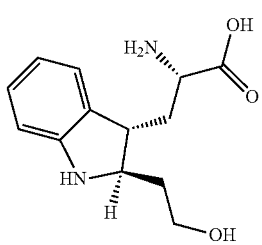 [SMILES: N[C@@H](C[C@H]1c2ccccc2N[C@@H]1CCO)C(=O)O] | (S)-2-amino-3-((2R,3S)-2-(2-hydroxyethyl)indolin-3-yl)propanoic acid |
| 01374 | 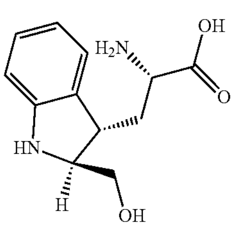 [SMILES: N[C@@H](C[C@H]1c2ccccc2N[C@@H]1CO)C(=O)O] | (S)-2-amino-3-((2S,3S)-2-(hydroxylmethyl)indolin-3-yl)propanoic acid |

TABLE 1-continued

| Cmpd # | Structure | Name |
|---|---|---|
| 01375 | 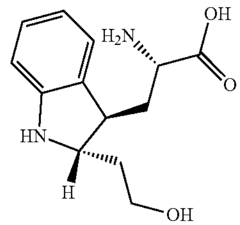 [SMILES: N[C@@H](C[C@@H]1c2ccccc2N[C@H]1CCO)C(=O)O] | (S)-2-amino-3-((2S,3R)-2-(2-hydroxyethyl)indolin-3-yl)propanoic acid |
| 01376 | 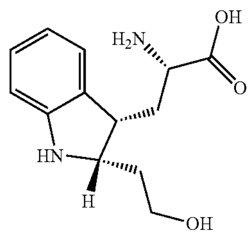 [SMILES: N[C@@H](C[C@H]1c2ccccc2N[C@H]1CCO)C(=O)O] | (S)-2-amino-3-((2S,3S)-2-(2-hydroxyethyl)indolin-3-yl)propanoic acid |
| 01378 | 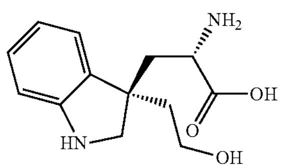 [SMILES: N[C@@H](C[C@@]1(CCO)CNc2ccccc21)C(=O)O] | (S)-2-amino-3-((S)-3-(2-hydroxyethyl)indolin-3-yl)propanoic acid |
| 01379 | 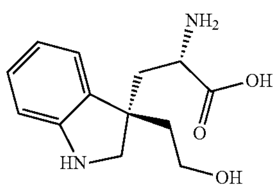 [SMILES: N[C@@H](C[C@]1(CCO)CNc2ccccc21)C(=O)O] | (S)-2-amino-3-((R)3-(2-hydroxyethyl)indolin-3-yl)propanoic acid |
| 01382 | 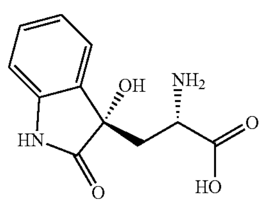 [SMILES: N[C@@H](C[C@@]1(O)C(=O)Nc2ccccc21)C(=O)O] | (S)-2-amino-3-((S)-3-hydroxy-2-oxoindolin-3-yl)propanoic acid |
| 01383 | 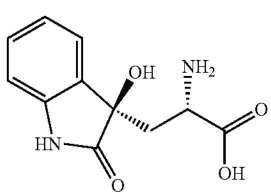 [SMILES: N[C@@H](C[C@]1(O)C(=O)Nc2ccccc21)C(=O)O] | (S)-2-amino-3-((R)3-hydroxy-2-oxoindolin-3-yl)propanoic acid |
| 01387 | 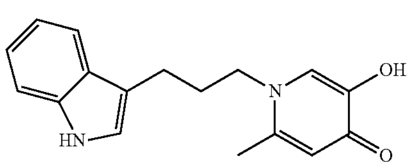 [SMILES: Cc1cc(=O)c(O)cn1CCCc1c[nH]c2ccccc12] | 1-(3-(1H-indol-3-yl)propyl)-5-hydroxy-2-methylpyridin-4(1H)-one |
| 01391 | 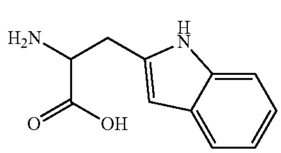 [SMILES: NC(Cc1cc2ccccc2[nH]1)C(=O)O] | 2-amino-3-(1H-indol-2-yl)propanoic acid |

TABLE 1-continued

| Cmpd # | Structure | Name |
|---|---|---|
| 01392 | 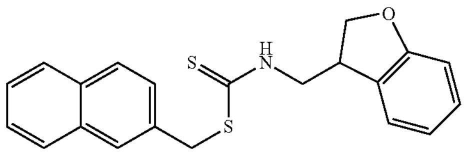 [SMILES: S=C(NCC1COc2ccccc21)SCc1ccc2ccccc2c1] | naphthalen-2-ylmethyl (2,3-dihydrobenzofuran-3-yl)methylcarbamodithioate |
| 01403 | 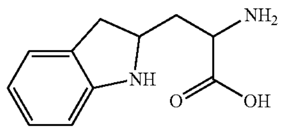 [SMILES: NC(CC1Cc2ccccc2N1)C(=O)O] | 2-amino-3-(indolin-2-yl)propanoic acid |
| 01418 | 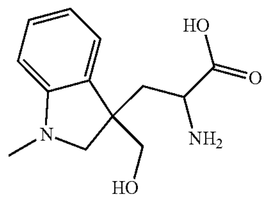 [SMILES: CN1CC(CO)(CC(N)C(=O)O)c2ccccc21] | 2-amino-3-(3-(hydroxymethyl)-1-methylindolin-3-yl)propanoic acid |
| 01419 | 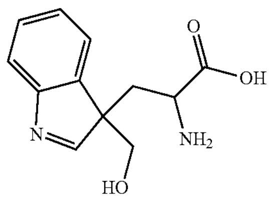 [SMILES: NC(CC1(CO)C=Nc2ccccc21)C(=O)O] | 2-amino-3-(3-(hydroxymethyl)-3H-indol-3-yl)propanoic acid |
| 01424 | 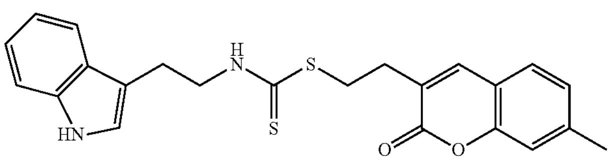 [SMILES: Cc1ccc2cc(CCSC(=S)NCCc3c[nH]c4ccccc34)c(=O)oc2c1] | 2-(7-methyl-2-oxo-2H-chromen-3-yl)ethyl 2-(1H-indol-3-yl)ethylcarbamodithioate |
| 01438 | 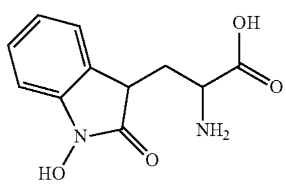 [SMILES: NC(CC1C(=O)N(O)c2ccccc21)C(=O)O] | 2-amino-3-(1-hydroxy-2-oxoindolin-3-yl)propanoic acid |
| 01443 | 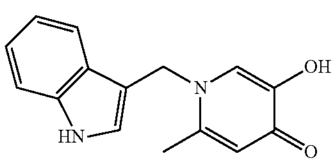 [SMILES: Cc1cc(=O)c(O)cn1Cc1c[nH]c2ccccc12] | 1-((1H-indol-3-yl)methyl)-5-hydroxy-2-methylpyridin-4(1H)-one |
| 01444 | 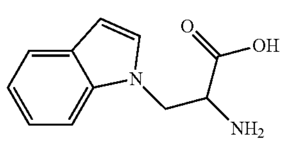 [SMILES: NC(Cn1ccc2ccccc21)C(=O)O] | 2-amino-3-(1H-indol-1-yl)propanoic acid |
| 01445 | 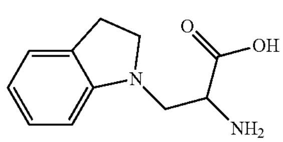 [SMILES: NC(CN1CCc2ccccc21)C(=O)O] | 2-amino-3-(indolin-1-yl)propanoic acid |

TABLE 1-continued

| Cmpd # | Structure | Name |
|---|---|---|
| 01446 | 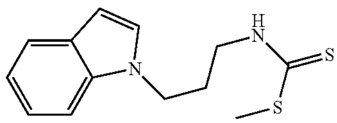 [SMILES: CSC(=S)NCCCn1ccc2ccccc21] | methyl 3-(1H-indol-1-yl)propylcarbamodithioate |
| 01447 | 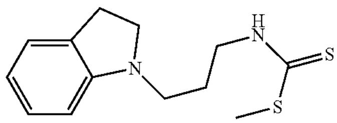 [SMILES: CSC(=S)NCCCN1CCc2ccccc21] | methyl 3-(indolin-1-yl)propyl-carbamodithioate |

TABLE 2

| Cmpd # | Structure | Name |
|---|---|---|
| 00523 | 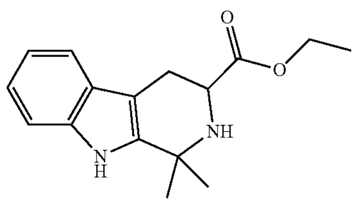 [SMILES: CCOC(=O)C1Cc2c([nH]c3ccccc23)C(C)(C)N1] | ethyl 1,1-dimethyl-2,3,4,9-tetrahydro-1H-pyrido[3,4-b]indole-3-carboxylate |
| 00525 | 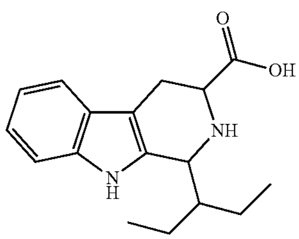 [SMILES: CCC(CC)C1NC(C(=O)O)Cc2c1[nH]c1ccccc21] | 1-(pentan-3-yl)-2,3,4,9-tetrahydro-1H-pyrido[3,4-b]indole-3-carboxylic acid |
| 00526 | 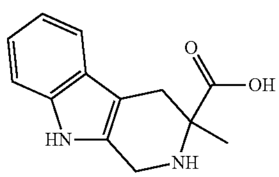 [SMILES: CC1(C(=O)O)Cc2c([nH]c3ccccc23)CN1] | 3-methyl-2,3,4,9-tetrahydro-1H-pyrido[3,4-b]indole-3-carboxylic acid |
| 00527 | 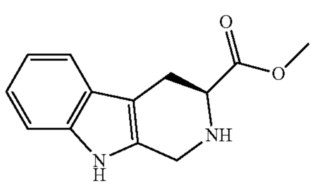 [SMILES: COC(=O)[C@@H]1Cc2c([nH]c3ccccc23)CN1] | (S)-methyl 2,3,4,9-tetrahydro-1H-pyrido[3,4-b]indole-3-carboxylate |
| 00528 | 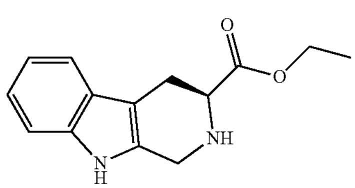 [SMILES: CCOC(=O)[C@@H]1Cc2c([nH]c3ccccc23)CN1] | (S)-ethyl 2,3,4,9-tetrahydro-1H-pyrido[3,4-b]indole-3-carboxylate |
| 00530 | 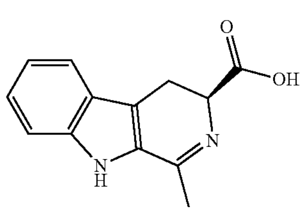 [SMILES: CC1=N[C@H](C(=O)O)Cc2c1[nH]c1ccccc21] | (S)-1-methyl-4,9-dihydro-3H-pyrido[3,4-b]indole-3-carboxylic acid |

TABLE 2-continued

| Cmpd # | Structure | Name |
|---|---|---|
| 00531 | 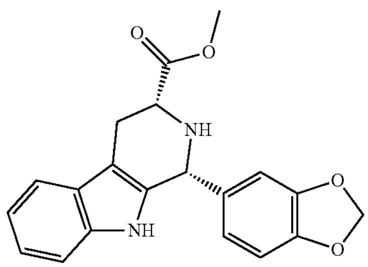 [SMILES: COC(=O)[C@H]1Cc2c([nH]c3ccccc23)[C@@H](c2ccc3c(c2)OCO3)N1] | (1R,3R)-methyl 1-(benzo[d][1,3]dioxol-5-yl)-2,3,4,9-tetrahydro-1H-pyrido[3,4-b]indole-3-carboxylate |
| 00532 | 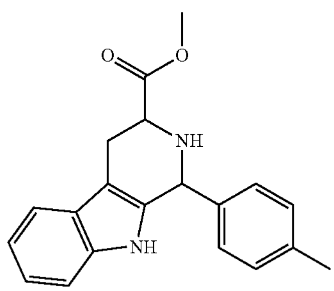 [SMILES: COC(=O)C1Cc2c([nH]c3ccccc23)C(c2ccc(C)cc2)N1] | methyl 1-p-tolyl-2,3,4,9-tetrahydro-1H-pyrido[3,4-b]indole-3-carboxylate |
| 00533 | 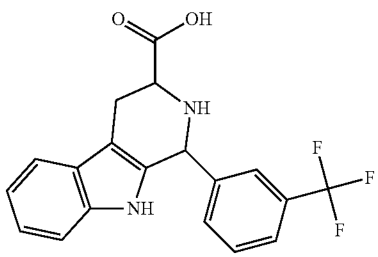 [SMILES: O=C(O)C1Cc2c([nH]c3ccccc23)C(c2cccc(C(F)(F)F)c2)N1] | 1-(3-(trifluoromethyl)phenyl)-2,3,4,9-tetrahydro-1H-pyrido[3,4-b]indole-3-carboxylic acid |
| 00535 | 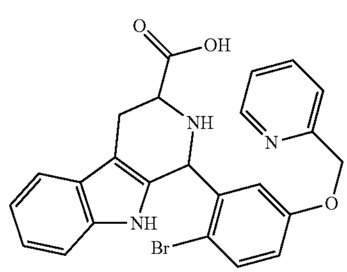 [SMILES: O=C(O)C1Cc2c([nH]c3ccccc23)C(c2cc(OCc3ccccn3)ccc2Br)N1] | 1-(2-bromo-5-(pyridin-2-ylmethoxy)phenyl)-2,3,4,9-tetrahydro-1H-pyrido[3,4-b]indole-3-carboxylic acid |
| 00539 | 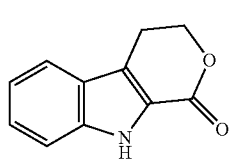 [SMILES: O=C1OCCc2c1[nH]c1ccccc21] | 3,4-dihydropyrano[3,4-b]indol-1(9H)-one |
| 00541 | 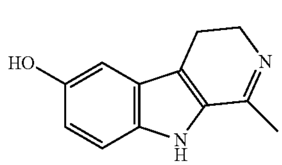 | 1-methyl-4,9-dihydro-3H-pyrido[3,4-b]indol-6-ol |

TABLE 2-continued

| Cmpd # | Structure | Name |
|---|---|---|
| 00545 | 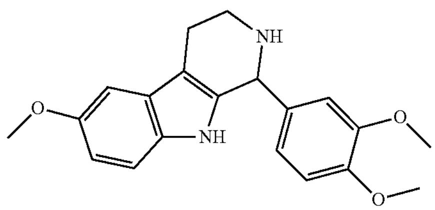 | 1-(3,4-dimethoxyphenyl)-6-methoxy-2,3,4,9-tetrahydro-1H-pyrido[3,4-b]indole |
| 00546 | 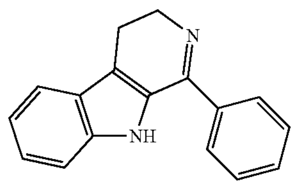 [SMILES: c1ccc(C2=NCCc3c2[nH]c2ccccc32)cc1] | 1-phenyl-4,9-dihydro-3H-pyrido[3,4-b]indole |
| 00549 | 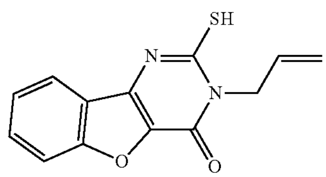 [SMILES: C=CCn1c(S)nc2c(oc3ccccc32)c1=O] | 3-allyl-2-mercaptobenzofuro[3,2-d]pyrimidin-4(3H)-one |
| 00550 | 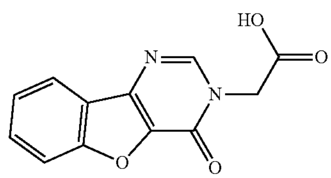 [SMILES: O=C(O)Cn1cnc2c(oc3ccccc32)c1=O] | 2-(4-oxobenzofuro[3,2-d]pyrimidin-3(4H)-yl)acetic acid |
| 01272 | 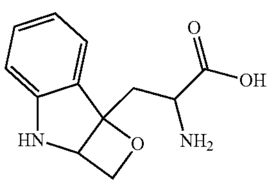 [SMILES: NC(CC12OCC1Nc1ccccc12)C(=O)O] | 2-amino-3-(2,2a,3,7b-tetrahydrooxeto[3,2-b]indol-7b-yl)propanoic acid |
| 01273 | 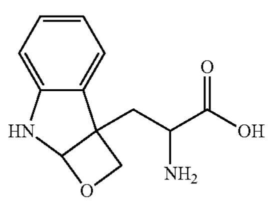 [SMILES: NC(CC12COC1Nc1ccccc12)C(=O)O] | 2-amino-3-(2,2a,7,7a-tetrahydrooxeto[2,3-b]indol-2a-yl)propanoic acid |
| 01276 | 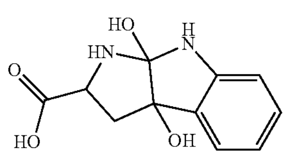 [SMILES: O=C(O)C1CC2(O)c3ccccc3NC2(O)N1] | 3a,8a-dihydroxy-1,2,3,3a,8,8a-hexahydropyrrolo[2,3-b]indole-2-carboxylic acid |
| 01289 | 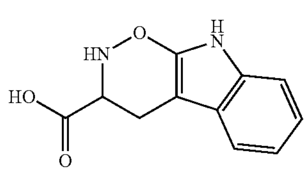 [SMILES: O=C(O)C1Cc2c([nH]c3ccccc23)ON1] | 2,3,4,9-tetrahydro-[1,2]oxazino[6,5-b]indole-3-carboxylic acid |

TABLE 2-continued

| Cmpd # | Structure | Name |
|---|---|---|
| 01290 | 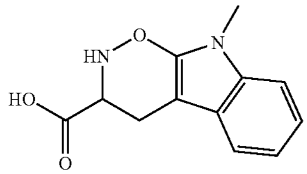 [SMILES: Cn1c2c(c3ccccc31)CC(C(=O)O)NO2] | 9-methyl-2,3,4,9-tetrahydro-[1,2]oxazino[6,5-b]indole-3-carboxylic acid |
| 01311 | 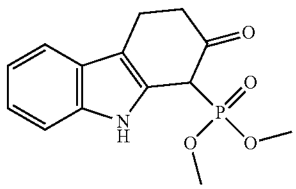 [SMILES: COP(=O)(OC)C1C(=O)CCc2c1[nH]c1ccccc21] | dimethyl 2-oxo-2,3,4,9-tetrahydro-1H-carbazol-1-ylphosphonate |
| 01365 | 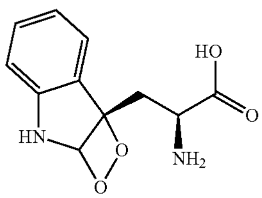 [SMILES: N[C@@H](C[C@@]12OOC1Nc1ccccc12)C(=O)O] | (2S)-2-amino-3-((7bS)-3,7b-dihydro-2aH-[1,2]dioxeto[3,4-b]indol-7b-yl)propanoic acid |
| 01366 | 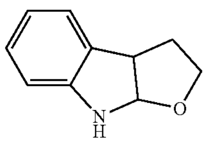 [SMILES: c1ccc2c(c1)NC1OCCC21] | 3,3a,8,8a-tetrahydro-2H-furo[2,3-b]indole |
| 01368 | 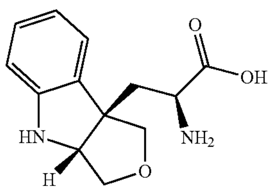 [SMILES: N[C@@H](C[C@@]12COC[C@@H]1Nc1ccccc12)C(=O)O] | (S)-2-amino-3-((3aR,8bS)-3a,4,8b-tetrahydro-1H-furo[3,4-b]indol-8b-yl)propanoic acid |
| 01369 | 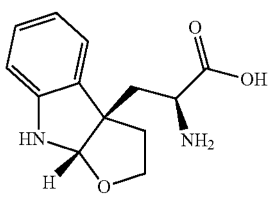 [SMILES: N[C@@H](C[C@@]12CCO[C@@H]1Nc1ccccc12)C(=O)O] | (S)-2-amino-3-((3aS,8aS)-3,3a,8,8a-tetrahydro-2H-furo[2,3-b]indol-3a-yl)propanoic acid |
| 01380 | 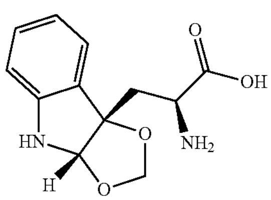 [SMILES: N[C@@H](C[C@@]12OCO[C@@H]1Nc1ccccc12)C(=O)O] | (S)-2-amino-3-((3aS,8bS)-4,8b-dihydro-3aH-[1,3]dioxolo[4,5-b]indol-8b-yl)propanoic acid |
| 01381 | 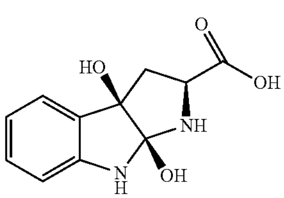 [SMILES: O=C(O)[C@@H]1C[C@@]2(O)c3ccccc3N[C@@]2(O)N1] | (2S,3aR,8aS)-3a,8a-dihydroxy-1,2,3,3a,8,8a-hexahydropyrrolo[2,3-b]indole-2-carboxylic acid |

TABLE 2-continued

| Cmpd # | Structure | Name |
|---|---|---|
| 01385 | 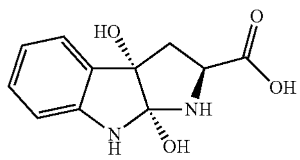 [SMILES: O=C(O)[C@@H]1C[C@]2(O)c3ccccc3N[C@]2(O)N1] | (2S,3aS,8aR)-3a,8a-dihydroxy-1,2,3,3a,8,8a-hexahydropyrrolo[2,3-b]indole-2-carboxylic acid |
| 01388 | 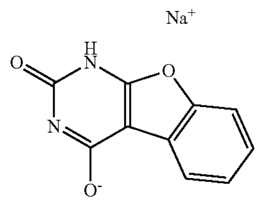 [SMILES: [Na+] ; O=c1nc([O-])c2c([nH]1)oc1ccccc12] | sodium 2-oxo-1,2-dihydrobenzofuro[2,3-d]-pyrimidin-4-olate |
| 01390 | 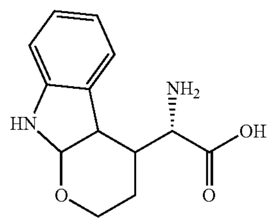 [SMILES: N[C@H](C(=O)O)C1CCOC2Nc3ccccc3C21] | (2S)-2-amino-2-(2,3,4,4a,9,9a-hexahydropyrano[2,3-b]indol-4-yl)acetic acid |
| 01410 | 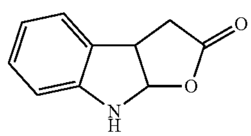 [SMILES: O=C1CC2c3ccccc3NC2O1] | 3,3a,8,8a-tetrahydro-2H-furo[2,3-b]indol-2-one |
| 01413 | 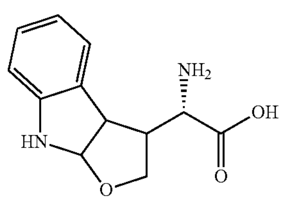 [SMILES: N[C@H](C(=O)O)C1COC2Nc3ccccc3C21] | (2S)-2-amino-2-(3,3a,8,8a-tetrahydro-2H-furo[2,3-b]indol-3-yl)acetic acid |
| 01425 | 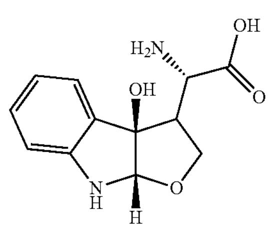 [SMILES: N[C@H](C(=O)O)C1CO[C@@H]2Nc3ccccc3[C@]12O] | (2S)-2-amino-2-((3aR,8aS)-3a-hydroxy-3,3a,8,8a-tetrahydro-2H-furo[2,3-b]indol-3-yl)acetic acid |
| 01427 | 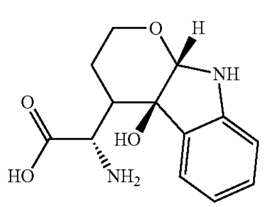 [SMILES: N[C@H](C(=O)O)C1CCO[C@@H]2Nc3ccccc3[C@]12O] | (2S)-2-amino-2-((4aR,9aS)-4a-hydroxy-2,3,3,4a,9,9a-hexahydropyrano[2,3-b]indol-4-yl)acetic acid |
| 01429 | 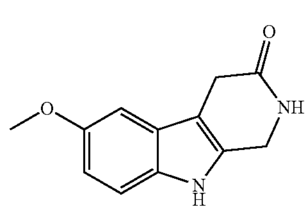 [SMILES: COc1ccc2[nH]c3c(c2c1)CC(=O)NC3] | 6-methoxy-4,9-dihydro-1H-pyrido[3,4-b]indol-3(2H)-one |

TABLE 2-continued

| Cmpd # | Structure | Name |
|---|---|---|
| 01430 | 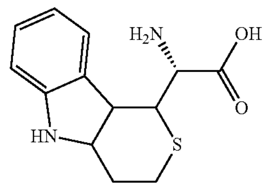 [SMILES: N[C@H](C(=O)O)C1SCCC2Nc3ccccc3C21] | (2R)-2-amino-2-(1,3,4,4a,5,9b-hexahydrothiopyrano[4,3-b]indol-1-yl)acetic acid |
| 01431 | 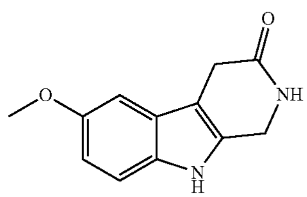 [SMILES: COc1ccc2[nH]c3c(c2c1)CC(=O)NC3] | 6-methoxy-4,9-dihydro-1H-pyrido[3,4-b]indol-3(2H)-one |
| 01432 | 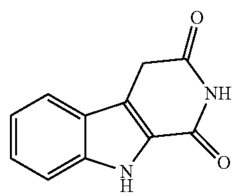 [SMILES: O=C1Cc2c([nH]c3ccccc23)C(=O)N1] | 4,9-dihydro-1H-pyrido[3,4-b]indole-1,3(2H)-dione |
| 01433 | 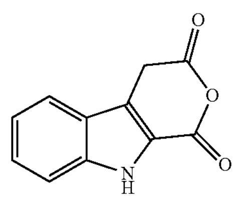 [SMILES: O=C1Cc2c([nH]c3ccccc23)C(=O)O1] | pyrano[3,4-b]indole-1,3(4H,9H)-dione |
| 01434 | 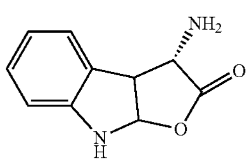 [SMILES: N[C@@H]1C(=O)OC2Nc3ccccc3C21] | (3S)-3-amino-3,3a,8,8a-tetrahydro-2H-furo[2,3-b]indol-2-one |
| 01448 | 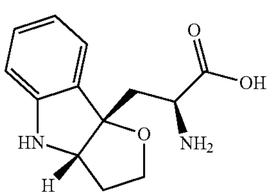 [SMILES: N[C@@H](C[C@@]12OCC[C@@H]1Nc1ccccc12)C(=O)O] | (S)-2-amino-3-((3aS,8bS)-3,3a,4,8b-tetrahydro-2H-furo[3,2-b]indol-8b-yl)propanoic acid |
| 01449 | 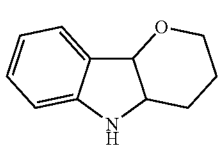 [SMILES: c1ccc2c(c1)NC1CCCOC21] | 2,3,4,4a,5,9b-hexahydropyrano[3,2-b]indole |
| 01458 | 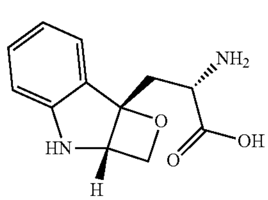 [SMILES: N[C@@H](C[C@@]12OC[C@@H]1Nc1ccccc12)C(=O)O] | (S)-2-amino-3-((2aS,7bS)-2,2a,3,7b-tetrahydrooxeto[3,2-b]indol-7b-yl)propanoic acid |

TABLE 2-continued

| Cmpd # | Structure | Name |
|---|---|---|
| 01459 | 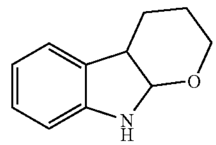 [SMILES: c1ccc2c(c1)NC1OCCCC21] | 2,3,4,4a,9,9a-hexahydropyrano[2,3-b]indole |
| 01460 | 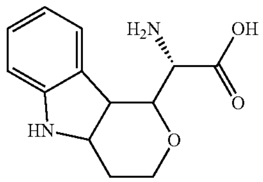 [SMILES: N[C@H](C(=O)O)C1OCCC2Nc3ccccc3C21] | (2S)-2-amino-2-(1,3,4,4a,5,9b-hexahydropyrano[4,3-b]indol-1-yl)acetic acid |
| 01461 | 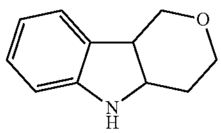 [SMILES: c1ccc2c(c1)NC1CCOCC21] | 1,3,4,4a,5,9b-hexahydropyrano[4,3-b]indole |
| 01470 | 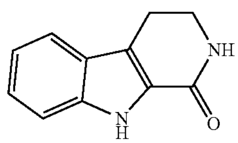 [SMILES: O=C1NCCc2c1[nH]c1ccccc21] | 2,3,4,9-tetrahydro-1H-pyrido[3,4-b]indol-1-one |
| 01479 | 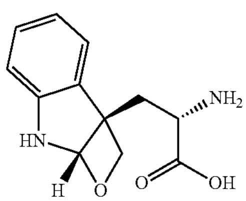 [SMILES: N[C@@H](C[C@@]12CO[C@@H]1Nc1ccccc12)C(=O)O] | (S)-2-amino-3-((2aR,7aS)-2,2a,7,7a-tetrahydrooxeto[2,3-b]indol-2a-yl)propanoic acid |
| 01490 | 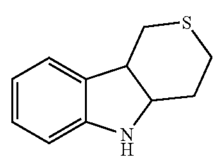 [SMILES: c1ccc2c(c1)NC1CCSCC21] | 1,3,4,4a,5,9b-hexahydrothiopyrano[4,3-b]indole |

TABLE 3

| Cmpd # | Structure | Name |
|---|---|---|
| 01363 | 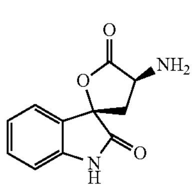 [SMILES: N[C@H]1C[C@@]2(OC1=O)C(=O)Nc1ccccc12] | (2S,4S)-4-amino-3H-spiro[furan-2,3'-indoline]-2',5(4H)-dione |
| 01377 | 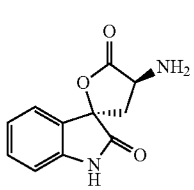 [SMILES: N[C@H]1C[C@]2(OC1=O)C(=O)Nc1ccccc12] | (2R,4S)-4-amino-3H-spiro[furan-2,3'-indoline]-2',5(4H)-dione |

TABLE 3-continued

| Cmpd # | Structure | Name |
|---|---|---|
| 01402 | 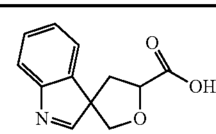 | 4,5-dihydro-2H-spiro[furan-3,3'-indole]-5-carboxylic acid |
| 01414 | 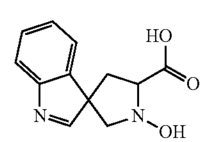 [SMILES: O=C(O)C1CC2(C=Nc3ccccc32)CN1O] | 1'-hydroxyspiro[indole-3,3'-pyrrolidine]-5'-carboxylic acid |
| 01417 | 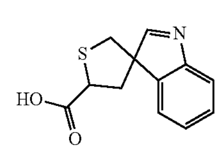 [SMILES: O=C(O)C1CC2(C=Nc3ccccc32)CS1] | 4',5'-dihydro-2'H-spiro[indole-3,3'-thiophene]-5'-carboxylic acid |

TABLE 3-continued

| Cmpd # | Name |
|---|---|
| 01439 | (S)-2'-thioxospiro[indoline-3,5'-oxazolidin]-2-one |
| 01451 | (S)-2'-thioxospiro[indoline-3,5'-thiazolidin]-2-one |
| 01452 | 1'-hydroxyspiro[indoline-3,3'-pyrrolidine]-5'-carboxylic acid |
| 01455 | spiro[indoline-3,3'-pyrrolidin]-2-one |
| 01456 | 4,5-dihydro-2H-spiro[furan-3,3'-indolin]-2'-one |
| 01457 | spiro[indoline-3,2'-oxiran]-2-one |
| 01462 | 3H-spiro[furan-2,3'-indoline] |
| 01463 | 1",2"-dihydrodispiro[cyclopentane-1,2'-oxirane-3',3"-indole] |
| 01464 | (S)-spiro[indoline-3,5'-oxazolidine]-2,2'-dione |
| 01471 | 1-methyl-4',5'-dihydro-2'H-spiro[indoline-3,3'-thiophene]-5'-carboxylic acid |
| 01472 | 1'-methyl-4,5-dihydro-2H-spiro[furan-3,3'-indoline]-5-carboxylic acid |
| 01473 | 1,1'-dimethylspiro[indoline-3,3'-pyrrolidine]-5'-carboxylic acid |
| 01474 | 1'-hydroxy-1-methylspiro[indoline-3,3'-pyrrolidine]-5'-carboxylic acid |
| 01475 | 4',5'-dihydro-2'H-spiro[indoline-3,3'-thiophene]-5'-carboxylic acid |
| 01476 | 4,5-dihydro-2H-spiro[furan-3,3'-indoline]-5-carboxylic acid |
| 01489 | 1'-methylspiro[indole-3,3'-pyrrolidine]-5'-carboxylic acid |
| 01491 | 1'-methylspiro[indoline-3,3'-pyrrolidine]-5'-carboxylic acid |

TABLE 4

| Cmpd # | Name |
|---|---|
| 00218 | 4,5-bis(2-hydroxyethylthio)-1,3-dithiol-2-one |
| 00738 | 3-(3-methyl-2-oxo-2,3-dihydro-1H-benzo[d]imidazol-1-yl)propanoic acid |
| 01069 | 4,5-dihydroxy-1,3-bis(hydroxylmethyl)-imidazolidin-2-one |

TABLE 4-continued

| Cmpd # | Structure | Name |
|---|---|---|
| 01110 | | 4,5-dihydroxy-1,3-bis(methoxymethyl)-imidazolidin-2-one |
| 01129 | | 4,5-bis(2-aminoethylthio)-1,3-dithiole-2-thione |
| 01160 | | 4-hydroxy-1,3-bis(hydroxymethyl)-5-methoxyimidazolidin-2-one |
| 01181 | | 1-ethyl-3-propyl-1H-benzo[d]imidazol-2(3H)-imine |
| 01192 | | 3,3'-(2-oxo-1,3-dithiole-4,5-diyl)bis-(sulfanediyl)dipropanenitrile |
| 01202 | | 1-tert-butyl-4,5-dihydroxy-3-methylimidazolidin-2-one |
| 01222 | | 4,5-dihydroxy-1-(hydroxymethyl)-3-(methoxymethyl)imidazolidin-2-one |
| 01237 | 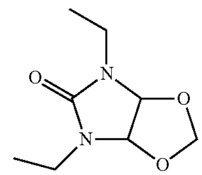 | 4,6-diethyldihydro-3aH-[1,3]dioxolo[4,5-d]imidazol-5(4H)-one |
| 01242 | 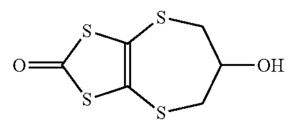 [SMILES: O=c1sc2c(s1)SCC(O)CS2] | 6-hydroxy-6,7-dihydro-5H-[1,3]dithiolo[4,5-b][1,4]dithiepin-2-one |
| 01245 | 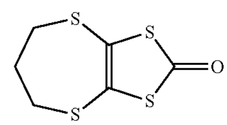 [SMILES: O=c1sc2c(s1)SCCCS2] | 6,7-dihydro-5H-[1,3]dithiolo[4,5-b][1,4]dithiepin-2-one |
| 01251 | 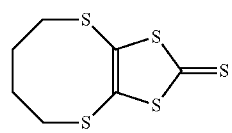 [SMILES: S=c1sc2c(s1)SCCCCS2] | 5,6,7,8-tetrahydro-[1,3]dithiolo[4,5-b][1,4]dithiocine-2-thione |
| 01252 | 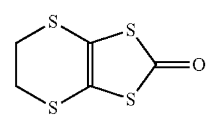 | 5,6-dihydro-[1,3]dithiolo[4,5-b][1,4]dithiin-2-one |
| 01420 | 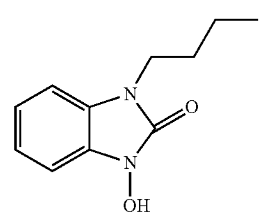 | 1-butyl-3-hydroxy-1H-benzo[d]imidazol-2(3H)-one |
| 01421 | 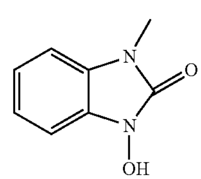 | 1-hydroxy-3-methyl-1H-benzo[d]imidazol-2(3H)-one |
| 01422 | 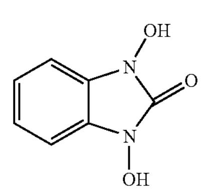 [SMILES: O=c1n(O)c2ccccc2n1O] | 1,3-dihydroxy-1H-benzo[d]imidazol-2(3H)-one |

TABLE 5

| Cmpd # | Structure | Name |
|---|---|---|
| 00157 | 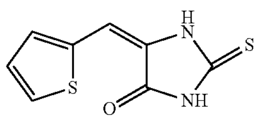 [SMILES: O=C1NC(=S)N/C1=C/c1cccs1] | (E)-5-(thiophen-2-ylmethylene)-2-thioxoimidazolidin-4-one |
| 00209 | 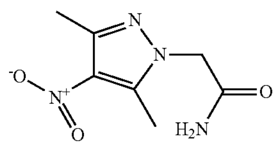 | 2-(3,5-dimethyl-4-nitro-1H-pyrazol-1-yl)acetamide |
| 00214 | 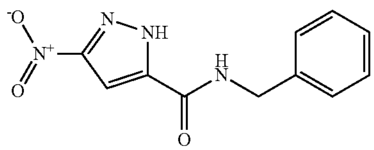 | N-benzyl-3-nitro-1H-pyrazole-5-carboxamide |
| 00217 | 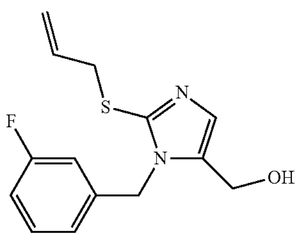 [SMILES: C=CCSc1ncc(CO)n1Cc1cccc(F)c1] | (2-(allylthio)-1-(3-fluorobenzyl)-1H-imidazol-5-yl)methanol |
| 00219 | 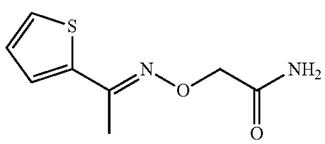 | (E)-2-(1-(thiophen-2-yl)ethylideneaminooxy)acetamide |
| 00224 | 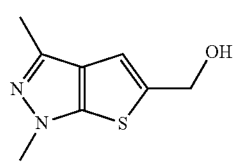 | (1,3-dimethyl-1H-thieno[2,3-c]pyrazol-5-yl)methanol |
| 00225 | 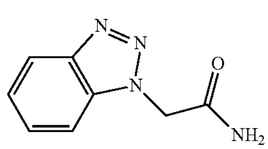 [SMILES: NC(=O)Cn1nnc2ccccc21] | 2-(1H-benzo[d][1,2,3]triazol-1-yl)acetamide |
| 00233 | 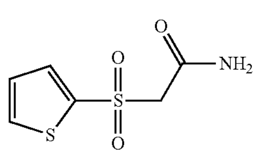 [SMILES: NC(=O)CS(=O)(=O)c1cccs1] | 2-(thiophen-2-ylsulfonyl)acetamide |
| 00240 | 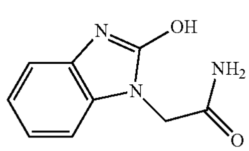 [SMILES: NC(=O)Cn1c(O)nc2ccccc21] | 2-(2-hydroxy-1H-benzo[d]imidazol-1-yl)acetamide |

TABLE 5-continued

| Cmpd # | Structure | Name |
| --- | --- | --- |
| 00268 | 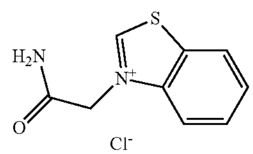 [SMILES: NC(=O)C[n+]1csc2ccccc21 ; [Cl-]] | 3-(2-amino-2-oxoethyl)benzo[d]thiazol-3-ium chloride |
| 00379 | 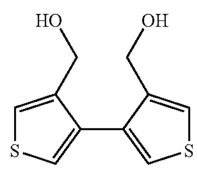 [SMILES: OCc1cscc1-c1cscc1CO] | 3,3'-bithiophene-4,4'-diyldimethanol |
| 00593 | 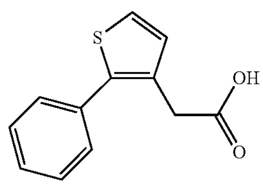 [SMILES: O=C(O)Cc1ccsc1-c1ccccc1] | 2-(2-phenylthiophen-3-yl)acetic acid |
| 00599 | 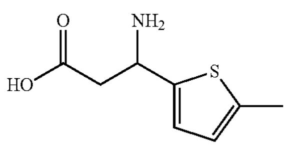 | 3-amino-3-(5-methylthiophen-2-yl)propanoic acid |
| 00602 | 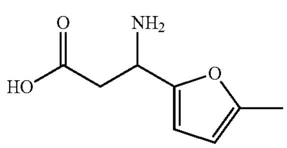 | 3-amino-3-(5-methylfuran-2-yl)propanoic acid |
| 00621 | 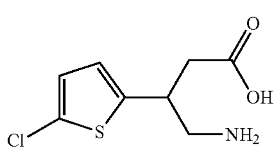 [SMILES: NCC(CC(=O)O)c1ccc(Cl)s1] | 4-amino-3-(5-chlorothiophen-2-yl)butanoic acid |
| 00649 | 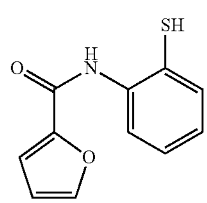 [SMILES: O=C(Nc1ccccc1S)c1ccco1] | N-(2-mercaptophenyl)furan-2-carboxamide |
| 00650 | 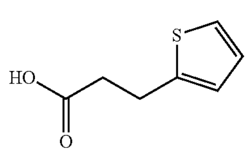 | 3-(thiophen-2-yl)propanoic acid |
| 00668 | 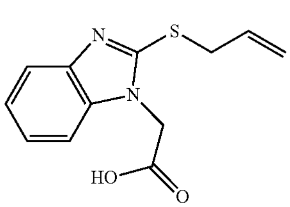 [SMILES: C=CCSc1nc2ccccc2n1CC(=O)O] | 2-(2-(allylthio)-1H-benzo[d]imidazol-1-yl)acetic acid |

TABLE 5-continued

| Cmpd # | Structure | Name |
|---|---|---|
| 00671 | 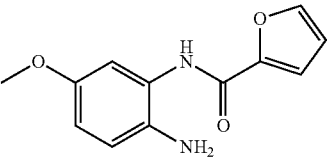 [SMILES: COc1ccc(N)c(NC(=O)c2ccco2)c1] | N-(2-amino-5-methoxyphenyl)furan-2-carboxamide |
| 00697 | 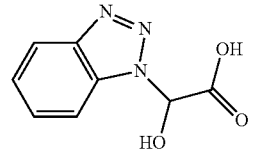 [SMILES: O=C(O)C(O)n1nnc2ccccc21] | 2-(1H-benzo[d][1,2,3]triazol-1-yl)-2-hydroxyacetic acid |
| 00722 | 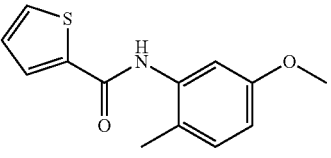 [SMILES: COc1ccc(C)c(NC(=O)c2cccs2)c1] | N-(5-methoxy-2-methylphenyl)thiophene-2-carboxamide |
| 00753 | 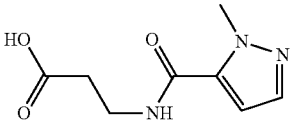 | 3-(1-methyl-1H-pyrazole-5-carboxamido)propanoic acid |
| 00761 | 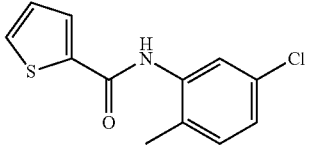 [SMILES: Cc1ccc(Cl)cc1NC(=O)c1cccs1] | N-(5-chloro-2-methylphenyl)thiophene-2-carboxamide |
| 00781 | 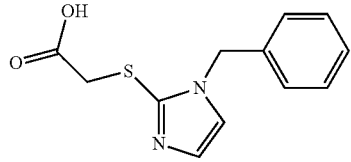 [SMILES: O=C(O)CSc1nccn1Cc1ccccc1] | 2-(1-benzyl-1H-imidazol-2-ylthio)acetic acid |
| 00791 | 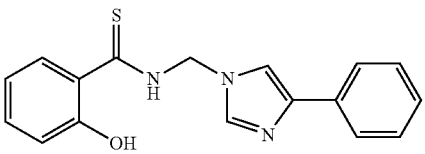 [SMILES: Oc1ccccc1C(=S)NCn1cnc(-c2ccccc2)c1] | 2-hydroxy-N-((4-phenyl-1H-imidazol-1-yl)methyl)benzothioamide |
| 00828 | 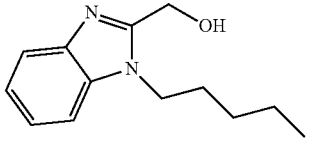 [SMILES: CCCCCn1c(CO)nc2ccccc21] | (1-pentyl-1H-benzo[d]imidazol-2-yl)methanol |
| 00835 | 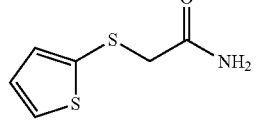 | 2-(thiophen-2-ylthio)acetamide |

TABLE 5-continued

| Cmpd # | Structure | Name |
|---|---|---|
| 00836 | 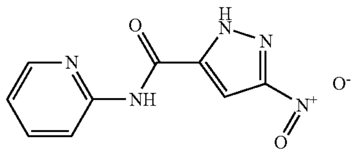 | 3-nitro-N-(pyridin-2-yl)-1H-pyrazole-5-carboxamide |
| 00855 | 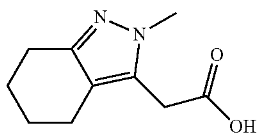 | 2-(2-methyl-4,5,6,7-tetrahydro-2H-indazol-3-yl)acetic acid |
| 00857 | 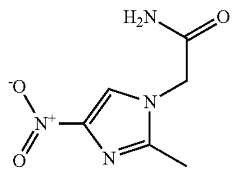 | 2-(2-methyl-4-nitro-1H-imidazol-1-yl)acetamide |
| 00861 | 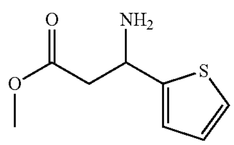 | methyl 3-amino-3-(thiophen-2-yl)propanoate |
| 00867 | 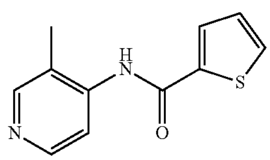 | N-(3-methylpyridin-4-yl)thiophene-2-carboxamide |
| 00868 | 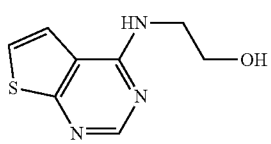 [SMILES: OCCNc1ncnc2sccc12] | 2-(thieno[2,3-d]pyrimidin-4-ylamino)ethanol |
| 00870 | 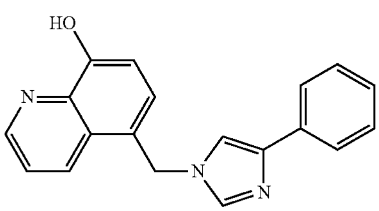 [SMILES: Oc1ccc(Cn2cnc(-c3ccccc3)c2)c2cccnc12] | 5-((4-phenyl-1H-imidazol-1-yl)methyl)quinolin-8-ol |
| 00874 | 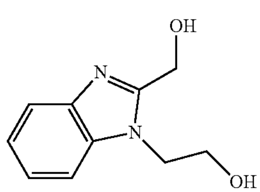 [SMILES: OCCn1c(CO)nc2ccccc21] | 2-(2-(hydroxymethyl)-1H-benzo[d]imidazol-1-yl)ethanol |
| 00883 | 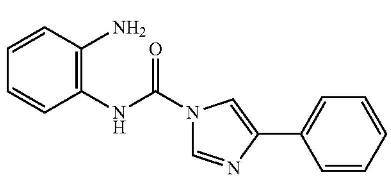 [SMILES: Nc1ccccc1NC(=O)n1cnc(-c2ccccc2)c1] | N-(2-aminophenyl)-4-phenyl-1H-imidazole-1-carboxamide |

TABLE 5-continued

| Cmpd # | Structure | Name |
|---|---|---|
| 00887 | 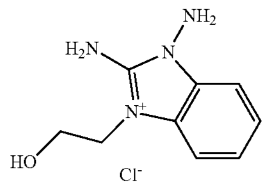 [SMILES: Nc1n(N)c2ccccc2[n+]1CCO ; [Cl-]] | 1,2-diamino-3-(2-hydroxyethyl)-1H-benzo[d]imidazol-3-ium chloride |
| 00891 | 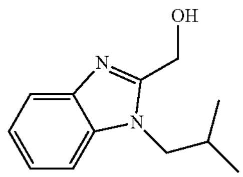 | (1-isobutyl-1H-benzo[d]imidazol-2-yl)methanol |
| 00892 | 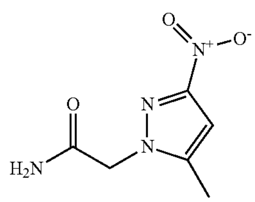 | 2-(5-methyl-3-nitro-1H-pyrazol-1-yl)acetamide |
| 00897 | 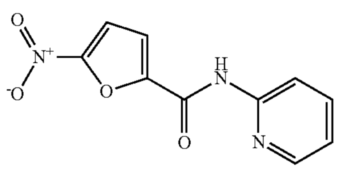 | 5-nitro-N-(pyridin-2-yl)furan-2-carboxamide |
| 00906 | 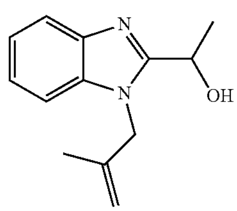 [SMILES: C=C(C)Cn1c(C(C)O)nc2ccccc21] | 1-(1-(2-methylallyl)-1H-benzo[d]imidazol-2-yl)ethanol |
| 00910 | 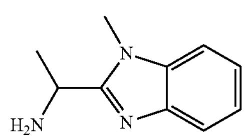 | 1-(1-methyl-1H-benzo[d]imidazol-2-yl)ethanamine |
| 00913 | 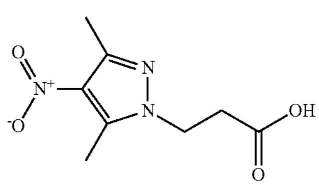 | 3-(3,5-dimethyl-4-nitro-1H-pyrazol-1-yl)propanoic acid |
| 00916 | 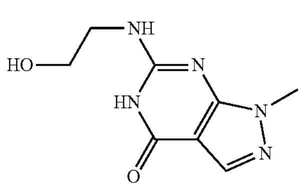 | 6-(2-hydroxyethylamino)-1-methyl-1H-pyrazolo[3,4-d]pyrimidin-4(5H)-one |
| 00918 | 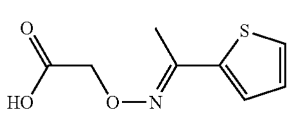 | (E)-2-(1-(thiophen-2-yl)ethylideneaminooxy)acetic acid |

TABLE 5-continued

| Cmpd # | Structure | Name |
| --- | --- | --- |
| 00921 | 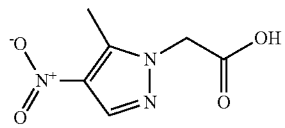 | 2-(5-methyl-4-nitro-1H-pyrazol-1-yl)acetic acid |
| 00927 | 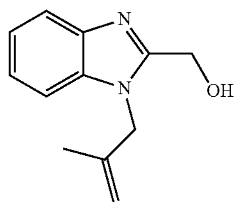 | (1-(2-methylallyl)-1H-benzo[d]imidazol-2-yl)methanol |
| 00930 | 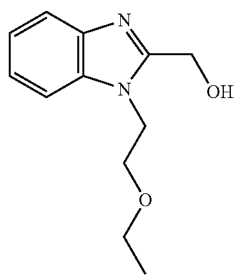 [SMILES: CCOCCn1c(CO)nc2ccccc21] | (1-(2-ethoxyethyl)-1H-benzo[d]imidazol-2-yl)methanol |
| 00944 | 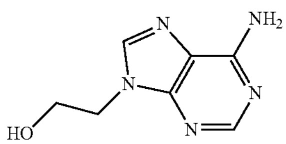 [SMILES: Nc1ncnc2c1ncn2CCO] | 2-(6-amino-9H-purin-9-yl)ethanol |
| 00959 | 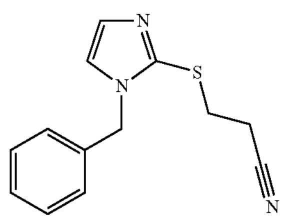 [SMILES: N#CCCSc1nccn1Cc1ccccc1] | 3-(1-benzyl-1H-imidazol-2-ylthio)propanenitrile |
| 00961 | 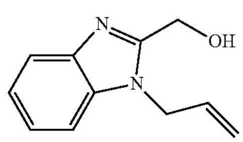 | (1-allyl-1H-benzo[d]imidazol-2-yl)-methanol |
| 00965 | 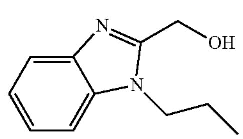 | (1-propyl-1H-benzo[d]imidazol-2-yl)-methanol |
| 00977 | 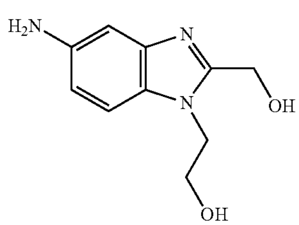 [SMILES: Nc1ccc2c(c1)nc(CO)n2CCO] | 2-(5-amino-2-(hydroxymethyl)-1H-benzo-[d]imidazol-1-yl)ethanol |

TABLE 5-continued

| Cmpd # | Structure | Name |
|---|---|---|
| 00979 | 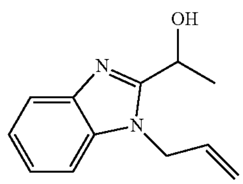 | 1-(1-allyl-1H-benzo[d]imidazol-2-yl)-ethanol |
| 00981 | 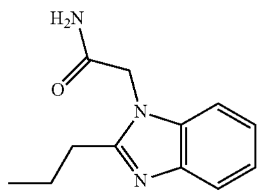 [SMILES: CCCc1nc2ccccc2n1CC(N)=O] | 2-(2-propyl-1H-benzo[d]imidazol-1-yl)-acetamide |
| 00999 | 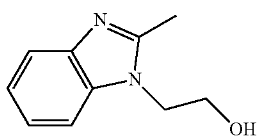 | 2-(2-methyl-1H-benzo[d]imidazol-1-yl)-ethanol |
| 01004 | 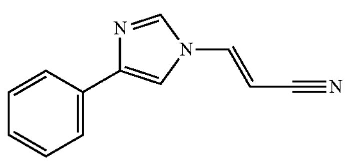 [SMILES: N#C/C=C/n1cnc(-c2ccccc2)c1] | (E)-3-(4-phenyl-1H-imidazol-1-yl)acrylonitrile |
| 01008 | 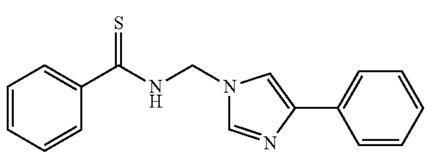 [SMILES: S=C(NCn1cnc(-c2ccccc2)c1)c1ccccc1] | N-((4-phenyl-1H-imidazol-1-yl)methyl)benzothioamide |
| 01012 | 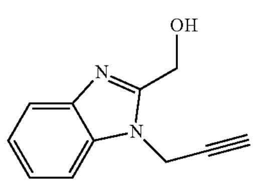 | (1-(prop-2-ynyl)-1H-benzo[d]imidazol-2-yl)methanol |
| 01018 | 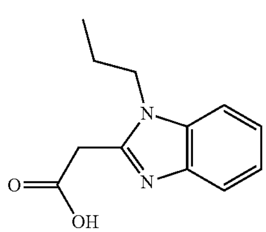 [SMILES: CCCn1c(CC(=O)O)nc2ccccc21] | 2-(1-propyl-1H-benzo[d]imidazol-2-yl)-acetic acid |
| 01021 | 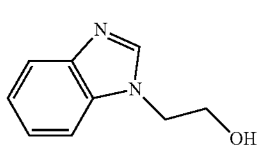 [SMILES: OCCn1cnc2ccccc21] | 2-(1H-benzo[d]imidazol-1-yl)ethanol |

TABLE 5-continued

| Cmpd # | Structure | Name |
| --- | --- | --- |
| 01034 | 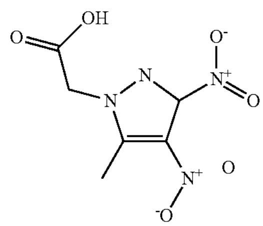 | 2-(5-methyl-3,4-dinitro-1H-pyrazol-1-yl)acetic acid |
| 01045 | 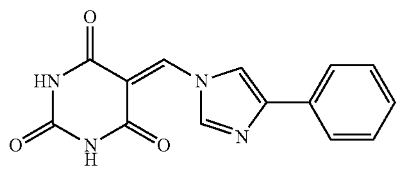 [SMILES: O=C1NC(=O)C(=Cn2cnc(-c3ccccc3)c2)C(=O)N1] | 5-((4-phenyl-1H-imidazol-1-yl)methylene)pyrimidine-2,4,6(1H,3H,5H)-trione |
| 01057 | 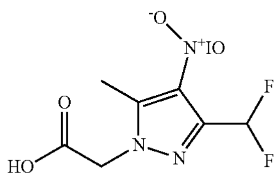 | 2-(3-(difluoromethyl)-5-methyl-4-nitro-1H-pyrazol-1-yl)acetic acid |
| 01064 | 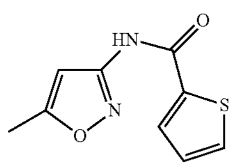 | N-(5-methylisoxazol-3-yl)thiophene-2-carboxamide |
| 01071 | 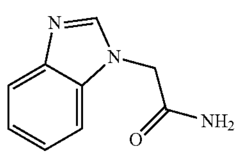 [SMILES: NC(=O)Cn1cnc2ccccc21] | 2-(1H-benzo[d]imidazol-1-yl)acetamide |
| 01078 | 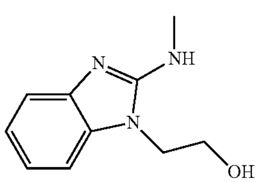 | 2-(2-(methylamino)-1H-benzo[d]imidazol-1-yl)ethanol |
| 01115 | 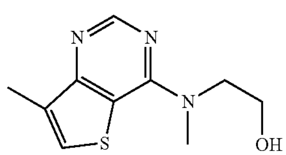 | 2-(methyl(7-methylthieno[3,2-d]pyrimidin-4-yl)amino)ethanol |
| 01124 | 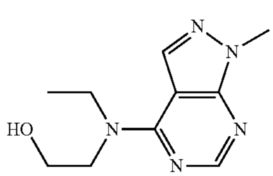 [SMILES: CCN(CCO)c1ncnc2c1cnn2C] | 2-(ethyl(1-methyl-1H-pyrazolo[3,4-d]pyrimidin-4-yl)amino)ethanol |

TABLE 5-continued

| Cmpd # | Structure | Name |
|---|---|---|
| 01142 | 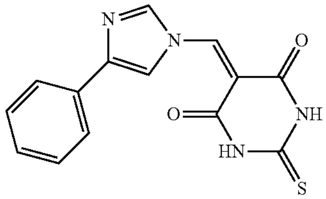 [SMILES: O=C1NC(=S)NC(=O)C1=Cn1cnc(-c2ccccc2)c1] | 5-((4-phenyl-1H-imidazol-1-yl)methylene)-2-thioxodihydropyrimidine-4,6(1H,5H)-dione |
| 01146 | 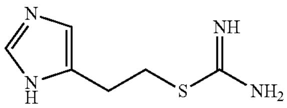 [SMILES: N=C(N)SCCc1cnc[nH]1] | 2-(1H-imidazol-5-yl)ethyl carbamimidothioate |
| 01147 | 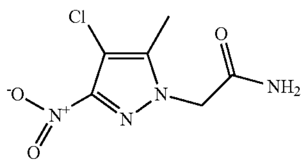 | 2-(4-chloro-5-methyl-3-nitro-1H-pyrazol-1-yl)acetamide |
| 01159 | 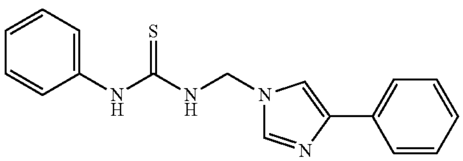 [SMILES: S=C(NCn1cnc(-c2ccccc2)c1)Nc1ccccc1] | 1-phenyl-3-((4-phenyl-1H-imidazol-1-yl)methyl)thiourea |
| 01171 | 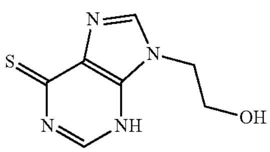 [SMILES: OCCn1cnc2c(=S)nc[nH]c21] | 9-(2-hydroxyethyl)-3H-purine-6(9H)-thione |
| 01173 | 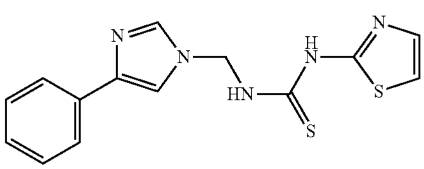 [SMILES: S=C(NCn1cnc(-c2ccccc2)c1)Nc1nccs1] | 1-((4-phenyl-1H-imidazol-1-yl)methyl)-3-(thiazol-2-yl)thiourea |
| 01179 | 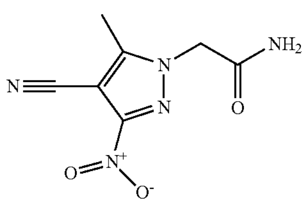 | 2-(4-cyano-5-methyl-3-nitro-1H-pyrazol-1-yl)acetamide |
| 01191 | 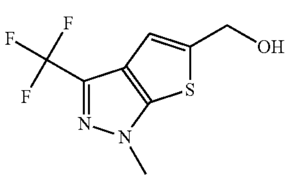 | (1-methyl-3-(trifluoromethyl)-1H-thieno[2,3-c]pyrazol-5-yl)methanol |
| 01205 | 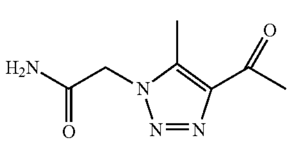 | 2-(4-acetyl-5-methyl-1H-1,2,3-triazol-1-yl)acetamide |

TABLE 5-continued

| Cmpd # | Structure | Name |
|---|---|---|
| 01225 | 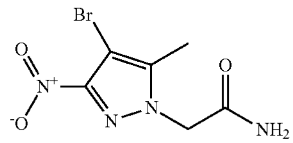 | 2-(4-bromo-5-methyl-3-nitro-1H-pyrazol-1-yl)acetamide |
| 01234 | 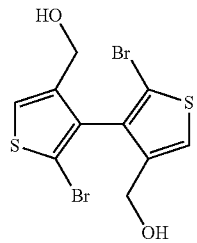 [SMILES: OCc1csc(Br)c1-c1c(CO)csc1Br] | (2,2'-dibromo-3,3'-bithiophene-4,4'-diyl)-dimethanol |
| 01255 | 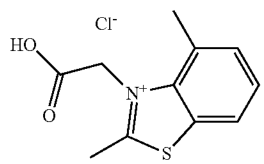 | 3-(carboxymethyl)-2,4-dimethylbenzo[d]thiazol-3-ium chloride |
| 01440 | 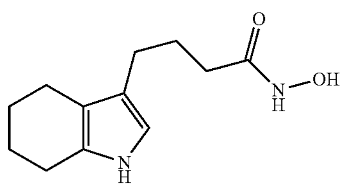 [SMILES: O=C(CCCc1c[nH]c2c1CCCC2)NO] | N-hydroxy-4-(4,5,6,7-tetrahydro-1H-indol-3-yl)butanamide |
| 01442 | 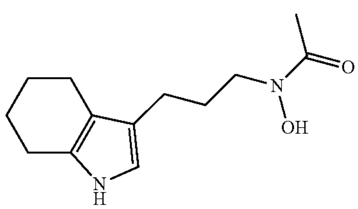 [SMILES: CC(=O)N(O)CCCc1c[nH]c2c1CCCC2] | N-hydroxy-N-(3-(4,5,6,7-tetrahydro-1H-indol-3-yl)propyl)acetamide |

TABLE 6

| Cmpd # | Structure | Name |
|---|---|---|
| 00155 | 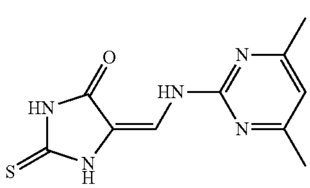 [SMILES: Cc1cc(C)nc(N/C=C2/NC(=S)NC2=O)n1] | (E)-5-((4,6-dimethylpyrimidin-2-ylamino)methylene)-2-thioxoimidazolidin-4-one |
| 00220 | 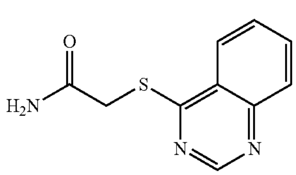 [SMILES: NC(=O)CSc1ncnc2ccccc12] | 2-(quinazolin-4-ylthio)acetamide |

TABLE 6-continued

| Cmpd # | Structure | Name |
|---|---|---|
| 00662 | 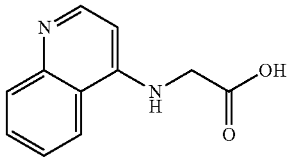 [SMILES: O=C(O)CNc1ccnc2ccccc12] | 2-(quinolin-4-ylamino)acetic acid |
| 00678 | 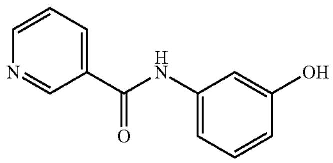 [SMILES: O=C(Nc1cccc(O)c1)c1cccnc1] | N-(3-hydroxyphenyl)nicotinamide |
| 00687 | 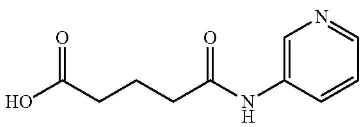 [SMILES: O=C(O)CCCC(=O)Nc1cccnc1] | 5-oxo-5-(pyridin-3-ylamino)pentanoic acid |
| 00699 | 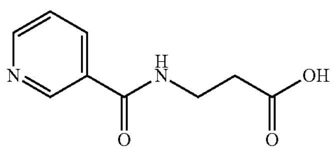 [SMILES: O=C(O)CCNC(=O)c1cccnc1] | 3-(nicotinamido)propanoic acid |
| 00732 | 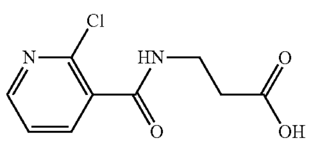 [SMILES: O=C(O)CCNC(=O)c1cccnc1Cl] | 3-(2-chloronicotinamido)propanoic acid |
| 00766 | 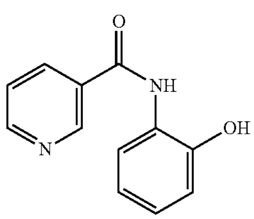 [SMILES: O=C(Nc1ccccc1O)c1cccnc1] | N-(2-hydroxyphenyl)nicotinamide |
| 00767 | 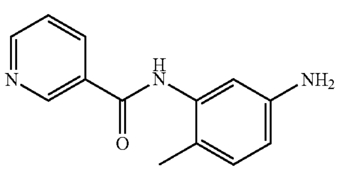 [SMILES: Cc1ccc(N)cc1NC(=O)c1cccnc1] | N-(5-amino-2-methylphenyl)nicotinamide |
| 00772 | 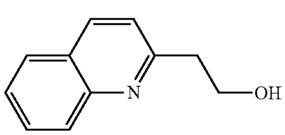 [SMILES: OCCc1ccc2ccccc2n1] | 2-(quinolin-2-yl)ethanol |
| 00787 | 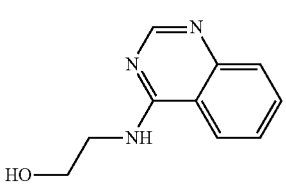 [SMILES: OCCNc1ncnc2ccccc12] | 2-(quinazolin-4-ylamino)ethanol |

TABLE 6-continued

| Cmpd # | Structure | Name |
|---|---|---|
| 00809 | 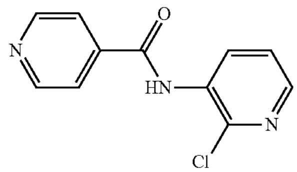 [SMILES: O=C(Nc1cccnc1Cl)c1ccncc1] | N-(2-chloropyridin-3-yl)isonicotinamide |
| 00834 | 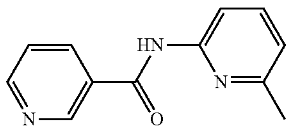 [SMILES: Cc1cccc(NC(=O)c2cccnc2)n1] | N-(6-methylpyridin-2-yl)nicotinamide |
| 00902 | 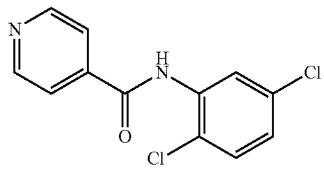 [SMILES: O=C(Nc1cc(Cl)ccc1Cl)c1ccncc1] | N-(2,5-dichlorophenyl)isonicotinamide |
| 00929 | 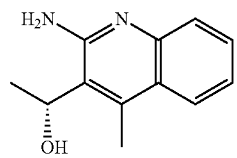 | (R)-1-(2-amino-4-methylquinolin-3-yl)ethanol |
| 00955 | 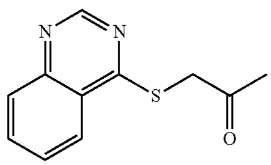 | 1-(quinazolin-4-ylthio)propan-2-one |
| 00960 | 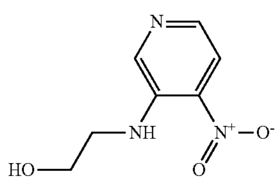 [SMILES: O=[N+]([O-])c1ccncc1NCCO] | 2-(4-nitropyridin-3-ylamino)ethanol |
| 00967 | 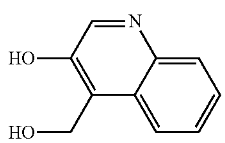 | 4-(hydroxymethyl)quinolin-3-ol |
| 01011 | 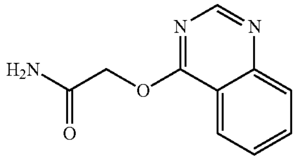 [SMILES: NC(=O)COc1ncnc2ccccc12] | 2-(quinazolin-4-yloxy)acetamide |
| 01016 | 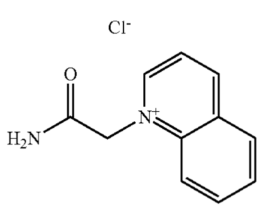 [SMILES: [Cl-] ; NC(=O)C[n+]1cccc2ccccc21] | 1-(2-amino-2-oxoethyl)quinolinium chloride |

TABLE 6-continued

| Cmpd # | Structure | Name |
|---|---|---|
| 01066 | 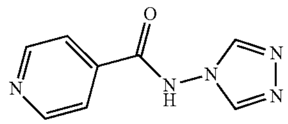 [SMILES: O=C(Nn1cnnc1)c1ccncc1] | N-(4H-1,2,4-triazol-4-yl)isonicotinamide |
| 01089 | 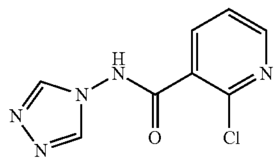 [SMILES: O=C(Nn1cnnc1)c1cccnc1Cl] | 2-chloro-N-(4H-1,2,4-triazol-4-yl)nicotinamide |
| 01141 | 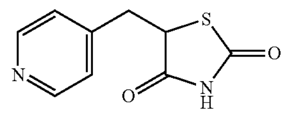 [SMILES: O=C1NC(=O)C(Cc2ccncc2)S1] | 5-(pyridin-4-ylmethyl)thiazolidine-2,4-dione |
| 01199 | 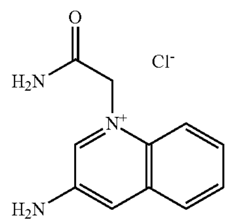 | 3-amino-1-(2-amino-2-oxoethyl)quinolinium chloride |

TABLE 7

| Cmpd # | Structure | Name |
|---|---|---|
| 00077 | 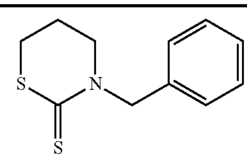 | 3-benzyl-1,3-thiazinane-2-thione |
| 00079 | 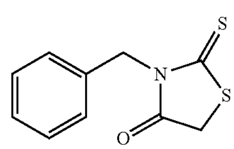 [SMILES: O=C1CSC(=S)N1Cc1ccccc1] | 3-benzyl-2-thioxothiazolidin-4-one |
| 00081 | 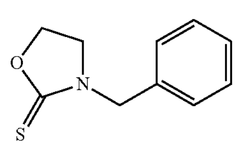 [SMILES: S=C1OCCN1Cc1ccccc1] | 3-benzyloxazolidine-2-thione |
| 00138 | 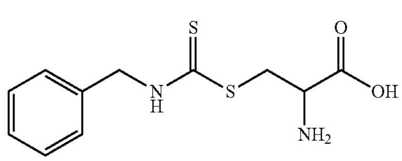 [SMILES: NC(CSC(=S)NCc1ccccc1)C(=O)O] | 2-amino-3-(benzylcarbamothioylthio)-propanoic acid |
| 00140 | 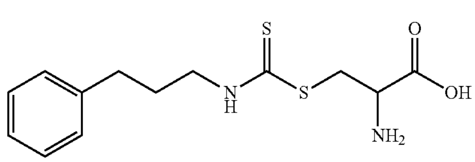 [SMILES: NC(CSC(=S)NCCCc1ccccc1)C(=O)O] | 2-amino-3-(3-phenylpropyl-carbamothioylthio)propanoic acid |

TABLE 7-continued

| Cmpd # | Structure | Name |
|---|---|---|
| 00148 | 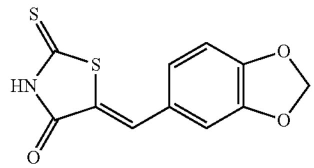 [SMILES: O=C1NC(=S)S/C1=C\c1ccc2c(c1)OCO2] | (Z)-5-(benzo[d][1,3]dioxol-5-ylmethylene)-2-thioxothiazolidin-4-one |
| 00150 | 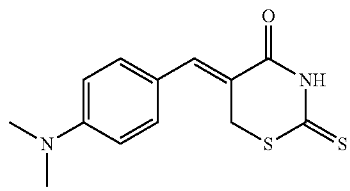 [SMILES: CN(C)c1ccc(/C=C2\CSC(=S)NC2=O)cc1] | (Z)-5-(4-(dimethylamino)benzylidene)-2-thioxo-1,3-thiazinan-4-one |
| 00154 | 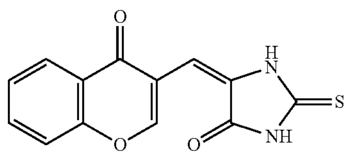 [SMILES: O=C1NC(=S)N/C1=C/c1coc2ccccc2c1=O] | (E)-5-((4-oxo-4H-chromen-3-yl)methylene)-2-thioxoimidazolidin-4-one |
| 00221 | 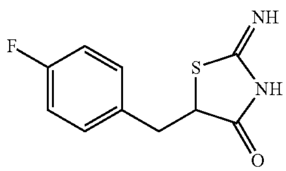 [SMILES: N=C1NC(=O)C(Cc2ccc(F)cc2)S1] | 5-(4-fluorobenzyl)-2-iminothiazolidin-4-one |
| 00261 | 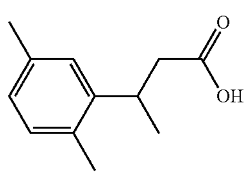 | 3-(2,5-dimethylphenyl)butanoic acid |
| 00262 | 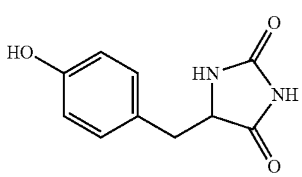 [SMILES: O=C1NC(=O)C(Cc2ccc(O)cc2)N1] | 5-(4-hydroxybenzyl)imidazolidine-2,4-dione |
| 00282 | 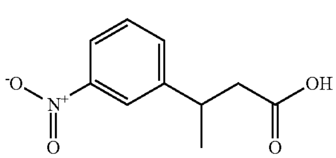 | 3-(3-nitrophenyl)butanoic acid |
| 00291 | 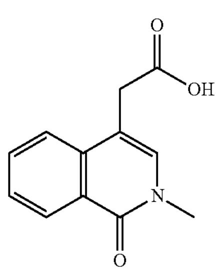 [SMILES: Cn1cc(CC(=O)O)c2ccccc2c1=O] | 2-(2-methyl-1-oxo-1,2-dihydroisoquinolin-4-yl)acetic acid |

TABLE 7-continued

| Cmpd # | Structure | Name |
| --- | --- | --- |
| 00292 | 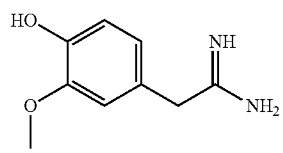 | 2-(4-hydroxy-3-methoxyphenyl)-acetimidamide |
| 00313 | 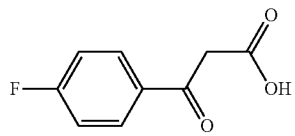 [SMILES: O=C(O)CC(=O)c1ccc(F)cc1] | 3-(4-fluorophenyl)-3-oxopropanoic acid |
| 00317 | 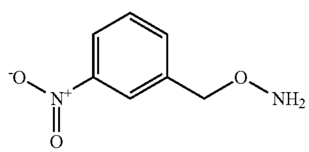 | O-(3-nitrobenzyl)hydroxylamine |
| 00346 | 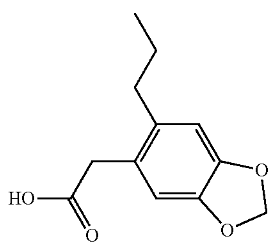 [SMILES: CCCc1cc2c(cc1CC(=O)O)OCO2] | 2-(6-propylbenzo[d][1,3]dioxol-5-yl)acetic acid |
| 00360 | 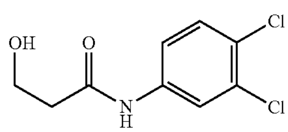 [SMILES: O=C(CCO)Nc1ccc(Cl)c(Cl)c1] | N-(3,4-dichlorophenyl)-3-hydroxypropanamide |
| 00389 | 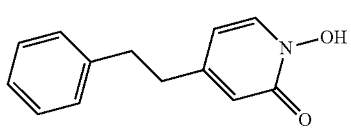 [SMILES: O=c1cc(CCc2ccccc2)ccn1O] | 1-hydroxy-4-phenethylpyridin-2(1H)-one |
| 00394 | 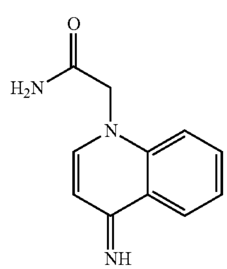 [SMILES: N=c1ccn(CC(N)=O)c2ccccc12] | 2-(4-iminoquinolin-1(4H)-yl)acetamide |
| 00567 | 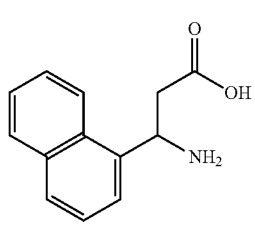 [SMILES: NC(CC(=O)O)c1cccc2ccccc12] | 3-amino-3-(naphthalen-1-yl)propanoic acid |

TABLE 7-continued

| Cmpd # | Structure | Name |
|---|---|---|
| 00572 | 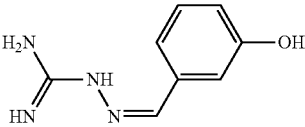 | (Z)-2-(3-hydroxybenzylidene)-hydrazinecarboximidamide |
| 00587 | 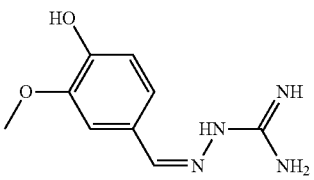 | (Z)-2-(4-hydroxy-3-methoxybenzylidene)-hydrazinecarboximidamide 2-(2-(1H-pyrrol-1-yl)phenyl)acetate |
| 00591 | 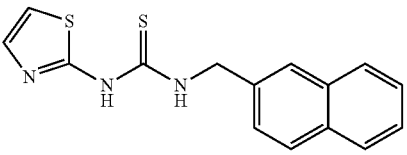 [SMILES: S=C(NCc1ccc2ccccc2c1)Nc1nccs1] | 1-(naphthalen-2-ylmethyl)-3-(thiazol-2-yl)thiourea |
| 00607 | 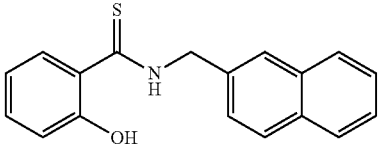 [SMILES: Oc1ccccc1C(=S)NCc1ccc2ccccc2c1] | 2-hydroxy-N-(naphthalen-2-ylmethyl)benzothioamide |
| 00616 | 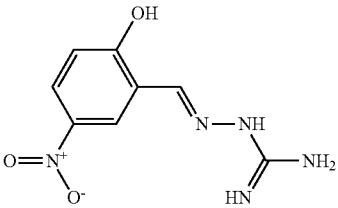 [SMILES: N=C(N)N/N=C/c1cc([N+](=O)[O-])ccc1O] | (E)-2-(2-hydroxy-5-nitrobenzylidene)-hydrazinecarboximidamide |
| 00620 | 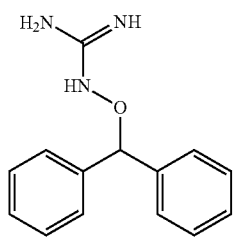 [SMILES: N=C(N)NOC(c1ccccc1)c1ccccc1] | 1-(benzhydryloxy)guanidine |
| 00627 | 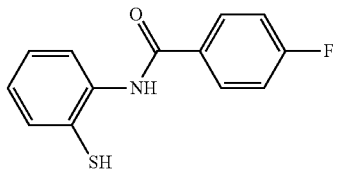 [SMILES: O=C(Nc1ccccc1S)c1ccc(F)cc1] | 4-fluoro-N-(2-mercaptophenyl)benzamide |
| 00634 | 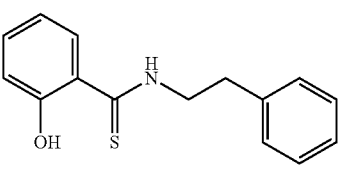 [SMILES: Oc1ccccc1C(=S)NCCc1ccccc1] | 2-hydroxy-N-phenethylbenzothioamide |

TABLE 7-continued

| Cmpd # | Structure | Name |
|---|---|---|
| 00656 | 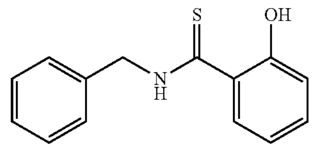 [SMILES: Oc1ccccc1C(=S)NCc1ccccc1] | N-benzyl-2-hydroxybenzothioamide |
| 00657 | 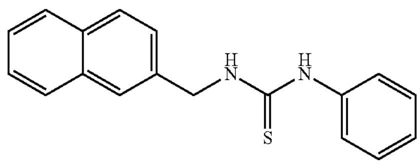 [SMILES: S=C(NCc1ccc2ccccc2c1)Nc1ccccc1] | 1-(naphthalen-2-ylmethyl)-3-phenylthiourea |
| 00664 | 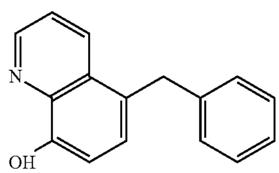 [SMILES: Oc1ccc(Cc2ccccc2)c2cccnc12] | 5-benzylquinolin-8-ol |
| 00665 | 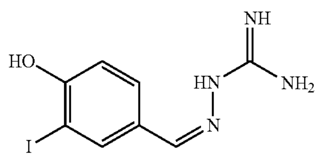 [SMILES: N=C(N)N/N=C\c1ccc(O)c(I)c1] | (Z)-2-(4-hydroxy-3-iodobenzylidene)-hydrazinecarboximidamide |
| 00683 | 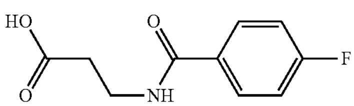 | 3-(4-fluorobenzamido)propanoic acid |
| 00686 | 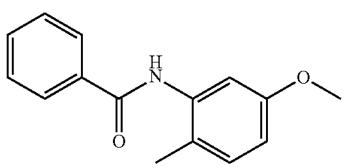 [SMILES: COc1ccc(C)c(NC(=O)c2ccccc2)c1] | N-(5-methoxy-2-methylphenyl)benzamide |
| 00688 | 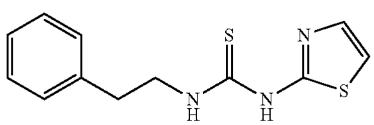 [SMILES: S=C(NCCc1ccccc1)Nc1nccs1] | 1-phenethyl-3-(thiazol-2-yl)thiourea |
| 00689 | 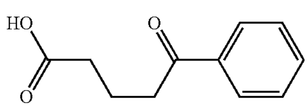 [SMILES: O=C(O)CCCC(=O)c1ccccc1] | 5-oxo-5-phenylpentanoic acid |
| 00691 | 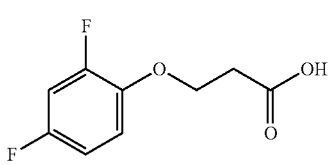 [SMILES: O=C(O)CCOc1ccc(F)cc1F] | 3-(2,4-difluorophenoxy)propanoic acid |
| 00698 | 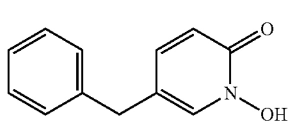 [SMILES: O=c1ccc(Cc2ccccc2)cn1O] | 5-benzyl-1-hydroxypyridin-2(1H)-one |

TABLE 7-continued

| Cmpd # | Structure | Name |
|---|---|---|
| 00711 | 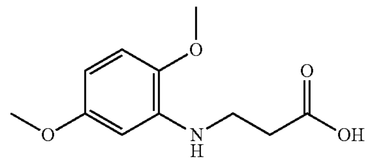 [SMILES: COc1ccc(OC)c(NCCC(=O)O)c1] | 3-(2,5-dimethoxyphenylamino)propanoic acid |
| 00720 | 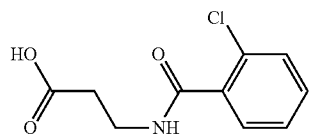 [SMILES: O=C(O)CCNC(=O)c1ccccc1Cl] | 3-(2-chlorobenzamido)propanoic acid |
| 00721 | 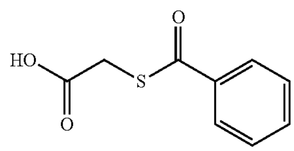 [SMILES: O=C(O)CSC(=O)c1ccccc1] | 2-(benzoylthio)acetic acid |
| 00724 | 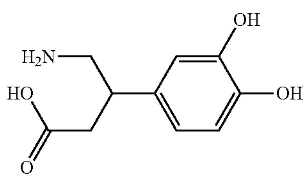 [SMILES: NCC(CC(=O)O)c1ccc(O)c(O)c1] | 4-amino-3-(3,4-dihydroxyphenyl)butanoic acid |
| 00744 | 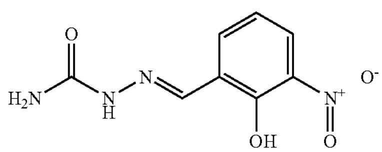 | (E)-2-(2-hydroxy-3-nitrobenzylidene)hydrazinecarboxamide |
| 00748 | 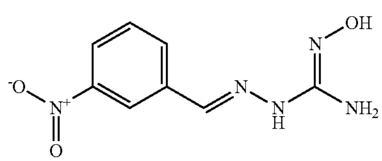 | (1E,2E)-N'-hydroxy-2-(3-nitro-benzylidene)hydrazinecarboximidamide |
| 00752 | 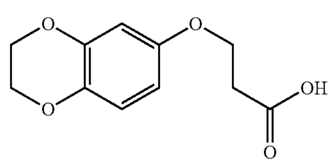 [SMILES: O=C(O)CCOc1ccc2c(c1)OCCO2] | 3-(2,3-dihydrobenzo[b][1,4]dioxin-6-yloxy)propanoic acid |
| 00755 | 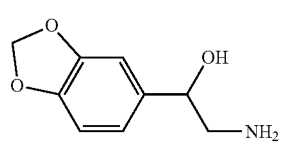 | 2-amino-1-(benzo[d][1,3]dioxol-5-yl)-ethanol |
| 00760 | 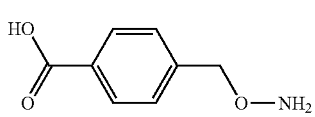 | O-(4-carboxybenzyl)hydroxylamine |
| 00762 | 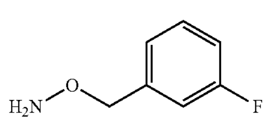 | O-(3-fluorobenzyl)hydroxylamine |

TABLE 7-continued

| Cmpd # | Structure | Name |
| --- | --- | --- |
| 00773 | 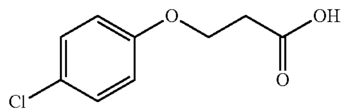 [SMILES: O=C(O)CCOc1ccc(Cl)cc1] | 3-(4-chlorophenoxy)propanoic acid |
| 00774 | 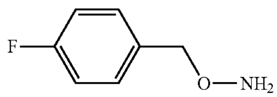 | O-(4-fluorobenzyl)hydroxylamine |
| 00775 | 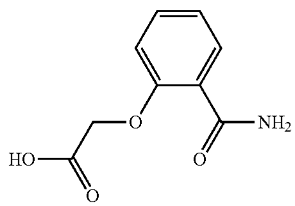 [SMILES: NC(=O)c1ccccc1OCC(=O)O] | 2-(2-carbamoylphenoxy)acetic acid |
| 00778 | 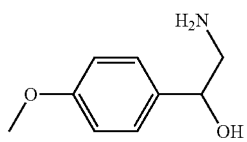 | 2-amino-1-(4-methoxyphenyl)ethanol |
| 00786 | 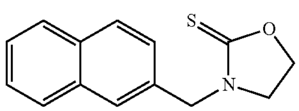 [SMILES: S=C1OCCN1Cc1ccc2ccccc2c1] | 3-(naphthalen-2-ylmethyl)oxazolidine-2-thione |
| 00788 | 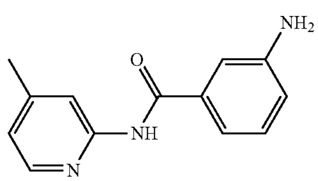 [SMILES: Cc1ccnc(NC(=O)c2cccc(N)c2)c1] | 3-amino-N-(4-methylpyridin-2-yl)-benzamide |
| 00801 | 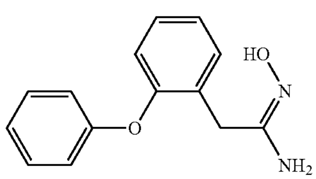 | (E)-N'-hydroxy-2-(2-phenoxyphenyl)-acetimidamide |
| 00808 | 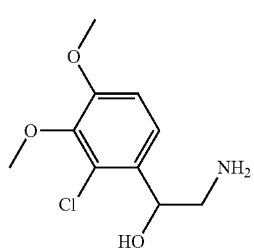 | 2-amino-1-(2-chloro-3,4-dimethoxyphenyl)ethanol |
| 00810 | 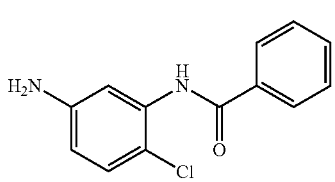 [SMILES: Nc1ccc(Cl)c(NC(=O)c2ccccc2)c1] | N-(5-amino-2-chlorophenyl)benzamide |

TABLE 7-continued

| Cmpd # | Structure | Name |
|---|---|---|
| 00811 | 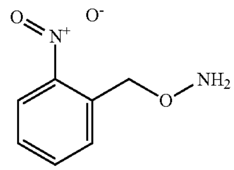 | O-(2-nitrobenzyl)hydroxylamine |
| 00827 | 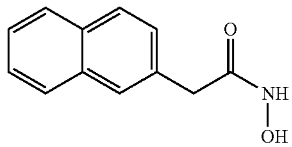 [SMILES: O=C(Cc1ccc2ccccc2c1)NO] | N-hydroxy-2-(naphthalen-2-yl)acetamide |
| 00830 | 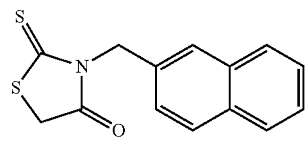 [SMILES: O=C1CSC(=S)N1Cc1ccc2ccccc2c1] | 3-(naphthalen-2-ylmethyl)-2-thioxothiazolidin-4-one |
| 00848 | 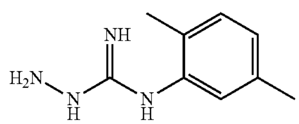 | N-(2,5-dimethylphenyl)hydrazinecarboximidamide |
| 00849 | 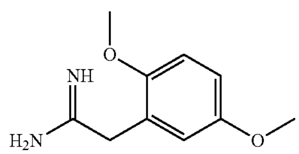 | 2-(2,5-dimethoxyphenyl)acetimidamide |
| 00862 | 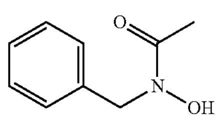 | N-benzyl-N-hydroxyacetamide |
| 00864 | 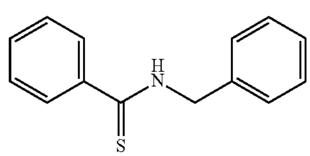 [SMILES: S=C(NCc1ccccc1)c1ccccc1] | N-benzylbenzothioamide |
| 00869 | 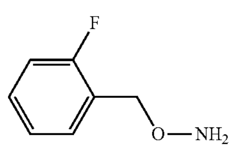 | O-(2-fluorobenzyl)hydroxylamine |
| 00880 | 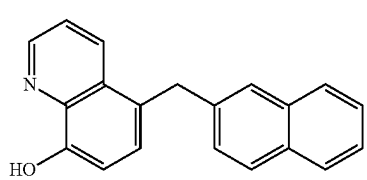 [SMILES: Oc1ccc(Cc2ccc3ccccc3c2)c2cccnc12] | 5-(naphthalen-2-ylmethyl)quinolin-8-ol |
| 00889 | 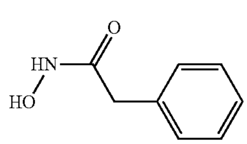 [SMILES: O=C(Cc1ccccc1)NO] | N-hydroxy-2-phenylacetamide |

TABLE 7-continued

| Cmpd # | Structure | Name |
| --- | --- | --- |
| 00890 | 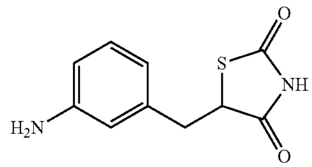 [SMILES: Nc1cccc(CC2SC(=O)NC2=O)c1] | 5-(3-aminobenzyl)thiazolidine-2,4-dione |
| 00895 | 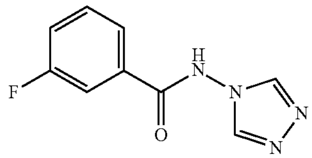 [SMILES: O=C(Nn1cnnc1)c1cccc(F)c1] | 3-fluoro-N-(4H-1,2,4-triazol-4-yl)benzamide |
| 00900 | 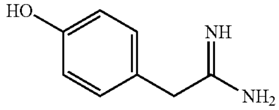 | 2-(4-hydroxyphenyl)acetimidamide |
| 00914 | 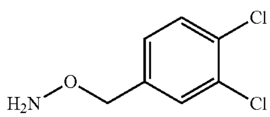 | O-(3,4-dichlorobenzyl)hydroxylamine |
| 00917 | 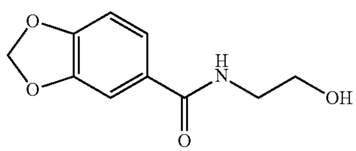 [SMILES: O=C(NCCO)c1ccc2c(c1)OCO2] | N-(2-hydroxyethyl)benzo[d][1,3]dioxole-5-carboxamide |
| 00920 | 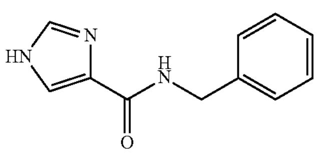 [SMILES: O=C(NCc1ccccc1)c1c[nH]cn1] | N-benzyl-1H-imidazole-4-carboxamide |
| 00922 | 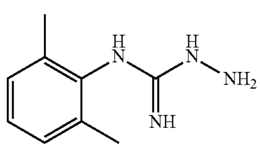 | N-(2,6-dimethylphenyl)hydrazine-carboximidamide |
| 00934 | 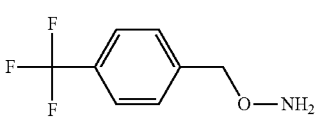 [SMILES: NOCc1ccc(C(F)(F)F)cc1] | O-(4-(trifluoromethyl)benzyl)-hydroxylamine |
| 00945 | 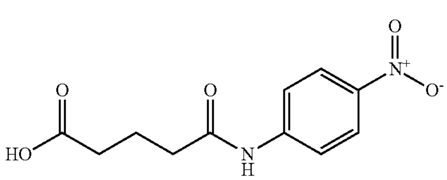 [SMILES: O=C(O)CCCC(=O)Nc1ccc([N+](=O)[O-])cc1] | 5-(4-nitrophenylamino)-5-oxopentanoic acid |
| 00947 | 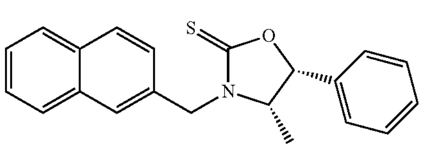 [SMILES: C[C@H]1[C@@H](c2ccccc2)OC(=S)N1Cc1ccc2ccccc2c1] | (4S,5R)-4-methyl-3-(naphthalen-2-ylmethyl)-5-phenyloxazolidine-2-thione |

TABLE 7-continued

| Cmpd # | Structure | Name |
| --- | --- | --- |
| 00951 | 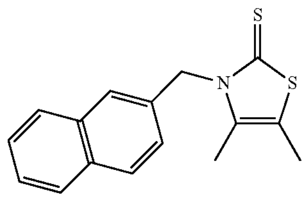 [SMILES: Cc1sc(=S)n(Cc2ccc3ccccc3c2)c1C] | 4,5-dimethyl-3-(naphthalen-2-ylmethyl)thiazole-2(3H)-thione |
| 00964 | 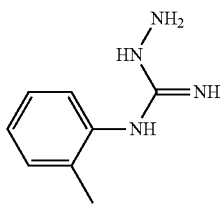 | N-o-tolylhydrazinecarboximidamide |
| 00969 | 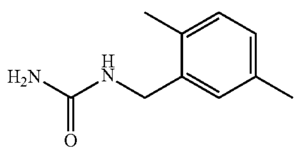 | 1-(2,5-dimethylbenzyl)urea |
| 00970 | 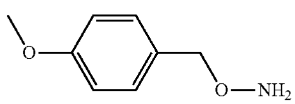 | O-(4-methoxybenzyl)hydroxylamine |
| 00974 | 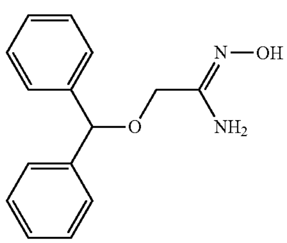 [SMILES: N/C(COC(c1ccccc1)c1ccccc1)=N\O] | (Z)-2-(benzhydryloxy)-N'-hydroxyacetimidamide |
| 00976 | 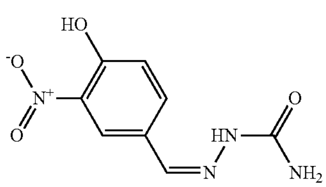 | (Z)-2-(4-hydroxy-3-nitrobenzylidene)-hydrazinecarboxamide |
| 00978 | 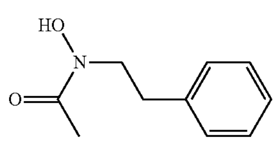 | N-hydroxy-N-phenethylacetamide |
| 00982 | 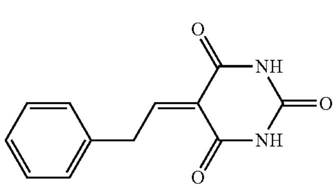 [SMILES: O=C1NC(=O)C(=CCc2ccccc2)C(=O)N1] | 5-(2-phenylethylidene)pyrimidine-2,4,6(1H,3H,5H)-trione |

TABLE 7-continued

| Cmpd # | Structure | Name |
| --- | --- | --- |
| 00990 | 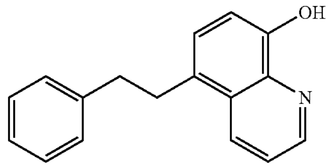 [SMILES: Oc1ccc(CCc2ccccc2)c2cccnc12] | 5-phenethylquinolin-8-ol |
| 00994 | 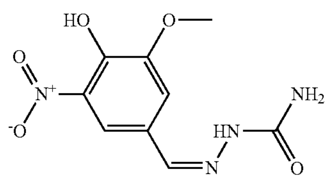 | (Z)-2-(4-hydroxy-3-methoxy-5-nitrobenzylidene)hydrazinecarboxamide |
| 00995 | 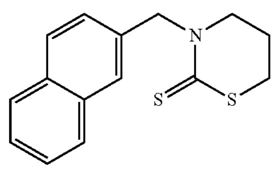 [SMILES: S=C1SCCCN1Cc1ccc2ccccc2c1] | 3-(naphthalen-2-ylmethyl)-1,3-thiazinane-2-thione |
| 00996 | 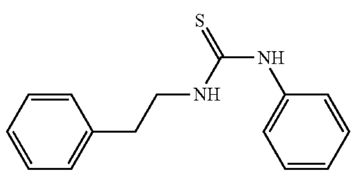 [SMILES: S=C(NCCc1ccccc1)Nc1ccccc1] | 1-phenethyl-3-phenylthiourea |
| 01013 | 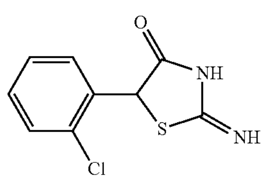 [SMILES: N=C1NC(=O)C(c2ccccc2Cl)S1] | 5-(2-chlorophenyl)-2-iminothiazolidin-4-one |
| 01014 | 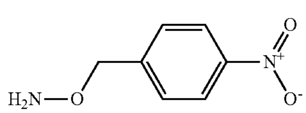 | O-(4-nitrobenzyl)hydroxylamine |
| 01028 | 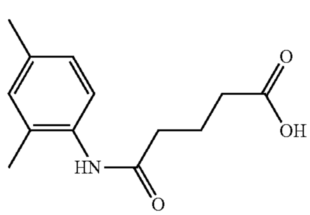 [SMILES: Cc1ccc(NC(=O)CCCC(=O)O)c(C)c1] | 5-(2,4-dimethylphenylamino)-5-oxopentanoic acid |
| 01031 | 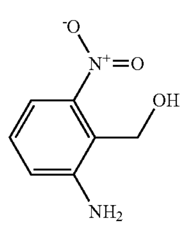 | (2-amino-6-nitrophenyl)methanol |
| 01033 | 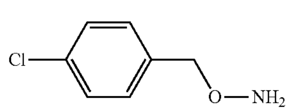 | O-(4-chlorobenzyl)hydroxylamine |

TABLE 7-continued

| Cmpd # | Structure | Name |
| --- | --- | --- |
| 01039 | 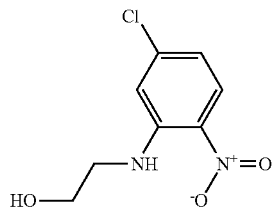 | 2-(5-chloro-2-nitrophenylamino)ethanol |
| 01051 | 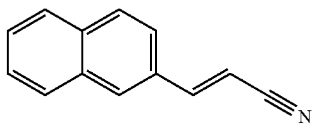 [SMILES: N#C/C=C/c1ccc2ccccc2c1] | (E)-3-(naphthalen-2-yl)acrylonitrile |
| 01056 | 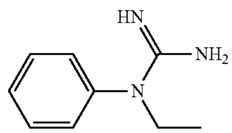 | 1-ethyl-1-phenylguanidine |
| 01059 | 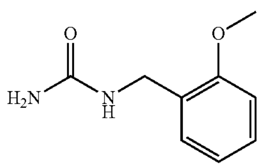 | 1-(2-methoxybenzyl)urea |
| 01062 | 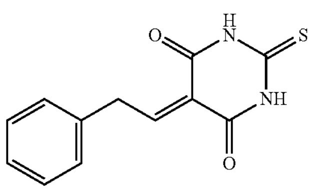 [SMILES: O=C1NC(=S)NC(=O)C1=CCc1ccccc1] | 5-(2-phenylethylidene)-2-thioxodihydropyrimidine-4,6(1H,5H)-dione |
| 01065 | 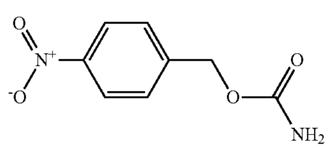 | 4-nitrobenzyl carbamate |
| 01070 | 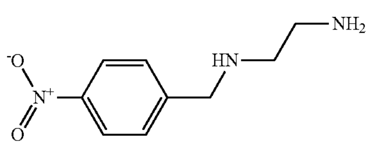 | N1-(4-nitrobenzyl)ethane-1,2-diamine |
| 01076 | 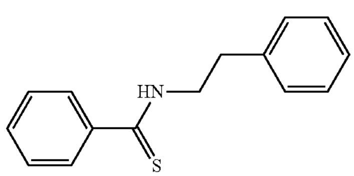 [SMILES: S=C(NCCc1ccccc1)c1ccccc1] | N-phenethylbenzothioamide |
| 01077 | 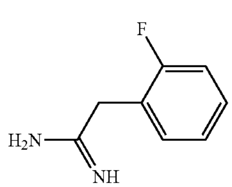 [SMILES: N=C(N)Cc1ccccc1F] | 2-(2-fluorophenyl)acetimidamide |

TABLE 7-continued

| Cmpd # | Structure | Name |
| --- | --- | --- |
| 01081 | 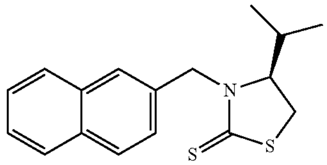 [SMILES: CC(C)[C@H]1CSC(=S)N1Cc1ccc2ccccc2c1] | (S)-4-isopropyl-3-(naphthalen-2-ylmethyl)-thiazolidine-2-thione |
| 01083 | 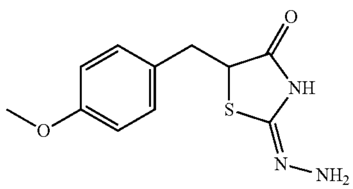 [SMILES: COc1ccc(CC2S/C(=N/N)NC2=O)cc1] | (E)-2-hydrazono-5-(4-methoxybenzyl)thiazolidin-4-one |
| 01088 | 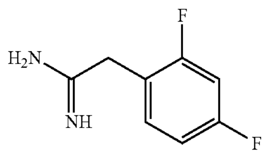 [SMILES: N=C(N)Cc1ccc(F)cc1F] | 2-(2,4-difluorophenyl)acetimidamide |
| 01099 | 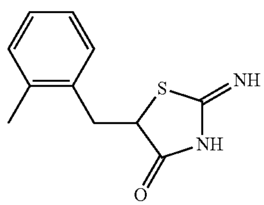 | 2-imino-5-(2-methylbenzyl)thiazolidin-4-one |
| 01100 | 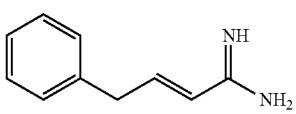 | (E)-4-phenylbut-2-enimidamide |
| 01101 | 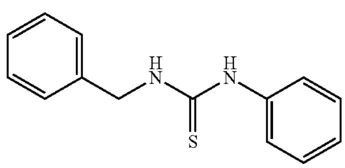 [SMILES: S=C(NCc1ccccc1)Nc1ccccc1] | 1-benzyl-3-phenylthiourea |
| 01107 | 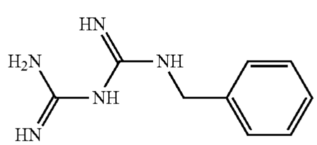 [SMILES: N=C(N)NC(=N)NCc1ccccc1] | N-(benzyl)imidodicarbonimidic diamide |
| 01116 | 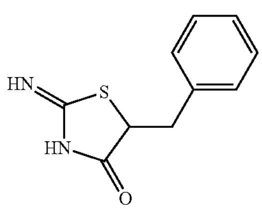 [SMILES: N=C1NC(=O)C(Cc2ccccc2)S1] | 5-benzyl-2-iminothiazolidin-4-one |
| 01131 | 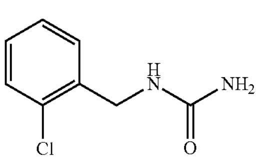 [SMILES: NC(=O)NCc1ccccc1Cl] | 1-(2-chlorobenzyl)urea |

TABLE 7-continued

| Cmpd # | Structure | Name |
|---|---|---|
| 01138 | 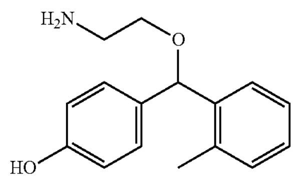 [SMILES: Cc1ccccc1C(OCCN)c1ccc(O)cc1] | 4-((2-aminoethoxy)(o-tolyl)methyl)phenol |
| 01139 | 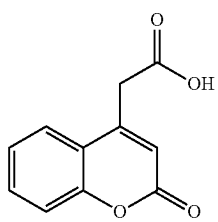 [SMILES: O=C(O)Cc1cc(=O)oc2ccccc12] | 2-(2-oxo-2H-chromen-4-yl)acetic acid |
| 01140 | 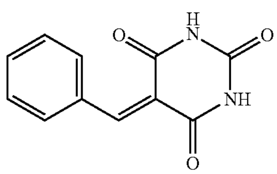 [SMILES: O=C1NC(=O)C(=Cc2ccccc2)C(=O)N1] | 5-benzylidenepyrimidine-2,4,6(1H,3H,5H)-trione |
| 01144 | 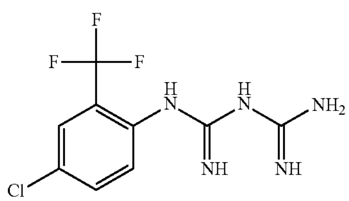 [SMILES: N=C(N)NC(=N)Nc1ccc(Cl)cc1C(F)(F)F] | N-(2-trifluromethyl-4-chloro)imidodicarbonimidic diamide |
| 01145 | 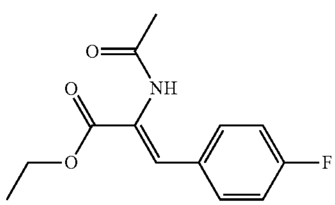 [SMILES: CCOC(=O)/C(=C/c1ccc(F)cc1)NC(C)=O] | (Z)-ethyl 2-acetamido-3-(4-fluorophenyl)acrylate |
| 01149 | 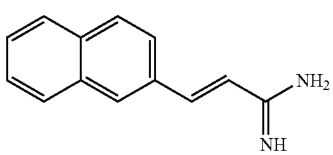 [SMILES: N=C(N)/C=C/c1ccc2ccccc2c1] | (E)-3-(naphthalen-2-yl)acrylimidamide |
| 01151 | 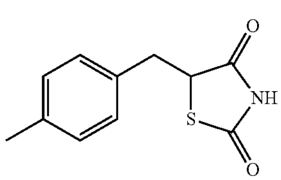 | 5-(4-methylbenzyl)thiazolidine-2,4-dione |
| 01156 | 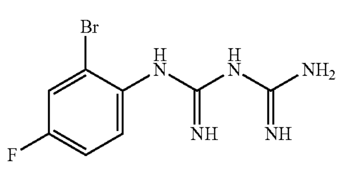 [SMILES: N=C(N)NC(=N)Nc1ccc(F)cc1Br] | N-(2-bromo-4-fluoro)imidodicarbonimidic diamide |

TABLE 7-continued

| Cmpd # | Structure | Name |
| --- | --- | --- |
| 01168 | 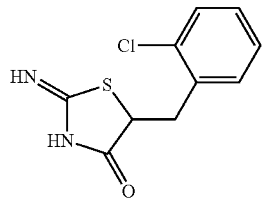 [SMILES: N=C1NC(=O)C(Cc2ccccc2Cl)S1] | 5-(2-chlorobenzyl)-2-iminothiazolidin-4-one |
| 01170 | 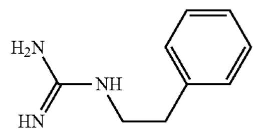 [SMILES: N=C(N)NCCc1ccccc1] | 1-phenethylguanidine |
| 01174 | 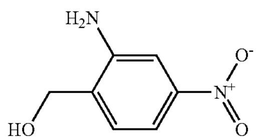 [SMILES: Nc1cc([N+](=O)[O-])ccc1CO] | (2-amino-4-nitrophenyl)methanol |
| 01177 | 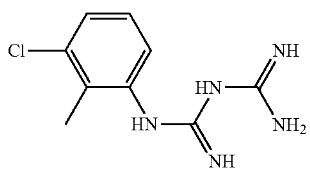 | N-(2-methyl-3-chloro)imidodicarbonimidic diamide |
| 01193 | 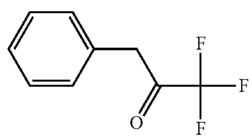 [SMILES: O=C(Cc1ccccc1)C(F)(F)F] | 1,1,1-trifluoro-3-phenylpropan-2-one |
| 01197 | 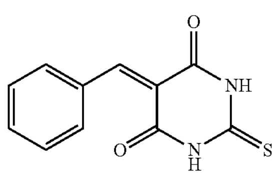 [SMILES: O=C1NC(=S)NC(=O)C1=Cc1ccccc1] | 5-benzylidene-2-thioxodihydropyrimidine-4,6(1H,5H)-dione |
| 01209 | 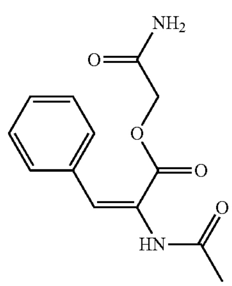 [SMILES: CC(=O)N/C(=C/c1ccccc1)C(=O)OCC(N)=O] | (E)-2-amino-2-oxoethyl 2-acetamido-3-phenylacrylate |
| 01210 | 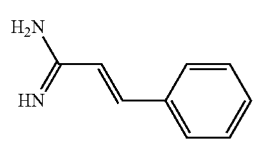 [SMILES: N=C(N)/C=C/c1ccccc1] | cinnamimidamide |
| 01217 | 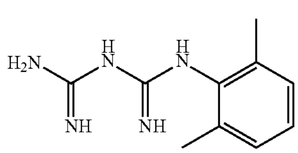 | N-(2,6-dimethyl)imidodicarbonimidic diamide |

TABLE 7-continued

| Cmpd # | Structure | Name |
| --- | --- | --- |
| 01218 | 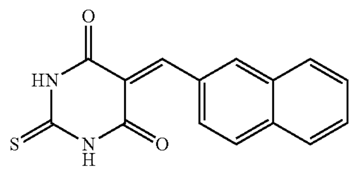 [SMILES: O=C1NC(=S)NC(=O)C1=Cc1ccc2ccccc2c1] | 5-(naphthalen-2-ylmethylene)-2-thioxodi-hydropyrimidine-4,6(1H,5H)-dione |
| 01229 | 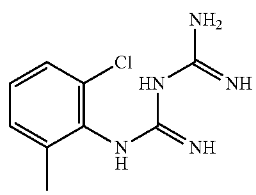 | N-(2-methyl-6-chloro)imidodicarbonimidic diamide |
| 01231 | 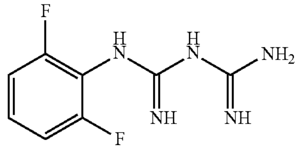 [SMILES: N=C(N)NC(=N)Nc1c(F)cccc1F] | N-(2,6-difluorophenyl) imidodicarbonimidic diamide |
| 01248 | 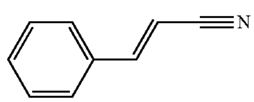 | cinnamonitrile |

TABLE 8

| Cmpd # | Structure | Name |
| --- | --- | --- |
| 00347 | 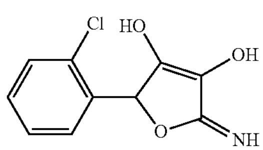 [SMILES: N=C1OC(c2ccccc2Cl)C(O)=C1O] | 2-(2-chlorophenyl)-5-imino-2,5-dihydrofuran-3,4-diol |
| 00356 | 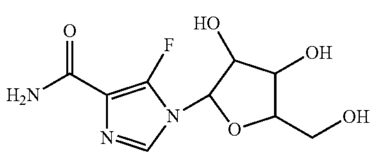 [SMILES: NC(=O)c1ncn(C2OC(CO)C(O)C2O)c1F] | 1-(3,4-dihydroxy-5-(hydroxymethyl)-tetrahydrofuran-2-yl)-5-fluoro-1H-imidazole-4-carboxamide |
| 00871 | 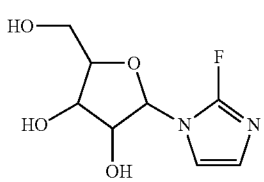 [SMILES: OCC1OC(n2ccnc2F)C(O)C1O] | 2-(2-fluoro-1H-imidazol-1-yl)-5-(hydroxyl-methyl)tetrahydrofuran-3,4-diol |
| 01042 | 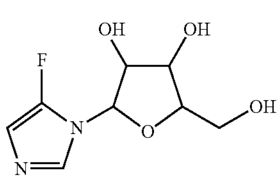 [SMILES: OCC1OC(n2cncc2F)C(O)C1O] | 2-(5-fluoro-1H-imidazol-1-yl)-5-(hydroxymethyl) tetrahydrofuran-3,4-diol |

TABLE 8-continued

| Cmpd # | Structure | Name |
|---|---|---|
| 01111 | 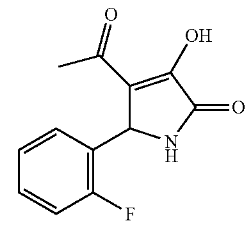 [SMILES: CC(=O)C1=C(O)C(=O)NC1c1ccccc1F] | 4-acetyl-5-(2-fluorophenyl)-3-hydroxy-1H-pyrrol-2(5H)-one |
| 01150 | 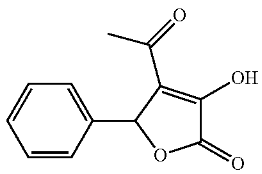 [SMILES: CC(=O)C1=C(O)C(=O)OC1c1ccccc1] | 4-acetyl-3-hydroxy-5-phenylfuran-2(5H)-one |
| 01163 | 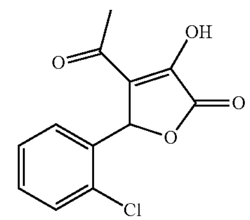 [SMILES: CC(=O)C1=C(O)C(=O)OC1c1ccccc1Cl] | 4-acetyl-5-(2-chlorophenyl)-3-hydroxy-1H-pyrrol-2(5H)-one |
| 01187 | 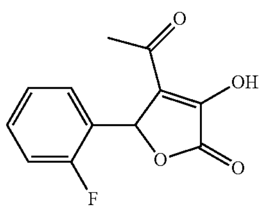 [SMILES: CC(=O)C1=C(O)C(=O)OC1c1ccccc1F] | 4-acetyl-5-(2-fluorophenyl)-3-hydroxyfuran-2(5H)-one |
| 01198 | 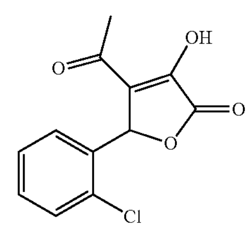 [SMILES: CC(=O)C1=C(O)C(=O)OC1c1ccccc1Cl] | 4-acetyl-5-(2-chlorophenyl)-3-hydroxyfuran-2(5H)-one |
| 01226 | 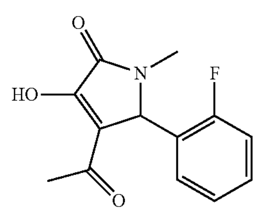 [SMILES: CC(=O)C1=C(O)C(=O)N(C)C1c1ccccc1F] | 4-acetyl-5-(2-fluorophenyl)-3-hydroxy-1-methyl-1H-pyrrol-2(5H)-one |
| 01240 | 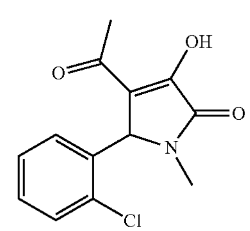 [SMILES: CC(=O)C1=C(O)C(=O)N(C)C1c1ccccc1Cl] | 4-acetyl-5-(2-chlorophenyl)-3-hydroxy-1-methyl-1H-pyrrol-2(5H)-one |

TABLE 9

| Cmpd # | Structure | Name |
|---|---|---|
| 01465 | 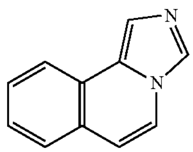 [SMILES: c1ccc2c(c1)ccn1cncc21] | imidazo[5,1-a]isoquinoline |
| 01469 | 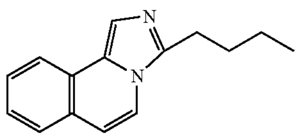 [SMILES: CCCCc1ncc2c3ccccc3ccn12] | 3-butylimidazo[5,1-a]isoquinoline |
| 01481 | 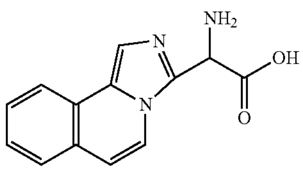 [SMILES: NC(C(=O)O)c1ncc2c3ccccc3ccn12] | 2-amino-2-(imidazo[5,1-a]isoquinolin-3-yl)acetic acid |

TABLE 9-continued

| Cmpd # | Structure | Name |
|---|---|---|
| 01482 | 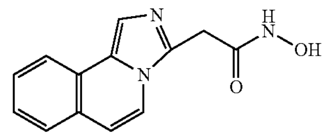 [SMILES: O=C(Cc1ncc2c3ccccc3ccn12)NO] | N-hydroxy-2-(imidazo[5,1-a]isoquinolin-3-yl)acetamide |
| 01483 | 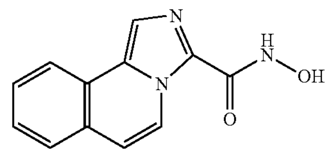 [SMILES: O=C(NO)c1ncc2c3ccccc3ccn12] | N-hydroxyimidazo[5,1-a]isoquinoline-3-carboxamide |

TABLE 10

| Cmpd # | Structure | Name |
|---|---|---|
| 01386 | 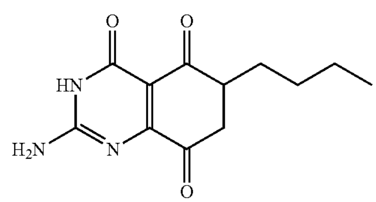 [SMILES: CCCCC1CC(=O)c2nc(N)[nH]c(=O)c2C1=O] | 2-amino-6-butyl-6,7-dihydroquinazoline-4,5,8(3H)-trione |
| 01394 | 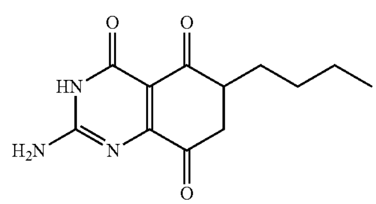 [SMILES: CCCCC1CC(=O)c2nc(N)[nH]c(=O)c2C1=O] | 2-amino-6-butyl-6,7-dihydroquinazoline-4,5,8(3H)-trione |
| 01395 | 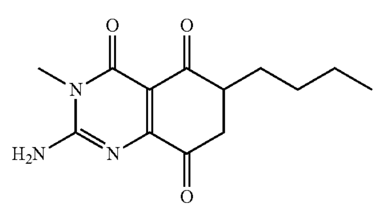 [SMILES: CCCCC1CC(=O)c2nc(N)n(C)c(=O)c2C1=O] | 2-amino-6-butyl-3-methyl-6,7-dihydroquinazoline-4,5,8(3H)-trione |
| 01396 | 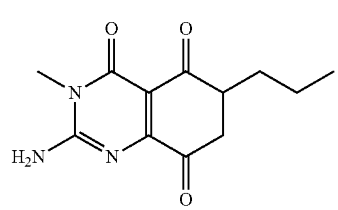 [SMILES: CCCC1CC(=O)c2nc(N)n(C)c(=O)c2C1=O] | 2-amino-3-methyl-6-propyl-6,7-dihydroquinazoline-4,5,8(3H)-trione |

TABLE 10-continued

| Cmpd # | Structure | Name |
|---|---|---|
| 01398 | 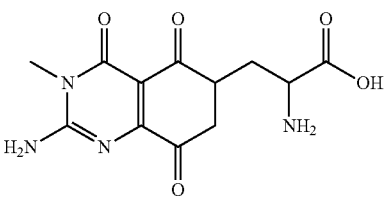 [SMILES: Cn1c(N)nc2c(c1=O)C(=O)C(CC(N)C(=O)O)CC2=O] | 2-amino-3-(2-amino-3-methyl-4,5,8-trioxo-3,4,5,6,7,8-hexahydroquinazolin-6-yl)propanoic acid |
| 01400 | 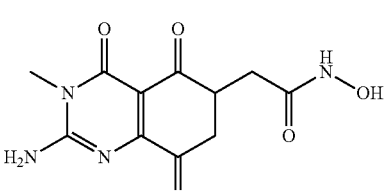 | 2-(2-amino-3-methyl-4,5,8-trioxo-3,4,5,6,7,8-hexahydroquinazolin-6-yl)-N-hydroxyacetamide |
| 01401 | 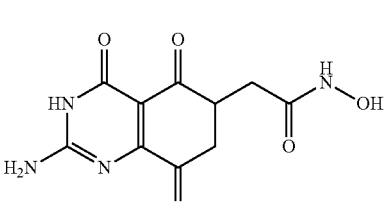 | 2-(2-amino-4,5,8-trioxo-3,4,5,6,7,8-hexahydroquinazolin-6-yl)-N-hydroxyacetamide |
| 01406 | 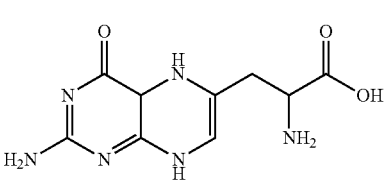 [SMILES: NC1=NC(=O)C2NC(CC(N)C(=O)O)=CNC2=N1] | 2-amino-3-(2-amino-4-oxo-4,4a,5,8-tetrahydropteridin-6-yl)propanoic acid |
| 01411 | 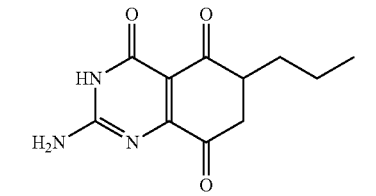 | 2-amino-6-propyl-6,7-dihydroquinazoline-4,5,8(3H)-trione |
| 01478 | 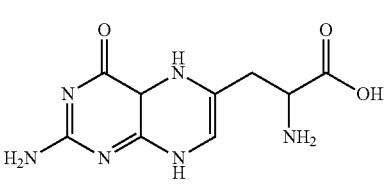 [SMILES: NC1=NC(=O)C2NC(CC(N)C(=O)O)=CNC2=N1] | 2-amino-3-(2-amino-4-oxo-4,4a,5,8-tetrahydropteridin-6-yl)propanoic acid |
| 01480 | 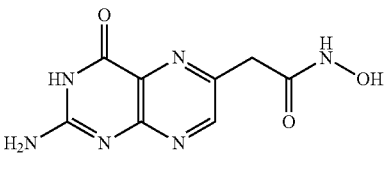 | 2-(2-amino-4-oxo-3,4-dihydropteridin-6-yl)-N-hydroxyacetamide |
| 01484 | 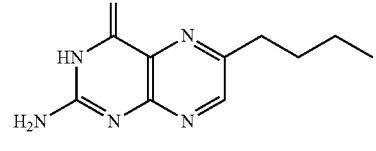 | 2-amino-6-butylpteridin-4(3H)-one |

TABLE 10-continued

| Cmpd # | Structure | Name |
| --- | --- | --- |
| 01485 | 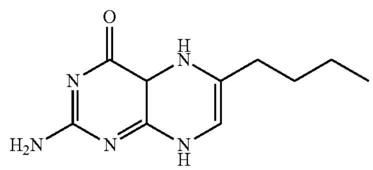 [SMILES: CCCCC1=CNC2=NC(N)=NC(=O)C2N1] | 2-amino-6-butyl-4a,5-dihydropteridin-4(8H)-one |
| 01486 | 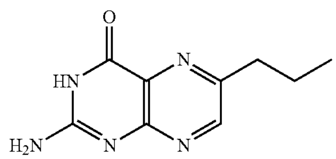 | 2-amino-6-propylpteridin-4(3H)-one |
| 01487 | 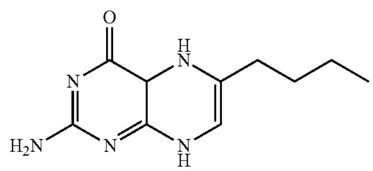 [SMILES: CCCCC1=CNC2=NC(N)=NC(=O)C2N1] | 2-amino-6-butyl-4a,5-dihydropteridin-4(8H)-one |
| 01488 | 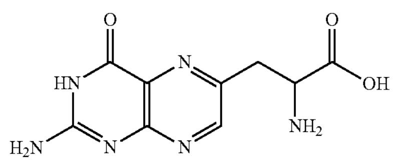 [SMILES: Nc1nc2ncc(CC(N)C(=O)O)nc2c(=O)[nH]1] | 2-amino-3-(2-amino-4-oxo-3,4-dihydropteridin-6-yl)propanoic acid |

TABLE 11

| Cmpd # | Structure | Name |
| --- | --- | --- |
| 00027 | 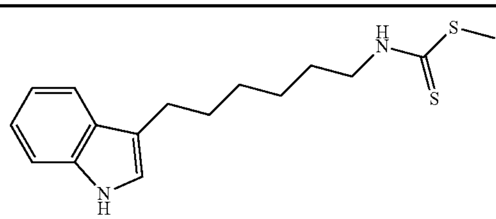 | methyl 6-(1H-indol-3-yl)hexylcarbamodithioate |
| 00028 | 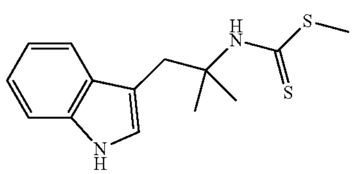 [SMILES: CSC(=S)NC(C)(C)Cc1c[nH]c2ccccc12] | methyl 1-(1H-indol-3-yl)-2-methylpropan-2-ylcarbamodithioate |
| 00063 | 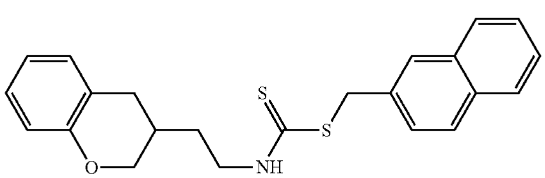 [SMILES: S=C(NCCC1COc2ccccc2C1)SCc1ccc2ccccc2c1] | naphthalen-2-ylmethyl 2-(chroman-3-yl)ethylcarbamodithioate |
| 00064 | 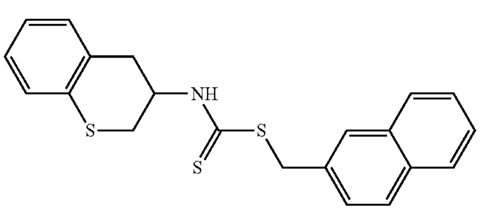 [SMILES: S=C(NC1CSc2ccccc2C1)SCc1ccc2ccccc2c1] | naphthalen-2-ylmethyl thiochroman-3-ylcarbamodithioate |

TABLE 11-continued
| Cmpd # | Structure | Name |
|---|---|---|
| 00141 | 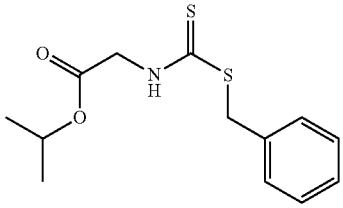 [SMILES: CC(C)OC(=O)CNC(=S)SCc1ccccc1] | isopropyl 2-(benzylthio-carbonothioylamino)acetate |
| 00142 | 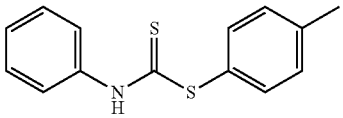 [SMILES: Cc1ccc(SC(=S)Nc2ccccc2)cc1] | p-tolyl phenylcarbamodithioate |
| 00144 | 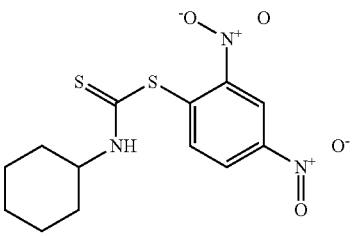 | 2,4-dinitrophenyl cyclohexylcarbamodithioate |
| 00145 | 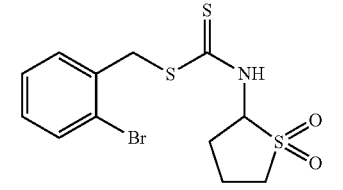 [SMILES: O=S1(=O)CCCC1NC(=S)SCc1ccccc1Br] | 2-bromobenzyl sulpholan-2-yl carbamodithioate |
| 00146 | 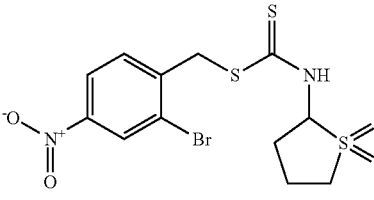 | 2-bromo-4-nitrobenzyl sulpholan-2-yl carbamodithioate |
| 00147 | 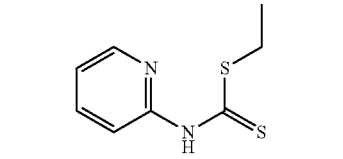 | ethyl pyridin-2-ylcarbamodithioate |
| 00149 | 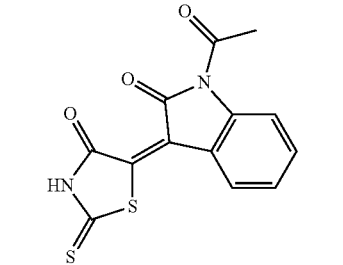 [SMILES: CC(=O)N1C(=O)/C(=C2/SC(=S)NC2=O)c2ccccc21] | (E)-5-(1-acetyl-2-oxoindolin-3-ylidene)-2-thioxothiazolidin-4-one |

TABLE 11-continued

| Cmpd # | Structure | Name |
| --- | --- | --- |
| 00151 | 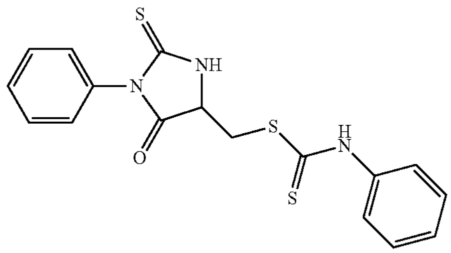 [SMILES: O=C1C(CSC(=S)Nc2ccccc2)NC(=S)N1c1ccccc1] | (5-oxo-1-phenyl-2-thioxoimidazolidin-4-yl)methyl phenylcarbamodithioate |
| 00152 | 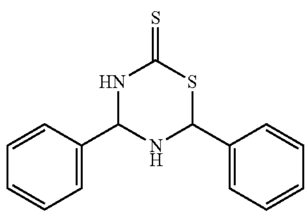 [SMILES: S=C1NC(c2ccccc2)NC(c2ccccc2)S1] | 4,6-diphenyl-1,3,5-thiadiazinane-2-thione |
| 00167 | 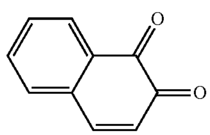 [SMILES: O=C1C=Cc2ccccc2C1=O] | naphthalene-1,2-dione |
| 00168 | 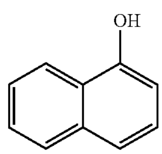 [SMILES: Oc1cccc2ccccc12] | naphthalen-1-ol |
| 00210 | 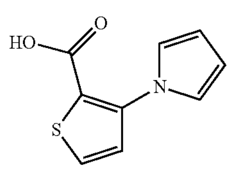 [SMILES: O=C(O)c1sccc1-n1cccc1] | 3-(1H-pyrrol-1-yl)thiophene-2-carboxylic acid |
| 00215 | 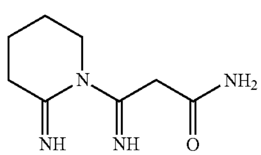 [SMILES: N=C1CCCCN1C(=N)CC(N)=O] | 3-imino-3-(2-iminopiperidin-1-yl)-propanamide |
| 00216 | 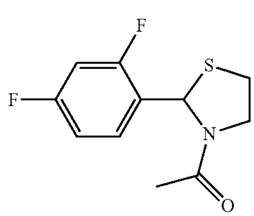 [SMILES: CC(=O)N1CCSC1c1ccc(F)cc1F] | 1-(2-(2,4-difluorophenyl)thiazolidin-3-yl)ethanone |
| 00222 | 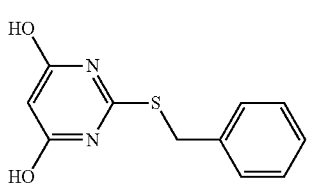 [SMILES: Oc1cc(O)nc(SCc2ccccc2)n1] | 2-(benzylthio)pyrimidine-4,6-diol |

TABLE 11-continued

| Cmpd # | Structure | Name |
| --- | --- | --- |
| 00226 | 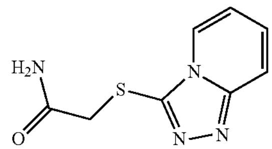 [SMILES: NC(=O)CSc1nnc2ccccn12] | 2-([1,2,4]triazolo[4,3-a]pyridin-3-ylthio)acetamide |
| 00230 | 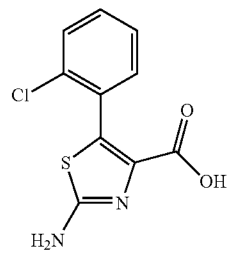 [SMILES: Nc1nc(C(=O)O)c(-c2ccccc2Cl)s1] | 2-amino-5-(2-chlorophenyl)thiazole-4-carboxylic acid |
| 00252 | 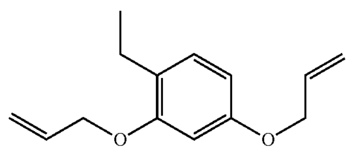 [SMILES: C=CCOc1ccc(CC)c(OCC=C)c1] | 2,4-bis(allyloxy)-1-ethylbenzene |
| 00254 | 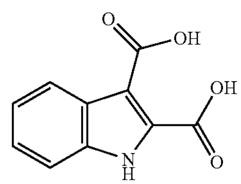 [SMILES: O=C(O)c1[nH]c2ccccc2c1C(=O)O] | 1H-indole-2,3-dicarboxylic acid |
| 00256 | 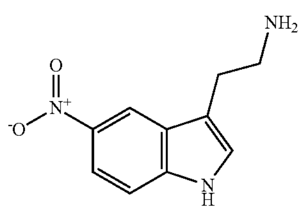 | 2-(5-nitro-1H-indol-3-yl)ethanamine |
| 00267 | 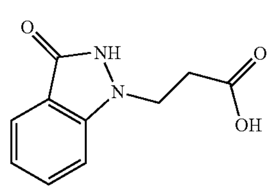 [SMILES: O=C(O)CCn1[nH]c(=O)c2ccccc21] | 3-(3-oxo-2,3-dihydro-1H-indazol-1-yl)propanoic acid |
| 00269 | 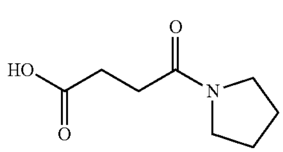 [SMILES: O=C(O)CCC(=O)N1CCCC1] | 4-oxo-4-(pyrrolidin-1-yl)butanoic acid |
| 00271 | 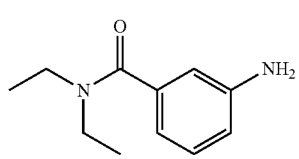 | 3-amino-N,N-diethylbenzamide |

TABLE 11-continued

| Cmpd # | Structure | Name |
|---|---|---|
| 00272 | 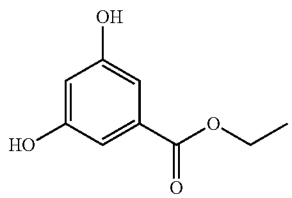 | ethyl 3,5-dihydroxybenzoate |
| 00281 | 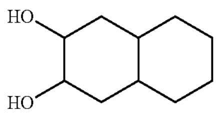 [SMILES: OC1CC2CCCCC2CC1O] | decahydronaphthalene-2,3-diol |
| 00289 | 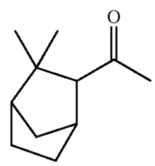 | 1-(3,3-dimethylbicyclo[2.2.1]heptan-2-yl)ethanone |
| 00300 | 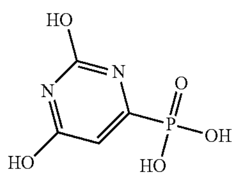 [SMILES: O=P(O)(O)c1cc(O)nc(O)n1] | 2,6-dihydroxypyrimidin-4-ylphosphonic acid |
| 00305 | 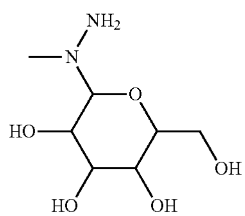 | 2-(hydroxymethyl)-6-(1-methylhydrazinyl)-tetrahydro-2H-pyran-3,4,5-triol |
| 00309 | 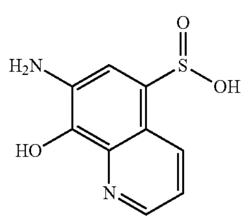 [SMILES: Nc1cc(S(=O)O)c2cccnc2c1O] | 7-amino-8-hydroxyquinoline-5-sulfinic acid |
| 00310 | 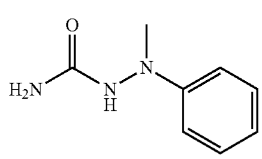 | 2-methyl-2-phenylhydrazinecarboxamide |
| 00311 | 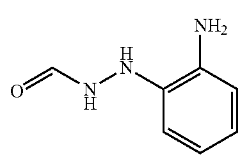 [SMILES: Nc1ccccc1NNC=O] | N'-(2-aminophenyl)formohydrazide |
| 00312 | 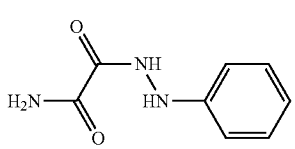 [SMILES: NC(=O)C(=O)NNc1ccccc1] | 2-oxo-2-(2-phenylhydrazinyl)acetamide |

TABLE 11-continued

| Cmpd # | Structure | Name |
|---|---|---|
| 00319 | 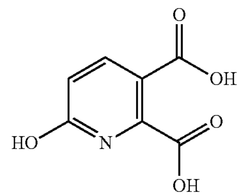 [SMILES: O=C(O)c1ccc(O)nc1C(=O)O] | 6-hydroxypyridine-2,3-dicarboxylic acid |
| 00320 | 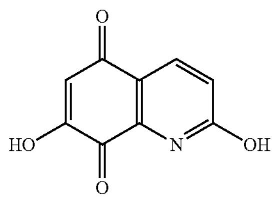 [SMILES: O=C1C=C(O)C(=O)c2nc(O)ccc21] | 2,7-dihydroxyquinoline-5,8-dione |
| 00324 | 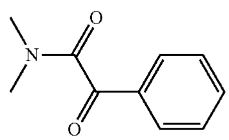 | N,N-dimethyl-2-oxo-2-phenylacetamide |
| 00332 | 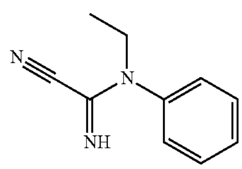 | N-ethyl-N-phenylcarbamimidoyl cyanide |
| 00334 | 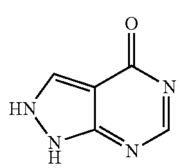 | 1H-pyrazolo[3,4-d]pyrimidin-4(2H)-one |
| 00337 | 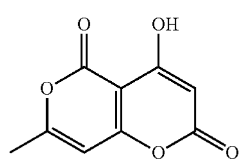 | 4-hydroxy-7-methylpyrano[4,3-b]pyran-2,5-dione |
| 00342 | 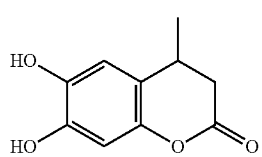 | 6,7-dihydroxy-4-methylchroman-2-one |
| 00343 | 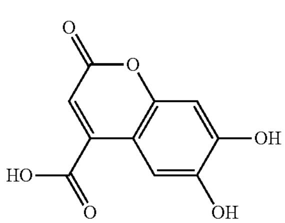 [SMILES: O=C(O)c1cc(=O)oc2cc(O)c(O)cc12] | 6,7-dihydroxy-2-oxo-2H-chromene-4-carboxylic acid |

TABLE 11-continued

| Cmpd # | Structure | Name |
|---|---|---|
| 00345 | 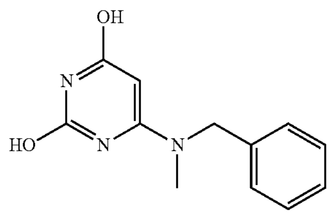 [SMILES: CN(Cc1ccccc1)c1cc(O)nc(O)n1] | 6-(benzyl(methyl)amino)pyrimidine-2,4-diol |
| 00348 | 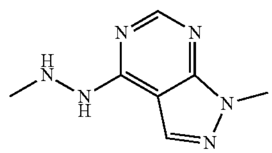 | 1-methyl-4-(2-methylhydrazinyl)-1H-pyrazolo[3,4-d]pyrimidine |
| 00352 | 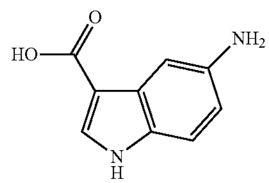 [SMILES: Nc1ccc2[nH]cc(C(=O)O)c2c1] | 5-amino-1H-indole-3-carboxylic acid |
| 00363 | 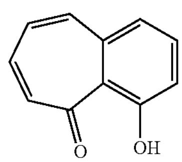 [SMILES: O=c1ccccc2cccc(O)c12] | (6Z,8Z)-4-hydroxy-5H-benzo[7]annulen-5-one |
| 00364 | 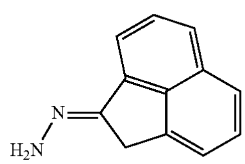 [SMILES: N/N=C1\Cc2cccc3cccc1c23] | (E)-acenaphthylen-1(2H)-ylidenehydrazine |
| 00366 | 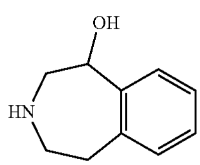 [SMILES: OC1CNCCc2ccccc21] | 2,3,4,5-tetrahydro-1H-benzo[d]azepin-1-ol |
| 00367 | 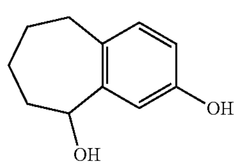 [SMILES: Oc1ccc2c(c1)C(O)CCCC2] | 6,7,8,9-tetrahydro-5H-benzo[7]annulene-2,9-diol |
| 00368 | 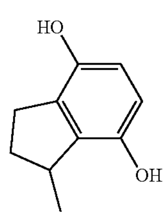 | 1-methyl-2,3-dihydro-1H-indene-4,7-diol |
| 00378 | 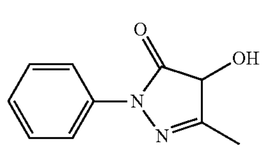 | 4-hydroxy-3-methyl-1-phenyl-1H-pyrazol-5(4H)-one |

TABLE 11-continued

| Cmpd # | Structure | Name |
| --- | --- | --- |
| 00380 | 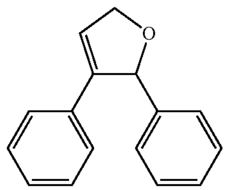 [SMILES: C1=C(c2ccccc2)C(c2ccccc2)OC1] | 2,3-diphenyl-2,5-dihydrofuran |
| 00382 | 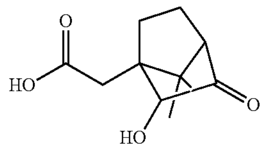 | 2-(2-hydroxy-7,7-dimethyl-3-oxobicyclo[2.2.1]heptan-1-yl)acetic acid |
| 00385 | 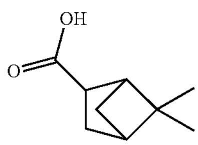 | 5,5-dimethylbicyclo[2.1.1]hexane-2-carboxylic acid |
| 00396 | 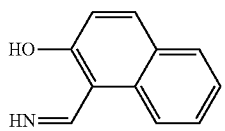 [SMILES: N=Cc1c(O)ccc2ccccc12] | 1-(iminomethyl)naphthalen-2-ol |
| 00398 | 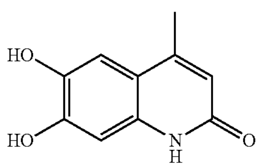 | 6,7-dihydroxy-4-methylquinolin-2(1H)-one |
| 00464 | 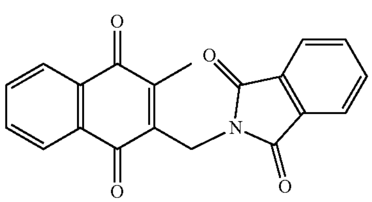 [SMILES: CC1=C(CN2C(=O)c3ccccc3C2=O)C(=O)c2ccccc2C1=O] | 2-((3-methyl-1,4-dioxo-1,4-dihydronaphthalen-2-yl)methyl)isoindoline-1,3-dione |
| 00477 | 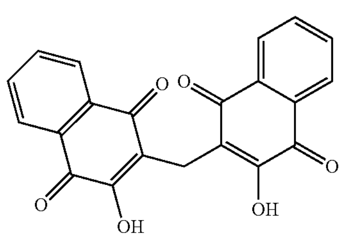 [SMILES: O=C1C(O)=C(CC2=C(O)C(=O)c3ccccc3C2=O)C(=O)c2ccccc21] | 3,3'-methylenebis(2-hydroxynaphthalene-1,4-dione) |
| 00507 | 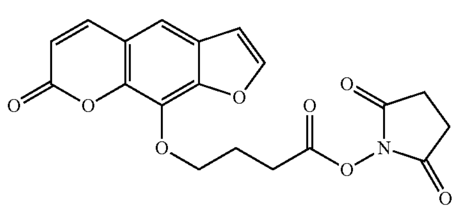 [SMILES: O=C(CCCOc1c2occc2cc2ccc(=O)oc12)ON1C(=O)CCC1=O] | 2,5-dioxopyrrolidin-1-yl 4-(7-oxo-7H-furo[3,2-g]chromen-9-yloxy)butanoate |

TABLE 11-continued

| Cmpd # | Structure | Name |
|---|---|---|
| 00515 | 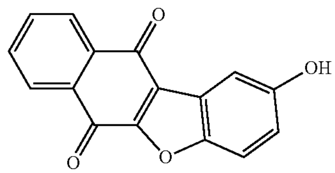 [SMILES: O=C1c2ccccc2C(=O)c2c1oc1ccc(O)cc21] | 2-hydroxybenzo[d]naphtho[2,3-b]furan-6,11-dione |
| 00516 | 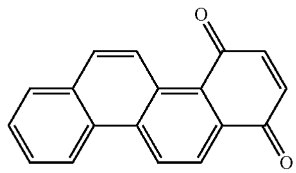 [SMILES: O=C1C=CC(=O)c2c1ccc1c2ccc2ccccc21] | chrysene-1,4-dione |
| 00561 | 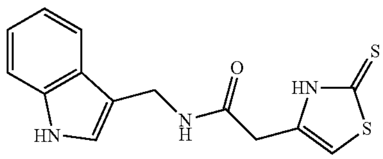 [SMILES: O=C(Cc1csc(=S)[nH]1)NCc1c[nH]c2ccccc12] | N-((1H-indol-3-yl)methyl)-2-(2-thioxo-2,3-dihydrothiazol-4-yl)acetamide |
| 00578 | 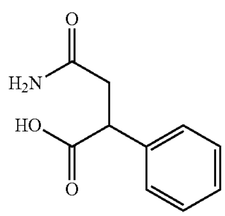 [SMILES: NC(=O)CC(C(=O)O)c1ccccc1] | 4-amino-4-oxo-2-phenylbutanoic acid |
| 00586 | 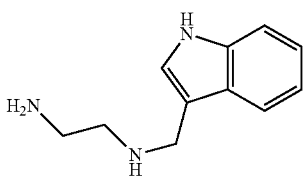 [SMILES: NCCNCc1c[nH]c2ccccc12] | N1-((1H-indol-3-yl)methyl)ethane-1,2-diamine |
| 00605 | 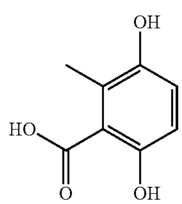 | 3,6-dihydroxy-2-methylbenzoic acid |
| 00608 | 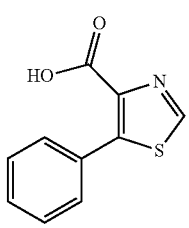 [SMILES: O=C(O)c1ncsc1-c1ccccc1] | 5-phenylthiazole-4-carboxylic acid |
| 00610 | 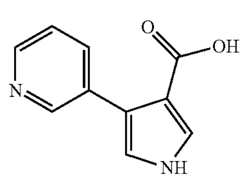 [SMILES: O=C(O)c1c[nH]cc1-c1cccnc1] | 4-(pyridin-3-yl)-1H-pyrrole-3-carboxylic acid |

TABLE 11-continued

| Cmpd # | Structure | Name |
|---|---|---|
| 00622 | 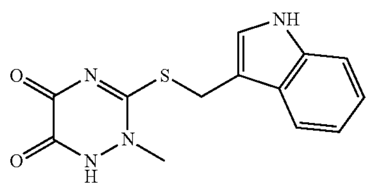 [SMILES: Cn1[nH]c(=O)c(=O)nc1SCc1c[nH]c2ccccc12] | 3-((1H-indol-3-yl)methylthio)-2-methyl-1,2-dihydro-1,2,4-triazine-5,6-dione |
| 00623 | 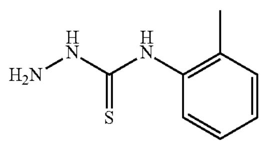 | N-o-tolylhydrazinecarbothioamide |
| 00628 | 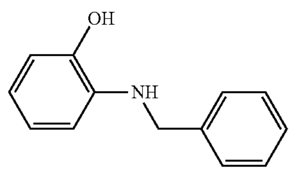 [SMILES: Oc1ccccc1NCc1ccccc1] | 2-(benzylamino)phenol |
| 00645 | 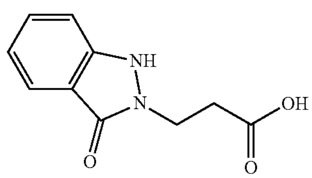 [SMILES: O=C(O)CCn1[nH]c2ccccc2c1=O] | 3-(3-oxo-1H-indazol-2(3H)-yl)propanoic acid |
| 00658 | 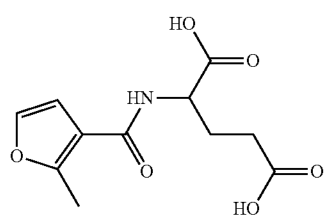 [SMILES: Cc1occc1C(=O)NC(CCC(=O)O)C(=O)O] | 2-(2-methylfuran-3-carboxamido)pentanedioic acid |
| 00663 | 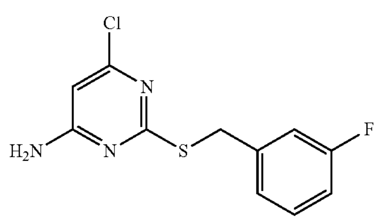 [SMILES: Nc1cc(Cl)nc(SCc2cccc(F)c2)n1] | 6-chloro-2-(3-fluorobenzylthio)pyrimidin-4-amine |
| 00669 | 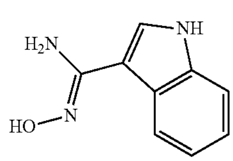 [SMILES: N/C(=N\O)c1c[nH]c2ccccc12] | (Z)-N'-hydroxy-1H-indole-3-carboximidamide |
| 00670 | 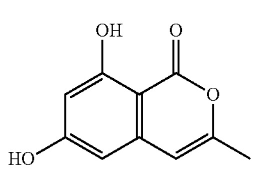 | 6,8-dihydroxy-3-methyl-1H-isochromen-1-one |

TABLE 11-continued

| Cmpd # | Structure | Name |
| --- | --- | --- |
| 00675 | 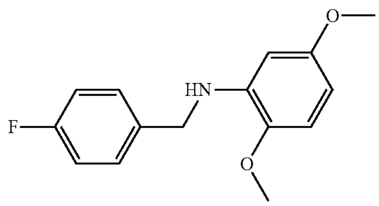 [SMILES: COc1ccc(OC)c(NCc2ccc(F)cc2)c1] | N-(4-fluorobenzyl)-2,5-dimethoxyaniline |
| 00681 | 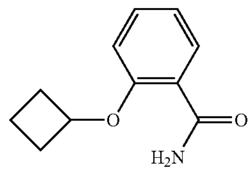 [SMILES: NC(=O)c1ccccc1OC1CCC1] | 2-cyclobutoxybenzamide |
| 00682 | 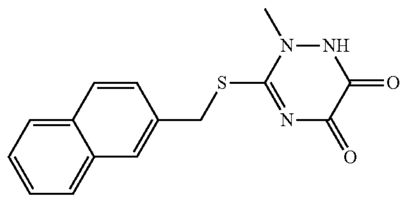 [SMILES: Cn1[nH]c(=O)c(=O)nc1SCc1ccc2ccccc2c1] | 2-methyl-3-(naphthalen-2-ylmethylthio)-1,2-dihydro-1,2,4-triazine-5,6-dione |
| 00685 | 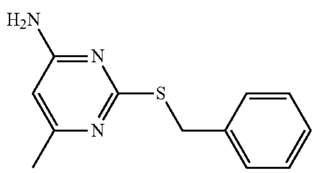 [SMILES: Cc1cc(N)nc(SCc2ccccc2)n1] | 2-(benzylthio)-6-methylpyrimidin-4-amine |
| 00690 | 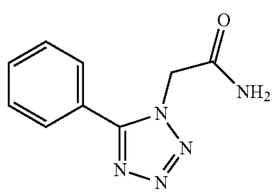 [SMILES: NC(=O)Cn1nnnc1-c1ccccc1] | 2-(5-phenyl-1H-tetrazol-1-yl)acetamide |
| 00692 | 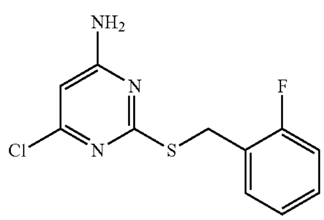 [SMILES: Nc1cc(Cl)nc(SCc2ccccc2F)n1] | 6-chloro-2-(2-fluorobenzylthio)pyrimidin-4-amine |
| 00700 | 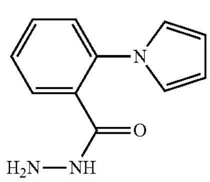 [SMILES: NNC(=O)c1ccccc1-n1cccc1] | 2-(1H-pyrrol-1-yl)benzohydrazide |
| 00701 | 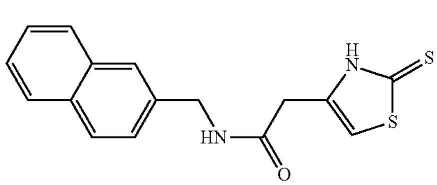 [SMILES: O=C(Cc1csc(=S)[nH]1)NCc1ccc2ccccc2c1] | N-(naphthalen-2-ylmethyl)-2-(2-thioxo-2,3-dihydrothiazol-4-yl)acetamide |

| Cmpd # | Structure | Name |
| --- | --- | --- |
| 00705 | 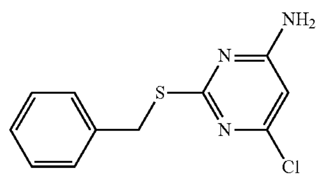 [SMILES: Nc1cc(Cl)nc(SCc2ccccc2)n1] | 2-(benzylthio)-6-chloropyrimidin-4-amine |
| 00707 | 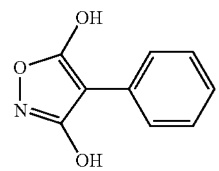 [SMILES: Oc1noc(O)c1-c1ccccc1] | 4-phenylisoxazole-3,5-diol |
| 00714 | 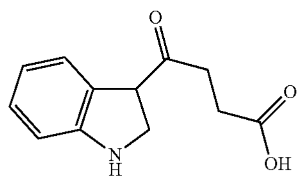 [SMILES: O=C(O)CCC(=O)C1CNc2ccccc21] | 4-(indolin-3-yl)-4-oxobutanoic acid |
| 00716 | 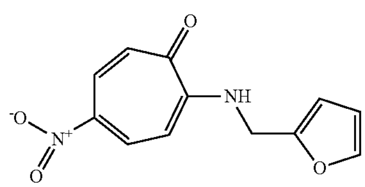 | (2E,4E,6Z)-2-(furan-2-ylmethylamino)-5-nitrocyclohepta-2,4,6-trienone |
| 00718 | 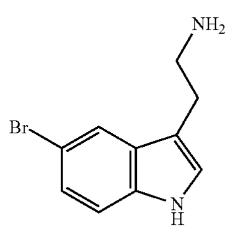 [SMILES: NCCc1c[nH]c2ccc(Br)cc12] | 2-(5-bromo-1H-indol-3-yl)ethanamine |
| 00727 | 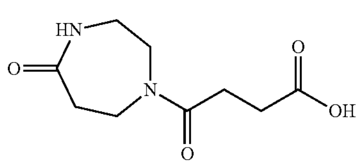 [SMILES: O=C(O)CCC(=O)N1CCNC(=O)CC1] | 4-oxo-4-(5-oxo-1,4-diazepan-1-yl)butanoic acid |
| 00740 | 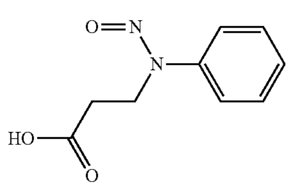 [SMILES: O=NN(CCC(=O)O)c1ccccc1] | 3-(nitroso(phenyl)amino)propanoic acid |
| 00746 | 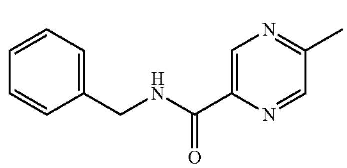 [SMILES: Cc1cnc(C(=O)NCc2ccccc2)cn1] | N-benzyl-5-methylpyrazine-2-carboxamide |

TABLE 11-continued

| Cmpd # | Structure | Name |
|---|---|---|
| 00750 | 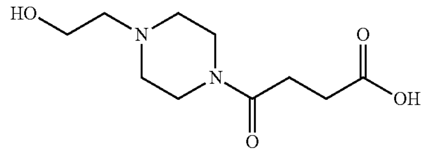 [SMILES: O=C(O)CCC(=O)N1CCN(CCO)CC1] | 4-(4-(2-hydroxyethyl)piperazin-1-yl)-4-oxobutanoic acid |
| 00751 | 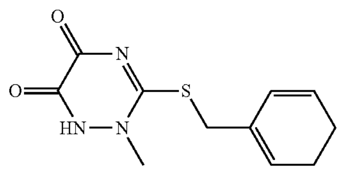 [SMILES: Cn1[nH]c(=O)c(=O)nc1SCC1=CCCC=C1] | 3-(cyclohexa-1,5-dienylmethylthio)-2-methyl-1,2-dihydro-1,2,4-triazine-5,6-dione |
| 00757 | 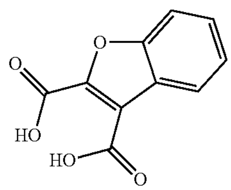 [SMILES: O=C(O)c1oc2ccccc2c1C(=O)O] | benzofuran-2,3-dicarboxylic acid |
| 00759 | 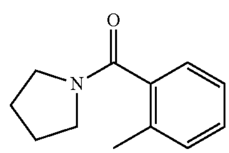 | pyrrolidin-1-yl(o-tolyl)methanone |
| 00768 | 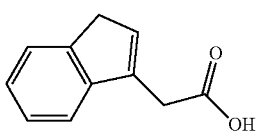 [SMILES: O=C(O)CC1=CCc2ccccc21] | 2-(1H-inden-3-yl)acetic acid |
| 00770 | 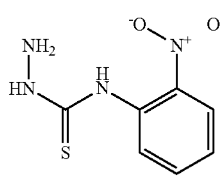 | N-(2-nitrophenyl)hydrazinecarbothioamide |
| 00777 | 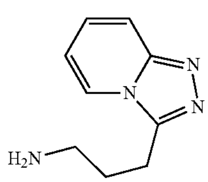 [SMILES: NCCCc1nnc2ccccn12] | 3-([1,2,4]triazolo[4,3-a]pyridin-3-yl)propan-1-amine |
| 00782 | 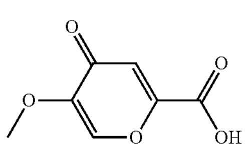 | 5-methoxy-4-oxo-4H-pyran-2-carboxylic acid |
| 00783 | 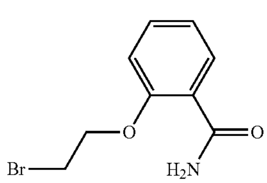 | 2-(2-bromoethoxy)benzamide |

TABLE 11-continued

| Cmpd # | Structure | Name |
|---|---|---|
| 00784 | 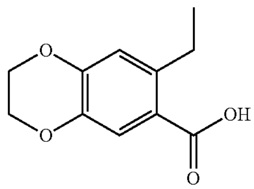 | 7-ethyl-2,3-dihydrobenzo[b][1,4]dioxine-6-carboxylic acid |
| 00793 | 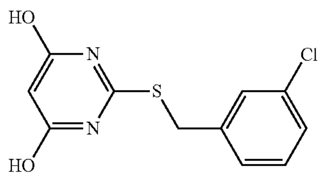 [SMILES: Oc1cc(O)nc(SCc2cccc(Cl)c2)n1] | 2-(3-chlorobenzylthio)pyrimidine-4,6-diol |
| 00797 | 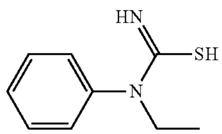 | N-ethyl-N-phenylcarbamimidothioic acid |
| 00799 | 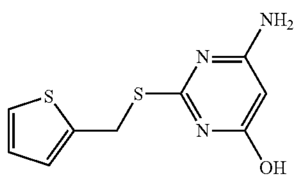 [SMILES: Nc1cc(O)nc(SCc2cccs2)n1] | 6-amino-2-(thiophen-2-ylmethylthio)pyrimidin-4-ol |
| 00803 | 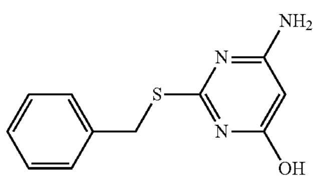 [SMILES: Nc1cc(O)nc(SCc2ccccc2)n1] | 6-amino-2-(benzylthio)pyrimidin-4-ol |
| 00805 | 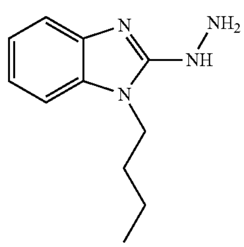 | 1-butyl-2-hydrazinyl-1H-benzo[d]imidazole |
| 00806 | 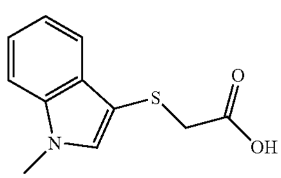 | 2-(1-methyl-1H-indol-3-ylthio)acetic acid |
| 00807 | 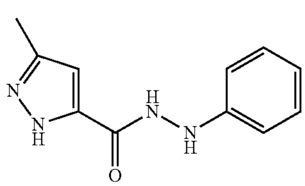 [SMILES: Cc1cc(C(=O)NNc2ccccc2)[nH]n1] | 3-methyl-N'-phenyl-1H-pyrazole-5-carbohydrazide |

TABLE 11-continued

| Cmpd # | Structure | Name |
|---|---|---|
| 00812 | 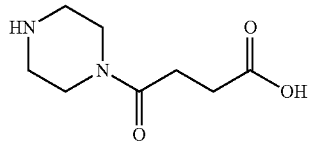 [SMILES: O=C(O)CCC(=O)N1CCNCC1] | 4-oxo-4-(piperazin-1-yl)butanoic acid |
| 00814 | 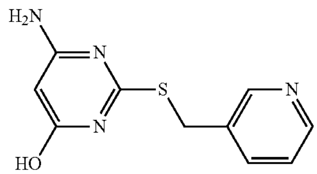 [SMILES: Nc1cc(O)nc(SCc2cccnc2)n1] | 6-amino-2-(pyridin-3-ylmethylthio)pyrimidin-4-ol |
| 00815 | 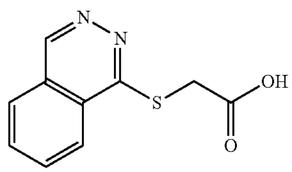 [SMILES: O=C(O)CSc1nncc2ccccc12] | 2-(phthalazin-1-ylthio)acetic acid |
| 00821 | 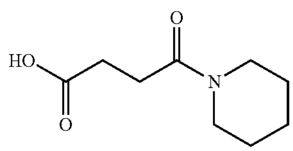 [SMILES: O=C(O)CCC(=O)N1CCCCC1] | 4-oxo-4-(piperidin-1-yl)butanoic acid |
| 00822 | 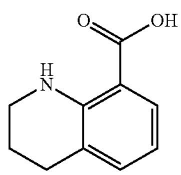 [SMILES: O=C(O)c1cccc2c1NCCC2] | 1,2,3,4-tetrahydroquinoline-8-carboxylic acid |
| 00824 | 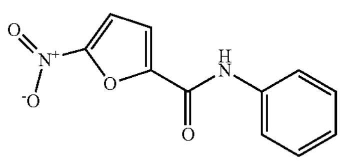 | 5-nitro-N-phenylfuran-2-carboxamide |
| 00837 | 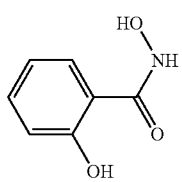 [SMILES: O=C(NO)c1ccccc1O] | N,2-dihydroxybenzamide |
| 00856 | 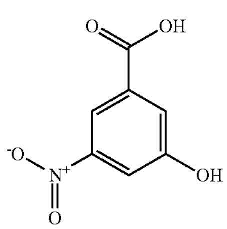 | 3-hydroxy-5-nitrobenzoic acid |
| 00858 | 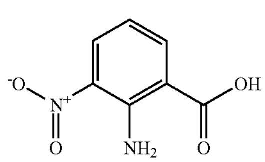 | 2-amino-3-nitrobenzoic acid |

TABLE 11-continued

| Cmpd # | Structure | Name |
| --- | --- | --- |
| 00875 | 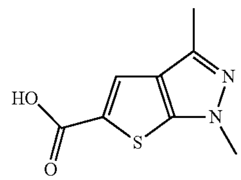 | 1,3-dimethyl-1H-thieno[2,3-c]pyrazole-5-carboxylic acid |
| 00877 | 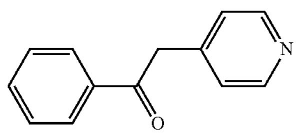 [SMILES: O=C(Cc1ccncc1)c1ccccc1] | 1-phenyl-2-(pyridin-4-yl)ethanone |
| 00881 | 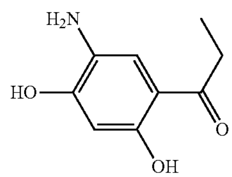 | 1-(5-amino-2,4-dihydroxyphenyl)propan-1-one |
| 00886 | 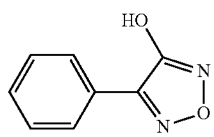 [SMILES: Oc1nonc1-c1ccccc1] | 4-phenyl-1,2,5-oxadiazol-3-ol |
| 00896 | 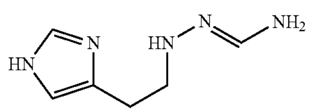 [SMILES: N/C=N/NCCc1c[nH]cn1] | (E)-N'-(2-(1H-imidazol-4-yl)ethyl)formohydrazonamide |
| 00899 | 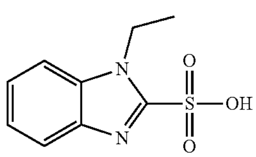 | 1-ethyl-1H-benzo[d]imidazole-2-sulfonic acid |
| 00901 | 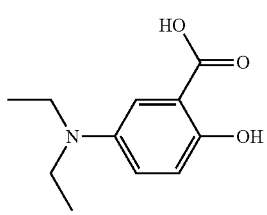 | 5-(diethylamino)-2-hydroxybenzoic acid |
| 00903 | 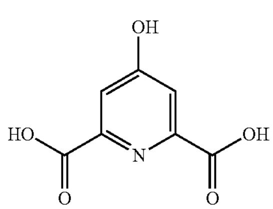 [SMILES: O=C(O)c1cc(O)cc(C(=O)O)n1] | 4-hydroxypyridine-2,6-dicarboxylic acid |
| 00905 | 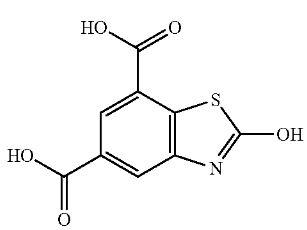 [SMILES: O=C(O)c1cc(C(=O)O)c2sc(O)nc2c1] | 2-hydroxybenzo[d]thiazole-5,7-dicarboxylic acid |

TABLE 11-continued

| Cmpd # | Structure | Name |
| --- | --- | --- |
| 00909 | 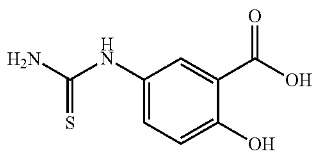 [SMILES: NC(=S)Nc1ccc(O)c(C(=O)O)c1] | 2-hydroxy-5-thioureidobenzoic acid |
| 00912 | 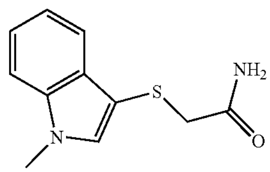 | 2-(1-methyl-1H-indol-3-ylthio)acetamide |
| 00915 | 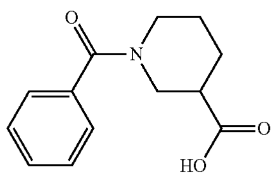 [SMILES: O=C(O)C1CCCN(C(=O)c2ccccc2)C1] | 1-benzoylpiperidine-3-carboxylic acid |
| 00919 | 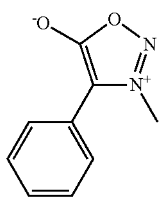 | 3-methyl-4-phenyl-1,2,3-oxadiazol-3-ium-5-olate |
| 00932 | 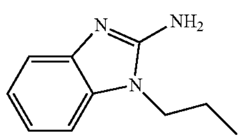 | 1-propyl-1H-benzo[d]imidazol-2-amine |
| 00935 | 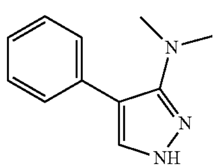 | N,N-dimethyl-4-phenyl-1H-pyrazol-3-amine |
| 00938 | 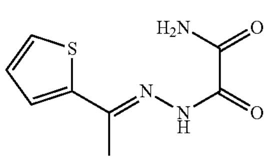 | (E)-2-oxo-2-(2-(1-(thiophen-2-yl)-ethylidene)hydrazinyl)acetamide |
| 00939 | 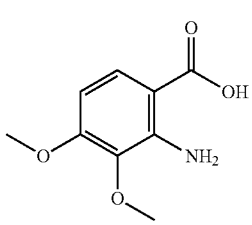 | 2-amino-3,4-dimethoxybenzoic acid |

TABLE 11-continued

| Cmpd # | Structure | Name |
|---|---|---|
| 00943 | 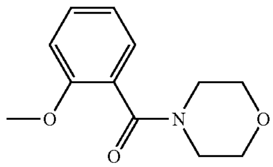 [SMILES: COc1ccccc1C(=O)N1CCOCC1] | (2-methoxyphenyl)(morpholino)methanone |
| 00946 | 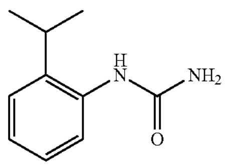 | 1-(2-isopropylphenyl)urea |
| 00954 | 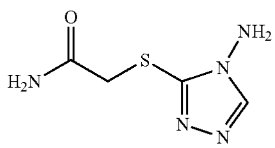 [SMILES: NC(=O)CSc1nncn1N] | 2-(4-amino-4H-1,2,4-triazol-3-ylthio)acetamide |
| 00958 | 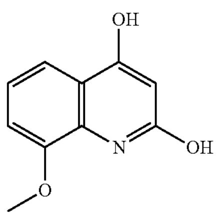 | 8-methoxyquinoline-2,4-diol |
| 00966 | 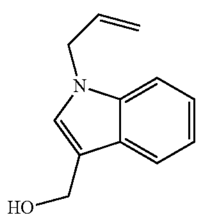 | (1-allyl-1H-indol-3-yl)methanol |
| 00973 | 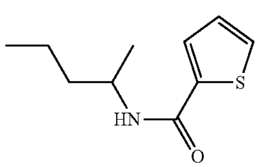 | N-(pentan-2-yl)thiophene-2-carboxamide |
| 00975 | 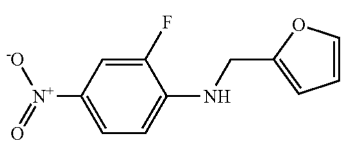 | 2-fluoro-N-(furan-2-ylmethyl)-4-nitroaniline |
| 00980 | 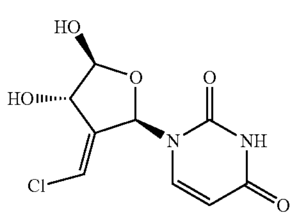 [SMILES: O=c1ccn([C@@H]2O[C@H](O)[C@@H](O)/C2=C\Cl)c(=O)[nH]1] | 1-((2R,4S,5S,E)-3-(chloromethylene)-4,5-dihydroxytetrahydrofuran-2-yl)pyrimidine-2,4(1H,3H)-dione |

TABLE 11-continued
| Cmpd # | Structure | Name |
|---|---|---|
| 00983 | 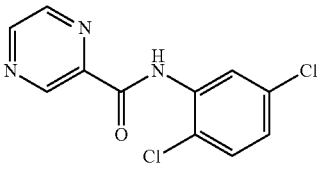 [SMILES: O=C(Nc1cc(Cl)ccc1Cl)c1cnccn1] | N-(2,5-dichlorophenyl)pyrazine-2-carboxamide |
| 00984 | 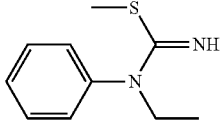 | methyl ethyl(phenyl)carbamimidothioate |
| 00988 | 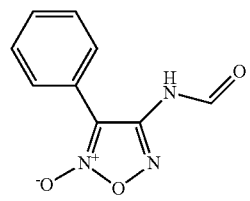 | 4-formamido-3-phenyl-1,2,5-oxadiazole 2-oxide |
| 00991 | 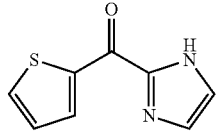 [SMILES: O=C(c1ncc[nH]1)c1cccs1] | (1H-imidazol-2-yl)(thiophen-2-yl)methanone |
| 00993 | 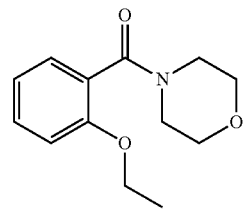 [SMILES: CCOc1ccccc1C(=O)N1CCOCC1] | (2-ethoxyphenyl)(morpholino)methanone |
| 00997 | 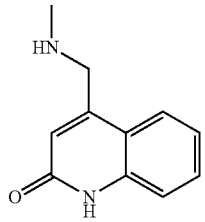 | 4-((methylamino)methyl)quinolin-2(1H)-one |
| 01000 | 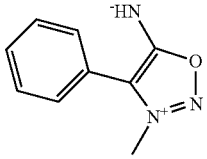 | (3-methyl-4-phenyl-1,2,3-oxadiazol-3-ium-5-yl)amide |
| 01003 | 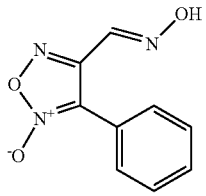 | (E)-4-((hydroxyimino)methyl)-3-phenyl-1,2,5-oxadiazole 2-oxide |

| Cmpd # | Structure | Name |
| --- | --- | --- |
| 01010 | 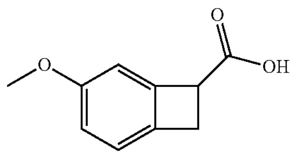 | 5-methoxy-1,2-dihydrocyclobutabenzene-1-carboxylic acid |
| 01019 | 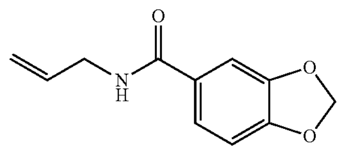 | N-allylbenzo[d][1,3]dioxole-5-carboxamide |
| 01020 | 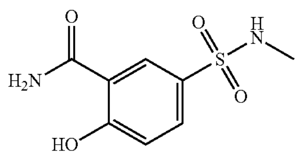 | 2-hydroxy-5-(N-methylsulfamoyl)benzamide |
| 01022 | 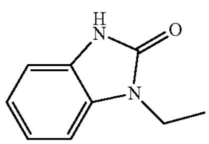 | 1-ethyl-1H-benzo[d]imidazol-2(3H)-one |
| 01024 | 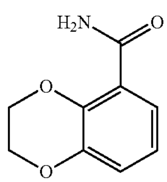 [SMILES: NC(=O)c1cccc2c1OCCO2] | 2,3-dihydrobenzo[b][1,4]dioxine-5-carboxamide |
| 01026 | 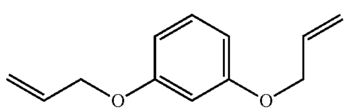 | 1,3-bis(allyloxy)benzene |
| 01029 | 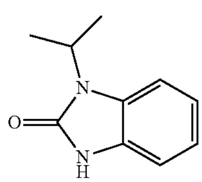 | 1-isopropyl-1H-benzo[d]imidazol-2(3H)-one |
| 01030 | 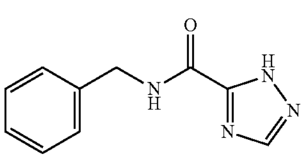 [SMILES: O=C(NCc1ccccc1)c1ncn[nH]1] | N-benzyl-1H-1,2,4-triazole-5-carboxamide |
| 01036 | 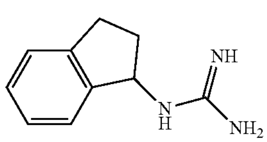 [SMILES: N=C(N)NC1CCc2ccccc21] | 1-(2,3-dihydro-1H-inden-1-yl)guanidine |

TABLE 11-continued

| Cmpd # | Structure | Name |
|---|---|---|
| 01037 | 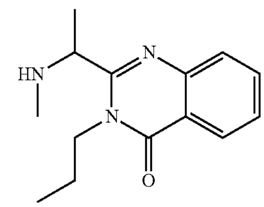 [SMILES: CCCn1c(C(C)NC)nc2ccccc2c1=O] | 2-(1-(methylamino)ethyl)-3-propylquinazolin-4(3H)-one |
| 01038 | 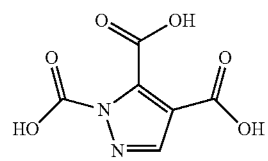 [SMILES: O=C(O)c1cnn(C(=O)O)c1C(=O)O] | 1H-pyrazole-1,4,5-tricarboxylic acid |
| 01040 | 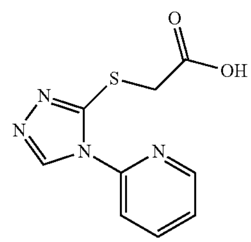 [SMILES: O=C(O)CSc1nncn1-c1ccccn1] | 2-(4-(pyridin-2-yl)-4H-1,2,4-triazol-3-ylthio)acetic acid |
| 01041 | 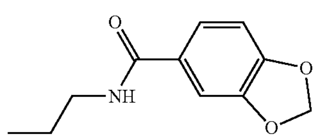 | N-propylbenzo[d][1,3]dioxole-5-carboxamide |
| 01044 | 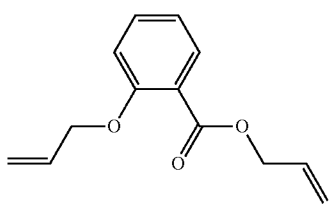 [SMILES: C=CCOC(=O)c1ccccc1OCC=C] | allyl 2-(allyloxy)benzoate |
| 01046 | 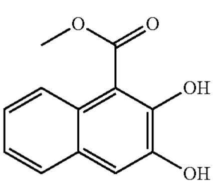 [SMILES: COC(=O)c1c(O)c(O)cc2ccccc12] | methyl 2,3-dihydroxy-1-naphthoate |
| 01052 | 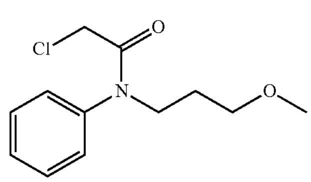 [SMILES: COCCCN(C(=O)CCl)c1ccccc1] | 2-chloro-N-(3-methoxypropyl)-N-phenyl-acetamide |
| 01058 | 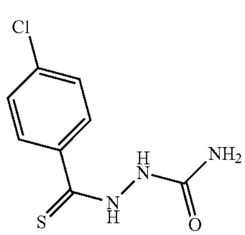 [SMILES: NC(=O)NNC(=S)c1ccc(Cl)cc1] | 2-(4-chlorophenylcarbonothioyl)hydrazinecarboxamide |

TABLE 11-continued

| Cmpd # | Structure | Name |
|---|---|---|
| 01061 | 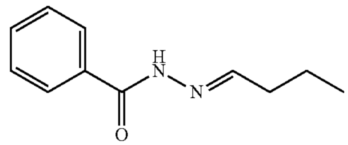 | (E)-N'-butylidenebenzohydrazide |
| 01067 | 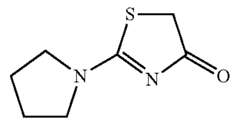 [SMILES: O=C1CSC(N2CCCC2)=N1] | 2-(pyrrolidin-1-yl)thiazol-4(5H)-one |
| 01068 | 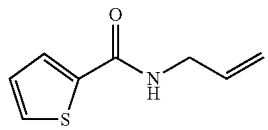 | N-allylthiophene-2-carboxamide |
| 01072 | 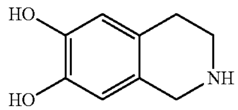 [SMILES: Oc1cc2c(cc1O)CNCC2] | 1,2,3,4-tetrahydroisoquinoline-6,7-diol |
| 01073 | 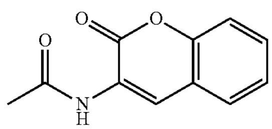 | N-(2-oxo-2H-chromen-3-yl)acetamide |
| 01074 | 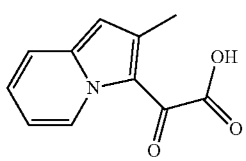 | 2-(2-methylindolizin-3-yl)-2-oxoacetic acid |
| 01075 | 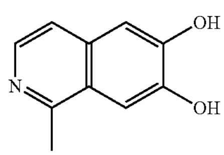 | 1-methylisoquinoline-6,7-diol |
| 01079 | 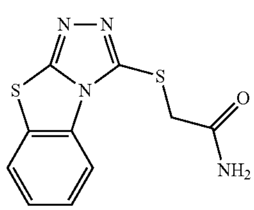 [SMILES: NC(=O)CSc1nnc2sc3ccccc3n12] | 2-benzo[4,5]thiazolo[2,3-c][1,2,4]triazol-3-ylsulfanyl-acetamide |
| 01080 | 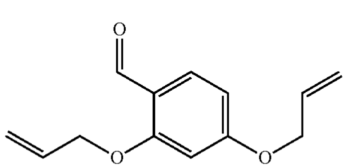 [SMILES: C=CCOc1ccc(C=O)c(OCC=C)c1] | 2,4-bis(allyloxy)benzaldehyde |
| 01082 | 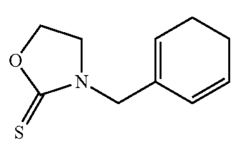 [SMILES: S=C1OCCN1CC1=CCCC=C1] | 3-(cyclohexa-1,5-dienylmethyl)oxazolidine-2-thione |

| Cmpd # | Structure | Name |
| --- | --- | --- |
| 01090 | 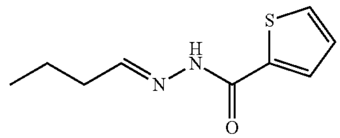 | (E)-N'-butylidenethiophene-2-carbohydrazide |
| 01092 | 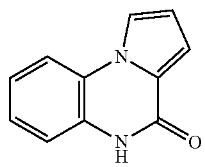 [SMILES: O=c1[nH]c2ccccc2n2cccc12] | pyrrolo[1,2-a]quinoxalin-4(5H)-one |
| 01093 | 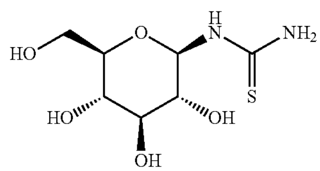 [SMILES: NC(=S)N[C@@H]1O[C@H](CO)[C@@H](O)[C@H](O)[C@H]1O] | 1-((2R,3R,4S,5S,6R)-3,4,5-trihydroxy-6-(hydroxymethyl)tetrahydro-2H-pyran-2-yl)thiourea |
| 01096 | 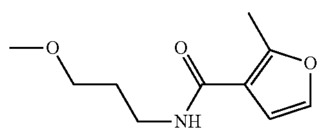 | N-(3-methoxypropyl)-2-methylfuran-3-carboxamide |
| 01098 | 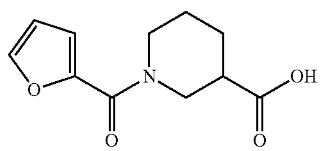 [SMILES: O=C(O)C1CCCN(C(=O)c2ccco2)C1] | 1-(furan-2-carbonyl)piperidine-3-carboxylic acid |
| 01104 | 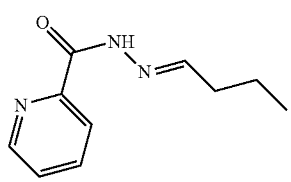 | (E)-N'-butylidenepicolinohydrazide |
| 01105 | 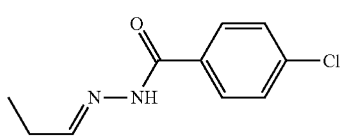 | (E)-4-chloro-N'-propylidenebenzohydrazide |
| 01106 | 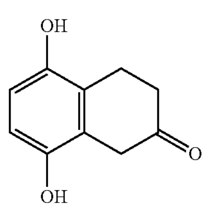 [SMILES: O=C1CCc2c(O)ccc(O)c2C1] | 5,8-dihydroxy-3,4-dihydronaphthalen-2(1H)-one |
| 01108 | 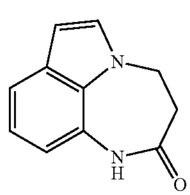 [SMILES: O=C1CCn2ccc3cccc(c32)N1] | 3,4-dihydro-[1,4]diazepino[3,2,1-hi]indol-2(1H)-one |

TABLE 11-continued

| Cmpd # | Structure | Name |
|---|---|---|
| 01109 | 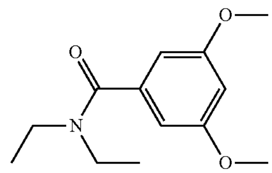 [SMILES: CCN(CC)C(=O)c1cc(OC)cc(OC)c1] | N,N-diethyl-3,5-dimethoxybenzamide |
| 01113 | 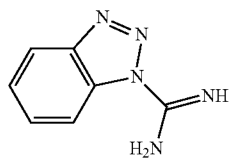 [SMILES: N=C(N)n1nnc2ccccc21] | 1H-benzo[d][1,2,3]triazole-1-carboximidamide |
| 01118 | 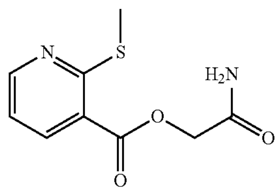 | 2-amino-2-oxoethyl 2-(methylthio)nicotinate |
| 01121 | 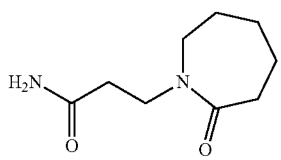 [SMILES: NC(=O)CCN1CCCCCC1=O] | 3-(2-oxoazepan-1-yl)propanamide |
| 01123 | 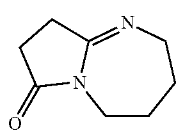 [SMILES: O=C1CCC2=NCCCCN12] | (Z)-4,5,8,9-tetrahydro-2H-pyrrolo[1,2-a][1,3]diazepin-7(3H)-one |
| 01126 | 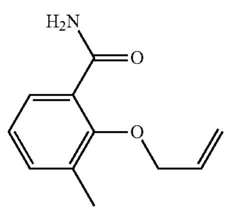 | 2-(allyloxy)-3-methylbenzamide |
| 01130 | 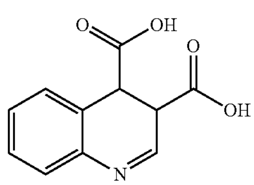 [SMILES: O=C(O)C1C=Nc2ccccc2C1C(=O)O] | quinoline-3,4-dicarboxylic acid |
| 01134 | 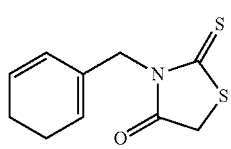 [SMILES: O=C1CSC(=S)N1CC1=CCCC=C1] | 3-(cyclohexa-1,5-dienylmethyl)-2-thioxothiazolidin-4-one |
| 01137 | 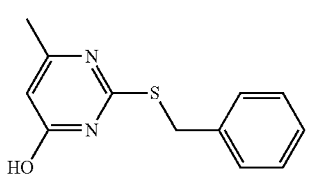 [SMILES: Cc1cc(O)nc(SCc2ccccc2)n1] | 2-(benzylthio)-6-methylpyrimidin-4-ol |

TABLE 11-continued

| Cmpd # | Structure | Name |
|---|---|---|
| 01148 | 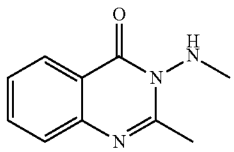 | 2-methyl-3-(methylamino)quinazolin-4(3H)-one |
| 01152 | 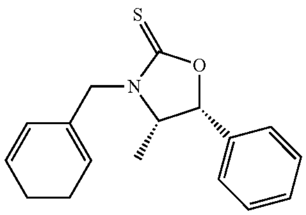 [SMILES: C[C@H]1[C@@H](c2ccccc2)OC(=S)N1CC1=CCCC=C1] | (4S,5R)-3-(cyclohexa-1,5-dienylmethyl)-4-methyl-5-phenyloxazolidine-2-thione |
| 01154 | 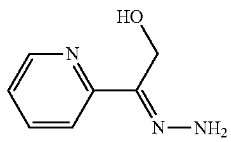 | (Z)-2-hydrazono-2-(pyridin-2-yl)ethanol |
| 01158 | 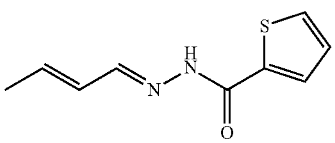 | (E)-N'-((E)-but-2-enylidene)thiophene-2-carbohydrazide |
| 01161 | 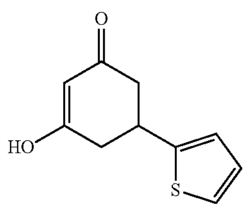 [SMILES: O=C1C=C(O)CC(c2cccs2)C1] | 3-hydroxy-5-(thiophen-2-yl)cyclohex-2-enone |
| 01164 | 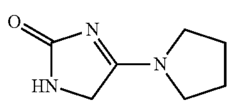 [SMILES: O=C1N=C(N2CCCC2)CN1] | 4-(pyrrolidin-1-yl)-1H-imidazol-2(5H)-one |
| 01167 | 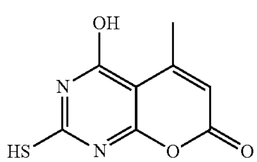 | 4-hydroxy-2-mercapto-5-methyl-7H-pyrano[2,3-d]pyrimidin-7-one |
| 01175 | 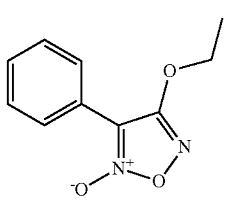 | 4-ethoxy-3-phenyl-1,2,5-oxadiazole 2-oxide |
| 01178 | 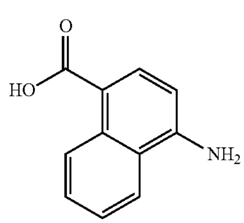 [SMILES: Nc1ccc(C(=O)O)c2ccccc12] | 4-amino-1-naphthoic acid |

TABLE 11-continued

| Cmpd # | Structure | Name |
|---|---|---|
| 01180 | 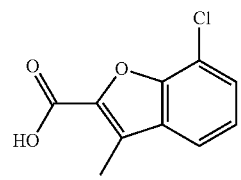 | 7-chloro-3-methylbenzofuran-2-carboxylic acid |
| 01182 | 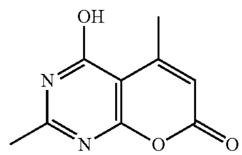 | 4-hydroxy-2,5-dimethyl-7H-pyrano[2,3-d]pyrimidin-7-one |
| 01184 | 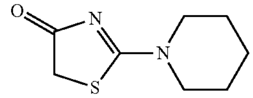 [SMILES: O=C1CSC(N2CCCCC2)=N1] | 2-(piperidin-1-yl)thiazol-4(5H)-one |
| 01189 | 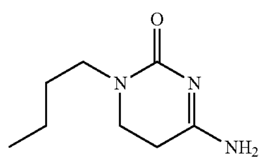 | 4-amino-1-butyl-5,6-dihydropyrimidin-2(1H)-one |
| 01194 | 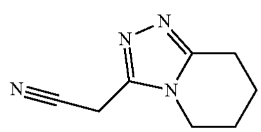 [SMILES: N#CCc1nnc2n1CCCC2] | 2-(5,6,7,8-tetrahydro-[1,2,4]triazolo[4,3-a]pyridin-3-yl)acetonitrile |
| 01195 | 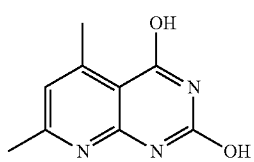 | 5,7-dimethylpyrido[2,3-d]pyrimidine-2,4-diol |
| 01196 | 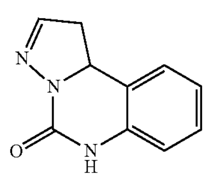 [SMILES: O=C1Nc2ccccc2C2CC=NN12] | 1,10b-dihydropyrazolo[1,5-c]quinazolin-5(6H)-one |
| 01204 | 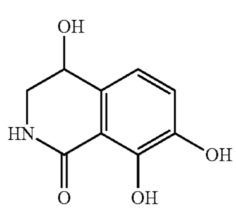 [SMILES: O=C1NCC(O)c2ccc(O)c(O)c21] | 4,7,8-trihydroxy-1-oxo-1,2,3,4-tetrahydro-isoquinoline |
| 01207 | 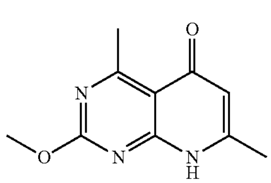 | 2-methoxy-4,7-dimethylpyrido[2,3-d]-pyrimidin-5(8H)-one |

TABLE 11-continued

| Cmpd # | Structure | Name |
|---|---|---|
| 01212 | 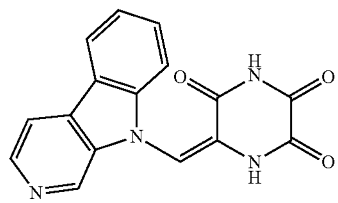 [SMILES: O=C1NC(=O)/C(=C\n2c3ccccc3c3ccncc32)NC1=O] | (E)-6-((9H-pyrido[3,4-b]indol-9-yl)-methylene)piperazine-2,3,5-trione |
| 01213 | 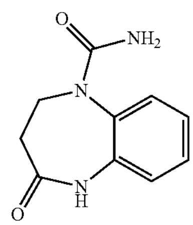 [SMILES: NC(=O)N1CCC(=O)Nc2ccccc21] | 4-oxo-2,3,4,5-tetrahydro-1H-benzo[b][1,4]diazepine-1-carboxamide |
| 01215 | 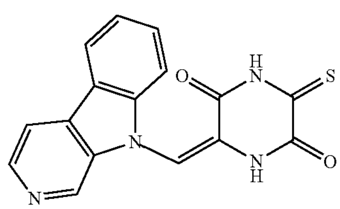 | (E)-3-((9H-pyrido[3,4-b]indol-9-yl)methylene)-6-thioxopiperazine-2,5-dione |
| 01220 | 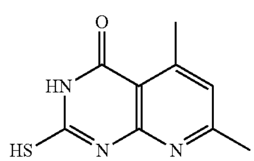 | 2-mercapto-5,7-dimethylpyrido[2,3-d]pyrimidin-4(3H)-one |
| 01224 | 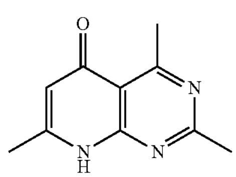 | 2,4,7-trimethylpyrido[2,3-d]pyrimidin-5(8H)-one |
| 01236 | 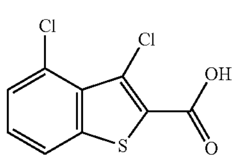 [SMILES: O=C(O)c1sc2cccc(Cl)c2c1Cl] | 3,4-dichlorobenzo[b]thiophene-2-carboxylic acid |
| 01239 | 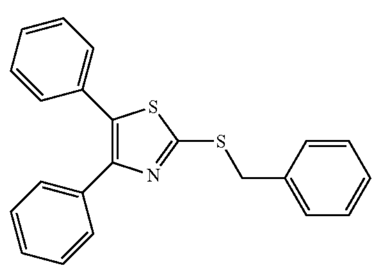 [SMILES: c1ccc(CSc2nc(-c3ccccc3)c(-c3ccccc3)s2)cc1] | 2-(benzylthio)-4,5-diphenylthiazole |

TABLE 11-continued

| Cmpd # | Structure | Name |
|---|---|---|
| 01243 | 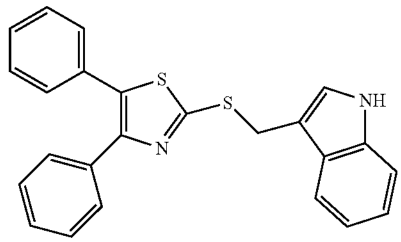 [SMILES: c1ccc(-c2nc(SCc3c[nH]c4ccccc34)sc2-c2ccccc2)cc1] | 2-((1H-indol-3-yl)methylthio)-4,5-diphenylthiazole |
| 01250 | 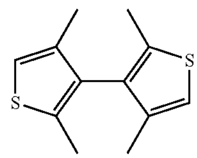 | 2,2',4,4'-tetramethyl-3,3'-bithiophene |
| 01253 | 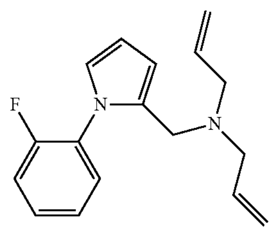 [SMILES: C=CCN(CC=C)Cc1cccn1-c1ccccc1F] | N-allyl-N-((1-(2-fluorophenyl)-1H-pyrrol-2-yl)methyl)prop-2-en-1-amine |
| 01257 | 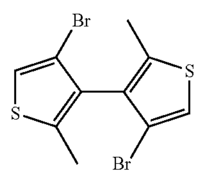 | 4,4'-dibromo-2,2'-dimethyl-3,3'-bithiophene |
| 01360 | 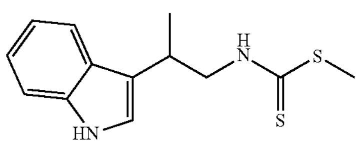 [SMILES: CSC(=S)NCC(C)c1c[nH]c2ccccc12] | methyl 2-(1H-indol-3-yl)propylcarbamodithioate |
| 01384 | 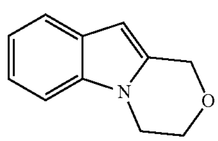 [SMILES: c1ccc2c(c1)cc1n2CCOC1] | 3,4-dihydro-1H-[1,4]oxazino[4,3-a]indole |
| 01389 | 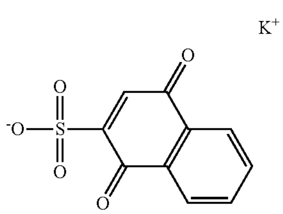 | potassium 1,4-dioxo-1,4-dihydronaphthalene-2-sulfonate |
| 01393 | 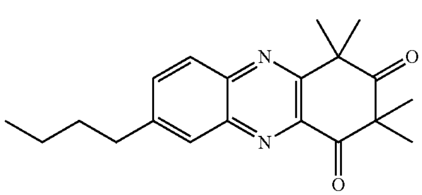 [SMILES: CCCCc1ccc2nc3c(nc2c1)C(=O)C(C)(C)C(=O)C3(C)C] | 8-butyl-2,2,4,4-tetramethylphenazine-1,3(2H,4H)-dione |

TABLE 11-continued

| Cmpd # | Structure | Name |
|---|---|---|
| 01397 | 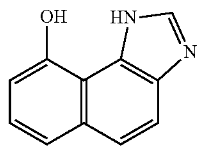 [SMILES: Oc1cccc2ccc3nc[nH]c3c12] | 1H-naphtho[1,2-d]imidazol-9-ol |
| 01399 | 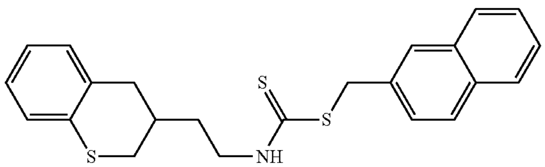 [SMILES: S=C(NCCC1CSc2ccccc2C1)SCc1ccc2ccccc2c1] | naphthalen-2-ylmethyl 2-(thiochroman-3-yl)ethylcarbamodithioate |
| 01404 | 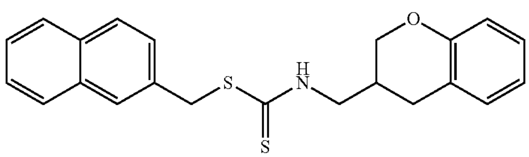 [SMILES: S=C(NCC1COc2ccccc2C1)SCc1ccc2ccccc2c1] | naphthalen-2-ylmethyl chroman-3-ylmethylcarbamodithioate |
| 01407 | 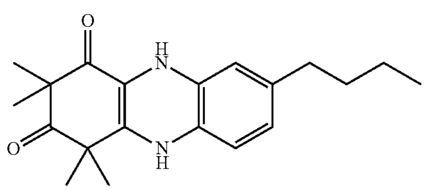 [SMILES: CCCCc1ccc2c(c1)NC1=C(N2)C(C)(C)C(=O)C(C)(C)C1=O] | 8-butyl-2,2,4,4-tetramethyl-5,10-dihydrophenazine-1,3(2H,4H)-dione |
| 01408 | 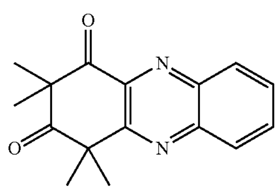 [SMILES: CC1(C)C(=O)c2nc3ccccc3nc2C(C)(C)C1=O] | 2,2,4,4-tetramethylphenazine-1,3(2H,4H)-dione |
| 01409 | 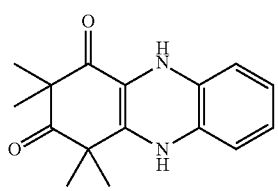 [SMILES: CC1(C)C(=O)C2=C(Nc3ccccc3N2)C(C)(C)C1=O] | 2,2,4,4-tetramethyl-5,10-dihydrophenazine-1,3(2H,4H)-dione |
| 01412 | 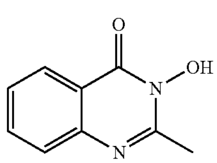 | 3-hydroxy-2-methylquinazolin-4(3H)-one |
| 01415 | 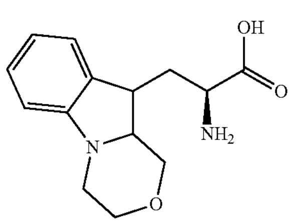 [SMILES: N[C@@H](CC1c2ccccc2N2CCOCC12)C(=O)O] | (2S)-2-amino-3-(3,4,10,10a-tetrahydro-1H-[1,4]oxazino[4,3-a]indol-10-yl)propanoic acid |

TABLE 11-continued

| Cmpd # | Structure | Name |
| --- | --- | --- |
| 01416 | 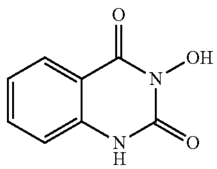 [SMILES: O=c1[nH]c2ccccc2c(=O)n1O] | 3-hydroxyquinazoline-2,4(1H,3H)-dione |
| 01423 | 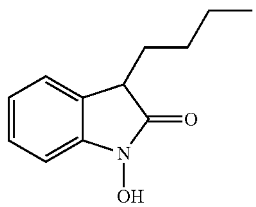 | 3-butyl-1-hydroxyindolin-2-one |
| 01435 | 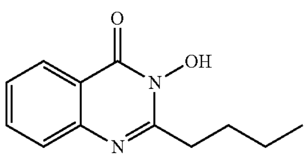 [SMILES: CCCCc1nc2ccccc2c(=O)n1O] | 2-butyl-3-hydroxyquinazolin-4(3H)-one |
| 01436 | 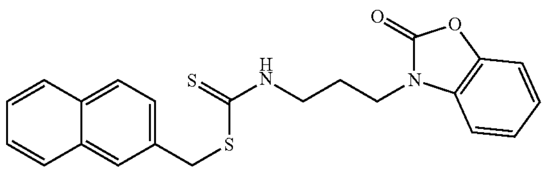 [SMILES: O=c1oc2ccccc2n1CCCNC(=S)SCc1ccc2ccccc2c1] | naphthalen-2-ylmethyl 3-(2-oxobenzo[d]oxazol-3(2H)-yl)propylcarbamodithioate |
| 01450 | 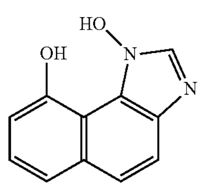 [SMILES: Oc1cccc2ccc3ncn(O)c3c12] | 1H-naphtho[1,2-d]imidazole-1,9-diol |
| 01453 | 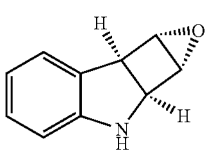 [SMILES: c1ccc2c(c1)N[C@@H]1[C@H]3O[C@H]3[C@H]21] | (1aR,1bS,6bR,6cS)-1b,2,6b,6c-tetrahydro-1aH-oxireno[3,4]cyclobuta[1,2-b]indole |
| 01454 | 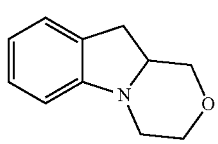 [SMILES: c1ccc2c(c1)CC1COCCN21] | 3,4,10,10a-tetrahydro-1H-[1,4]oxazino[4,3-a]indole |
| 01467 | 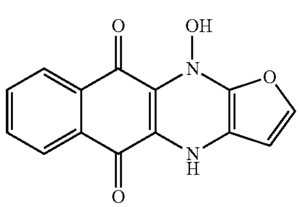 [SMILES: O=c1c2[nH]c3ccoc3n(O)c=2c(=O)c2ccccc12] | 11-hydroxybenzo[g]furo[3,2-b]quinoxaline-5,10(4H,11H)-dione |

In a twelfth aspect, the compounds as provided as listed in Table 12.

TABLE 12

| Cmpd # | Structure | Name |
| --- | --- | --- |
| 00001 | 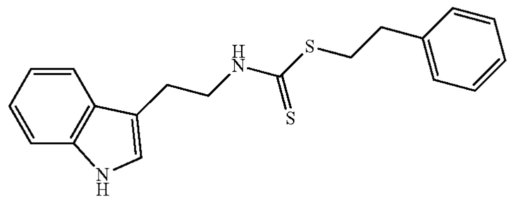 [SMILES: S=C(NCCc1c[nH]c2ccccc12)SCCc1ccccc1] | phenethyl 2-(1H-indol-3-yl)ethylcarbamodithioate |
| 00002 | 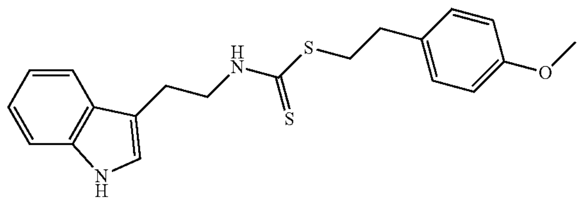 [SMILES: COc1ccc(CCSC(=S)NCCc2c[nH]c3ccccc23)cc1] | 4-methoxyphenethyl 2-(1H-indol-3-yl)ethylcarbamodithioate |
| 00003 | 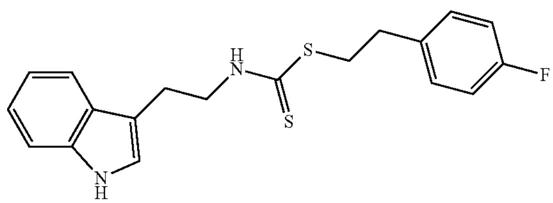 [SMILES: Fc1ccc(CCSC(=S)NCCc2c[nH]c3ccccc23)cc1] | 4-fluorophenethyl 2-(1H-indol-3-yl)ethylcarbamodithioate |
| 00004 | 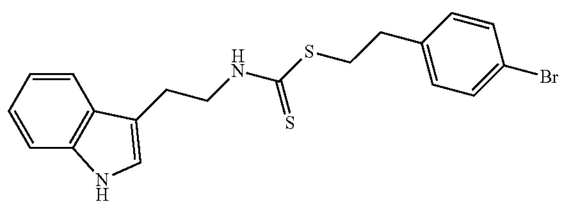 [SMILES: S=C(NCCc1c[nH]c2ccccc12)SCCc1ccc(Br)cc1] | 4-bromophenethyl 2-(1H-indol-3-yl)ethylcarbamodithioate |
| 00006 | 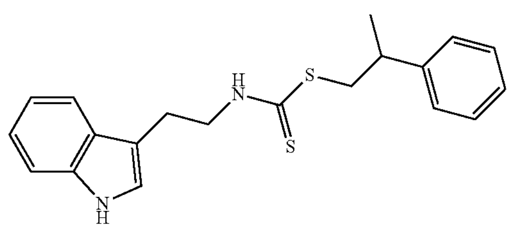 [SMILES: CC(CSC(=S)NCCc1c[nH]c2ccccc12)c1ccccc1] | 2-phenylpropyl 2-(1H-indol-3-yl)ethylcarbamodithioate |
| 00007 | 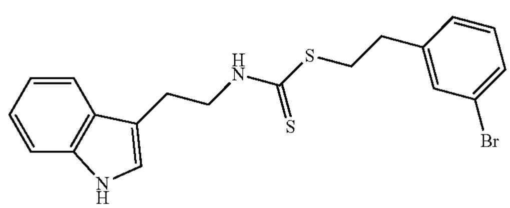 | 3-bromophenethyl 2-(1H-indol-3-yl)ethylcarbamodithioate |
| 00008 | 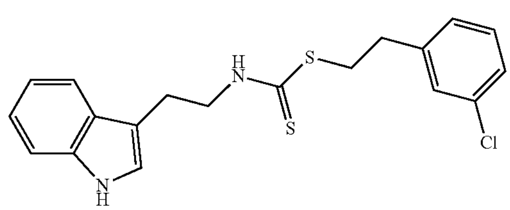 [SMILES: S=C(NCCc1c[nH]c2ccccc12)SCCc1cccc(Br)c1] | 3-chlorophenethyl 2-(1H-indol-3-yl)ethylcarbamodithioate |

TABLE 12-continued

| Cmpd # | Structure | Name |
|---|---|---|
| 00009 | 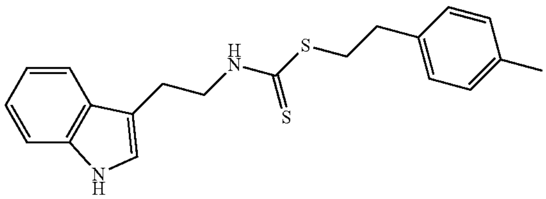 [SMILES: Cc1ccc(CCSC(=S)NCCc2c[nH]c3ccccc23)cc1] | 4-methylphenethyl 2-(1H-indol-3-yl)ethylcarbamodithioate |
| 00010 | 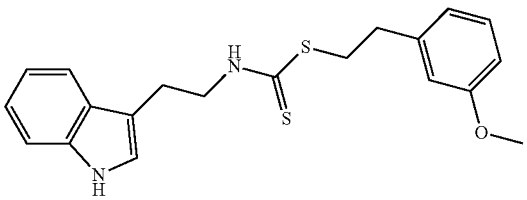 [SMILES: COc1cccc(CCSC(=S)NCCc2c[nH]c3ccccc23)c1] | 3-methoxyphenethyl 2-(1H-indol-3-yl)ethylcarbamodithioate |
| 00023 | 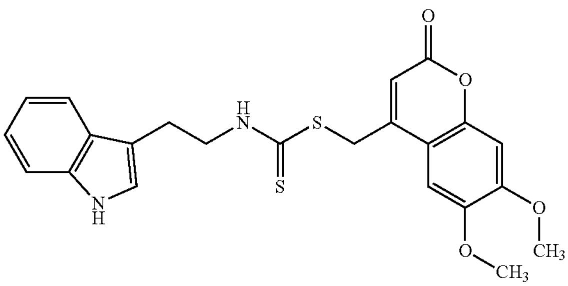 [SMILES: COc1cc2oc(=O)cc(CSC(=S)NCCc3c[nH]c4ccccc34)c2cc1OC] | (6,7-Dimethoxy-2-oxo-2H-chromen-4-yl)methyl 2-(1H-indol-3-yl)ethyl-carbamodithioate |
| 00030 | 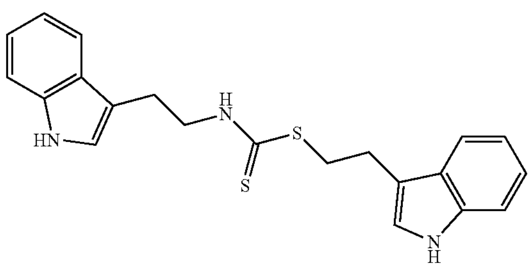 [SMILES: S=C(NCCc1c[nH]c2ccccc12)SCCc1c[nH]c2ccccc12] | 2-(1H-indol-3-yl)ethyl 2-(1H-indol-3-yl)ethylcarbamodithioate |
| 00038 | 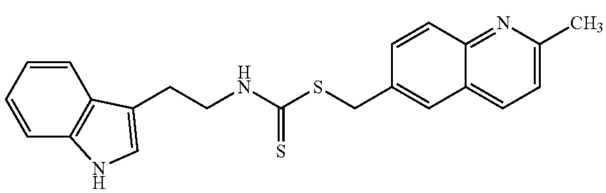 [SMILES: Cc1ccc2cc(CSC(=S)NCCc3c[nH]c4ccccc34)ccc2n1] | (2-Methylquinolin-6-yl)methyl 2-(1H-indol-3-yl)ethylcarbamodithioate |
| 00047 | 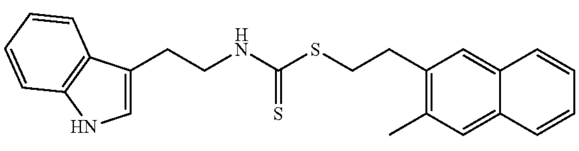 [SMILES: Cc1cc2ccccc2cc1CCSC(=S)NCCc1c[nH]c2ccccc12] | 2-(3-methylnaphthalen-2-yl)ethyl 2-(1H-indol-3-yl)ethylcarbamodithioate |
| 00049 | 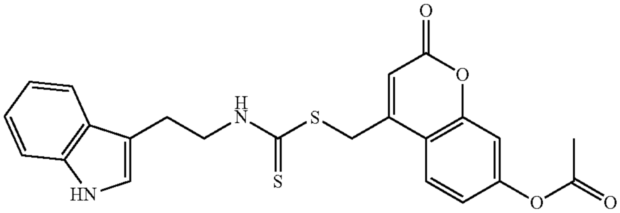 [SMILES: CC(=O)Oc1ccc2c(CSC(=S)NCCc3c[nH]c4ccccc34)cc(=O)oc2c1] | 4-((2-(1H-indol-3-yl)ethylcarbamothioylthio)methyl)-2-oxo-2H-chromen-7-yl acetate |

TABLE 12-continued

| Cmpd # | Structure | Name |
|---|---|---|
| 00050 | 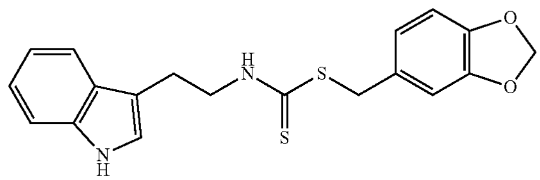 [SMILES: S=C(NCCc1c[nH]c2ccccc12)SCc1ccc2c(c1)OCO2] | Benzo[d][1,3]dioxol-5-ylmethyl 2-(1H-indol-3-yl)ethylcarbamodithioate |
| 00052 | 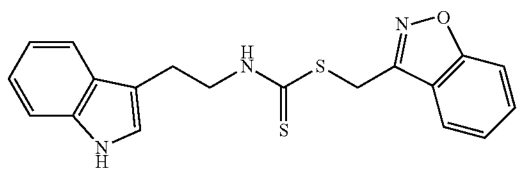 [SMILES: S=C(NCCc1c[nH]c2ccccc12)SCc1noc2ccccc12] | Benzo[d]isoxazol-3-ylmethyl 2-(1H-indol-3-yl)ethylcarbamodithioate |
| 00053 | 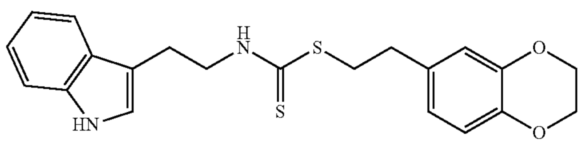 [SMILES: S=C(NCCc1c[nH]c2ccccc12)SCCc1ccc2c(c1)OCCO2] | 2-(2,3-dihydrobenzo[b][1,4]dioxin-6-yl)ethyl 2-(1H-indol-3-yl)ethylcarbamodithioate |
| 00065 | 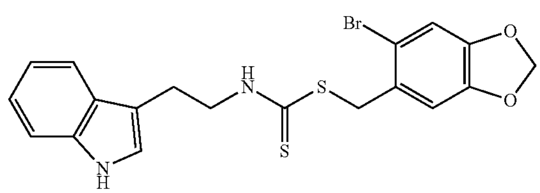 [SMILES: S=C(NCCc1c[nH]c2ccccc12)SCc1cc2c(cc1Br)OCO2] | (6-Bromobenzo[d][1,3]dioxol-5-yl)methyl 2-(1H-indol-3-yl)ethylcarbamodithioate |
| 00066 | 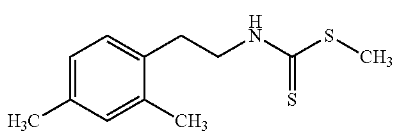 | Methyl 2,4-dimethylphenethyl-carbamodithioate |
| 00069 | 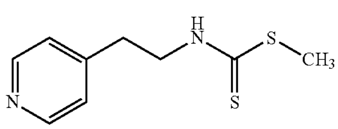 | Methyl 2-(pyridin-4-yl)ethylcarbamodithioate |
| 00786 | 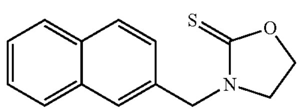 [SMILES: S=C1OCCN1Cc1ccc2ccccc2c1] | 3-(naphthalen-2-ylmethyl)oxazolidine-2-thione |
| 00830 | 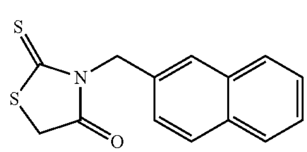 [SMILES: O=C1CSC(=S)N1Cc1ccc2ccccc2c1] | 3-(naphthalen-2-ylmethyl)-2-thioxothiazolidin-4-one |

In a thirteenth aspect is provided a compound of the formula (XIII),

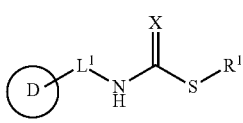

(XIII)

or a pharmaceutically acceptable salt thereof, wherein
$L^1$ is —$C_2$-$C_6$alkyl-;
X is =O or =S;
ring D is an aryl or heteroaryl group, each optionally substituted with one to four R groups;
$R^1$ is -$L^2$-$R^2$, wherein $L^2$ is —$C_2$-$C_6$alkyl-; and $R^2$ is (i) hydrogen; (ii) aryl optionally substituted with one to four R groups; or (iii) heteroaryl optionally substituted with one to four R groups; and
each R is independently halogen, cyano, nitro, $C_1$-$C_6$alkyl, $C_2$-$C_6$alkenyl, $C_2$-$C_6$alkynyl, —$OR^3$, —$SR^3$, —N(R³)₂, —OC(O)R³, —C(O)OR³, —C(O)N(R³)₂, —N(R³)C(O)R³, —S(O)R³, or —S(O)₂R³, wherein each R³ is independently hydrogen or $C_1$-$C_6$alkyl;

provided that when ring D is an aryl or unsubstituted indol-3-yl, benzofuran-3-yl, or benzothien-3-yl group, and $L^1$ is —$C_2$-$C_3$alkyl-, then (a) R² is not hydrogen.

In an embodiment of the thirteenth aspect, the compound is according to formula (XIII), wherein ring D is aryl.

In an embodiment of the thirteenth aspect, the compound is according to formula (XIII), wherein ring D is heteroaryl.

In an embodiment of the thirteenth aspect, the compound is according to formula (XIII), wherein ring D is phenyl, naphthyl, azulenyl, indolyl, benzothienyl, benzofuranyl, pyridyl, pyrazinyl, pyrimidinyl, thienyl, furanyl, pyrrolyl, pyrazolyl, imidazolyl, thiazolyl, oxazolyl, isoxazolyl, isothiazolyl, quinolinyl, or quinazolinyl, each optionally substituted with one to four R groups.

In an embodiment of the thirteenth aspect, the compound is according to formula (XIII), wherein ring D is phenyl or naphthyl, each optionally substituted with one to four R groups.

In an embodiment of the thirteenth aspect, the compound is according to formula (XIII), wherein ring D is indolyl, benzothienyl, benzofuranyl, pyridyl, pyrazinyl, pyrimidinyl, thienyl, furanyl, pyrrolyl, pyrazolyl, imidazolyl, thiazolyl, oxazolyl, isoxazolyl, isothiazolyl, quinolinyl, or quinazolinyl, each optionally substituted with one to four R groups.

In an embodiment of the thirteenth aspect, the compound is according to formula (XIII), wherein ring D is indolyl, benzothienyl, benzofuranyl, quinolinyl, or quinazolinyl, each optionally substituted with one to four R groups.

In an embodiment of the thirteenth aspect, the compound is according to formula (XIII), wherein ring D is indolyl, benzothienyl, or benzofuranyl, each optionally substituted with one to four R groups.

In an embodiment of the thirteenth aspect, the compound is according to formula (XIII), wherein X is =S.

In an embodiment of the thirteenth aspect, the compound is according to formula (XIII), wherein X is =O.

In an embodiment of the thirteenth aspect, the compound is according to one of formulae (XIIIa-c),

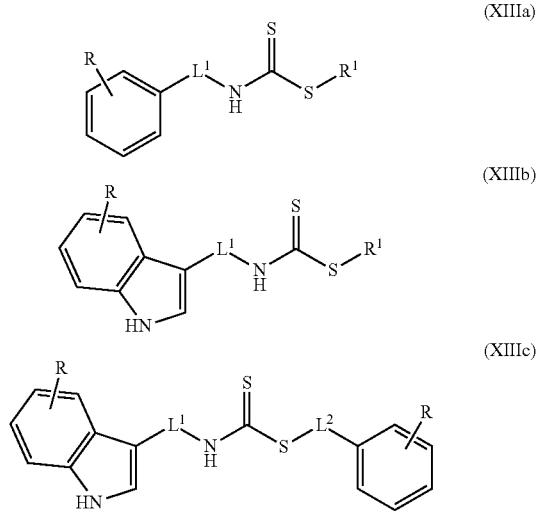

In an embodiment of the thirteenth aspect, the compound is according to one of formulae (XIII and XIIIa-c), wherein $L^1$ is —CH₂CH₂—.

In an embodiment of the thirteenth aspect, the compound is according to one of formulae (XIII and XIIIa-c), wherein $L^2$ is —CH₂CH₂—.

In an embodiment of the thirteenth aspect, the compound is according to one of formulae (XIII and XIIIa-c), wherein $L^1$ and $L^2$ are both is —CH₂CH₂—.

In an embodiment of the thirteenth aspect, the compound is a compound listed in Table 12.

In a fourteenth aspect, methods are provided for (a) modulating an activity of indoleamine 2,3-dioxygenase comprising contacting an indoleamine 2,3-dioxygenase with a modulation effective amount a compound of formula (XXI); (b) treating indoleamine 2,3-dioxygenase (IDO) mediated immunosuppression in a subject in need thereof, comprising administering an effective indoleamine 2,3-dioxygenase inhibiting amount of a compound of formula (XXI); (c) treating a medical conditions that benefit from the inhibition of enzymatic activity of indoleamine-2,3-dioxygenase comprising administering an effective indoleamine 2,3-dioxygenase inhibiting amount of a compound of formula (XXI); (d) enhancing the effectiveness of an anti-cancer treatment comprising administering an anti-cancer agent and a compound of formula (XXI), (e) treating tumor-specific immunosuppression associated with cancer comprising administering an effective indoleamine 2,3-dioxygenase inhibiting amount of a compound of formula (XXI); and (f) treating immunsupression associated with an infectious disease, e.g., HIV-1 infection, comprising administering an effective indoleamine 2,3-dioxygenase inhibiting amount of a compound of formula (XXI),

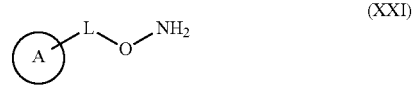

(XXI)

and pharmaceutically acceptable salts thereof, wherein ring A is aryl, heteroaryl, $C_5$-$C_{10}$ cycloalkyl, or heterocyclyl, each optionally substituted with one or more $R^A$ groups, wherein each $R^A$ is independently halogen, cyano, nitro, —N(R^{41})₂, —OR^{41}, —ON(R^{41})₂, —N(R^{41})N(R^{41})₂, —SR^{41}, —C(O)R^{41}, —C(O)OR^{41}, —C(O)N(R^{41})₂, —S(O)R^{41}, —S(O)OR^{41}, —S(O)N(R^{41})₂, —S(O)₂R^{41}, —S(O)₂OR^{41}, —S(O)₂N(R^{41})₂, —OC(O)R^{41}, —OC(O)OR^{41}, —OC(O)N(R^{41})₂, —N(R^{41})C(O)OR^{41}, —N(R^{41})C(O)N(R^{41})₂, —$C_1$-$C_6$ alkyl, —$C_1$-$C_6$ haloalkyl, —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more halogen, cyano, nitro, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, -heterocyclyl, —N(R^{41})₂, —OR^{41}, —ON(R^{41})₂, —N(R^{41})N(R^{41})₂, —SR^{41}, —C(O)R^{41}, —C(O)OR^{41}, —C(O)N(R^{41})₂, —S(O)R^{41}, —S(O)OR^{41}, —S(O)N(R^{41})₂, —S(O)₂R^{41}, —S(O)₂OR^{41}, —S(O)₂N(R^{41})₂, —OC(O)R^{41}, —OC(O)OR^{41}, —OC(O)N(R^{41})₂, —N(R^{41})C(O)OR^{41}, or —N(R^{41})C(O)N(R^{41})₂, wherein each $R^{41}$ is independently hydrogen, —$C_1$-$C_6$ alkyl, —$C_1$-$C_6$ haloalkyl, —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more halogen, cyano, nitro, —N(R$^{A2}$)$_2$, —OR$^{A2}$, —ON(R$^{A2}$)$_2$, —N(R$^{A2}$)N(R$^{A2}$)$_2$, —SR$^{A2}$, —C(O)R$^{A2}$, —C(O)OR$^{A2}$, —C(O)N(R$^{A2}$)$_2$, —S(O)R$^{A2}$, —S(O)OR$^{A2}$, —S(O)N(R$^{A2}$)$_2$, —S(O)$_2$R$^{A2}$, —S(O)$_2$OR$^{A2}$, —S(O)$_2$N(R$^{A2}$)$_2$, —OC(O)R$^{A2}$, —OC(O)OR$^{A2}$, —OC(O)N(R$^{A2}$)$_2$, —N(R$^{A2}$)C(O)OR$^{A2}$, or —N(R$^{A2}$)C(O)N(R$^{A2}$)$_2$, wherein each R$^{A2}$ is independently hydrogen, —C$_1$-C$_6$ alkyl, aryl, or —C$_1$-C$_6$ alkylaryl; and L is a bond or —X-L$^1$-, wherein X is bonded to A, and is a bond, —O—, —S—, —N(R$^X$)—, —C(Y)—, —S(O)—, —S(O)$_2$—, —C(O)O—, —OC(O)—, —OC(O)O—, —OC(O)N(R$^X$)—, —N(R$^X$)C(O)O—, —C(O)N(R$^X$)—, —N(R$^X$)C(O)—, —N(R$^X$)C(O)N(R$^X$)—, —S(O)O—, —OS(O)—, —S(O)N(R$^X$)—, —N(R$^X$)S(O)—, —S(O)$_2$O—, —OS(O)$_2$—, —S(O)$_2$N(R$^X$)—, —N(R$^X$)S(O)$_2$—, —C$_1$-C$_3$ alkylO—, —C$_1$-C$_3$alkylS—, —C$_1$-C$_3$alkylN(R$^X$)—, —C$_1$-C$_3$alkylC(Y)—, —C$_1$-C$_3$alkylS(O)—, —C$_1$-C$_3$alkylS(O)$_2$—, —C$_1$-C$_3$alkylC(O)O—, —C$_1$-C$_3$alkylO—C(O)—, —C$_1$-C$_3$alkylOC(O)O—, —C$_1$-C$_3$alkylN(R$^X$)C(O)O—, —C$_1$-C$_3$alkylOC(O)N(R$^X$)—, —C$_1$-C$_3$ alkyl-C(O)N(R$^X$)—, —C$_1$-C$_3$alkylN(R$^X$)C(O)—, —C$_1$-C$_3$ alkylN(R$^X$)C(O)N(R$^X$)—, —C$_1$-C$_3$alkylS(O)O—, —C$_1$-C$_3$alkylOS(O)—, —C$_1$-C$_3$alkylS(O)N(R$^X$)—, —C$_1$-C$_3$alkylN(R$^X$)S(O)—, —C$_1$-C$_3$alkylS(O)$_2$O—, —C$_1$-C$_3$alkylOS(O)$_2$—, —C$_1$-C$_3$alkylS(O)$_2$N(R$^X$)—, or —C$_1$-C$_3$alkylN(R$^X$)S(O)$_2$—, wherein each R$^X$ is independently hydrogen or —C$_1$-C$_6$ alkyl;

Y is =O, =S, or =NH; and

L$^1$ is —C$_1$-C$_6$alkyl-, or —C$_2$-C$_6$alkenyl-, wherein the alkyl and alkenyl are each optionally substituted with one or two R$^L$ groups, wherein each R$^L$ is independently halogen, cyano, nitro, —N(R$^{L1}$)$_2$, —OR$^{L1}$, —ON(R$^{L1}$)$_2$, —N(R$^{L1}$)N(R$^{L1}$)$_2$, —N(R$^{L1}$)C(O)R$^{L1}$, —SR$^{L1}$, —C(O)R$^{L1}$, —C(O)OR$^{L1}$, —C(O)N(R$^{L1}$)$_2$, —S(O)R$^{L1}$, —S(O)OR$^{L1}$, —S(O)N(R$^{L1}$)$_2$, —S(O)$_2$R$^{L1}$, —S(O)$_2$OR$^{L1}$, —S(O)$_2$N(R$^{L1}$)$_2$, —OC(O)R$^{L1}$, —OC(O)OR$^{L1}$, —OC(O)N(R$^{L1}$)$_2$, —N(R$^{L1}$)C(O)OR$^{L1}$, —N(R$^{L1}$)C(O)N(R$^{L1}$)$_2$, —C$_1$-C$_6$ alkyl, —C$_1$-C$_6$ haloalkyl, —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, —C$_1$-C$_6$ alkylC$_3$-C$_8$ cycloalkyl, -heterocyclyl, or —C$_1$-C$_6$ alkylheterocyclyl, wherein each alkyl, haloalkyl, alkenyl, alkynyl, aryl, alkylaryl, heteroaryl, alkylheteroaryl, cycloalkyl, and heterocyclyl is optionally substituted with one or two halogen, cyano, nitro, —N(R$^{L1}$)$_2$, —OR$^{L1}$, —ON(R$^{L1}$)$_2$, —N(R$^{L1}$)N(R$^{L1}$)$_2$, —SR$^{L1}$, —C(O)R$^{L1}$, —C(O)OR$^{L1}$, —C(O)N(R$^{L1}$)$_2$, —S(O)R$^{L1}$, —S(O)OR$^{L1}$, —S(O)N(R$^{L1}$)$_2$, —S(O)$_2$R$^{L1}$, —S(O)$_2$OR$^{L1}$, —S(O)$_2$N(R$^{L1}$)$_2$, —OC(O)R$^{L1}$, —OC(O)OR$^{L1}$, —OC(O)N(R$^{L1}$)$_2$, —N(R$^{L1}$)C(O)R$^{L1}$, —N(R$^{L1}$)C(O)OR$^{L1}$, or —N(R$^{L1}$)C(O)N(R$^{L1}$)$_2$, wherein each R$^{L1}$ is independently hydrogen, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more halogen, cyano, nitro, —N(R$^{L2}$)$_2$, —OR$^{L2}$, —ON(R$^{L2}$)$_2$, —N(R$^{L2}$)N(R$^{L2}$)$_2$, —SR$^{L2}$, —C(O)R$^{L2}$, —C(O)OR$^{L2}$, —C(O)N(R$^{L2}$)$_2$, —S(O)R$^{L2}$, —S(O)OR$^{L2}$, —S(O)N(R$^{L2}$)$_2$, —S(O)$_2$R$^{L2}$, —S(O)$_2$OR$^{L2}$, —S(O)$_2$N(R$^{L2}$)$_2$, —OC(O)R$^{L2}$, —OC(O)OR$^{L2}$, —OC(O)N(R$^{L2}$)$_2$, —N(R$^{L2}$)C(O)OR$^{L2}$, or —N(R$^{L2}$)C(O)N(R$^{L2}$)$_2$, wherein each R$^{L2}$ is independently hydrogen, —C$_1$-C$_6$ alkyl, aryl, or —C$_1$-C$_6$ alkylaryl.

A preferred subgenus of the fourteenth aspect includes compounds in which ring A is substituted with at least one R$^A$. Preferably, ring A is substituted with one or two R$^A$. More preferably, ring A is substituted with two R$^A$.

Another preferred subgenus of the fourteenth aspect includes compounds in which ring A is aryl, heteroaryl, or heterocyclyl, each optionally substituted with one or more R$^A$ groups.

Another preferred subgenus of the fourteenth aspect includes compounds in which ring A is aryl, heteroaryl, or heterocyclyl, each optionally substituted with one or more R$^A$ groups, provided that ring A is not piperidinyl. Compounds of this subgenus are preferably used for treating cancer, infectious disease, trauma, and age-related cataracts as described herein below, although they are also suitable for the other uses described in the "Methods of Use" section hereinbelow.

Another preferred subgenus of the fourteenth aspect includes compounds in which ring A is aryl or heteroaryl optionally substituted with one or more R$^A$ groups. Preferably, ring A is aryl or heteroaryl, each substituted with one or two R$^A$ groups.

Another preferred subgenus of the fourteenth aspect includes compounds in which ring A is aryl optionally substituted with one or more R$^A$ groups. Preferably, ring A is phenyl or naphthyl, each substituted with one or two R$^A$ groups. More preferably, ring A is phenyl substituted with one or two R$^A$ groups. Even more preferably, ring A is phenyl substituted with one or two R$^A$ groups, wherein at least one R$^A$ group is meta- or ortho- to L.

Another preferred subgenus of the fourteenth aspect includes compounds in which ring A is indolinyl, dihydrobenzofuranyl, dihydrobenzothienyl, benzooxazolinyl, benzimidazolidinyl, benzothioxazolinyl, cromanyl, 2,3-dihydrobenzo[b][1,4]dioxanyl, benzo[d][1,3]dioxolyl, tetrahydronaphthyl, indenyl, or dihydroindenyl, each optionally substituted with one or more R$^A$ groups, or preferably, each substituted with one or two R$^A$ groups.

Another preferred subgenus of the fourteenth aspect includes compounds in which ring A is tetrahydroquinolinyl, 4,5,6,7-tetrahydrobenzimidazolyl, 4,5,6,7-tetrahydrobenzothienyl, 4,5,6,7-tetrahydrobenzo-furanyl, 4,5,6,7-tetrahydroindolyl, 4,5,6,7-tetrahydrobenzoxazolyl, 4,5,6,7-tetrahydrobenzo-thioxazolyl, each optionally substituted with one or more R$^A$ groups, or preferably, each substituted with one or two R$^A$ groups.

Another preferred subgenus of the fourteenth aspect includes compounds in which ring A is heteroaryl optionally substituted with one or more R$^A$ groups, or preferably, each substituted with one or two R$^A$ groups. Preferably, ring A is pyrrolyl, furanyl, thienyl, benzothienyl, indolyl, pyridinyl, pyrimidinyl, pyrazinyl, 1,3,5-triazinyl, benzofuranyl, benzimidazolyl, benzoxazolyl, benzothioxazolyl, benzotriazolyl, quinolinyl, or quinazolinyl, each optionally substituted with one or more R$^A$ groups, or preferably, each substituted with one or two R$^A$ groups. More preferably, ring A is pyridinyl, pyrimidinyl, pyrazinyl, or 1,3,5-triazinyl, each optionally substituted with one or more R$^A$ groups, or preferably, each substituted with one or two R$^A$ groups. In an alternative embodiment, ring A is benzothienyl, indolyl, benzofuranyl, benzimidazolyl, benzoxazolyl, benzothioxazolyl, or benzotriazolyl, each optionally substituted with one or more R$^A$ groups, or preferably, each substituted with one or two R$^A$ groups. Preferably, ring A is benzothienyl, indolyl, or benzofuranyl, each optionally substituted with one or more R$^A$ groups, or preferably, each substituted with one or two R$^A$ groups.

Another preferred subgenus of the fourteenth aspect includes compounds in which ring A is $C_5$-$C_{10}$ cycloalkyl substituted with one or two $R^A$ groups. Preferably, ring A is $C_5$-$C_7$ cycloalkyl substituted with one or two $R^A$ groups.

In a preferred subgenus of any of the preceding subgenera of the fourteenth aspect, (a) at least one $R^A$ is halogen, cyano, nitro, —N($R^{411}$)$_2$, —$OR^{411}$, —ON($R^{411}$)$_2$, —N($R^{411}$)N($R^{411}$)$_2$, —$SR^{411}$, —C(O)$R^{411}$, —C(O)O$R^{411}$, —C(O)N($R^{411}$)$_2$, —S(O)$R^{411}$, —S(O)O$R^{411}$, —S(O)N($R^{411}$)$_2$, —S(O)$_2$$R^{411}$, —S(O)$_2$O$R^{411}$, —S(O)$_2$N($R^{411}$)$_2$, —OC(O)$R^{411}$, —OC(O)O$R^{411}$, —OC(O)N($R^{411}$)$_2$, —N($R^{411}$)C(O)O$R^{411}$, or —N($R^{411}$)C(O)N($R^{411}$)$_2$, each $R^{411}$ is independently hydrogen, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more groups which are each independently halogen, cyano, nitro, —N($R^{412}$)$^2$, —$OR^{412}$, —ON($R^{412}$)$_2$, —N($R^{412}$)N($R^{412}$)$_2$, —$SR^{412}$, —C(O)$R^{412}$, —C(O)O$R^{412}$, —C(O)N($R^{412}$)$_2$, —S(O)$R^{412}$, —S(O)O$R^{412}$, —S(O)N($R^{412}$)$_2$, —S(O)$_2$$R^{412}$, —S(O)$_2$O$R^{412}$, —S(O)$_2$N($R^{412}$)$_2$, —OC(O)$R^{412}$, —OC(O)O$R^{412}$, —OC(O)N($R^{412}$)$_2$, —N($R^{412}$)C(O)O$R^{412}$, or —N($R^{412}$)C(O)N($R^{412}$)$_2$, wherein each $R^{412}$ is independently hydrogen, —$C_1$-$C_6$ alkyl, aryl, or —$C_1$-$C_6$ alkylaryl.

(b) at least one $R^A$ is halogen, cyano, nitro, —NH$_2$, —OH, —ONH$_2$, —NHNH$_2$, —C(O)OH, or —C(O)NH$_2$.

(c) only one $R^A$ is present and $R^A$ is halogen, cyano, nitro, —NH$_2$, —OH, —ONH$_2$, —NHNH$_2$, —C(O)OH, or —C(O)NH$_2$;

(d) at least one $R^A$ is —N($R^{411}$)$_2$ or —$OR^{411}$, wherein each $R^{411}$ is independently hydrogen, —$C_1$-$C_6$ alkyl, -aryl, —$C_1$-$C_6$ alkylaryl, -heteroaryl, or —$C_1$-$C_6$ alkylheteroaryl, wherein each alkyl, aryl, alkylaryl, heteroaryl, and alkylheteroaryl is optionally substituted with one or more groups which are each independently halogen, cyano, nitro, —N($R^{412}$)$^2$, —$OR^{412}$, —ON($R^{412}$)$_2$, —N($R^{412}$)N($R^{412}$)$_2$, —$SR^{412}$, —C(O)$R^{412}$, —C(O)O$R^{412}$, —C(O)N($R^{412}$)$_2$, —S(O)$R^{412}$, —S(O)O$R^{412}$, —S(O)N($R^{412}$)$_2$, —S(O)$_2$$R^{412}$, —S(O)$_2$O$R^{412}$, —S(O)$_2$N($R^{412}$)$_2$, —OC(O)$R^{412}$, —OC(O) O$R^{412}$, —OC(O)N($R^{412}$)$_2$, —N($R^{412}$)C(O)O$R^{412}$, or —N($R^{412}$)C(O)N($R^{412}$)$_2$, wherein each $R^{412}$ is independently hydrogen, or —$C_1$-$C_6$ alkyl;

(e) at least one $R^A$ is —NHR$^{411}$ or —$OR^{411}$, wherein $R^{411}$ is phenyl or pyridinyl, each optionally substituted with one or more groups which are each independently halogen, cyano, nitro, —N($R^{412}$)$^2$, —$OR^{412}$, —ON($R^{412}$)$_2$, —N($R^{412}$)N($R^{412}$)$_2$, —$SR^{412}$, —C(O)$R^{412}$, —C(O)O$R^{412}$, —C(O)N($R^{412}$)$_2$, —S(O)$_2$$R^{412}$, —S(O)$_2$O$R^{412}$, —S(O)$_2$N($R^{412}$)$_2$, —OC(O)$R^{412}$, —OC(O)O$R^{412}$, —OC(O)N($R^{412}$)$_2$, —N($R^{412}$)C(O)O$R^{412}$, or —N($R^{412}$)C(O)N($R^{412}$)$_2$, —$C_1$-$C_6$ alkyl, -aryl, or -heteroaryl, wherein each $R^{412}$ is independently hydrogen, —$C_1$-$C_6$ alkyl (f) at least one $R^A$ is —NHR$^{411}$, wherein $R^{411}$ is phenyl or pyridinyl, each optionally substituted with one or two groups which are each independently halogen, cyano, nitro, —N($R^{412}$)$^2$, —$OR^{412}$, —ON($R^{412}$)$_2$, —N($R^{412}$)N($R^{412}$)$_2$, —$SR^{412}$, —C(O)$R^{412}$, —C(O)O$R^{412}$, —C(O)N($R^{412}$)$_2$, —S(O)$_2$$R^{412}$, —S(O)$_2$O$R^{412}$, —S(O)$_2$N($R^{412}$)$_2$, —OC(O)$R^{412}$, —OC(O)O$R^{412}$, —OC(O)N($R^{412}$)$_2$, —N($R^{412}$)C(O)O$R^{412}$, or —N($R^{412}$)C(O)N($R^{412}$)$_2$, —$C_1$-$C_6$ alkyl, -aryl, or -heteroaryl, wherein each $R^{412}$ is independently hydrogen, —$C_1$-$C_6$ alkyl, aryl, or —$C_1$-$C_6$ alkyl. Even more preferably, only one $R^A$ is present and $R^A$ is —NHR$^{411}$, wherein $R^{411}$ is phenyl or pyridinyl, each optionally substituted with one or two groups which are each independently halogen, cyano, nitro, —N($R^{412}$)$^2$, —$OR^{412}$, —ON($R^{412}$)$_2$, —N($R^{412}$)N($R^{412}$)$_2$, —$SR^{412}$, —C(O)$R^{412}$, —C(O)O$R^{412}$, —C(O)N($R^{412}$)$_2$, —S(O)$R^{412}$, —S(O)$_2$$R^{412}$, —S(O)$_2$O$R^{412}$, —S(O)$_2$N($R^{412}$)$_2$, —OC(O)$R^{412}$, —OC(O)O$R^{412}$, —OC(O)N($R^{412}$)$_2$, —N($R^{412}$)C(O)O$R^{412}$, or —N($R^{412}$)C(O)N($R^{412}$)$_2$, —$C_1$-$C_6$ alkyl, -aryl, or -heteroaryl, wherein each $R^{412}$ is independently hydrogen, —$C_1$-$C_6$ alkyl;

(g) at least one $R^A$ is —$C_1$-$C_6$ alkyl, -aryl, —$C_1$-$C_6$ alkylaryl, -heteroaryl, or —$C_1$-$C_6$ alkylheteroaryl, wherein each alkyl, aryl, alkylaryl, heteroaryl, and alkylheteroaryl, is optionally substituted with one or more groups which are each independently halogen, cyano, nitro, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, -heterocyclyl, —N($R^{421}$)$_2$, —$OR^{421}$, —ON($R^{421}$)$_2$, —N($R^{421}$)N($R^{421}$)$_2$, —$SR^{421}$, —C(O)$R^{421}$, —C(O)O$R^{421}$, —C(O)N($R^{421}$)$_2$, —S(O)$R^{421}$, —S(O) O$R^{421}$, —S(O)N($R^{421}$)$_2$, —S(O)$_2$$R^{421}$, —S(O)$_2$O$R^{421}$, —S(O)$_2$N($R^{421}$)$_2$, —OC(O)$R^{421}$, —OC(O)O$R^{421}$, —OC(O)N($R^{421}$)$_2$, —N($R^{421}$)C(O)O$R^{421}$, or —N($R^{421}$)C(O)N($R^{421}$)$_2$, wherein each $R^{421}$ is independently hydrogen, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl;

(h) at least one $R^A$ is -aryl or -heteroaryl, each optionally substituted with one or more groups which are each independently halogen, cyano, nitro, —$C_1$-$C_6$ alkyl, —$C_1$-$C_6$haloalkyl; -aryl, -heteroaryl, —N($R^{421}$)$_2$, —$OR^{421}$, —ON($R^{421}$)$_2$, —N($R^{421}$)N($R^{421}$)$_2$, —$SR^{421}$, —C(O)$R^{421}$, —C(O)O$R^{421}$, —C(O)N($R^{421}$)$_2$, —S(O)$_2$$R^{421}$, —S(O)$_2$O$R^{421}$, —S(O)$_2$N($R^{421}$)$_2$, —OC(O)$R^{421}$, —OC(O)O$R^{421}$, —OC(O)N($R^{421}$)$_2$, —N($R^{421}$)C(O)O$R^{421}$, or —N($R^{421}$)C(O)N($R^{421}$)$_2$, wherein each $R^{421}$ is independently hydrogen, —$C_1$-$C_6$ alkyl, —$C_1$-$C_6$ haloalkyl; -aryl, —$C_1$-$C_6$ alkylaryl, -heteroaryl, —$C_1$-$C_6$ alkylheteroaryl, —$C_3$-$C_8$ cycloalkyl, or -heterocyclyl.

(i) only one $R^A$ is present and $R^A$ is -aryl or -heteroaryl, each optionally substituted with one or more groups which are each independently halogen, cyano, nitro, —$C_1$-$C_6$ alkyl, —$C_1$-$C_6$ haloalkyl; -aryl, -heteroaryl, —N($R^{421}$)$_2$, —$OR^{421}$, —ON($R^{421}$)$_2$, —N($R^{421}$)N($R^{421}$)$_2$, —$SR^{421}$, —C(O)$R^{421}$, —C(O)O$R^{421}$, —C(O)N($R^{421}$)$_2$, —S(O)$_2$$R^{421}$, —S(O)$_2$O$R^{421}$, —S(O)$_2$N($R^{421}$)$_2$, —OC(O)$R^{421}$, —OC(O)O$R^{421}$, —OC(O)N($R^{421}$)$_2$, —N($R^{421}$)C(O)O$R^{421}$, or —N($R^{421}$)C(O)N($R^{421}$)$_2$, wherein each $R^{421}$ is independently hydrogen, —$C_1$-$C_6$ alkyl, —$C_1$-$C_6$ haloalkyl; -aryl, —$C_1$-$C_6$ alkylaryl, -heteroaryl, —$C_1$-$C_6$ alkylheteroaryl, —$C_3$-$C_8$ cycloalkyl, or -heterocyclyl;

(j) one of two $R^A$ are present and one $R^A$ is phenyl optionally substituted with one or more groups which are each independently halogen, cyano, nitro, —$C_1$-$C_6$ alkyl, —$C_1$-$C_6$ haloalkyl; -aryl, -heteroaryl, —N($R^{421}$)$_2$, —$OR^{421}$, —ON($R^{421}$)$_2$, —N($R^{421}$)N($R^{421}$)$_2$, —$SR^{421}$, —C(O)$R^{421}$, —C(O)O$R^{421}$, —C(O)N($R^{421}$)$_2$, —S(O)$_2$$R^{421}$, —S(O)$_2$O$R^{421}$, —S(O)$_2$N($R^{421}$)$_2$, —OC(O)$R^{421}$, —OC(O)O$R^{421}$, —OC(O)N($R^{421}$)$_2$, —N($R^{421}$)C(O)O$R^{421}$, or —N($R^{421}$)C(O)N($R^{421}$)$_2$, wherein each $R^{421}$ is independently hydrogen, —$C_1$-$C_6$ alkyl, —$C_1$-$C_6$ haloalkyl; -aryl, —$C_1$-$C_6$ alkylaryl, -heteroaryl, —$C_1$-$C_6$ alkylheteroaryl, —$C_3$-$C_8$ cycloalkyl, or -heterocyclyl;

(k) one or two $R^A$ are present, one $R^A$ is phenyl optionally substituted with one or more groups which are each independently halogen, cyano, nitro, —$C_1$-$C_6$ alkyl, —$C_1$-$C_6$ haloalkyl; -aryl, -heteroaryl, —N($R^{421}$)$_2$, —$OR^{421}$, —ON($R^{421}$)$_2$, —N($R^{421}$)N($R^{421}$)$_2$, —$SR^{421}$, —C(O)$R^{421}$, —C(O)OR$^{A21}$, —C(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl, where the optionally substituted phenyl is ortho or meta to L;

(l) one or two R$^A$ are present, one R$^A$ is phenyl optionally substituted with one or more groups which are each independently halogen, cyano, nitro, —C$_1$-C$_6$ alkyl, —C$_1$-C$_6$ haloalkyl; -aryl, -heteroaryl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl, where the optionally substituted phenyl is ortho to L;

(m) at least one R$^A$ is —C$_1$-C$_6$ alkyl optionally substituted with one or more groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O(OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl.

(n) at least one R$^A$ is —C$_1$-C$_6$ alkyl optionally substituted with one or more groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen or —C$_1$-C$_6$ alkyl;

(o) at least one R$^A$ is —C$_1$-C$_6$ alkyl substituted with one or two groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen or —C$_1$-C$_6$ alkyl; or (p) only one R$^A$ is present and R$^A$ is —C$_1$-C$_6$ alkyl substituted with one or two groups which are each independently halogen, cyano, nitro, —C$_1$-C$_6$ alkyl, —C$_1$-C$_6$ haloalkyl; alkenyl, —C$_2$-C$_6$ alkynyl, -aryl, —C$_1$-C$_6$ alkylaryl, -heteroaryl, alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen or —C$_1$-C$_6$ alkyl.

A preferred subgenus of any of the preceding subgenera includes compounds in which L is (a) a bond;
(b) —X-L$^1$, wherein L$^1$ is -linear C$_1$-C$_6$alkyl- optionally substituted with one or two R$^L$ groups
(c) -linear C$_1$-C$_6$alkyl- substituted with one or two R$^L$ groups
(d) -linear C$_1$-C$_6$alkyl- substituted with one R$^L$ group;
(e) -linear C$_1$-C$_3$alkyl- substituted with one R$^L$ group;
(f). -linear C$_1$-C$_6$alkyl-,
(g) —CH(R$^L$)— or
(h) —CH$_2$—.

A preferred subgenus of any of the preceding subgenera includes compounds in which X is (a) a bond;
(b) —O—, —S—, or —N(R$^X$)—;
(c) —O—;
(d) —C(Y)—, —S(O)—, —S(O)$_2$, —OC(O)—, —N(R$^X$)C(O)—, —N(R$^X$)S(O)—, —OS(O)$_2$, or —N(R$^X$)S(O)$_2$—;
(e) —C(O)—, —C(=NH)—, or —N(H)C(O)—;
(f) —C$_1$-C$_3$alkylOC(O)—, —C$_1$-C$_3$alkylN(R$^X$)C(O)—, —C$_1$-C$_3$alkylN(R$^X$)S(O)—, —C$_1$-C$_3$alkylOS(O)$_2$, or —C$_1$-C$_3$alkylN(R$^X$)S(O)$_2$—;
(g) —C$_1$-C$_3$alkylN(R$^X$)C(O)—; or
(h) —C$_1$-C$_2$alkylN(H)C(O)—.

A preferred subgenus of any of the preceding subgenera includes compounds in which (a) at least one R$^L$ is —C$_1$-C$_6$ alkyl optionally substituted with one or two groups which are each independently halogen, cyano, nitro, —N(R$^{L11}$)$_2$, —OR$^{L11}$, —ON(R$^{L11}$)$_2$, —N(R$^{L11}$)N(R$^{L11}$)$_2$, —SR$^{L11}$, —C(O)R$^{L11}$, —C(O)OR$^{L11}$, —C(O)N(R$^{L11}$)$_2$, —S(O)R$^{L11}$, —S(O)OR$^{L11}$, —S(O)N(R$^{L11}$)$_2$, —S(O)$_2$R$^{L11}$, —S(O)$_2$OR$^{L11}$, —S(O)$_2$N(R$^{L11}$)$_2$, —OC(O)R$^{L11}$, —OC(O)OR$^{L11}$, —OC(O)N(R$^{L11}$)$_2$, —N(R$^{L11}$)C(O)OR$^{L11}$, or —N(R$^{L11}$)C(O)—N(R$^{L11}$)$_2$, wherein each R$^{L11}$ is independently hydrogen or —C$_1$-C$_6$ alkyl;

(b) at least one R$^L$ is —C$_1$-C$_6$ alkyl-OR$^{L21}$, —C$_1$-C$_6$ alkyl-NH—R$^{L21}$, —C$_1$-C$_6$ alkyl-NHC(O)R$^{L21}$, —C$_2$-C$_6$ alkenyl-OR$^{L21}$, —C$_2$-C$_6$ alkenyl-NH—R$^{L21}$, or —C$_2$-C$_6$ alkenyl-NHC(O)R$^{L21}$, wherein each R$^{L21}$ is independently hydrogen, —C$_1$-C$_6$ alkyl, -aryl, —C$_1$-C$_6$ alkylaryl, -heteroaryl, or —C$_1$-C$_6$ alkylheteroaryl, wherein each alkyl, aryl, alkylaryl, heteroaryl, cycloalkyl, and alkylheteroaryl, is optionally substituted with one or more groups which are each independently halogen, cyano, nitro, —N(R$^{L22}$)$_2$, —OR$^{L22}$, —ON(R$^{L22}$)$_2$, —N(R$^{L22}$)N(R$^{L22}$)$_2$, —SR$^{L22}$, —C(O)R$^{L22}$, —C(O)OR$^{L22}$, —C(O)N(R$^{L22}$)$_2$, —S(O)R$^{L22}$, —S(O)OR$^{L22}$, —S(O)N(R$^{L22}$)$_2$, —S(O)$_2$R$^{L22}$, —S(O)$_2$OR$^{L22}$, —S(O)$_2$N(R$^{L22}$)$_2$, —OC(O)R$^{L22}$, —OC(O)OR$^{L22}$, —OC(O)N(R$^{L22}$)$_2$, —N(R$^{L22}$)C(O)OR$^{L22}$, or —N(R$^{L22}$)C(O)N(R$^{L22}$)$_2$, wherein each R$^{L22}$ is independently hydrogen, —C$_1$-C$_6$ alkyl, aryl, or —C$_1$-C$_6$ alkylaryl;

(c) at least one R$^L$ is —N(R$^{L21}$)$_2$, —OR$^{L21}$, —ON(R$^{L21}$)$_2$, —N(R$^{L21}$)N(R$^{L21}$)$_2$, —C(O)R$^{L21}$, —C(O)OR$^{L21}$, —C(O)N(R$^{L21}$)$_2$, —OC(O)R$^{L21}$, —OC(O)OR$^{L21}$, —OC(O)N(R$^{L21}$)$_2$, —N(R$^{L21}$)C(O)OR$^{L21}$, or —N(R$^{L21}$)C(O)N(R$^{L21}$)$_2$, wherein each R$^{L21}$ is independently hydrogen, —C$_1$-C$_6$ alkyl, -aryl, —C$_1$-C$_6$ alkylaryl, -heteroaryl, or —C$_1$-C$_6$ alkylheteroaryl, wherein each alkyl, aryl, alkylaryl, heteroaryl, cycloalkyl, and alkylheteroaryl, is optionally substituted with one or more groups which are each independently halogen, cyano, nitro, —N($R^{L22}$)$_2$, —O$R^{L22}$, —ON($R^{L22}$)$_2$, —N($R^{L22}$)N($R^{L22}$)$_2$, —S$R^{L22}$, —C(O)$R^{L22}$, —C(O)O$R^{L22}$, —C(O)N($R^{L22}$)$_2$, —S(O)$R^{L22}$, —S(O)O$R^{L22}$, —S(O)N($R^{L22}$)$_2$, —S(O)$_2$$R^{L22}$, —S(O)$_2$O$R^{L22}$, —S(O)$_2$N($R^{L22}$)$_2$, —OC(O)$R^{L22}$, —OC(O)O$R^{L22}$, —OC(O)N($R^{L22}$)$_2$, —N($R^{L22}$)C(O)O$R^{L22}$, or —N($R^{L22}$)C(O)N($R^{L22}$)$_2$, wherein each $R^{L22}$ is independently hydrogen, —$C_1$-$C_6$ alkyl, aryl, or —$C_1$-$C_6$ alkylaryl;

or (d) at least one $R^L$ is —N($R^{L21}$)$_2$ or —O$R^{L21}$, wherein each $R^{L21}$ is independently hydrogen, —$C_1$-$C_6$ alkyl, -aryl, —$C_1$-$C_6$ alkylaryl, -heteroaryl, or —$C_1$-$C_6$ alkylheteroaryl, wherein each alkyl, aryl, alkylaryl, heteroaryl, and alkylheteroaryl, is optionally substituted with one or more halogen, cyano, nitro, —N($R^{L22}$)$_2$, —O$R^{L22}$, —ON($R^{L22}$)$_2$, —C(O)O$R^{L22}$, or —C(O)N($R^{L22}$)$_2$, wherein each $R^{L22}$ is independently hydrogen, —$C_1$-$C_6$ alkyl, aryl, or —$C_1$-$C_6$ alkylaryl.

Another preferred genus of the fourteenth aspect includes compounds in which the compound of formula (XXI) is according to one of the formulas (XXII)-(XXIX), (XXII)

(XXIII)

(XXIV)

(XXV)

(XXVI)

(XXVII)

(XXVIII)

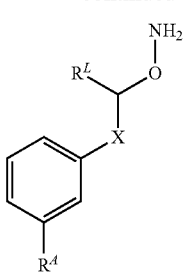

(XXIX)

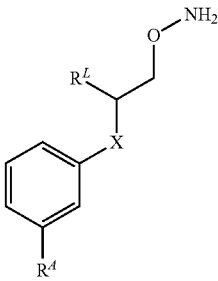

(XXX)

(XXXI)

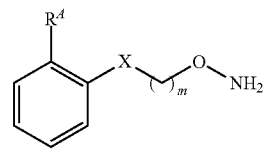

(XXXII)

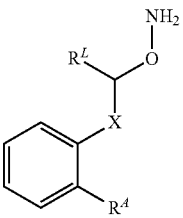

(XXXIII)

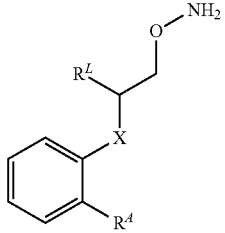

wherein m is 0, 1, 2, or 3; and n is 0, 1, 2, 3, 4, or 5.

A preferred subgenus of any of the formulas (XXV)-(XXVII) includes compounds in which n is 1, 2, 3, 4, or 5. Preferably, n is 1 or 2. More preferably, n is 1.

A preferred subgenus of any of the formulas (XXII), (XXV), and (XXVIII), includes compounds in which m is 1.

A preferred subgenus of any of the formulas (XXII)-(XXIV), includes compounds in which ring A indolinyl, dihydrobenzofuranyl, dihydrobenzothienyl, benzooxazolinyl, benzimidazolidinyl, benzothioxazolinyl, cromanyl, 2,3-dihydrobenzo[b][1,4]dioxanyl, benzo[d][1,3]dioxolyl, tetrahydronaphthyl, indenyl, or dihydroindenyl, each optionally substituted with one or more $R^A$ groups, and preferably, substituted with one or two $R^A$ groups.

Another preferred subgenus of any of the formulas (XXII)-(XXIV), includes compounds in which ring A is (a) heteroaryl optionally substituted with one or more $R^A$ groups, and preferably, substituted with one or two $R^A$ groups.

(b) pyrrolyl, furanyl, thienyl, imidazolyl, benzothienyl, indolyl, pyridinyl, pyrimidinyl, pyrazinyl, 1,3,5-triazinyl, benzofuranyl, benzimidazolyl, benzoxazolyl, benzothioxazolyl, benzotriazolyl, quinolinyl, or quinazolinyl, each optionally substituted with one or more $R^A$ groups, and preferably, substituted with one or two $R^A$ groups;

(c) pyridinyl, pyrimidinyl, pyrazinyl, or 1,3,5-triazinyl, each optionally substituted with one or more $R^A$ groups, and preferably, substituted with one or two $R^A$ groups;

(d) benzothienyl, indolyl, benzofuranyl, benzimidazolyl, benzoxazolyl, benzothioxazolyl, or benzotriazolyl, each optionally substituted with one or more $R^A$ groups, and preferably, substituted with one or two $R^A$ groups; or (e) benzothienyl, indolyl, or benzofuranyl, each optionally substituted with one or more $R^A$ groups, and preferably, substituted with one or two $R^A$ groups.

Another preferred subgenus of any of formulas (XXII)-(XXIV), includes compounds in which ring A is tetrahydroquinolinyl, 4,5,6,7-tetrahydrobenzimidazolyl, 4,5,6,7-tetrahydrobenzothienyl, 4,5,6,7-tetrahydrobenzo-furanyl, 4,5,6,7-tetrahydroindolyl, 4,5,6,7-tetrahydrobenzoxazolyl, 4,5,6,7-tetrahydrobenzo-thioxazolyl, each optionally substituted with one or more $R^A$ groups, and preferably, substituted with one or two $R^A$ groups.

Another preferred subgenus of any of formulas (XXII)-(XXIV), includes compounds in which ring A is $C_5$-$C_{10}$ cycloalkyl substituted with one or two $R^A$ groups. Preferably, ring A is $C_5$-$C_7$ cycloalkyl substituted with one or two $R^A$ groups.

A preferred subgenus of any of the preceding subgenera of formulas (XXII)-(XXXIII), includes compounds in which (a) at least one $R^A$ is halogen, cyano, nitro, —N($R^{A11}$)$_2$, —O$R^{A11}$, —ON($R^{A11}$)$_2$, —N($R^{A11}$)N($R^{A11}$)$_2$, —S$R^{A11}$, —C(O)$R^{A11}$, —C(O)O$R^{A11}$, —C(O)N($R^{A11}$)$_2$, —S(O)$R^{A11}$, —S(O)O$R^{A11}$, —S(O)N($R^{A11}$)$_2$, —S(O)$_2$$R^{A11}$, —S(O)$_2$O$R^{A11}$, —S(O)$_2$N($R^{A11}$)$_2$, —OC(O)$R^{A11}$, —OC(O)O$R^{A11}$, —OC(O)N($R^{A11}$)$_2$, —N($R^{A11}$)C(O)O$R^{A11}$, or —N($R^{A11}$)C(O)N($R^{A11}$)$_2$, wherein each $R^{A11}$ is independently hydrogen, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more groups which are each independently halogen, cyano, nitro, —N($R^{A12}$)$_2$, —O$R^{A12}$, —ON($R^{A12}$)$_2$, —N($R^{A12}$)N($R^{A12}$)$_2$, —S$R^{A12}$, —C(O)$R^{A12}$, —C(O)O$R^{A12}$, —C(O)N($R^{A12}$)$_2$, —S(O)$R^{A12}$, —S(O)O$R^{A12}$, —S(O)N($R^{A12}$)$_2$, —S(O)$_2$$R^{A12}$, —S(O)$_2$O$R^{A12}$, —S(O)$_2$N($R^{A12}$)$_2$, —OC(O)$R^{A12}$, —OC(O)O$R^{A12}$, —OC(O)N($R^{A12}$)$_2$, —N($R^{A12}$)C(O)O$R^{A12}$, or —N($R^{A12}$)C(O)N($R^{A12}$)$_2$, wherein each $R^{A12}$ is independently hydrogen, —$C_1$-$C_6$ alkyl, aryl, or —$C_1$-$C_6$ alkylaryl.

(b) at least one $R^A$ is halogen, cyano, nitro, —NH$_2$, —OH, —ONH$_2$, —NHNH$_2$, —C(O)OH, or —C(O)NH$_2$;

(c) only one $R^A$ is present and $R^A$ is halogen, cyano, nitro, —NH$_2$, —OH, —ONH$_2$, —NHNH$_2$, —C(O)OH, or —C(O)NH$_2$;

(d) at least one $R^A$ is —N($R^{A11}$)$_2$ or —O$R^{A11}$, wherein each $R^{A11}$ is independently hydrogen, —$C_1$-$C_6$ alkyl, -aryl, —$C_1$-$C_6$ alkylaryl, -heteroaryl, or —$C_1$-$C_6$ alkylheteroaryl, wherein each alkyl, aryl, alkylaryl, heteroaryl, and alkylheteroaryl is optionally substituted with one or more groups which are each independently halogen, cyano, nitro, —N($R^{A12}$)$_2$, —O$R^{A12}$, —ON($R^{A12}$)$_2$, —N($R^{A12}$)N($R^{A12}$)$_2$, —S$R^{A12}$, —C(O)$R^{A12}$, —C(O)O$R^{A12}$, —C(O)N($R^{A12}$)$_2$, —S(O)$R^{A12}$, —S(O)O$R^{A12}$, —S(O)N($R^{A12}$)$_2$, —S(O)$_2$$R^{A12}$, —S(O)$_2$O$R^{A12}$, —S(O)$_2$N($R^{A12}$)$_2$, —OC(O)$R^{A12}$, —OC(O) O$R^{A12}$, —OC(O)N($R^{A12}$)$_2$, —N($R^{A12}$)C(O)O$R^{A12}$, or —N($R^{A12}$)C(O)N($R^{A12}$)$_2$, wherein herein each $R^{A12}$ is independently hydrogen or —$C_1$-$C_6$ alkyl;

(e) at least one $R^A$ is —NH$R^{A11}$ or —O$R^{A11}$, wherein $R^{A11}$ is phenyl or pyridinyl, each optionally substituted with one or more groups which are each independently halogen, cyano, nitro, —N($R^{A12}$)$_2$, —O$R^{A12}$, —ON($R^{A12}$)$_2$, —N($R^{A12}$)N($R^{A12}$)$_2$, —S$R^{A12}$, —C(O)$R^{A12}$, —C(O)O$R^{A12}$, —C(O)N($R^{A12}$)$_2$, —S(O)$_2$$R^{A12}$, —S(O)$_2$O$R^{A12}$, —S(O)$_2$N($R^{A12}$)$_2$, —OC(O)$R^{A12}$, —OC(O)O$R^{A12}$, —OC(O)N($R^{A12}$)$_2$, —N($R^{A12}$)C(O)O$R^{A12}$, or —N($R^{A12}$)C(O)N($R^{A12}$)$_2$, —$C_1$-$C_6$ alkyl, -aryl, or -heteroaryl, wherein each $R^{A12}$ is independently hydrogen or —$C_1$-$C_6$ alkyl;

(f) at least one $R^A$ is —NH$R^{A11}$, wherein $R^{A11}$ is phenyl or pyridinyl, each optionally substituted with one or two groups which are each independently halogen, cyano, nitro, —N($R^{A12}$)$_2$, —O$R^{A12}$, —ON($R^{A12}$)$_2$, —N($R^{A12}$)N($R^{A12}$)$_2$, —S$R^{A12}$, —C(O)$R^{A12}$, —C(O)O$R^{A12}$, —C(O)N($R^{A12}$)$_2$, —S(O)$_2$$R^{A12}$, —S(O)$_2$O$R^{A12}$, —S(O)$_2$N($R^{A12}$)$_2$, —OC(O)$R^{A12}$, —OC(O)O$R^{A12}$, —OC(O)N($R^{A12}$)$_2$, —N($R^{A12}$)C(O)O$R^{A12}$, or —N($R^{A12}$)C(O)N($R^{A12}$)$_2$, —$C_1$-$C_6$ alkyl, -aryl, or -heteroaryl, wherein each $R^{A12}$ is independently hydrogen or —$C_1$-$C_6$ alkyl;

(g) only one $R^A$ is present and $R^A$ is —NH$R^{A11}$, wherein $R^{A11}$ is phenyl or pyridinyl, each optionally substituted with one or two groups which are each independently halogen, cyano, nitro, —N($R^{A12}$)$_2$, —O$R^{A12}$, —ON($R^{A12}$)$_2$, —N($R^{A12}$)N($R^{A12}$)$_2$, —S$R^{A12}$, —C(O)$R^{A12}$, —C(O)O$R^{A12}$, —C(O)N($R^{A12}$)$_2$, —S(O)$_2$$R^{A12}$, —S(O)$_2$O$R^{A12}$, —S(O)$_2$N($R^{A12}$)$_2$, —OC(O)$R^{A12}$, —OC(O)O$R^{A12}$, —OC(O)N($R^{A12}$)$_2$, —N($R^{A12}$)C(O)O$R^{A12}$, or —N($R^{A12}$)C(O)N($R^{A12}$)$_2$, —$C_1$-$C_6$ alkyl, -aryl, or -heteroaryl, wherein each $R^{A12}$ is independently hydrogen or —$C_1$-$C_6$ alkyl;

(h) at least one $R^A$ is —$C_1$-$C_6$ alkyl, -aryl, —$C_1$-$C_6$ alkylaryl, -heteroaryl, or —$C_1$-$C_6$ alkylheteroaryl, wherein each alkyl, aryl, alkylaryl, heteroaryl, and alkylheteroaryl, is optionally substituted with one or more groups which are each independently halogen, cyano, nitro, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, —N($R^{A21}$)$_2$, —O$R^{A21}$, —ON($R^{A21}$)$_2$, —N($R^{A21}$)N($R^{A21}$)$_2$, —S$R^{A21}$, —C(O)$R^{A21}$, —C(O)O$R^{A21}$, —C(O)N($R^{A21}$)$_2$, —S(O)$R^{A21}$, —S(O)O$R^{A21}$, —S(O)N($R^{A21}$)$_2$, —S(O)$_2$$R^{A21}$, —S(O)$_2$O$R^{A21}$, —S(O)$_2$N($R^{A21}$)$_2$, —OC(O)$R^{A21}$, —OC(O)O$R^{A21}$, —OC(O)N($R^{A21}$)$_2$, —N($R^{A21}$)C(O)O$R^{A21}$, or —N($R^{A21}$)C(O)N($R^{A21}$)$_2$, wherein each $R^{A21}$ is independently hydrogen, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl;

(i) at least one $R^A$ is -aryl or -heteroaryl, each optionally substituted with one or more groups which are each independently halogen, cyano, nitro, —$C_1$-$C_6$ alkyl, —$C_1$-$C_6$ haloalkyl; -aryl, -heteroaryl, —N($R^{A21}$)$_2$, —O$R^{A21}$, —ON($R^{A21}$)$_2$, —N($R^{A21}$)N($R^{A21}$)$_2$, —S$R^{A21}$, —C(O)$R^{A21}$, —C(O)O$R^{A21}$, —C(O)N($R^{A21}$)$_2$, —S(O)$_2$$R^{A21}$, —S(O)$_2$O$R^{A21}$, —S(O)$_2$N($R^{A21}$)$_2$, —OC(O)$R^{A21}$, —OC(O)O$R^{A21}$, —OC(O)N($R^{A21}$)$_2$, —N($R^{A21}$)C(O)O$R^{A21}$, or —N($R^{A21}$)C(O)N($R^{A21}$)$_2$, wherein each $R^{A21}$ is independently hydrogen, —$C_1$-$C_6$ alkyl, $C_1$-$C_6$ haloalkyl; -aryl, —$C_1$-$C_6$ alkylaryl, -heteroaryl, —$C_1$-$C_6$ alkylheteroaryl, —$C_3$-$C_8$ cycloalkyl, or -heterocyclyl;

(j) only one $R^A$ is present and $R^A$ is -aryl or -heteroaryl, each optionally substituted with one or more groups which are each independently halogen, cyano, nitro, —$C_1$-$C_6$ alkyl, —$C_1$-$C_6$ haloalkyl; -aryl, -heteroaryl, —N($R^{A21}$)$_2$, —O$R^{A21}$, —ON($R^{A21}$)$_2$, —N($R^{A21}$)N($R^{A21}$)$_2$, —S$R^{A21}$, —C(O)R$^{A21}$, —C(O)OR$^{A21}$, —C(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl;

(j) one of two R$^A$ are present and one R$^A$ is phenyl optionally substituted with one or more groups which are each independently halogen, cyano, nitro, —C$_1$-C$_6$ alkyl, —C$_1$-C$_6$ haloalkyl; -aryl, -heteroaryl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl;

(k) one or two R$^A$ are present, one R$^A$ is phenyl optionally substituted with one or more groups which are each independently halogen, cyano, nitro, —C$_1$-C$_6$ alkyl, —C$_1$-C$_6$ haloalkyl; -aryl, -heteroaryl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl, where the optionally substituted phenyl is ortho or meta to X;

(l) one or two R$^A$ are present, one R$^A$ is phenyl optionally substituted with one or more groups which are each independently halogen, cyano, nitro, —C$_1$-C$_6$ alkyl, —C$_1$-C$_6$ haloalkyl; -aryl, -heteroaryl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl, where the optionally substituted phenyl is ortho to X;

(k) one R$^A$ is —C$_1$-C$_6$ alkyl optionally substituted with one or more groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen, —C$_1$-C$_6$ alkyl, —C$_1$-C$_6$ haloalkyl; -aryl, —C$_1$-C$_6$ alkylaryl, -heteroaryl, —C$_1$-C$_6$ alkylheteroaryl, —C$_3$-C$_8$ cycloalkyl, or -heterocyclyl;

(l) at least one R$^A$ is —C$_1$-C$_6$ alkyl optionally substituted with one or more groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen or —C$_1$-C$_6$ alkyl;

(m) at least one R$^A$ is —C$_1$-C$_6$ alkyl substituted with one or two groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen or —C$_1$-C$_6$ alkyl; or (n) only one R$^A$ is present and R$^A$ is —C$_1$-C$_6$ alkyl substituted with one or two groups which are each independently halogen, cyano, nitro, —C$_1$-C$_6$ alkyl, —C$_1$-C$_6$ haloalkyl; —C$_2$-C$_6$ alkenyl, —C$_2$-C$_6$ alkynyl, -aryl, —C$_1$-C$_6$ alkylaryl, -heteroaryl, —C$_1$-C$_6$ alkylheteroaryl, —C$_3$-C$_8$ cycloalkyl, -heterocyclyl, —N(R$^{A21}$)$_2$, —OR$^{A21}$, —ON(R$^{A21}$)$_2$, —N(R$^{A21}$)N(R$^{A21}$)$_2$, —SR$^{A21}$, —C(O)R$^{A21}$, —C(O)OR$^{A21}$, —C(O)N(R$^{A21}$)$_2$, —S(O)R$^{A21}$, —S(O)OR$^{A21}$, —S(O)N(R$^{A21}$)$_2$, —S(O)$_2$R$^{A21}$, —S(O)$_2$OR$^{A21}$, —S(O)$_2$N(R$^{A21}$)$_2$, —OC(O)R$^{A21}$, —OC(O)OR$^{A21}$, —OC(O)N(R$^{A21}$)$_2$, —N(R$^{A21}$)C(O)OR$^{A21}$, or —N(R$^{A21}$)C(O)N(R$^{A21}$)$_2$, wherein each R$^{A21}$ is independently hydrogen or —C$_1$-C$_6$ alkyl.

A preferred subgenus of any of the preceding subgenera of formulas (XXII)-(XXXIII), includes compounds in which
(a) X is a bond;
(b) X is —O—, —S—, or —N(R$^X$)—;
(c) X is —O—;
(d) X is —C(Y)—, —S(O)—, —S(O)$_2$—, —OC(O)—, —N(R$^X$)C(O)—, —N(R$^X$)S(O)—, —OS(O)$_2$—, or —N(R$^X$)S(O)$_2$—;
(e) X is —C(O)—, —C(=NH)—, or —N(H)C(O)—;
(f) X is —C$_1$-C$_3$alkylOC(O)—, —C$_1$-C$_3$alkylN(R$^X$)C(O)—, —C$_1$-C$_3$alkylN(R$^X$)—S(O)—, —C$_1$-C$_3$alkylOS(O)$_2$—, or —C$_1$-C$_3$alkylN(R$^X$)S(O)$_2$—;
(g) X is —C$_1$-C$_3$alkylN(R$^X$)C(O)—; or
(h) X is —C$_1$-C$_2$alkylN(H)C(O)—.

A preferred subgenus of any of the preceding subgenera of formulas (XXII), (XXV), and (XXVIII), includes compounds in which
(a) m is 1, 2, or 3, and X is —C(Y)—, —S(O)—, —S(O)$_2$—, —OC(O)—, —N(R$^X$)C(O)—, —N(R$^X$)S(O)—, —OS(O)$_2$—, or —N(R$^X$)S(O)$_2$—;
(b) m is 1 or 2, and X is —C(O)—, —C(=NH)—, or —N(H)C(O)—;
(c) m is 1, 2, or 3, and X is —O—, —S—, or —N(R$^X$)—;
(d) m is 1 or 2, and X is —O—;
(e) m is 1, 2, or 3, and X is —C$_1$-C$_3$alkylOC(O)—, —C$_1$-C$_3$alkylN(R$^X$)C(O)—, —C$_1$-C$_3$alkylN(R$^X$)S(O)—, —C$_1$-C$_3$alkylOS(O)$_2$—, or —C$_1$-C$_3$alkylN(R$^X$)S(O)$_2$—;
(f) m is 1, 2, or 3, and X is —C$_1$-C$_3$alkylN(R$^X$)C(O)—; or
(g) m is 1 or 2, and X is —C$_1$-C$_2$alkylN(H)C(O)—.

A preferred subgenus of any of the preceding subgenera of formulas (XXII)-(XXXIII), includes compounds in which
(a) one R$^L$ is —C$_1$-C$_6$ alkyl optionally substituted with one or two groups which are each independently halogen, cyano, nitro, —N(R$^{L11}$)$_2$, —OR$^{L11}$, —ON(R$^{L11}$)$_2$, —N(R$^{L11}$)N(R$^{L11}$)$_2$, —SR$^{L11}$, —C(O)R$^{L11}$, —C(O)OR$^{L11}$, —C(O)N(R$^{L11}$)$_2$, —S(O)R$^{L11}$, —S(O)OR$^{L11}$, —S(O)N(R$^{L11}$)$_2$, —S(O)$_2$R$^{L11}$, —S(O)$_2$OR$^{L11}$, —S(O)$_2$N(R$^{L11}$)$_2$, —OC(O)R$^{L11}$, —OC(O)OR$^{L11}$, —OC(O)N(R$^{L11}$)$_2$, —N(R$^{L11}$)C(O)OR$^{L11}$, or —N(R$^{L11}$)C(O)N(R$^{L11}$)$_2$, wherein each R$^{L11}$ is independently hydrogen or —C$_1$-C$_6$ alkyl;

(b) one R$^L$ is —C$_1$-C$_6$ alkyl-OR$^{L21}$, —C$_1$-C$_6$ alkyl-NH—R$^{L21}$, —C$_1$-C$_6$ alkyl-NHC(O)R$^{L21}$, —C$_2$-C$_6$ alkenyl-OR$^{L21}$, —C$_2$-C$_6$ alkenyl-NH—R$^{L21}$, or —C$_2$-C$_6$ alkenyl-NHC(O)R$^{L21}$, wherein each R$^{L21}$ is independently hydrogen, —C$_1$-C$_6$ alkyl, -aryl, —C$_1$-C$_6$ alkylaryl, -heteroaryl, or —C$_1$-C$_6$ alkylheteroaryl, wherein each alkyl, aryl, alkylaryl, heteroaryl, cycloalkyl, and alkylheteroaryl, is optionally substituted with one or more groups which are each independently halogen, cyano, nitro, —N(R$^{L22}$)$_2$, —OR$^{L22}$, —ON(R$^{L22}$)$_2$, —N(R$^{L22}$)N(R$^{L22}$)$_2$, —SR$^{L22}$, —C(O)R$^{L22}$, —C(O)OR$^{L22}$, —C(O)N(R$^{L22}$)$_2$, —S(O)R$^{L22}$, —S(O)OR$^{L22}$, —S(O)N(R$^{L22}$)$_2$, —S(O)$_2$R$^{L22}$, —S(O)$_2$OR$^{L22}$, —S(O)$_2$N(R$^{L22}$)$_2$, —OC(O)R$^{L22}$, —OC(O)OR$^{L22}$, —OC(O)N(R$^{L22}$)$_2$, —N(R$^{L22}$)C(O)OR$^{L22}$, or —N(R$^{L22}$)C(O)N(R$^{L22}$)$_2$, wherein each R$^{L22}$ is independently hydrogen, —C$_1$-C$_6$ alkyl, aryl, or —C$_1$-C$_6$ alkylaryl;

(c) one R$^L$ is —N(R$^{L21}$)$_2$, —OR$^{L21}$, —ON(R$^{L21}$)$_2$, —N(R$^{L21}$)N(R$^{L21}$)$_2$, —C(O)R$^{L21}$, —C(O)OR$^{L21}$, —C(O)N(R$^{L21}$)$_2$, —OC(O)R$^{L21}$, —OC(O)OR$^{L21}$, —OC(O)N(R$^{L21}$)$_2$, —N(R$^{L21}$)C(O)OR$^{L21}$, or —N(R$^{L21}$)C(O)N(R$^{L21}$)$_2$, wherein each R$^{L21}$ is independently hydrogen, —C$_1$-C$_6$ alkyl, -aryl, —C$_1$-C$_6$ alkylaryl, -heteroaryl, or —C$_1$-C$_6$ alkylheteroaryl, wherein each alkyl, aryl, alkylaryl, heteroaryl, and alkylheteroaryl, is optionally substituted with one or more groups which are each independently halogen, cyano, nitro, —N(R$^{L22}$)$_2$, —OR$^{L22}$, —ON(R$^{L22}$)$_2$, —N(R$^{L22}$)N(R$^{L22}$)$_2$, —SR$^{L22}$, —C(O)R$^{L22}$, —C(O)OR$^{L22}$, —C(O)N(R$^{L22}$)$_2$, —S(O)R$^{L22}$, —S(O)OR$^{L22}$, —S(O)N(R$^{L22}$)$_2$, —S(O)$_2$R$^{L22}$, —S(O)$_2$OR$^{L22}$, —S(O)$_2$N(R$^{L22}$)$_2$, —OC(O)R$^{L22}$, —OC(O)OR$^{L22}$, —OC(O)N(R$^{L22}$)$_2$, —N(R$^{L22}$)C(O)OR$^{L22}$, or —N(R$^{L22}$)C(O)N(R$^{L22}$)$_2$, wherein each R$^{L22}$ is independently hydrogen, —C$_1$-C$_6$ alkyl, aryl, or —C$_1$-C$_6$ alkylaryl; or (d) one R$^L$ is —N(R$^{L21}$)$_2$ or —OR$^{L21}$, wherein each R$^{L21}$ is independently hydrogen, —C$_1$-C$_6$ alkyl, -aryl, —C$_1$-C$_6$ alkylaryl, -heteroaryl, or —C$_1$-C$_6$ alkylheteroaryl, wherein each alkyl, aryl, alkylaryl, heteroaryl, and alkylheteroaryl, is optionally substituted with one or more halogen, cyano, nitro, —N(R$^{L22}$)$_2$, —OR$^{L22}$, —ON(R$^{L22}$)$_2$, —C(O)OR$^{L22}$, or —C(O)N(R$^{L22}$)$_2$, wherein each R$^{L22}$ is independently hydrogen, —C$_1$-C$_6$ alkyl, aryl, or —C$_1$-C$_6$ alkylaryl.

In our study of the activities of the foregoing compounds, we made the following observations and conclusions:

(1) The —O— in the aminoxy group is essential.

(2) A primary —NH$_2$ group in aminoxy group is required for activity;

(3) The order of R—O—NH$_2$ is essential (4) Substitution of the 3-NO$_2$ group by 3-Cl; 3-Br; 3-I; 3,5-Cl; increases activity ~3-fold.

(5) The preferred position for phenyl substitution with small groups is in meta, followed by ortho and para.

(6) Multiple substitutions on the phenyl ring are accepted.

(7) Mono or bicyclic heterocycles, aromatic or non-aromatic can substitute the phenyl ring.

(8) Substitutions of the phenyl ring with another phenyl ring (substituted in para with Cl, —OCH$_3$ or —CH$_3$) is accepted in ortho and in meta. The preferred position of substitution on the main phenyl ring depends on the secondary substituents in the secondary phenyl ring.

(9) A secondary aromatic ring can be linked to the main phenyl ring either directly, or through a linker. The longer the linker, the lesser the activity, though the activity is greatly affected by the nature of the substituents on the secondary phenyl ring.

(10) Several aromatic heterocycles can be joined to the C6 position of the main phenyl ring, alone or in combination with 3-Cl substitution on the main phenyl ring.

(11) Rigidification of the aminoxy group into a co-planar or non co-planar structure with the phenyl ring, generally diminishes compound activity.

(12) Increasing linker length decreases activity.

(13) Linker L substitutions with R$^L$ groups are accepted.

(14) Substitutions of the benzylic position with ester and amides are well tolerated and increase activity compared to the unsubstituted parent compound.

(15) Substitution of the benzylic carbon with a phenyl group via a C0-C3 carbon or ether linker maintains the activity with respect to the unsubstituted benzylic carbon. On the contrary, substitution with a non-aromatic ring such as cyclohexyl or N-morpholino generally reduces the activity (especially for the N-morpholino).

(16) The length of the R$^L$ groups have an influence on the activity. A C0 linker results in the highest activity, followed by a C2 linker and then by a C1 linker, for both aromatic or non-aromatic rings.

(17) Inclusion of an ether linker in R$^L$ increases the activity compared to the corresponding alkyl linker.

The foregoing points are presented as a general guide of preferred characteristics of the compounds of the invention only and are not intended and should not be construed as limiting all aspects or embodiments of the compounds.

In a fifteenth aspect, the invention provides a pharmaceutical composition comprising a compound described in any of the preceding aspects (and any embodiment thereof), and a pharmaceutically acceptable carrier, diluent, or excipient, provided the compound is not 2-(6-hydroxy-2,5,7,8-tetramethylchroman-2-yl)-1-(aminooxy)ethane. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient.

In a sixteenth aspect, the invention provides a use of compounds of described in any of the preceding aspects (and any embodiment thereof), as defined above, for the preparation of a medicament for the treatment of medical conditions that benefit from the inhibition of enzymatic activity of indoleamine-2,3-dioxygenase. Medical conditions contemplated in this sixteenth aspect include all the conditions described herein.

In a seventeenth aspect, the invention provides a use of compounds of described in any of the preceding aspects (and any embodiment thereof), as defined above, for the preparation of a medicament to stimulate T cell proliferation or to reverse an immunologic state of anergy or immunosuppression.

In an embodiment of the seventeenth aspect, the anergy or immunosuppression is caused by expression of the enzyme indoleamine-2,3-dioxygenase.

In a eighteenth aspect, the invention provides a use of compounds of described in any of the preceding aspects (and any embodiment thereof), as defined above, for the preparation of a medicament for the treatment of immunosuppression associated with cancer, infectious diseases, or viral infections.

In one embodiment of the eighteenth aspect, the invention provides the use of compounds of described in any of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

In another embodiment of the eighteenth aspect, the invention the use of compounds described in any of the preceding aspects (and any embodiment thereof), as defined above, and embodiments thereof as defined above, for the preparation of a medicament for the treatment of infectious diseases. Preferably, the infections disease is tuberculosis or *Leishmaniasis*.

In another embodiment of the eighteenth aspect, the invention provides the use of compounds described in any of the preceding aspects (and any embodiment thereof), as defined above, and embodiments thereof as defined above, for the preparation of a medicament for the treatment of infectious diseases where the infectious disease is a viral infection. Preferably, the viral infection is selected from the group consisting of: hepatitis C virus (HCV), human papilloma virus (HPV), cytomegalovirus (CMV), Epstein-Barr virus (EBV), varicella zoster virus, poliovirus, coxsackie virus, and human immunodeficiency virus (HIV). More preferably, the viral infection is human immunodeficiency virus (HIV).

In a nineteenth aspect, the invention provides pharmaceutical composition comprising a pharmaceutically acceptable excipient, diluent, or carrier and a compound of the formula (XL),

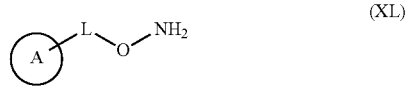

(XL)

or a pharmaceutically acceptable salt thereof, wherein
ring A is phenyl, tetrahydronaphthyl, quinolinyl, indolyl, benzothienyl, benzothiazolyl, benzodioxanyl, benzopyranyl, benzofuranyl, pyridyl or pyrimidinyl, each optionally substituted with one or more $R^4$ groups, wherein each $R^A$ is independently halogen, cyano, nitro, —N($R^{A1}$)$_2$, —O$R^{A1}$, —N($R^{A1}$)N($R^{A1}$)$_2$, —S$R^{A1}$, —C(O)$R^{A1}$, —C(O)O$R^{A1}$, —C(O)N($R^{A1}$)$_2$, —S(O)$R^{A1}$, —S(O)O$R^{A1}$, —S(O)N($R^{A1}$)$_2$, —S(O)$_2$$R^{A1}$, —S(O)$_2$O$R^{A1}$, —S(O)$_2$N($R^{A1}$)$_2$, —OC(O)$R^{A1}$, —OC(O)O$R^{A1}$, —OC(O)N($R^{A1}$)$_2$, —N($R^{A1}$)C(O)O$R^{A1}$, —N($R^{A1}$)S(O)$_2$$R^{A1}$, —N($R^{A1}$)C(O)O$R^{A1}$, —N($R^{A1}$)C(O)N($R^{A1}$)$_2$, —$C_1$-$C_6$ alkyl, —$C_1$-$C_6$ haloalkyl, —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more halogen, cyano, nitro, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, -heterocyclyl, —N($R^{A1}$)$_2$, —O$R^{A1}$, —N($R^{A1}$)N($R^{A1}$)$_2$, —S$R^{A1}$, —C(O)$R^{A1}$, —C(O)O$R^{A1}$, —C(O)N($R^{A1}$)$_2$, —S(O)$R^{A1}$, —S(O)O$R^{A1}$, —S(O)N($R^{A1}$)$_2$, —S(O)$_2$$R^{A1}$, —S(O)$_2$O$R^{A1}$, —S(O)$_2$N($R^{A1}$)$_2$, —OC(O)$R^{A1}$, —OC(O)O$R^{A1}$, —OC(O)N($R^{A1}$)$_2$, —N($R^{A1}$)C(O)O$R^{A1}$, or —N($R^{A1}$)C(O)N($R^{A1}$)$_2$, wherein each $R^{A1}$ is independently hydrogen, —$C_1$-$C_6$ alkyl, —$C_1$-$C_6$ haloalkyl, —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more halogen, cyano, nitro, —N($R^{A2}$)$_2$, —O$R^{A2}$, —N($R^{A2}$)N($R^{A2}$)$_2$, —S$R^{A2}$, —C(O)$R^{A2}$, —C(O)O$R^{A2}$, —C(O)N($R^{A2}$)$_2$, —S(O)$R^{A2}$, —S(O)O$R^{A2}$, —S(O)N($R^{A2}$)$_2$, —S(O)$_2$$R^{A2}$, —S(O)$_2$O$R^{A2}$, —S(O)$_2$N($R^{A2}$)$_2$, —OC(O)$R^{A2}$, —OC(O)O$R^{A2}$, —OC(O)N($R^{A2}$)$_2$, —N($R^{A2}$)C(O)O$R^{A2}$, or —N($R^{A2}$)C(O)N($R^{A2}$)$_2$, wherein each $R^{A2}$ is independently hydrogen, —$C_1$-$C_6$ alkyl, aryl, or —$C_1$-$C_6$ alkylaryl; and L is a bond or —C(H)($R^L$)—, wherein $R^L$ is hydrogen, halogen, cyano, nitro, —N($R^{L1}$)$_2$, —O$R^{L1}$, —ON($R^{L1}$)$_2$, —N($R^{L1}$)N($R^{L1}$)$_2$, —N($R^{L1}$)C(O)$R^{L1}$, —N($R^{L1}$)S(O)$_2$$R^{L1}$, —S$R^{L1}$, —C(O)$R^{L1}$, —C(O)O$R^{L1}$, —C(O)N($R^{L1}$)$_2$, —S(O)$R^{L1}$, —S(O)O$R^{L1}$, —S(O)N($R^{L1}$)$_2$, —S(O)$_2$$R^{L1}$, —S(O)$_2$O$R^{L1}$, —S(O)$_2$N($R^{L1}$)$_2$, —OC(O)$R^{L1}$, —OC(O)O$R^{L1}$, —OC(O)N($R^{L1}$)$_2$, —N($R^{L1}$)C(O)O$R^{L1}$, —N($R^{L1}$)C(O)N($R^{L1}$)$_2$, —$C_1$-$C_6$ alkyl, —$C_1$-$C_6$ haloalkyl, —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, —$C_1$-$C_6$ alkyl($C_3$-$C_8$)cycloalkyl, -heterocyclyl, or —$C_1$-$C_6$ alkylheterocyclyl, wherein each alkyl, haloalkyl, alkenyl, alkynyl, aryl, alkylaryl, heteroaryl, alkylheteroaryl, cycloalkyl, alkylcycloalkyl, heterocyclyl, and alkylheterocyclyl is optionally substituted with one halogen, cyano, nitro, —N($R^{L1}$)$_2$, —N($R^{L1}$)C(O)$R^{L1}$, —O$R^{L1}$, —N($R^{L1}$)N($R^{L1}$)$_2$, —S$R^{L1}$, —C(O)$R^{L1}$, —C(O)O$R^{L1}$, —C(O)N($R^{L1}$)$_2$, —S(O)$R^{L1}$, —S(O)O$R^{L1}$, —S(O)N($R^{L1}$)$_2$, —S(O)$_2$$R^{L1}$, —S(O)$_2$O$R^{L1}$, —S(O)$_2$N($R^{L1}$)$_2$, —OC(O)$R^{L1}$, —OC(O)O$R^{L1}$, —OC(O)N($R^{L1}$)$_2$, —N($R^{L1}$)C(O)O$R^{L1}$, or —N($R^{L1}$)C(O)N($R^{L1}$)$_2$, wherein each $R^{L1}$ is independently hydrogen, —$C_1$-$C_6$ alkyl, -aryl, —$C_1$-$C_6$ alkylaryl, -heteroaryl, —$C_1$-$C_6$ alkylheteroaryl, —$C_3$-$C_8$ cycloalkyl, —$C_1$-$C_6$ alkyl($C_3$-$C_8$)cycloalkyl, or -heterocyclyl, wherein alkyl, aryl, alkylaryl, heteroaryl, alkylheteroaryl, cycloalkyl, alkylcycloalkyl, and heterocyclyl, is optionally substituted with one or more groups which are each independently halo en cyano nitro, —N($R^{L11}$)$_2$, —O$R^{L11}$, —ON($R^{L11}$)$_2$, —N($R^{L11}$)N($R^{L11}$)$_2$, —S$R^{L11}$, —C(O)$R^{L11}$, —C(O)O$R^{L11}$, —C(O)N($R^{L11}$)$_2$, —S(O)$R^{L11}$, —S(O)O$R^{L11}$, —S(O)N($R^{L11}$)$_2$—S(O)$_2$$R^{L11}$, —S(O)$_2$O$R^{L11}$, —S(O)$_2$N($R^{L11}$)$_2$, —OC(O)$R^{L11}$, —OC(O)O$R^{L11}$, —OC(O)N($R^{L11}$)$_2$, —N($R^{L11}$)C(O)O$R^{L11}$, —N($R^{L11}$)C(O)N($R^{L11}$)$_2$, wherein each $R^{L11}$ is independently hydrogen, —$C_1$-$C_6$ alkyl, aryl, or —$C_1$-$C_6$ alkylaryl, provided that (i) when ring A is phenyl and $R^L$ is hydrogen, then ring A is substituted with at least one $R^A$;

(ii) when ring A is phenyl and $R^L$ is hydrogen, —COOH, unsubstituted $C_1$-$C_6$ alkyl, —$C_1$-$C_6$ alkyl-COOH, or unsubstituted phenyl, then ring A is substituted with at least one $R^A$ that is not halogen, hydroxy, trifluoromethyl, $C_1$-$C_5$ alkyl, $C_1$-$C_4$ alkoxy, nitro, amino, $C_1$-$C_4$alkylthio, benzyloxy, or —OC(O)$R^{L1}$;

(iii) when ring A is phenyl and $R^L$ is hydrogen, then $R^A$ is not hydroxy, —C(O)N(H)(isopropyl), or —CH$_2$C(O)O$R^{A1}$;

(iv) when ring A is phenyl and L is a bond, then ring A is substituted with at least one $R^A$ that is not halogen, nitro, trifluoromethyl, or methyl.

In one embodiment of the nineteenth aspect, the compound is according to formula (XLI),

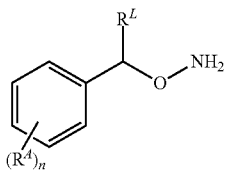

(XLI)

or a pharmaceutically acceptable salt thereof, wherein n is 0, 1, 2, or 3.

In another embodiment of the nineteenth aspect, the compound is according to formula (XLII),

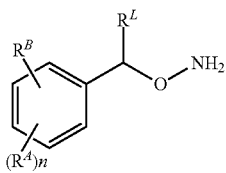

(XLII)

or a pharmaceutically acceptable salt thereof, wherein n is 0, 1, or 2; and $R^B$ is aryl or heteroaryl, each optionally substituted with one or more halogen, cyano, nitro, —$C_1$-$C_6$ alkyl, —$C_1$-$C_6$ haloalkyl; —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, -heterocyclyl, —N($R^{B1}$)$_2$, —O$R^{B1}$, —N($R^{B1}$)N($R^{B1}$)$_2$, —S$R^{B1}$, —C(O)$R^{B1}$, —C(O)O$R^{B1}$, —C(O)N($R^{B1}$)$_2$, —S(O)$R^{B1}$, —S(O)O$R^{B1}$, —S(O)N($R^{B1}$)$_2$, —S(O)$_2R^{B1}$, —S(O)$_2$O$R^{B1}$, —S(O)$_2$N($R^{B1}$)$_2$, —OC(O)$R^{B1}$, —OC(O)O$R^{B1}$, —OC(O)N($R^{B1}$)$_2$, —N($R^{B1}$)C(O)O$R^{B1}$, or —N($R^{B1}$)C(O)N($R^{B1}$)$_2$, wherein each $R^{B1}$ is independently hydrogen, —$C_1$-$C_6$ alkyl, —$C_1$-$C_6$ haloalkyl, —$C_2$-$C_6$ alkenyl, —$C_2$-$C_6$ alkynyl, -aryl, —$C_1$-$C_6$ alkylaryl, -heteroaryl, —$C_1$-$C_6$ alkylheteroaryl, —$C_3$-$C_8$ cycloalkyl, or -heterocyclyl, wherein each alkyl, haloalkyl, alkenyl, alkynyl, aryl, alkylaryl, heteroaryl, alkylheteroaryl, cycloalkyl, and heterocyclyl is optionally substituted with one or more halogen, cyano, nitro, —N($R^{B2}$)$_2$, —O$R^{B2}$, —N($R^{B2}$)N($R^{B2}$)$_2$, —S$R^{B2}$, —C(O)$R^{B2}$, —C(O)O$R^{B2}$, —C(O)N($R^{B2}$)$_2$, —S(O)$R^{B2}$, —S(O)O$R^{B2}$, —S(O)N($R^{B2}$)$_2$, —S(O)$_2R^{B2}$, —S(O)$_2$O$R^{B2}$, —S(O)$_2$N($R^{B2}$)$_2$, —OC(O)$R^{B2}$, —OC(O)O$R^{B2}$, —OC(O)N($R^{B2}$)$_2$, —N($R^{B2}$)C(O)O$R^{B2}$, or —N($R^{B2}$)C(O)N($R^{B2}$)$_2$, wherein each $R^{B2}$ is independently hydrogen, —$C_1$-$C_6$ alkyl, aryl, or —$C_1$-$C_6$ alkylaryl.

In another embodiment of the nineteenth aspect, the compound is according to formula (XLII),

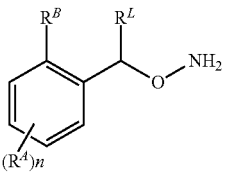

(XLIII)

or a pharmaceutically acceptable salt thereof.

In an embodiment of formulae (XLII) and (XLIII), $R^B$ is phenyl optionally substituted with one or more halogen, —$C_1$-$C_6$ alkyl, —$C_1$-$C_6$ haloalkyl; —N($R^{B1}$)$_2$, —O$R^{B1}$, or —C(O)O$R^{B1}$, wherein each $R^{B1}$ is independently hydrogen, —$C_1$-$C_6$ alkyl, -aryl, —$C_1$-$C_6$ alkylaryl, wherein each $R^{B2}$ is independently hydrogen, —$C_1$-$C_6$ alkyl, aryl, or —$C_1$-$C_6$ alkylaryl.

In another embodiment of formulae (XLII) and (XLIII), $R^B$ is phenyl optionally substituted with one halogen, —$C_1$-$C_6$ alkyl, —$C_1$-$C_6$ haloalkyl; —N($R^{B1}$)$_2$, —O$R^{B1}$, or —C(O)O$R^{B1}$, wherein each $R^{B1}$ is independently hydrogen, —$C_1$-$C_6$ alkyl, -aryl, —$C_1$-$C_6$ alkylaryl, wherein each $R^{B2}$ is independently hydrogen, —$C_1$-$C_6$ alkyl, aryl, or —$C_1$-$C_6$ alkylaryl.

In an embodiment of formulae (XLII) and (XLIII), $R^B$ is thienyl, pyrimidinyl, indolyl, or pyridyl.

In another embodiment of the nineteenth aspect, the compound is according to formula (XLIV),

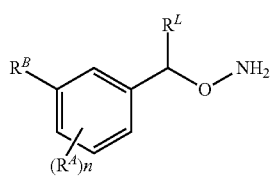

(XLIV)

or a pharmaceutically acceptable salt thereof.

In an embodiment of formulae (XLIV), $R^B$ is phenyl optionally substituted with one or more halogen, —$C_1$-$C_6$ alkyl, —$C_1$-$C_6$ haloalkyl; —N($R^{B1}$)$_2$, —O$R^{B1}$, or —C(O)O$R^{B1}$, wherein each $R^{B1}$ is independently hydrogen, —$C_1$-$C_6$ alkyl, -aryl, —$C_1$-$C_6$ alkylaryl, wherein each $R^{B2}$ is independently hydrogen, —$C_1$-$C_6$ alkyl, aryl, or —$C_1$-$C_6$ alkylaryl.

In another embodiment of formulae (XLIV), $R^B$ is phenyl optionally substituted with one halogen, —$C_1$-$C_6$ alkyl, —$C_1$-$C_6$ haloalkyl; —N($R^{B1}$)$^2$, —O$R^{B1}$, or —C(O)O$R^{B1}$, wherein each $R^{B1}$ is independently hydrogen, —$C_1$-$C_6$ alkyl, -aryl, —$C_1$-$C_6$ alkylaryl, wherein each $R^{B2}$ is independently hydrogen, —$C_1$-$C_6$ alkyl, aryl, or —$C_1$-$C_6$ alkylaryl.

In another embodiment of formulae (XLIV), $R^B$ is thienyl, pyrimidinyl, indolyl, or pyridyl.

In any of formulae (XL)-(XLIV), and any of the preceding embodiments thereof, RL is one of the following:

(a) $R^L$ is hydrogen;

(b) —$C_1$-$C_6$ alkyl-O$R^{L21}$, —$C_1$-$C_6$ alkyl-NH—$R^{L21}$, —$C_1$-$C_6$ alkyl-NHC(O)$R^{L21}$, —$C_2$-$C_6$ alkenyl-O$R^{L21}$, —$C_2$-$C_6$ alkenyl-NH—$R^{L21}$ or —$C_2$-$C_6$ alkenyl-NHC(O)$R^{L21}$ wherein each $R^{L21}$ is independently hydrogen, —$C_1$-$C_6$ alkyl, -aryl, —$C_1$-$C_6$ alkylaryl, -heteroaryl, —$C_1$-$C_6$ alkylheteroaryl, —$C_3$-$C_8$ cycloalkyl, —$C_1$-$C_6$ alkyl($C_3$-$C_8$)cycloalkyl, or -heterocyclyl, wherein alkyl, aryl, alkylaryl, heteroaryl, alkylheteroaryl, cycloalkyl, alkylcycloalkyl, and heterocyclyl, is optionally substituted with one or more groups which are each independently halogen, cyano, nitro, —N($R^{L22}$)$_2$, —O$R^{L22}$, —ON($R^{L22}$)$_2$—N($R^{L22}$)N($R^{L22}$)$_2$, —S$R^{L22}$, —C(O)$R^{L22}$, —C(O)O$R^{L22}$, —C(O)N($R^{L22}$)$_2$, —S(O)$R^{L22}$, —S(O)O$R^{L22}$, —S(O)N($R^{L22}$)$_2$, —S(O)$_2R^{L22}$, —S(O)$_2$O$R^{L22}$, —S(O)$_2$N($R^{L22}$)$_2$, —OC(O)$R^{L22}$, —OC(O)O$R^{L22}$, —OC(O)N($R^{L22}$)$_2$, —N($R^{L22}$)C(O)O$R^{L22}$, or —N($R^{L22}$)C(O)N($R^{L22}$)$_2$, wherein each $R^{L22}$ is independently hydrogen, —$C_1$-$C_6$ alkyl, aryl, or —$C_1$-$C_6$ alkylaryl;

(c) —$C_1$-$C_6$ alkyl-O$R^{L21}$, —$C_1$-$C_6$ alkyl-NH—$R^{L21}$, or —$C_1$-$C_6$ alkyl-NHC(O)$R^{L21}$, wherein each $R^{L21}$ is independently hydrogen, —$C_1$-$C_6$ alkyl, -aryl, —$C_1$-$C_6$ alkylaryl, -heteroaryl, —$C_1$-$C_6$ alkylheteroaryl, —$C_3$-$C_8$ cycloalkyl, —$C_1$-$C_6$ alkyl($C_3$-$C_8$)cycloalkyl, or -heterocyclyl, wherein alkyl, aryl, alkylaryl, heteroaryl, alkylheteroaryl, cycloalkyl, alkylcycloalkyl, and heterocyclyl, is optionally substituted with one or more groups which are each independently halogen, cyano, nitro, —N($R^{L22}$)$_2$, —O$R^{L22}$, —ON($R^{L22}$)$_2$, —N($R^{L22}$)N($R^{L22}$)$_2$, —S$R^{L22}$, —C(O)$R^{L22}$, —C(O)O$R^{L22}$, —C(O)N($R^{L22}$)$_2$, —S(O)$R^{L22}$, —S(O)O$R^{L22}$, —S(O)N($R^{L22}$)$_2$, —S(O)$_2$$R^{L22}$, —S(O)$_2$O$R^{L22}$, —S(O)$_2$N($R^{L22}$)$_2$, —OC(O)$R^{L22}$, —OC(O)O$R^{L22}$, —OC(O)N($R^{L22}$)$_2$, —N($R^{L22}$)C(O)O$R^{L22}$, or —N($R^{L22}$)C(O)N($R^{L22}$)$_2$, wherein each $R^{L22}$ is independently hydrogen, —$C_1$-$C_6$ alkyl, aryl, or —$C_1$-$C_6$ alkylaryl;

(d) —$C_2$-$C_6$ alkenyl-O$R^{L21}$, —$C_2$-$C_6$ alkenyl-NH—$R^{L21}$, or —$C_2$-$C_6$ alkenyl-NHC(O)$R^{L21}$, wherein each $R^{L21}$ is independently hydrogen, —$C_1$-$C_6$ alkyl, -aryl, —$C_1$-$C_6$ alkylaryl, -heteroaryl, —$C_1$-$C_6$ alkylheteroaryl, —$C_3$-$C_8$ cycloalkyl, —$C_1$-$C_6$ alkyl($C_3$-$C_8$)cycloalkyl, or -heterocyclyl, wherein alkyl, aryl, alkylaryl, heteroaryl, alkylheteroaryl, cycloalkyl, alkylcycloalkyl, and heterocyclyl, is optionally substituted with one or more groups which are each independently halogen, cyano, nitro, —N($R^{L22}$)$_2$, —O$R^{L22}$, —ON($R^{L22}$)$_2$, —N($R^{L22}$)N($R^{L22}$)$_2$, —S$R^{L22}$, —C(O)$R^{L22}$, —C(O)O$R^{L22}$, —C(O)N($R^{L22}$)$_2$, —S(O)$R^{L22}$, —S(O)O$R^{L22}$, —S(O)N($R^{L22}$)$_2$, —S(O)$_2$$R^{L22}$, —S(O)$_2$O$R^{L22}$, —S(O)$_2$N($R^{L22}$)$_2$, —OC(O)$R^{L22}$, —OC(O)O$R^{L22}$, —OC(O)N($R^{L22}$)$_2$, —N($R^{L22}$)C(O)O$R^{L22}$, or —N($R^{L22}$)C(O)N($R^{L22}$)$_2$, wherein each $R^{L22}$ is independently hydrogen, —$C_1$-$C_6$ alkyl, aryl, or —$C_1$-$C_6$ alkylaryl;

(e) —N($R^{L21}$)$_2$, —O$R^{L21}$, —ON($R^{L21}$)$_2$, —N($R^{L21}$)N($R^{L21}$)$_2$, —C(O)$R^{L21}$, —C(O)O$R^{L21}$, —C(O)N($R^{L21}$)$_2$, —OC(O)$R^{L21}$, —OC(O)O$R^{L21}$, —OC(O)N($R^{L21}$)$_2$, —N($R^{L21}$)C(O)O$R^{L21}$, or —N($R^{L21}$)C(O)N($R^{L21}$)$_2$, wherein each $R^{L21}$ is independently hydrogen, —$C_1$-$C_6$ alkyl, -aryl, —$C_1$-$C_6$ alkylaryl, -heteroaryl, —$C_1$-$C_6$ alkylheteroaryl, —$C_3$-$C_8$ cycloalkyl, —$C_1$-$C_6$ alkyl($C_3$-$C_8$)cycloalkyl, or -heterocyclyl, wherein alkyl, aryl, alkylaryl, heteroaryl, alkylheteroaryl, cycloalkyl, alkylcycloalkyl, and heterocyclyl, is optionally substituted with one or more groups which are each independently halogen, cyano, nitro, —N($R^{L22}$)$_2$, —O$R^{L22}$, —ON($R^{L22}$)$_2$, —N($R^{L22}$)N($R^{L22}$)$_2$, —S$R^{L22}$, —C(O)$R^{L22}$, —C(O)O$R^{L22}$, —C(O)N($R^{L22}$)$_2$, —S(O)$R^{L22}$, —S(O)O$R^{L22}$, —S(O)N($R^{L22}$)$_2$, —S(O)$_2$$R^{L22}$, —S(O)$_2$O$R^{L22}$, —S(O)$_2$N($R^{L22}$)$_2$, —OC(O)$R^{L22}$, —OC(O)O$R^{L22}$, —OC(O)N($R^{L22}$)$_2$, —N($R^{L22}$)C(O)O$R^{L22}$, or —N($R^{L22}$)C(O)N($R^{L22}$)$_2$, wherein each $R^{L22}$ is independently hydrogen, —$C_1$-$C_6$ alkyl, aryl, or —$C_1$-$C_6$ alkylaryl;

(f) —$C_1$-$C_2$ alkyl-N($R^{L1}$)$_2$;
(g) —$C_1$-$C_2$ alkyl-N($R^{L1}$)C(O)$R^{L1}$;
(h) —$C_1$-$C_2$ alkyl-O$R^{L1}$;
(i) —$C_1$-$C_2$ alkyl-C(O)O$R^{L1}$;
(j) —$C_1$-$C_2$ alkyl-C(O)N($R^{L1}$)$_2$;
(k) —$C_1$-$C_2$ alkyl-N($R^{L1}$)C(O)O$R^{L1}$; or
(l) —C(O)N($R^{L1}$)$_2$.

In a twentieth aspect, the invention provides pharmaceutical compositions comprising a pharmaceutically acceptable excipient, diluent, or carrier and a compound in Table 15 (infra).

In a twenty-first aspect, the invention provides methods for treating indoleamine 2,3-dioxygenase (IDO) mediated immunosuppression in a subject in need thereof, comprising administering an effective indoleamine 2,3-dioxygenase inhibiting amount of a pharmaceutical composition of the nineteenth of twentieth aspects.

In an embodiment of the twenty-first aspect, the immunosuppression is associated with an infectious disease, or cancer.

In another embodiment of the twenty-first aspect, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In an embodiment of the twenty-first aspect, the immunosuppression is immunsupression associated with HIV-1 infection.

In another embodiment of the twenty-first aspect, the immunosuppression is associated with an infectious disease and the infectious disease is tuberculosis or *Leishmaniasis*.

In another embodiment of the twenty-first aspect, the immunosuppression is associated with a cancer.

In an embodiment of the twenty-first aspect, the immunosuppression is tumor-specific immunosuppression associated with cancer.

In another embodiment of the twenty-first aspect, the immunosuppression is associated with a cancer, wherein the cancer is colon, pancreas, breast, prostate, lung, brain, ovary, cervix, testes, renal, head, or neck cancer, or lymphoma, leukemia, or melanoma.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "linear alkenyl" as used herein means straight chain hydrocarbon containing from 2 to 10 carbons, unless otherwise specified, and containing at least one carbon-carbon double bond. Representative examples of alkenyl include, but are not limited to, ethenyl, 2-propenyl, 3-butenyl, 4-pentenyl, 5-hexenyl, 2-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "linear alkyl" as used herein, means a straight chain hydrocarbon containing from 1 to 10 carbon atoms, unless otherwise specified. Linear alkyl includes methyl, ethyl, n-propyl, n-butyl, n-pentyl, n-hexyl, n-heptyl, n-octyl, n-nonyl, and n-decyl. When a "linear alkyl" group is a linking group between two other moieties, then it is also a straight chain; examples include, but are not limited to —CH₂—, —CH₂CH₂—, and —CH₂CH₂CH₂—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl (i.e., monocyclic aryl), or a bicyclic ring system containing at least one aromatic ring containing only carbon atoms in the aromatic ring. The bicyclic aryl can be naphthyl, or a phenyl fused to a cycloalkyl, or a phenyl fused to a cycloalkenyl, or a phenyl fused to a heterocyclyl. The bicyclic aryl can be attached to the parent molecular moiety through any atom contained within the bicyclic aryl. Representative examples of the bicyclic aryl include, but are not limited to, dihydroindenyl, indenyl, naphthyl, dihydronaphthalenyl, tetrahydronaphthalenyl, 2,3-dihydrobenzofuranyl, or benzo[d][1,3]di-oxolyl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carboxy" as used herein, means a —CO₂H group.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a monocyclic, bicyclic, or tricyclic ring systems, where such groups can be saturated or unsaturated, but not aromatic. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The term "formyl" as used herein, means a —C(O)H group.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle, where such groups can be saturated or unsaturated, but not aromatic. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a cycloalkyl, or a monocyclic heterocycle fused to a cycloalkenyl, or a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzo dioxinyl, 2,3-dihydro-1-benzofuranyl, 2,3-dihydro-1-benzothienyl, 2,3-dihydro-1H-indolyl, and 1,2,3,4-tetrahydroquinolinyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "saturated" as used herein means the referenced chemical structure does not contain any multiple carbon-carbon bonds. For example, a saturated cycloalkyl group as defined herein includes cyclohexyl, cyclopropyl, and the like.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound includes the administration of a compound described herein to an individual or patient, such as a human, having IDO, as well as, for example, introducing a compound into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., IDO modulation or tryptophan degradation inhibition).

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalisis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hyrdoiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

Compounds described herein can modulate activity of the enzyme indoleamine-2,3-dioxygenase (IDO). The term "modulate" is meant to refer to an ability to increase or decrease activity of an enzyme or receptor. Accordingly, compounds described herein can be used in methods of modulating IDO by contacting the enzyme with any one or more of the compounds or compositions described herein. In some embodiments, the compounds described herein can act as inhibitors of IDO. In further embodiments, the compounds described herein can be used to modulate activity of IDO in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing IDO such as a tissue, living organism, or cell culture. In some embodiments methods of altering (e.g., increasing) extracellular tryptophan levels in a mammal comprise administering an effective amount of a compound of composition provided herein. Methods of measuring tryptophan levels and tryptophan degradation are routine in the art.

Further provided are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, IDO-mediated immunosuppression associated with viral infection, is associated with a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

Further provided are methods for treating immunsupression associated with an infectious disease, e.g., HIV-1 infection, in a patient by administering to the patient an effective amount of a compound or composition recited herein.

In other examples, IDO-mediated immunosuppression associated with and infectious diseases is associated with tuberculosis or *Leishmaniasis*.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods of treating diseases associated with activity or expression, including abnormal activity and/or overexpression, of IDO in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity.

Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.
Combination Therapy One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds described herein for treatment of IDO-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)—FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4,4-1BB and PD-1, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds described herein can be administered in the form of pharmaceutical compositions which is a combination of a compound described herein and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

Screening of IDO Inhibitory Compounds
Molecular Modeling Methods

Protein structure information, typically in the form of the atomic structure coordinates, can be used in a variety of computational or computer-based methods to design, screen for or identify compounds that bind to the catalytic site of IDO. Such information is useful to design improved analogues of known IDO inhibitors or to design novel classes of compounds based on the structure of reaction intermediates of IDO—complexed with its substrates oxygen and tryptophan.

In one embodiment, compounds whose structure mimics the reaction intermediates of tryptophan dioxygenation catalyzed by IDO can also be deduced from the proposed reaction mechanism.

In still another embodiment, the structure of the IDO catalytic domain and enzyme active site can be used to computationally screen small molecule databases for functional groups or compounds that can bind in whole, or in part, to IDO. In this screening, the quality of fit of such entities or compounds to the binding site may be judged by methods such as estimated interaction energy or by shape complementarity. See, for example, Meng et al., (1992), J. Comp. Chem., 13:505-524.

Compounds fitting the catalytic site serve as a starting point for an iterative design, synthesis and test cycle in which new compounds are selected and optimized for desired properties including affinity, efficacy, and selectivity. For example, the compounds can be subjected to additional modification, such as replacement or addition of R-group substituents of a core structure identified for a particular class of binding compounds, modeling or activity screening if desired, and then subjected to additional rounds of testing.

By "modeling" is intended to mean quantitative and qualitative analysis of molecular structure and/or function based on atomic structural information and interaction models of a receptor and a ligand agonist or antagonist. Modeling thus includes conventional numeric-based molecular dynamic and energy minimization models, interactive computer graphic models, modified molecular mechanics models, distance geometry and other structure-based constraint models. Modeling is performed using a computer running specialized software.

Molecular Docking

Identification of IDO protein structure complexed with the IDO inhibitor 4-phenylimidazole and identification of the catalytic site structure has made it possible to apply the principles of molecular recognition to evaluate a variety of compound structures which are complementary to the structure of the site. Accordingly, computer programs that employ various docking algorithms can be used to identify compounds that fit into the catalytic site of IDO and can interact with amino acids defining such catalytic pocket, or with its heme cofactor, thus preventing binding and/or processing of its natural substrate, tryptophan. Fragment-based docking can also be used to build molecules de novo inside the catalytic site by placing molecular fragments that have a complementary fit with the site, thereby optimizing intermolecular interactions and subsequently synthesizing molecules that contain several of the molecular fragments that interact with amino acids in the catalytic pocket. Techniques of computational chemistry can further be used to optimize the geometry of the bound conformations.

Docking may be accomplished using commercially available software such as GLIDE (available from Schrodinger, Inc., Portland, Oreg.); DOCK (Kuntz et al., (1982), J. Mol. Biol., 161:269-288, available from University of California, San Francisco, Calif.); AUTODOCK (Goodsell & Olsen, (1990), Proteins: Structure, Function, and Genetics 8:195-202, available from Scripps Research Institute, La Jolla, Calif.; GOLD (Jones, et al., (1995), J. Mol. Biol., 245:43-53, available from the Cambridge Crystallographic Data Centre, 12 Union Road. Cambridge, U.K.; QUANTA (available from Accelrys, a subsidiary of Pharmacopeia, Inc.); SYBYL, (available from Tripos, Inc., 1700 South Hanley Road, St. Louis, Mo.), and ICM (Abagayan, et al., available from MolSoft, L.L.C., 3366 North Torrey Pines Court, Suite 300, La Jolla, Calif.).

Docking is typically followed by energy minimization and molecular dynamics simulations of the docked molecule, using molecular mechanics force fields such as MM2 (see, e.g., Rev. Comp. Chem., 3, 81 (1991)), MM3 (Allinger, N. L., Bowen, J. P., and coworkers, University of Georgia; see, J. Comp. Chem., 17:429 (1996); available from Tripos, Inc., 1699 South Hanley Road, St. Louis, Mo.), CHARMM (see, e.g., B. R. Brooks, R. E. Bruccoleri, B. D. Olafson, D. J. States, S. Swaminathan, and M. Karplus, "CHARMM: A Program for Macromolecular Energy, Minimization, and Dynamics Calculations," J. Comp. Chem., 4, 187-217, (1983)), a version of AMBER such as version 7, (Kollman, P. A., et al., School of Pharmacy, Department of Pharmaceutical Chemistry, University of California at San Francisco), and Discover (available from Accelrys, a subsidiary of Pharmacopeia, Inc.).

Constructing Molecules that Bind to IDO

A compound that binds to the catalytic site of IDO, thereby exerting a modulatory or other effect on its function, may be computationally designed and evaluated by means of a series of steps in which functional groups or other fragments are screened and selected for their ability to associate with the individual binding pockets or other areas of the IDO catalytic pocket. One of ordinary skill in the art may use one of several methods to screen functional groups and fragments for their ability to associate with IDO. Selected fragments or functional groups may then be positioned in a variety of orientations, or docked, within the catalytic pocket of IDO as described above.

Specialized computer programs may assist in the process of selecting fragments or functional groups, or whole molecules that can fit into and populate a binding site, or can be used to build virtual libraries of compounds. These include: GRID (Goodford, (1985), J. Med. Chem., 28:849-857, available from Oxford University, Oxford, UK); and MCSS (Miranker & Karplus, (1991), Proteins: Structure, Function and Genetics 11:29-34, available from Accelrys, a subsidiary of Pharmacopeia, Inc., as part of the Quanta package).

Once suitable functional groups or fragments have been selected, they can be assembled into a single compound or inhibitor. Assembly may be performed by visual inspection and by manual model building using software such as QUANTA or SYBYL, while observing the relationship of the fragments to each other in relation to a three-dimensional image of the structure coordinates of IDO catalytic pocket.

Alternatively, fragment assembly can be performed using the software CAVEAT (Bartlett et al., "CAVEAT: A Program to Facilitate the Structure-Derived Design of Biologically Active Molecules," in Molecular Recognition in Chemical and Biological Problems, Special Pub., Royal Chem. Soc. 78:182-196, (1989); available from the University of California, Berkeley, Calif.); and HOOK (available from Accelrys, a subsidiary of Pharmacopeia, Inc., as part of the Quanta package).

In another embodiment, IDO inhibitor molecules may be designed as a whole or de novo using either an empty active site. Software programs for achieving this include: LUDI (Bohm, J. Comp. Aid. Molec. Design, 6:61-78, (1992), available from Accelrys, a subsidiary of Pharmacopeia, Inc.); LEGEND (Nishibata and Itai, Tetrahedron, 47:8985, (1991), available from Molecular Simulations, Burlington, Mass.); and LeapFrog (available from Tripos, Inc., 1699 South Hanley Road, St. Louis, Mo.).

Quantifying Potential of IDO Binding Molecules

Once a compound has been designed or selected by methods such as those described above, the efficiency with which that compound may bind to the catalytic site of IDO may be tested and optimized by computational evaluation. For example, a compound that has been designed or selected to function as an inhibitor (antagonist) preferably occupies a volume that overlaps with the volume occupied by the native substrate at the active site. An effective IDO inhibitor preferably displays a relatively small difference in energy between its bound and free states (i.e., it has a small deformation energy of binding). Thus, the most efficient inhibitors of IDO should preferably be designed with a deformation energy of binding of not greater than about 10 kcal/mol or, even more preferably, not greater than about 7 kcal/mol.

A compound selected or designed for binding to the IDO catalytic site may be further computationally optimized so that in its bound state it would lack repulsive electrostatic interactions with amino acids of the IDO catalytic pocket and it has favorable hydrogen bond formation, attractive electrostatic interactions with such amino acids. Such favorable or repulsive electrostatic interactions include charge-charge, dipole-dipole and charge-dipole interactions. Specifically, the sum of all electrostatic interactions between the inhibitor and the binding pocket when the inhibitor is bound to it preferably make a neutral or favorable contribution to the enthalpy of binding.

Specific computer software is available to evaluate compound deformation energy and electrostatic interaction. Examples of programs designed for such uses fall into approximately three levels of sophistication. The first level of approximation, molecular mechanics, is also the cheapest to compute and can most usefully be used to calculate deformation energies. Molecular mechanics programs find application for calculations on small organic molecules as well as polypeptides, nucleic acids, proteins, and most other biomolecules. Examples of programs which have implemented molecular mechanics force fields include: AMBER (Kollman, P. A., et al., School of Pharmacy, Department of Pharmaceutical Chemistry, University of California at San Francisco); CHARMM (see B. R. Brooks, R. E. Bruccoleri, B. D. Olafson, D. J. States, S. Swaminathan, and M. Karplus, "CHARMM: A Program for Macromolecular Energy, Minimization, and Dynamics Calculations," J. Comp. Chem., 4, 187-217, (1983); A. D. MacKerell, Jr., B. Brooks, C. L. Brooks, III, L. Nilsson, B. Roux, Y. Won, and M. Karplus, "CHARMM: The Energy Function and Its Parameterization with an Overview of the Program," in The Encyclopedia of Computational Chemistry, 1, 271-277, P. v. R. Schleyer et al., eds, John Wiley & Sons, Chichester, (1998)); and QUANTA/CHARMm (available from Accelrys, a subsidiary of Pharmacopeia, Inc.).

An intermediate level of sophistication comprises the so-called "semi-empirical" methods, which are relatively inexpensive to compute and are most frequently employed for calculating deformation energies of organic molecules. Examples of program packages that provide semi-empirical capability are MOPAC 2000 (Stewart, J. J. P., et al., available from Schrodinger, Inc., 1500 S.W. First Avenue, Suite 1180, Portland, Oreg.) and AMPAC (Holder, A., et al., available from Tripos, Inc., 1699 South Hanley Road, St. Louis, Mo.).

The highest level of sophistication is achieved by those programs that employ so-called ab initio quantum chemical methods and methods of density functional theory, for example: Gaussian 03, (available from Gaussian, Inc., Carnegie Office Park, Building 6, Suite 230. Carnegie, Pa.); and Q-Chem2.0 ("A high-performance ab initio electronic structure program," J. Kong, et al., J. Comput. Chem., 21, 1532-1548, (2000)).

Virtual Screening

Databases containing the structural coordinates of thousands of small molecules can be computationally screened to identify molecules that are likely to bind to the catalytic site of IDO. In such screening, the quality of fit of molecules to the binding site in question may be evaluated by any of a number of methods that are familiar to one of ordinary skill in the art, including shape complementarity (see, e.g., DesJalais, et al., J. Med. Chem., 31:722-729, (1988)) or by estimated energy of interaction (Meng, et al., J. Comp. Chem., 13:505-524, (1992)).

In an method, potential binding compounds may be obtained by rapid computational screening. Such a screening comprises testing a large number, which may be hundreds, or may preferably be thousands, or more preferably tens of thousands, or even more preferably hundreds of thousands of molecules whose formulae are known and for which at least one conformation can be readily computed.

The databases of small molecules include any virtual or physical database, such as electronic and physical compound library databases. Preferably, the molecules are obtained from one or more molecular structure databases that are available in electronic form, for example, the "Available Chemicals Directory" (ACD), the MDL Drug Data Report and/or the Comprehensive Medicinal Chemistry Database (available from MDL Information Systems, Inc., 14600 Catalina Street, San Leandro, Calif.); the Cambridge Structural Database; the Fine Chemical Database (Rusinko, Chem. Des. Auto. News, 8:44-47 (1993)); the National Cancer Institute database and any proprietary database of compounds with known medicinal properties, as is found in large or small pharmaceutical companies.

The molecules in such databases are preferably stored as a connection table, with or without a 2D representation that comprises coordinates in just 2 dimensions, say x and y, for facilitating visualization on a computer display. The molecules are more preferably stored as at least one set of 3D coordinates corresponding to an experimentally derived or computer-generated molecular conformation. If the molecules are only stored as a connection table or a 2D set of coordinates, then it could be necessary to generate a 3D structure for each molecule before proceeding with a computational screen. Programs for converting 2D molecular structures or molecule connection tables to 3D structures include Converter (available from Accelrys, a subsidiary of Pharmacopeia, Inc.) and CONCORD (A. Rusinko III, J. M. Skell, R. Balducci, C. M. McGarity, and R. S. Pearlman, "CONCORD, A Program for the Rapid Generation of High Quality Approximate 3-Dimensional Molecular Structures," (1988) The University of Texas at Austin and Tripos Associates, available from Tripos, Inc., 1699 South Hanley Road, St. Louis, Mo.).

To perform the virtual screening of IDO inhibitory compounds, each 3D structure is docked to the IDO catalytic site using high-throughput screening software. Such a procedure can normally be subjected to a number of user-defined parameters and thresholds according to desired speed of throughput and accuracy of result. Such parameters include the number of different starting positions from which to start a docking simulation and the number of energy calculations to carry out before rejecting or accepting a docked structure. Such parameters and their choices are familiar to one of ordinary skill in the art. Structures from the database can be selected for synthesis to test their ability to modulate nuclear receptor activity if their docked energy is below a certain threshold. Methods of docking are further described elsewhere herein. For example the high throughput virtual screening can be performed by using the computer software GLIDE (Schrodinger, Inc., Portland, Oreg.). GLIDE searches the protein active site for the best possible location and orientation for the docked ligand. Its docking algorithm examines the conformational space, employing a heuristic screening process that eliminates unfavorable conformations. The software generates a score that rewards favorable lipophilic, hydrogen bonding, and metal ligation contacts and penalizes frozen rotatable bonds and steric clashes. In addition, the score takes into account an evaluation of the Coulomb-van der Walls interactions, as well as a small number of potential energy terms that reward hydrogen bond donors found in the active site's hydrophilic regions and penalizes hydrogen bond donors and acceptors found in the hydrophobic regions. The software yields a Docking Score value for each compound, expressed in energy units of kcal/mol.

Alternatively, it is possible to carry out a "molecular similarity" search for molecules that are potential IDO inhibitors. A similarity search attempts to find molecules in a database that have at least one favorable 3D conformation whose structure overlap favorably with a pharmacophore that has been previously defined as a favorable IDO inhibitor. For example, a pharmacophore may bind to a lipophilic pocket at a particular position, a hydrogen-bond acceptor site at another position and a hydrogen bond donor site at yet another specified position accompanied by distance ranges between them. A molecule that could potentially fit into the active site is one that can adopt a conformation in which a H-bond donor in the active site can reach the H-bond acceptor site on the pharmacophore, a H-bond acceptor in the active site can simultaneously reach the H-bond donor site of the pharmacophore and, for example, a group such as a phenyl ring can orient itself into the lipophilic pocket.

Even where a pharmacophore has not been developed, molecular similarity principles may be employed in a database searching regime (see, for example, Johnson, M. A.; Maggiora, G. M., Eds. Concepts and Applications of Molecular Similarity, New York: John Wiley & Sons (1990)) if at least one molecule that fits well in the IDO catalytic site is known.

In one embodiment, it is possible to search for molecules that have certain properties in common with those of the molecule(s) known to bind. For example, such properties include numbers of hydrogen bond donors or numbers of hydrogen bond acceptors, or overall hydrophobicity within a particular range of values. Alternatively, even where a pharmacophore is not known, similar molecules may be selected on the basis of optimizing an overlap criterion with the molecule of interest.

Considerations of the Rational Design of IDO Inhibitors

Molecules that bind to the IDO catalytic site can be designed by a number of methods, including: 1) structural analogy to known IDO inhibitor or 2) structural analogy to intermediates structures participating in the mechanism of tryptophan dioxygenation catalyzed by IDO.

In another embodiment, IDO inhibitors can be design by mimicking the structures of molecular species representing the transition state of tryptophan dioxygenation. The current understanding of the mechanism catalyzed by IDO involves the formation of an adduct between the indole core of tryptophan, oxygen and the iron atom present in the heme cofactor. Reviewed in Malachowski et al, Drugs of Future 2005, 30(9), 1-9 and Sugimoto H et al., 2006, Proc. Natl. Acad. Sci. USA 103(8), 2611-2616. There are three suggested mechanism proposed for the formation of this adduct that involve an ionic mechanism, a pericyclic mechanism or a radical mechanism. The adduct suffers a molecular reorganization that involves electron transfer with a base aminoacid present at the catalytic site. The molecular reorganization of the adduct proceeds either through a Criegee-type of rearrangement or through a dioxetane retro-cycloaddition mechanism to yield kynurenine and the free enzyme. Further provided are the structures of IDO inhibitory molecules designed by mimicking the structural features of these intermediate molecular species, or structurally modified substrate mimics that do not allow progression of one of the mechanistic steps of the reaction.

The design of molecules that inhibit IDO generally involves consideration of two factors. The molecule must be capable of first physically, and second structurally, associating with IDO. The physical interactions supporting this association can be covalent or non-covalent. For example, covalent interactions may be important for designing irreversible or "suicide" inhibitors of a protein. Non-covalent molecular interactions that are important in the association of IDO with molecules that bind to it include hydrogen bonding, ionic, van der Waals, and hydrophobic interactions. Structurally, the compound must be able to assume a conformation that allows it to associate with the heme cofactor at the IDO catalytic active site.

In general, the potential inhibitory or binding effect of a compound on IDO may be analyzed prior to its actual synthesis and testing by the use of computer modeling techniques. If the theoretical structure of the given compound suggests insufficient interaction and association between it and the IDO active site, synthesis and testing of the compound need not be carried out. However, if computer modeling indicates a strong interaction, the molecule may then be synthesized and tested for its ability to bind to the IDO catalytic pocket and thereby inhibit its activity. In this manner, synthesis of ineffective compounds may be avoided.

Among the computational techniques that enable the rational design of molecules that bind to IDO, it is key to have access to visualization tools, programs for calculating properties of molecules, and programs for fitting ligand structures into three-dimensional representations of the receptor binding site. Computer program packages for facilitating each of these capabilities have been referred to herein, and are available to one of ordinary skill in the art. Visualization of molecular properties, such as field properties that vary through space, can also be particularly important and may be aided by computer programs such as MOLCAD (Brickmann, J., and coworkers, see, for example, J. Comp.-Aid. Molec. Des., 7:503, (1993); available from Tripos, Inc., 1699 South Hanley Road, St. Louis, Mo.).

A molecular property of particular interest when assessing suitability of drug compounds is its hydrophobicity. An accepted and widespread measure of hydrophobicity is Log P, the Log 10 of the octanol-water partition coefficient. It is customary to use the value of Log P for a designed molecule to assess whether the molecule could be suitable for transport across a cell membrane, if it were to be administered as a drug. Measured values of Log P are available for many compounds. Methods and programs for calculating Log P are also available, and are particularly useful for molecules that have not been synthesized or for which no experimental value of Log P is available. See for example: CLOGP (Hansch, C., and Leo, A.; available from Biobyte, Inc., Pomona, Calif.) and ACD/Log P DB (Advanced Chemistry Development Inc., 90 Adelaide Street West, Suite 702, Toronto, Ontario, Canada).

Labeled Compounds and Assay Methods

Another aspect relates to fluorescent dye, spin label, heavy metal or radio-labeled derivatives of the compounds described herein that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, further provided are IDO enzyme assays that contain such labeled compounds.

Further provided are isotopically-labeled compounds of the compounds described herein. An "isotopically" or "radio-labeled" compound is a compound described herein where one or more atoms are replaced or substituted by an atom having an atomic mass or mass number different from the atomic mass or mass number typically found in nature (i.e., naturally occurring). Suitable radionuclides that may be include but are not limited to 2H (also written as D for deuterium), 3H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and a $^{131}$I. The radionuclide that is incorporated in the instant radio-labeled compounds will depend on the specific application of that radio-labeled compound. For example, for in vitro IDO enzyme labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br.

Synthetic methods for incorporating radio-isotopes into organic compounds are applicable to compounds described herein and are well known in the art.

A radio-labeled compound described herein can be used in a screening assay to identify/evaluate compounds. In general terms, a newly synthesized or identified compound (i.e., test compound) can be evaluated for its ability to reduce binding of the radio-labeled compound described herein to the IDO enzyme. Accordingly, the ability of a test compound to compete with the radio-labeled compound for binding to the IDO enzyme directly correlates to its binding affinity.

Kits

Also included are pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO according to one or more of the assays described herein.

EXAMPLES

General Experimental Methods

All reagents and solvents were purchased from commercial sources and used as received without further purification. The reactions were monitored using analytical thin layer chromatography (TLC) with 0.25 mm EM Science silica gel plates (60E-254). The developed TLC plates were visualized by immersion in potassium permanganate solution followed by heating on a hot plate. Flash chromatography was performed with Selecto Scientific silica gel, 32-63 μm particle sizes. All reactions were performed in flame- or oven-dried glassware under a nitrogen atmosphere. All reactions were stirred magnetically at ambient temperature unless otherwise indicated. $^1$H NMR and $^{13}$C NMR spectra were obtained with a Bruker DRX400, Varian VXR300 and VXR400. $^1$H NMR spectra were reported in parts per million (δ) relative to CDCl$_3$ (7.27 ppm), CD$_3$OD (4.80) or DMSO-d$_6$ (2.50) as an internal reference.

The following compounds were synthesized by known literature procedures: (2-(benzylamino)phenyl)methanol (Organic Letters 2002, 581-584), (3-(benzylamino)phenyl)methanol (European Patent Application 1989, 91 pp), (2-(phenylamino)phenyl)methanol (Journal of Heterocyclic Chemistry 1986, 23, 223-224), tert-butyl 2-hydroxy-2-phenylethylcarbamate (Bioorganic and Medicinal Chemistry 2004, 12, 1483-1491), tert-butyl 3-hydroxy-3-phenylpropylcarbamate (US Patent 2000, 5 pp), methyl 4-hydroxy-4-phenylbutanoate (Journal of Medicinal Chemistry 1986, 230-238), 3-morpholino-1-phenylpropan-1-ol (Chemistry Letters 1978, 11, 1285-1288), 1,2-diphenylethanol (Organic Letters 2006, 8, 773-776), 2-morpholino-1-phenylethanol (Organic Letters 2005, 7, 3649-3651), cyclohexyl(phenyl)methanol (Tetrahedron Letters 1989, 30, 6709-6712), (R)-3-(tert-butyldimethylsilyloxy)-1-phenylpropan-1-ol (Bioorganic and Medicinal Chemistry Letters 2005, 15, 4130-4135), biphenyl-3-ylmethanol (European Journal of Medicinal Chemistry 2007, 42, 293-306), biphenyl-2-ylmethanol (Journal of the American Chemical Society 1999, 121, 9550-9561), (4'-methylbiphenyl-3-yl)methanol (Tetrahedron 1994, 50, 8301-16), (4'-methylbiphenyl-2-yl)methanol (Tetrahedron Letters 2000, 41, 6415-6418), (4'-methoxybiphenyl-2-yl)methanol (Journal of Organic Chemistry 1987, 52, 4953-61), (4'-methoxybiphenyl-3-yl)methanol (Synlett 1998, 6, 671-675), 2-hydroxy-N-methyl-2-phenylacetamide (Journal of Organic Chemistry 1992, 57, 5700-7), 2-cyclohexyl-1-phenylethanol (Journal of Organic Chemistry 1936, 1, 288-99), 2-phenoxy-1-phenylethanol (Tetrahedron 2008, 64, 3867-3876).

Example 1

Method A: Syntheses of Dithiocarbamates with Variations in S-Alkyl Groups (Scheme 1)

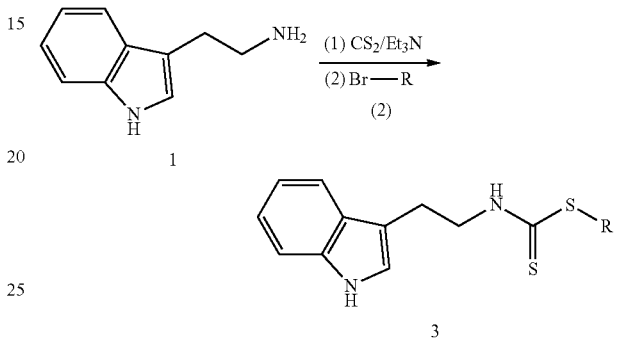

A solution of tryptamine 1 (1.0 equiv) in anhydrous CH$_2$Cl$_2$ (10 mL) at 0° C. was treated sequentially with triethylamine (1.1 equiv) then carbon disulfide (1.1 equiv) and stirred for 30 min. After this time, alkyl bromide 2 (1.2 equiv unless indicated otherwise) was added and the reaction was allowed to warm to room temperature and stirred overnight. The reaction mixture was then poured into 1 M H$_2$SO$_4$ and extracted with EtOAc (3×10 mL). The combined organic layers were washed with brine, dried over anhydrous Na$_2$SO$_4$, filtered and concentrated. Purification by flash chromatography (silica, EtOAc/hexanes) afforded the desired product. The dithiocarbamate product typically exists as a ≈7:3 mixture of tautomers observed by $^1$H NMR, and are listed with spectral data.

Example 2

Phenethyl 2-(1H-indol-3-yl)ethylcarbamodithioate [Compound 00001]

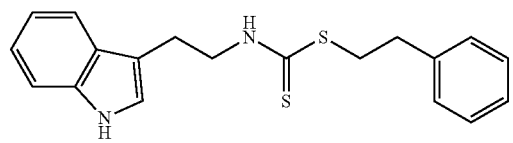 [SMILES: S=C(NCCc1c[nH]c2ccccc12)SCCc1ccccc1]

The reaction of 1 with (2-bromoethyl)benzene (1.2 equiv) was performed as described in Method A. Purification by flash chromatography (silica, gradient of 12% EtOAc/Hexanes to 100% EtOAc) afforded product 00001 (0.148 g, 35%) as a yellow oil: $^1$H NMR (500 MHz, CDCl$_3$) δ 8.04 (br s, 1H), 7.62 (d, J=7.5 Hz, 1H), 7.38 (d, J=8.0 Hz, 1H), 7.32-7.25 (m, 2H), 7.25-7.20 (m, 4H), 7.16-7.13 (m, 1H), 7.07-7.05 (m, 1H), 6.92 (br s, 1H), 4.11-4.06 (m, 2H), 3.48-3.45 (m, 2H), 3.13 (t, J=6.5 Hz, 2H), 2.97-2.94 (m, 2H) and signals due to a minor tautomer (ca. 31%): 3.78-3.74

(m), 3.59-3.55 (m), 3.10-3.08 (m), 3.05-3.01 (m); ESI MS m/z 341 [M+H]$^+$, HPLC (Method 1)>99% (AUC), $t_R$=13.9 min.

Example 3

4-Fluorophenethyl 2-(1H-indol-3-yl)ethylcarbamodithioate [Compound 00003]

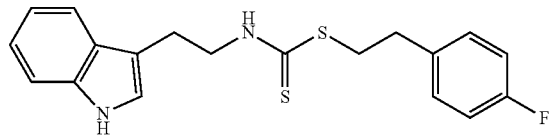 [SMILES: Fc1ccc(CCSC(=S)NCCc2c[nH]c3ccccc23)cc1]

The reaction of 1 with 4-fluorophenethyl bromide (0.6 equiv) was performed as described in Method A. Purification by flash chromatography (silica, gradient of 12% EtOAc/Hexanes to 100% EtOAc) afforded product 00003 (0.084 g, 31%) as a yellow oil: $^1$H NMR (500 MHz, CDCl$_3$) δ 8.04 (br s, 1H), 7.63 (d, J=8.0 Hz, 1H), 7.39 (d, J=8.0 Hz, 1H), 7.24-7.13 (m, 4H), 7.08-7.04 (m, 1H), 7.00-6.94 (m, 2H), 6.92 (br s, 1H), 4.11-4.07 (m, 2H), 3.46-3.43 (m, 2H), 3.14 (t, J=7.0 Hz, 2H), 2.94-2.91 (m, 2H) and signals due to a minor tautomer (ca. 31%): 3.79-3.75 (m), 3.55-3.52 (m), 3.11-3.09 (m), 3.01-2.98 (m); ESI MS m/z 359 [M+H]$^+$, HPLC (Method 1) 95.3% (AUC), $t_R$=13.7 min.

Example 4

3-Methoxyphenethyl 2-1H-indol-3-yl)ethylcarbamodithioate [Compound 00010]

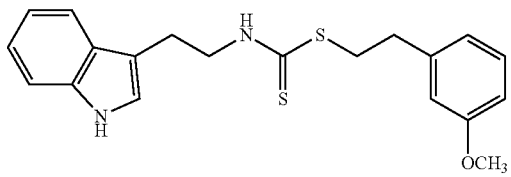 [SMILES: COc1cccc(CCSC(=S)NCCc2c[nH]c3ccccc23)c1]

The reaction of 1 with 3-methoxyphenethyl bromide (0.6 equiv) was performed as described in Method A. Purification by flash chromatography (silica, gradient of 12% EtOAc/Hexanes to 100% EtOAc) afforded product 00010 (0.094 g, 33%) as a yellow oil: $^1$H NMR (500 MHz, CDCl$_3$) δ 8.04 (br s, 1H), 7.62 (d, J=7.5 Hz, 1H), 7.38 (d, J=8.5 Hz, 1H), 7.24-7.19 (m, 2H), 7.16-7.13 (m, 1H), 7.07-7.06 (m, 1H), 6.92 (br s, 1H), 6.83-6.75 (m, 3H), 4.10-4.06 (m, 2H), 3.80 (s, 3H), 3.48-3.45 (m, 2H), 3.13 (t, J=6.5 Hz, 2H), 2.95-2.92 (m, 2H) and signals due to a minor tautomer (ca. 31%): 3.79-3.76 (m), 3.59-3.55 (m), 3.10-3.09 (m), 3.02-2.99 (m); ESI MS m/z 371 [M+H]$^+$, HPLC (Method 1) 97.3% (AUC), $t_R$=13.1 min.

Example 5

4-Methoxyphenethyl 2-(1H-indol-3-yl)ethylcarbamodithioate [Compound 00002]

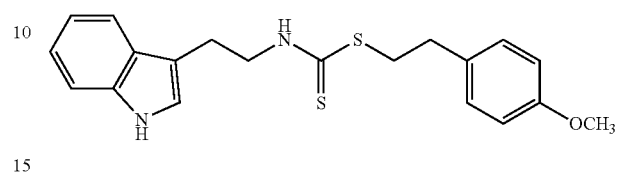

The reaction of 1 with 4-methoxyphenethyl bromide (0.6 equiv) was performed as described in Method A. Purification by flash chromatography (silica, gradient of 12% EtOAc/Hexanes to 100% EtOAc) afforded product 00002 (0.078 g, 28%) as a yellow oil: $^1$H NMR (500 MHz, CDCl$_3$) δ 8.03 (br s, 1H), 7.62 (d, J=8.0 Hz, 1H), 7.38 (d, J=8.0 Hz, 1H), 7.24-7.18 (m, 2H), 7.16-7.13 (m, 3H), 7.08-7.05 (m, 1H), 6.92 (br s, 1H), 6.85-6.82 (m, 2H), 4.10-4.06 (m, 2H), 3.78 (s, 3H), 3.45-3.42 (m, 2H), 3.13 (t, J=6.5, 2H), 2.91-2.88 (m, 2H) and signals due to a minor tautomer (ca. 31%): 3.78-3.76 (m), 3.55-3.52 (m), 3.11-3.09 (m), 2.98-2.95 (m); ESI MS m/z 371 [M+H]$^+$, HPLC (Method 1) 96.5% (AUC), $t_R$=13.3 min.

Example 6

4-Bromophenethyl 2-(1H-indol-3-yl)ethylcarbamodithioate [Compound 00004]

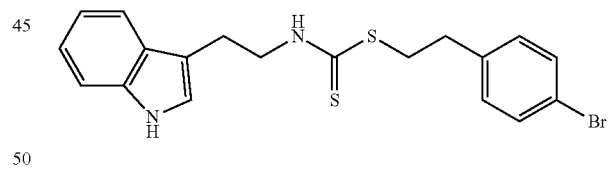

The reaction of 1 with 4-bromophenethyl bromide (1.2 equiv) was performed as described in Method A. Purification by flash chromatography (silica, gradient of 12% EtOAc/Hexanes to 100% EtOAc) afforded product 00004 (0.245 g, 46%) as a yellow oil: $^1$H NMR (500 MHz, CDCl$_3$) δ 8.04 (br s, 1H), 7.62 (d, J=8.0 Hz, 1H), 7.43-7.38 (m, 3H), 7.25-7.22 (m, 1H), 7.16-7.05 (m, 4H), 6.92 (br s, 1H), 4.10-4.06 (m, 2H), 3.46-3.42 (m, 2H), 3.14 (t, J=6.5 Hz, 2H), 2.93-2.90 (m, 2H) and signals due to a minor tautomer (ca. 32%): 3.78-3.74 (m), 3.55-3.52 (m), 3.11-3.09 (m), 3.00-2.97 (m); ESI MS m/z 419 [M+H]$^+$, HPLC (Method 1)>99% (AUC), $t_R$=15.6 min.

Example 7

3-Bromophenethyl 2-(1H-indol-3-yl)ethylcarbamodithioate [Compound 00007]

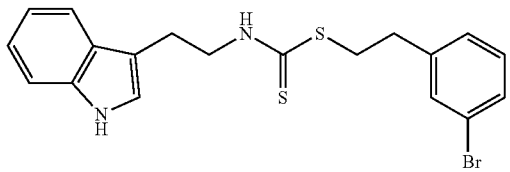 [SMILES: S=C(NCCc1c[nH]c2ccccc12)SCCc1cccc(Br)c1]

The reaction of 1 with 3-bromophenethyl bromide (1.2 equiv) was performed as described in Method A. Purification by flash chromatography (silica, gradient of 12% EtOAc/Hexanes to 100% EtOAc) afforded product 00007 (0.329 g, 62%) as a yellow oil: $^1$H NMR (500 MHz, CDCl$_3$) δ 8.04 (br s, 1H), 7.62 (d, J=7.5 Hz, 1H), 7.42-7.34 (m, 3H), 7.24-7.20 (m, 1H), 7.18-7.13 (m, 3H), 7.07-7.06 (m, 1H), 6.93 (br s, 1H), 4.11-4.06 (m, 2H), 3.46-3.43 (m, 2H), 3.14 (t, J=7.0 Hz, 2H), 2.94-2.91 (m, 2H) and signals due to a minor tautomer (ca. 32%): 3.78-3.74 (m), 3.55-3.52 (m), 3.11-3.09 (m), 3.01-2.98 (m); ESI MS m/z 419 [M+H]$^+$, HPLC (Method 1)>99% (AUC), $t_R$=15.5 min.

Example 8

3-Methylphenethyl 2-(1H-indol-3-yl)ethylcarbamodithioate [Compound 00020]

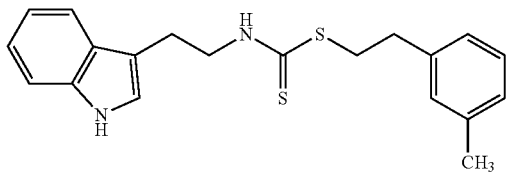

The reaction of 1 with 1-(2-bromoethyl)-3-methyl-benzene (1.0 equiv) was performed as described in Method A. Purification by flash chromatography (silica, gradient of 12% EtOAc/Hexanes to 100% EtOAc) afforded product 00020 (0.039 g, 22%) as a yellow oil: $^1$H NMR (500 MHz, CDCl$_3$) δ 8.03 (br s, 1H), 7.63 (d, J=8.0 Hz, 1H), 7.39 (d, J=8.0 Hz, 1H), 7.24-7.13 (m, 4H), 7.06-7.02 (m, 3H), 6.92 (br s, 1H), 4.10-4.06 (m, 2H), 3.47-3.44 (m, 2H), 3.13 (t, J=7.0 Hz, 2H) Hz, 2.93-2.90 (m, 2H) and signals due to a minor tautomer (ca. 32%): 3.79-3.75 (m), 3.57-3.54 (m), 3.11-3.09 (m), 3.01-2.98 (m); ESI MS m/z 355 [M+H]$^+$, HPLC (Method 1) 96.3% (AUC), $t_R$=15.1 min.

Example 9

2-Phenylpropyl 2-(1H-indol-3-yl)ethylcarbamodithioate [Compound 00006]

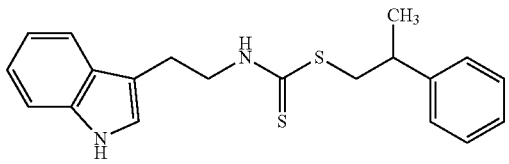 [SMILES: CC(CSC(=S)NCCc1c[nH]c2ccccc12)c1ccccc1]

The reaction of 1 with 1-bromo-2-phenylpropane (1.2 equiv) was performed as described in Method A. The reaction was at reflux (55° C.) overnight instead of room temperature. Purification by flash chromatography (silica, gradient of 12% EtOAc/Hexanes to 100% EtOAc) afforded product 00006 (0.022 g, 5%) as a yellow oil: $^1$H NMR (500 MHz, CDCl$_3$) δ 8.01 (br s, 1H), 7.61 (d, J=7.5 Hz, 1H), 7.38 (d, J=8.5 Hz, 1H), 7.33-7.20 (m, 6H), 7.15-7.12 (m, 1H), 7.05-7.04 (m, 1H), 6.88 (br s, 1H), 4.08-4.04 (m, 2H), 3.48-3.45 (m, 2H), 3.12-3.06 (m, 3H), 1.53 (s, 3H) and signals due to a minor tautomer (ca. 30%) 3.75-3.71 (m), 3.21-3.18 (m); ESI MS m/z 355 [M+H]$^+$, HPLC (Method 1) 96.2% (AUC), $t_R$=14.3 min.

Example 10

(6,7-Dimethoxy-2-oxo-2H-chromen-4-yl)methyl 2-(1H-indol-3-yl)ethyl-carbamodithioate [Compound 00023]

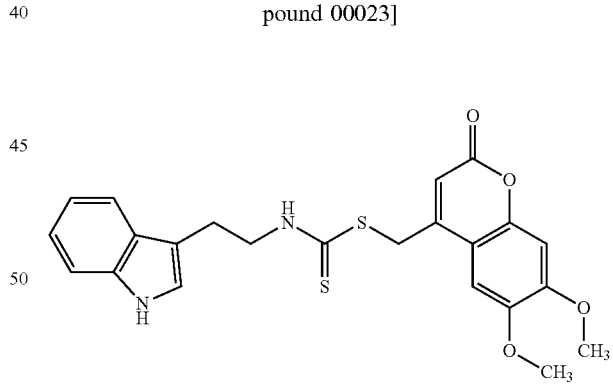

The reaction of 1 with 4-(bromomethyl)-6,7-dimethoxycoumarin (1.2 equiv) was performed as described in Method A. Purification by flash chromatography (silica, gradient of 12% EtOAc/Hexanes to 100% EtOAc) afforded product 00023 (0.063 g, 11%) as an off white solid: $^1$H NMR (500 MHz, CDCl$_3$) δ 8.15 (br s, 1H), 7.60 (d, J=8.0 Hz, 1H), 7.40-7.38 (m, 1H), 7.24-7.21 (m, 1H), 7.15-7.12 (m, 2H), 7.05-7.01 (m, 2H), 6.85-6.84 (m, 1H), 6.33 (s, 1H), 4.70 (s, 2H), 4.13-4.09 (m, 2H), 3.94 (s, 3H), 3.89 (s, 3H), 3.17 (t, J=6.5 Hz, 2H) and signals due to a minor tautomer (ca. 23%): 3.14-3.10 (m); ESI MS m/z 455 [M+H]$^+$, HPLC (Method 1) 96.5% (AUC), $t_R$=11.5 min, MP=175-177° C.

Example 11

2-(1H-Indol-3-yl)ethyl 2-(1H-indol-3-yl)ethylcarbamodithioate [Compound 00030]

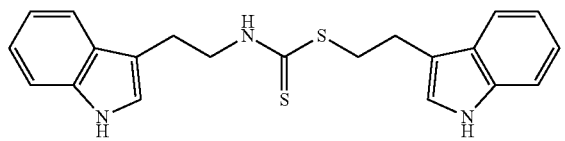 [SMILES: S=C(NCCc1c[nH]c2ccccc12)SCCc1c[nH]c2ccccc12]

The reaction of 1 with 3-(2-bromoethyl)indole (1.2 equiv) was performed as described in Method A. Purification by flash chromatography (silica, gradient of 12% EtOAc/Hexanes to 100% EtOAc) afforded product 00030 (0.086 g, 18%) as an off white solid: $^1$H NMR (500 MHz, CDCl$_3$) δ 7.98-7.93 (m, 2H), 7.68 (d, J=8.0 Hz, 1H), 7.61 (d, J=8.0 Hz, 1H), 7.37-7.34 (m, 2H), 7.23-7.18 (m, 2H), 7.15-7.11 (m, 2H), 7.06-7.01 (m, 2H), 6.89 (s, 1H), 4.05-4.02 (m, 2H), 3.53 (t, J=7.5 Hz, 2H), 3.13-3.07 (m, 4H), and signals due to a minor tautomer (ca. 31%): 3.76-3.75 (m), 3.68 (t, J=7.5 Hz), 3.20 (t, J=7.5); ESI MS m/z 380 [M+H]$^+$, HPLC (Method 1)>99% (AUC), t$_R$=12.4 min, MP=125-127° C.

Example 12

(2-Methylquinolin-6-yl)methyl 2-(1H-indol-3-yl)ethylcarbamodithioate [Compound 00038]

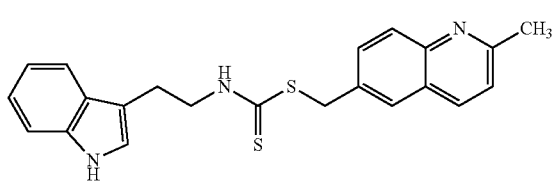 [SMILES: Cc1ccc2cc(CSC(=S)NCCc3c[nH]c4ccccc34)ccc2n1]

The reaction of 1 with 6-(bromomethyl)-2-methylquinoline (1.2 equiv) was performed as described in Method A. Purification by flash chromatography (silica, gradient of 12% EtOAc/Hexanes to 100% EtOAc) afforded product 00038 (0.079 g, 16%) as an off white solid: $^1$H NMR (500 MHz, CDCl$_3$) δ 8.00-7.93 (m, 2H) 7.71 (s, 1H), 7.63-7.55 (m, 3H), 7.37 (d, J=8.0 Hz, 1H), 7.29-7.20 (m, 2H), 7.14-7.11 (m, 1H), 6.98-6.95 (m, 2H), 4.66 (s, 2H), 4.10-4.06 (m, 2H), 3.12 (t, J=7.0 Hz, 2H), 2.73 (s, 3H), and signals due to a minor tautomer (ca. 27%): 3.79-3.78 (m), 3.12-3.09 (m); ESI MS m/z 392 [M+H]$^+$, HPLC (Method 1) 98.5% (AUC), t$_R$=8.2 min, MP=72-75° C.

Example 13

(3-Methylnaphthalen-2-yl)methyl 2-(1H-indol-3-yl)ethylcarbamodithioate [Compound 00047]

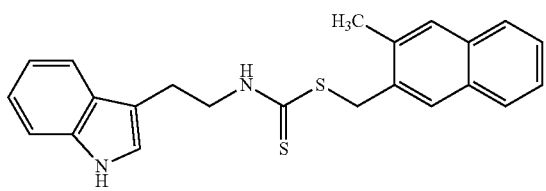 [SMILES: Cc1cc2ccccc2cc1CSC(=S)NCCc1c[nH]c2ccccc12]

The reaction of 1 with 2-bromomethyl-3-methyl-naphthalene (1.2 equiv) was performed as described in Method A. Purification by flash chromatography (silica, gradient of 12% EtOAc/Hexanes to 100% EtOAc) afforded product 00047 (0.097 g, 71%) as an off white solid: $^1$H NMR (500 MHz, CDCl$_3$) δ 7.93 (br s, 1H), 7.87 (br s, 1H), 7.76-7.71 (m, 1H), 7.64-7.60 (m, 1H), 7.43-7.35 (m, 4H), 7.21 (t, J=8.0 Hz, 1H), 7.13 (t, J=8.0 Hz, 1H), 6.99-6.94 (m, 2H), 4.64 (s, 2H), 4.10-4.06 (m, 2H), 3.13 (t, J=6.5 Hz, 2H), 2.50 (s, 3H), and signals due to a minor tautomer (ca. 33%): 4.7 (s), 3.77-3.76 (m), 3.12-3.08 (m); ESI MS m/z 391 [M+H]$^+$, HPLC (Method 1)>99% (AUC), t$_R$=16.1 min, MP=129-131° C.

Example 14

(6-Bromobenzo[d][1,3]dioxol-5-yl)methyl 2-(1H-indol-3-yl)ethylcarbamodithioate [Compound 00065]

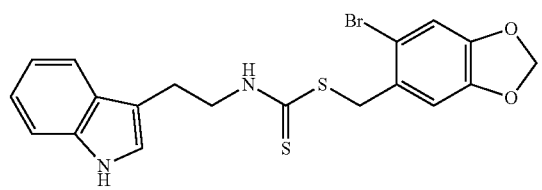 [SMILES: S=C(NCCc1c[nH]c2ccccc12)SCc1cc2c(cc1Br)OCO2]

The reaction of 1 with 5-bromo-6-bromomethyl-1,3-benzodioxole (1.2 equiv) was performed as described in Method A. Purification by flash chromatography (silica, gradient of 12% EtOAc/Hexanes to 100% EtOAc) afforded product 00065 (0.368 g, 66%) as a clear oil: $^1$H NMR (500 MHz, CDCl$_3$) δ 8.02 (br s, 1H), 7.60 (d, J=8.0 Hz, 1H), 7.37 (d, J=8.5 Hz, 1H), 7.22 (t, J=8.0 Hz, 1H), 7.13 (t, J=7.5 Hz, 1H), 7.06 (s, 1H), 7.03 (s, 1H), 6.96 (s, 1H), 6.92 (br s, 1H), 5.94 (s, 2H), 4.58 (s, 2H), 4.09-4.05 (m, 2H), 3.12 (t, J=7.0 Hz, 2H), and signals due to a minor tautomer (ca. 29%): 4.68 (s), 3.77-3.76 (m), 3.11-3.08 (m); ESI MS m/z 450 [M+H]$^+$, HPLC (Method 1) 98.7% (AUC), t$_R$=14.4 min.

Example 15

Benzo[d]isoxazol-3-ylmethyl 2-(1H-indol-3-yl)ethylcarbamodithioate [Compound 00052]

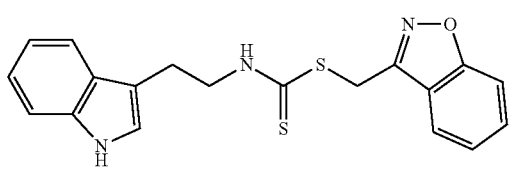 [SMILES: S=C(NCCc1c[nH]c2ccccc12)SCc1noc2ccccc12]

The reaction of 1 with 3-(bromomethyl)-1,2-benzisoxazole (1.2 equiv) was performed as described in Method A. Purification by flash chromatography (silica, gradient of 12% EtOAc/Hexanes to 100% EtOAc) afforded product 00052 (0.304 g, 66%) as a yellow oil: $^1$H NMR (500 MHz, CDCl$_3$) δ 8.03 (br s, 1H), 7.82 (d, J=8.0 Hz, 1H), 7.61 (d, J=8.0 Hz, 1H), 7.56-7.55 (m, 1H), 7.37 (d, J=8.0 Hz, 1H), 7.32-7.29 (m, 1H), 7.22-7.20 (m, 2H), 7.15-7.10 (m, 1H), 7.07-7.05 (m, 1H), 4.90 (s, 2H), 4.14-4.09 (m, 2H), 3.16 (t, J=6.5 Hz, 2H), and signals due to a minor tautomer (ca. 20%): 5.10 (s), 3.83-3.78 (m), 3.12-3.10 (m); ESI MS m/z 368 [M+H]⁺, HPLC (Method 1) 98.8% (AUC), $t_R$=12.4 min.

Example 16

2-Chlorophenethyl 2-(1H-indol-3-yl)ethylcarbamodithioate [Compound 00021]

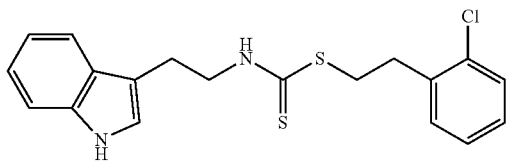 [SMILES: S=C(NCCc1c[nH]c2ccccc12)SCCc1ccccc1Cl]

The reaction of 1 with 2-chlorophenethyl bromide (1.2 equiv) was performed as described in Method A. Purification by flash chromatography (silica, gradient of 12% EtOAc/Hexanes to 100% EtOAc) afforded product 00021 (0.054 g, 11%) as a yellow oil: ¹H NMR (500 MHz, CDCl₃) δ 8.02 (br s, 1H), 7.63 (d, J=8.0 Hz, 1H), 7.39 (d, J=8.0 Hz, 1H), 7.39-7.29 (m, 2H), 7.24-7.13 (m, 4H), 7.08-7.04 (m, 1H), 6.95 (br s, 1H), 4.11-4.07 (m, 2H), 3.49-3.46 (m, 2H), 3.16-3.13 (m, 2H), 3.11-3.07 (m, 2H), and signals due to a minor tautomer (ca. 30%): 3.80-3.76 (m), 3.60-3.57 (m), 3.18-3.14 (m); ESI MS m/z 375 [M+H]⁺, HPLC (Method 1) 97.4% (AUC), $t_R$=16.0 min.

Example 17

4-Methylphenethyl 2-(1H-indol-3-yl)ethylcarbamodithioate [Compound 00009]

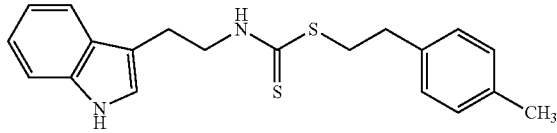 [SMILES: Cc1ccc(CCSC(=S)NCCc2c[nH]c3ccccc23)cc1]

The reaction of 1 with 4-methylphenethyl bromide (1.2 equiv) was performed as described in Method A. Purification by flash chromatography (silica, gradient of 12% EtOAc/Hexanes to 100% EtOAc) afforded product 00009 (0.225 g, 50%) as a yellow oil: ¹H NMR (500 MHz, CDCl₃) δ 8.02 (br s, 1H), 7.62 (d, J=8.0 Hz, 1H), 7.37 (d, J=8.5 Hz, 1H), 7.24-7.20 (m, 1H), 7.17-7.08 (m, 5H), 7.03 (s, 1H), 6.91 (br s, 1H), 4.08 (m, 2H), 3.45-3.42 (m, 2H), 3.11 (t, J=7.0 Hz, 2H), 2.93-2.90 (m, 2H), and signals due to a minor tautomer (ca. 32%): 3.77-3.73 (m), 3.56-3.53 (m), 3.10-3.07 (m), 3.00-2.97 (m); ESI MS m/z 355 [M+H]⁺, HPLC (Method 1) 95.3% (AUC), $t_R$=16.1 min.

Example 18

4-((2-(1H-Indol-3-yl)ethylcarbamothioylthio) methyl)-2-oxo-2H-chromen-7-yl acetate [Compound 00049]

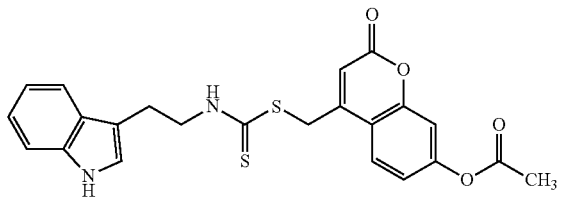 [SMILES: CC(=O)Oc1ccc2c(CSC(=S)NCCc3c[nH]c4ccccc34)cc(=O)oc2c1]

The reaction of 1 with 7-acetoxy-4(bromomethyl) coumarine (1.2 equiv) was performed as described in Method A. Purification by flash chromatography (silica, gradient of 12% EtOAc/Hexanes to 100% EtOAc) afforded product 00049 (0.130 g, 28%) as an off white solid: ¹H NMR (500 MHz, CDCl₃) δ 8.18 (br s, 1H), 7.71 (d, J=9.0 Hz, 1H), 7.60 (d, J=8.0 Hz, 1H), 7.39-7.37 (m, 1H), 7.23-7.20 (m, 1H), 7.15-7.11 (m, 2H), 7.09-7.06 (m, 2H), 7.01-7.00 (m, 1H), 6.49 (s, 1H), 4.66 (s, 2H), 4.11-4.08 (m, 2H), 3.16 (t, J=6.5 Hz, 2H), 2.34 (s, 3H), and signals due to a minor tautomer (ca. 21%): 4.71 (s), 3.83-3.80 (m), 3.12-3.10 (m); ESI MS m/z 453 [M+H]⁺, HPLC (Method 1) 95.6% (AUC), $t_R$=11.5 min, MP=132-134° C.

Example 19

3-Chlorophenethyl 2-(1H-indol-3-yl)ethylcarbamodithioate [Compound 00008]

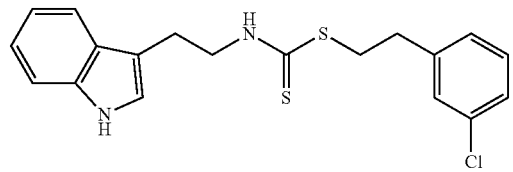

The reaction of 1 with 1-(2-bromoethyl)-3-chlorobenzene (1.2 equiv) was performed as described in Method A. Purification by flash chromatography (silica, gradient of 12% EtOAc/Hexanes to 100% EtOAc) afforded product 00008 (0.290 g, 61%) as a yellow oil: ¹H NMR (500 MHz, CDCl₃) δ 8.04 (br s, 1H), 7.62 (d, J=8.0 Hz, 1H), 7.39 (d, J=8.0 Hz, 1H), 7.27-7.18 (m, 4H), 7.16-7.11 (m, 2H), 7.08-7.06 (m, 1H), 6.93 (br s, 1H) 4.12-4.07 (m, 2H), 3.47-3.44 (m, 2H), 3.14 (t, J=6.5 Hz, 2H), 2.95-2.92 (m, 2H), and signals due to a minor tautomer (ca. 34%): 3.79-3.75 (m), 3.56-3.53 (m), 3.13-3.09 (m), 3.02-2.99 (m); ESI MS m/z 375 [M+H]⁺, HPLC (Method 1) 97.5% (AUC), $t_R$=15.4 min.

Example 20

2-(2,3-Dihydrobenzo[b][1,4]dioxin-6-yl)ethyl 2-(1H-indol-3-yl)ethyl-carbamodithioate (6, Scheme 2) [Compound 00053]

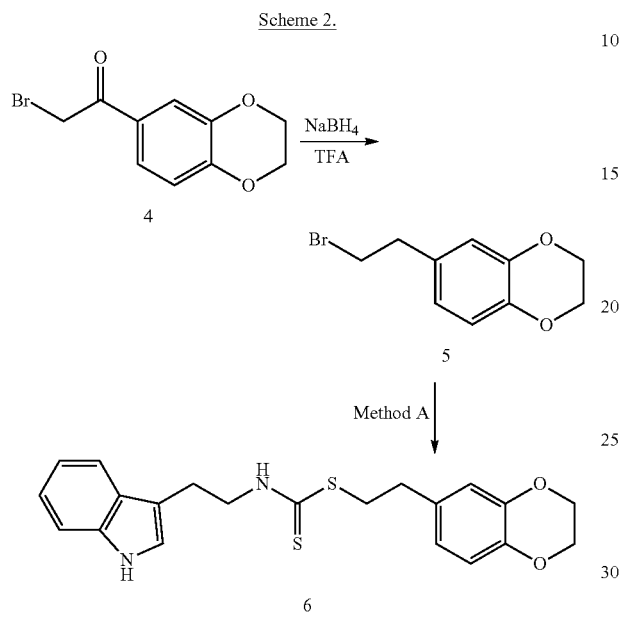

Sodium borohydride (18 mmol, 12 equiv) was added to stirred trifluoroacetic acid (0.19 mL, 1.38 mmol) over a period of 30 min. To the mixture was then added a solution of 2-bromo-1-(2,3-dihydro-1,4-benzodioxin-6-yl)ethan-1-one 4 in $CH_2Cl_2$ over 30 min. After the addition of 4 was complete, the reaction was stirred at room temperature overnight. After this time, the reaction mixture was diluted with $H_2O$ (75 mL), cooled with an ice/water bath, and pH was adjusted to 12 with the addition of NaOH beads. The aqueous layer was separated, and extracted with $CH_2Cl_2$ (3×50 mL). The combined organic solutions were washed with brine, dried over anhydrous $Na_2SO_4$, and concentrated to afford crude product which was purified by chromatography (silica, hexanes-EtOAc), affording 5 (55 mg, 15%) as a yellow oil: $^1$H NMR (500 MHz, $CDCl_3$) δ 6.79 (d, J=8.0 Hz, 1H), 6.71 (d, J=2.0 Hz, 1H), 6.67-6.65 (m, 1H), 4.23 (s, 4H), 3.50 (t, J=8.0 Hz, 2H), 3.04 (t, J=7.5 Hz, 2H).

Coupling of tryptamine 1 with 5 following Method A afforded product 6 (00053, 40 mg, 54% yield) as a yellow oil: $^1$H NMR (500 MHz, $CDCl_3$) 08.04 (br s, 1H), 7.62 (d, J=8.0 Hz, 1H), 7.39 (d, J=8.0 Hz, 1H), 7.22 (t, J=8.0 Hz, 1H), 7.14 (t, J=8.0 Hz, 1H), 7.07-7.05 (m, 1H), 6.91 (br s, 1H), 6.78-6.68 (m, 3H), 4.25-4.22 (m, 4H), 4.09-4.05 (m, 2H), 3.43-3.40 (m, 2H), 3.13 (t, J=6.5 Hz, 2H), 2.86-2.83 (m, 2H), and signals due to a minor tautomer (ca. 31%): 3.77-3.76 (m), 3.52-3.50 (m), 3.12-3.09 (m), 2.93-2.91 (m); ESI MS m/z 399 [M+H]$^+$, HPLC (Method 1) 97.9% (AUC), $t_R$=13.1 min.

Example 21

Benzo[d][1,3]dioxol-5-ylmethyl 2-(1H-indol-3-yl) ethylcarbamodithioate [Compound 00050] (Scheme 4)

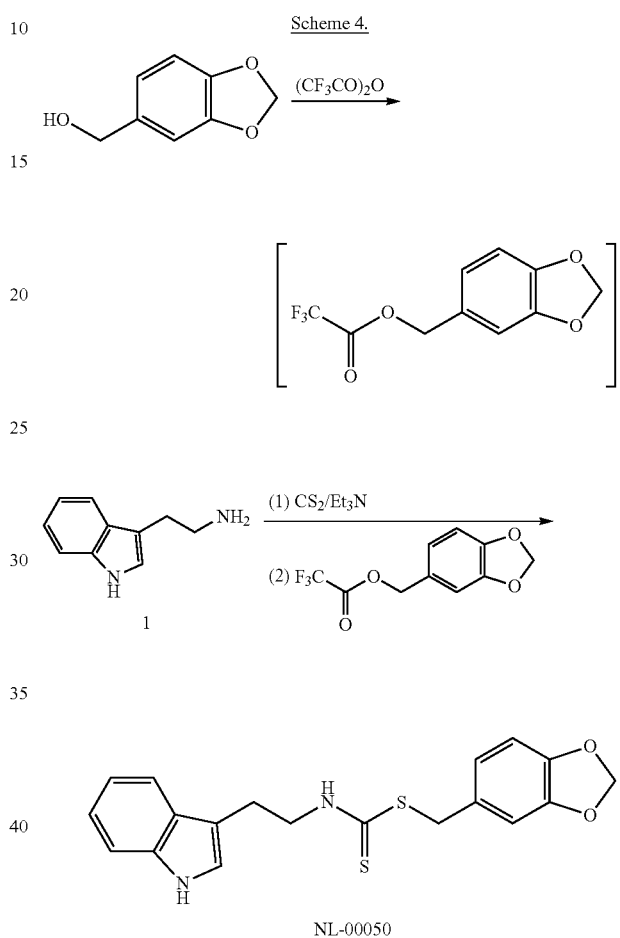

NL-00050

Piperonyl alcohol (1.25 mmol, 1 equiv) was dissolved in anhydrous $CH_2Cl_2$ (10 mL) at 0° C., trifluoroacetic anhydride (1.38 mmol, 1.1 equiv) added, and the reaction mixture was stirred for 1 hour, concentrated to about 3 mL. This material was then treated with 1 following general Method A. Purification by flash chromatography (silica, gradient of 12% EtOAc/Hexanes to 100% EtOAc) afforded product 00050 (0.103 g, 88%) as a yellow oil: $^1$H NMR (500 MHz, $CDCl_3$) δ 8.03 (br s, 1H), 7.61 (d, J=8.0 Hz, 1H), 7.38 (d, J=8.0 Hz, 1H), 7.24-7.21 (m, 1H), 7.16-7.13 (m, 1H), 7.04-7.03 (m, 1H), 6.92-6.82 (m, 2H), 6.75-6.74 (m, 1H), 6.68-6.67 (m, 1H), 5.92 (s, 2H), 4.40 (s, 2H), 4.09-4.06 (m, 2H), 3.12 (t, J=6.5 Hz, 2H), and signals due to a minor tautomer (ca. 31%): 5.94 (s), 4.52 (m), 3.77-3.76 (m), 3.11-3.08 (m); ESI MS m/z 371 [M+H]$^+$, HPLC (Method 1)>99% (AUC), $t_R$=12.6 min.

Example 22

Method B: Syntheses of Dithiocarbamates of the Brassinin Family where the Indole Group is Replaced by Other Cyclic Structures (Scheme 5)

Scheme 5. General procedure for synthesis of targets in series 5

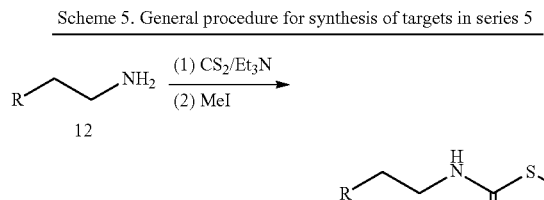

To a solution of amine 12 (Scheme 5, 1.0 equiv) in anhydrous $CH_2Cl_2$ (10 mL) cooled in an ice/water bath were sequentially added triethylamine (1.1 equiv) and then carbon disulfide (1.1 equiv). The solution was stirred for 30 min at 0° C. After this time, methyl iodide (1.2 equiv) was then added and the reaction was allowed to warm to room temperature and stirred overnight. The reaction mixture was then poured into 1 M $H_2SO_4$ and extracted with EtOAc (3×10 mL). The combined organic solutions were washed with brine, dried over anhydrous $Na_2SO_4$, and concentrated to afford crude material 13 which was purified by chromatography (silica, EtOAc/hexanes). The majority of the dithiocarbamates exist in tautomeric form (25% to 35%) as observed by $^1$H NMR, and are listed with spectral data.

Example 23

Methyl 3-chlorophenethylcarbamodithioate [Compound 00014]

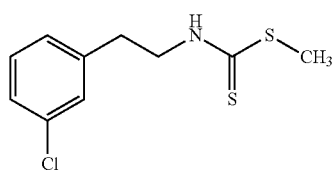

Compound 00014 was synthesized as described in EP 656351 (1995). Briefly, 2-(3-Chlorophenyl)ethylamine (1 equiv) was used as amine 12 (Scheme 5) as described in Method B. Purification by flash chromatography (silica, gradient of 12% EtOAc/Hexanes to 100% EtOAc) afforded product 00014 (0.220 g, 69%) as a yellow oil: $^1$H NMR (500 MHz, $CDCl_3$) δ 7.27-7.21 (m, 3H), 7.10 (d, J=7.0 Hz, 1H), 6.93 (br s, 1H), 4.00-3.96 (m, 2H), 2.96 (t, J=7.0 Hz, 2H), 2.62 (s, 3H), and signals due to a minor tautomer (ca. 28%): 3.70-3.69 (m), 2.69 (s); ESI MS m/z 246 [M+H]$^+$, HPLC (Method 1) 98.2% (AUC), $t_R$=12.0 min.

Example 24

Methyl 2-(pyridin-4-yl)ethylcarbamodithioate [Compound 00069]

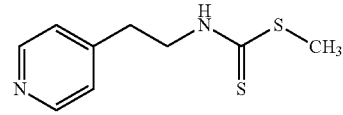

4-(2-Aminoethyl)pyridine (1 equiv) was used as amine 12 (Scheme 5) as described in Method B. In addition to the general method, the acidic aqueous layer was neutralized with 1 M NaOH and extracted with EtOAc (3×30 mL). Purification by flash chromatography (silica, gradient of 12% EtOAc/Hexanes to 100% EtOAc) afforded product 00069 (0.093 g, 26%) as a white solid: $^1$H NMR (500 MHz, $CDCl_3$) δ 8.54-8.53 (m, 2H), 7.15 (d, J=5.5 Hz, 2H), 7.02 (br s, 1H), 4.04-4.01 (m, 2H), 3.00 (t, J=7.0 Hz, 2H), 2.64 (s, 3H); ESI MS m/z 213 [M+H]$^+$, HPLC (Method 1) 98.6% (AUC), $t_R$=9.6 min, MP=94-96° C.

Example 25

Methyl 2,4-dimethylphenethylcarbamodithioate [Compound 00066]

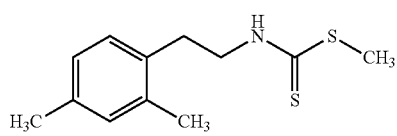

2,4-Dimethylphenethylamine (1 equiv) was used as amine 12 (Scheme 5) as described in Method B. Purification by flash chromatography (silica, gradient of 12% EtOAc/Hexanes to 100% EtOAc) afforded product 00066 (0.161 g, 52%) as a yellow oil: $^1$H NMR (500 MHz, $CDCl_3$) δ 7.08 (d, J=7.5 Hz, 1H), 7.03-6.87 (m, 3H), 3.99-3.93 (m, 2H), 2.95-2.86 (m, 2H), 2.60 (s, 3H), 2.29 (s, 3H), 2.25 (s, 3H); ESI MS m/z 240 [M+H]$^+$, HPLC (Method 1) 97.5% (AUC), $t_R$=12.9 min.

Example 26

Method C: Syntheses of Dithiocarbamate Isostere Equivalents (Scheme 9)

Scheme 9.

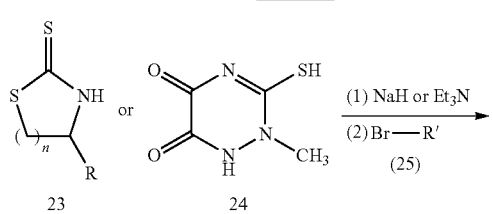

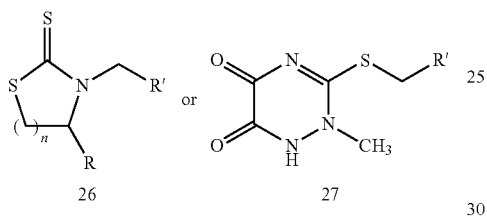

R = H, = O or (S)-i-Pr
n = 1 or 2
R' = Ph or naphthyl

To a solution of 23 (such as thiazole-2-thiol, 1.0 equiv, R═H, n=1) in anhydrous THF (10 mL) cooled in an ice/water bath was added NaH (1.1 eq unless indicated otherwise), and the solution was stirred for 2 h at 0° C. After this time, a bromide 25 (1.2 equiv) was added and the reaction was allowed to warm to room temperature and stirred overnight. Reaction mixture was then quenched by addition of a few drops of $H_2O$ and concentrated. The residue was taken up into EtOAc, washed with brine, dried over anhydrous $Na_2SO_4$, and concentrated. Purification of the residue by chromatography (silica) afforded the desired product.

Example 27

3-Benzyloxazolidine-2-thione [Compound 00081]

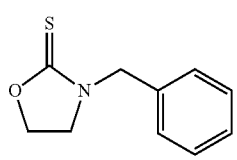 [SMILES: S=C1OCCN1Cc1ccccc1]

Compound 00081 was previously described by Baba, et al, Bull. Chem. Soc. Jpn., 1986, 59(1), 341-343; b) and Y. Nagao, et al, Chem. Pharma. Bull., Jpn., 1988, 36(11), 4293-4300). Its synthesis was achieved by treating 2-Thioxotetrahydro-1,3-oxazole with NaH (3.0 equiv instead of 1.1 equiv) as described in Method C. Purification by flash chromatography (silica, gradient of 12% EtOAc/Hexanes to 100% EtOAc) afforded product 00081 (0.198 g, 53%) as a clear oil: $^1$H NMR (500 MHz, $CDCl_3$) δ 7.38-7.36 (m, 2H), 7.32-7.29 (m, 2H), 7.27-7.25 (m, 1H), 4.35 (t, J=9.0 Hz, 2H), 4.26 (s, 2H), 3.90 (t, J=9.0 Hz, 2H); ESI MS m/z 194 [M+H]$^+$, HPLC (Method 1) 96.2% (AUC), $t_R$=7.8 min.

Example 28

3-Benzyl-1,3-thiazinane-2-thione [Compound 00077]

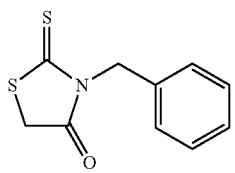 [SMILES: O=C1CSC(=S)N1Cc1ccccc1]

Synthesis of compound 0077 was performed as described by W. Hanefeld, Archiv der Pharmazie, 1977, 310(5), 409-417; b) W. Hanefeld, et al, J. Heterocycl. Chem. 1997, 34(5), 1621-1624). Briefly, 1,3-Thiazinane-2-thine was treated with 1.5 equiv NaH (instead of 1.1 equiv) as described in Method C. Purification by flash chromatography (silica, gradient of 12% EtOAc/Hexanes to 100% EtOAc) afforded product 00077 (0.020 g, 6%) as a yellow oil: $^1$H NMR (300 MHz, $CDCl_3$) δ 7.34-7.22 (m, 5H), 4.23 (s, 2H), 3.77 (t, J=5.7 Hz, 2H), 3.06 (t, J=6.0 Hz, 2H), 1.95-1.88 (m, 2H); ESI MS m/z 224 [M+H]$^+$, HPLC (Method 1) 98.5% (AUC), $t_R$=7.9 min.

Example 29

3-Benzyl-2-thioxothiazolidin-4-one [Compound 00079]

Synthesis of compound 00079 was performed as described in A. Martinez, et al, J. Med. Chem., 2005, 48(23), 7103-7112; and in M. Pulici, et al, Tetrahedron Lett., 2005,

Example 30

3-(Naphthalen-2-ylmethyl)-2-thioxothiazolidin-4-one [Compound 00830]

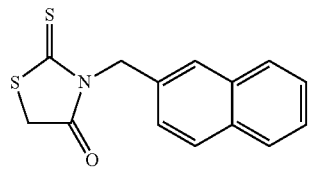 [SMILES: O=C1CSC(=S)N1Cc1ccc2ccccc2c1]

Rhodanine (1.0 equiv) was reacted with 2-(bromomethyl)naphthalene (1.5 equiv) as described in Method C. Purification by flash chromatography (silica, gradient of 12% EtOAc/Hexanes to 100% EtOAc) afforded product 00830 (0.093 g, 30%) as a yellow oil: $^1$H NMR (500 MHz, CDCl$_3$) δ 7.86-7.81 (m, 4H), 7.50-7.46 (m, 3H), 4.76 (s, 2H), 4.00 (s, 2H); ESI MS m/z 274 [M+H]$^+$, HPLC (Method 1) 95.8% (AUC), t$_R$=8.5 min, MP=120-123° C.

Example 31

3-(Naphthalen-2-ylmethyl)oxazolidine-2-thione [Compound 00786]

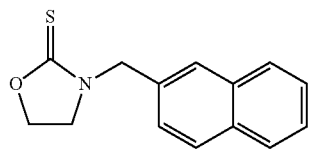 [SMILES: S=C1OCCN1Cc1ccc2ccccc2c1]

2-Thioxotetrahydro-1,3-oxazole was reacted with 2-(bromomethyl)naphthalene (1.5 equiv) as described in Method C. Purification by flash chromatography (silica, gradient of 12% EtOAc/Hexanes to 100% EtOAc) afforded product 00786 (0.292 g, 61%) as a yellow oil: $^1$H NMR (500 MHz, CDCl$_3$) δ 7.82-7.79 (m, 4H), 7.50-7.45 (m, 3H), 4.42 (s, 2H), 4.37 (t, J=9.5 Hz, 2H), 3.92 (t, J=9.5 Hz, 2H); ESI MS m/z 244 [M+H]$^+$, HPLC (Method 1) 95.9% (AUC), t$_R$=8.5 min, MP=120-123° C.

Example 32

2-Methyl-3-(naphthalen-2-ylmethylthio)-1,2-dihydro-1,2,4-triazine-5,6-dione [Compound 00682]

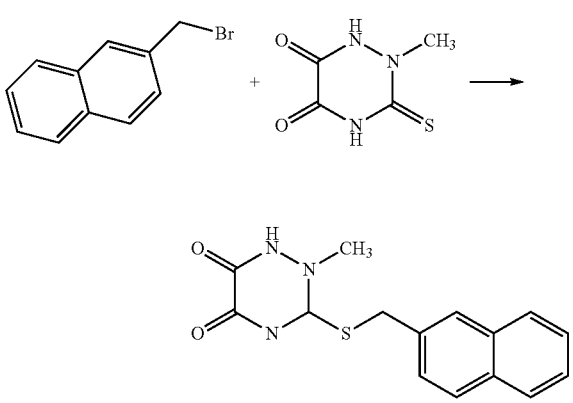

| Entry | Scale | Yield | Conditions |
|---|---|---|---|
| 1 | 1.00 g | 1.10 g (58%) | K$_2$CO$_3$, DMF, 50° C., 3 h, |

Example 33

Naphthalen-2-ylmethyl-2-(benzo[b]thiophen-3-yl)ethylcarbamodithioate [Compound 00060]

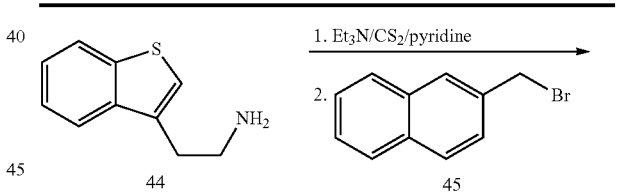

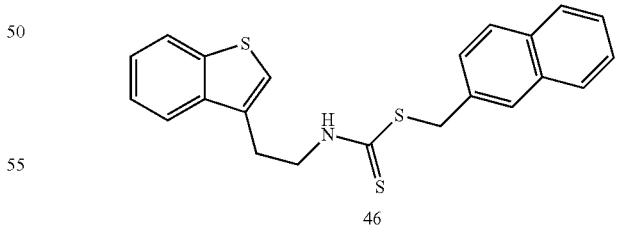

| Scale | Yield | Conditions |
|---|---|---|
| 0.41 g | 0.35 g (31%) | 44, Et$_3$N (1.1 equiv), CS$_2$ (1.2 equiv), 45 (1.2 equiv), pyridine, 0° C. tort, 15 h; product consistent by ESI-MS and $^1$H NMR analysis. |

Example 34

Naphthalen-2-ylmethyl-2-(benzo[d]isoxazol-3-yl)ethylcarbamodithioate [Compound 00058]

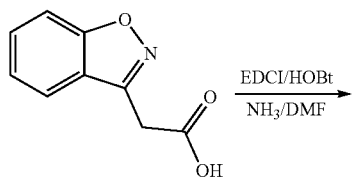

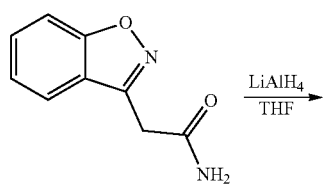

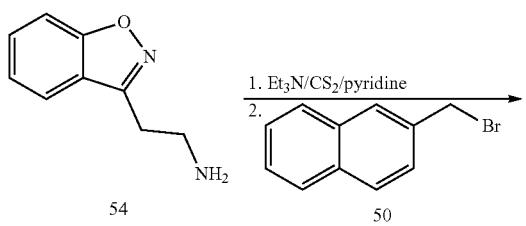

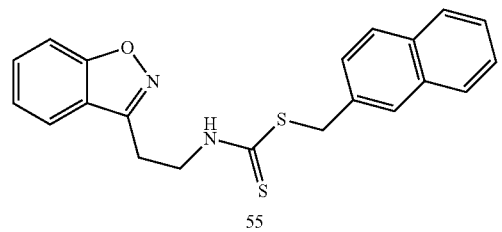

| Reaction | Scale | Yield | Conditions |
|---|---|---|---|
| 52 to 53 | 0.10 g | 0.090 g (89%) | EDCI (1.2 equiv), HOBt (0.5 equiv), NH$_3$ (1.2 equiv), DMF, rt, 4 h; product consistent by ESI-MS and $^1$H NMR analysis. |
| 53 to 54 | 0.090 g | 0.10 g (crude) | LiAlH$_4$ (4 equiv), THF, 40° C., overnight; crude used for next step. |
| 54 to 55 | 0.14 g | 0.04 g (12%) | Et$_3$N (1.1 equiv), CS$_2$ (1.2 equiv), 50 (1.2 equiv), pyridine, 0° C. to r.t.: product consistent by ESI-MS and $^1$H NMR analysis. |

Example 35

Methyl 2-(5,7-dichloro-1H-indol-3-yl)ethylcarbamodithioate [Compound 00042]

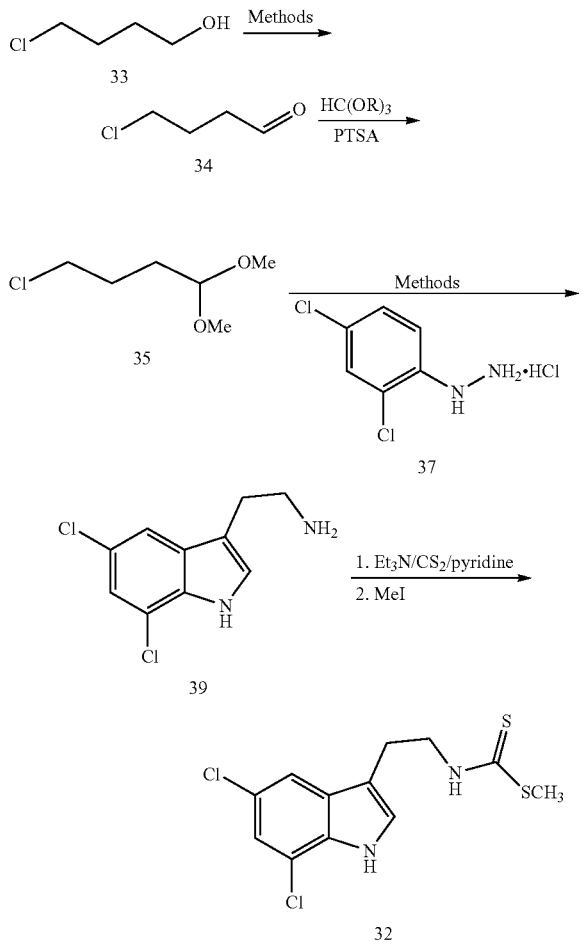

| Reaction | Scale | Yield | Conditions |
|---|---|---|---|
| 33 to 34 | 1.00 g | 0.46 g (47%) | PCC (1.2 equiv), rt; 2.5 h, DCM; product consistent by ESI-MS and $^1$H NMR analysis. |
| 33 to 34 | 3.00 g | 2.30 g (78%) | DMSO (2 equiv), Et$_3$N (5 equiv), (COCl)$_2$ (1.5 equiv), DCM, -78° C. to rt; product consistent by ESI-MS and $^1$H NMR analysis. |
| 34 to 35 | 1.00 g | 1.20 g (84%) | HC(OMe)$_3$ (excess as neat), PTSA (0.1 equiv), rt; product consistent by ESI-MS and $^1$H NMR analysis. |
| 37 to 39 | 0.10 g | 0.021 g (16%) | 37 (1.05 equiv), 35 (1.0 equiv), EtOH/H$_2$O, 100° C., 4.5 h; product consistent by ESI-MS and $^1$H NMR analysis. |
| 37 to 39 | 0.10 g | 0.035 g (27%) | 37 (1.05 equiv), 35 (1.0 equiv), EtOH/H$_2$O, 100° C., overnight; product consistent by ESI-MS and $^1$H NMR analysis. |
| 37 to 39 | 0.10 g | 0.011 g (8.5%) | 37 (1.05 equiv), 35 (1.0 equiv), 4% aq. H$_2$SO$_4$, 70° C., 4 h; product consistent by ESI-MS and $^1$H NMR analysis. |
| 37 to 39 | 0.50 g | 0.138 g (21%) | 37 (1.05 equiv), 35 (1.0 equiv), EtOH/H$_2$O, 100° C., overnight; product consistent by ESI-MS and $^1$H NMR analysis. |
| 39 to 40 | 0.090 g | 72 mg (68%) | 39, Et$_3$N (1.1 equiv), CS$_2$ (1.2 equiv), MeI (1.2 equiv), pyridine, 0° C. to rt, 15 h; product consistent by ESI-MS and $^1$H NMR analysis, 97% pure by HPLC. |

Example 36
Methyl 2-(4,6-dichloro-1H-indol-3-yl)ethylcarbamodithioate [Compound 00043]
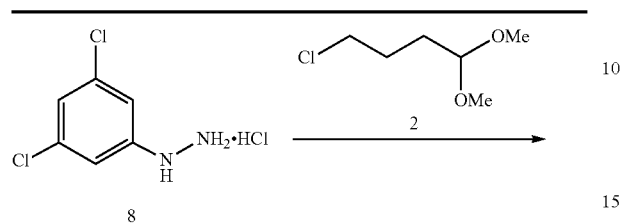
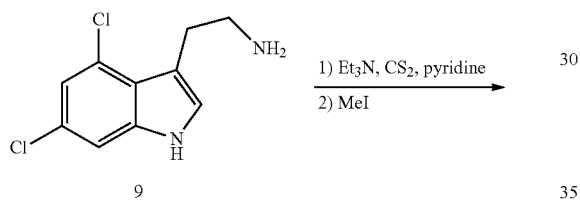
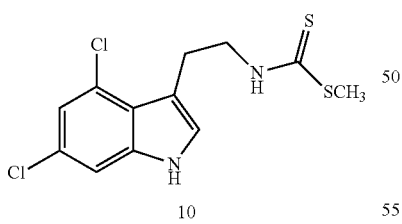
| Reaction | Scale | Yield | Conditions |
|---|---|---|---|
| 8 to 9 | 1.00 g | 0.346 g (32%) | 8, (1.05 equiv), 2 (1.0 equiv), EtOH/H$_2$O, microwave, 150° C., 15 min; product consistent by LCMS and $^1$H NMR analysis. |
| 9 to 10 | 0.320 g | 0.240 g (55%) | 9, Et$_3$N (1.1 equiv), CS$_2$ (1.2 equiv), MeI (1.2 equiv), pyridine, 0° C. to rt, 16 h; product consistent by LCMS and $^1$H NMR analysis. |

Example 37

Methyl 2-(4,5,6-trifluoro-1H-indol-3-yl)ethylcarbamodithioate [Compound 00045]

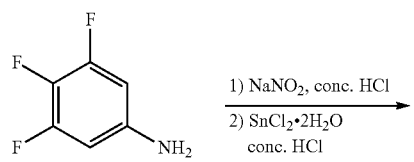

5
Ref 1: *J. Med. Chem.*, 1993, 36, 1529
Ref 2: *Bioorg. Med. Chem.*, 2004, 12, 2013

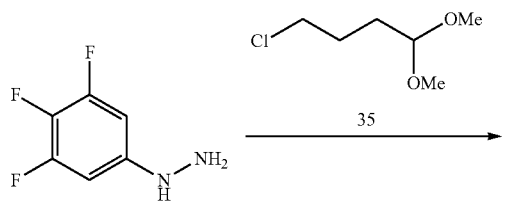

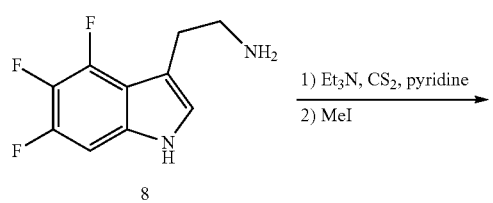 [SMILES: NCCc1c[nH]c2cc(F)c(F)c(F)c12]

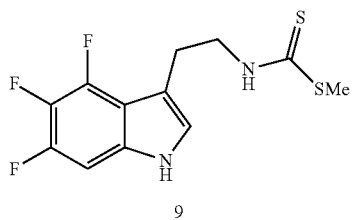 [SMILES: CSC(=S)NCCc1c[nH]c2cc(F)c(F)c(F)c12]

| Reaction | Scale | Yield | Conditions |
|---|---|---|---|
| 5 to 6 | 0.250 g | 0.050 g (18%) | Ref 1; 5, NaNO$_2$ (1.05 equiv), conc. HCl, 0° C., 30 min followed by SnCl$_2$•2H$_2$O (3.5 equiv), conc. HCl, 0° C. to rt, 1 h; product consistent by $^1$H NMR and LCMS analysis. |
| 5 to 6 | 0.500 g | 0.450 g (81%) | Ref 2; 5, NaNO$_2$ (1.2 equiv), conc. HCl, 0° C., 1 h followed by SnCl$_2$•2H$_2$O (2.2 equiv), conc. HCl, rt, 1 h; product consistent by $^1$H NMR and LCMS analysis. |
| 6 to 8 | 0.430 g | 0.122 g (19%) | 6 (1.05 equiv), 35 (1.0 equiv), EtOH/H$_2$O, conc. HCl (1.1 equiv), microwave, 130° C., 10 min; product consistent by $^1$H NMR and LCMS analysis. |
| 8 to 9 | 0.120 g | 0.105 g (61%) | 8, Et$_3$N (1.1 equiv), CS$_2$ (1.2 equiv), MeI (1.2 equiv), pyridine, 0° C. to rt; product consistent by $^1$H NMR and LCMS analysis. |

Example 38

Methyl 2-(5-amino-1H-indol-3-yl)ethylcarbamodithioate [Compound 00039] and Methyl 2-(5-nitro-1H-indol-3-yl)ethylcarbamodithioate [Compound 00040]

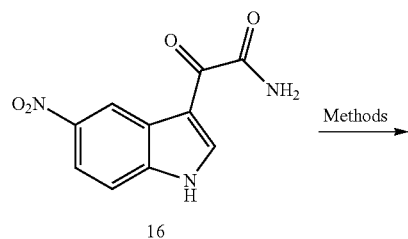 [SMILES: NC(=O)C(=O)c1c[nH]c2ccc([N+](=O)[O-])cc12]

16

Methods →

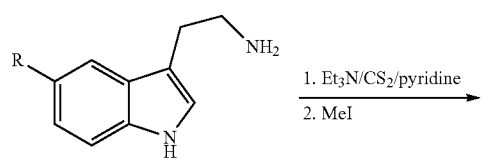

17a: R = NO₂
17b: R = NH₂

1. Et₃N/CS₂/pyridine
2. MeI

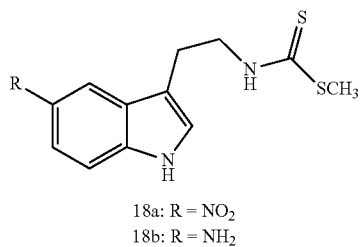

18a: R = NO₂
18b: R = NH₂

| Reaction | Scale | Yield | Conditions |
|---|---|---|---|
| 16 to 17a | 1.00 g | 0.225 g (crude) | 16, BH₃•THF (3 equiv), 35° C., 4 h followed by CsF, Na₂CO₃, EtOH, reflux, 16 h; purified by silica gel chromatography; product consistent by ¹H NMR gel and LCMS analysis. |
| 17a to 18a | 0.100 g | 0.048 g (33%) | 17a, Et₃N (1.1 equiv), CS₂ (1.2 equiv), MeI (1.2 equiv), pyridine, 0° C. to rt, 15 h; product consistent by ESI-MS and ¹H NMR analysis. |
| 17a to 17b | 0.125 g | 0.115 g (crude) | 17a, H₂, 10% Pd/C (20 mol%), 40 psi, 8 h; product confirmed by ¹H NMR analysis. |
| 17b to 18b | 0.115 g | 0.035 g (crude) | 17b, Et₃N (1.1 equiv), CS₂ (1.2 equiv), MeI (1.2 equiv) pyridine 0° C. to rt, 15 h; product consistent by ESI-MS and ¹H NMR analysis. |

Example 39

Methyl 2-(4,6-bis(trifluoromethyl)-1H-indol-3-yl)ethylcarbamodithioate [Compound 00044]

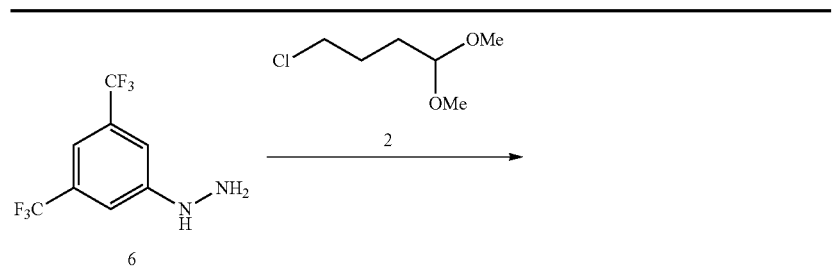

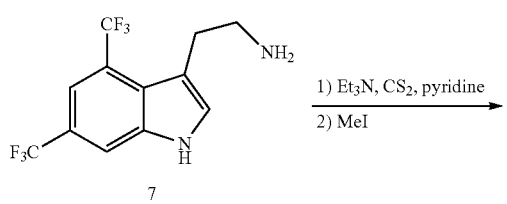 [SMILES: NCCc1c[nH]c2cc(C(F)(F)F)cc(C(F)(F)F)c12]

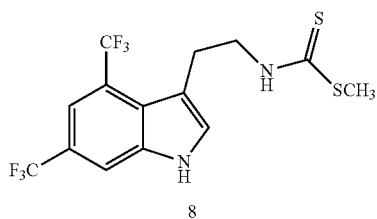 [SMILES: CSC(=S)NCCc1c[nH]c2cc(C(F)(F)F)cc(C(F)(F)F)c12]

| Reaction | Scale | Yield | Conditions |
| --- | --- | --- | --- |
| 6 to 7 | 0.010 g | 0.005 g (crude) | 6 (1.05 equiv), 2 (1.0 equiv), EtOH/H$_2$O, conc. HCl (1.1 equiv), microwave, 130° C., 15 min; 40% conversion by LCMS analysis. |
| 6 to 7 | 0.030 g | — | 6 (1.05 equiv), 2 (1.0 equiv), EtOH/H$_2$O, conc. HCl (1.1 equiv), microwave, 130° C., 20 min; 30% conversion to desired product By LCMS analysis. |
| 6 to 7 | 0.040 g | — | 6 (1.05 equiv), 2 (1.0 equiv), EtOH/H$_2$O, conc. HCl (1.1 equiv), microwave, 120° C., 10 min followed by 130° C., 10 min; 25% conversion by LCMS analysis. |
| 6 to 7 | 0.005 g | — | 6 (1.05 equiv), 2 (1.0 equiv), EtOH/H$_2$O, conc. HCl (1.1 equiv), microwave, 120° C., 15 min; 45% conversion by LCMS analysis. |
| 6 to 7 | 0.165 g | 0.035 g (crude) | 6 (1.05 equiv), 2 (1.0 equiv), EtOH/H$_2$O, conc. HCl (1.1 equiv), microwave, 120° C., 15 min; 45% conversion by LCMS analysis; 85% pure by HPLC analysis. |
| 7 to 8 | 0.030 g | 0.020 g (51%) | 3, Et$_3$N (1.1 equiv), CS$_2$ (1.2 equiv), MeI (1.2 equiv), pyridine, 0° C. to rt; product consistent by ESI-MS and $^1$H NMR analysis. |

Example 40 benzo[b]thiophen-3-ylmethyl 2-(1H-indol-3-yl)eth-ylcarbamodithioate [Compound 00054]

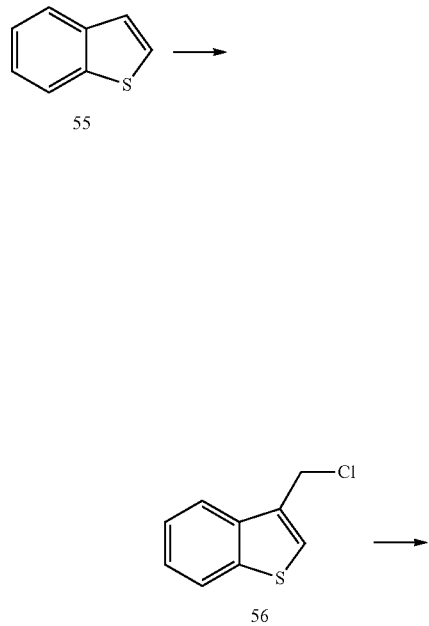

| SM | Scale | Yield | Conditions |
|---|---|---|---|
| 55 | 8.00 g | 1.956 g (18%) | 55, formaldehyde, HCl (gas), 65° C. vacuum distillation. NMR. |
| 56 | 0.274 g | 0.068 g (14%) | tryptamine, CS$_2$, standard procedure. 98% by HPLC (254 nm), but ca. 90% by NMR. further purification needed. |
| 55 | 8.00 g | 3.06 g (28%) | 55, formaldehyde, HCl (gas), 65° C. vacuum distillation. NMR, GCMS. |
| 56 | 0.457 g | 0.208 g (26%) | tryptamine, CS$_2$, standard procedure. Pure by HPLC and NMR. |

Example 41

2-Hydroxy-N-phenethylbenzothioamide [Compound 00634]

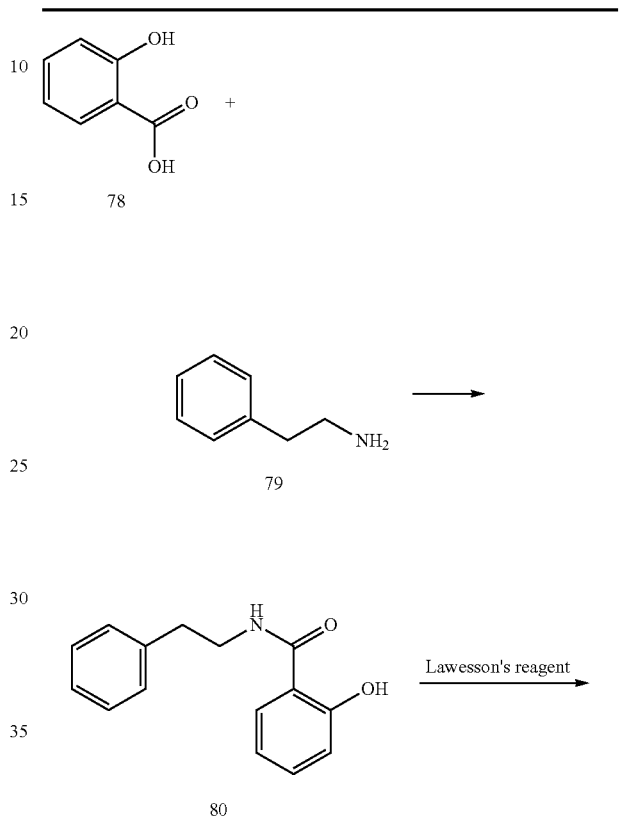

| SM | Scale | Yield | Conditions |
|---|---|---|---|
| 78 | 1.380 g | 2.388 g (99%) | 78 CDI, DKE, 1 h, rt, then 79, overnight rt. Purity: 80% by NMR, 89% by HPLC-MS. |
| 80 | 2.390 g | 0.254 g (10%) | 80, toulene, Lawesson's reagent, reflux, 2 h. Purity: 98% by NMR, 100% by HPLC-MS. |

Example 42

3-((1H-indol-3-yl)methyl)-2-thioxothiazolidin-4-one [Compound 00078]

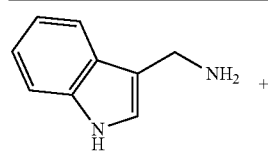

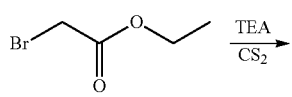

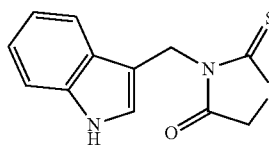

| SM | Scale | Yield | Conditions |
|----|-------|-------|------------|
| 70 | 0.22 g | 0.132 g (33%) | 70, MeOH, TEA (1 equiv.), CS$_2$ (1.5 equiv.), rt, 30 min. 71(1.05 equiv.), reflux, 1 h; HPLC, NMR. |

Example 43

Naphthalen-2-ylmethyl 2-(thiochroman-3-yl)ethylcarbamodithioate [Compound 00064]

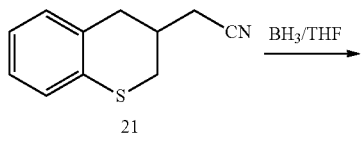

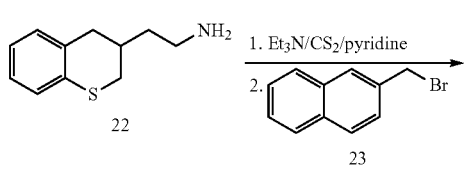

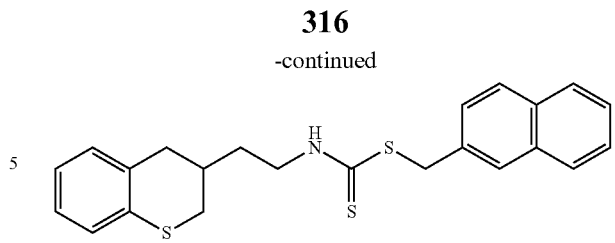

Example 44

N-((1H-indol-3-yl)methyl)-2-(2-thioxo-2,3-dihydrothiazol-4-yl)acetamide [Compound 00561]

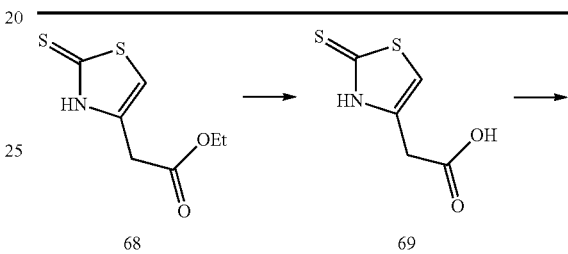

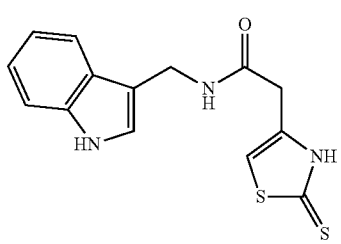

| SM | Scale | Yield | Conditions |
|----|-------|-------|------------|
| 68 | 5.00 g | 2.70 g (63%) | NaOH, EtOH, water, 50° C., 4 h. |
| 69 | 0.114 g | 0.018 g | PS-DCC, DCM. HPLC: 87 %. |
| 69 | 0.26 g | 0.10 g | CDI, DCE, N$_2$, rt. |

Example 45

N-Benzyl-2-hydroxybenzothioamide [Compound 00656]

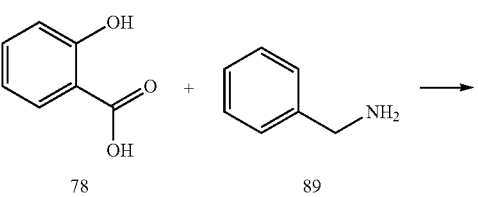 [SMILES: O=C(O)c1ccccc1O ; NCc1ccccc1]

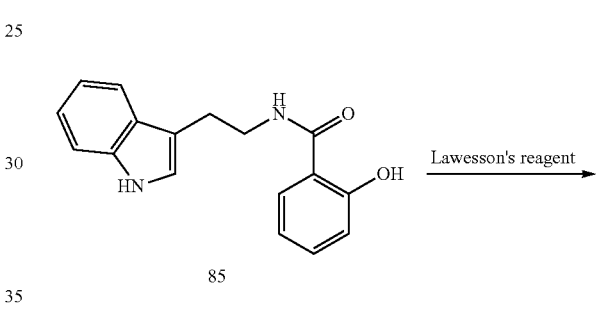

| SM | Scale | Yield | Conditions |
|---|---|---|---|
| 78 | 6.90 g | 10.100 g (89 %) | 78, CDI, CHCl$_3$, 1 h, rt, then 89, overnight, rt. Purity: 60% by NMR, 88% by HPLC-MS. |
| 90 | 10.10 g | 0.647 g (6 %) | 90, toulene, Lawesson's reagent, reflux, 2 h. Purity: 98% by NMR, 100% by HPLC-MS. |

Example 46

N-(2-(1H-indol-3-yl)ethyl)-2-hydroxybenzothioamide [Compound 00644]

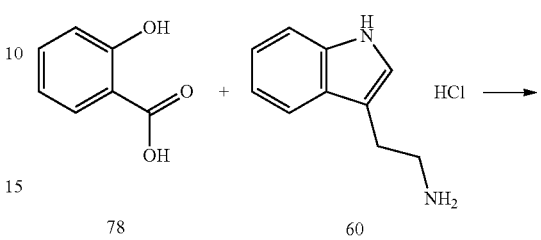

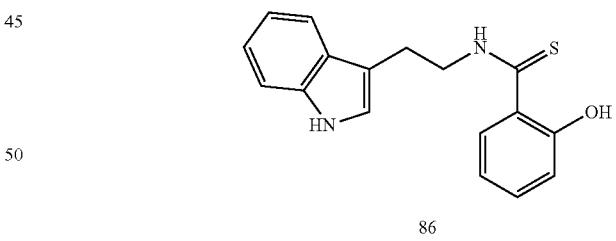

| SM | Scale | Yield | Conditions |
|---|---|---|---|
| 78 | 4.14 g | 6.22 g (74%) | 78 CDI, DCM, 1 h, rt, then DIPEA and 60, overnight, rt. Purity: 98% by NMR, 96% by HPLC-MS. |
| 85 | 6.22 g | 1.24 g (19%) | 85, toulene, Lawesson's reagent, reflux, 2 h. Purity: 97% by NMR, 100% by HPLC-MS. |

Example 47

N-(2-(benzo[b]thiophen-3-yl)ethyl)-2-hydroxybenzothioamide [Compound 00672]

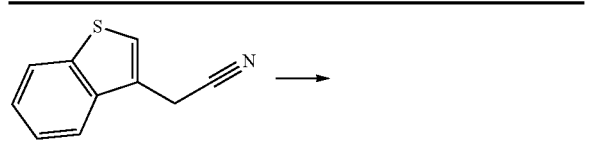

74

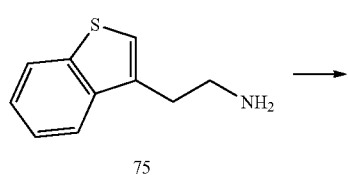 [SMILES: NCCc1csc2ccccc12]

75

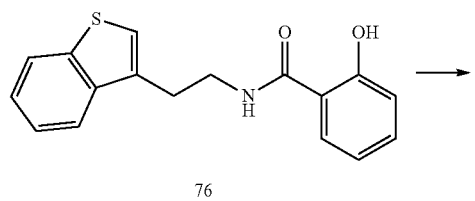 [SMILES: O=C(NCCc1csc2ccccc12)c1ccccc1O]

76

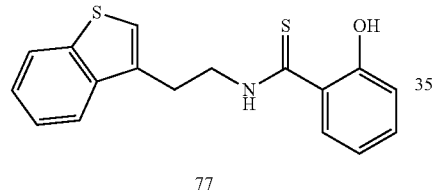

77

| SM | Scale | Yield | Conditions |
|----|-------|-------|------------|
| 74 | 0.45 g | 0.14 g (31%) | LAH, ether, reflux. |
| 74 | 1.00 g | 0.90 g (88%) | LAH, AlCl₃, ether, 30 min, reflux. |
| 75 | 0.50 g | | CDI, DCE rt. |

Example 48

N-(Naphthalen-2-ylmethyl)-2-(2-thioxo-2,3-dihydrothiazol-4-yl)acetamide [Compound 00701]

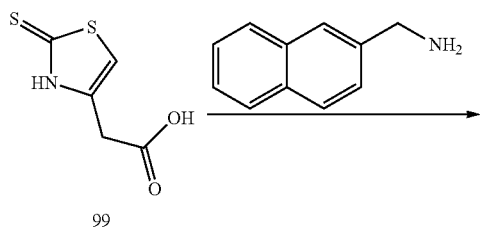

99

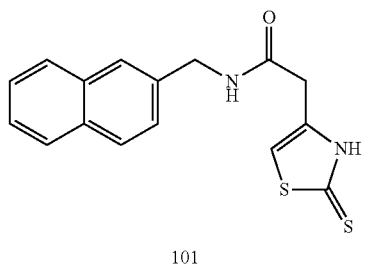

101

Example 49

Methyl 6-(1H-indol-3-yl)hexylcarbamodithioate [Compound 00027]

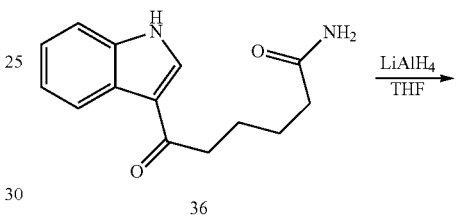

36

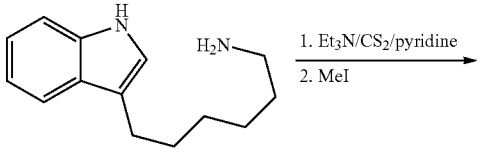

37

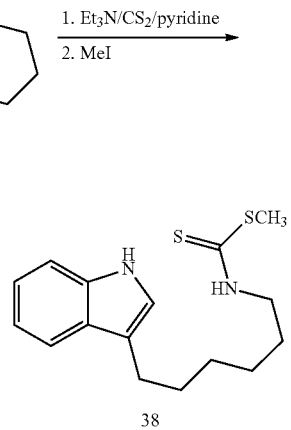

38

| Reaction | Scale | Yield | Conditions |
|----------|-------|-------|------------|
| 36 to 37 | 0.80 g | 0.80 g (Crude) | LiAlH₄ (6 equiv), dioxane, reflux, 36 h; product consistent by ESI-MS analysis. |
| 37 to 38 | 0.80 g | 0.09 g (8%) | Et₃N (1.1 equiv), CS₂ (1.2 equiv), MeI (1.2 equiv), pyridine, 0° C. to r.t., 15 h; product consistent by ESI-MS and ¹H NMR analysis |

Example 50

Methyl 1-(1H-indol-3-yl)-2-methylpropan-2-ylcarbamodithioate [Compound 00028]

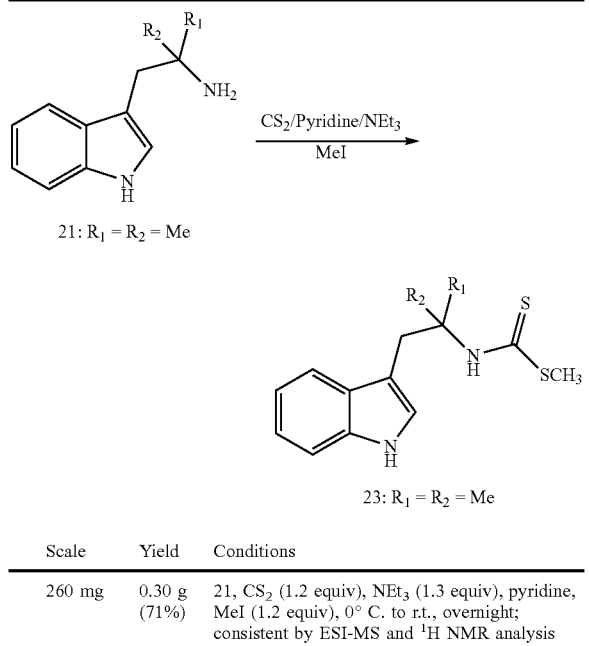

21: R₁ = R₂ = Me

23: R₁ = R₂ = Me

| Scale | Yield | Conditions |
|---|---|---|
| 260 mg | 0.30 g (71%) | 21, CS₂ (1.2 equiv), NEt₃ (1.3 equiv), pyridine, MeI (1.2 equiv), 0° C. to r.t., overnight; consistent by ESI-MS and ¹H NMR analysis |

Example 51

Methyl 2-(5-chloro-1H-indol-3-yl)ethylcarbamodithioate [Compound 00032]

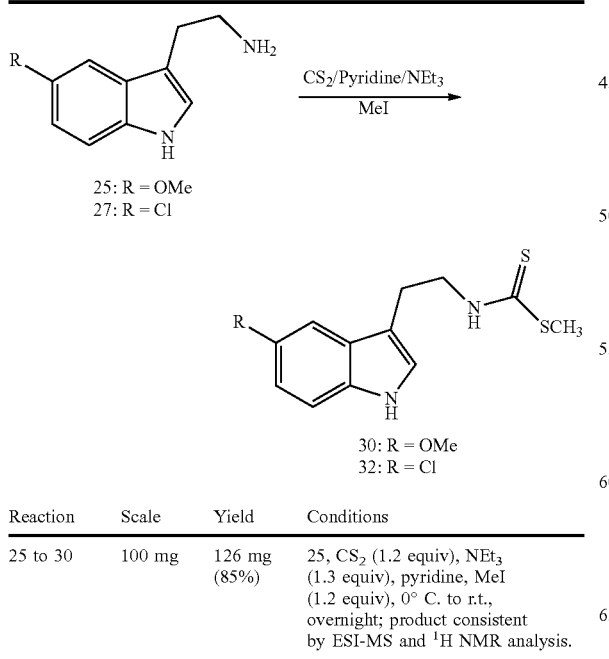

25: R = OMe
27: R = Cl

30: R = OMe
32: R = Cl

| Reaction | Scale | Yield | Conditions |
|---|---|---|---|
| 25 to 30 | 100 mg | 126 mg (85%) | 25, CS₂ (1.2 equiv), NEt₃ (1.3 equiv), pyridine, MeI (1.2 equiv), 0° C. to r.t., overnight; product consistent by ESI-MS and ¹H NMR analysis. |

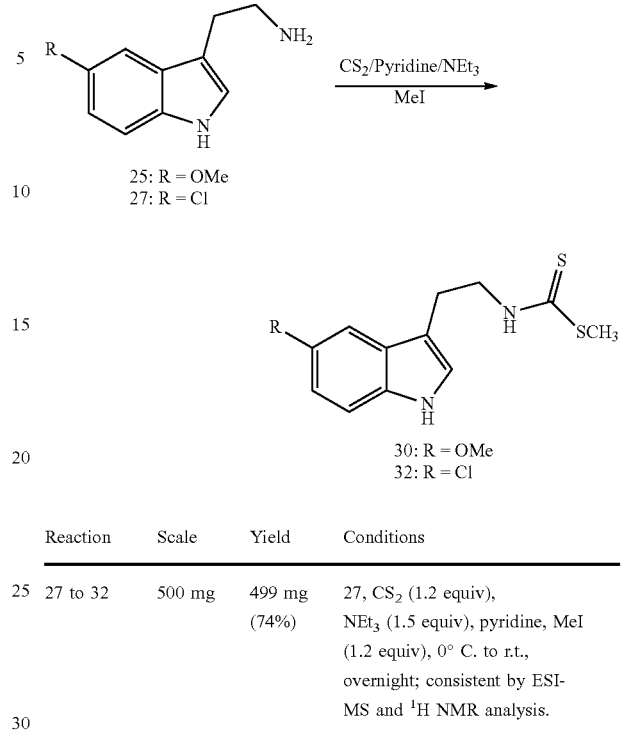

25: R = OMe
27: R = Cl

30: R = OMe
32: R = Cl

| Reaction | Scale | Yield | Conditions |
|---|---|---|---|
| 27 to 32 | 500 mg | 499 mg (74%) | 27, CS₂ (1.2 equiv), NEt₃ (1.5 equiv), pyridine, MeI (1.2 equiv), 0° C. to r.t., overnight; consistent by ESI-MS and ¹H NMR analysis. |

Example 52

Naphthalen-2-ylmethyl 2-(benzofuran-3-yl)ethylcarbamodithioate [Compound 00057]

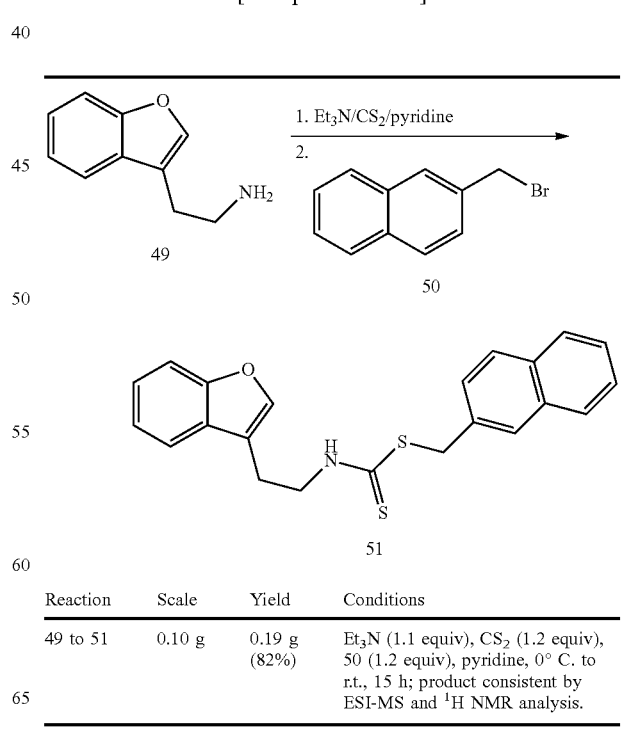

49

50

51

| Reaction | Scale | Yield | Conditions |
|---|---|---|---|
| 49 to 51 | 0.10 g | 0.19 g (82%) | Et₃N (1.1 equiv), CS₂ (1.2 equiv), 50 (1.2 equiv), pyridine, 0° C. to r.t., 15 h; product consistent by ESI-MS and ¹H NMR analysis. |

323
Example 53
N-(2-aminophenyl)-3-phenylpropanamide
[Compound 00581]
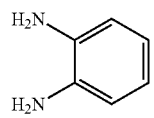
38
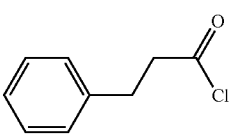
41
DCE, rt →
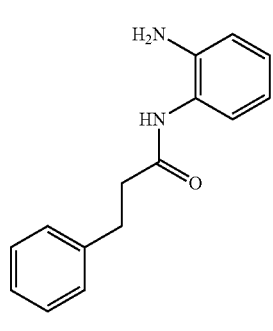
42
| SM | Scale | Yield | Conditions |
|----|-------|-------|------------|
| 41 | 1.00 g | 0.345 g (24%) | 38 (3 equiv), DCE, 41, rt, 10 min. Chromatographic purification. 95% pure by HPLC, MS, NMR. |
324
Example 54
N-(2-aminophenyl)-4-(1H-indol-3-yl)butanamide
[Compound 00588]
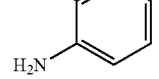
45
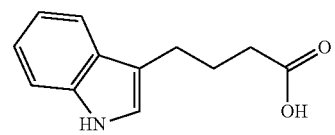
54
CDI, DMF
40° C. →
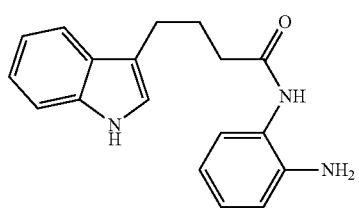
55
| SM | Scale | Yield | Conditions |
|----|-------|-------|------------|
| 45 | 1.00 g | 0.751 g (52%) | purity: 98% by HPLC-MS. |

Example 55

N-(2-aminophenyl)-3-(benzo[b]thiophen-3-yl)propanamide [Compound 00739]

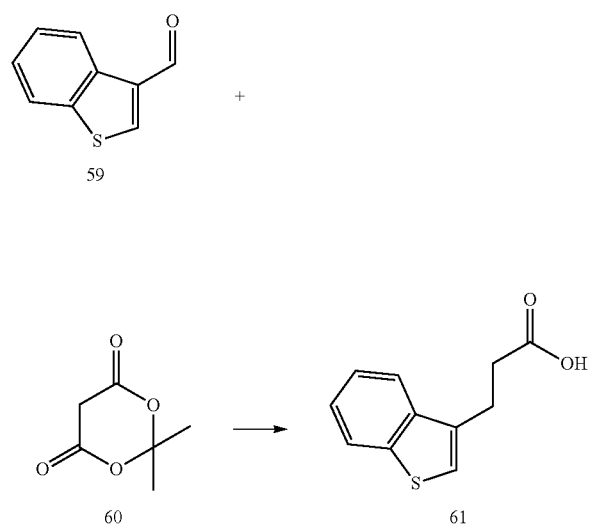

| SM | Scale | Yield | Conditions |
|----|-------|-------|------------|
| 59 | 1.00 g | 1.00 g (79 %) | 59, Meldrum's acid, triethylamine formate, 100° C., 2 h. HPLC: 94%, NMR: 95%. |
| 61 | 0.50 g | 0.13 g (18%) | 61, CDI, DCE, rt, 1 h. 62, rt, 16 h. LCMS, NMR. |

Example 56

N-hydroxy-2-(naphthalen-2-yl)acetamide [Compound 00827]

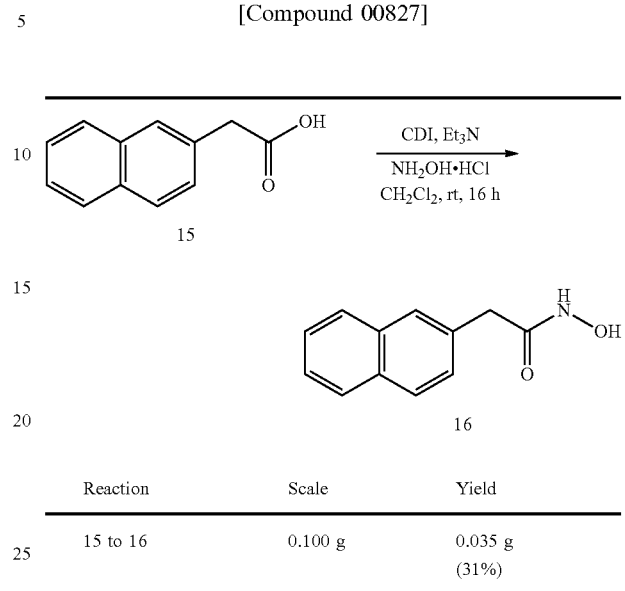

| Reaction | Scale | Yield |
|----------|-------|-------|
| 15 to 16 | 0.100 g | 0.035 g (31%) |

Example 57

5-((1H-indol-3-yl)methyl)quinolin-8-ol [Compound 00655]

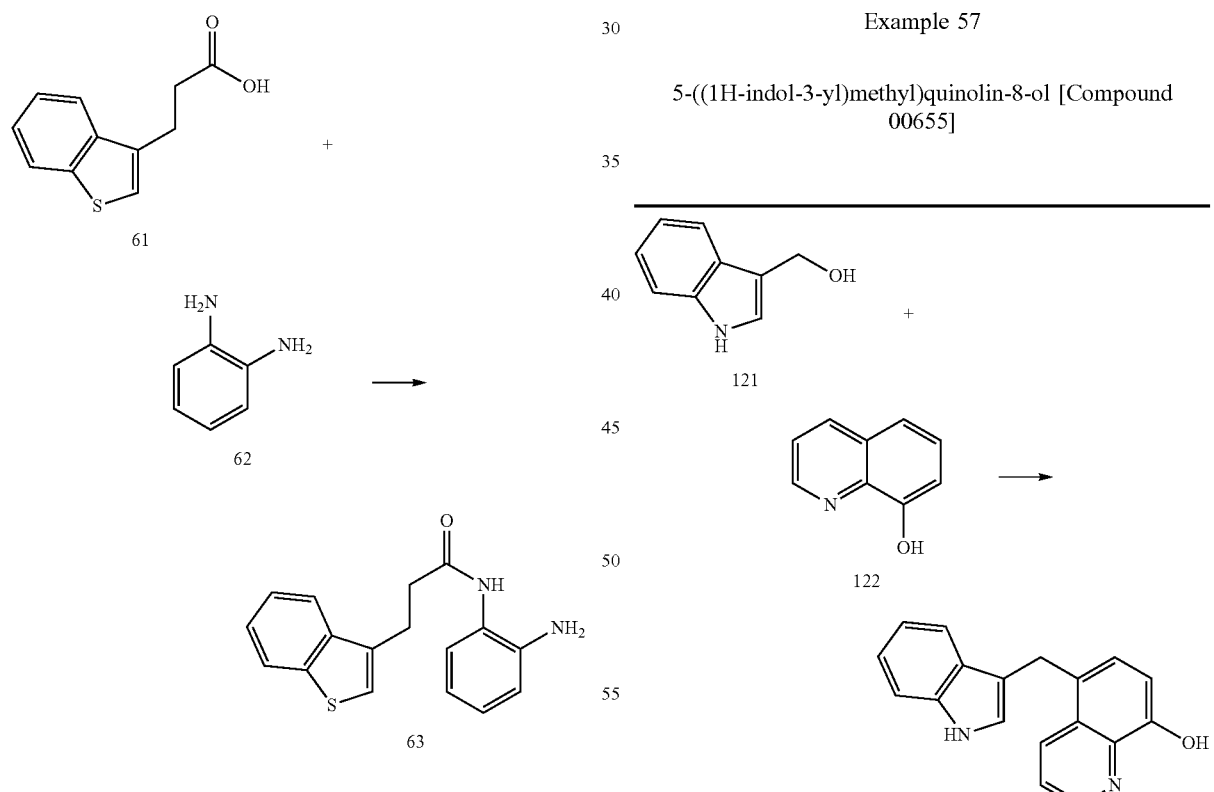

| SM | Scale | Yield | Conditions |
|----|-------|-------|------------|
| 121 | 2.00 g | | Ethanol, cat. piperidine acetate, reflux, 16 h. crude: 15% product by HPLC, after chrom. 29%. |

Example 58

5-Benzylquionolin-8-ol [Compound 00664]

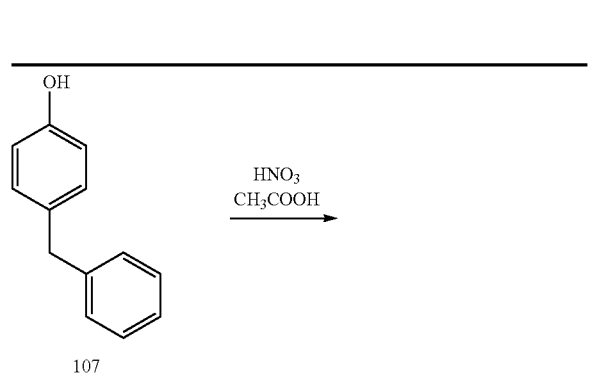

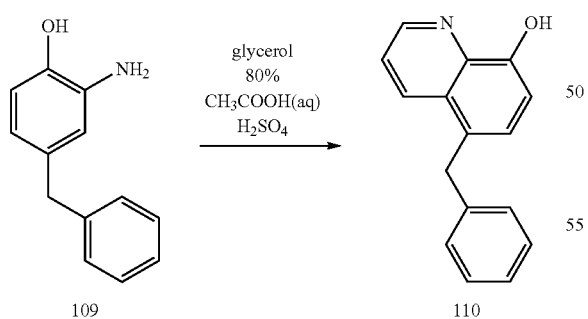

| SM | Scale | Yield | Comments |
|---|---|---|---|
| 107 | 5.00 g | 5.00 g (80%) | 65% HNO₃(aq.), acetic acid, 12-15° C., 0.5 h. HPLC 97%, NMR. |
| 108 | 2.29 g | 1.80 g (90%) | 20% HCl-solution, Sn powder (3.1 equiv.), reflux, 2 h. LC-MS: 96%, NMR. |
| 109 | 0.50 g | 0.135 g (14%) | 109 (0.57 equiv.), glycerol (5.5 equiv.), acetic acid (80% aq. solution), sulfuric acid; |

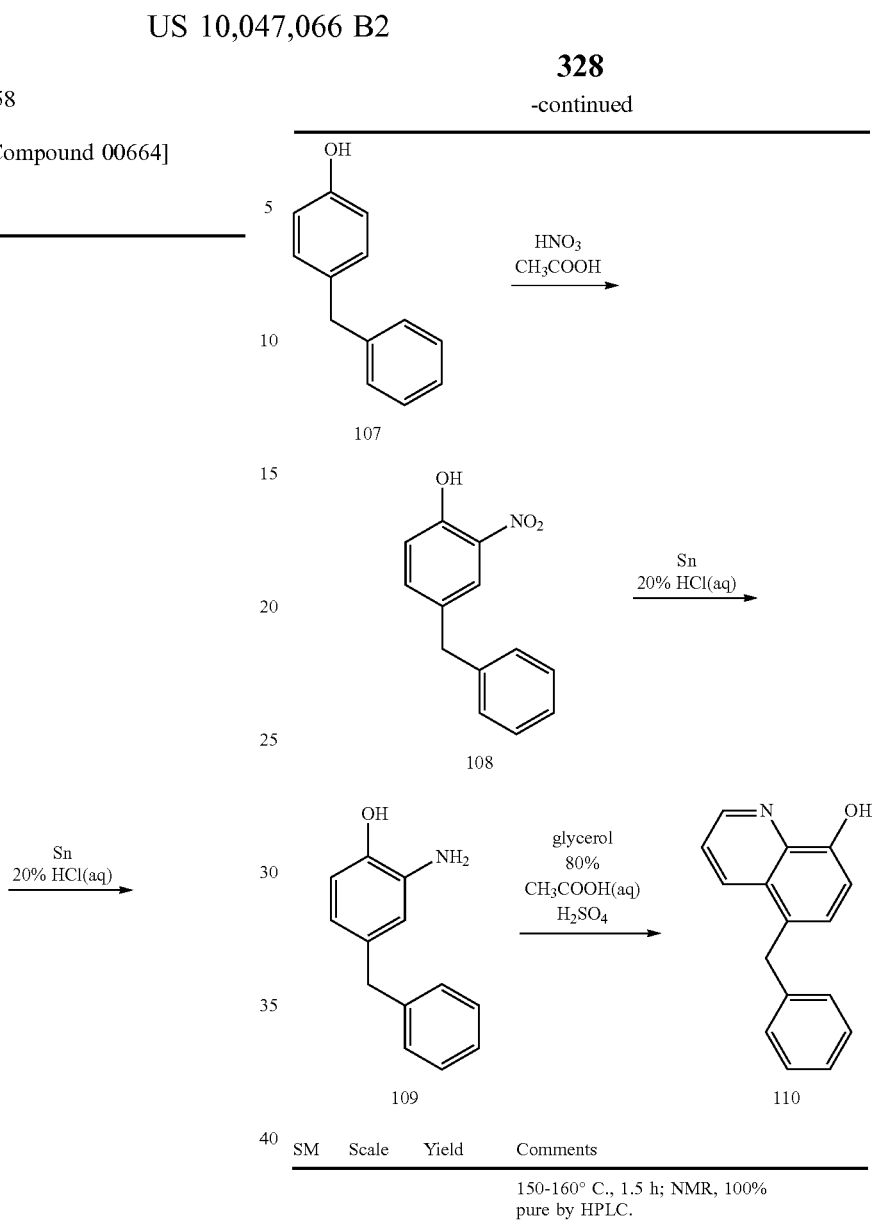

| SM | Scale | Yield | Comments |
|---|---|---|---|
| | | | 150-160° C., 1.5 h; NMR, 100% pure by HPLC. |

Example 59

General Method for Synthesis of Hydroxylamine Compounds

Alcohol (1.0 equiv.), N-hydroxypthalimide (1.1 equiv.) and triphenylphosphine (1.1 equiv.) were dissolved in dichloromethane (6 mL). Diethyl azodicarboxylate (DEAD) (1.1 equiv.) was added dropwise while stirring to the solution and the reaction mixture was stirred overnight at room temperature. The reaction mixture was diluted with dichloromethane (20 mL). The combined dichloromethane was washed with 10% NaOH (2×15 mL), water (2×15 mL) and brine (15 mL). The solvent was removed under reduced pressure and the crude product was used for the next step. The crude product was dissolved in ethanol (8 mL) and hydrazine monohydrate (2.0 equiv.) was added. The reaction was refluxed for 2 h and filtered. Ethanol was removed under reduced pressure. The crude product was purified by flash column chromatography on silica gel.

The following compounds (Table A) were prepared essentially according to the preceding example with the proper substitution of starting materials:

TABLE A

| Compound | Yield (%) | ¹H NMR (CDCl₃ unless otherwise noted): δ (ppm) |
|---|---|---|
| O-(3-Nitrobenzyl)hydroxylamine | 53 | 4.75 (s, 2 H), 5.53 (br s, 2 H), 7.48-7.54 (m, 1 H), 7.66 (d, 1 H, J = 10 Hz), 8.13 (d, 1 H, J = 11 Hz), 8.20 (s, 1 H) |
| O-(Pyridin-2-ylmethyl)hydroxylamine | 11 | 4.77 (s, 2 H), 5.58 (br s, 2 H), 7.16 (dd, 1 H, J = 4.8, 6.8 Hz), 7.32 (d, 1 H, J = 7.6 Hz), 7.64 (dt, 1 H, J = 2, 8 Hz), 8.54 (d, 1 H, J = 4.8 Hz) |
| O-(Pyridin-3-ylmethyl)hydroxylamine | 10 | 4.66 (s, 2 H), 5.44 (br s, 2 H), 7.23-7.27 (m, 1 H), 7.65 (d, 1 H, J = 8 Hz), 8.53 (d, 1 H, J = 4.4 Hz), 8.58 (s, 1 H) |
| O-(Pyridin-4-ylmethyl)hydroxylamine | 37 | 4.64 (s, 2 H), 5.53 (br s, 2 H), 7.20 (dd, 2 H, J = 1.6, 4.4 Hz), 8.53 (dd, 2 H, J = 1.6, 4.4 Hz) |
| O-(Benzo[d][1,3]dioxol-5-ylmethyl)hydroxylamine | 48 | 4.56 (s, 2 H), 5.35 (br s, 2 H), 5.94 (s, 2 H), 6.76-6.85 (m, 3 H) |
| O-((5-Chlorobenzo[b]thiophen-3-yl)methyl)hydroxylamine | 51 | 4.87 (s, 2 H), 5.44 (br s, 2 H), 7.30 (dd, 2 H, J = 2, 8.8 Hz), 7.45 (s, 1 H), 7.74 (dd, 1 H, J = 0.4, 8.4 Hz), 7.87 (d, 1 H, J = 1.6 Hz) |
| O-(Naphthalen-2-ylmethyl)hydroxylamine | 61 | 4.84 (s, 2 H), 5.42 (br s, 2 H), 7.46-7.49 (m, 3 H), 7.80-7.85 (m, 4 H) |
| O-(Quinolin-6-ylmethyl)hydroxylamine | 55 | 4.79 (s, 2 H), 5.46 (br s, 2 H), 7.32 (dd, 1 H, J = 4.4, 8.4 Hz), 7.36-7.40 (m, 1 H), 7.65 (dd, 1 H, J = 1.6, 8.4 Hz), 7.71 (d, 1 H, J = 0.8 Hz), 8.03-8.07 (m, 2 H) |
| O-((2,3-Dihydrobenzo[b][1,4]dioxin-6-yl)methyl)hydroxylamine | 61 | 4.20 (s, 4 H), 4.52 (s, 2 H), 5.32 (br s, 2 H), 6.80-6.81 (m, 2 H), 6.85 (d, 1 H, J = 1.2 Hz). |
| O-(Chroman-2-ylmethyl)hydroxylamine | 43 | 1.71-1.82 (m, 1 H), 1.95-1.99 (m, 1 H), 2.71-2.77 (m, 1 H), 2.81-2.90 (m, 1 H), 3.80-3.91 (m, 2 H), 4.25-4.31 (m, 1 H), 5.52 (br s, 2 H), 6.80-6.85 (m, 2 H), 7.01-7.08 (m, 1 H). |
| O-(Benzo[d]thiazol-2-ylmethyl)hydroxylamine | 39 | 5.05 (s, 2 H), 5.78 (br s, 2 H), 7.34-7.38 (m, 1 H), 7.43-7.47 (m, 1 H), 7.87 (dd, 1 H, J = 0.4, 7.6 Hz), 7.99 (d, 1 H, J = 8 Hz). |
| O-((4-Methyl-2-phenylpyrimidin-5-yl)methyl)hydroxylamine | 53 | 2.59 (s, 3 H), 4.69 (s, 2 H), 5.47 (br s, 2 H), 7.44-7.45 (m, 3 H), 8.40-8.43 (m, 2 H), 8.59 (s, 1 H). |
| O-(Benzofuran-2-ylmethyl)hydroxylamine | 28 | 4.76 (s, 2 H), 5.55 (br s, 2 H), 6.72 (s, 1 H), 7.18-7.29 (m, 2 H), 7.47 (d, 1 H, J = 8 Hz), 7.54 (d, 1 H, J = 7.6 Hz). |
| O-(3-Fluorobenzyl)hydroxylamine | 42 | 4.65 (s, 2 H), 5.42 (br s, 2 H), 6.95-7.11 (m, 3 H), 7.23-7.29 (m, 1 H) |
| O-(3,5-Difluorobenzyl)hydroxylamine | 47 | 4.63 (s, 2 H), 5.47 (br s, 2 H), 6.69-6.72 (m, 1 H), 6.84-6.86 (m, 2 H). |
| O-(3-(Trifluoromethyl)benzyl)hydroxylamine | 57 | 4.71 (s, 2 H), 5.45 (br s, 2 H), 7.46-7.56 (m, 3 H), 7.61 (s, 1 H). |
| O-(3,5-Dichlorobenzyl)hydroxylamine | 44 | 4.63 (s, 2 H), 5.50 (br s, 2 H), 7.25-7.27 (m, 2 H), 7.30 (d, 1 H, J = 1.8 Hz). |
| O-(3-Bromobenzyl)hydroxylamine | 58 | 4.62 (s, 2 H), 5.42 (br s, 2 H), 7.18-7.26 (m, 2 H), 7.40-7.43 (m, 1 H), 7.50 (s, 1 H). |
| O-(2,5-Dimethoxybenzyl)hydroxylamine | 49 | 3.78 (s, 3 H), 3.80 (s, 3 H), 4.74 (s, 2 H), 5.44 (br s, 2 H), 6.82 (d, 2 H, J = 2 Hz), 6.95 (s, 1 H). |
| O-(4-(Trifluoromethyl)benzyl)hydroxylamine | 54 | 4.72 (s, 2 H), 5.45 (br s, 2 H), 7.45 (d, 2 H, J = 8 Hz), 7.60 (d, 2 H, J = 8 Hz). |
| O-(4-Fluorobenzyl)hydroxylamine | 57 | 4.61 (s, 2 H), 5.38 (br s, 2 H), 6.99-7.03 (m, 2 H), 7.28-7.31 (m, 2 H). |
| O-(2-Chloro-4-fluorobenzyl)hydroxylamine | 48 | 4.74 (s, 2 H), 5.46 (br s, 2 H), 6.97 (dt, 1 H, J = 2.4, 8.4 Hz), 7.11 (dd, 1 H, J = 2.4, 8.4 Hz), 7.39 (dd, 1 H, J = 6.4, 8.4 Hz). |
| O-(2-Chloro-6-fluorobenzyl)hydroxylamine | 39 | 4.86 (s, 2 H), 5.47 (br s, 2 H), 6.96-7.01 (m, 1 H), 7.17-7.25 (m, 2 H). |
| O-(2-Bromobenzyl)hydroxylamine | 56 | 4.78 (s, 2 H), 5.49 (br s, 2 H), 7.15 (dt, 1 H, J = 1.6, 7.6 Hz), 7.29 (dt, 1 H, J = 1.2, 7.6 Hz), 7.41 (dd, 1 H, J = 1.2, 7.6 Hz), 7.54 (dd, 1 H, J = 1.2, 7.6 Hz). |
| O-(3-Methylbenzyl)hydroxylamine | 58 | 2.34 (s, 3 H), 4.64 (s, 2 H), 5.36 (br s, 2 H), 7.10-7.16 (m, 3 H), 7.21-7.25 (m, 1 H). |
| Methyl 4-(aminooxymethyl)benzoate | 35 | 3.89 (s, 3 H), 4.72 (s, 2 H), 5.44 (br s, 2 H), 7.38 (d, 2 H, J = 7.6 Hz), 7.99 (d, 2 H, J = 6.8 Hz). |
| O-(3-Chloro-4-fluorobenzyl)hydroxylamine | 42 | 4.59 (s, 2 H), 5.41 (br s, 2 H), 7.07-7.12 (m, 1 H), 7.18-7.19 (m, 1 H), 7.40 (dd, 1 H, J = 1.6, 6.8 Hz). |
| O-(2-Methoxybenzyl)hydroxylamine | 48 | 3.82 (s, 3 H), 4.74 (s, 2 H), 5.39 (br s, 2 H), 6.87 (d, 1 H, J = 8 Hz), 6.93 (t, 1 H, J = 7.6 Hz), 7.25-7.32 (m, 2 H). |
| O-(2-(Trifluoromethyl)benzyl)hydroxylamine | 52 | 4.91 (s, 2 H), 5.54 (br s, 2 H), 7.39-7.43 (m, 1 H), 7.55-7.62 (m, 3 H). |
| O-(2-Nitrobenzyl)hydroxylamine | 39 | 5.05 (s, 2 H), 5.54 (br s, 2 H), 7.41-7.44 (m, 1 H), 7.61-7.63 (m, 2 H), 7.99-8.01 (m, 1 H). |
| O-(3-Chloro-5-fluorobenzyl)hydroxylamine | 35 | 4.61 (s, 2 H), 5.47 (br s, 2 H), 6.94-6.97 (m, 1 H), 7.01 (td, 1 H, J = 2, 8.4 Hz), 7.12 (s, 1 H). |

TABLE A-continued

| Compound | Yield (%) | $^1$H NMR (CDCl$_3$ unless otherwise noted): δ (ppm) |
|---|---|---|
| O-(Perfluorobenzyl)hydroxylamine | 30 | 4.77 (s, 2 H), 5.51 (br s, 2 H). |
| O-(3-Nitrophenethyl)hydroxylamine | 47 | 2.97 (t, 2 H, J = 6.8 Hz), 3.88 (t, 2 H, J = 6.8 Hz), 5.40 (br s, 2 H), 7.40-7.43 (m, 1 H), 7.51-7.53 (m, 1 H), 8.01-8.05 (m, 2 H). |
| O-(4-Methoxybenzyl)hydroxylamine | 49 | 3.80 (s, 3 H), 4.62 (s, 2 H), 5.33 (br s, 2 H), 6.89 (d, 2 H, J = 8.4 Hz), 7.29 (d, 2 H, J = 8.4 Hz). |
| O-(4-Iodobenzyl)hydroxylamine | 52 | 4.59 (s, 2 H), 5.38 (br s, 2 H), 7.08 (d, 2 H, J = 7.6 Hz), 7.66 (d, 2 H, J = 7.6 Hz). |
| O-(3-Iodobenzyl)hydroxylamine | 61 | 4.59 (s, 2 H), 5.41 (br s, 2 H), 7.07 (t, 1 H, J = 7.6 Hz), 7.29 (d, 1 H, J = 7.2 Hz), 7.62 (d, 1 H, J = 7.6 Hz), 7.70 (s, 1 H). |
| O-(2-Iodobenzyl)hydroxylamine | 57 | 4.71 (s, 2 H), 5.49 (br s, 2 H), 6.95-7.00 (m, 1 H), 7.30-7.38 (m, 2 H), 7.82 (d, 1 H, J = 8 Hz). |
| 2-(aminooxymethyl)-N-phenylaniline | 32 | 4.72 (s, 2 H), 5.35 (br s, 2 H), 6.88-6.92 (m, 2 H), 7.04-7.06 (m, 2 H), 7.22-7.27 (m, 4 H), 7.37-7.39 (d, 1 H, J = 8 Hz) |
| 2-(aminooxymethyl)-N-benzylaniline | 28 | 4.37 (s, 2 H), 4.73 (s, 2 H), 5.30 (br s, 3 H), 6.61-6.69 (m, 2 H), 7.11-7.13 (dd, 1 H, J = 1.6, 7.6 Hz), 7.16-7.20 (dt, 1 H, J = 1.6, 8.4 Hz), 7.23-7.27 (m, 1 H), 7.30-7.35 (m, 4 H) |
| 3-(aminooxymethyl)-N-benzylaniline | 39 | (CD$_3$OD) 4.59 (s, 2 H), 5.06 (s, 2 H), 7.38-7.40 (m, 6 H), 7.48-7.56 (m, 3 H) |
| O-benzhydrylhydroxylamine | 65 | 5.30 (br s, 2 H), 5.64 (s, 1 H), 7.23-7.35 (m, 10 H) |
| O-(cyclohexyl(phenyl)methyl)hydroxylamine | 57 | 0.81-1.25 (m, 6 H), 1.55-1.60 (m, 2 H), 1.71 (d, 1 H, J = 12.4 Hz), 2.00 (d, 1 H, J = 12.8 Hz), 4.17 (d, 1H, J = 8 Hz), 5.10 (br s, 2 H), 7.23-7.32 (m, 5 H) |
| O-(3-morpholino-1-phenylpropyl)hydroxylamine | 52 | 1.64-1.65 (m, 1 H), 1.89-1.93 (m, 1 H), 2.21-2.28 (m, 6 H), 3.56-3.57 (m, 4 H), 4.45-4.46 (m, 1 H), 5.09 (br s, 2 H), 7.20-7.25 (m, 5 H) |
| O-(1,2-diphenylethyl)hydroxylamine | 58 | 2.86-2.91 (dd, 1 H, J = 5.6, 13.6 Hz), 3.10-3.15 (dd, 1 H, J = 7.6, 13.6 Hz). 4.71-4.74 (dd, 1 H, J = 6, 7.6 Hz), 5.18 (br s, 2 H), 7.12 (d, 1 H, J = 6.8 Hz), 7.16-7.30 (m, 8 H) |
| O-(2-morpholino-1-phenylethyl)hydroxylamine | 64 | 2.35-2.39 (dd, 1 H, J = 3.2, 13.6 Hz), 2.48-2.58 (m, 4 H), 2.73-2.78 (dd, 1 H, J = 9.6, 13.6 Hz), 3.67-3.76 (m, 4 H), 4.74-4.77 (dd, 1 H, J = 3.2, 9.2 Hz), 5.24 (br s, 2 H), 7.27-7.36 (m, 5 H) |
| 4-(aminooxy)-N-methyl-4-phenylbutanamide | 41 | 1.98-2.11 (m, 2 H), 2.17-2.21 (m, 2 H), 2.75 (d, 3 H, J = 4 Hz), 4.48-4.51 (dd, 1 H, J = 5.6, 7.6 Hz), 5.20 (br s, 2 H), 5.56 (br s, 1 H), 7.24-7.32 (m, 5 H) |
| 4-(aminooxy)-N-cyclohexyl-4-phenylbutanamide | 38 | 1.05-1.18 (m, 2 H), 1.26-1.41 (m, 2 H), 1.62-1.74 (m, 4 H), 1.88-1.97 (m, 2 H), 1.99-2.21 (m, 4 H), 3.71-3.77 (m, 1 H), 4.50-4.55 (dd, 1 H, J = 7.6, 10 Hz), 5.22 (br s, 2 H), 5.35 (d, 1 H, J = 10 Hz), 7.27-7.39 (m, 5 H) |
| methyl 4-(aminooxy)-4-phenylbutanoate | 49 | 1.95-1.99 (m, 1 H), 2.06-2.11 (m, 1 H), 2.34-2.38 (dd, 2 H, J = 1.2, 8.4 Hz), 3.63 (s, 3 H), 4.49-4.52 (dd, 1 H, J = 5.6, 7.6 Hz), 5.22 (br s, 2 H), 7.26-7.36 (m, 5 H) |
| 2-(aminooxy)-2-phenylethanamine | 52 | (CD$_3$OD) 3.22-3.71 (m, 2 H), 5.31-5.34 (m, 1 H), 7.41-7.45 (m, 5 H) |
| 3-(aminooxy)-3-phenylpropan-1-amine | 45 | 1.78-1.85 (m, 1 H), 1.87-1.94 (m, 1 H), 3.13-3.24 (m, 2 H), 4.52-4.55 (m, 1 H), 4.76 (br s, 2 H), 5.22 (br s, 2 H), 7.23-7.32 (m, 5 H) |
| O-((3',4-dichlorobiphenyl-2-yl)methyl)hydroxylammonium chloride | 33 | 4.56 (s, 2H), 5.45 (br s, 2H), 7.19-7.23 (m, 2H), 7.33-7.36 (m, 4H), 7.54 (d, 1H, J = 1.5 Hz) |
| O-((3',4,4'-trichlorobiphenyl-2-yl)methyl)hydroxylammonium chloride | 62 | 4.54 (s, 2H), 5.46 (br s, 2H), 7.18-7.21 (m, 2H), 7.33-7.36 (dd, 1H, J = 1.5, 4.5 Hz), 7.47-7.49 (m, 2H), 7.54 (s, 1H) |
| O-((4-chloro-4'-(trifluoromethyl)biphenyl-2-yl)methyl)hydroxylamine | 31 | 4.54 (s, 2H), 5.46 (br s, 2H), 7.21 (d, 1H, J = 6.30 Hz), 7.36 (d, 1H, J = 4.8 Hz), 7.47 (d, 2H, J = 6.0 Hz), 7.56 (d, 1H, J = 1.5 Hz), 7.68 (d, 2H, J = 6.0 Hz) |
| O-(5-chloro-2-(pyrimidin-5-yl)benzyl)hydroxylamine | 45 | 4.52 (s, 2H), 5.48 (br s, 2H), 7.18-7.24 (m, 1H), 7.39 (d, 1H, J = 4.8 Hz), 7.57 (s, 1H), 8.75-8.82 (m, 2H), 9.21 (s, 1H) |
| O-(5-chloro-2-(thiophen-3-yl)benzyl)hydroxylamine | 62 | 4.64 (s, 2H), 5.42 (br s, 2H), 7.17 (dd, 1H, J = 1.32, 3.54 Hz), 7.31-7.39 (m, 4H), 7.53 (s, 1H) |
| O-(5-chloro-2-(thiophen-2-yl)benzyl)hydroxylamine | 36 | 4.71 (s, 2H), 5.30 (br s, 2H), 7.08-7.13 (m, 2H), 7.25-7.41 (m, 3H), 7.53 (d, 1H, J = 1.83 Hz) |
| O-((4'-chlorobiphenyl-2-yl)methyl)hydroxylamine | 67 | 4.58 (s, 2H), 4.36 (s, 2H), 7.23-7.27 (m, 1H), 7.30-7.33 (dd, 2H, J = 2, 6.6 Hz), 7.35-7.40 (m, 4H), 7.51-7.53 (m, 1H) |

TABLE A-continued

| Compound | Yield (%) | ¹H NMR (CDCl₃ unless otherwise noted): δ (ppm) |
|---|---|---|
| O-((4'-chlorobiphenyl-3-yl)methyl)hydroxylamine hydrochloride | 78 | DMSO-d6 5.10 (s, 2H), 7.43-7.45 (d, 1H, J = 7.6 Hz), 7.51-7.64 (m, 4H), 7.71-7.73 (m, 3H), 11.02 (br s, 3H) |
| O-((4'-methylbiphenyl-3-yl)methyl)hydroxylamine | 65 | 2.68 (s, 3H), 4.73 (s, 2H), 5.41 (s, 2H), 7.22-7.24 (d, 2H, 7.9 Hz), 7.30-7.32 (d, 1H, J = 7.5 Hz), 7.39-7.42 (t, 1H, J = 7.6 Hz), 7.48-7.53 (m, 3H), 7.57 (s, 1H) |
| O-((4'-methoxybiphenyl-3-yl)methyl)hydroxylamine | 62 | 3.84 (s, 3H), 4.74 (s, 2H), 5.43 (br s, 2H), 6.96-6.98 (dd, 2H, J = 1.8, 6.9 Hz), 7.29-7.31 (d, 1H, J = 7.5 Hz), 7.39-7.42 (t, 1H, J = 7.5 Hz), 7.49-7.55 (m, 4H) |
| O-(3-(pyridin-4-yl)benzyl)hydroxylamine | 49 | 4.77 (s, 2H), 5.51 (br s, 2H), 7.43-7.53 (m, 4H), 7.58-7.60 (d, 2H, J = 7.6 Hz), 7.64 (s, 1H), 8.65-8.67 (dd, 2H, J = 1.6, 4.5 Hz) |
| O-(2-(pyridin-4-yl)benzyl)hydroxylamine | 50 | 4.60 (s, 2H), 5.42 (br s, 2H), 7.28-7.31 (dd, 1H, J = 1.9, 7.8 Hz), 7.34-7.36 (dd, 2H, J = 1.4, 4.5 Hz), 7.40-7.47 (m, 2H), 7.55-7.58 (dd, 1H, J = 2.0, 7.8 Hz), 8.65-8.66 (d, 2H, J = 5.9 Hz) |
| 2-(aminooxy)-N-methyl-2-phenylacetamide | 44 | 2.79-2.81 (d, 3H, J = 5.0 Hz), 5.00 (s, 1H), 5.66 (br s, 2H), 6.68 (br s, 1H), 7.31-7.39 (m, 5H) |
| tert-butyl 2-(aminooxy)-2-phenylethyl(methyl)carbamate | 70 | 1.42 (s, 9H), 2.85 (s, 3H), 3.28-3.33 (dd, 1H, J = 7.7, 14.5 Hz), 3.44-3.49 (dd, 1H, J = 4.5, 14.8 Hz), 4.74-4.79 (m, 1H), 5.21 (br s, 2H), 7.28-7.36 (m, 5H) |
| O-(naphthalen-1-ylmethyl)hydroxylamine | 90 | 5.13 (s, 2H), 5.40 (br s, 2H), 7.40-7.54 (m, 4H), 7.80-7.86 (m, 2H), 8.14 (d, 1H, J = 6.18 Hz) |
| O-((4,4'-dichlorobiphenyl-2-yl)methyl)hydroxylamine | 85 | 4.55 (s, 2H), 5.43 (br s, 2H), 7.19 (d, 1H, J = 6.18 Hz), 7.25-7.40 (m, 5H), 7.54 (d, 1H, J = 1.47 Hz) |
| O-((4',5-dichlorobiphenyl-3-yl)methyl)hydroxylamine | 75 | 4.70 (s, 2H), 5.49 (br s, 2H), 7.34 (s, 1H), 7.39-7.49 (m, 6 H) |
| 2-(aminooxy)-N-methyl-2-phenylethanamine dihydrochloride | 70 | DMSO-d6 2.61 (s, 3H), 3.21 (dd, 1H, J = 2.5, 11.3 Hz), 3.43 (dd, 1H, J = 9.74, 3.78 Hz), 5.60 (d, 1H, J = 7.3 Hz), 7.46 (s, 5H), 10.06 (br s, 3H) |
| O-((4-chlorobiphenyl-2-yl)methyl)hydroxylamine | 62 | 4.58 (s, 2H), 5.41 (br s, 2H), 7.22 (d, 1H, J = 6.2 Hz), 7.31-7.43 (m, 6H), 7.54 (d, 1H, J = 1.5 Hz) |
| O-((4-chloro-4'-methoxybiphenyl-2-yl)methyl)hydroxylamine | 57 | 3.85 (s, 3H), 4.58 (s, 2H), 5.42 (br s, 2H), 6.94 (d, 2H, J = 6.5 Hz), 7.19-7.32 (m, 4H), 7.52 (d, 1H, 1.6 Hz), |
| O-((2',4-dichlorobiphenyl-2-yl)methyl)hydroxylamine | 10 | 4.40 (d, 1H, J = 9.45 Hz), 4.53 (d, 1H, J = 9.5 Hz), 5.35 (br s, 2H), 7.13 (d, 1H, J = 6.2 Hz), 7.22-7.35 (m, 4H), 7.45-7.47 (m, 1H), 7.54 (d, 1H, J = 1.4 Hz) |
| O-(5-chloro-2-(1H-indol-5-yl)benzyl)hydroxylamine | 82 | 4.64 (s, 2H), 5.38 (br s, 2H), 6.56 (s, 1H), 7.13 (dd, 1H, J = 1.1, 5.2 Hz), 7.21-7.39 (m, 4H), 7.54-7.56 (m, 2H), 8.30 (br s, 1H) |
| 2'-(aminooxymethyl)-4'-chloro-N,N-dimethylbiphenyl-4-amine | 71 | 2.99 (s, 6H), 4.63 (s, 2H), 5.40 (br s, 2H), 6.76 (d, 2H, J = 6.72 Hz), 7.20-7.30 (m, 4H), 7.51 (s, 1H) |
| methyl 2'-(aminooxymethyl)-4'-chlorobiphenyl-4-carboxylate | 83 | 3.95 (s, 3H), 4.56 (s, 2H), 5.44 (br s, 2H), 7.22-7.24 (d, 1H, J = 8.2 Hz), 7.34-7.37 (dd, 1H, J = 2.2, 8.2 Hz), 7.41-7.43 (d, 2H, J = 8.4 Hz), 7.55-7.56 (d, 1H, J = 2.1 Hz), 8.08-8.10 (d, 2H, J = 8.3 Hz) |
| O-(biphenyl-3-ylmethyl)hydroxylamine | 47 | 4.75 (s, 2 H), 5.43 (br s, 2 H), 7.33-7.36 (m, 2 H), 7.41-7.45 (m, 3 H), 7.54 (d, 1 H, J = 8 Hz), 7.59-7.61 (m, 3 H). |
| O-(biphenyl-2-ylmethyl)hydroxylamine | 28 | 4.64 (s, 2 H), 5.36 (br s, 2 H), 7.30-7.45 (m, 8 H), 7.53-7.56 (m, 1 H). |
| (S)—O-(3-(tert-butyldimethylsilyloxy)-1-phenylpropyl)hydroxylamine | 28 | 0.01 (s, 3 H), 0.02 (s, 3 H), 0.08 (s, 9 H), 1.75-1.82 (m, 1 H), 1.93-2.06 (m, 1 H), 3.52-3.54 (m, 1 H), 3.68-3.75 (m, 1 H), 4.63-4.65 (m, 1 H), 5.14 (br s, 2 H), 7.23-7.33 (m, 5 H). |
| O-(4-cyanobenzyl)hydroxylamine | 61 | 4.67 (s, 2 H), 5.48 (br s, 2 H), 7.39 (d, 2 H, J = 8.0 Hz), 7.57 (d, 2 H, J = 8.0 Hz) |
| O-(1,2,3,4-tetrahydronaphthalen-1-yl)hydroxylammonium chloride | 23 | 1.66-1.84 (m, 3 H), 2.29-2.32 (m, 1 H), 2.58-2.77 (m, 2 H), 5.33-5.35 (m, 1 H), 7.11 (d, 1 H, J = 7.6 Hz), 7.16-7.26 (m, 2 H), 7.41 (d, 1 H, J = 7.6 Hz), 11.10 (s, 3 H) |
| O-(2-cyclohexyl-1-phenylethyl)hydroxylammonium chloride | 37 | 0.79-1.25 (m, 5 H), 1.35-1.82 (m, 6 H), 2.38-2.46 (m, 2 H), 7.34-7.39 (m, 5 H), 10.75 (s, 3 H) |
| O-(2-phenoxy-1-phenylethyl)hydroxylammonium chloride | 47 | 4.18-4.22 (m, 1 H), 4.29-4.40 (m, 1 H), 5.41-5.51 (m, 1 H), 6.89-6.94 (m, 3 H), 7.23-7.27 (m, 2 H), 7.38-7.44 (m, 3 H), 7.46-7.52 (m, 2 H), 11.02 (br. s, 3 H) |
| O-(2-(benzyloxy)-1-phenylethyl)hydroxylammonium chloride | 52 | 3.58-3.62 (m, 1 H), 3.75-3.82 (m, 1 H), 4.48-4.57 (m, 2 H), 5.33-5.38 (m, 1 H), 7.16-7.35 (m, 5 H), 7.36-7.41 (m, 5 H), 10.98 (br. s, 3 H) |
| O-(1,3-diphenylpropyl)hydroxylammonium chloride | 73 | 1.96-2.01 (m, 1 H), 2.15-2.28 (m, 1 H), 2.33-2.65 (m, 2 H), 5.00-5.15 (m, 1 H), 7.10-7.18 (m, 3 H), 7.19-7.27 (m, 2 H), 7.32-7.45 (m, 5 H), 11.00 (br. s, 3 H) |

TABLE A-continued

| Compound | Yield (%) | $^1$H NMR (CDCl$_3$ unless otherwise noted): δ (ppm) |
|---|---|---|
| O-(3-cyclohexyl-1-phenylpropyl)hydroxylammonium chloride | 42 | 0.93-1.25 (m, 7 H), 1.56-1.86 (m, 8 H), 4.98-5.10 (m, 1 H), 7.15-7.39 (m, 5 H), 10.81 (br. s, 3 H) |

Example 60

General Method for Synthesis of bis(hydroxylamine) Compounds

Alcohol (1.0 equiv.), N-hydroxypthalimide (2.2 equiv.) and triphenylphosphine (2.2 equiv.) were dissolved in dichloromethane (6 mL). Diethyl azodicarboxylate (DEAD) (2.2 equiv.) was added dropwise while stirring to the solution and the reaction mixture was stirred overnight at room temperature. The reaction mixture was diluted with dichloromethane (20 mL). The combined dichloromethane was washed with 10% NaOH (2×15 mL), water (2×15 mL) and brine (15 mL). The solvent was removed under reduced pressure and the crude product was used for the next step. The crude product was dissolved in ethanol (8 mL) and hydrazine monohydrate (4.0 equiv.) was added. The reaction was refluxed for 2 h and filtered. Ethanol was removed under reduced pressure. The crude product was purified by flash column chromatography on silica gel.

The following compounds (Table B) were prepared essentially according to the preceding example with the proper substitution of starting materials:

TABLE B

| Compound | Yield (%) | $^1$H NMR (CDCl$_3$ unless otherwise noted): δ (ppm) |
|---|---|---|
| O,O'-(1,3-phenylenebis(methylene))-bis(hydroxylamine) | 28 | 4.67 (s, 4 H), 5.42 (br s, 4 H), 7.28-7.33 (m, 4 H). |
| O,O'-(1,2-phenylenebis(methylene))-bis(hydroxylamine) | 36 | 4.80 (s, 4 H), 5.42 (br s, 4 H), 7.30-7.40 (m, 4 H). |
| O,O'-(1,4-phenylenebis(methylene))-bis(hydroxylamine) | 32 | 4.67 (s, 4 H), 5.40 (br s, 4 H), 7.34-7.36 (m, 4 H). |

Example 61

Synthesis of O-(1-(3-Nitrophenyl)but-3-enyl)hydroxylamine

3-Nitrobenzaldehyde (296 mg, 1.96 mmol) was dissolved in THF (4 mL) and cooled to −78° C. Allyl magnesium bromide (1 M in butyl ether, 2.4 mL, 2.35 mmol) was added dropwise and the reaction mixture was stirred at −78° C. for 1 h. It was then quenched with saturated ammonium chloride (5 mL) and extracted with ethyl acetate (2×30 mL). The combined organic layers were dried over Na$_2$SO$_4$ and concentrated. The crude product was purified by flash column chromatography on silica gel using 25% EtOAc/hexanes as eluent to yield the desired product as yellow oil which was used in the next step. 1-(3-Nitrophenyl)but-3-en-1-ol (139 mg, 0.720), N-hydroxyphthalimide (129 mg, 0.792 mmol) and triphenylphosphine (208 mg, 0.792 mmol) were dissolved in dichloromethane (6 mL). Diethyl azodicarboxylate (DEAD) (0.13 mL, 0.792 mmol) was added dropwise while stirring to the solution and the reaction mixture was stirred overnight at room temperature. The reaction mixture was diluted with dichloromethane (20 mL). The combined dichloromethane was washed with 10% NaOH (2×15 mL), water (2×15 mL) and brine (15 mL). The solvent was removed under reduced pressure and the crude product was used for the next step. The crude product was dissolved in ethanol (6 mL) and hydrazine monohydrate (0.16 mL, 3.22 mmol) was added. The reaction was refluxed for 2 h and filtered. Ethanol was removed under reduced pressure. The crude product was purified by flash column chromatography on silica gel using 20%-35% EtOAc/hexanes as eluent to yield the desired product as colorless oil. $^1$H NMR (CDCl$_3$, 400 MHz): δ (ppm) 2.38-2.43 (m, 1H), 2.53-2.59 (m, 1H), 4.67 (t, 1H, J=6.8 Hz), 5.00-5.04 (m, 2H), 5.35 (br s, 2H), 5.67-5.74 (m, 2H), 7.49-7.53 (m, 1H), 7.62 (d, 1H, J=7.6 Hz), 8.11-8.16 (m, 2H).

Example 62

Synthesis of N-Boc-Indole-3-carbinol

To a solution of indole-3-carbinol (250 mg, 1.70 mmol) and (Boc)$_2$O (371 mg, 1.70 mmol) in dichloromethane (6 mL) was added triethylamine (0.47 mL, 3.40 mmol) followed by DMAP (21 mg, 0.170 mmol). The reaction mixture was stirred at room temperature for 1 h and poured into water. The dichloromethane layer was separated, dried over Na$_2$SO$_4$ and concentrated. The crude product was purified by flash column chromatography on silica gel using 20%-30% EtOAc/hexanes as eluent to afford Boc protected indole as solid (60 mg, 0.243 mmol, 15%). $^1$H NMR (CDCl$_3$, 300 MHz): δ (ppm) 1.66 (s, 9H), 1.84 (br s, 1H), 4.82 (s, 2H), 7.22-7.36 (m, 2H), 7.57 (s, 1H), 7.64 (dd, 1H, J=0.6, 7.5 Hz), 8.14 (d, 1H, J=8.1 Hz).

Example 63

Synthesis of O-((1H-Indol-3-yl)methyl)hydroxylamine hydrochloride

N-Boc-Indole-3-carbinol (120 mg, 0.486 mmol), N-hydroxyphthalimide (87 mg, 0.534 mmol) and triphenylphosphine (140 mg, 0.534 mmol) were dissolved in dichloromethane (6 mL). Diethyl azodicarboxylate (DEAD) (0.08 mL, 0.534 mmol) was added dropwise while stirring to the solution and the reaction mixture was stirred overnight at room temperature. The reaction mixture was diluted with dichloromethane (20 mL). The combined dichloromethane was washed with 10% NaOH (2×15 mL), water (2×15 mL) and brine (15 mL). The solvent was removed under reduced pressure and the crude product was used for the next step. The crude product was dissolved in ethanol (5 mL) and hydrazine monohydrate (0.07 mL, 1.42 mmol) was added. The reaction was refluxed for 2 h and filtered. Ethanol was removed under reduced pressure. The crude product was purified by flash column chromatography on silica gel using 20%-35% EtOAc/hexanes as eluent to yield the desired product as colorless oil. The product was dissolved in dioxane (1 mL) and HCl (4M in dioxane, 2 mL) was added. The reaction was stirred at room temperature for 20 h and concentrated. The crude product was triturated with 20% EtOAc/hexanes and dried to afford the final product as hydrochloride salt (34 mg, 0.171, 35% over two steps). $^1$H NMR (CD$_3$OD, 400 MHz): δ (ppm) 3.62 (s, 2H), 7.27-7.36 (m, 2H), 7.67-7.69 (m, 1H), 7.87 (s, 1H), 8.17 (d, 1H, J=8.4 Hz).

Example 64

General Method for the Synthesis of Sulfonamides

To a solution of O-(3-nitrobenzyl)hydroxylamine (1.0 equiv.) in dichloromethane (2 mL) was sequentially added pyridine (2.0 equiv.) and sulfonylchloride (1.2 equiv.). The reaction mixture was stirred at room temperature for 18 h and then poured into water (5 mL). The aqueous layer was extracted with dichloromethane (2×15 mL). The combined organic layers were concentrated and the crude product was purified by flash column chromatography on silica gel using 10%-27% EtOAc/hexanes as eluent.

The following compounds (Table C) were prepared essentially according to the preceding example with the proper substitution of starting materials:

TABLE C

| Compound | Yield (%) | $^1$H NMR (CDCl$_3$ unless otherwise noted): δ (ppm) |
| --- | --- | --- |
| 4-Methyl-N-(3-nitrobenzyloxy)-benzenesulfonamide | 62 | 2.41 (s, 3 H), 5.03 (d, 2 H), 7.17 (s, 1 H), 7.31 (d, 2 H, J = 8 Hz), 7.47-7.51 (m, 1 H), 7.63 (d, 1 H, J = 7.6 Hz), 7.78 (d, 2 H, J = 8 Hz), 8.13-8.15 (m, 2 H). |
| N-(3-Nitrobenzyloxy)-methanesulfonamide | 71 | 3.08 (s, 3 H), 5.09 (s, 2 H), 6.93 (s, 1 H), 7.55 (t, 1 H, J = 7.6 Hz), 7.70 (d, 1 H, J = 7.6 Hz), 8.20-8.24 (m, 2 H). |
| 2-Methyl-5-nitro-N-(3-nitrobenzyloxy)-benzenesulfonamide | 65 | 2.73 (s, 3 H), 5.02 (s, 2 H), 7.40 (s, 1 H), 7.50-7.53 (m, 1 H), 7.64 (d, 1 H, J = 7.6 Hz), 8.09 (s, 1 H), 8.14-8.16 (m, 1 H), 8.31 (dd, 1 H, J = 2.4, 8.4 Hz), 8.82 (d, 1 H, J = 2.4 Hz). |

Example 65

Synthesis of (3-(aminooxymethyl)phenyl)methanamine

3-Cyanobenzyl alcohol (308 mg, 2.32 mmol), N-hydroxyphthalimide (416 mg, 2.55 mmol) and triphenylphosphine (668 mg, 2.55 mmol) were dissolved in THF (8 mL). Diethyl azodicarboxylate (DEAD) (0.40 mL, 2.55 mmol) was added dropwise while stirring to the solution and the reaction mixture was stirred at room temperature for 2 h. The reaction mixture was filtered and the residue washed with THF (4 mL) and dried under high vacuum. The crude product (1.24 g, 4.46 mmol) was dissolved in ethanol (8 mL) and hydrazine monohydrate (0.43 mL, 8.92 mmol) was added. The reaction was refluxed for 2 h and filtered. Ethanol was removed under reduced pressure and the residue suspended in ethyl ether. The ethyl ether layer was washed with 3% Na$_2$CO$_3$ (2×10 mL), brine (10 mL) and concentrated. The crude product (830 mg, 5.61 mmol) was dissolved in THF (15 mL) and cooled to 0° C. Lithium aluminum hydride (1 M in THF, 11.2 mL, 11.2 mmol) was added dropwise and the reaction was stirred overnight at room temperature. It was then quenched with methanol (10 mL) and water (2 mL). The mixture for stirred for a further 30 min. The salts were filtered off and the solvent removed by evaporation in vacuo. The crude product was purified by silica gel flash column chromatography using 20% MeOH/dichloromethane as eluent to afford the desired product as white solid (59 mg, 0.388 mmol, 17% over 3 steps). $^1$H NMR (CDCl$_3$, 300 MHz): δ (ppm) 4.07 (s, 2H), 4.63 (s, 2H), 5.18 (s, 4H), 7.36-7.44 (m, 4H).

Example 66

General Procedure for Suzuki Reaction

To a degassed solution of appropriate halo-substituted benzyl alcohol (1.5 mmol), aryl boronic acid (1.5 equiv), and sodium carbonate (2.0 equiv) in DME/water (6 mL/3 mL) was added Pd(PPh$_3$)$_4$ (2 mol %). The mixture was heated to 85° C. until the reaction was complete as indicated by TLC. The mixture was allowed to cool to room temperature, and then partition between EtOAc and water. The layers were separated and the aqueous layer was extracted with EtOAc (2×20 mL) and the combined organic layers were washed with water (10 mL), brine (10 mL), and dried over sodium sulfate. The solvent was removed under reduced pressure and the crude product was purified by silica gel flash column chromatography.

The following compounds (Table D) were prepared essentially according to the preceding example with the proper substitution of starting materials:

TABLE D

| Compound | Yield (%) | $^1$H NMR (CDCl$_3$ unless otherwise noted): δ (ppm) |
| --- | --- | --- |
| (3-(pyridin-4-yl)phenyl)methanol | 91 | 4.22 (br s, 1H), 4.78 (s, 2H), 7.44-7.52 (m, 5H), 7.63 (s, 1H), 8.53-8.54 (dd, 2H, J = 4.8 Hz) |
| (2-(pyridin-4-yl)phenyl)methanol | 40 | 4.56 (s, 2H), 4.68 (br s, 1H), 7.20-7.23 (dd, 1H, J = 1.6, 7.4 Hz), 7.30-7.32 (dd, 2H, J = 1.6, 4.5 Hz), 7.34-7.43 (m, 2H), 7.58-7.61 (dd, 1H, J = 1.1, 7.9 Hz), 8.45-8.47 (dd, 2H, J = 1.6, 4.5 Hz) |
| (4'-chlorobiphenyl-3-yl)methanol | 67 | 2.51 (br s, 1H), 4.66 (s, 2H), 7.27-7.28 (d, 1H, J = 7.1 Hz), 7.33-7.38 (dt, 3H, J = 1.9, 6.6 Hz), 7.41-7.45 (m, 3H), 7.48 (s, 1H) |
| (4'-chlorobiphenyl-2-yl)methanol | 75 | 2.08 (br s, 1H), 4.51 (s, 2H), 7.21-7.23 (m, 1H), 7.26-7.27 (t, 1H, J = 2.2 Hz), 7.28-7.29 (t, 1H, J = 2.2 Hz), 7.31-7.39 (m, 4H), 7.49-7.51 (dd, 1H, J = 1.6, 7.4 Hz) |

TABLE D-continued

| Compound | Yield (%) | $^1$H NMR (CDCl$_3$ unless otherwise noted): δ (ppm) |
|---|---|---|
| (4,4'-dichlorobiphenyl-2-yl)methanol | 89 | 1.73-1.75 (t, 1H, J = 5.7 Hz), 4.55-4.56 (d, 2H, J = 5.7 Hz), 7.16-7.18 (d, 1H, J = 8.1 Hz) 7.25-7.27 (d, 2H, J = 8.3 Hz), 7.31-7.33 (dd, 1H, J = 2.1, 8.2 Hz), 7.39-7.40 (d, 2H, J = 8.3 Hz), 7.56-7.57 (d, 1H, J = 2.0 Hz) |
| (4-chlorobiphenyl-2-yl)methanol | 91 | 2.02 (br s, 1H), 4.53 (s, 2H), 7.16-7.19 (d, 1H, J = 8.2 Hz), 7.26-7.43 (m, 6H), 7.54-7.55 (d, 1H, J = 2.9 Hz) |
| (4-chloro-4'-methoxybiphenyl-2-yl)methanol | 98 | 2.31 (br s, 1H), 3.82 (s, 3H), 4.52 (s, 2H), 6.89-6.94 (td, 2H, J = 2.2, 8.7 Hz), 7.13-7.28 (m 4H), 7.50-7.51 (d, 1H, J = 2.1 Hz) |
| (2',4-dichlorobiphenyl-2-yl)methanol | 96 | 1.77-1.80 (t, 1H, J = 5.8 Hz), 4.35-4.40 (dd, 1H, J = 5.9, 13.5 Hz), 4.45-4.50 (dd, 1H, J = 5.1, 13.4 Hz), 7.09-7.11 (d, 1H, J = 8.0 Hz), 7.20-7.22 (m, 1H), 7.31-7.36 (m, 3H), 7.45-7.48 (m, 1H), 7.60-7.61 (d, 1H, J = 1.8 Hz) |
| methyl 4'-chloro-2'-(hydroxymethyl)biphenyl-4-carboxylate | 92 | 1.73 (br s, 1H), 3.95 (s, 3H), 4.57 (s, 2H), 7.20-7.22 (d, 1H, 8.2 Hz), 7.33-7.36 (dd, 1H, J = 2.1, 8.2 Hz), 7.39-7.42 (d, 2H, J = 8.4 Hz), 7.61-7.62 (d, 1H, J = 1.8 Hz), 7.08-8.11 (d, 2H, J = 8.4 Hz) |
| (4',5-dichlorobiphenyl-3-yl)methanol | 95 | 2.01 (br s, 1H), 4.72 (s, 2H), 7.34 (s, 1H), 7.39-7.48 (m, 6H) |
| (5-chloro-2-(1H-indol-5-yl)phenyl)methanol | 97 | 1.72 (br s, 1H), 7.62 (s, 2H), 6.56-6.58 (m, 1H), 7.10-7.13 (dd, 1H, J = 1.5, 8.4 Hz), 7.21-7.26 (m, 2H merged with CDCl$_3$), 7.29-7.32 (dd, 1H, J = 2.2, 8.2 Hz), 7.39-7.42 (d, 1H, J = 8.3 Hz), 7.55 (s, 2H), 8.29 (br s, 1H) |
| (4-chloro-4'-(dimethylamino)biphenyl-2-yl)methanol | 37 | 1.25 (br s, 1H), 2.96 (s, 6H), 4.60 (s, 2H), 6.75-6.77 (d, 2H, J = 8.4 Hz), 7.17-7.28 (m, 4H), 7.51-7.52 (d, 1H, J = 2.0 Hz) |
| (3',4-dichlorobiphenyl-2-yl)methanol | 88 | 1.77 (br s, 1H), 4.56 (d, 2H, J = 3.3 Hz), 7.16-7.57 (m, 6H), 7.58 (s, 1H) |
| (4-chloro-4'-(trifluoromethyl)biphenyl-2-yl)methanol | 78 | 1.68 (t, 1H, J = 3.9 HZ), 4.56 (d, 2H, J = 3.9 HZ), 7.19 (d, 1H, J = 6.3 Hz), 7.34-7.36 (m, 1H), 7.46 (d, 2H, J = 6.3 Hz), 7.60 (d, 1H, J = 1.5 Hz), 7.68 (d, 2H, J = 6.3 Hz) |
| (3',4,4'-trichlorobiphenyl-2-yl)methanol | 83 | 1.73 (t, 1H, J = 4.2 Hz), 4.56 (d, 2H, J = 4.2 Hz), 7.16-7.19 (m, 2H), 7.32-7.57 (m, 3H), 7.58 (s, 1H) |
| (5-chloro-2-(thiophen-3-yl)phenyl)methanol | 87 | 1.67 (s, 1H), 4.64 (s, 2H), 7.13 (d, 1H, J = 0.9 Hz), 7.15-7.39 (m, 4H), 7.52 (s, 1H) |
| (5-chloro-2-(thiophen-2-yl)phenyl)methanol | 62 | 1.96 (s, 1H), 4.69 (s, 2H), 7.06-7.09 (m, 2H), 7.23-7.35 (m, 3H), 7.55 (d, 1H, J = 1.5 Hz) |
| (5-chloro-2-(pyrimidin-5-yl)phenyl)methanol | 88 | 2.46 (br s, 1H), 4.56 (s, 2H), 7.21 (d, 1H, J = 8.19 Hz), 7.39-7.65 (m, 2H), 8.78 (s, 2H), 9.21 (s, 1H) |

Example 67

Synthesis of (3-(phenylamino)phenyl)methanol

To a degassed solution of racemic-BINAP (67 mg, 0.107 mmol) in toluene (6 mL) was added palladium (II) acetate (36 mg, 0.054 mmol) and stirred at room temperature for 10 min. 3-Bromobenzyl alcohol (200 mg, 1.07 mmol) and aniline (149 mg, 1.60 mmol) were added and stirred for 5 min, cesium carbonate (522 mg, 1.60 mmol) was then added and stirred for 5 min. The mixture was then heated at 90° C. for 16 h diluted with ether (containing 1% triethylamine) and filtered. The solvent was removed under reduced pressure and the crude product was purified by silica gel flash column chromatography using 15-30% EtOAc/hexanes as eluent to afford the desired product as yellow oil (67 mg, 0.337 mmol, 32%). $^1$H NMR (CDCl$_3$, 400 MHz): δ (ppm) 1.74 (br s, 1H), 4.61 (s, 2H), 5.72 (br s, 1H), 6.87-7.07 (m, 6H), 7.21-7.28 (m, 3H).

Example 68

Synthesis of 3-(aminooxymethyl)-N-phenylaniline (3-(Phenylamino)phenyl)methanol (67 mg, 0.337 mmol), N-hydroxyphthalimide (66 mg, 0.404 mmol) and triphenyl-phosphine (106 mg, 0.404 mmol) were dissolved in THF (4 mL). Diethyl azodicarboxylate (DEAD) (0.07 mL, 0.404 mmol) was added dropwise while stirring to the solution and the reaction mixture was stirred at room temperature for 2 h. THF was evaporated under reduced pressure and the residue dissolved in dichloromethane (20 mL). The dichloromethane solution was washed with 10% NaOH (2×15 mL), water (2×15 mL) and brine (15 mL). The solvent was removed under reduced pressure and the crude product was used for the next step. The crude product (267 mg, 0.778 mmol) was dissolved in ethanol (4 mL) and hydrazine monohydrate (0.08 mL, 1.56 mmol) was added. The reaction was refluxed for 2 h and filtered. Ethanol was removed under reduced pressure. The crude product was purified by flash column chromatography on silica gel using 20%-40% EtOAc/hexanes as eluent to yield the desired product as white solid (50 mg, 0.234 mmol, 69% over 2 steps). $^1$H NMR (CDCl$_3$, 300 MHz): δ (ppm) 4.65 (s, 2H), 5.41 (br s, 2H), 5.74 (br s, 1H), 6.90-7.09 (m, 5H), 7.22-7.30 (m, 4H).

Example 69

Synthesis of 2-(aminooxy)-2-phenylethanol

Methyl 2-aminooxy-2-phenylacetate (35 mg, 0.193 mmol) was dissolved in ether (3 mL) and LAH (1 M in THF, 0.39 mL, 0.387 mmol) was added at 0° C. The mixture was allowed to warm to room temperature over 2 h, and then quenched with water (0.3 mL) and 10% NaOH (0.3 mL) and additional water (1 mL). The product was extracted with ethyl acetate and the organic phase was washed with brine, dried and evaporated. The crude product was purified by silica gel flash column chromatography using 48% EtOAc/hexanes as eluent to yield the desired alcohol as clear oil (15 mg, 0.098 mmol, 51%). $^1$H NMR (CDCl$_3$, 400 MHz): δ (ppm) 2.38 (br s, 1H), 2.82 (br s, 2H), 3.62-3.67 (dd, 1H, J=8, 11.2 Hz), 3.73-3.76 (dd, 1H, J=3.6, 11.6 Hz), 4.79-4.82 (dd, 1H, J=3.2, 8 Hz), 7.25-7.36 (m, 5H).

Example 70

Synthesis of 4-(aminooxy)-4-phenylbutan-1-ol

Methyl 4-(aminooxy)-4-phenylbutanoate (45 mg, 0.215 mmol) was dissolved in ether (3 mL) and LAH (1 M in THF, 0.4 mL, 0.431 mmol) was added at 0° C. The mixture was allowed to warm to room temperature over 2 h, and then quenched with water (0.3 mL) and 10% NaOH (0.3 mL) and additional water (1 mL). The product was extracted with ethyl acetate and the organic phase was washed with brine, dried and evaporated. The crude product was purified by silica gel flash column chromatography using 48% EtOAc/hexanes as eluent to yield the desired alcohol as clear oil (18 mg, 0.099 mmol, 46%). $^1$H NMR (CDCl$_3$, 400 MHz): δ (ppm) 1.62-1.68 (m, 2H), 1.80-1.87 (m, 2H), 2.68 (br s, 2H), 3.62-3.67 (m, 2H), 4.68-4.72 (m, 1H), 7.24-7.33 (m, 5H).

Example 71

Synthesis of (S)-3-(aminooxy)-3-phenylpropan-1-ol

A solution of TBS protected (R)-1-phenyl-1-aminooxy-3-propanol (199 mg, 0.708 mmol) in THF (3 mL) at was cooled to 0° C. TBAF (1 M in THF, 1.4 mL, 1.42 mmol) was added dropwise. The reaction mixture was stirred at RT for 1 h and concentrated. The residue was dissolved in EtOAc (40 mL), washed with 3% sodium carbonate (10 mL) and dried over sodium sulfate. The solvent was removed under reduced pressure and the crude product was purified by silica gel flash column chromatography using 25%-40% EtOAc/hexanes as eluent to afford the desired alcohol as colorless oil (75 mg, 0.449 mmol, 63%). $^1$H NMR (CDCl$_3$, 400 MHz): δ (ppm) 1.82-1.88 (m, 2H), 2.02-2.09 (m, 2H), 2.28 (br s, 1H), 3.69-3.77 (m, 2H), 4.70-4.73 (dd, 1H, J=4.4, 8.8 Hz), 5.27 (br s, 2H), 7.27-7.38 (m, 5H).

Example 72

General Method for the Synthesis of Aryl Hydroxylamine Compounds

In a 20 mL vial containing N-hydroxypthalamide (1 equiv), CuCl (1 equiv), freshly activated 4 Å molecular sieves (500 mg), and 1-naphthaleneboronic acid (2 equiv). The 1,2-dichloroethane solvent (5 mL) was added followed by pyridine (1.1 equiv), resulting in a light brown suspension. The cap was loosely applied such that the reaction was open to the atmosphere. Reaction progress was followed by TLC and was complete in 48 h. The reaction mixture became green as the reaction proceeded. The reaction products were adsorbed to SiO2 and the solvent was removed under reduced pressure. Chromatography of the reaction mixture (hexanes followed by DCM) afforded product as a light brown liquid. To the solution of phthalimide protected hydroxylamine and ethanol at room temperature, hydrazine hydrate (2 equiv) was added drop wise. The reaction was allowed to run for 1 hour at 50° C. The solution was filtered to remove the white precipitate and was concentrated under reduced pressure. To the concentrated mixture ethyl ether was added and the resulting solution was filtered and dried in to give pure product.

The following compounds (Table E) were prepared essentially according to the preceding example with the proper substitution of starting materials:

TABLE E

| Compound | Yield (%) | $^1$H NMR (CDCl$_3$ unless otherwise noted): δ (ppm) |
|---|---|---|
| O-phenylhydroxylamine | 43 | 6.84-6.89 (m, 1 H), 7.03-7.09 (m, 2 H), 7.19-7.25 (m, 2 H) |
| O-(naphthalen-1-yl)hydroxylamine | 35 | 7.16 (dd, 1 H, J = 9 Hz), 7.24-7.32 (m, 1 H), 7.35-7.42 (m, 1 H), 7.55 (d, 1 H, J = 2 Hz), 7.67-7.76 (m, 3 H) |

Example 73

Synthesis of 2-(benzyloxy)-1-phenylethanol

A solution of benzoyloxyacetaldehyde (350 mg, 2.33 mmol) and THF (10 mL) was flushed with nitrogen and cooled to 0° C. and phenylmagnesium bromide (2.6 mL, 2.6 mmol, 1M in THF) was added drop wise. The resulting solution was allowed to stir for additional 12 hours at room temperature. After reaction was finished the reaction mixture was cooled to 0° C. and 1 mL of water was added drop wise. The mixture was concentrated in vacuum and diluted with DCM washed with NaHCO$_3$ solution, water, and brine respectively. The organic layer was dried with Na$_2$SO$_4$ and concentrated. The crude product was purified by column chromatography using hexanes and EtOAc (10:1) as eluent. The pure product was obtained as colorless oil in 83% yield. $^1$H NMR (DMSO-d6, 400 MHz): 3.36-3.50 (m, 2H), 4.65 (s, 2H), 4.69-4.73 (m, 1H), 5.37 (d, 1H, J=4.4 Hz), 5.20-5.33 (m, 1H), 7.18-7.32 (m, 10H).

Example 74

Synthesis of 1,3-diphenylpropan-1-ol

Solution of hydrocinnamaldehyde (540 mg, 4.0 mmol) and THF was flushed with nitrogen and cooled to 0° C. and Phenylmagnesium bromide (4.4 mL, 1M in THF) was added dropwise. The resulting solution was allowed to stir for additional 12 hours at room temperature. After reaction was finished the reaction mixture was cooled to 0° C. and 1 mL of water was added dropwise. The mixture was concentrated in vacuum and diluted with DCM washed with NaHCO$_3$ solution, water, and brine respectively. The organic layer was dried with Na$_2$SO$_4$ and concentrated. The crude product was purified by column chromatography using hexanes and EtOAc (10:1) as eluent. The product was obtained as pale yellow oil in 58% yield. $^1$H NMR (DMSO-d6, 400 MHz): 1.80-1.87 (m, 2H), 2.52-2.62 (m, 2H), 4.46-4-51 (m, 1H), 5.24 (d, 1H, J=4.8 Hz), 7.09-7.14 (m, 3H), 7.16-7.25 (m, 3H) 7.27-7.31 (m, 4H).

Example 75

Synthesis of 3-cyclohexyl-1-phenylpropan-1-ol

To the stirred solution of CuI and THF (5 mL) at −78° C. and under nitrogen cyclohexylmethyl magnesium bromide (7.2 mL, 3.6 mmol, 0.5 M in THF) was added. This mixture was allowed to stir for additional 10 minutes and styrene oxide (360.5 mg, 3 mmol) dissolved in 1 mL of THF was added. The resulting mixture was stir overnight at room temperature. After the reaction was over water 5 mL was added. The mixture was concentrated in vacuum and diluted with DCM washed with $NaHCO_3$ solution, water, and brine respectively. The organic layer was dried with $Na_2SO_4$ and concentrated. The crude mixture was purified by column chromatography using EtOAc/Hexanes (1:10) to give the desired product as colorless liquid in 17% yield. $^1$H NMR ($CDCl_3$, 400 MHz): 0.71-0.90 (m, 2H), 1.08-1.34 (m, 6H), 1.60-1.82 (m, 7H), 1.90 (br. s, 1H), 4.58-5.59 (m, 1H), 7.31-7.34 (m, 1H) 7.23-7.28 (m, 4H).

Example 76

Synthesis of tert-Butyl 2-hydroxy-2-phenylethylcarbamate

To a solution of 2-amino-1-phenylethanol (685 mg, 5.0 mmol) in dichloromethane (20 mL), triethylamine (1.04 mL, 7.5 mmol) followed by di-tert-butyl dicarbonate (1.14 mL, 5.0 mmol) were added. The reaction mixture was stirred overnight at room temperature then saturated ammonium chloride solution added. The phases were separated and the aqueous layer extracted with dichloromethane (2×30 mL). The combined organic layers were dried over sodium sulfate, filtered and concentrated. The product was purified by column chromatography using EtOAc/hexanes (1:2) as eluent to give desired product as white solid in 83% yield. $^1$H NMR ($CDCl_3$, 400 MHz): 1.45 (s, 9H); 3.0 (s, 1H), 3.27-3.47 (m, 2H), 4.84 (m, 1H), 4.91 (br. s, 1H), 7.28-7.37 (m, 5H).

Example 77

Synthesis of tert-Butyl 2-(1,3-dioxoisoindolin-2-yloxy)-2-phenylethylcarbamate

To the solution of tert-Butyl 2-hydroxy-2-phenylethylcarbamate (878.0 mg, 3.6 mmol), N-hydroxyphthalimide (664.2 mg, 4.06 mmol), and triphenylphosphine (1067.6 mg, 4.06 mmol) in THF (16 mL), Diethyl azodicarboxylate (DEAD) (1.66 mL, 4.06 mmol, 40 wt % in toluene) was added dropwise. The solution was allowed to stir at 50° C. for 12 h. Water (5 mL) was added after the reaction was over. The organic layer was extracted in DCM and was dried over sodium sulfate. After concentrating in vacuum the crude product was purified by silica gel flash column chromatography using EtOAc/hexanes (1:2) as eluent to give desired product as off white solid in 69% yield. $^1$H NMR ($CDCl_3$, 400 MHz): 1.42 (s, 9H); 3.52-3.68 (m, 2H), 5.25-5.50 (m, 1H), 5.56 (br. s, 1H), 7.25-7.40 (m, 3H), 7.41-7.59 (m, 2H), 7.72-7.82 (m, 4H).

Example 78

Synthesis of 2-(2-amino-1-phenylethoxy)isoindoline-1,3-dione

To a solution of tert-Butyl 2-aminooxy-2-phenylethylcarbamate (554.4 mg, 2.2 mmol) in dichloromethane (5 ml) was added trifluoroacetic acid (2 ml). The mixture was stirred at room temperature for 1 h and concentrated under reduced pressure to yield the desired crude product as clear oil. The crude product was then purified by column chromatography using MeOH/DCM (10:90) as an eluent to give the product as colorless oil in 72% yield. $^1$H NMR ($CDCl_3$, 400 MHz): 3.40-3.51 (m, 1H); 3.57-3.66 (m, 1H); 5.50-5.52 (m, 1H), 7.32-7.45 (m, 3H), 7.46-7.51 (m, 2H), 7.57-7.62 (m, 4H). 8.61 (br, s, 2H).

Example 79

Synthesis of N-(2-(1,3-dioxoisoindolin-2-yloxy)-2-phenylethyl)acetamide

To a solution of 2-amino-1-phenylethanol (400.0 mg, 1.41 mmol) in THF (5 mL) was added $NaHCO_3$ (238 mg, 2.83 mmol) and cooled to 0° C. Acetyl chloride (0.11 mL, 1.56 mmol) was added and the reaction mixture stirred at room temperature for 4 h. The THF was removed under reduced pressure and 5 mL of water was added to the remaining solution. The aqueous layer was extracted with dichloromethane (3×10 mL). The combined organic layers were dried over sodium sulfate, filtered and concentrated. The crude product was then purified by column chromatography using ethyl acetate as an eluent to give the product as colorless oil in 71% yield. $^1$H NMR ($CDCl_3$, 400 MHz): 2.06 (s, 3H); 3.63-3.68 (m, 1H); 3.82-3.88 (m, 1H), 5.17-5.20 (m, 1H), 6.82 (br, s, 1H), 7.15-7.42 (m, 3H), 7.45-7.50 (m, 2H), 7.67-7.91 (m, 4H).

Example 80

Synthesis of N-(2-(aminooxy)-2-phenylethyl)acetamide

To the solution of N-(2-(1,3-dioxoisoindolin-2-yloxy)-2-phenylethyl)acetamide (83 mg, 0.25 mmol) and ethanol (3 mL), methyl hydrazine (0.25 mL, 1M solution in Ethanol) was added drop wise. The reaction was allowed to run for 1 hour at room temperature. The solution was filtered to remove the white precipitate and was concentrated. Ethyl ether was added and the resulting solution was filtered and dried in vacuum to give the desired product as white solid in 51% yield. $^1$H NMR (DMSO, 400 MHz): 1.75 (s, 3H); 3.22-3.32 (m, 1H), 4.43-4.62 (m, 1H), 5.89 (br, s, 2H), 7.03-7.25 (m, 3H), 7.26-7.34 (m, 2H), 7.89 (br, s, 1H).

Example 81

Synthesis of tert-Butyl 3-hydroxy-3-phenylpropyl(methyl)carbamate

To a solution of 3-(methylamino)-1-phenylpropan-1-ol (495 mg, 3 mmol) in dichloromethane (8 mL), triethylamine (0.62 mL, 4.5 mmol), followed by di-tert-butyl dicarbonate (0.68 mL, 3 mmol) were added. The reaction mixture was stirred overnight at room temperature then saturated ammonium chloride solution added. The phases were separated and the aqueous layer extracted with dichloromethane (2×30 mL). The combined organic layers were dried over sodium sulfate, filtered and concentrated and purified by column chromatography using EtOAc/hexanes (1:5) as an eluent to give the product as colorless oil in 67% yield. $^1$H NMR (300 MHz, $CDCl_3$): 1.46 (s, 9H), 1.86-2.02 (m, 2H), 2.86 (s, 3H), 3.08 (br, s, 1H), 3.86 (br, s, 1H), 4.59 (d, 1H, J=7.7 Hz), 7.35-7.23 (m, 5H).

Example 82

Synthesis of tert-Butyl 3-(1,3-dioxoisoindolin-2-yloxy)-3-phenylpropyl(methyl)carbamate To the solution of tert-Butyl 2-hydroxy-2-phenylethylcarbamate (785.0 mg, 3.0 mmol), N-hydroxyphthalimide (579.0 mg, 3.55 mmol), and triphenylphosphine (930.1 mg, 3.55 mmol) in THF (12 mL), Diethyl azodicarboxylate (DEAD) (1.50 mL, 3.55 mmol, 40 wt % in toluene) was added dropwise. The solution was allowed to stir at 50° C. for 12 h. Water (5 mL) was added after the reaction was over. The organic layer was extracted in DCM and was dried over sodium sulfate. After concentrating in vacuum the crude product was purified by silica gel flash column chromatography using EtOAc/hexanes (1:2) as eluent to give desired product as off white solid in 69% yield. $^1$H NMR (CDCl$_3$, 400 MHz): 1.38 (s, 9H); 1.98-2.2 (m, 1H), 2.30-2.42 (m, 1H), 2.85 (s, 3H), 3.25-3.44 (m, 2H), 5.25-5.32 (m, 1H), 7.22-7.35 (m, 3H), 7.38-7.47 (m, 2H), 7.55-7.72 (m, 4H).

Example 83

Synthesis of 3-(Ammoniooxy)-N-methyl-3-phenylpropan-1-aminium chloride

To the solution of tert-butyl 3-(1,3-dioxoisoindolin-2-yloxy)-3-phenylpropyl(methyl)carbamate (410 mg, 1 mmol) and ethanol (3 mL) at room temperature Hydrazine Hydrate (3 mL, 1M solution in Ethanol) was added drop wise. The reaction was allowed to run for 1 hour. The solution was filtered to remove the white precipitate and was concentrated. Ethyl ether was added and the resulting solution was filtered and dried in vacuum. Resulting solid was dissolved in 2 mL of dioxane and solution of HCl (2 mL, 4M in Dioxane) was added drop wise. The resulting solution was allowed to stir for 24 h at room temperature. The white precipitate was collected by filtration and dried in vacuum to give the desired product in 83% overall yield. $^1$H NMR (CDCl$_3$, 400 MHz): 2.0-2.10 (m, 1H), 2.14-2.32 (m, 1H), 2.46 (s, 3H), 2.64-3.00 (m, 2H), 5.20-5.33 (m, 1H), 7.31-7.48 (m, 5H), 9.21 (br, s, 2H), 11.05 (br, s, 3H).

Example 84

Virtual Screening of IDO Inhibitors and Molecular Docking

The published crystal structure of human IDO complexed with cyanide (pdb code:2D01) or with the IDO inhibitor 4-phenylimidazole (pdb code:2D0T) has been published by Sugimoto et al. (Sugimoto et at 2006, Proc. Natl. Acad. Sci. USA, 103(8) 2611-2616). Additionally, site directed mutagenesis and comparison with the mouse IDO aminoacid sequence identified aminoacids important for catalysis and substrate binding.

All molecular modeling studies including docking were carried out using GLIDE v4.0 (SCHRODINGER L.L.C, New York). The published X-ray crystal structure of the human IDO complexed with 4-phenylimidazole provided the structural framework for molecular docking studies.

A database with a library of 400,000 compounds was obtained from Albany Molecular Research Inc (Albany, N.Y.). Glide scores were obtained for known IDO inhibitors and used as reference to evaluate the results for other series of compounds. The known IDO inhibitors docked were: a) 1-methyl-tryptophan (Docking Score: −9.31), b) 4-phenylimidazole (Docking Score: −7.96), c) brassinin (Docking Score: −5.07) and d) 3-butyl-b-carboline (a non-competitive inhibitor, docking score: N/A). The more negative the value of the docking score, the better the result for the respective compounds. The calculations for known reference competitive inhibitors of IDO suggested that values between −7 kcal/mol and −10 kcal/mol would indicate compounds that are likely inhibitors of IDO. The library of 400,000 compounds was docked at the active site of IDO, yielding 852 structures with acceptable binding. The top 10% of these structures (88 compounds) were selected and used as a query in a 2D similarity search on a more extensive library of compounds (ACD). This broadened the diversity set of compounds to ~30000 structures, which were subsequently docked using more stringent docking parameters (fine tuning of structures), yielding ~800 structures with good docking scores (shown in Tables 1-11).

In addition to compounds identified via virtual screening, several rationally designed IDO inhibitors were docked to IDO to evaluate their potential as good IDO inhibitors. Such compounds belong to families of known IDO inhibitors such as derivatives of brassinin, analogs of tryptophan, indole derivatives, known metal chelators, naphtoquinones, and compounds that mimic the transition state of tryptophan dioxygenation. The whole focused set of compounds was re-docked, yielding ~1200 compounds with favorable docking scores (shown in Tables 1-11 of the present application). Docking scores for the compounds in Tables 1-12 are report in Table 13.

TABLE 13

| Cmpd # | Docking Score (kcal/mol) |
|---|---|
| 00001 | −8.56 |
| 00002 | −7.98 |
| 00003 | −8.71 |
| 00004 | −8.25 |
| 00006 | −8.24 |
| 00007 | −8.8 |
| 00008 | −8.91 |
| 00009 | −7.24 |
| 00010 | −7.83 |
| 00012 | −8.6 |
| 00020 | −6.56 |
| 00021 | −8.07 |
| 00027 | −8.5 |
| 00028 | −7.61 |
| 00030 | −8.61 |
| 00047 | −6.1 |
| 00053 | −8.58 |
| 00062 | −8.18 |
| 00063 | −7.62 |
| 00064 | −7.28 |
| 00077 | −6.04 |
| 00078 | −8.13 |
| 00079 | −7.23 |
| 00080 | −8.24 |
| 00081 | −7.6 |
| 00138 | −9.56 |
| 00140 | −9.05 |
| 00141 | −7.36 |
| 00142 | −7 |
| 00144 | −6.73 |
| 00145 | −6.84 |
| 00146 | −6.62 |
| 00147 | −6.95 |
| 00148 | −6.03 |
| 00149 | −5.25 |
| 00150 | −6.63 |
| 00151 | −7.35 |

TABLE 13-continued

| Cmpd # | Docking Score (kcal/mol) |
|---|---|
| 00152 | −5.6 |
| 00154 | −6.64 |
| 00155 | −6.73 |
| 00157 | −5.93 |
| 00167 | −6.48 |
| 00168 | −7.75 |
| 00209 | −6.69 |
| 00210 | −9.02 |
| 00214 | −7.58 |
| 00215 | −8.4 |
| 00216 | −6.17 |
| 00217 | −7.27 |
| 00218 | −6.57 |
| 00219 | −7.73 |
| 00220 | −7 |
| 00221 | −6.4 |
| 00222 | −7.49 |
| 00224 | −6.14 |
| 00225 | −7.6 |
| 00226 | −7.64 |
| 00228 | −7.09 |
| 00230 | −8.61 |
| 00233 | −7.24 |
| 00239 | −7.9 |
| 00240 | −8.6 |
| 00252 | −7.06 |
| 00254 | −8.31 |
| 00256 | −8.65 |
| 00261 | −8 |
| 00262 | −7.39 |
| 00267 | −8.27 |
| 00268 | −6.56 |
| 00271 | −7.65 |
| 00272 | −6.37 |
| 00281 | −6.3 |
| 00282 | −8.22 |
| 00288 | −8.8 |
| 00289 | −5.52 |
| 00291 | −5.65 |
| 00292 | −8.32 |
| 00293 | −8.08 |
| 00300 | −8.62 |
| 00305 | −6.9 |
| 00307 | −7.65 |
| 00309 | −6.08 |
| 00310 | −8.44 |
| 00311 | −6.97 |
| 00312 | −7.84 |
| 00313 | −8.24 |
| 00317 | −8.06 |
| 00319 | −8.03 |
| 00320 | −6.2 |
| 00324 | −6.77 |
| 00325 | −8.82 |
| 00327 | −8.78 |
| 00332 | −7.66 |
| 00334 | −6.05 |
| 00335 | −9.29 |
| 00337 | −6.49 |
| 00342 | −6.78 |
| 00343 | −8.63 |
| 00345 | −6.81 |
| 00346 | −7.18 |
| 00347 | −8.11 |
| 00348 | −6.75 |
| 00352 | −9.49 |
| 00356 | −6.91 |
| 00360 | −7.44 |
| 00363 | −6.97 |
| 00364 | −6.31 |
| 00366 | −7.53 |
| 00367 | −7.43 |
| 00368 | −8.02 |
| 00378 | −7.53 |
| 00379 | −8.44 |
| 00380 | −6.79 |

TABLE 13-continued

| Cmpd # | Docking Score (kcal/mol) |
|---|---|
| 00382 | −5.85 |
| 00385 | −7.62 |
| 00386 | −9.31 |
| 00388 | −9.05 |
| 00389 | −8.63 |
| 00390 | −8.94 |
| 00391 | −5.82 |
| 00392 | −5.93 |
| 00394 | −7.85 |
| 00396 | −7.84 |
| 00398 | −6.07 |
| 00464 | −6.29 |
| 00477 | −6.12 |
| 00507 | −6.55 |
| 00515 | −5.22 |
| 00516 | −4.69 |
| 00523 | −3.79 |
| 00525 | −4.28 |
| 00526 | −7.67 |
| 00527 | −6.32 |
| 00528 | −6.41 |
| 00530 | −5.91 |
| 00531 | −4.57 |
| 00532 | −5.24 |
| 00533 | −6.16 |
| 00535 | −6.64 |
| 00539 | −6.2 |
| 00541 | −5.54 |
| 00545 | −6.99 |
| 00546 | −6.97 |
| 00549 | −6.44 |
| 00550 | −6.87 |
| 00552 | −9.11 |
| 00553 | −9.64 |
| 00554 | −8.12 |
| 00555 | −8.23 |
| 00561 | −10.64 |
| 00562 | −10.44 |
| 00563 | −10.3 |
| 00564 | −10.27 |
| 00565 | −10.22 |
| 00566 | −10.17 |
| 00567 | −10.11 |
| 00568 | −9.96 |
| 00571 | −9.87 |
| 00572 | −9.83 |
| 00577 | −9.72 |
| 00578 | −9.65 |
| 00586 | −9.49 |
| 00587 | −9.46 |
| 00588 | −9.45 |
| 00589 | −9.45 |
| 00590 | −9.42 |
| 00591 | −9.38 |
| 00592 | −9.35 |
| 00593 | −9.32 |
| 00596 | −9.29 |
| 00599 | −9.21 |
| 00601 | −9.19 |
| 00602 | −9.18 |
| 00603 | −9.14 |
| 00604 | −9.14 |
| 00605 | −9.13 |
| 00606 | −9.11 |
| 00607 | −9.11 |
| 00608 | −9.1 |
| 00610 | −9.09 |
| 00611 | −9.08 |
| 00613 | −9.04 |
| 00616 | −9 |
| 00620 | −8.97 |
| 00621 | −8.97 |
| 00622 | −8.97 |
| 00623 | −8.95 |
| 00627 | −8.92 |
| 00628 | −8.92 |

TABLE 13-continued

| Cmpd # | Docking Score (kcal/mol) |
|---|---|
| 00630 | −8.89 |
| 00632 | −8.88 |
| 00634 | −8.86 |
| 00636 | −8.85 |
| 00637 | −8.84 |
| 00644 | −8.8 |
| 00645 | −8.79 |
| 00646 | −8.78 |
| 00649 | −8.76 |
| 00650 | −8.75 |
| 00655 | −8.71 |
| 00656 | −8.71 |
| 00657 | −8.7 |
| 00658 | −8.69 |
| 00660 | −8.68 |
| 00662 | −8.67 |
| 00663 | −8.66 |
| 00664 | −8.65 |
| 00665 | −8.64 |
| 00667 | −8.64 |
| 00668 | −8.63 |
| 00669 | −8.61 |
| 00670 | −8.61 |
| 00671 | −8.61 |
| 00672 | −8.58 |
| 00673 | −8.58 |
| 00674 | −8.57 |
| 00675 | −8.57 |
| 00678 | −8.56 |
| 00681 | −8.53 |
| 00682 | −8.53 |
| 00683 | −8.53 |
| 00685 | −8.52 |
| 00686 | −8.5 |
| 00687 | −8.49 |
| 00688 | −8.49 |
| 00689 | −8.49 |
| 00690 | −8.48 |
| 00691 | −8.48 |
| 00692 | −8.47 |
| 00695 | −8.46 |
| 00697 | −8.46 |
| 00698 | −8.45 |
| 00699 | −8.44 |
| 00700 | −8.44 |
| 00701 | −8.44 |
| 00705 | −8.43 |
| 00707 | −8.42 |
| 00711 | −8.4 |
| 00714 | −8.4 |
| 00716 | −8.39 |
| 00717 | −8.39 |
| 00718 | −8.38 |
| 00720 | −8.37 |
| 00721 | −8.36 |
| 00722 | −8.36 |
| 00724 | −8.36 |
| 00725 | −8.36 |
| 00727 | −8.35 |
| 00729 | −8.34 |
| 00732 | −8.34 |
| 00737 | −8.31 |
| 00738 | −8.3 |
| 00739 | −8.3 |
| 00740 | −8.29 |
| 00741 | −8.29 |
| 00744 | −8.28 |
| 00745 | −8.26 |
| 00746 | −8.26 |
| 00748 | −8.26 |
| 00749 | −8.25 |
| 00750 | −8.25 |
| 00751 | −8.62 |
| 00752 | −8.25 |
| 00753 | −8.25 |
| 00755 | −8.23 |
| 00757 | −8.21 |
| 00758 | −8.21 |
| 00759 | −8.21 |
| 00760 | −8.2 |
| 00761 | −8.2 |
| 00762 | −8.2 |
| 00764 | −8.18 |
| 00766 | −8.17 |
| 00767 | −8.16 |
| 00768 | −8.15 |
| 00770 | −8.15 |
| 00772 | −8.15 |
| 00773 | −8.14 |
| 00774 | −8.14 |
| 00775 | −8.14 |
| 00777 | −8.14 |
| 00778 | −8.13 |
| 00781 | −8.12 |
| 00782 | −8.11 |
| 00783 | −8.11 |
| 00784 | −8.09 |
| 00786 | −8.08 |
| 00787 | −8.07 |
| 00788 | −8.07 |
| 00789 | −8.06 |
| 00791 | −8.04 |
| 00793 | −8.03 |
| 00796 | −8 |
| 00797 | −8 |
| 00799 | −8 |
| 00801 | −8 |
| 00803 | −7.99 |
| 00805 | −7.99 |
| 00806 | −7.99 |
| 00807 | −7.98 |
| 00808 | −7.98 |
| 00809 | −7.97 |
| 00810 | −7.97 |
| 00811 | −7.97 |
| 00812 | −7.96 |
| 00813 | −7.96 |
| 00814 | −7.96 |
| 00815 | −7.96 |
| 00819 | −7.95 |
| 00820 | −7.95 |
| 00821 | −7.94 |
| 00822 | −7.94 |
| 00824 | −7.94 |
| 00827 | −7.94 |
| 00828 | −7.92 |
| 00830 | −7.92 |
| 00834 | −7.91 |
| 00835 | −7.9 |
| 00836 | −7.9 |
| 00837 | −7.89 |
| 00840 | −7.89 |
| 00843 | −7.88 |
| 00848 | −7.87 |
| 00849 | −7.86 |
| 00850 | −7.86 |
| 00852 | −7.85 |
| 00855 | −7.84 |
| 00856 | −7.84 |
| 00857 | −7.83 |
| 00858 | −7.83 |
| 00861 | −7.81 |
| 00862 | −7.81 |
| 00864 | −7.81 |
| 00867 | −7.79 |
| 00868 | −7.79 |
| 00869 | −7.78 |
| 00870 | −7.77 |
| 00871 | −7.77 |
| 00872 | −7.77 |
| 00874 | −7.76 |
| 00875 | −7.76 |

TABLE 13-continued

| Cmpd # | Docking Score (kcal/mol) |
|---|---|
| 00877 | −7.76 |
| 00880 | −7.74 |
| 00881 | −7.74 |
| 00882 | −7.74 |
| 00883 | −7.73 |
| 00886 | −7.72 |
| 00887 | −7.72 |
| 00888 | −7.71 |
| 00889 | −7.71 |
| 00890 | −7.71 |
| 00891 | −7.68 |
| 00892 | −7.68 |
| 00894 | −7.67 |
| 00895 | −7.67 |
| 00896 | −7.67 |
| 00897 | −7.66 |
| 00898 | −7.66 |
| 00899 | −7.66 |
| 00900 | −7.65 |
| 00901 | −7.65 |
| 00902 | −7.65 |
| 00903 | −7.64 |
| 00905 | −7.62 |
| 00906 | −7.62 |
| 00909 | −8 |
| 00910 | −7.61 |
| 00912 | −7.61 |
| 00913 | −7.6 |
| 00914 | −7.59 |
| 00915 | −7.59 |
| 00916 | −7.59 |
| 00917 | −7.59 |
| 00918 | −7.59 |
| 00919 | −7.59 |
| 00920 | −7.58 |
| 00921 | −7.57 |
| 00922 | −7.57 |
| 00924 | −7.57 |
| 00927 | −7.56 |
| 00929 | −7.52 |
| 00930 | −7.52 |
| 00931 | −7.52 |
| 00932 | −7.51 |
| 00934 | −7.5 |
| 00935 | −7.5 |
| 00938 | −7.48 |
| 00939 | −7.47 |
| 00940 | −7.47 |
| 00943 | −7.46 |
| 00944 | −7.45 |
| 00945 | −7.45 |
| 00946 | −7.45 |
| 00947 | −7.45 |
| 00949 | −7.45 |
| 00950 | −7.45 |
| 00951 | −7.45 |
| 00952 | −7.44 |
| 00953 | −7.44 |
| 00954 | −7.44 |
| 00955 | −7.44 |
| 00957 | −7.43 |
| 00958 | −7.43 |
| 00959 | −7.43 |
| 00960 | −7.42 |
| 00961 | −7.42 |
| 00963 | −7.42 |
| 00964 | −7.41 |
| 00965 | −7.41 |
| 00966 | −7.4 |
| 00967 | −7.4 |
| 00969 | −7.39 |
| 00970 | −7.39 |
| 00973 | −7.37 |
| 00974 | −7.35 |
| 00975 | −7.35 |
| 00976 | −7.35 |
| 00977 | −7.35 |
| 00978 | −7.35 |
| 00979 | −7.35 |
| 00980 | −7.34 |
| 00981 | −7.34 |
| 00982 | −7.34 |
| 00983 | −7.33 |
| 00984 | −7.33 |
| 00985 | −7.33 |
| 00988 | −7.31 |
| 00989 | −7.31 |
| 00990 | −7.31 |
| 00991 | −7.3 |
| 00993 | −7.29 |
| 00994 | −7.29 |
| 00995 | −7.29 |
| 00996 | −7.28 |
| 00997 | −7.28 |
| 00998 | −7.27 |
| 00999 | −7.27 |
| 01000 | −7.27 |
| 01001 | −7.26 |
| 01003 | −7.26 |
| 01004 | −7.26 |
| 01007 | −7.24 |
| 01008 | −7.24 |
| 01009 | −7.24 |
| 01010 | −7.24 |
| 01011 | −7.24 |
| 01012 | −7.24 |
| 01013 | −7.23 |
| 01014 | −7.23 |
| 01015 | −7.22 |
| 01016 | −7.22 |
| 01017 | −7.21 |
| 01018 | −7.21 |
| 01019 | −7.2 |
| 01020 | −7.2 |
| 01021 | −7.2 |
| 01022 | −7.19 |
| 01024 | −7.18 |
| 01026 | −7.17 |
| 01027 | −7.16 |
| 01028 | −7.16 |
| 01029 | −7.16 |
| 01030 | −7.16 |
| 01031 | −7.15 |
| 01033 | −7.15 |
| 01034 | −7.15 |
| 01036 | −7.14 |
| 01037 | −7.14 |
| 01038 | −7.13 |
| 01039 | −7.11 |
| 01040 | −7.11 |
| 01041 | −7.11 |
| 01042 | −7.1 |
| 01043 | −7.1 |
| 01044 | −7.09 |
| 01045 | −7.07 |
| 01046 | −7.07 |
| 01048 | −7.04 |
| 01051 | −7.04 |
| 01052 | −7.03 |
| 01056 | −7.01 |
| 01057 | −7 |
| 01058 | −7 |
| 01059 | −6.99 |
| 01060 | −6.97 |
| 01061 | −6.97 |
| 01062 | −6.97 |
| 01063 | −6.97 |
| 01064 | −6.96 |
| 01065 | −6.96 |
| 01066 | −6.94 |
| 01067 | −6.94 |
| 01068 | −6.94 |

TABLE 13-continued

| Cmpd # | Docking Score (kcal/mol) |
|---|---|
| 01069 | −6.92 |
| 01070 | −6.92 |
| 01071 | −6.92 |
| 01072 | −6.92 |
| 01073 | −6.91 |
| 01074 | −6.91 |
| 01075 | −6.91 |
| 01076 | −6.91 |
| 01077 | −6.91 |
| 01078 | −6.9 |
| 01079 | −6.9 |
| 01080 | −6.89 |
| 01081 | −6.89 |
| 01082 | −6.89 |
| 01083 | −6.88 |
| 01087 | −6.86 |
| 01088 | −6.86 |
| 01089 | −6.85 |
| 01090 | −6.85 |
| 01091 | −6.85 |
| 01092 | −6.84 |
| 01093 | −6.84 |
| 01094 | −6.83 |
| 01096 | −6.82 |
| 01098 | −6.81 |
| 01099 | −6.81 |
| 01100 | −6.81 |
| 01101 | −6.81 |
| 01104 | −6.79 |
| 01105 | −6.79 |
| 01106 | −6.78 |
| 01107 | −6.78 |
| 01108 | −6.78 |
| 01109 | −6.78 |
| 01110 | −6.77 |
| 01111 | −6.76 |
| 01113 | −6.74 |
| 01114 | −6.74 |
| 01115 | −6.73 |
| 01116 | −6.72 |
| 01118 | −6.72 |
| 01119 | −6.7 |
| 01120 | −6.7 |
| 01121 | −6.7 |
| 01123 | −6.69 |
| 01124 | −6.68 |
| 01125 | −6.68 |
| 01126 | −6.66 |
| 01127 | −6.64 |
| 01128 | −6.64 |
| 01129 | −6.63 |
| 01130 | −6.63 |
| 01131 | −6.63 |
| 01133 | −6.61 |
| 01134 | −6.6 |
| 01135 | −6.59 |
| 01137 | −6.58 |
| 01138 | −6.57 |
| 01139 | −6.57 |
| 01140 | −6.56 |
| 01141 | −6.56 |
| 01142 | −6.56 |
| 01143 | −6.55 |
| 01144 | −6.54 |
| 01145 | −6.52 |
| 01146 | −6.52 |
| 01147 | −6.51 |
| 01148 | −6.51 |
| 01149 | −6.51 |
| 01150 | −6.49 |
| 01151 | −6.48 |
| 01152 | −6.46 |
| 01153 | −6.46 |
| 01154 | −6.46 |
| 01156 | −6.44 |
| 01158 | −6.43 |

TABLE 13-continued

| Cmpd # | Docking Score (kcal/mol) |
|---|---|
| 01159 | −6.43 |
| 01160 | −6.42 |
| 01161 | −6.42 |
| 01163 | −6.4 |
| 01164 | −6.4 |
| 01165 | −6.39 |
| 01167 | −6.39 |
| 01168 | −6.38 |
| 01169 | −6.38 |
| 01170 | −6.38 |
| 01171 | −6.35 |
| 01173 | −6.33 |
| 01174 | −6.32 |
| 01175 | −6.32 |
| 01177 | −6.29 |
| 01178 | −6.29 |
| 01179 | −6.26 |
| 01180 | −6.26 |
| 01181 | −6.26 |
| 01182 | −6.25 |
| 01183 | −6.24 |
| 01184 | −6.23 |
| 01185 | −6.21 |
| 01187 | −6.21 |
| 01188 | −6.19 |
| 01189 | −6.19 |
| 01190 | −6.19 |
| 01191 | −6.16 |
| 01192 | −6.16 |
| 01194 | −6.13 |
| 01195 | −6.11 |
| 01196 | −6.1 |
| 01197 | −6.1 |
| 01198 | −6.07 |
| 01199 | −6.05 |
| 01200 | −6.03 |
| 01202 | −6.01 |
| 01204 | −6 |
| 01205 | −6 |
| 01206 | −5.98 |
| 01207 | −5.97 |
| 01209 | −5.95 |
| 01210 | −5.95 |
| 01212 | −5.92 |
| 01213 | −5.92 |
| 01214 | −5.91 |
| 01215 | −5.9 |
| 01217 | −5.88 |
| 01218 | −5.88 |
| 01219 | −5.86 |
| 01220 | −5.84 |
| 01222 | −5.8 |
| 01224 | −5.75 |
| 01225 | −5.74 |
| 01226 | −5.66 |
| 01228 | −5.6 |
| 01229 | −5.6 |
| 01230 | −5.56 |
| 01231 | −5.54 |
| 01232 | −5.51 |
| 01233 | −5.49 |
| 01234 | −5.48 |
| 01235 | −5.47 |
| 01236 | −5.42 |
| 01237 | −5.42 |
| 01238 | −5.34 |
| 01239 | −5.33 |
| 01240 | −5.26 |
| 01241 | −5.19 |
| 01242 | −5.14 |
| 01243 | −5.14 |
| 01244 | −5.1 |
| 01245 | −5.09 |
| 01246 | −5.03 |
| 01247 | −5.01 |
| 01248 | −4.91 |

TABLE 13-continued

| Cmpd # | Docking Score (kcal/mol) |
|---|---|
| 01249 | −4.87 |
| 01250 | −4.86 |
| 01251 | −4.82 |
| 01252 | −4.82 |
| 01253 | −4.8 |
| 01254 | −4.67 |
| 01255 | −4.66 |
| 01256 | −4.52 |
| 01257 | −3.63 |
| 01258 | −3.5 |
| 01259 | −3.43 |
| 01260 | −8.06 |
| 01261 | −8.68 |
| 01262 | −9.34 |
| 01263 | −7.45 |
| 01264 | −7.51 |
| 01265 | −6.92 |
| 01266 | −7.48 |
| 01267 | −7.87 |
| 01268 | −8.81 |
| 01269 | −8.32 |
| 01270 | −8.9 |
| 01271 | −9.3 |
| 01272 | −8.3 |
| 01273 | −8.75 |
| 01274 | −8.41 |
| 01275 | −8.54 |
| 01276 | −9 |
| 01277 | −8.11 |
| 01278 | −8.88 |
| 01279 | −8.71 |
| 01280 | −8.61 |
| 01281 | −8.29 |
| 01282 | −7.3 |
| 01283 | −9.08 |
| 01284 | −6.02 |
| 01285 | −8.67 |
| 01286 | −8.42 |
| 01287 | −8.11 |
| 01288 | −7.4 |
| 01289 | −7.76 |
| 01290 | −7.47 |
| 01291 | −8.03 |
| 01292 | −6.99 |
| 01293 | −8.52 |
| 01294 | −7.91 |
| 01295 | −7.17 |
| 01296 | −6.95 |
| 01298 | −7.27 |
| 01299 | −8.39 |
| 01300 | −8.57 |
| 01301 | −8.72 |
| 01302 | −8.12 |
| 01305 | −9.18 |
| 01306 | −8.99 |
| 01307 | −8.93 |
| 01308 | −9.24 |
| 01309 | −8.99 |
| 01310 | −9.21 |
| 01311 | −5.72 |
| 01360 | −8.27 |
| 01361 | −8.01 |
| 01362 | −6.42 |
| 01363 | −6.38 |
| 01364 | −6.77 |
| 01365 | −8.65 |
| 01366 | −5.7 |
| 01367 | −8.92 |
| 01368 | −8.89 |
| 01369 | −8.57 |
| 01370 | −7.91 |
| 01371 | −7.65 |
| 01372 | −7.96 |
| 01373 | −6.63 |
| 01374 | −8.06 |
| 01375 | −7.4 |
| 01376 | −5.83 |
| 01377 | −6.24 |
| 01378 | −7.85 |
| 01379 | −7.04 |
| 01380 | −7.8 |
| 01381 | −7.7 |
| 01382 | −7.91 |
| 01383 | −6.63 |
| 01384 | −6.69 |
| 01385 | −6.81 |
| 01386 | −3.58 |
| 01387 | −10.21 |
| 01388 | −5.56 |
| 01389 | −6.8 |
| 01390 | −5.2 |
| 01391 | −9.34 |
| 01392 | −8.41 |
| 01393 | −6.19 |
| 01394 | −3.58 |
| 01395 | −4.35 |
| 01396 | −4.24 |
| 01397 | −6.7 |
| 01398 | −7.22 |
| 01399 | −7.35 |
| 01400 | −4.29 |
| 01401 | −5.75 |
| 01402 | −6.96 |
| 01403 | −8.93 |
| 01404 | −7.78 |
| 01406 | −8.09 |
| 01407 | −5.12 |
| 01408 | −5.23 |
| 01409 | −4.43 |
| 01410 | −5.44 |
| 01410 | −5.44 |
| 01411 | −4.19 |
| 01412 | −7.09 |
| 01413 | −6.52 |
| 01414 | −7.71 |
| 01415 | −6.1 |
| 01416 | −5.18 |
| 01417 | −6.51 |
| 01418 | −5.29 |
| 01419 | −5.33 |
| 01420 | −8.16 |
| 01421 | −7.05 |
| 01422 | −7.38 |
| 01423 | −6.99 |
| 01424 | −7.05 |
| 01425 | −6.76 |
| 01427 | −4.02 |
| 01429 | −7.11 |
| 01430 | −5.3 |
| 01431 | −7.11 |
| 01432 | −5.86 |
| 01433 | −6.42 |
| 01434 | −6.1 |
| 01435 | −7.28 |
| 01436 | −8.59 |
| 01438 | −6.91 |
| 01439 | −5.89 |
| 01440 | −9.26 |
| 01442 | −9.3 |
| 01443 | −8.26 |
| 01444 | −9.85 |
| 01445 | −9.38 |
| 01446 | −8.11 |
| 01447 | −8.13 |
| 01448 | −8.52 |
| 01449 | −6.89 |
| 01450 | −4.88 |
| 01451 | −6.51 |
| 01452 | −4.98 |
| 01453 | −6.97 |
| 01454 | −4.33 |
| 01455 | −5.72 |

TABLE 13-continued

| Cmpd # | Docking Score (kcal/mol) |
|---|---|
| 01456 | −5.63 |
| 01457 | −5.72 |
| 01458 | −8.89 |
| 01459 | −5.73 |
| 01460 | −5.42 |
| 01461 | −6.68 |
| 01462 | −6.51 |
| 01463 | −6.02 |
| 01464 | −6.15 |
| 01465 | −6.55 |
| 01467 | −5.56 |
| 01469 | −5.9 |
| 01470 | −6.25 |
| 01471 | −4.97 |
| 01472 | −5.25 |
| 01473 | −6.81 |
| 01474 | −6.22 |
| 01475 | −6.86 |
| 01476 | −6.96 |
| 01478 | −8.09 |
| 01479 | −8.31 |
| 01480 | −5.93 |
| 01481 | −6.41 |
| 01482 | −6.83 |
| 01483 | −5.77 |
| 01484 | −5.96 |
| 01485 | −5.34 |
| 01486 | −5.61 |
| 01487 | −5.34 |
| 01488 | −7.08 |
| 01489 | −6.71 |
| 01490 | −6.47 |
| 01491 | −6.95 |

Example 85

Human IDO Protein Cloning, Expression and Purification

Expression vectors for human indoleamine-2,3-dioxygenase (IDO) protein were prepared by amplification of a 1219 bp fragment of the sequence present in vector phIDO6His cDNA with primers 5'-ggagcatgctaATGGCA-CACGCTATGGAAAAC-3' and 5'-gagagatctACCTTCCT-TCAAAAGGGATTTC-3' and cloning the SphI-BglII 1213 bp fragment into pQE70 (Qiagen), to yield vector pQE70-hIDO. This construct adds 2 extra amino acids and a 6-Histidine tag to the C-terminus of the natural human IDO protein while preserving intact the natural start codon and N-terminus amino acid sequence. The amplified allele of human IDO shows two polymorphisms with respect to the sequence deposited in accession file P14902 of SwissProt database. These polymorphisms result in a P110S and E119G amino acid changes.

Plasmid pQE70-hIDO was transformed into M15(pREP4) cells (Qiagen) and clones were selected in LB-agar plates supplemented with carbenicillin 50 µg/mL and kanamycin 30 µg/mL. Protein expression was carried out by growing an overnight culture of the M15pREP4/pQE70-hIDO clone in 100 mL LB supplemented with 100 µg/mL carbenicillin, 50 µg/mL kanamycin and 50 µg/mL of L-tryptophan (LBCKT medium). 40 mL of this culture were inoculated into 750 mL of LBCKT for 4 hours at 37° C. This culture was diluted 1:10 into LBCKT medium and cultured for another 2 hours at 37° C. until OD600 was higher than 0.8. At this point the cultures were inoculated with Hemin to 7 µM and L-Tryptophan to 75 µg/mL and incubated at 37° C. for 2 h. Induction of protein expression was carried out by supplementing the cultures with IPTG to 1 mM, PMSF to 200 µM, EDTA to 1 mM and L-tryptophan to 50 µg/mL. Incubation was continued for additional 16 h at 25° C. Cells were collected by centrifugation, and the cell pellets were washed with PBS buffer supplemented with 200 µM PMSF and 1 mM EDTA and stored at −80° C. until protein purification.

The equivalent of 16 L of culture were processed in one batch of purification. Cell pellets were thawed, resuspended in 50 mM potassium phosphate buffer pH 7.0, 200 µM PMSF, 1 mM EDTA, 1 mg/mL lysozyme to 10 mL per liter of bacterial culture and incubated 30 minutes on ice. Cells were then lysed by sonication. Cell lysates were centrifuged 20 min at 20000 g and the supernatant was filtered through 0.45 µm filters. The filtered supernatant was loaded onto a 60 mL phosphocellulose column equilibrated with 50 mM potassium phosphate buffer pH 6.5 (KPB) at 1-3 mL/min. The column was washed with 3 volumes of 50 mM KPB, 3 volumes of 100 mM KPB and the protein was eluted with 15 volumes of a linear gradient of 100-500 mM KPB. Fractions were collected and IDO activity assay was performed by measuring kynurenine production. This was carried out by mixing 50 µL of each fraction with 100 µL of reaction mix to yield a final concentration of 50 mM KPB buffer, 20 mM ascorbic acid, 200 µg/mL catalase, 20 µM methylene blue and 400 µM L-tryptophan. Fractions demonstrating IDO activity were loaded onto a Ni-NTA purification column (15 mL). This affinity purification column was washed with 10 volumes of 250 mM KPB, 150 mM NaCl, 50 mM imidazole pH 8, and eluted with 10 volumes of buffer containing 250 mM KPB, 150 mM NaCl and a 50 to 250 mM imidazole linear gradient. Collected fractions were assayed by IDO enzymatic assay described above and the positive fractions were pooled and concentrated by ultrafiltration and dialyzed against a buffer containing 250 mM KPB, 50% glycerol. This process yields ~8-10 mg of pure protein (>98%) with a specific activity of 170 µmol/h/mg.

Example 86

Testing of IDO Inhibitory Compounds by Enzymatic IDO Assay

The $IC_{50}$ values for each compound were determined by testing the activity of IDO in a mixture containing 50 mM potassium phosphate buffer at pH 6.5; 70 nM purified human IDO protein, 200 µM L-tryptophan, 20 mM ascorbate, 20 µM methylene blue, 0.1% DMSO. The inhibitors were initially diluted in DMSO at 100 mM and were diluted in potassium phosphate 50 mM, added to the reaction mixture at final concentrations raging from 1 mM to 5 nM and preincubated with the enzyme for 5 min at 25° C. The reaction was started by addition of L-tryptophan to 200 µM and incubated 15 min at 37° C. The reaction was stopped by addition of 0.5 vol of 30% trichloroacetic acid and incubated 30 min at 60° C. to hydrolyze N-formylkynurenine to kynurenine. The reaction was centrifuged at 3400 g for 5 min to remove precipitated protein and the supernatant was reacted with 2% (w/v) of p-dimethylaminobenzaldehyde in acetic acid. The reaction was incubated 10 min at 25° C. and read at 480 nm in a spectrophotometer. Control samples with no IDO inhibitor, or with no IDO enzyme or with the reference inhibitors 1-methyl-tryptophan (200 µM) and menadione (1.2 µM) were used as controls to set the parameters for the non-linear regressions necessary for determination of the $IC_{50}$ for each compound. Nonlinear regressions and determination of the $IC_{50}$ values were performed using the GraphPad Prism 4 software. Compounds with an $IC_{50}$ of less than 500 μM were considered as active inhibitors in this assay.

Example 87

Determination of IDO Inhibitory Activity and Toxicity in Cell Based IDO/Kynurenine Assay 293-T-REx™ cells (Invitrogen) constitutively express a tet operator binding repressor protein and are maintained in DMEM, 10% FBS, 1× Penicillin+Streptomycin, 2 mM L-glutamine, 5 μg/mL blasticidin at 37° C. with a 5% $CO_2$ in air atmosphere and typically split prior to confluency. Cells were passed by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium, 10% DMSO), stored in 1.8 mL cryopreservation vials (~2–5×10$^6$ cells per vial), in liquid nitrogen vapor storage tanks.

IDOL—expressing 293-T-Rex™ cell lines were generated by stable transfection of plasmid pcDNA-tetO-IDO expressing human IDO or murine IDO under the control of the doxycycline-inducible CMV-tet promoter. Transfected cells were selected in DBZ medium (DMEM, 10% FBS, 1× Penicillin+Streptomycin, 2 mM L-glutamine, 5 μg/mL blasticidin and 25 μg/ml Zeocin) at 37° C. with a 5% $CO_2$ in air atmosphere. Individual clones were isolated by limiting dilution cloning from these populations. These clones were assayed for IDO activity and the clones that showed the highest levels of IDO activity inducible by doxycycline were used for subsequent cell based IDO assays.

To setup an IDO cell based activity assay, IDO-293-T-Rex cells were harvested and resuspended in DBZ media at 10$^6$ cells/mL, and split into poly-D-lysine coated 96-well plates at 100,000 cells per well. 100 μL of Neutral medium (DBZ medium, 200 μM L-tryptophan) or Induction media (Neutral medium supplemented with 5 μM doxycycline) are added to the cells and incubated 28 h at 37° C. After the IDO induction period, medium is removed and replaced with Induction or Neutral medium containing different concentrations of each inhibitor (1 mM to 0.5 nM). The cells incubated in Neutral medium serve as negative control of the assay. The cells incubated in Induction medium and without inhibitor serve as the positive control of the assay. The incubation is carried out for 16 h at 37° C. in a cell culture incubator. 200 μL of medium are transferred to U-bottom polypropylene 96-well plates containing 25 μL of 30% TCA, incubated 30 minutes at 60° C. and centrifuged at 3400 g for 5 minutes. 150 μL of the clear supernatant is transferred to a polystyrene 96-well plate containing 50 μL of 4% (w/v) of p-dimethylaminobenzaldehyde in acetic acid, incubated for 10 min. Kynurenine concentration is determined by measuring the absorbance at 480 nm.

To measure the toxicity of each compound after 16 h incubation with cells, cell viability is measured via a WST-1 assay (Roche) according to instructions from the manufacturer. Briefly, after the incubation with each compound, medium is aspirated and replaced with 100 mL of WST-1 reagent, and incubated 30 min at 37° C. Absorbance at 540 nm is correlated with the number of viable cells. Determination of $IC_{50}$ (Kynurenine assay) or $LD_{50}$ (WST-1 assay) is performed via non-linear regression analysis using GraphPad Prism software.

Example 88

Reversal of IDO-Mediated Suppression of T-Cell Proliferation by IDO Inhibitors

Human monocytes were collected from peripheral mononuclear cells by leukoapheresis and cultured overnight at 10$^6$ cells/well in a 96-well plate in RPMI 1640 medium supplemented with 10% fetal calf serum and 2 mM L-glutamine. Adherent cells were retained and cultured for 7 days with 200 ng/ml IL-4, 100 ng/ml GM-CSF. Cells were matured for 2 days with a cytokine cocktail containing TNF-α, IL-β, IL-6 and PGE2 for additional 2 days to induce dendritic cell maturation. At the end of maturation, loosely adherent cells were detached by gentle aspiration and plated in V-bottom 96 well plates, at 5000 cells/well. These cells are >80% IDO+ dendritic cells. Human allogeneic T cells (3×10$^5$) from normal donors were resuspended in RPMI 1640 supplemented with 100-200 U/mL IL-2 and 100 ng/mL anti-CD3 antibody and added to the wells. Serial dilutions of IDO compounds dissolved in phenol red-free RPMI was added to yield a final concentration of IDOi between 500 and 1 μM. After incubation for 2-4 days, T cell proliferation was measured by BrdU incorporation assay after an overnight pulse with BrdU labeling mix (Roche Molecular Biochemicals). At the en of the pulse, the cells were fixed and incubated with 100 μL/well anti-BrdU-POD antibody following the instructions from the manufacturer. Plates were read in a microplate reader.

Alternatively, testing of IDO inhibitors in an in vitro mouse model of IDO-mediated suppression of T cell proliferation is performed by the following procedure. C57b16 mice are inoculated with 1×10$^6$ B78H1-GMCSF tumor cells in the right flank. After 10-12 days, tumor draining lymph nodes are collected and cells are stained with anti-CD11c and anti-B220 monoclonal antibodies. Cells are sorted by high-speed fluorescence activated cell sorting and the CD11c+/B220+ plasmacytoid dendritic cells are collected and seeded at 2000 cells/well in 96 well V-bottom plates. Splenocytes were collected from BM3 transgenic mice (in CBA background) and collected by nylon wool enrichment. BM3 T cells (10$^5$ cells/well) are added to each well in 200 μL of RPMI, 10% FCS, 50 μM β-mercaptoetanol. Alternatively, T cells are obtained from spleens of OT-I transgenic mice and added to the culture in combination with OVA peptide. IDO inhibitors are added dissolved in RPMI at final concentrations ranging from 1 mM to 10 nM. After 3 days of stimulation, cells are pulsed by 16 h with BrdU or $^3$H-thymidine. Cells are collected, fixed and tested for BrdU incorporation following the instructions from the BrdU labeling kit manufacturer (Roche Diagnostics). If $^3$H-tymidine is used to measure T cell proliferation, cells are harvested and dpm counts are measured in a scintillation counter following procedures widely known in the art. Control CD11c$^+$ cells taken from the contralateral lymph node or CD11c$^+$/B220$^-$ cells (IDO$^-$ population) from the TDLN are used as positive control for proliferation.

Example 89

In Vivo Testing of IDO Inhibitors for Antitumor Activity in Combination with Chemotherapeutic Agents In vivo anti-tumor efficacy can be tested using modified tumor allograft protocols. For instance, it has been described in the literature that IDO inhibition can syngerize with cytotoxic chemotherapy in immune-competent mice. Due to different susceptibilities of different tumor cell lines to chemotherapeutic drugs and to immune mediated rejection, each IDO inhibitor is tested alone and in combination with 2 different chemotherapeutic drugs in 4 different animal tumor models, represented by 4 different mouse tumor cell lines, of different tissue origin (colorectal, bladder, mammary and lung carcinoma), implanted subcutaneously in syngeneic strains of mice. These cell lines have been selected based on their known susceptibility to chemotherapeutic drugs, their partial response to IDO inhibitors as single agents, their presumed pattern of IDO expression according to their tissue of origin, and their ability to elicit an immune reaction.

For every animal tumor model, 2 different chemotherapeutic drugs are tested in separate groups of mice according to the following list: 1] LLC tumor: cyclophosphamide and paclitaxel; 2] EMT6 tumor: cyclophosphamide and paclitaxel; 3] CT26 tumor: cyclophosphamide and doxorubicin; and 4] MB49 tumor: cyclophosphamide and gemcitabine.

The following chemotherapeutic drugs are used, at the indicated doses. The maximum tolerated dose for the following chemotherapeutic agents in mice depends on the formulation, concentration, frequency of administration, route of administration and number of doses. The chemotherapeutic drugs administered in conjunction with each IDO inhibitor drug are: 1] Paclitaxel: 20 mg/kg/day i.p, every 4 days, 4 times (q4d×4) (in Cremophor); 2] Doxorubicin: mg/kg, once a week for 3 weeks (q7d×3); 3] Cyclophosphamide: 100 mg/kg, I.P., every 4 days, 4 times (q4d×4); 4] Gemcitabine: 80 mg/kg every 4 days, 4 times, i.p. (q4d×4).

All animals receive a subcutaneous injection of a tumor forming dose of live tumor cells (~50000-1000000 cells) suspended in 0.1 mL of PBS or saline on day 1. Subcutaneous injection forms a localized tumor that allows monitoring tumor growth over time.

To mimic the effect of IDO inhibitor drugs as therapeutic compositions, administration of IDO inhibitor drugs begins at day 5-8 after tumor inoculation. Dosing, route of administration, dosing frequency varies depending on the toxicity and pharmacokinetics profile of each drug. Duration of the treatment is 2 weeks. Most preferably, drug is administered continuously via oral gavage or dissolution in the drinking water. Alternatively, subcutaneous slow release pellets containing 100 mg of each drug are implanted under the skin by surgical procedure. IDO inhibitor drug are administered at the maximum tolerated dose or at a concentration corresponding to the $LD_{10}$.

Example 90

Pharmacological Values

Tables 14-16 report pharmacological values for compounds tested according to one or more of the preceding examples, including, Human IDO $IC_{50}$: this is the concentration of the compound at which we observe 50% of enzymatic activity using recombinant human IDO under the assay conditions described in one of the examples;

Human IDO $EC_{50}$: This is the concentration of the compound at which we observe 50% of kynurenine production in a cell based assay using a 293T cell lines stably transfected with an expression cassette expressing human IDO. The conditions of the assay were as described in the examples.

Human IDO $LD_{50}$: This is the concentration of the compound at which we observe 50% of cell viability loss in the IDO cell based assay. Viability was measure by the WST assay as described in one of the examples.

In Table 14, values are reported in ranges: A: 1-10 mM; B: 0.1-1 mM; C: 20-100 µM; D: <20 µM.

TABLE 14

| Cmpd # | hIDO $IC_{50}$ | hIDO $EC_{50}$ | hIDO $LD_{50}$ | Docking_Score |
|---|---|---|---|---|
| 1 | B | B | B | −8.56 |
| 2 | B | B | B | −7.98 |
| 3 | B | B | B | −8.71 |
| 4 | B | C | B | −8.25 |
| 6 | B | B | B | −8.24 |
| 7 | B | B | B | −8.8 |
| 8 | B | B | B | −8.91 |
| 9 | B | C | B | −7.24 |
| 10 | B | B | B | −7.83 |
| 12 | B | B | B | −8.6 |
| 13 | B | | | −7.88 |
| 14 | B | B | B | −7.19 |
| 20 | B | | | −6.56 |
| 21 | B | B | B | −8.07 |
| 23 | B | C | C | −4.45 |
| 27 | B | B | B | −8.5 |
| 28 | B | C | A | −7.61 |
| 30 | B | C | B | −8.61 |
| 32 | B | C | B | −7.57 |
| 38 | B | C | C | −6.22 |
| 40 | B | B | B | −8.29 |
| 42 | B | B | B | −6.13 |
| 43 | B | B | B | −6.31 |
| 44 | B | A | A | −5.34 |
| 45 | B | B | B | −7.39 |
| 47 | B | C | C | −6.1 |
| 50 | C | C | C | −8.92 |
| 52 | C | C | B | −9.51 |
| 53 | B | C | C | −8.58 |
| 57 | D | C | B | −8.73 |
| 58 | B | C | C | −7.84 |
| 60 | C | C | B | −8.04 |
| 63 | C | C | B | −7.62 |
| 64 | B | C | B | −7.28 |
| 65 | C | C | B | −8.57 |
| 66 | B | B | B | −6.05 |
| 69 | B | | | −7.19 |
| 77 | B | | | −6.04 |
| 78 | B | B | A | −8.13 |
| 79 | C | D | A | −7.23 |
| 81 | B | | | −7.6 |
| 138 | B | C | C | −9.56 |
| 140 | B | C | C | −9.05 |
| 142 | D | B | A | −7 |
| 148 | B | B | B | −6.03 |
| 149 | B | C | B | −5.25 |
| 150 | B | B | C | −6.63 |
| 151 | B | B | B | −7.35 |
| 152 | C | C | A | −5.6 |
| 162 | D | B | B | −6.26 |
| 163 | D | D | D | −5.85 |
| 167 | D | C | B | −6.48 |
| 168 | B | B | A | −7.75 |
| 209 | B | A | B | −6.69 |
| 222 | B | C | B | −7.49 |
| 252 | B | C | A | −7.06 |
| 261 | B | C | B | −8 |
| 267 | B | | | −8.27 |
| 280 | B | A | A | −8.02 |
| 282 | B | A | A | −8.22 |
| 289 | B | A | A | −5.52 |
| 307 | D | A | B | −7.65 |
| 309 | C | B | B | −6.08 |
| 312 | D | D | A | −7.84 |
| 313 | B | B | A | −8.24 |

TABLE 14-continued

| Cmpd # | hIDO IC$_{50}$ | hIDO EC$_{50}$ | hIDO LD$_{50}$ | Docking_Score |
|---|---|---|---|---|
| 317 | D | D | A | −8.06 |
| 320 | D | A | A | −6.2 |
| 321 | B | B | B | −8.37 |
| 325 | B | A | A | −8.82 |
| 352 | B | A | A | −9.49 |
| 463 | C |   |   | −5.49 |
| 464 | C | A | A | −6.29 |
| 477 | D | C | A | −6.12 |
| 525 | B |   |   | −4.28 |
| 552 | B | C | A | −9.11 |
| 561 | B | C | A | −10.64 |
| 565 | B |   |   | −10.22 |
| 568 | B |   |   | −9.96 |
| 581 | B | B | A | −9.6 |
| 588 | B | B | B | −9.45 |
| 591 | B |   |   | −9.38 |
| 592 | B |   |   | −9.35 |
| 606 | B |   |   | −9.11 |
| 607 | C | C | B | −9.11 |
| 634 | B | B | A | −8.86 |
| 644 | B | C | B | −8.8 |
| 656 | B | C | C | −8.71 |
| 664 | B |   |   | −8.65 |
| 672 | B | C | B | −8.58 |
| 673 | B |   |   | −8.58 |
| 682 | B | B | A | −8.53 |
| 701 | B | B | A | −8.44 |
| 707 | B |   |   | −8.42 |
| 739 | B | B | A | −8.3 |
| 786 | B |   |   | −8.08 |
| 827 | B | C | B | −7.94 |
| 830 | C | C | A | −7.92 |
| 889 | B |   |   | −7.71 |
| 1359 | B | C | B | −9.52 |

In Tables 15 and 16, values are reported in ranges: A: <10 µM; B: 10-100 µM; C: 100-1000 µM; D>1000 µM.

TABLE 15

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1769 |   | O-(3,5-dichlorobenzyl)hydroxylamine | A | A | D | A | D |
| 1914 |   | O-((4-chloro-4'-methoxybiphenyl-2-yl)methyl)hydroxylamine | A | A | C | B | D |
| 1935 |   | methyl 2'-(aminooxymethyl)-4'-chlorobiphenyl-4-carboxylate | A | A | C |   |   |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1892 | 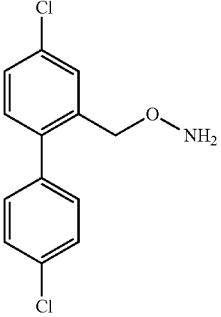 [SMILES: NOCc1cc(Cl)ccc1-c1ccc(Cl)cc1] | O-((4,4'-dichlorobiphenyl-2-yl)methyl)hydroxylamine | A | A | B | A | D |
| 1932 | 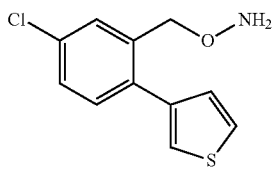 [SMILES: NOCc1cc(Cl)ccc1-c1ccsc1] | O-(5-chloro-2-(thiophen-3-yl)benzyl)hydroxylamine | A | A | D | | |
| 1918 | 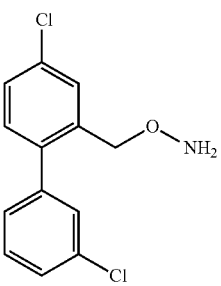 [SMILES: NOCc1cc(Cl)ccc1-c1cccc(Cl)c1] | O-((3',4-dichlorobiphenyl-2-yl)methyl)hydroxylamine | A | A | D | B | C |
| 1916 | 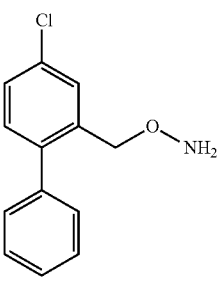 [SMILES: NOCc1cc(Cl)ccc1-c1ccccc1] | O-((4-chlorobiphenyl-2-yl)methyl)hydroxylamine | A | A | C | B | C |
| 1937 | 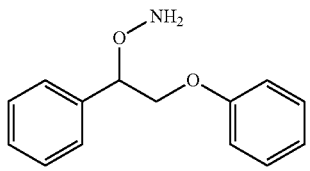 [SMILES: NOC(COc1ccccc1)c1ccccc1] | O-(2-phenoxy-1-phenylethyl)hydroxylamine | A | A | C | | |
| 1825 | 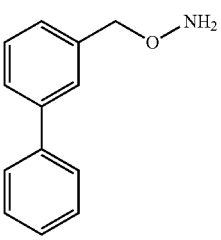 | O-(biphenyl-3-ylmethyl)hydroxylamine | A | A | D | B | D |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1879 | 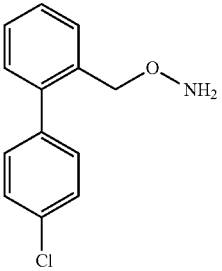 [SMILES: NOCc1ccccc1-c1ccc(Cl)cc1] | O-((4'-chlorobiphenyl-2-yl)methyl)hydroxylamine | A | A | D | B | D |
| 1931 | 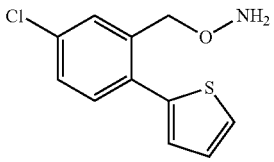 [SMILES: NOCc1cc(Cl)ccc1-c1cccs1] | O-(5-chloro-2-(thiophen-2-yl)benzyl)hydroxylamine | A | A | D | | |
| 1743 | 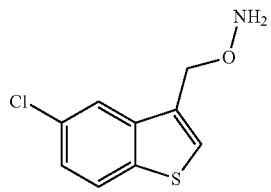 [SMILES: NOCc1csc2ccc(Cl)cc12] | O-((5-chlorobenzo[b]thiophen-3-yl)methyl)hydroxylamine | A | A | D | B | D |
| 1880 | 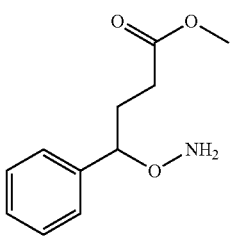 | methyl 4-(aminooxy)-4-phenylbutanoate | A | A | D | C | D |
| 1915 | 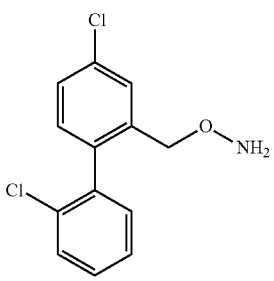 [SMILES: NOCc1cc(Cl)ccc1-c1ccccc1Cl] | O-((2',4-dichlorobiphenyl-2-yl)methyl)hydroxylamine | A | B | C | C | C |
| 1749 | 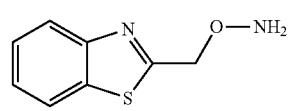 [SMILES: NOCc1nc2ccccc2s1] | O-(benzo[d]thiazol-2-ylmethyl)hydroxylamine | A | A | D | A | D |
| 1878 | 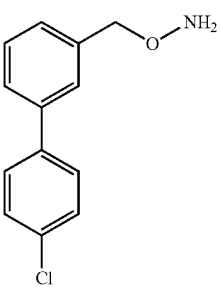 [SMILES: NOCc1cccc(-c2ccc(Cl)cc2)c1] | O-((4'-chlorobiphenyl-3-yl)methyl)hydroxylamine | A | A | D | B | D |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1919 | 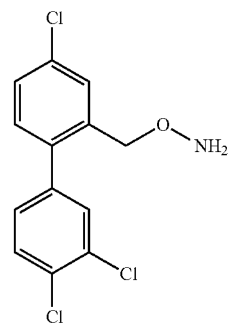 [SMILES: NOCc1cc(Cl)ccc1-c1ccc(Cl)c(Cl)c1] | O-((3',4,4'-trichlorobiphenyl-2-yl)methyl)hydroxylamine | A | A | C | B | C |
| 1923 | 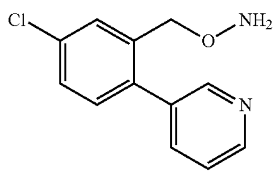 [SMILES: NOCc1cc(Cl)ccc1-c1cccnc1] | O-(5-chloro-2-(pyrimidin-5-yl)benzyl)hydroxylamine | A | A | C | A | D |
| 1774 | 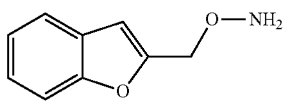 [SMILES: NOCc1cc2ccccc2o1] | O-(benzofuran-2-ylmethyl)hydroxylamine | A | A | D | A | D |
| 1882 | 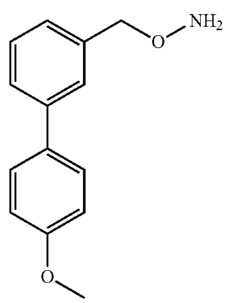 [SMILES: COc1ccc(-c2cccc(CON)c2)cc1] | O-((4'-methoxybiphenyl-3-yl)methyl)hydroxylamine | A | A | D | B | D |
| 1930 | 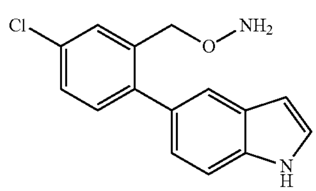 [SMILES: NOCc1cc(Cl)ccc1-c1ccc2[nH]ccc2c1] | O-(5-chloro-2-(1H-indol-5-yl)benzyl)hydroxylamine | A | A | C | | |
| 1873 | 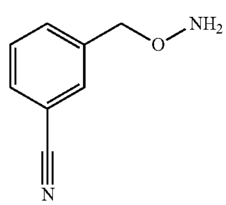 [SMILES: N#Cc1cccc(CON)c1] | 3-(aminooxymethyl)benzonitrile | A | A | D | A | D |
| 2033 | 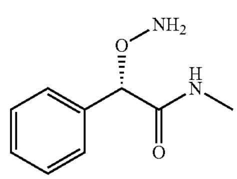 | (S)-2-(aminooxy)-N-methyl-2-phenylacetamide | A | | | | |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1770 | | O-(3,5-difluorobenzyl) hydroxylamine | A | A | D | 2.3 | D |
| 1886 | | methyl 2-(aminooxy)-2-phenylacetate | A | A | D | A | D |
| 1924 | | O-(1,3-diphenylpropyl)hydroxylamine | A | A | C | B | C |
| 1829 | | 3-(aminooxymethyl)-N-phenylaniline | A | A | D | A | C |
| 1933 | | O-(2-(benzyloxy)-1-phenylethyl)hydroxylamine | A | A | D | | |
| 1827 | | O-(biphenyl-2-ylmethyl)hydroxylamine | A | A | D | B | D |
| 1660 | | O-(3-chloro-5-fluorobenzyl)hydroxylamine | A | A | D | A | D |
| 1903 | | O-(naphthalen-1-yl)hydroxylamine | A | B | B | B | B |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1893 | 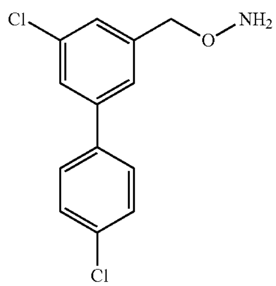 [SMILES: NOCc1cc(Cl)cc(-c2ccc(Cl)cc2)c1] | O-((4',5-dichlorobiphenyl-3-yl)methyl)hydroxylamine | A | A | D | B | D |
| 1662 | 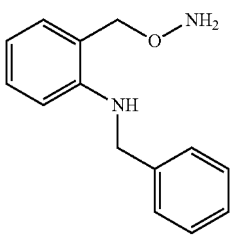 [SMILES: NOCc1ccccc1NCc1ccccc1] | 2-(aminooxymethyl)-N-benzylaniline | A | A | D | C | D |
| 1771 | 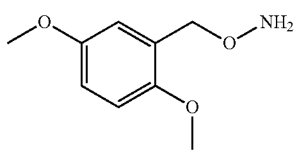 | O-(2,5-dimethoxybenzyl)hydroxylamine | A | A | D | A | D |
| 1938 | 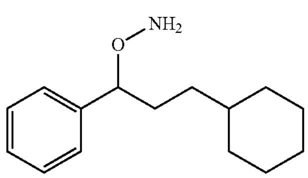 [SMILES: NOC(CCC1CCCCC1)c1ccccc1] | O-(3-cyclohexyl-1-phenylpropyl)hydroxylamine | A | A | C | | |
| 1871 | 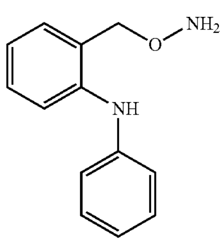 [SMILES: NOCc1ccccc1Nc1ccccc1] | 2-(aminooxymethyl)-N-phenylaniline | A | A | D | B | D |
| 1736 | 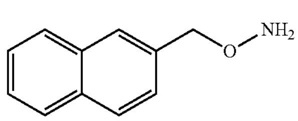 [SMILES: NOCc1ccc2ccccc2c1] | O-(naphthalen-2-ylmethyl)hydroxylamine | A | A | D | A | D |
| 1920 | 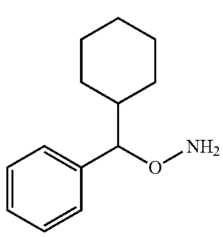 [SMILES: NOC(c1ccccc1)C1CCCCC1] | O-(cyclohexyl(phenyl)methyl)hydroxylamine | A | A | D | B | B |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1917 | 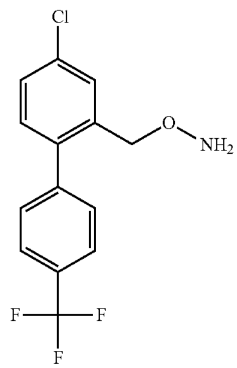 [SMILES: NOCc1cc(Cl)ccc1-c1ccc(C(F)(F)F)cc1] | O-((4-chloro-4'-(trifluoromethyl)biphenyl-2-yl)methyl)hydroxylamine | A | A | C | B | C |
| 1744 | 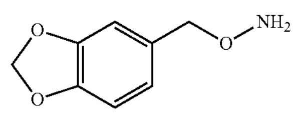 [SMILES: NOCc1ccc2c(c1)OCO2] | O-(benzo[d][1,3]dioxol-5-ylmethyl)hydroxylamine | A | A | D | B | D |
| 1897 | 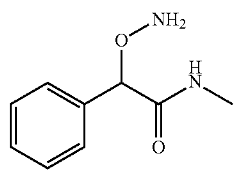 | 2-(aminooxy)-N-methyl-2-phenylacetamide | A | A | D | A | D |
| 1921 | 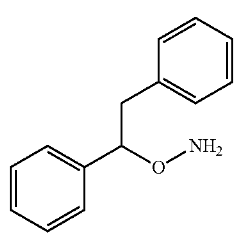 [SMILES: NOC(Cc1ccccc1)c1ccccc1] | O-(1,2-diphenylethyl)hydroxylamine | A | A | C | B | D |
| 1895 | 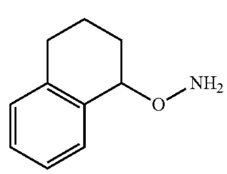 [SMILES: NOC1CCCc2ccccc21] | O-(1,2,3,4-tetrahydronaphthalen-1-yl)hydroxylamine | A | A | D | B | D |
| 1676 | 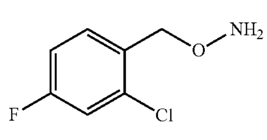 [SMILES: NOCc1ccc(F)cc1Cl] | O-(2-chloro-4-fluorobenzyl)hydroxylamine | A | A | D | B | D |
| 1896 | 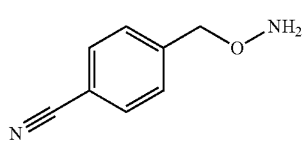 [SMILES: N#Cc1ccc(CON)cc1] | 4-(aminooxymethyl)benzonitrile | A | A | D | B | D |
| 1768 | 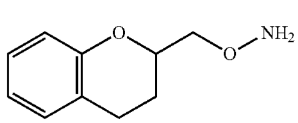 [SMILES: NOCC1CCc2ccccc2O1] | O-(chroman-2-ylmethyl)hydroxylamine | A | A | D | A | D |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1872 | 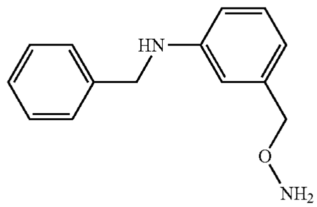 [SMILES: NOCc1cccc(NCc2ccccc2)c1] | 3-(aminooxymethyl)-N-benzylaniline | A | A | D | A | D |
| 1934 | 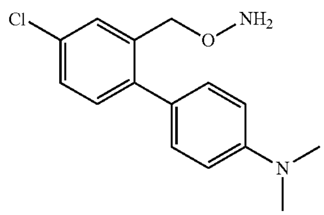 [SMILES: CN(C)c1ccc(-c2ccc(Cl)cc2CON)cc1] | 2'-(aminooxymethyl)-4'-chloro-N,N-dimethylbiphenyl-4-amine | A | A | D | | |
| 1739 | 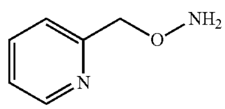 | O-(pyridin-2-ylmethyl)hydroxylamine | B | A | D | A | D |
| 1674 | 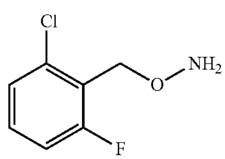 [SMILES: NOCc1c(F)cccc1Cl] | O-(2-chloro-6-fluorobenzyl)hydroxylamine | B | A | D | B | D |
| 1889 | 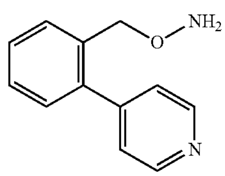 [SMILES: NOCc1ccccc1-c1ccncc1] | O-(2-(pyridin-4-yl)benzyl)hydroxylamine | B | A | D | C | D |
| 1742 | 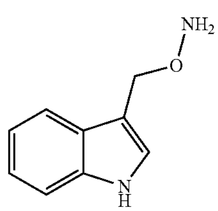 [SMILES: NOCc1c[nH]c2ccccc12] | O-((1H-indol-3-yl)methyl)hydroxylamine | B | A | D | A | D |
| 1737 | 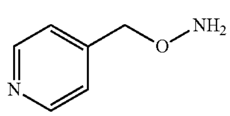 | O-(pyridin-4-ylmethyl)hydroxylamine | B | A | D | A | D |
| 1738 | 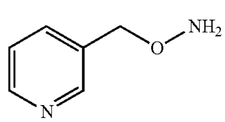 | O-(pyridin-3-ylmethyl)hydroxylamine | B | A | D | B | D |
| 1888 | 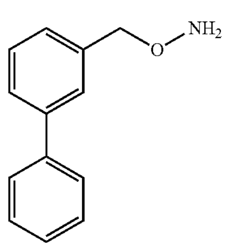 [SMILES: NOCc1cccc(-c2ccccc2)c1] | O-(3-(pyridin-4-yl)benzyl)hydroxylamine | B | A | D | C | D |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1750 | 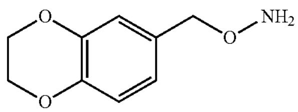 [SMILES: NOCc1ccc2c(c1)OCCO2] | O-((2,3-dihydrobenzo[b][1,4]dioxin-6-yl)methyl)hydroxylamine | B | A | D | B | B |
| 1824 | 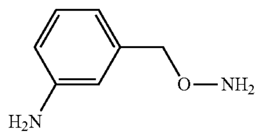 | 3-(aminooxymethyl)aniline | B | A | D | B | D |
| 1741 | 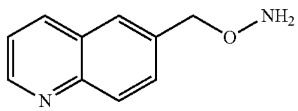 [SMILES: NOCc1ccc2ncccc2c1] | O-(quinolin-6-ylmethyl)hydroxylamine | B | A | D | A | D |
| 1925 | 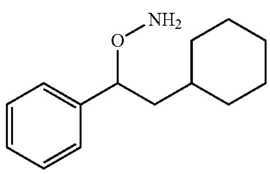 [SMILES: NOC(CC1CCCCC1)c1ccccc1] | O-(2-cyclohexyl-1-phenylethyl)hydroxylamine | B | A | C | B | C |
| 1881 | 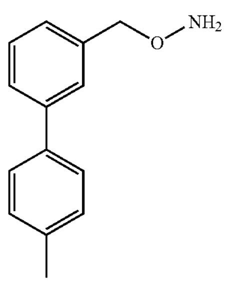 [SMILES: Cc1ccc(-c2cccc(CON)c2)cc1] | O-((4'-methylbiphenyl-3-yl)methyl)hydroxylamine | B | A | D | B | D |
| 1898 | 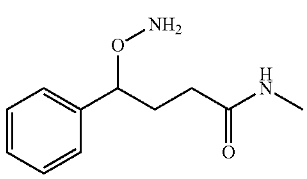 | 4-(aminooxy)-N-methyl-4-phenylbutanamide | B | A | D | B | B |
| 1875 | 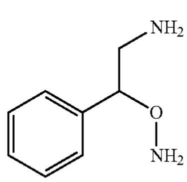 [SMILES: NCC(ON)c1ccccc1] | 2-(aminooxy)-2-phenylethanamine | B | D | D | | |
| 1877 | 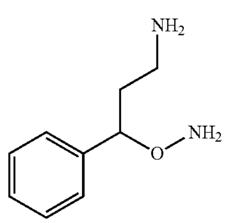 [SMILES: NCCC(ON)c1ccccc1] | 3-(aminooxy)-3-phenylpropan-1-amine | B | | | | |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 1936 | 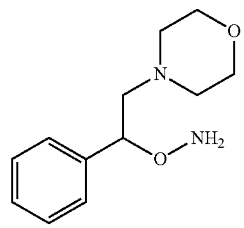 [SMILES: NOC(CN1CCOCC1)c1ccccc1] | O-(2-morpholino-1-phenylethyl)hydroxylamine | B | | | | |
| 1740 | 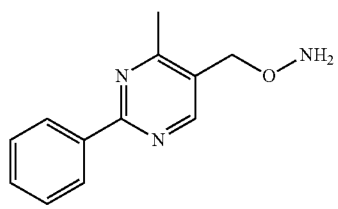 [SMILES: Cc1nc(-c2ccccc2)ncc1CON] | O-((4-methyl-2-phenylpyrimidin-5-yl)methyl)hydroxylamine | B | A | D | A | D |
| 1828 | 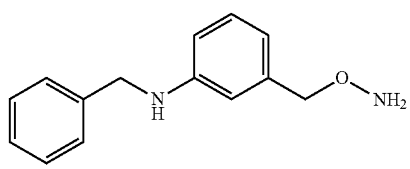 [SMILES: NOCc1cccc(NCc2ccccc2)c1] | 3-(aminooxymethyl)-N-benzylaniline | C | B | D | C | C |
| 1902 | 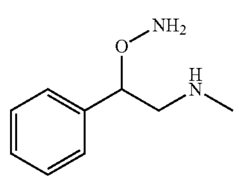 | 2-(aminooxy)-N-methyl-2-phenylethanamine | C | | | | |
| 1901 | 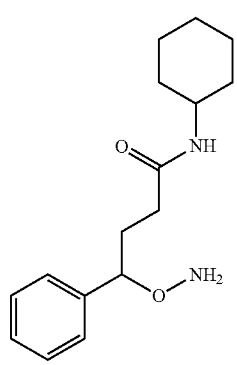 [SMILES: NOC(CCC(=O)NC1CCCCC1)c1ccccc1] | 4-(aminooxy)-N-cyclohexyl-4-phenylbutanamide | C | | | | |
| 1876 | 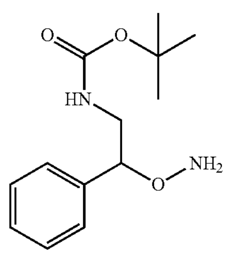 [SMILES: CC(C)(C)OC(=O)NCC(ON)c1ccccc1] | tert-butyl 2-(aminooxy)-2-phenylethylcarbamate | C | | | | |

TABLE 15-continued

| Cpd # | Structure | Name | hIDO IC$_{50}$ | hIDO EC$_{50}$ | hIDO LD$_{50}$ | mIDO EC$_{50}$ | mIDO LD$_{50}$ |
|---|---|---|---|---|---|---|---|
| 2034 | 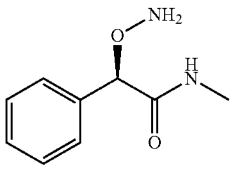 | (R)-2-(aminooxy)-N-methyl-2-phenylacetamide | C | | | | |
| 1904 | 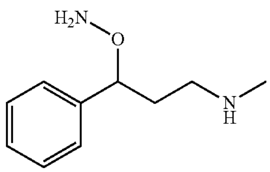 | 3-(aminooxy)-N-methyl-3-phenylpropan-1-amine | C | | | | |
| 1899 | 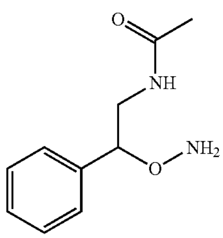 | N-(2-(aminooxy)-2-phenylethyl)acetamide | C | | | | |
| 1929 | 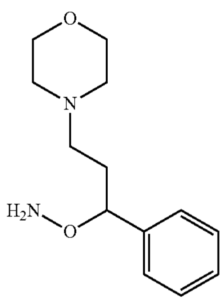 [SMILES: NOC(CCN1CCOCC1)c1ccccc1] | O-(3-morpholino-1-phenylpropyl)hydroxylamine | C | | | | |
| 1883 | 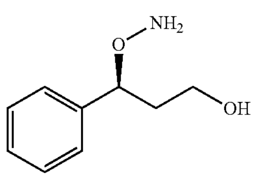 [SMILES: NO[C@@H](CCO)c1ccccc1] | (S)-3-(aminooxy)-3-phenylpropan-1-ol | C | | | | |

TABLE 16

| Cpd # | Structure | Name | hIDO IC50 | hIDO EC50 | hIDO LD50 | mIDO EC50 | mIDO LD50 |
|---|---|---|---|---|---|---|---|
| 1656 | 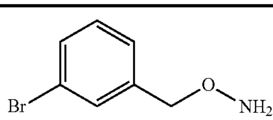 | O-(3-bromobenzyl)hydroxylamine | A | A | D | A | D |
| 1672 | 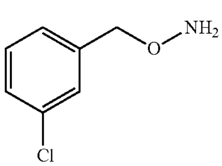 | O-(3-chlorobenzyl)hydroxylamine | A | A | D | A | D |

TABLE 16-continued

| Cpd # | Structure | Name | hIDO IC50 | hIDO EC50 | hIDO LD50 | mIDO EC50 | mIDO LD50 |
|---|---|---|---|---|---|---|---|
| 1775 | 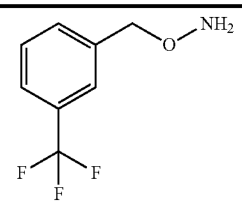 | O-(3-(trifluoromethyl)benzyl)hydroxylamine | A | A | D | A | D |
| 1816 | 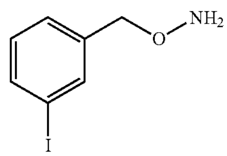 | O-(3-iodobenzyl)hydroxylamine | A | A | D | B | D |
| 317 | 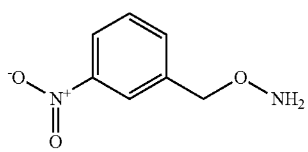 | O-(3-nitrobenzyl)hydroxylamine | A | A | D | A | D |
| 762 | 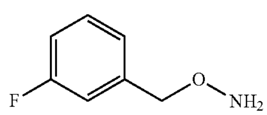 | O-(3-fluorobenzyl)hydroxylamine | A | A | D | A | D |
| 1817 | 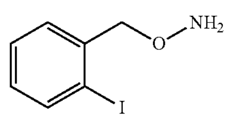 | O-(2-iodobenzyl)hydroxylamine | A | A | D | B | D |
| 1657 | 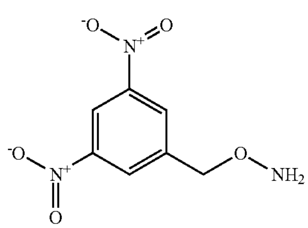 | O-(3,5-dinitrobenzyl)hydroxylamine | A | A | D | A | D |
| 1767 | 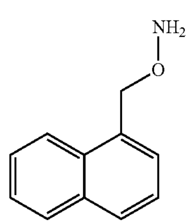 [SMILES: NOCc1cccc2ccccc12] | O-(naphthalen-1-ylmethyl)hydroxylamine | A | A | D | B | D |
| 1922 | 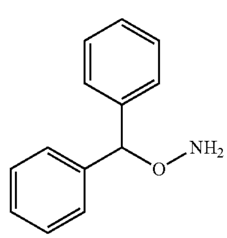 [SMILES: NOC(c1ccccc1)c1ccccc1] | O-benzhydrylhydroxylamine | A | A | C | A | C |
| 1666 | 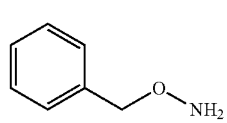 | O-benzylhydroxylamine | A | A | D | A | D |

TABLE 16-continued

| Cpd # | Structure | Name | hIDO IC50 | hIDO EC50 | hIDO LD50 | mIDO EC50 | mIDO LD50 |
|---|---|---|---|---|---|---|---|
| 774 | 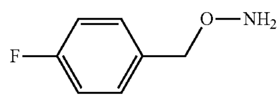 | O-(4-fluorobenzyl) hydroxylamine | A | A | D | A | D |
| 1677 | 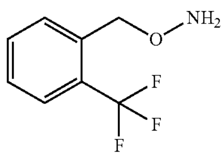 [SMILES: NOCc1ccccc1C(F)(F)F] | O-(2-(trifluoromethyl)benzyl) hydroxylamine | A | A | D | B | D |
| 1818 | 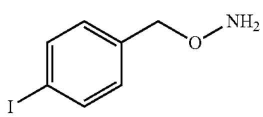 | O-(4-iodobenzyl)hydroxylamine | A | A | D | B | D |
| 934 | 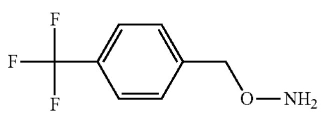 [SMILES: NOCc1ccc(C(F)(F)F)cc1] | O-(4-(trifluoromethyl)benzyl) hydroxylamine | A | A | D | A | D |
| 1679 | 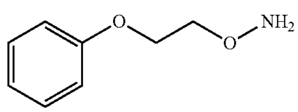 [SMILES: NOCCOc1ccccc1] | O-(2-phenoxyethyl) hydroxylamine | A | A | D | A | D |
| 1682 | 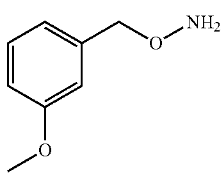 | O-(3-methoxybenzyl) hydroxylamine | A | A | D | A | D |
| 1752 | 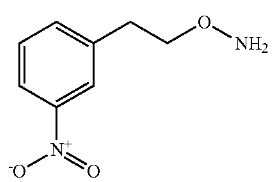 | O-(3-nitrophenethyl) hydroxylamine | A | A | D | A | D |
| 1675 | 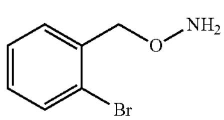 | O-(2-bromobenzyl) hydroxylamine | A | A | D | A | D |
| 1755 | 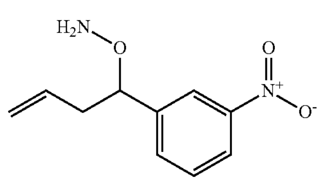 | O-(1-(3-nitrophenyl)but-3-enyl) hydroxylamine | A | A | D | A | D |
| 1684 | 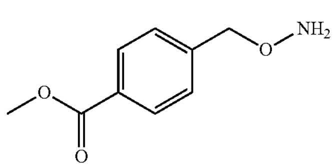 | methyl 4-(aminooxymethyl) benzoate | A | A | D | B | D |

TABLE 16-continued

| Cpd # | Structure | Name | hIDO IC50 | hIDO EC50 | hIDO LD50 | mIDO EC50 | mIDO LD50 |
|---|---|---|---|---|---|---|---|
| 811 | 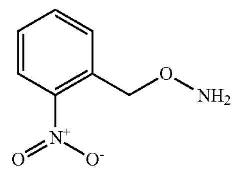 [SMILES: NOCc1ccccc1[N+](=O)[O-]] | O-(2-nitrobenzyl) hydroxylamine | A | A | D | B | D |
| 1669 | 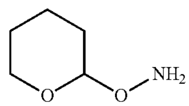 | O-(tetrahydro-2H-pyran-2-yl) hydroxylamine | B | A | D | A | D |
| 1692 | 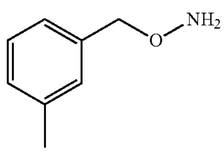 | O-(3-methylbenzyl) hydroxylamine | B | A | D | B | D |
| 1822 | 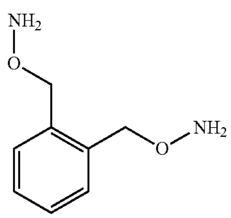 [SMILES: NOCc1ccccc1CON] | O,O'-(1,2-phenylenebis(methylene)) bis(hydroxylamine) | B | B | D | B | D |
| 1667 | 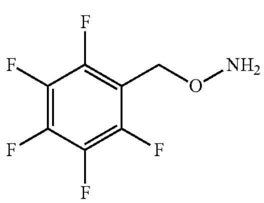 [SMILES: NOCc1c(F)c(F)c(F)c(F)c1F] | O-(perfluorobenzyl) hydroxylamine | B | A | D | B | D |
| 1823 | 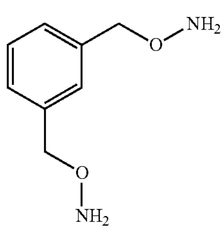 [SMILES: NOCc1cccc(CON)c1] | O,O'-(1,3-phenylenebis(methylene)) bis(hydroxylamine) | B | B | D | A | D |
| 1678 | 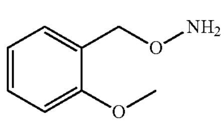 | O-(2-methoxybenzyl) hydroxylamine | B | A | D | B | D |
| 1492 | 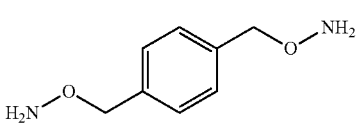 [SMILES: NOCc1ccc(CON)cc1] | O,O'-(1,4-phenylenebis(methylene)) bis(hydroxylamine) | B | A | D | B | C |
| 1815 | 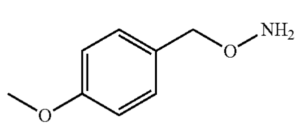 | O-(4-methoxybenzyl) hydroxylamine | B | A | D | B | C |

TABLE 16-continued

| Cpd # | Structure | Name | hIDO IC50 | hIDO EC50 | hIDO LD50 | mIDO EC50 | mIDO LD50 |
|---|---|---|---|---|---|---|---|
| 1014 | 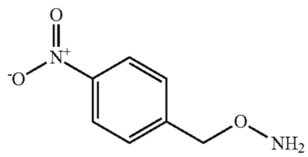 | O-(4-nitrobenzyl)hydroxylamine | B | A | D | B | D |
| 1900 | 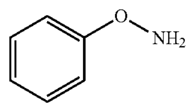 | O-phenylhydroxylamine | B | | | | |
| 1693 | 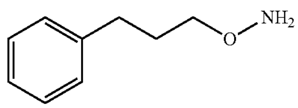 [SMILES: NOCCCc1ccccc1] | O-(3-phenylpropyl)hydroxylamine | B | A | D | B | D |
| 1673 | 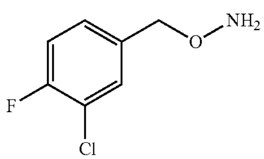 [SMILES: NOCc1ccc(F)c(Cl)c1] | O-(3-chloro-4-fluorobenzyl)hydroxylamine | C | A | C | D | DS |
| 1690 | 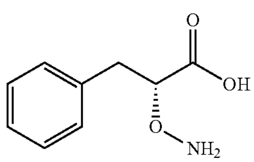 [SMILES: NO[C@H](Cc1ccccc1)C(=O)O] | (R)-2-(aminooxy)-3-phenylpropanoic acid | C | | | | |

We claim:

1. A solid pharmaceutical composition comprising a pharmaceutically acceptable excipient, diluent, or carrier and a compound selected from the group consisting of:
O-((4,4'-dichlorobiphenyl-2-yl)methyl)hydroxylamine;
O-(5-chloro-2-(thiophen-3-yl)benzyl)hydroxylamine;
O-((4'-chlorobiphenyl-2-yl)methyl)hydroxylamine;
O-(5-chloro-2-(thiophen-2-yl)benzyl)hydroxylamine;
methyl 4-(aminooxy)-4-phenylbutanoate;
O-((4'-chlorobiphenyl-3-yl)methyl)hydroxylamine;
O-((3',4,4'-trichlorobiphenyl-2-yl)methyl)hydroxylamine;
O-(5-chloro-2-(pyrimidin-5-yl)benzyl)hydroxylamine;
O-(5-chloro-2-(1H-indol-5-yl)benzyl)hydroxylamine;
(S)-2-(aminooxy)-N-methyl-2-phenylacetamide;
methyl 2-(aminooxy)-2-phenylacetate;
O-(1,3-diphenylpropyl)hydroxylamine;
3-(aminooxymethyl)-N-phenylaniline;
O-((4',5-dichlorobiphenyl-3-yl)methyl)hydroxylamine;
2-(aminooxymethyl)-N-benzylaniline;
O-(3-cyclohexyl-1-phenylpropyl)hydroxylamine;
2-(aminooxymethyl)-N-phenylaniline;
O-(cyclohexyl(phenyl)methyl)hydroxylamine;
2-(aminooxy)-N-methyl-2-phenylacetamide;
O-(1,2-diphenylethyl)hydroxylamine;
O-(1,2,3,4-tetrahydronaphthalen-1-yl)hydroxylamine;
3-(aminooxymethyl)-N-benzylaniline;
O-(2-(pyridin-4-yl)benzyl)hydroxylamine;
O-(3-(pyridin-4-yl)benzyl)hydroxylamine;
O-(2-cyclohexyl-1-phenylethyl)hydroxylamine;
4-(aminooxy)-N-methyl-4-phenylbutanamide;
2-(aminooxy)-2-phenylethanamine;
3-(aminooxy)-3-phenylpropan-1-amine;
O-(2-morpholino-1-phenylethyl)hydroxylamine;
3-(aminooxymethyl)-N-benzylaniline;
2-(aminooxy)-N-methyl-2-phenylethanamine;
4-(aminooxy)-N-cyclohexyl-4-phenylbutanamide;
tert-butyl 2-(aminooxy)-2-phenylethylcarbamate;
(R)-2-(aminooxy)-N-methyl-2-phenylacetamide;
3-(aminooxy)-N-methyl-3-phenylpropan-1-amine;
N-(2-(aminooxy)-2-phenylethyl)acetamide;
O-(3-morpholino-1-phenylpropyl)hydroxylamine; and
(S)-3-(aminooxy)-3-phenylpropan-1-ol;
or a pharmaceutically acceptable salt thereof.

* * * * *